US012781202B2

(12) United States Patent
Böhm et al.

(10) Patent No.: US 12,781,202 B2
(45) Date of Patent: Nov. 3, 2026

(54) RECOMBINANT HUMAN DIAMINE OXIDASE AND METHODS FOR TREATMENT OF EXCESS HISTAMINE CONDITIONS USING THE SAME

(71) Applicants: Medizinische Universität Wien, Vienna (AT); Universität für Bodenkultur Wien, Vienna (AT)

(72) Inventors: Thomas Böhm, Vienna (AT); Bernd Jilma, Vienna (AT); Nicole Borth, Vienna (AT); Elisabeth Gludovacz, Vienna (AT)

(73) Assignees: UNIVERSITÄT FÜR BOEDENKULTUR WIEN, Vienna (AT); MEDIZINESCHE UNIVERSITÄT WIEN, Vienna (AT)

( * ) Notice: Subject to any disclaimer, the term of this patent is extended or adjusted under 35 U.S.C. 154(b) by 943 days.

(21) Appl. No.: 17/430,714

(22) PCT Filed: Feb. 18, 2020

(86) PCT No.: PCT/EP2020/054197
§ 371 (c)(1),
(2) Date: Aug. 12, 2021

(87) PCT Pub. No.: WO2020/169577
PCT Pub. Date: Aug. 27, 2020

(65) Prior Publication Data

US 2022/0145269 A1 May 12, 2022

(30) Foreign Application Priority Data

Feb. 19, 2019 (EP) .................................... 19157932

(51) Int. Cl.

| | |
|---|---|
| ***C12N 9/06*** | (2006.01) |
| ***C07K 14/765*** | (2006.01) |
| ***C12N 15/85*** | (2006.01) |
| *A61K 38/00* | (2006.01) |

(52) U.S. Cl.
CPC .......... *C12N 9/0022* (2013.01); *C07K 14/765* (2013.01); *C12N 15/85* (2013.01); *C12Y 104/03022* (2013.01); *A61K 38/00* (2013.01); *C07K 2319/30* (2013.01); *C07K 2319/31* (2013.01)

(58) Field of Classification Search
None
See application file for complete search history.

(56) References Cited

U.S. PATENT DOCUMENTS

| | | | | |
|---|---|---|---|---|
| 7,745,391 | B2 * | 6/2010 | Mintz ..................... | A61P 37/00 514/19.3 |
| 8,586,006 | B2 * | 11/2013 | Hood ...................... | A61P 35/00 424/9.1 |
| 2005/0255114 | A1 | 11/2005 | Labat et al. | |

FOREIGN PATENT DOCUMENTS

| | | | |
|---|---|---|---|
| JP | 08317793 | A2 | 12/1996 |
| JP | 2001510044 | A | 7/2001 |
| JP | 2008505869 | A | 2/2008 |
| JP | 2014518632 | A | 8/2014 |
| JP | 2017532045 | A | 11/2017 |
| WO | 0243745 | A2 | 6/2002 |
| WO | 2004032830 | A2 | 4/2004 |
| WO | 2012028891 | A1 | 3/2012 |
| WO | 2023122254 | A | 6/2023 |

OTHER PUBLICATIONS

Lingueglia et al. (Eur. J. Biochem., 216, 679-687, 1993).*
Ahlmark A., Acta Physiol. Scand. Suppl., 1944, vol. 9, p. 28.
Bardsley W.G. et al., Biochem. J., 1972, vol. 127, pp. 875-879.
Bartko J. et al., Alcohol, 2016, vol. 54, pp. 1-9.
Best C H., J. Physiol., 1929, vol. 67, No. 3, pp. 256-263.
Boehm T. et al., Clinical Biochemistry, 2017, vol. 50, pp. 444-451.
Brew O. and Sullivan M.H.F., J. Reprod. Immunol., 2006, vol. 72, pp. 94-107.
Database UniProt, XP2792064A, 2011.
Database UniProt, XP2792065A, 2000.
Du-Cuny L et al., Bioorganic & Med. Chem., 2009, vol. 17, No. 19, pp. 6983-6992.
Elmore BO. et al., J. Biol. Inorg. Chem., 2002, vol. 7, pp. 565-579.
Gludovacz E. et al., J Biotechnol., 2016, vol. 227, pp. 120-130.
Gludovacz E. et al., J. Biol. Chem., 2018, vol. 293, No. 3, pp. 1070-1087.
Holmstedt B.O. and Tham R., Acta Physiol. Scand., 1959, vol. 45, pp. 152-163.
Kilkenny C et al., Br. J. Pharmacol., 2010, vol. 160, pp. 1577-1579.

(Continued)

*Primary Examiner* — Hope A Robinson
(74) *Attorney, Agent, or Firm* — Michael Fedrick; LOZA & LOZA, LLP

(57) ABSTRACT

The invention refers to a recombinant human diamine oxidase (DAO) with decreased glycosaminoglycan binding affinity, wherein said DAO comprises at least one amino acid modification in the glycosaminoglycan (GAG) binding domain. The present invention also refers to the use of the DAO in the treatment of a condition associated with excess histamine, specifically in the treatment of chronic allergic diseases, more specifically in the treatment of anaphylaxis, anaphylactic shock, chronic urticaria, acute urticaria, asthma, hay fever, allergic rhinitis, allergic conjunctivitis, histamine intoxication, headache, atopic dermatitis inflammatory diseases, mastocytosis, mast cell activation syndrome (MCAS), pre-eclampsia, hyperemesis gravidarum, pre-term labor, peptic ulcers, acid reflux, pruritus, and sepsis.

20 Claims, 61 Drawing Sheets

Figure 2:
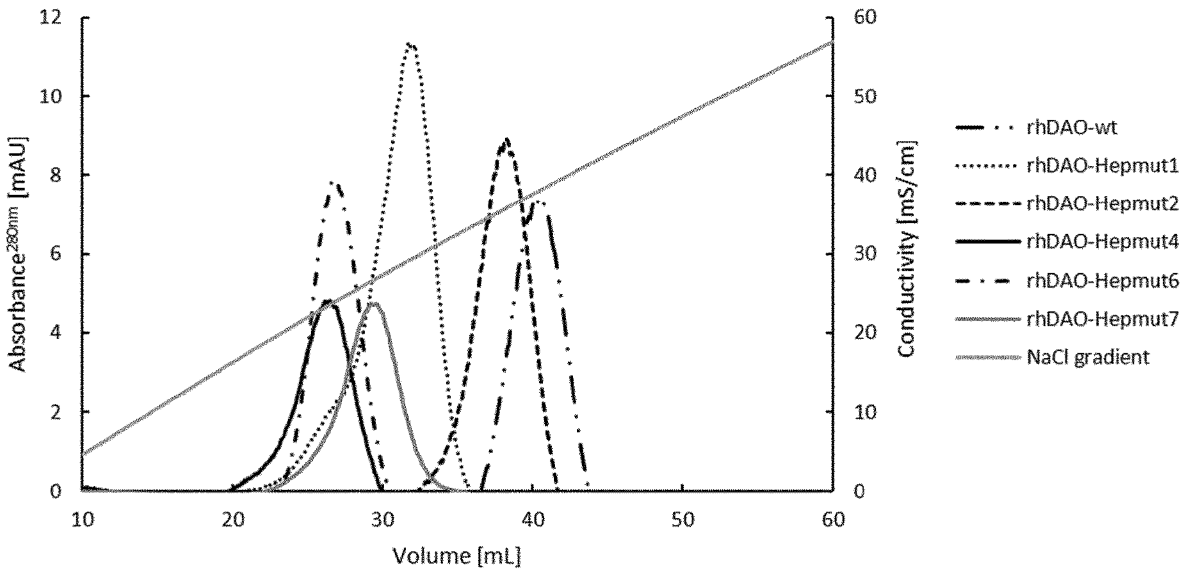

Specification includes a Sequence Listing.

(56) References Cited

OTHER PUBLICATIONS

Maintz L. et al., Am.J.Clin.Nutr., 2007, vol. 85, pp. 1185-1196.
Maintz L. et al., Human Reproduction Update, 2008, vol. 14, No. 5, pp. 485-495.
Marino S M and Gladyshev V N, J Mol Biol., 2010, vol. 404, No. 5, pp. 902-916.
McGrath A P et al., Biochemistry, 2009, vol. 48, No. 41, pp. 9810-9822.
Novotny W F et al., J. Biol. Chem., 1994, vol. 269, No. 13, pp. 9921-9925.
Okuyama T. and Kobayashi Y., Archives Biochem. Biophys., 1961, vol. 95, pp. 242-250.
Paolucci F. et al., Biochimie, 1971, vol. 53, No. 6, pp. 735-749.
Shore P. A. et al., J. Pharmacol. Exptl. Therap., 1959, vol. 127, p. 182.
Tufvesson G, Scand. J Clin. Lab. Invest., 1978, vol. 38, No. 5, pp. 463-472.
Wilflingseder et al., Inflamm Res., 2002, vol. 51, Suppl 1, pp. 89-90.
European Patent Application No. 19157932.5-1120, Extended European Search Report dated Jun. 27, 2019.
International Patent Application No. PCT/EP2020/054197, International Preliminary Report on Patentability dated Aug. 10, 2021.
International Patent Application No. PCT/EP2020/054197, International Search Report dated Apr. 21, 2020.
International Patent Application No. PCT/EP2020/054197, Written Opinion of the International Search Report dated Aug. 27, 2020.
Avalos, A M et al., "Neuronal Thy-1 induces astrocyte adhesion by engaging syndecan-4 in a cooperative interaction with v 3 integrin that activates PKC and RHO", J of Cell Science, 2009, vol. 122, pp. 3462-3471.
Gludovacz, E et al. "Neuronal Thy-1 induces astrocyte adhesion by engaging syndecan-4 in a cooperative interaction with v 3 integrin that activates PKC and RhoA", eLife, 2021, vol. 10, e68542.
Gludovacz, E et al. "Glycosylation site Asn168 is important for slow in vivo clearance of recombinant human diamine oxidase heparin-binding motif mutants", Glycobiology, 2022, vol. 32, No. 5, pp. 404-413.
Ishihara, J et al. "The heparin binding domain of von Willebrand factor binds to growth factors and promotes angiogenesis in wound healing", Blood, 2019, vol. 133, No. 24, pp. 2559-2569.
Kan, M et al."An Essential Heparin-Binding Domain in the Fibroblast Growth Factor Receptor Kinase", Science, 1993, vol. 259, pp. 1918-1921.
Kloker, J et al. "Continuous administration of heparin in patients with deep vein thrombosis can increase plasma levels of diamine oxidase", Vascul Pharmacol., 2004, vol. 40, No. 6, pp. 293-300.
Lau, E K et al. "Identification of the Glycosaminoglycan Binding Site of the CC Chemokine, MCP-1", the J of Biol Chem., 2004, vol. 279, No. 21, pp. 22294-22305.
Luria-Perez, R et al. "Amino acid residues involved in the heparin-binding activity of murine IL-12 in the context of an antibody-cytokine fusion protein", Cytokine, 2019, vol. 120, pp. 220-226.
Picard, V et al. "Two new antithrombin variants support a role for K114 and R13 in heparin binding", Letters to the Editors, 2002, pp. 386-387.
Sandström, J et al. "10-Fold Increase in Human Plasma Extracellular Superoxide Dismutase Content Caused by a Mutation in Heparin-binding Domain", The J of Biol Chem., 1994, vol. 269, No. 29, pp. 19163-19166.
Scherer, S.W. et al. "Amiloride binding protein 1 (amine oxidase (copper-containing)) [*Homo sapiens*]", GenBank, EAL24490, 2004, 2 pgs.
Sendak, R et al."Identification of a heparin-binding domain in the distal carboxyl-terminal region of lipoprotein lipase by site-directed mutagenesis", Journal of Lipid Research, 1998, vol. 39, pp. 1310-1315.
Amine oxidase of Gorilla gorilla gorilla (Western Iowland gorilla), UniProtKB accession No. G3QJ02, UniProt: the Universal Protein Knowledgebase, release No. 2024_02/2024_02, Mar. 27, 2024.
Amine oxidase of *Pisum sativum* (Garden pea), UniProtKB accession no: Q9SXW5, UniProt: the Universal Protein Knowledgebase, release No. 2024_01/2024_01, Jan. 24, 2024.
Intention to Grant (Communication under Rule 71(3) EPC) for corresponding European Patent Application No. EP20704547.7, dated Mar. 17, 2025.
Granted claims of corresponding Chinese Patent No. 113785052B with machine translation.
Gludovacz et al., "Heparin-binding motif mutations of human diamine oxidase allow the development of a first-in-class histamine-degrading biopharmaceutical," eLife, 10:e68542 (Sep. 3, 2021).

* cited by examiner

Figure 1 hDAO-wildtype

MPALGWAVAAILMLQTAMAEPSPGTLPRKAGVFSDLSNQELKAVHSFLWSKKELRLQPSSTTTMAKNT
VFLIEMLLPKKYHVLRFLDKGERHPVREARAVIFFGDQEHPNVTEFAVGPLPGPCYMRALSPRPGYQSS
WASRPISTAEYALLYHTLQEATKPLHQFFLNTTGFSFQDCHDRCLAFTDVAPRGVASGQRRSWLIIQRY
VEGYFLHPTGLELLVDHGSTDAGHWAVEQVWYNGKFYGSPEELARKYADGEVDVVVLEDPLPGGKGH
DSTEEPPLFSSHKPRGDFPSPIHVSGPRLVQPHGPRFRLEGNAVLYGGWSFAFRLRSSSGLQVLNVHF
GGERIAYEVSVQEAVALYGGHTPAGMQTKYLDVGWGLGSVTHELAPGIDCPETATFLDTFHYYDADDP
VHYPRALCLFEMPTGVPLRRHFNSNFKGGFNFYAGLKGQVLVLRTTSTVYNYDYIWDFIFYPNGVMEAK
MHATGYVHATFYTPEGLRHGTRLHTHLIGNIHTHLVHYRVDLDVAGTKNSFQTLQMKLENITNPWSPRH
RVVQPTLEQTQYSWERQAAFRFKRKLPKYLLFTSPQENPWGHKRSYRLQIHSMADQVLPPGWQEEQA
ITWARYPLAVTKYRESELCSSSIYHQNDPWHPPVVFEQFLHNNENIENEDLVAWVTVGFLHIPHSEDIPN
TATPGNSVGFLLRPFNFFPEDPSLASRDTVIVWPRDNGPNYVQRWIPEDRDCSMPPPFSYNGTYRPV
(SEQ ID NO:1)

hDAO-Hepmut1

MPALGWAVAAILMLQTAMAEPSPGTLPRKAGVFSDLSNQELKAVHSFLWSKKELRLQPSSTTTMAKNT
VFLIEMLLPKKYHVLRFLDKGERHPVREARAVIFFGDQEHPNVTEFAVGPLPGPCYMRALSPRPGYQSS
WASRPISTAEYALLYHTLQEATKPLHQFFLNTTGFSFQDCHDRCLAFTDVAPRGVASGQRRSWLIIQRY
VEGYFLHPTGLELLVDHGSTDAGHWAVEQVWYNGKFYGSPEELARKYADGEVDVVVLEDPLPGGKGH
DSTEEPPLFSSHKPRGDFPSPIHVSGPRLVQPHGPRFRLEGNAVLYGGWSFAFRLRSSSGLQVLNVHF
GGERIAYEVSVQEAVALYGGHTPAGMQTKYLDVGWGLGSVTHELAPGIDCPETATFLDTFHYYDADDP
VHYPRALCLFEMPTGVPLRRHFNSNFKGGFNFYAGLKGQVLVLRTTSTVYNYDYIWDFIFYPNGVMEAK
MHATGYVHATFYTPEGLRHGTRLHTHLIGNIHTHLVHYRVDLDVAGTKNSFQTLQMKLENITNPWSPRH
RVVQPTLEQTQYSWERQAAFSFKRKLPKYLLFTSPQENPWGHKRSYRLQIHSMADQVLPPGWQEEQA
ITWARYPLAVTKYRESELCSSSIYHQNDPWHPPVVFEQFLHNNENIENEDLVAWVTVGFLHIPHSEDIPN
TATPGNSVGFLLRPFNFFPEDPSLASRDTVIVWPRDNGPNYVQRWIPEDRDCSMPPPFSYNGTYRPV
(SEQ ID NO:2)

hDAO-Hepmut2

MPALGWAVAAILMLQTAMAEPSPGTLPRKAGVFSDLSNQELKAVHSFLWSKKELRLQPSSTTTMAKNT
VFLIEMLLPKKYHVLRFLDKGERHPVREARAVIFFGDQEHPNVTEFAVGPLPGPCYMRALSPRPGYQSS
WASRPISTAEYALLYHTLQEATKPLHQFFLNTTGFSFQDCHDRCLAFTDVAPRGVASGQRRSWLIIQRY
VEGYFLHPTGLELLVDHGSTDAGHWAVEQVWYNGKFYGSPEELARKYADGEVDVVVLEDPLPGGKGH
DSTEEPPLFSSHKPRGDFPSPIHVSGPRLVQPHGPRFRLEGNAVLYGGWSFAFRLRSSSGLQVLNVHF
GGERIAYEVSVQEAVALYGGHTPAGMQTKYLDVGWGLGSVTHELAPGIDCPETATFLDTFHYYDADDP
VHYPRALCLFEMPTGVPLRRHFNSNFKGGFNFYAGLKGQVLVLRTTSTVYNYDYIWDFIFYPNGVMEAK
MHATGYVHATFYTPEGLRHGTRLHTHLIGNIHTHLVHYRVDLDVAGTKNSFQTLQMKLENITNPWSPRH
RVVQPTLEQTQYSWERQAAFRFKRKLPTYLLFTSPQENPWGHKRSYRLQIHSMADQVLPPGWQEEQA
ITWARYPLAVTKYRESELCSSSIYHQNDPWHPPVVFEQFLHNNENIENEDLVAWVTVGFLHIPHSEDIPN
TATPGNSVGFLLRPFNFFPEDPSLASRDTVIVWPRDNGPNYVQRWIPEDRDCSMPPPFSYNGTYRPV
(SEQ ID NO:3)

hDAO-Hepmut3

MPALGWAVAAILMLQTAMAEPSPGTLPRKAGVFSDLSNQELKAVHSFLWSKKELRLQPSSTTTMAKNT
VFLIEMLLPKKYHVLRFLDKGERHPVREARAVIFFGDQEHPNVTEFAVGPLPGPCYMRALSPRPGYQSS
WASRPISTAEYALLYHTLQEATKPLHQFFLNTTGFSFQDCHDRCLAFTDVAPRGVASGQRRSWLIIQRY
VEGYFLHPTGLELLVDHGSTDAGHWAVEQVWYNGKFYGSPEELARKYADGEVDVVVLEDPLPGGKGH
DSTEEPPLFSSHKPRGDFPSPIHVSGPRLVQPHGPRFRLEGNAVLYGGWSFAFRLRSSSGLQVLNVHF
GGERIAYEVSVQEAVALYGGHTPAGMQTKYLDVGWGLGSVTHELAPGIDCPETATFLDTFHYYDADDP
VHYPRALCLFEMPTGVPLRRHFNSNFKGGFNFYAGLKGQVLVLRTTSTVYNYDYIWDFIFYPNGVMEAK
MHATGYVHATFYTPEGLRHGTRLHTHLIGNIHTHLVHYRVDLDVAGTKNSFQTLQMKLENITNPWSPRH
RVVQPTLEQTQYSWERQAAFRFKTKLPKYLLFTSPQENPWGHKRSYRLQIHSMADQVLPPGWQEEQA
ITWARYPLAVTKYRESELCSSSIYHQNDPWHPPVVFEQFLHNNENIENEDLVAWVTVGFLHIPHSEDIPN
TATPGNSVGFLLRPFNFFPEDPSLASRDTVIVWPRDNGPNYVQRWIPEDRDCSMPPPFSYNGTYRPV
(SEQ ID NO:4)

Figure 1 continued hDAO-Hepmut4

MPALGWAVAAILMLQTAMAEPSPGTLPRKAGVFSDLSNQELKAVHSFLWSKKELRLQPSSTTTMAKNT
VFLIEMLLPKKYHVLRFLDKGERHPVREARAVIFFGDQEHPNVTEFAVGPLPGPCYMRALSPRPGYQSS
WASRPISTAEYALLYHTLQEATKPLHQFFLNTTGFSFQDCHDRCLAFTDVAPRGVASGQRRSWLIIQRY
VEGYFLHPTGLELLVDHGSTDAGHWAVEQVWYNGKFYGSPEELARKYADGEVDVVVLEDPLPGGKGH
DSTEEPPLFSSHKPRGDFPSPIHVSGPRLVQPHGPRFRLEGNAVLYGGWSFAFRLRSSSGLQVLNVHF
GGERIAYEVSVQEAVALYGGHTPAGMQTKYLDVGWGLGSVTHELAPGIDCPETATFLDTFHYYDADDP
VHYPRALCLFEMPTGVPLRRHFNSNFKGGFNFYAGLKGQVLVLRTTSTVYNYDYIWDFIFYPNGVMEAK
MHATGYVHATFYTPEGLRHGTRLHTHLIGNIHTHLVHYRVDLDVAGTKNSFQTLQMKLENITNPWSPRH
RVVQPTLEQTQYSWERQAAFSFKTKLPKYLLFTSPQENPWGHKRSYRLQIHSMADQVLPPGWQEEQAI
TWARYPLAVTKYRESELCSSSIYHQNDPWHPPVVFEQFLHNNENIENEDLVAWVTVGFLHIPHSEDIPN
TATPGNSVGFLLRPFNFFPEDPSLASRDTVIVWPRDNGPNYVQRWIPEDRDCSMPPPFSYNGTYRPV
(SEQ ID NO:5)

hDAO-Hepmut5

MPALGWAVAAILMLQTAMAEPSPGTLPRKAGVFSDLSNQELKAVHSFLWSKKELRLQPSSTTTMAKNT
VFLIEMLLPKKYHVLRFLDKGERHPVREARAVIFFGDQEHPNVTEFAVGPLPGPCYMRALSPRPGYQSS
WASRPISTAEYALLYHTLQEATKPLHQFFLNTTGFSFQDCHDRCLAFTDVAPRGVASGQRRSWLIIQRY
VEGYFLHPTGLELLVDHGSTDAGHWAVEQVWYNGKFYGSPEELARKYADGEVDVVVLEDPLPGGKGH
DSTEEPPLFSSHKPRGDFPSPIHVSGPRLVQPHGPRFRLEGNAVLYGGWSFAFRLRSSSGLQVLNVHF
GGERIAYEVSVQEAVALYGGHTPAGMQTKYLDVGWGLGSVTHELAPGIDCPETATFLDTFHYYDADDP
VHYPRALCLFEMPTGVPLRRHFNSNFKGGFNFYAGLKGQVLVLRTTSTVYNYDYIWDFIFYPNGVMEAK
MHATGYVHATFYTPEGLRHGTRLHTHLIGNIHTHLVHYRVDLDVAGTKNSFQTLQMKLENITNPWSPRH
RVVQPTLEQTQYSWERQAAFRFKTKLPTYLLFTSPQENPWGHKRSYRLQIHSMADQVLPPGWQEEQAI
TWARYPLAVTKYRESELCSSSIYHQNDPWHPPVVFEQFLHNNENIENEDLVAWVTVGFLHIPHSEDIPN
TATPGNSVGFLLRPFNFFPEDPSLASRDTVIVWPRDNGPNYVQRWIPEDRDCSMPPPFSYNGTYRPV
(SEQ ID NO:6)

hDAO-Hepmut6

MPALGWAVAAILMLQTAMAEPSPGTLPRKAGVFSDLSNQELKAVHSFLWSKKELRLQPSSTTTMAKNT
VFLIEMLLPKKYHVLRFLDKGERHPVREARAVIFFGDQEHPNVTEFAVGPLPGPCYMRALSPRPGYQSS
WASRPISTAEYALLYHTLQEATKPLHQFFLNTTGFSFQDCHDRCLAFTDVAPRGVASGQRRSWLIIQRY
VEGYFLHPTGLELLVDHGSTDAGHWAVEQVWYNGKFYGSPEELARKYADGEVDVVVLEDPLPGGKGH
DSTEEPPLFSSHKPRGDFPSPIHVSGPRLVQPHGPRFRLEGNAVLYGGWSFAFRLRSSSGLQVLNVHF
GGERIAYEVSVQEAVALYGGHTPAGMQTKYLDVGWGLGSVTHELAPGIDCPETATFLDTFHYYDADDP
VHYPRALCLFEMPTGVPLRRHFNSNFKGGFNFYAGLKGQVLVLRTTSTVYNYDYIWDFIFYPNGVMEAK
MHATGYVHATFYTPEGLRHGTRLHTHLIGNIHTHLVHYRVDLDVAGTKNSFQTLQMKLENITNPWSPRH
RVVQPTLEQTQYSWERQAAFRFGQTLPKYLLFTSPQENPWGHKRSYRLQIHSMADQVLPPGWQEEQA
ITWARYPLAVTKYRESELCSSSIYHQNDPWHPPVVFEQFLHNNENIENEDLVAWVTVGFLHIPHSEDIPN
TATPGNSVGFLLRPFNFFPEDPSLASRDTVIVWPRDNGPNYVQRWIPEDRDCSMPPPFSYNGTYRPV
(SEQ ID NO:7)

hDAO-Hepmut7

MPALGWAVAAILMLQTAMAEPSPGTLPRKAGVFSDLSNQELKAVHSFLWSKKELRLQPSSTTTMAKNT
VFLIEMLLPKKYHVLRFLDKGERHPVREARAVIFFGDQEHPNVTEFAVGPLPGPCYMRALSPRPGYQSS
WASRPISTAEYALLYHTLQEATKPLHQFFLNTTGFSFQDCHDRCLAFTDVAPRGVASGQRRSWLIIQRY
VEGYFLHPTGLELLVDHGSTDAGHWAVEQVWYNGKFYGSPEELARKYADGEVDVVVLEDPLPGGKGH
DSTEEPPLFSSHKPRGDFPSPIHVSGPRLVQPHGPRFRLEGNAVLYGGWSFAFRLRSSSGLQVLNVHF
GGERIAYEVSVQEAVALYGGHTPAGMQTKYLDVGWGLGSVTHELAPGIDCPETATFLDTFHYYDADDP
VHYPRALCLFEMPTGVPLRRHFNSNFKGGFNFYAGLKGQVLVLRTTSTVYNYDYIWDFIFYPNGVMEAK
MHATGYVHATFYTPEGLRHGTRLHTHLIGNIHTHLVHYRVDLDVAGTKNSFQTLQMKLENITNPWSPRH
RVVQPTLEQTQYSWERQAAFSFKRKLPTYLLFTSPQENPWGHKRSYRLQIHSMADQVLPPGWQEEQA
ITWARYPLAVTKYRESELCSSSIYHQNDPWHPPVVFEQFLHNNENIENEDLVAWVTVGFLHIPHSEDIPN
TATPGNSVGFLLRPFNFFPEDPSLASRDTVIVWPRDNGPNYVQRWIPEDRDCSMPPPFSYNGTYRPV
(SEQ ID NO:8)

Figure 1 continued hDAO-Cysmut

MPALGWAVAAILMLQTAMAEPSPGTLPRKAGVFSDLSNQELKAVHSFLWSKKELRLQPSSTTTMAKNT
VFLIEMLLPKKYHVLRFLDKGERHPVREARAVIFFGDQEHPNVTEFAVGPLPGPAYMRALSPRPGYQSS
WASRPISTAEYALLYHTLQEATKPLHQFFLNTTGFSFQDCHDRCLAFTDVAPRGVASGQRRSWLIIQRY
VEGYFLHPTGLELLVDHGSTDAGHWAVEQVWYNGKFYGSPEELARKYADGEVDVVVLEDPLPGGKGH
DSTEEPPLFSSHKPRGDFPSPIHVSGPRLVQPHGPRFRLEGNAVLYGGWSFAFRLRSSSGLQVLNVHF
GGERIAYEVSVQEAVALYGGHTPAGMQTKYLDVGWGLGSVTHELAPGIDCPETATFLDTFHYYDADDP
VHYPRALCLFEMPTGVPLRRHFNSNFKGGFNFYAGLKGQVLVLRTTSTVYNYDYIWDFIFYPNGVMEAK
MHATGYVHATFYTPEGLRHGTRLHTHLIGNIHTHLVHYRVDLDVAGTKNSFQTLQMKLENITNPWSPRH
RVVQPTLEQTQYSWERQAAFRFKRKLPKYLLFTSPQENPWGHKRSYRLQIHSMADQVLPPGWQEEQA
ITWARYPLAVTKYRESELCSSSIYHQNDPWHPPVVFEQFLHNNENIENEDLVAWVTVGFLHIPHSEDIPN
TATPGNSVGFLLRPFNFFPEDPSLASRDTVIVWPRDNGPNYVQRWIPEDRDCSMPPPFSYNGTYRPV
(SEQ ID NO:9)

hDAO-Hepmut1-Cysmut

MPALGWAVAAILMLQTAMAEPSPGTLPRKAGVFSDLSNQELKAVHSFLWSKKELRLQPSSTTTMAKNT
VFLIEMLLPKKYHVLRFLDKGERHPVREARAVIFFGDQEHPNVTEFAVGPLPGPAYMRALSPRPGYQSS
WASRPISTAEYALLYHTLQEATKPLHQFFLNTTGFSFQDCHDRCLAFTDVAPRGVASGQRRSWLIIQRY
VEGYFLHPTGLELLVDHGSTDAGHWAVEQVWYNGKFYGSPEELARKYADGEVDVVVLEDPLPGGKGH
DSTEEPPLFSSHKPRGDFPSPIHVSGPRLVQPHGPRFRLEGNAVLYGGWSFAFRLRSSSGLQVLNVHF
GGERIAYEVSVQEAVALYGGHTPAGMQTKYLDVGWGLGSVTHELAPGIDCPETATFLDTFHYYDADDP
VHYPRALCLFEMPTGVPLRRHFNSNFKGGFNFYAGLKGQVLVLRTTSTVYNYDYIWDFIFYPNGVMEAK
MHATGYVHATFYTPEGLRHGTRLHTHLIGNIHTHLVHYRVDLDVAGTKNSFQTLQMKLENITNPWSPRH
RVVQPTLEQTQYSWERQAAFSFKRKLPKYLLFTSPQENPWGHKRSYRLQIHSMADQVLPPGWQEEQA
ITWARYPLAVTKYRESELCSSSIYHQNDPWHPPVVFEQFLHNNENIENEDLVAWVTVGFLHIPHSEDIPN
TATPGNSVGFLLRPFNFFPEDPSLASRDTVIVWPRDNGPNYVQRWIPEDRDCSMPPPFSYNGTYRPV
(SEQ ID NO:10)

hDAO-Hepmut2-Cysmut

MPALGWAVAAILMLQTAMAEPSPGTLPRKAGVFSDLSNQELKAVHSFLWSKKELRLQPSSTTTMAKNT
VFLIEMLLPKKYHVLRFLDKGERHPVREARAVIFFGDQEHPNVTEFAVGPLPGPAYMRALSPRPGYQSS
WASRPISTAEYALLYHTLQEATKPLHQFFLNTTGFSFQDCHDRCLAFTDVAPRGVASGQRRSWLIIQRY
VEGYFLHPTGLELLVDHGSTDAGHWAVEQVWYNGKFYGSPEELARKYADGEVDVVVLEDPLPGGKGH
DSTEEPPLFSSHKPRGDFPSPIHVSGPRLVQPHGPRFRLEGNAVLYGGWSFAFRLRSSSGLQVLNVHF
GGERIAYEVSVQEAVALYGGHTPAGMQTKYLDVGWGLGSVTHELAPGIDCPETATFLDTFHYYDADDP
VHYPRALCLFEMPTGVPLRRHFNSNFKGGFNFYAGLKGQVLVLRTTSTVYNYDYIWDFIFYPNGVMEAK
MHATGYVHATFYTPEGLRHGTRLHTHLIGNIHTHLVHYRVDLDVAGTKNSFQTLQMKLENITNPWSPRH
RVVQPTLEQTQYSWERQAAFRFKRKLPTYLLFTSPQENPWGHKRSYRLQIHSMADQVLPPGWQEEQA
ITWARYPLAVTKYRESELCSSSIYHQNDPWHPPVVFEQFLHNNENIENEDLVAWVTVGFLHIPHSEDIPN
TATPGNSVGFLLRPFNFFPEDPSLASRDTVIVWPRDNGPNYVQRWIPEDRDCSMPPPFSYNGTYRPV
(SEQ ID NO:11)

hDAO-Hepmut3-Cysmut

MPALGWAVAAILMLQTAMAEPSPGTLPRKAGVFSDLSNQELKAVHSFLWSKKELRLQPSSTTTMAKNT
VFLIEMLLPKKYHVLRFLDKGERHPVREARAVIFFGDQEHPNVTEFAVGPLPGPAYMRALSPRPGYQSS
WASRPISTAEYALLYHTLQEATKPLHQFFLNTTGFSFQDCHDRCLAFTDVAPRGVASGQRRSWLIIQRY
VEGYFLHPTGLELLVDHGSTDAGHWAVEQVWYNGKFYGSPEELARKYADGEVDVVVLEDPLPGGKGH
DSTEEPPLFSSHKPRGDFPSPIHVSGPRLVQPHGPRFRLEGNAVLYGGWSFAFRLRSSSGLQVLNVHF
GGERIAYEVSVQEAVALYGGHTPAGMQTKYLDVGWGLGSVTHELAPGIDCPETATFLDTFHYYDADDP
VHYPRALCLFEMPTGVPLRRHFNSNFKGGFNFYAGLKGQVLVLRTTSTVYNYDYIWDFIFYPNGVMEAK
MHATGYVHATFYTPEGLRHGTRLHTHLIGNIHTHLVHYRVDLDVAGTKNSFQTLQMKLENITNPWSPRH
RVVQPTLEQTQYSWERQAAFRFKTKLPKYLLFTSPQENPWGHKRSYRLQIHSMADQVLPPGWQEEQA
ITWARYPLAVTKYRESELCSSSIYHQNDPWHPPVVFEQFLHNNENIENEDLVAWVTVGFLHIPHSEDIPN
TATPGNSVGFLLRPFNFFPEDPSLASRDTVIVWPRDNGPNYVQRWIPEDRDCSMPPPFSYNGTYRPV
(SEQ ID NO:12)

Figure 1 continued hDAO-Hepmut4-Cysmut

MPALGWAVAAILMLQTAMAEPSPGTLPRKAGVFSDLSNQELKAVHSFLWSKKELRLQPSSTTTMAKNT
VFLIEMLLPKKYHVLRFLDKGERHPVREARAVIFFGDQEHPNVTEFAVGPLPGPAYMRALSPRPGYQSS
WASRPISTAEYALLYHTLQEATKPLHQFFLNTTGFSFQDCHDRCLAFTDVAPRGVASGQRRSWLIIQRY
VEGYFLHPTGLELLVDHGSTDAGHWAVEQVWYNGKFYGSPEELARKYADGEVDVVVLEDPLPGGKGH
DSTEEPPLFSSHKPRGDFPSPIHVSGPRLVQPHGPRFRLEGNAVLYGGWSFAFRLRSSSGLQVLNVHF
GGERIAYEVSVQEAVALYGGHTPAGMQTKYLDVGWGLGSVTHELAPGIDCPETATFLDTFHYYDADDP
VHYPRALCLFEMPTGVPLRRHFNSNFKGGFNFYAGLKGQVLVLRTTSTVYNYDYIWDFIFYPNGVMEAK
MHATGYVHATFYTPEGLRHGTRLHTHLIGNIHTHLVHYRVDLDVAGTKNSFQTLQMKLENITNPWSPRH
RVVQPTLEQTQYSWERQAAFSFKTKLPKYLLFTSPQENPWGHKRSYRLQIHSMADQVLPPGWQEEQAI
TWARYPLAVTKYRESELCSSSIYHQNDPWHPPVVFEQFLHNNENIENEDLVAWVTVGFLHIPHSEDIPN
TATPGNSVGFLLRPFNFFPEDPSLASRDTVIVWPRDNGPNYVQRWIPEDRDCSMPPPFSYNGTYRPV
(SEQ ID NO:13)

hDAO-Hepmut5-Cysmut

MPALGWAVAAILMLQTAMAEPSPGTLPRKAGVFSDLSNQELKAVHSFLWSKKELRLQPSSTTTMAKNT
VFLIEMLLPKKYHVLRFLDKGERHPVREARAVIFFGDQEHPNVTEFAVGPLPGPAYMRALSPRPGYQSS
WASRPISTAEYALLYHTLQEATKPLHQFFLNTTGFSFQDCHDRCLAFTDVAPRGVASGQRRSWLIIQRY
VEGYFLHPTGLELLVDHGSTDAGHWAVEQVWYNGKFYGSPEELARKYADGEVDVVVLEDPLPGGKGH
DSTEEPPLFSSHKPRGDFPSPIHVSGPRLVQPHGPRFRLEGNAVLYGGWSFAFRLRSSSGLQVLNVHF
GGERIAYEVSVQEAVALYGGHTPAGMQTKYLDVGWGLGSVTHELAPGIDCPETATFLDTFHYYDADDP
VHYPRALCLFEMPTGVPLRRHFNSNFKGGFNFYAGLKGQVLVLRTTSTVYNYDYIWDFIFYPNGVMEAK
MHATGYVHATFYTPEGLRHGTRLHTHLIGNIHTHLVHYRVDLDVAGTKNSFQTLQMKLENITNPWSPRH
RVVQPTLEQTQYSWERQAAFRFKTKLPTYLLFTSPQENPWGHKRSYRLQIHSMADQVLPPGWQEEQAI
TWARYPLAVTKYRESELCSSSIYHQNDPWHPPVVFEQFLHNNENIENEDLVAWVTVGFLHIPHSEDIPN
TATPGNSVGFLLRPFNFFPEDPSLASRDTVIVWPRDNGPNYVQRWIPEDRDCSMPPPFSYNGTYRPV
(SEQ ID NO:14)

hDAO-Hepmut6-Cysmut

MPALGWAVAAILMLQTAMAEPSPGTLPRKAGVFSDLSNQELKAVHSFLWSKKELRLQPSSTTTMAKNT
VFLIEMLLPKKYHVLRFLDKGERHPVREARAVIFFGDQEHPNVTEFAVGPLPGPAYMRALSPRPGYQSS
WASRPISTAEYALLYHTLQEATKPLHQFFLNTTGFSFQDCHDRCLAFTDVAPRGVASGQRRSWLIIQRY
VEGYFLHPTGLELLVDHGSTDAGHWAVEQVWYNGKFYGSPEELARKYADGEVDVVVLEDPLPGGKGH
DSTEEPPLFSSHKPRGDFPSPIHVSGPRLVQPHGPRFRLEGNAVLYGGWSFAFRLRSSSGLQVLNVHF
GGERIAYEVSVQEAVALYGGHTPAGMQTKYLDVGWGLGSVTHELAPGIDCPETATFLDTFHYYDADDP
VHYPRALCLFEMPTGVPLRRHFNSNFKGGFNFYAGLKGQVLVLRTTSTVYNYDYIWDFIFYPNGVMEAK
MHATGYVHATFYTPEGLRHGTRLHTHLIGNIHTHLVHYRVDLDVAGTKNSFQTLQMKLENITNPWSPRH
RVVQPTLEQTQYSWERQAAFRFGQTLPKYLLFTSPQENPWGHKRSYRLQIHSMADQVLPPGWQEEQA
ITWARYPLAVTKYRESELCSSSIYHQNDPWHPPVVFEQFLHNNENIENEDLVAWVTVGFLHIPHSEDIPN
TATPGNSVGFLLRPFNFFPEDPSLASRDTVIVWPRDNGPNYVQRWIPEDRDCSMPPPFSYNGTYRPV
(SEQ ID NO:15)

hDAO-Hepmut7-Cysmut

MPALGWAVAAILMLQTAMAEPSPGTLPRKAGVFSDLSNQELKAVHSFLWSKKELRLQPSSTTTMAKNT
VFLIEMLLPKKYHVLRFLDKGERHPVREARAVIFFGDQEHPNVTEFAVGPLPGPAYMRALSPRPGYQSS
WASRPISTAEYALLYHTLQEATKPLHQFFLNTTGFSFQDCHDRCLAFTDVAPRGVASGQRRSWLIIQRY
VEGYFLHPTGLELLVDHGSTDAGHWAVEQVWYNGKFYGSPEELARKYADGEVDVVVLEDPLPGGKGH
DSTEEPPLFSSHKPRGDFPSPIHVSGPRLVQPHGPRFRLEGNAVLYGGWSFAFRLRSSSGLQVLNVHF
GGERIAYEVSVQEAVALYGGHTPAGMQTKYLDVGWGLGSVTHELAPGIDCPETATFLDTFHYYDADDP
VHYPRALCLFEMPTGVPLRRHFNSNFKGGFNFYAGLKGQVLVLRTTSTVYNYDYIWDFIFYPNGVMEAK
MHATGYVHATFYTPEGLRHGTRLHTHLIGNIHTHLVHYRVDLDVAGTKNSFQTLQMKLENITNPWSPRH
RVVQPTLEQTQYSWERQAAFSFKRKLPTYLLFTSPQENPWGHKRSYRLQIHSMADQVLPPGWQEEQA
ITWARYPLAVTKYRESELCSSSIYHQNDPWHPPVVFEQFLHNNENIENEDLVAWVTVGFLHIPHSEDIPN
TATPGNSVGFLLRPFNFFPEDPSLASRDTVIVWPRDNGPNYVQRWIPEDRDCSMPPPFSYNGTYRPV
(SEQ ID NO:16)

Figure 1 continued hDAO-wildtype atgccggccctgggctgggccgtggctgccatcctgatgctgcagacggccatggcggagccctccccggggactctgcccaggaa
ggcaggggtgttttcagacctaagcaaccaagagctgaaggcagtgcacagcttcctctggtccaagaaggagctgaggctgcagccctccagt
accaccaccatggccaagaacaccgtgtttctcatcgagatgctgctgcccaagaagtaccatgtgctgaggtttctggataaaggtgaaaggcat
cctgtgcgggaagcccgtgccgtcatcttctttggtgaccaggagcatcccaatgtcaccgagtttgctgtggggcccctgccagggccctgctaca
tgcgagcactgtcccccaggcctgggtaccagtcctcctgggcatcgaggcccatctccacagcagagtatgccctcctctaccacaccctgcag
gaagccaccaagcccctgcatcagttcttcctcaataccacaggcttctcattccaagactgccatgacagatgcctggccttcaccgatgtggccc
cccggggtgtggcttctggccagcgccgcagttggcttatcatacagcgctatgtagaaggctactttctgcaccccactgggctggagctcctcgtg
gatcatgggagcacagatgctgggcactgggccgtggagcaggtgtggtacaacgggaagttctatgggagcccagaggaactggctcggaa
gtatgcagatggagaggtggacgtggtggtcctggaggacccgctgcctgggggcaaggggcatgacagcacagaggagccgcccctcttctc
ctcccacaagccccgcggggacttccccagccccatccatgtgagcggcccccgcttggtccagccccacggccctcgcttcaggctggaggg
caacgctgtgctctacggcggctggagctttgccttccggctgcgctcctcctccgggctgcaggtcctgaacgtgcacttcggcggagagcgcatt
gcctatgaggtcagcgtgcaagaggcagtggcgctgtatggaggacacacacctgcaggcatgcagaccaagtacctcgatgtcggctggggc
ctgggcagcgtcactcatgagttagcccccggcatcgactgcccggagaccgccaccttcctggacactttccactactatgatgccgatgacccg
gtccattatccccgagccctctgcctctttgaaatgcccacaggggtgccccttcggcggcactttaattccaactttaaaggtggcttcaacttctatg
cggggctgaagggccaggtgctggtgctgcggacaacttcaactgtctacaattatgattacatttgggactttatcttctaccccaacggggtgatg
gaggccaagatgcatgccactggctacgtccacgccaccttctacacccccgaggggctgcgccacggcactcgcctgcacacccacctgattg
gcaacatacacactcacttggtgcactaccgcgtagacctggatgtggcaggcaccaagaacagcttccagacactgcagatgaagctagaaa
acatcaccaacccctggagcccaagacaccgcgtggtccagccaactctggagcagacgcagtactcctgggagcgccaggcggccttccgc
ttcaaaaggaagctgcccaagtacctgctctttaccagcccccaggagaacccctggggccacaagcgcagctaccgcctgcagatccactcc
atggccgaccaggtgctgcccccaggctggcaggaggagcaggccatcacctgggcaaggtacccccctggcagtgaccaagtaccgggagt
cggagctgtgcagcagcagcatctaccaccagaacgacccctggcacccgcccgtggtctttgagcagtttcttcacaacaacgagaacattga
aaatgaggacctggtggcctgggtgacggtgggcttcctgcacatcccccactcagaggacattcccaacacagccacacctgggaactccgtg
ggcttcctgctccggccattcaacttcttcccagaggacccctccctggcatccagagacactgtgatcgtgtggcctcgggacaacggccccaac
tacgtccagcgctggatccctgaggacagggactgctcgatgcctcccccttttagctacaatgggacctatagacctgtgtga (SEQ ID NO:17)

hDAO-Hepmut1 atgccggccctgggctgggccgtggctgccatcctgatgctgcagacggccatggcggagccctccccggggactctgcccaggaa
ggcaggggtgttttcagacctaagcaaccaagagctgaaggcagtgcacagcttcctctggtccaagaaggagctgaggctgcagccctccagt
accaccaccatggccaagaacaccgtgtttctcatcgagatgctgctgcccaagaagtaccatgtgctgaggtttctggataaaggtgaaaggcat
cctgtgcgggaagcccgtgccgtcatcttctttggtgaccaggagcatcccaatgtcaccgagtttgctgtggggcccctgccagggccctgctaca
tgcgagcactgtcccccaggcctgggtaccagtcctcctgggcatcgaggcccatctccacagcagagtatgccctcctctaccacaccctgcag
gaagccaccaagcccctgcatcagttcttcctcaataccacaggcttctcattccaagactgccatgacagatgcctggccttcaccgatgtggccc
cccggggtgtggcttctggccagcgccgcagttggcttatcatacagcgctatgtagaaggctactttctgcaccccactgggctggagctcctcgtg
gatcatgggagcacagatgctgggcactgggccgtggagcaggtgtggtacaacgggaagttctatgggagcccagaggaactggctcggaa
gtatgcagatggagaggtggacgtggtggtcctggaggacccgctgcctgggggcaaggggcatgacagcacagaggagccgcccctcttctc
ctcccacaagccccgcggggacttccccagccccatccatgtgagcggcccccgcttggtccagccccacggccctcgcttcaggctggaggg
caacgctgtgctctacggcggctggagctttgccttccggctgcgctcctcctccgggctgcaggtcctgaacgtgcacttcggcggagagcgcatt
gcctatgaggtcagcgtgcaagaggcagtggcgctgtatggaggacacacacctgcaggcatgcagaccaagtacctcgatgtcggctggggc
ctgggcagcgtcactcatgagttagcccccggcatcgactgcccggagaccgccaccttcctggacactttccactactatgatgccgatgacccg
gtccattatccccgagccctctgcctctttgaaatgcccacaggggtgccccttcggcggcactttaattccaactttaaaggtggcttcaacttctatg
cggggctgaagggccaggtgctggtgctgcggacaacttcaactgtctacaattatgattacatttgggactttatcttctaccccaacggggtgatg
gaggccaagatgcatgccactggctacgtccacgccaccttctacacccccgaggggctgcgccacggcactcgcctgcacacccacctgattg
gcaacatacacactcacttggtgcactaccgcgtagacctggatgtggcaggcaccaagaacagcttccagacactgcagatgaagctagaaa
acatcaccaacccctggagcccaagacaccgcgtggtccagccaactctggagcagacgcagtactcctgggagcgccaggcggccttcag
cttcaaaaggaagctgcccaagtacctgctctttaccagcccccaggagaacccctggggccacaagcgcagctaccgcctgcagatccactc
catggccgaccaggtgctgcccccaggctggcaggaggagcaggccatcacctgggcaaggtacccccctggcagtgaccaagtaccgggag
tcggagctgtgcagcagcagcatctaccaccagaacgacccctggcacccgcccgtggtctttgagcagtttcttcacaacaacgagaacattga
aaatgaggacctggtggcctgggtgacggtgggcttcctgcacatcccccactcagaggacattcccaacacagccacacctgggaactccgtg
ggcttcctgctccggccattcaacttcttcccagaggacccctccctggcatccagagacactgtgatcgtgtggcctcgggacaacggccccaac
tacgtccagcgctggatccctgaggacagggactgctcgatgcctcccccttttagctacaatgggacctatagacctgtgtga (SEQ ID NO:18)

Figure 1 continued hDAO-Hepmut2 atgccggccctgggctgggccgtggctgccatcctgatgctgcagacggccatggcggagccctccccggggactctgcccaggaa
ggcaggggtgttttcagacctaagcaaccaagagctgaaggcagtgcacagcttcctctggtccaagaaggagctgaggctgcagccctccagt
accaccaccatggccaagaacaccgtgtttctcatcgagatgctgctgcccaagaagtaccatgtgctgaggtttctggataaaggtgaaaggcat
cctgtgcgggaagcccgtgccgtcatcttctttggtgaccaggagcatcccaatgtcaccgagtttgctgtggggcccctgccagggccctgctaca
tgcgagcactgtcccccaggcctgggtaccagtcctcctgggcatcgaggcccatctccacagcagagtatgccctcctctaccacaccctgcag
gaagccaccaagcccctgcatcagttcttcctcaataccacaggcttctcattccaagactgccatgacagatgcctggccttcaccgatgtggccc
cccggggtgtggcttctggccagcgccgcagttggcttatcatacagcgctatgtagaaggctactttctgcaccccactgggctggagctcctcgtg
gatcatgggagcacagatgctgggcactggccgtggagcaggtgtggtacaacgggaagttctatgggagcccagaggaactggctcggaa
gtatgcagatggagaggtggacgtggtggtcctggaggacccgctgcctgggggcaaggggcatgacagcacagaggagccgcccctcttctc
ctcccacaagccccgcggggacttccccagccccatccatgtgagcggcccccgcttggtccagccccacggccctcgcttcaggctggaggg
caacgctgtgctctacggcggctggagctttgccttccggctgcgctcctcctccgggctgcaggtcctgaacgtgcacttcggcggagagcgcatt
gcctatgaggtcagcgtgcaagaggcagtggcgctgtatggaggacacacacctgcaggcatgcagaccaagtacctcgatgtcggctggggc
ctgggcagcgtcactcatgagttagcccccggcatcgactgcccggagaccgccaccttcctggacactttccactactatgatgccgatgacccg
gtccattatccccgagccctctgcctctttgaaatgcccacaggggtgccccttcggcggcactttaattccaactttaaaggtggcttcaacttctatg
cggggctgaagggccaggtgctggtgctgcggacaacttcaactgtctacaattatgattacatttgggactttatcttctaccccaacggggtgatg
gaggccaagatgcatgccactggctacgtccacgccaccttctacacccccgaggggctgcgccacggcactcgcctgcacacccacctgattg
gcaacatacacactcacttggtgcactaccgcgtagacctggatgtggcaggcaccaagaacagcttccagacactgcagatgaagctagaaa
acatcaccaacccctggagcccaagacaccgcgtggtccagccaactctggagcagacgcagtactcctgggagcgccaggcggccttccgc
ttcaaaaggaagctgcccacgtacctgctctttaccagcccccaggagaacccctggggccacaagcgcagctaccgcctgcagatccactcc
atggccgaccaggtgctgcccccaggctggcaggaggagcaggccatcacctgggcaaggtacccccctggcagtgaccaagtaccgggagt
cggagctgtgcagcagcagcatctaccaccagaacgacccctggcacccgcccgtggtctttgagcagtttcttcacaacaacgagaacattga
aaatgaggacctggtggcctgggtgacggtgggcttcctgcacatcccccactcagaggacattcccaacacagccacacctgggaactccgtg
ggcttcctgctccggccattcaacttcttcccagaggacccctccctggcatccagagacactgtgatcgtgtggcctcgggacaacggccccaac
tacgtccagcgctggatccctgaggacagggactgctcgatgcctcccccttttagctacaatgggacctatagacctgtgtga (SEQ ID NO:19)

hDAO-Hepmut3 atgccggccctgggctgggccgtggctgccatcctgatgctgcagacggccatggcggagccctccccggggactctgcccaggaa
ggcaggggtgttttcagacctaagcaaccaagagctgaaggcagtgcacagcttcctctggtccaagaaggagctgaggctgcagccctccagt
accaccaccatggccaagaacaccgtgtttctcatcgagatgctgctgcccaagaagtaccatgtgctgaggtttctggataaaggtgaaaggcat
cctgtgcgggaagcccgtgccgtcatcttctttggtgaccaggagcatcccaatgtcaccgagtttgctgtggggcccctgccagggccctgctaca
tgcgagcactgtcccccaggcctgggtaccagtcctcctgggcatcgaggcccatctccacagcagagtatgccctcctctaccacaccctgcag
gaagccaccaagcccctgcatcagttcttcctcaataccacaggcttctcattccaagactgccatgacagatgcctggccttcaccgatgtggccc
cccggggtgtggcttctggccagcgccgcagttggcttatcatacagcgctatgtagaaggctactttctgcaccccactgggctggagctcctcgtg
gatcatgggagcacagatgctgggcactggccgtggagcaggtgtggtacaacgggaagttctatgggagcccagaggaactggctcggaa
gtatgcagatggagaggtggacgtggtggtcctggaggacccgctgcctgggggcaaggggcatgacagcacagaggagccgcccctcttctc
ctcccacaagccccgcggggacttccccagccccatccatgtgagcggcccccgcttggtccagccccacggccctcgcttcaggctggaggg
caacgctgtgctctacggcggctggagctttgccttccggctgcgctcctcctccgggctgcaggtcctgaacgtgcacttcggcggagagcgcatt
gcctatgaggtcagcgtgcaagaggcagtggcgctgtatggaggacacacacctgcaggcatgcagaccaagtacctcgatgtcggctggggc
ctgggcagcgtcactcatgagttagcccccggcatcgactgcccggagaccgccaccttcctggacactttccactactatgatgccgatgacccg
gtccattatccccgagccctctgcctctttgaaatgcccacaggggtgccccttcggcggcactttaattccaactttaaaggtggcttcaacttctatg
cggggctgaagggccaggtgctggtgctgcggacaacttcaactgtctacaattatgattacatttgggactttatcttctaccccaacggggtgatg
gaggccaagatgcatgccactggctacgtccacgccaccttctacacccccgaggggctgcgccacggcactcgcctgcacacccacctgattg
gcaacatacacactcacttggtgcactaccgcgtagacctggatgtggcaggcaccaagaacagcttccagacactgcagatgaagctagaaa
acatcaccaacccctggagcccaagacaccgcgtggtccagccaactctggagcagacgcagtactcctgggagcgccaggcggccttccgc
ttcaaaacgaagctgcccaagtacctgctctttaccagcccccaggagaacccctggggccacaagcgcagctaccgcctgcagatccactcc
atggccgaccaggtgctgcccccaggctggcaggaggagcaggccatcacctgggcaaggtacccccctggcagtgaccaagtaccgggagt
cggagctgtgcagcagcagcatctaccaccagaacgacccctggcacccgcccgtggtctttgagcagtttcttcacaacaacgagaacattga
aaatgaggacctggtggcctgggtgacggtgggcttcctgcacatcccccactcagaggacattcccaacacagccacacctgggaactccgtg
ggcttcctgctccggccattcaacttcttcccagaggacccctccctggcatccagagacactgtgatcgtgtggcctcgggacaacggccccaac
tacgtccagcgctggatccctgaggacagggactgctcgatgcctcccccttttagctacaatgggacctatagacctgtgtga (SEQ ID NO:20)

Figure 1 continued hDAO-Hepmut4 atgccggccctgggctgggccgtggctgccatcctgatgctgcagacggccatggcggagccctccccggggactctgcccaggaa
ggcaggggtgttttcagacctaagcaaccaagagctgaaggcagtgcacagcttcctctggtccaagaaggagctgaggctgcagccctccagt
accaccaccatggccaagaacaccgtgtttctcatcgagatgctgctgcccaagaagtaccatgtgctgaggtttctggataaaggtgaaaggcat
cctgtgcgggaagcccgtgccgtcatcttctttggtgaccaggagcatcccaatgtcaccgagtttgctgtggggcccctgccagggccctgctaca
tgcgagcactgtcccccaggcctgggtaccagtcctcctgggcatcgaggcccatctccacagcagagtatgccctcctctaccacaccctgcag
gaagccaccaagcccctgcatcagttcttcctcaataccacaggcttctcattccaagactgccatgacagatgcctggccttcaccgatgtggccc
cccggggtgtggcttctggccagcgccgcagttggcttatcatacagcgctatgtagaaggctactttctgcaccccactgggctggagctcctcgtg
gatcatgggagcacagatgctgggcactgggccgtggagcaggtgtggtacaacgggaagttctatgggagcccagaggaactggctcggaa
gtatgcagatggagaggtggacgtggtggtcctggaggacccgctgcctgggggcaagggcatgacagcacagaggagccgcccctcttctc
ctcccacaagccccgcggggacttccccagccccatccatgtgagcggcccccgcttggtccagccccacggccctcgcttcaggctggaggg
caacgctgtgctctacggcggctggagctttgccttccggctgcgctcctcctccgggctgcaggtcctgaacgtgcacttcggcggagagcgcatt
gcctatgaggtcagcgtgcaagaggcagtggcgctgtatggaggacacacacctgcaggcatgcagaccaagtacctcgatgtcggctggggc
ctgggcagcgtcactcatgagttagcccccggcatcgactgcccggagaccgccaccttcctggacactttccactactatgatgccgatgacccg
gtccattatccccgagccctctgcctctttgaaatgcccacaggggtgccccttcggcggcactttaattccaactttaaaggtggcttcaacttctatg
cggggctgaagggccaggtgctggtgctgcggacaacttcaactgtctacaattatgattacatttgggactttatcttctaccccaacggggtgatg
gaggccaagatgcatgccactggctacgtccacgccaccttctacacccccgaggggctgcgccacggcactcgcctgcacacccacctgattg
gcaacatacacactcacttggtgcactaccgcgtagacctggatgtggcaggcaccaagaacagcttccagacactgcagatgaagctagaaa
acatcaccaacccctggagcccaagacaccgcgtggtccagccaactctggagcagacgcagtactcctgggagcgccaggcggccttcag
cttcaaaacgaagctgcccaagtacctgctctttaccagcccccaggagaacccctggggccacaagcgcagctaccgcctgcagatccactc
catggccgaccaggtgctgcccccaggctggcaggaggagcaggccatcacctgggcaaggtacccctggcagtgaccaagtaccgggag
tcggagctgtgcagcagcagcatctaccaccagaacgacccctggcacccgcccgtggtctttgagcagtttcttcacaacaacgagaacattga
aaatgaggacctggtggcctgggtgacggtgggcttcctgcacatcccccactcagaggacattcccaacacagccacacctgggaactccgtg
ggcttcctgctccggccattcaacttcttcccagaggacccctccctggcatccagagacactgtgatcgtgtggcctcgggacaacggccccaac
tacgtccagcgctggatccctgaggacagggactgctcgatgcctccccctttagctacaatgggacctatagacctgtgtga (SEQ ID NO:21)

hDAO-Hepmut5 atgccggccctgggctgggccgtggctgccatcctgatgctgcagacggccatggcggagccctccccggggactctgcccaggaa
ggcaggggtgttttcagacctaagcaaccaagagctgaaggcagtgcacagcttcctctggtccaagaaggagctgaggctgcagccctccagt
accaccaccatggccaagaacaccgtgtttctcatcgagatgctgctgcccaagaagtaccatgtgctgaggtttctggataaaggtgaaaggcat
cctgtgcgggaagcccgtgccgtcatcttctttggtgaccaggagcatcccaatgtcaccgagtttgctgtggggcccctgccagggccctgctaca
tgcgagcactgtcccccaggcctgggtaccagtcctcctgggcatcgaggcccatctccacagcagagtatgccctcctctaccacaccctgcag
gaagccaccaagcccctgcatcagttcttcctcaataccacaggcttctcattccaagactgccatgacagatgcctggccttcaccgatgtggccc
cccggggtgtggcttctggccagcgccgcagttggcttatcatacagcgctatgtagaaggctactttctgcaccccactgggctggagctcctcgtg
gatcatgggagcacagatgctgggcactgggccgtggagcaggtgtggtacaacgggaagttctatgggagcccagaggaactggctcggaa
gtatgcagatggagaggtggacgtggtggtcctggaggacccgctgcctgggggcaagggcatgacagcacagaggagccgcccctcttctc
ctcccacaagccccgcggggacttccccagccccatccatgtgagcggcccccgcttggtccagccccacggccctcgcttcaggctggaggg
caacgctgtgctctacggcggctggagctttgccttccggctgcgctcctcctccgggctgcaggtcctgaacgtgcacttcggcggagagcgcatt
gcctatgaggtcagcgtgcaagaggcagtggcgctgtatggaggacacacacctgcaggcatgcagaccaagtacctcgatgtcggctggggc
ctgggcagcgtcactcatgagttagcccccggcatcgactgcccggagaccgccaccttcctggacactttccactactatgatgccgatgacccg
gtccattatccccgagccctctgcctctttgaaatgcccacaggggtgccccttcggcggcactttaattccaactttaaaggtggcttcaacttctatg
cggggctgaagggccaggtgctggtgctgcggacaacttcaactgtctacaattatgattacatttgggactttatcttctaccccaacggggtgatg
gaggccaagatgcatgccactggctacgtccacgccaccttctacacccccgaggggctgcgccacggcactcgcctgcacacccacctgattg
gcaacatacacactcacttggtgcactaccgcgtagacctggatgtggcaggcaccaagaacagcttccagacactgcagatgaagctagaaa
acatcaccaacccctggagcccaagacaccgcgtggtccagccaactctggagcagacgcagtactcctgggagcgccaggcggccttccgc
ttcaaaacgaagctgcccacgtacctgctctttaccagcccccaggagaacccctggggccacaagcgcagctaccgcctgcagatccactcc
atggccgaccaggtgctgcccccaggctggcaggaggagcaggccatcacctgggcaaggtacccctggcagtgaccaagtaccgggagt
cggagctgtgcagcagcagcatctaccaccagaacgacccctggcacccgcccgtggtctttgagcagtttcttcacaacaacgagaacattga
aaatgaggacctggtggcctgggtgacggtgggcttcctgcacatcccccactcagaggacattcccaacacagccacacctgggaactccgtg
ggcttcctgctccggccattcaacttcttcccagaggacccctccctggcatccagagacactgtgatcgtgtggcctcgggacaacggccccaac
tacgtccagcgctggatccctgaggacagggactgctcgatgcctccccctttagctacaatgggacctatagacctgtgtga (SEQ ID NO:22)

Figure 1 continued hDAO-Hepmut6 atgccggccctgggctgggccgtggctgccatcctgatgctgcagacggccatggcggagccctccccggggactctgcccaggaa
ggcaggggtgttttcagacctaagcaaccaagagctgaaggcagtgcacagcttcctctggtccaagaaggagctgaggctgcagccctccagt
accaccaccatggccaagaacaccgtgtttctcatcgagatgctgctgcccaagaagtaccatgtgctgaggtttctggataaaggtgaaaggcat
cctgtgcgggaagcccgtgccgtcatcttctttggtgaccaggagcatcccaatgtcaccgagtttgctgtggggcccctgccagggccctgctaca
tgcgagcactgtcccccaggcctgggtaccagtcctcctgggcatcgaggcccatctccacagcagagtatgccctcctctaccacaccctgcag
gaagccaccaagcccctgcatcagttcttcctcaataccacaggcttctcattccaagactgccatgacagatgcctggccttcaccgatgtggccc
cccggggtgtggcttctggccagcgccgcagttggcttatcatacagcgctatgtagaaggctactttctgcaccccactgggctggagctcctcgtg
gatcatgggagcacagatgctgggcactgggccgtggagcaggtgtggtacaacgggaagttctatgggagcccagaggaactggctcggaa
gtatgcagatggagaggtggacgtggtggtcctggaggacccgctgcctgggggcaaggggcatgacagcacagaggagccgcccctcttctc
ctcccacaagccccgcggggacttccccagccccatccatgtgagcggcccccgcttggtccagccccacggccctcgcttcaggctggaggg
caacgctgtgctctacggcggctggagctttgccttccggctgcgctcctcctccgggctgcaggtcctgaacgtgcacttcggcggagagcgcatt
gcctatgaggtcagcgtgcaagaggcagtggcgctgtatggaggacacacacctgcaggcatgcagaccaagtacctcgatgtcggctggggc
ctgggcagcgtcactcatgagttagcccccggcatcgactgcccggagaccgccaccttcctggacactttccactactatgatgccgatgacccg
gtccattatccccgagccctctgcctctttgaaatgcccacaggggtgccccttcggcggcactttaattccaactttaaaggtggcttcaacttctatg
cggggctgaagggccaggtgctggtgctgcggacaacttcaactgtctacaattatgattacatttgggactttatcttctaccccaacggggtgatg
gaggccaagatgcatgccactggctacgtccacgccaccttctacacccccgaggggctgcgccacggcactcgcctgcacacccacctgattg
gcaacatacacactcacttggtgcactaccgcgtagacctggatgtggcaggcaccaagaacagcttccagacactgcagatgaagctagaaa
acatcaccaacccctggagcccaagacaccgcgtggtccagccaactctggagcagacgcagtactcctgggagcgccaggcggccttccgc
ttcggacagacgctgcccaagtacctgctctttaccagcccccaggagaacccctggggccacaagcgcagctaccgcctgcagatccactcc
atggccgaccaggtgctgcccccaggctggcaggaggagcaggccatcacctgggcaaggtacccccctggcagtgaccaagtaccgggagt
cggagctgtgcagcagcagcatctaccaccagaacgacccctggcacccgcccgtggtctttgagcagtttcttcacaacaacgagaacattga
aaatgaggacctggtggcctgggtgacggtgggcttcctgcacatcccccactcagaggacattcccaacacagccacacctgggaactccgtg
ggcttcctgctccggccattcaacttcttcccagaggacccctccctggcatccagagacactgtgatcgtgtggcctcgggacaacggccccaac
tacgtccagcgctggatccctgaggacagggactgctcgatgcctcccccttttagctacaatgggacctatagacctgtgtga (SEQ ID
NO:23)

hDAO-Hepmut7 atgccggccctgggctgggccgtggctgccatcctgatgctgcagacggccatggcggagccctccccggggactctgcccaggaa
ggcaggggtgttttcagacctaagcaaccaagagctgaaggcagtgcacagcttcctctggtccaagaaggagctgaggctgcagccctccagt
accaccaccatggccaagaacaccgtgtttctcatcgagatgctgctgcccaagaagtaccatgtgctgaggtttctggataaaggtgaaaggcat
cctgtgcgggaagcccgtgccgtcatcttctttggtgaccaggagcatcccaatgtcaccgagtttgctgtggggcccctgccagggccctgctaca
tgcgagcactgtcccccaggcctgggtaccagtcctcctgggcatcgaggcccatctccacagcagagtatgccctcctctaccacaccctgcag
gaagccaccaagcccctgcatcagttcttcctcaataccacaggcttctcattccaagactgccatgacagatgcctggccttcaccgatgtggccc
cccggggtgtggcttctggccagcgccgcagttggcttatcatacagcgctatgtagaaggctactttctgcaccccactgggctggagctcctcgtg
gatcatgggagcacagatgctgggcactgggccgtggagcaggtgtggtacaacgggaagttctatgggagcccagaggaactggctcggaa
gtatgcagatggagaggtggacgtggtggtcctggaggacccgctgcctgggggcaaggggcatgacagcacagaggagccgcccctcttctc
ctcccacaagccccgcggggacttccccagccccatccatgtgagcggcccccgcttggtccagccccacggccctcgcttcaggctggaggg
caacgctgtgctctacggcggctggagctttgccttccggctgcgctcctcctccgggctgcaggtcctgaacgtgcacttcggcggagagcgcatt
gcctatgaggtcagcgtgcaagaggcagtggcgctgtatggaggacacacacctgcaggcatgcagaccaagtacctcgatgtcggctggggc
ctgggcagcgtcactcatgagttagcccccggcatcgactgcccggagaccgccaccttcctggacactttccactactatgatgccgatgacccg
gtccattatccccgagccctctgcctctttgaaatgcccacaggggtgccccttcggcggcactttaattccaactttaaaggtggcttcaacttctatg
cggggctgaagggccaggtgctggtgctgcggacaacttcaactgtctacaattatgattacatttgggactttatcttctaccccaacggggtgatg
gaggccaagatgcatgccactggctacgtccacgccaccttctacacccccgaggggctgcgccacggcactcgcctgcacacccacctgattg
gcaacatacacactcacttggtgcactaccgcgtagacctggatgtggcaggcaccaagaacagcttccagacactgcagatgaagctagaaa
acatcaccaacccctggagcccaagacaccgcgtggtccagccaactctggagcagacgcagtactcctgggagcgccaggcggccttcag
cttcaaaaggaagctgcccacgtacctgctctttaccagcccccaggagaacccctggggccacaagcgcagctaccgcctgcagatccactc
catggccgaccaggtgctgcccccaggctggcaggaggagcaggccatcacctgggcaaggtacccccctggcagtgaccaagtaccgggag
tcggagctgtgcagcagcagcatctaccaccagaacgacccctggcacccgcccgtggtctttgagcagtttcttcacaacaacgagaacattga
aaatgaggacctggtggcctgggtgacggtgggcttcctgcacatcccccactcagaggacattcccaacacagccacacctgggaactccgtg
ggcttcctgctccggccattcaacttcttcccagaggacccctccctggcatccagagacactgtgatcgtgtggcctcgggacaacggccccaac
tacgtccagcgctggatccctgaggacagggactgctcgatgcctcccccttttagctacaatgggacctatagacctgtgtga (SEQ ID
NO:24)

Figure 1 continued hDAO-Cysmut atgccggccctgggctgggccgtggctgccatcctgatgctgcagacggccatggcggagccctccccggggactctgcccaggaa
ggcaggggtgttttcagacctaagcaaccaagagctgaaggcagtgcacagcttcctctggtccaagaaggagctgaggctgcagccctccagt
accaccaccatggccaagaacaccgtgtttctcatcgagatgctgctgcccaagaagtaccatgtgctgaggtttctggataaaggtgaaaggcat
cctgtgcgggaagcccgtgccgtcatcttctttggtgaccaggagcatcccaatgtcaccgagtttgctgtggggcccctgccagggcccgcctac
atgcgagcactgtcccccaggcctgggtaccagtcctcctgggcatcgaggcccatctccacagcagagtatgccctcctctaccacaccctgca
ggaagccaccaagcccctgcatcagttcttcctcaataccacaggcttctcattccaagactgccatgacagatgcctggccttcaccgatgtggcc
ccccggggtgtggcttctggccagcgccgcagttggcttatcatacagcgctatgtagaaggctactttctgcaccccactgggctggagctcctcgt
ggatcatgggagcacagatgctgggcactgggccgtggagcaggtgtggtacaacgggaagttctatgggagcccagaggaactggctcgga
agtatgcagatggagaggtggacgtggtggtcctggaggacccgctgcctgggggcaaggggcatgacagcacagaggagccgcccctcttc
tcctcccacaagccccgcggggacttccccagccccatccatgtgagcggcccccgcttggtccagccccacggccctcgcttcaggctggagg
gcaacgctgtgctctacggcggctggagctttgccttccggctgcgctcctcctccgggctgcaggtcctgaacgtgcacttcggcggagagcgca
ttgcctatgaggtcagcgtgcaagaggcagtggcgctgtatggaggacacacacctgcaggcatgcagaccaagtacctcgatgtcggctggg
gcctgggcagcgtcactcatgagttagcccccggcatcgactgcccggagaccgccaccttcctggacactttccactactatgatgccgatgacc
cggtccattatccccgagccctctgcctctttgaaatgcccacaggggtgccccttcggcggcactttaattccaactttaaaggtggcttcaacttcta
tgcggggctgaagggccaggtgctggtgctgcggacaacttcaactgtctacaattatgattacatttgggactttatcttctaccccaacggggtgat
ggaggccaagatgcatgccactggctacgtccacgccaccttctacacccccgaggggctgcgccacggcactcgcctgcacacccacctgatt
ggcaacatacacactcacttggtgcactaccgcgtagacctggatgtggcaggcaccaagaacagcttccagacactgcagatgaagctagaa
aacatcaccaacccctggagcccaagacaccgcgtggtccagccaactctggagcagacgcagtactcctgggagcgccaggcggccttccg
cttcaaaaggaagctgcccaagtacctgctctttaccagcccccaggagaacccctggggccacaagcgcagctaccgcctgcagatccactc
catggccgaccaggtgctgcccccaggctggcaggaggagcaggccatcacctgggcaaggtacccctggcagtgaccaagtaccgggag
tcggagctgtgcagcagcagcatctaccaccagaacgacccctggcacccgcccgtggtctttgagcagtttcttcacaacaacgagaacattga
aaatgaggacctggtggcctgggtgacggtgggcttcctgcacatcccccactcagaggacattcccaacacagccacacctgggaactccgtg
ggcttcctgctccggccattcaacttcttcccagaggacccctccctggcatccagagacactgtgatcgtgtggcctcgggacaacggccccaac
tacgtccagcgctggatccctgaggacagggactgctcgatgcctccccctttagctacaatgggacctatagacctgtgtga (SEQ ID NO:25)

hDAO-Hepmut1-Cysmut atgccggccctgggctgggccgtggctgccatcctgatgctgcagacggccatggcggagccctccccggggactctgcccaggaa
ggcaggggtgttttcagacctaagcaaccaagagctgaaggcagtgcacagcttcctctggtccaagaaggagctgaggctgcagccctccagt
accaccaccatggccaagaacaccgtgtttctcatcgagatgctgctgcccaagaagtaccatgtgctgaggtttctggataaaggtgaaaggcat
cctgtgcgggaagcccgtgccgtcatcttctttggtgaccaggagcatcccaatgtcaccgagtttgctgtggggcccctgccagggcccgcctac
atgcgagcactgtcccccaggcctgggtaccagtcctcctgggcatcgaggcccatctccacagcagagtatgccctcctctaccacaccctgca
ggaagccaccaagcccctgcatcagttcttcctcaataccacaggcttctcattccaagactgccatgacagatgcctggccttcaccgatgtggcc
ccccggggtgtggcttctggccagcgccgcagttggcttatcatacagcgctatgtagaaggctactttctgcaccccactgggctggagctcctcgt
ggatcatgggagcacagatgctgggcactgggccgtggagcaggtgtggtacaacgggaagttctatgggagcccagaggaactggctcgga
agtatgcagatggagaggtggacgtggtggtcctggaggacccgctgcctgggggcaaggggcatgacagcacagaggagccgcccctcttc
tcctcccacaagccccgcggggacttccccagccccatccatgtgagcggcccccgcttggtccagccccacggccctcgcttcaggctggagg
gcaacgctgtgctctacggcggctggagctttgccttccggctgcgctcctcctccgggctgcaggtcctgaacgtgcacttcggcggagagcgca
ttgcctatgaggtcagcgtgcaagaggcagtggcgctgtatggaggacacacacctgcaggcatgcagaccaagtacctcgatgtcggctggg
gcctgggcagcgtcactcatgagttagcccccggcatcgactgcccggagaccgccaccttcctggacactttccactactatgatgccgatgacc
cggtccattatccccgagccctctgcctctttgaaatgcccacaggggtgccccttcggcggcactttaattccaactttaaaggtggcttcaacttcta
tgcggggctgaagggccaggtgctggtgctgcggacaacttcaactgtctacaattatgattacatttgggactttatcttctaccccaacggggtgat
ggaggccaagatgcatgccactggctacgtccacgccaccttctacacccccgaggggctgcgccacggcactcgcctgcacacccacctgatt
ggcaacatacacactcacttggtgcactaccgcgtagacctggatgtggcaggcaccaagaacagcttccagacactgcagatgaagctagaa
aacatcaccaacccctggagcccaagacaccgcgtggtccagccaactctggagcagacgcagtactcctgggagcgccaggcggccttca
gcttcaaaaggaagctgcccaagtacctgctctttaccagcccccaggagaacccctggggccacaagcgcagctaccgcctgcagatccact
ccatggccgaccaggtgctgcccccaggctggcaggaggagcaggccatcacctgggcaaggtacccctggcagtgaccaagtaccggga
gtcggagctgtgcagcagcagcatctaccaccagaacgacccctggcacccgcccgtggtctttgagcagtttcttcacaacaacgagaacattg
aaaatgaggacctggtggcctgggtgacggtgggcttcctgcacatcccccactcagaggacattcccaacacagccacacctgggaactccgt
gggcttcctgctccggccattcaacttcttcccagaggacccctccctggcatccagagacactgtgatcgtgtggcctcgggacaacggcccca
actacgtccagcgctggatccctgaggacagggactgctcgatgcctccccctttagctacaatgggacctatagacctgtgtga (SEQ ID NO:26)

Figure 1 continued hDAO-Hepmut2-Cysmut atgccggccctgggctgggccgtggctgccatcctgatgctgcagacggccatggcggagccctccccggggactctgcccaggaaggcaggggtgttttcagacctaagcaaccaagagctgaaggcagtgcacagcttcctctggtccaagaaggagctgaggctgcagccctccagtaccaccaccatggccaagaacaccgtgtttctcatcgagatgctgctgcccaagaagtaccatgtgctgaggtttctggataaaggtgaaaggcatcctgtgcgggaagcccgtgccgtcatcttctttggtgaccaggagcatcccaatgtcaccgagtttgctgtggggcccctgccagggcccgcctacatgcgagcactgtcccccaggcctgggtaccagtcctcctgggcatcgaggcccatctccacagcagagtatgccctcctctaccacaccctgcaggaagccaccaagcccctgcatcagttcttcctcaataccacaggcttctcattccaagactgccatgacagatgcctggccttcaccgatgtggccccccggggtgtggcttctggccagcgccgcagttggcttatcatacagcgctatgtagaaggctactttctgcaccccactgggctggagctcctcgtggatcatgggagcacagatgctgggcactgggccgtggagcaggtgtggtacaacgggaagttctatgggagcccagaggaactggctcggaagtatgcagatggagaggtggacgtggtggtcctggaggacccgctgcctgggggcaaggggcatgacagcacagaggagccgcccctcttctcctcccacaagccccgcggggacttccccagccccatccatgtgagcggcccccgcttggtccagccccacggccctcgcttcaggctggagggcaacgctgtgctctacggcggctggagctttgccttccggctgcgctcctcctccgggctgcaggtcctgaacgtgcacttcggcggagagcgcattgcctatgaggtcagcgtgcaagaggcagtggcgctgtatggaggacacacacctgcaggcatgcagaccaagtacctcgatgtcggctggggcctgggcagcgtcactcatgagttagcccccggcatcgactgcccggagaccgccaccttcctggacactttccactactatgatgccgatgaccggtccattatccccgagccctctgcctctttgaaatgcccacaggggtgccccttcggcggcactttaattccaactttaaaggtggcttcaacttctatgcggggctgaagggccaggtgctggtgctgcggacaacttcaactgtctacaattatgattacatttgggactttatcttctaccccaacggggtgatggaggccaagatgcatgccactggctacgtccacgccaccttctacacccccgaggggctgcgccacggcactcgcctgcacacccacctgattggcaacatacacactcacttggtgcactaccgcgtagacctggatgtggcaggcaccaagaacagcttccagacactgcagatgaagctagaaaacatcaccaacccctggagcccaagacaccgcgtggtccagccaactctggagcagacgcagtactcctgggagcgccaggcggccttccgcttcaaaaggaagctgcccacgtacctgctctttaccagcccccaggagaacccctggggccacaagcgcagctaccgcctgcagatccactccatggccgaccaggtgctgcccccaggctggcaggaggagcaggccatcacctgggcaaggtacccccctggcagtgaccaagtaccgggagtcggagctgtgcagcagcagcatctaccaccagaacgacccctggcacccgcccgtggtctttgagcagtttcttcacaacaacgagaacattgaaaatgaggacctggtggcctgggtgacggtgggcttcctgcacatcccccactcagaggacattcccaacacagccacacctgggaactccgtgggcttcctgctccggccattcaacttcttcccagaggacccctccctggcatccagagacactgtgatcgtgtggcctcgggacaacggccccaactacgtccagcgctggatccctgaggacagggactgctcgatgcctcccccttttagctacaatgggacctatagacctgtgtga (SEQ ID NO:27)

hDAO-Hepmut3-Cysmut atgccggccctgggctgggccgtggctgccatcctgatgctgcagacggccatggcggagccctccccggggactctgcccaggaaggcaggggtgttttcagacctaagcaaccaagagctgaaggcagtgcacagcttcctctggtccaagaaggagctgaggctgcagccctccagtaccaccaccatggccaagaacaccgtgtttctcatcgagatgctgctgcccaagaagtaccatgtgctgaggtttctggataaaggtgaaaggcatcctgtgcgggaagcccgtgccgtcatcttctttggtgaccaggagcatcccaatgtcaccgagtttgctgtggggcccctgccagggcccgcctacatgcgagcactgtcccccaggcctgggtaccagtcctcctgggcatcgaggcccatctccacagcagagtatgccctcctctaccacaccctgcaggaagccaccaagcccctgcatcagttcttcctcaataccacaggcttctcattccaagactgccatgacagatgcctggccttcaccgatgtggccccccggggtgtggcttctggccagcgccgcagttggcttatcatacagcgctatgtagaaggctactttctgcaccccactgggctggagctcctcgtggatcatgggagcacagatgctgggcactgggccgtggagcaggtgtggtacaacgggaagttctatgggagcccagaggaactggctcggaagtatgcagatggagaggtggacgtggtggtcctggaggacccgctgcctgggggcaaggggcatgacagcacagaggagccgcccctcttctcctcccacaagccccgcggggacttccccagccccatccatgtgagcggcccccgcttggtccagccccacggccctcgcttcaggctggagggcaacgctgtgctctacggcggctggagctttgccttccggctgcgctcctcctccgggctgcaggtcctgaacgtgcacttcggcggagagcgcattgcctatgaggtcagcgtgcaagaggcagtggcgctgtatggaggacacacacctgcaggcatgcagaccaagtacctcgatgtcggctggggcctgggcagcgtcactcatgagttagcccccggcatcgactgcccggagaccgccaccttcctggacactttccactactatgatgccgatgaccggtccattatccccgagccctctgcctctttgaaatgcccacaggggtgccccttcggcggcactttaattccaactttaaaggtggcttcaacttctatgcggggctgaagggccaggtgctggtgctgcggacaacttcaactgtctacaattatgattacatttgggactttatcttctaccccaacggggtgatggaggccaagatgcatgccactggctacgtccacgccaccttctacacccccgaggggctgcgccacggcactcgcctgcacacccacctgattggcaacatacacactcacttggtgcactaccgcgtagacctggatgtggcaggcaccaagaacagcttccagacactgcagatgaagctagaaaacatcaccaacccctggagcccaagacaccgcgtggtccagccaactctggagcagacgcagtactcctgggagcgccaggcggccttccgcttcaaaacgaagctgcccaagtacctgctctttaccagcccccaggagaacccctggggccacaagcgcagctaccgcctgcagatccactccatggccgaccaggtgctgcccccaggctggcaggaggagcaggccatcacctgggcaaggtacccccctggcagtgaccaagtaccgggagtcggagctgtgcagcagcagcatctaccaccagaacgacccctggcacccgcccgtggtctttgagcagtttcttcacaacaacgagaacattgaaaatgaggacctggtggcctgggtgacggtgggcttcctgcacatcccccactcagaggacattcccaacacagccacacctgggaactccgtgggcttcctgctccggccattcaacttcttcccagaggacccctccctggcatccagagacactgtgatcgtgtggcctcgggacaacggccccaactacgtccagcgctggatccctgaggacagggactgctcgatgcctcccccttttagctacaatgggacctatagacctgtgtga (SEQ ID NO:28)

Figure 1 continued hDAO-Hepmut4-Cysmut atgccggccctgggctgggccgtggctgccatcctgatgctgcagacggccatggcggagccctccccggggactctgcccaggaa
ggcaggggtgttttcagacctaagcaaccaagagctgaaggcagtgcacagcttcctctggtccaagaaggagctgaggctgcagccctccagt
accaccaccatggccaagaacaccgtgtttctcatcgagatgctgctgcccaagaagtaccatgtgctgaggtttctggataaaggtgaaaggcat
cctgtgcgggaagcccgtgccgtcatcttctttggtgaccaggagcatcccaatgtcaccgagtttgctgtggggcccctgccagggcccgcctac
atgcgagcactgtcccccaggcctgggtaccagtcctcctgggcatcgaggcccatctccacagcagagtatgccctcctctaccacaccctgca
ggaagccaccaagcccctgcatcagttcttcctcaataccacaggcttctcattccaagactgccatgacagatgcctggccttcaccgatgtggcc
ccccggggtgtggcttctggccagcgccgcagttggcttatcatacagcgctatgtagaaggctactttctgcaccccactgggctggagctcctcgt
ggatcatgggagcacagatgctgggcactgggccgtggagcaggtgtggtacaacgggaagttctatgggagcccagaggaactggctcgga
agtatgcagatggagaggtggacgtggtggtcctggaggacccgctgcctgggggcaaggggcatgacagcacagaggagccgcccctcttc
tcctcccacaagccccgcggggacttccccagccccatccatgtgagcggcccccgcttggtccagccccacggccctcgcttcaggctggagg
gcaacgctgtgctctacggcggctggagctttgccttccggctgcgctcctcctccgggctgcaggtcctgaacgtgcacttcggcggagagcgca
ttgcctatgaggtcagcgtgcaagaggcagtggcgctgtatggaggacacacacctgcaggcatgcagaccaagtacctcgatgtcggctggg
gcctgggcagcgtcactcatgagttagcccccggcatcgactgcccggagaccgccaccttcctggacactttccactactatgatgccgatgacc
cggtccattatccccgagccctctgcctctttgaaatgcccacaggggtgccccttcggcggcactttaattccaactttaaaggtggcttcaacttcta
tgcggggctgaagggccaggtgctggtgctgcggacaacttcaactgtctacaattatgattacatttgggactttatcttctaccccaacggggtgat
ggaggccaagatgcatgccactggctacgtccacgccaccttctacacccccgaggggctgcgccacggcactcgcctgcacacccacctgatt
ggcaacatacacactcacttggtgcactaccgcgtagacctggatgtggcaggcaccaagaacagcttccagacactgcagatgaagctagaa
aacatcaccaacccctggagcccaagacaccgcgtggtccagccaactctggagcagacgcagtactcctgggagcgccaggcggccttca
gcttcaaaacgaagctgcccaagtacctgctctttaccagcccccaggagaacccctggggccacaagcgcagctaccgcctgcagatccact
ccatggccgaccaggtgctgcccccaggctggcaggaggagcaggccatcacctgggcaaggtacccccctggcagtgaccaagtaccggga
gtcggagctgtgcagcagcagcatctaccaccagaacgacccctggcacccgcccgtggtctttgagcagtttcttcacaacaacgagaacattg
aaaatgaggacctggtggcctgggtgacggtgggcttcctgcacatcccccactcagaggacattcccaacacagccacacctgggaactccgt
gggcttcctgctccggccattcaacttcttcccagaggacccctccctggcatccagagacactgtgatcgtgtggcctcgggacaacggccccaa
ctacgtccagcgctggatccctgaggacagggactgctcgatgcctcccccttttagctacaatgggacctatagacctgtgtga (SEQ ID NO:29)

hDAO-Hepmut5-Cysmut atgccggccctgggctgggccgtggctgccatcctgatgctgcagacggccatggcggagccctccccggggactctgcccaggaa
ggcaggggtgttttcagacctaagcaaccaagagctgaaggcagtgcacagcttcctctggtccaagaaggagctgaggctgcagccctccagt
accaccaccatggccaagaacaccgtgtttctcatcgagatgctgctgcccaagaagtaccatgtgctgaggtttctggataaaggtgaaaggcat
cctgtgcgggaagcccgtgccgtcatcttctttggtgaccaggagcatcccaatgtcaccgagtttgctgtggggcccctgccagggcccgcctac
atgcgagcactgtcccccaggcctgggtaccagtcctcctgggcatcgaggcccatctccacagcagagtatgccctcctctaccacaccctgca
ggaagccaccaagcccctgcatcagttcttcctcaataccacaggcttctcattccaagactgccatgacagatgcctggccttcaccgatgtggcc
ccccggggtgtggcttctggccagcgccgcagttggcttatcatacagcgctatgtagaaggctactttctgcaccccactgggctggagctcctcgt
ggatcatgggagcacagatgctgggcactgggccgtggagcaggtgtggtacaacgggaagttctatgggagcccagaggaactggctcgga
agtatgcagatggagaggtggacgtggtggtcctggaggacccgctgcctgggggcaaggggcatgacagcacagaggagccgcccctcttc
tcctcccacaagccccgcggggacttccccagccccatccatgtgagcggcccccgcttggtccagccccacggccctcgcttcaggctggagg
gcaacgctgtgctctacggcggctggagctttgccttccggctgcgctcctcctccgggctgcaggtcctgaacgtgcacttcggcggagagcgca
ttgcctatgaggtcagcgtgcaagaggcagtggcgctgtatggaggacacacacctgcaggcatgcagaccaagtacctcgatgtcggctggg
gcctgggcagcgtcactcatgagttagcccccggcatcgactgcccggagaccgccaccttcctggacactttccactactatgatgccgatgacc
cggtccattatccccgagccctctgcctctttgaaatgcccacaggggtgccccttcggcggcactttaattccaactttaaaggtggcttcaacttcta
tgcggggctgaagggccaggtgctggtgctgcggacaacttcaactgtctacaattatgattacatttgggactttatcttctaccccaacggggtgat
ggaggccaagatgcatgccactggctacgtccacgccaccttctacacccccgaggggctgcgccacggcactcgcctgcacacccacctgatt
ggcaacatacacactcacttggtgcactaccgcgtagacctggatgtggcaggcaccaagaacagcttccagacactgcagatgaagctagaa
aacatcaccaacccctggagcccaagacaccgcgtggtccagccaactctggagcagacgcagtactcctgggagcgccaggcggccttccg
cttcaaaacgaagctgcccacgtacctgctctttaccagcccccaggagaacccctggggccacaagcgcagctaccgcctgcagatccactc
catggccgaccaggtgctgcccccaggctggcaggaggagcaggccatcacctgggcaaggtacccccctggcagtgaccaagtaccgggag
tcggagctgtgcagcagcagcatctaccaccagaacgacccctggcacccgcccgtggtctttgagcagtttcttcacaacaacgagaacattga
aaatgaggacctggtggcctgggtgacggtgggcttcctgcacatcccccactcagaggacattcccaacacagccacacctgggaactccgtg
ggcttcctgctccggccattcaacttcttcccagaggacccctccctggcatccagagacactgtgatcgtgtggcctcgggacaacggccccaac
tacgtccagcgctggatccctgaggacagggactgctcgatgcctcccccttttagctacaatgggacctatagacctgtgtga (SEQ ID NO:30)

Figure 1 continued hDAO-Hepmut6-Cysmut atgccggccctgggctgggccgtggctgccatcctgatgctgcagacggccatggcggagccctccccggggactctgcccaggaa ggcaggggtgttttcagacctaagcaaccaagagctgaaggcagtgcacagcttcctctggtccaagaaggagctgaggctgcagccctccagt accaccaccatggccaagaacaccgtgtttctcatcgagatgctgctgcccaagaagtaccatgtgctgaggtttctggataaaggtgaaaggcat cctgtgcgggaagcccgtgccgtcatcttctttggtgaccaggagcatcccaatgtcaccgagtttgctgtggggcccctgccagggcccgcctac atgcgagcactgtcccccaggcctgggtaccagtcctcctgggcatcgaggcccatctccacagcagagtatgccctcctctaccacaccctgca ggaagccaccaagcccctgcatcagttcttcctcaataccacaggcttctcattccaagactgccatgacagatgcctggccttcaccgatgtggcc ccccggggtgtggcttctggccagcgccgcagttggcttatcatacagcgctatgtagaaggctactttctgcaccccactgggctggagctcctcgt ggatcatgggagcacagatgctgggcactgggccgtggagcaggtgtggtacaacgggaagttctatgggagcccagaggaactggctcgga agtatgcagatggagaggtggacgtggtggtcctggaggacccgctgcctgggggcaaggggcatgacagcacagaggagccgcccctcttc tcctcccacaagccccgcggggacttccccagccccatccatgtgagcggcccccgcttggtccagccccacggccctcgcttcaggctggagg gcaacgctgtgctctacggcggctggagctttgccttccggctgcgctcctcctccgggctgcaggtcctgaacgtgcacttcggcggagagcgca ttgcctatgaggtcagcgtgcaagaggcagtggcgctgtatggaggacacacacctgcaggcatgcagaccaagtacctcgatgtcggctggg gcctgggcagcgtcactcatgagttagcccccggcatcgactgcccggagaccgccaccttcctggacactttccactactatgatgccgatgacc cggtccattatccccgagccctctgcctctttgaaatgcccacaggggtgccccttcggcggcactttaattccaactttaaaggtggcttcaacttcta tgcggggctgaagggccaggtgctggtgctgcggacaacttcaactgtctacaattatgattacatttgggactttatcttctaccccaacggggtgat ggaggccaagatgcatgccactggctacgtccacgccaccttctacacccccgaggggctgcgccacggcactcgcctgcacacccacctgatt ggcaacatacacactcacttggtgcactaccgcgtagacctggatgtggcaggcaccaagaacagcttccagacactgcagatgaagctagaa aacatcaccaacccctggagcccaagacaccgcgtggtccagccaactctggagcagacgcagtactcctgggagcgccaggcggccttccg cttcggacagacgctgcccaagtacctgctctttaccagcccccaggagaacccctggggccacaagcgcagctaccgcctgcagatccactc catggccgaccaggtgctgcccccaggctggcaggaggagcaggccatcacctgggcaaggtacccccctggcagtgaccaagtaccgggag tcggagctgtgcagcagcagcatctaccaccagaacgacccctggcacccgcccgtggtctttgagcagtttcttcacaacaacgagaacattga aaatgaggacctggtggcctgggtgacggtgggcttcctgcacatcccccactcagaggacattcccaacacagccacacctgggaactccgtg ggcttcctgctccggccattcaacttcttcccagaggacccctccctggcatccagagacactgtgatcgtgtggcctcgggacaacggccccaac tacgtccagcgctggatccctgaggacagggactgctcgatgcctcccccttttagctacaatgggacctatagacctgtgtga (SEQ ID NO:31)

hDAO-Hepmut7-Cysmut atgccggccctgggctgggccgtggctgccatcctgatgctgcagacggccatggcggagccctccccggggactctgcccaggaa ggcaggggtgttttcagacctaagcaaccaagagctgaaggcagtgcacagcttcctctggtccaagaaggagctgaggctgcagccctccagt accaccaccatggccaagaacaccgtgtttctcatcgagatgctgctgcccaagaagtaccatgtgctgaggtttctggataaaggtgaaaggcat cctgtgcgggaagcccgtgccgtcatcttctttggtgaccaggagcatcccaatgtcaccgagtttgctgtggggcccctgccagggcccgcctac atgcgagcactgtcccccaggcctgggtaccagtcctcctgggcatcgaggcccatctccacagcagagtatgccctcctctaccacaccctgca ggaagccaccaagcccctgcatcagttcttcctcaataccacaggcttctcattccaagactgccatgacagatgcctggccttcaccgatgtggcc ccccggggtgtggcttctggccagcgccgcagttggcttatcatacagcgctatgtagaaggctactttctgcaccccactgggctggagctcctcgt ggatcatgggagcacagatgctgggcactgggccgtggagcaggtgtggtacaacgggaagttctatgggagcccagaggaactggctcgga agtatgcagatggagaggtggacgtggtggtcctggaggacccgctgcctgggggcaaggggcatgacagcacagaggagccgcccctcttc tcctcccacaagccccgcggggacttccccagccccatccatgtgagcggcccccgcttggtccagccccacggccctcgcttcaggctggagg gcaacgctgtgctctacggcggctggagctttgccttccggctgcgctcctcctccgggctgcaggtcctgaacgtgcacttcggcggagagcgca ttgcctatgaggtcagcgtgcaagaggcagtggcgctgtatggaggacacacacctgcaggcatgcagaccaagtacctcgatgtcggctggg gcctgggcagcgtcactcatgagttagcccccggcatcgactgcccggagaccgccaccttcctggacactttccactactatgatgccgatgacc cggtccattatccccgagccctctgcctctttgaaatgcccacaggggtgccccttcggcggcactttaattccaactttaaaggtggcttcaacttcta tgcggggctgaagggccaggtgctggtgctgcggacaacttcaactgtctacaattatgattacatttgggactttatcttctaccccaacggggtgat ggaggccaagatgcatgccactggctacgtccacgccaccttctacacccccgaggggctgcgccacggcactcgcctgcacacccacctgatt ggcaacatacacactcacttggtgcactaccgcgtagacctggatgtggcaggcaccaagaacagcttccagacactgcagatgaagctagaa aacatcaccaacccctggagcccaagacaccgcgtggtccagccaactctggagcagacgcagtactcctgggagcgccaggcggccttca gcttcaaaaggaagctgcccacgtacctgctctttaccagcccccaggagaacccctggggccacaagcgcagctaccgcctgcagatccact ccatggccgaccaggtgctgcccccaggctggcaggaggagcaggccatcacctgggcaaggtacccccctggcagtgaccaagtaccggga gtcggagctgtgcagcagcagcatctaccaccagaacgacccctggcacccgcccgtggtctttgagcagtttcttcacaacaacgagaacattg aaaatgaggacctggtggcctgggtgacggtgggcttcctgcacatcccccactcagaggacattcccaacacagccacacctgggaactccgt gggcttcctgctccggccattcaacttcttcccagaggacccctccctggcatccagagacactgtgatcgtgtggcctcgggacaacggccccaa ctacgtccagcgctggatccctgaggacagggactgctcgatgcctcccccttttagctacaatgggacctatagacctgtgtga (SEQ ID NO:32)

Figure 1 continued

Fc-hDAO

MPALGWAVAAILMLQTAMA*ECPPCPAPPVAGPSVFLFPPKPKDTLMISRTPEVTCVVVDVSHEDPEVKFNWYVDGVEVHNAKTKPREEQYNSTYRVVSVLTVLHQDWLNGKEYKCKVSNKGLPSSIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGKEPKSADKTHT*EPSPGTLPRKAGVFSDLSNQELKAVHSFLWSKKELRLQPSSTTTMAKNTVFLIEMLLPKKYHVLRFLDKGERHPVREARAVIFFGDQEHPNVTEFAVGPLPGPCYMRALSPRPGYQSSWASRPISTAEYALLYHTLQEATKPLHQFFLNTTGFSFQDCHDRCLAFTDVAPRGVASGQRRSWLIIQRYVEGYFLHPTGLELLVDHGSTDAGHWAVEQVWYNGKFYGSPEELARKYADGEVDVVVLEDPLPGGKGHDSTEEPPLFSSHKPRGDFPSPIHVSGPRLVQPHGPRFRLEGNAVLYGGWSFAFRLRSSSGLQVLNVHFGGERIAYEVSVQEAVALYGGHTPAGMQTKYLDVGWGLGSVTHELAPGIDCPETATFLDTFHYYDADDPVHYPRALCLFEMPTGVPLRRHFNSNFKGGFNFYAGLKGQVLVLRTTSTVYNYDYIWDFIFYPNGVMEAKMHATGYVHATFYTPEGLRHGTRLHTHLIGNIHTHLVHYRVDLDVAGTKNSFQTLQMKLENITNPWSPRHRVVQPTLEQTQYSWERQAAFRFKRKLPKYLLFTSPQENPWGHKRSYRLQIHSMADQVLPPGWQEEQAITWARYPLAVTKYRESELCSSSIYHQNDPWHPPVVFEQFLHNNENIENEDLVAWVTVGFLHIPHSEDIPNTATPGNSVGFLLRPFNFFPEDPSLASRDTVIVWPRDNGPNYVQRWIPEDRDCSMPPPFSYNGTYRPV (SEQ ID NO:39)

Fc-hDAO-Hepmut1

MPALGWAVAAILMLQTAMA*ECPPCPAPPVAGPSVFLFPPKPKDTLMISRTPEVTCVVVDVSHEDPEVKFNWYVDGVEVHNAKTKPREEQYNSTYRVVSVLTVLHQDWLNGKEYKCKVSNKGLPSSIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGKEPKSADKTHT*EPSPGTLPRKAGVFSDLSNQELKAVHSFLWSKKELRLQPSSTTTMAKNTVFLIEMLLPKKYHVLRFLDKGERHPVREARAVIFFGDQEHPNVTEFAVGPLPGPCYMRALSPRPGYQSSWASRPISTAEYALLYHTLQEATKPLHQFFLNTTGFSFQDCHDRCLAFTDVAPRGVASGQRRSWLIIQRYVEGYFLHPTGLELLVDHGSTDAGHWAVEQVWYNGKFYGSPEELARKYADGEVDVVVLEDPLPGGKGHDSTEEPPLFSSHKPRGDFPSPIHVSGPRLVQPHGPRFRLEGNAVLYGGWSFAFRLRSSSGLQVLNVHFGGERIAYEVSVQEAVALYGGHTPAGMQTKYLDVGWGLGSVTHELAPGIDCPETATFLDTFHYYDADDPVHYPRALCLFEMPTGVPLRRHFNSNFKGGFNFYAGLKGQVLVLRTTSTVYNYDYIWDFIFYPNGVMEAKMHATGYVHATFYTPEGLRHGTRLHTHLIGNIHTHLVHYRVDLDVAGTKNSFQTLQMKLENITNPWSPRHRVVQPTLEQTQYSWERQAAFSFKRKLPKYLLFTSPQENPWGHKRSYRLQIHSMADQVLPPGWQEEQAITWARYPLAVTKYRESELCSSSIYHQNDPWHPPVVFEQFLHNNENIENEDLVAWVTVGFLHIPHSEDIPNTATPGNSVGFLLRPFNFFPEDPSLASRDTVIVWPRDNGPNYVQRWIPEDRDCSMPPPFSYNGTYRPV (SEQ ID NO:40)

Fc-hDAO-Hepmut2

MPALGWAVAAILMLQTAMA*ECPPCPAPPVAGPSVFLFPPKPKDTLMISRTPEVTCVVVDVSHEDPEVKFNWYVDGVEVHNAKTKPREEQYNSTYRVVSVLTVLHQDWLNGKEYKCKVSNKGLPSSIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGKEPKSADKTHT*EPSPGTLPRKAGVFSDLSNQELKAVHSFLWSKKELRLQPSSTTTMAKNTVFLIEMLLPKKYHVLRFLDKGERHPVREARAVIFFGDQEHPNVTEFAVGPLPGPCYMRALSPRPGYQSSWASRPISTAEYALLYHTLQEATKPLHQFFLNTTGFSFQDCHDRCLAFTDVAPRGVASGQRRSWLIIQRYVEGYFLHPTGLELLVDHGSTDAGHWAVEQVWYNGKFYGSPEELARKYADGEVDVVVLEDPLPGGKGHDSTEEPPLFSSHKPRGDFPSPIHVSGPRLVQPHGPRFRLEGNAVLYGGWSFAFRLRSSSGLQVLNVHFGGERIAYEVSVQEAVALYGGHTPAGMQTKYLDVGWGLGSVTHELAPGIDCPETATFLDTFHYYDADDPVHYPRALCLFEMPTGVPLRRHFNSNFKGGFNFYAGLKGQVLVLRTTSTVYNYDYIWDFIFYPNGVMEAKMHATGYVHATFYTPEGLRHGTRLHTHLIGNIHTHLVHYRVDLDVAGTKNSFQTLQMKLENITNPWSPRHRVVQPTLEQTQYSWERQAAFRFKRKLPTYLLFTSPQENPWGHKRSYRLQIHSMADQVLPPGWQEEQAITWARYPLAVTKYRESELCSSSIYHQNDPWHPPVVFEQFLHNNENIENEDLVAWVTVGFLHIPHSEDIPNTATPGNSVGFLLRPFNFFPEDPSLASRDTVIVWPRDNGPNYVQRWIPEDRDCSMPPPFSYNGTYRPV (SEQ ID NO:41)

Figure 1 continued

Fc-hDAO-Hepmut3

MPALGWAVAAILMLQTAMA*ECPPCPAPPVAGPSVFLFPPKPKDTLMISRTPEVTCVVVDVSHEDPEVK*
*FNWYVDGVEVHNAKTKPREEQYNSTYRVVSVLTVLHQDWLNGKEYKCKVSNKGLPSSIEKTISKAKG*
*QPREPQVYTLPPSREEMTKNQVSLTCLVKGFYPSDIAVEWESNGQPENNYKTTPPVLDSDGSFFLYS*
*KLTVDKSRWQQGNVFSCSVMHEALHNHYTQKSLSLSPGKEPKSADKTHT*EPSPGTLPRKAGVFSDLS
NQELKAVHSFLWSKKELRLQPSSTTTMAKNTVFLIEMLLPKKYHVLRFLDKGERHPVREARAVIFFGDQ
EHPNVTEFAVGPLPGPCYMRALSPRPGYQSSWASRPISTAEYALLYHTLQEATKPLHQFFLNTTGFSFQ
DCHDRCLAFTDVAPRGVASGQRRSWLIIQRYVEGYFLHPTGLELLVDHGSTDAGHWAVEQVWYNGKF
YGSPEELARKYADGEVDVVVLEDPLPGGKGHDSTEEPPLFSSHKPRGDFPSPIHVSGPRLVQPHGPRF
RLEGNAVLYGGWSFAFRLRSSSGLQVLNVHFGGERIAYEVSVQEAVALYGGHTPAGMQTKYLDVGWG
LGSVTHELAPGIDCPETATFLDTFHYYDADDPVHYPRALCLFEMPTGVPLRRHFNSNFKGGFNFYAGLK
GQVLVLRTTSTVYNYDYIWDFIFYPNGVMEAKMHATGYVHATFYTPEGLRHGTRLHTHLIGNIHTHLVHY
RVDLDVAGTKNSFQTLQMKLENITNPWSPRHRVVQPTLEQTQYSWERQAAFRFKTKLPKYLLFTSPQE
NPWGHKRSYRLQIHSMADQVLPPGWQEEQAITWARYPLAVTKYRESELCSSSIYHQNDPWHPPVVFE
QFLHNNENIENEDLVAWVTVGFLHIPHSEDIPNTATPGNSVGFLLRPFNFFPEDPSLASRDTVIVWPRDN
GPNYVQRWIPEDRDCSMPPPFSYNGTYRPV (SEQ ID NO:42)

Fc-hDAO-Hepmut4

MPALGWAVAAILMLQTAMA*ECPPCPAPPVAGPSVFLFPPKPKDTLMISRTPEVTCVVVDVSHEDPEVK*
*FNWYVDGVEVHNAKTKPREEQYNSTYRVVSVLTVLHQDWLNGKEYKCKVSNKGLPSSIEKTISKAKG*
*QPREPQVYTLPPSREEMTKNQVSLTCLVKGFYPSDIAVEWESNGQPENNYKTTPPVLDSDGSFFLYS*
*KLTVDKSRWQQGNVFSCSVMHEALHNHYTQKSLSLSPGKEPKSADKTHT*EPSPGTLPRKAGVFSDLS
NQELKAVHSFLWSKKELRLQPSSTTTMAKNTVFLIEMLLPKKYHVLRFLDKGERHPVREARAVIFFGDQ
EHPNVTEFAVGPLPGPCYMRALSPRPGYQSSWASRPISTAEYALLYHTLQEATKPLHQFFLNTTGFSFQ
DCHDRCLAFTDVAPRGVASGQRRSWLIIQRYVEGYFLHPTGLELLVDHGSTDAGHWAVEQVWYNGKF
YGSPEELARKYADGEVDVVVLEDPLPGGKGHDSTEEPPLFSSHKPRGDFPSPIHVSGPRLVQPHGPRF
RLEGNAVLYGGWSFAFRLRSSSGLQVLNVHFGGERIAYEVSVQEAVALYGGHTPAGMQTKYLDVGWG
LGSVTHELAPGIDCPETATFLDTFHYYDADDPVHYPRALCLFEMPTGVPLRRHFNSNFKGGFNFYAGLK
GQVLVLRTTSTVYNYDYIWDFIFYPNGVMEAKMHATGYVHATFYTPEGLRHGTRLHTHLIGNIHTHLVHY
RVDLDVAGTKNSFQTLQMKLENITNPWSPRHRVVQPTLEQTQYSWERQAAFSFKTKLPKYLLFTSPQE
NPWGHKRSYRLQIHSMADQVLPPGWQEEQAITWARYPLAVTKYRESELCSSSIYHQNDPWHPPVVFE
QFLHNNENIENEDLVAWVTVGFLHIPHSEDIPNTATPGNSVGFLLRPFNFFPEDPSLASRDTVIVWPRDN
GPNYVQRWIPEDRDCSMPPPFSYNGTYRPV (SEQ ID NO:43)

Fc-hDAO-Hepmut5

MPALGWAVAAILMLQTAMA*ECPPCPAPPVAGPSVFLFPPKPKDTLMISRTPEVTCVVVDVSHEDPEVK*
*FNWYVDGVEVHNAKTKPREEQYNSTYRVVSVLTVLHQDWLNGKEYKCKVSNKGLPSSIEKTISKAKG*
*QPREPQVYTLPPSREEMTKNQVSLTCLVKGFYPSDIAVEWESNGQPENNYKTTPPVLDSDGSFFLYS*
*KLTVDKSRWQQGNVFSCSVMHEALHNHYTQKSLSLSPGKEPKSADKTHT*EPSPGTLPRKAGVFSDLS
NQELKAVHSFLWSKKELRLQPSSTTTMAKNTVFLIEMLLPKKYHVLRFLDKGERHPVREARAVIFFGDQ
EHPNVTEFAVGPLPGPCYMRALSPRPGYQSSWASRPISTAEYALLYHTLQEATKPLHQFFLNTTGFSFQ
DCHDRCLAFTDVAPRGVASGQRRSWLIIQRYVEGYFLHPTGLELLVDHGSTDAGHWAVEQVWYNGKF
YGSPEELARKYADGEVDVVVLEDPLPGGKGHDSTEEPPLFSSHKPRGDFPSPIHVSGPRLVQPHGPRF
RLEGNAVLYGGWSFAFRLRSSSGLQVLNVHFGGERIAYEVSVQEAVALYGGHTPAGMQTKYLDVGWG
LGSVTHELAPGIDCPETATFLDTFHYYDADDPVHYPRALCLFEMPTGVPLRRHFNSNFKGGFNFYAGLK
GQVLVLRTTSTVYNYDYIWDFIFYPNGVMEAKMHATGYVHATFYTPEGLRHGTRLHTHLIGNIHTHLVHY
RVDLDVAGTKNSFQTLQMKLENITNPWSPRHRVVQPTLEQTQYSWERQAAFRFKTKLPTYLLFTSPQE
NPWGHKRSYRLQIHSMADQVLPPGWQEEQAITWARYPLAVTKYRESELCSSSIYHQNDPWHPPVVFE
QFLHNNENIENEDLVAWVTVGFLHIPHSEDIPNTATPGNSVGFLLRPFNFFPEDPSLASRDTVIVWPRDN
GPNYVQRWIPEDRDCSMPPPFSYNGTYRPV (SEQ ID NO:44)

Figure 1 continued

Fc-hDAO-Hepmut6

MPALGWAVAAILMLQTAMA*ECPPCPAPPVAGPSVFLFPPKPKDTLMISRTPEVTCVVVDVSHEDPEVK*
*FNWYVDGVEVHNAKTKPREEQYNSTYRVVSVLTVLHQDWLNGKEYKCKVSNKGLPSSIEKTISKAKG*
*QPREPQVYTLPPSREEMTKNQVSLTCLVKGFYPSDIAVEWESNGQPENNYKTTPPVLDSDGSFFLYS*
*KLTVDKSRWQQGNVFSCSVMHEALHNHYTQKSLSLSPGKEPKSADKTHT*EPSPGTLPRKAGVFSDLS
NQELKAVHSFLWSKKELRLQPSSTTTMAKNTVFLIEMLLPKKYHVLRFLDKGERHPVREARAVIFFGDQ
EHPNVTEFAVGPLPGPCYMRALSPRPGYQSSWASRPISTAEYALLYHTLQEATKPLHQFFLNTTGFSFQ
DCHDRCLAFTDVAPRGVASGQRRSWLIIQRYVEGYFLHPTGLELLVDHGSTDAGHWAVEQVWYNGKF
YGSPEELARKYADGEVDVVVLEDPLPGGKGHDSTEEPPLFSSHKPRGDFPSPIHVSGPRLVQPHGPRF
RLEGNAVLYGGWSFAFRLRSSSGLQVLNVHFGGERIAYEVSVQEAVALYGGHTPAGMQTKYLDVGWG
LGSVTHELAPGIDCPETATFLDTFHYYDADDPVHYPRALCLFEMPTGVPLRRHFNSNFKGGFNFYAGLK
GQVLVLRTTSTVYNYDYIWDFIFYPNGVMEAKMHATGYVHATFYTPEGLRHGTRLHTHLIGNIHTHLVHY
RVDLDVAGTKNSFQTLQMKLENITNPWSPRHRVVQPTLEQTQYSWERQAAFRFGQTLPKYLLFTSPQE
NPWGHKRSYRLQIHSMADQVLPPGWQEEQAITWARYPLAVTKYRESELCSSSIYHQNDPWHPPVVFE
QFLHNNENIENEDLVAWVTVGFLHIPHSEDIPNTATPGNSVGFLLRPFNFFPEDPSLASRDTVIVWPRDN
GPNYVQRWIPEDRDCSMPPPFSYNGTYRPV (SEQ ID NO:45)

Fc-hDAO-Hepmut7

MPALGWAVAAILMLQTAMA*ECPPCPAPPVAGPSVFLFPPKPKDTLMISRTPEVTCVVVDVSHEDPEVK*
*FNWYVDGVEVHNAKTKPREEQYNSTYRVVSVLTVLHQDWLNGKEYKCKVSNKGLPSSIEKTISKAKG*
*QPREPQVYTLPPSREEMTKNQVSLTCLVKGFYPSDIAVEWESNGQPENNYKTTPPVLDSDGSFFLYS*
*KLTVDKSRWQQGNVFSCSVMHEALHNHYTQKSLSLSPGKEPKSADKTHT*EPSPGTLPRKAGVFSDLS
NQELKAVHSFLWSKKELRLQPSSTTTMAKNTVFLIEMLLPKKYHVLRFLDKGERHPVREARAVIFFGDQ
EHPNVTEFAVGPLPGPCYMRALSPRPGYQSSWASRPISTAEYALLYHTLQEATKPLHQFFLNTTGFSFQ
DCHDRCLAFTDVAPRGVASGQRRSWLIIQRYVEGYFLHPTGLELLVDHGSTDAGHWAVEQVWYNGKF
YGSPEELARKYADGEVDVVVLEDPLPGGKGHDSTEEPPLFSSHKPRGDFPSPIHVSGPRLVQPHGPRF
RLEGNAVLYGGWSFAFRLRSSSGLQVLNVHFGGERIAYEVSVQEAVALYGGHTPAGMQTKYLDVGWG
LGSVTHELAPGIDCPETATFLDTFHYYDADDPVHYPRALCLFEMPTGVPLRRHFNSNFKGGFNFYAGLK
GQVLVLRTTSTVYNYDYIWDFIFYPNGVMEAKMHATGYVHATFYTPEGLRHGTRLHTHLIGNIHTHLVHY
RVDLDVAGTKNSFQTLQMKLENITNPWSPRHRVVQPTLEQTQYSWERQAAFSFKRKLPTYLLFTSPQE
NPWGHKRSYRLQIHSMADQVLPPGWQEEQAITWARYPLAVTKYRESELCSSSIYHQNDPWHPPVVFE
QFLHNNENIENEDLVAWVTVGFLHIPHSEDIPNTATPGNSVGFLLRPFNFFPEDPSLASRDTVIVWPRDN
GPNYVQRWIPEDRDCSMPPPFSYNGTYRPV (SEQ ID NO:46)

Fc-hDAO-Cysmut

MPALGWAVAAILMLQTAMA*ECPPCPAPPVAGPSVFLFPPKPKDTLMISRTPEVTCVVVDVSHE*
*DPEVKFNWYVDGVEVHNAKTKPREEQYNSTYRVVSVLTVLHQDWLNGKEYKCKVSNKGLPSSIEKTI*
*SKAKGQPREPQVYTLPPSREEMTKNQVSLTCLVKGFYPSDIAVEWESNGQPENNYKTTPPVLDSDGS*
*FFLYSKLTVDKSRWQQGNVFSCSVMHEALHNHYTQKSLSLSPGKEPKSADKTHT*EPSPGTLPRKAGV
FSDLSNQELKAVHSFLWSKKELRLQPSSTTTMAKNTVFLIEMLLPKKYHVLRFLDKGERHPVREARAVIF
FGDQEHPNVTEFAVGPLPGPAYMRALSPRPGYQSSWASRPISTAEYALLYHTLQEATKPLHQFFLNTT
GFSFQDCHDRCLAFTDVAPRGVASGQRRSWLIIQRYVEGYFLHPTGLELLVDHGSTDAGHWAVEQVW
YNGKFYGSPEELARKYADGEVDVVVLEDPLPGGKGHDSTEEPPLFSSHKPRGDFPSPIHVSGPRLVQP
HGPRFRLEGNAVLYGGWSFAFRLRSSSGLQVLNVHFGGERIAYEVSVQEAVALYGGHTPAGMQTKYL
DVGWGLGSVTHELAPGIDCPETATFLDTFHYYDADDPVHYPRALCLFEMPTGVPLRRHFNSNFKGGFN
FYAGLKGQVLVLRTTSTVYNYDYIWDFIFYPNGVMEAKMHATGYVHATFYTPEGLRHGTRLHTHLIGNIH
THLVHYRVDLDVAGTKNSFQTLQMKLENITNPWSPRHRVVQPTLEQTQYSWERQAAFRFKRKLPKYLL
FTSPQENPWGHKRSYRLQIHSMADQVLPPGWQEEQAITWARYPLAVTKYRESELCSSSIYHQNDPWH
PPVVFEQFLHNNENIENEDLVAWVTVGFLHIPHSEDIPNTATPGNSVGFLLRPFNFFPEDPSLASRDTVIV
WPRDNGPNYVQRWIPEDRDCSMPPPFSYNGTYRPV (SEQ ID NO:47)

Figure 1 continued

Fc-hDAO-Hepmut1-Cysmut

MPALGWAVAAILMLQTAMA*ECPPCPAPPVAGPSVFLFPPKPKDTLMISRTPEVTCVVVDVSHEDPEVK*
*FNWYVDGVEVHNAKTKPREEQYNSTYRVVSVLTVLHQDWLNGKEYKCKVSNKGLPSSIEKTISKAKG*
*QPREPQVYTLPPSREEMTKNQVSLTCLVKGFYPSDIAVEWESNGQPENNYKTTPPVLDSDGSFFLYS*
*KLTVDKSRWQQGNVFSCSVMHEALHNHYTQKSLSLSPGKEPKSADKTHT*EPSPGTLPRKAGVFSDLS
NQELKAVHSFLWSKKELRLQPSSTTTMAKNTVFLIEMLLPKKYHVLRFLDKGERHPVREARAVIFFGDQ
EHPNVTEFAVGPLPGPAYMRALSPRPGYQSSWASRPISTAEYALLYHTLQEATKPLHQFFLNTTGFSFQ
DCHDRCLAFTDVAPRGVASGQRRSWLIIQRYVEGYFLHPTGLELLVDHGSTDAGHWAVEQVWYNGKF
YGSPEELARKYADGEVDVVVLEDPLPGGKGHDSTEEPPLFSSHKPRGDFPSPIHVSGPRLVQPHGPRF
RLEGNAVLYGGWSFAFRLRSSSGLQVLNVHFGGERIAYEVSVQEAVALYGGHTPAGMQTKYLDVGWG
LGSVTHELAPGIDCPETATFLDTFHYYDADDPVHYPRALCLFEMPTGVPLRRHFNSNFKGGFNFYAGLK
GQVLVLRTTSTVYNYDYIWDFIFYPNGVMEAKMHATGYVHATFYTPEGLRHGTRLHTHLIGNIHTHLVHY
RVDLDVAGTKNSFQTLQMKLENITNPWSPRHRVVQPTLEQTQYSWERQAAFSFKRKLPKYLLFTSPQE
NPWGHKRSYRLQIHSMADQVLPPGWQEEQAITWARYPLAVTKYRESELCSSSIYHQNDPWHPPVVFE
QFLHNNENIENEDLVAWVTVGFLHIPHSEDIPNTATPGNSVGFLLRPFNFFPEDPSLASRDTVIVWPRDN
GPNYVQRWIPEDRDCSMPPPFSYNGTYRPV (SEQ ID NO:48)

Fc-hDAO-Hepmut2-Cysmut

MPALGWAVAAILMLQTAMA*ECPPCPAPPVAGPSVFLFPPKPKDTLMISRTPEVTCVVVDVSHEDPEVK*
*FNWYVDGVEVHNAKTKPREEQYNSTYRVVSVLTVLHQDWLNGKEYKCKVSNKGLPSSIEKTISKAKG*
*QPREPQVYTLPPSREEMTKNQVSLTCLVKGFYPSDIAVEWESNGQPENNYKTTPPVLDSDGSFFLYS*
*KLTVDKSRWQQGNVFSCSVMHEALHNHYTQKSLSLSPGKEPKSADKTHT*EPSPGTLPRKAGVFSDLS
NQELKAVHSFLWSKKELRLQPSSTTTMAKNTVFLIEMLLPKKYHVLRFLDKGERHPVREARAVIFFGDQ
EHPNVTEFAVGPLPGPAYMRALSPRPGYQSSWASRPISTAEYALLYHTLQEATKPLHQFFLNTTGFSFQ
DCHDRCLAFTDVAPRGVASGQRRSWLIIQRYVEGYFLHPTGLELLVDHGSTDAGHWAVEQVWYNGKF
YGSPEELARKYADGEVDVVVLEDPLPGGKGHDSTEEPPLFSSHKPRGDFPSPIHVSGPRLVQPHGPRF
RLEGNAVLYGGWSFAFRLRSSSGLQVLNVHFGGERIAYEVSVQEAVALYGGHTPAGMQTKYLDVGWG
LGSVTHELAPGIDCPETATFLDTFHYYDADDPVHYPRALCLFEMPTGVPLRRHFNSNFKGGFNFYAGLK
GQVLVLRTTSTVYNYDYIWDFIFYPNGVMEAKMHATGYVHATFYTPEGLRHGTRLHTHLIGNIHTHLVHY
RVDLDVAGTKNSFQTLQMKLENITNPWSPRHRVVQPTLEQTQYSWERQAAFRFKRKLPTYLLFTSPQE
NPWGHKRSYRLQIHSMADQVLPPGWQEEQAITWARYPLAVTKYRESELCSSSIYHQNDPWHPPVVFE
QFLHNNENIENEDLVAWVTVGFLHIPHSEDIPNTATPGNSVGFLLRPFNFFPEDPSLASRDTVIVWPRDN
GPNYVQRWIPEDRDCSMPPPFSYNGTYRPV (SEQ ID NO:49)

Fc-hDAO-Hepmut3-Cysmut

MPALGWAVAAILMLQTAMA*ECPPCPAPPVAGPSVFLFPPKPKDTLMISRTPEVTCVVVDVSHEDPEVK*
*FNWYVDGVEVHNAKTKPREEQYNSTYRVVSVLTVLHQDWLNGKEYKCKVSNKGLPSSIEKTISKAKG*
*QPREPQVYTLPPSREEMTKNQVSLTCLVKGFYPSDIAVEWESNGQPENNYKTTPPVLDSDGSFFLYS*
*KLTVDKSRWQQGNVFSCSVMHEALHNHYTQKSLSLSPGKEPKSADKTHT*EPSPGTLPRKAGVFSDLS
NQELKAVHSFLWSKKELRLQPSSTTTMAKNTVFLIEMLLPKKYHVLRFLDKGERHPVREARAVIFFGDQ
EHPNVTEFAVGPLPGPAYMRALSPRPGYQSSWASRPISTAEYALLYHTLQEATKPLHQFFLNTTGFSFQ
DCHDRCLAFTDVAPRGVASGQRRSWLIIQRYVEGYFLHPTGLELLVDHGSTDAGHWAVEQVWYNGKF
YGSPEELARKYADGEVDVVVLEDPLPGGKGHDSTEEPPLFSSHKPRGDFPSPIHVSGPRLVQPHGPRF
RLEGNAVLYGGWSFAFRLRSSSGLQVLNVHFGGERIAYEVSVQEAVALYGGHTPAGMQTKYLDVGWG
LGSVTHELAPGIDCPETATFLDTFHYYDADDPVHYPRALCLFEMPTGVPLRRHFNSNFKGGFNFYAGLK
GQVLVLRTTSTVYNYDYIWDFIFYPNGVMEAKMHATGYVHATFYTPEGLRHGTRLHTHLIGNIHTHLVHY
RVDLDVAGTKNSFQTLQMKLENITNPWSPRHRVVQPTLEQTQYSWERQAAFRFKTKLPKYLLFTSPQE
NPWGHKRSYRLQIHSMADQVLPPGWQEEQAITWARYPLAVTKYRESELCSSSIYHQNDPWHPPVVFE
QFLHNNENIENEDLVAWVTVGFLHIPHSEDIPNTATPGNSVGFLLRPFNFFPEDPSLASRDTVIVWPRDN
GPNYVQRWIPEDRDCSMPPPFSYNGTYRPV (SEQ ID NO:50)

Figure 1 continued

Fc-hDAO-Hepmut4-Cysmut

MPALGWAVAAILMLQTAMA***ECPPCPAPPVAGPSVFLFPPKPKDTLMISRTPEVTCVVVDVSHEDPEVK
FNWYVDGVEVHNAKTKPREEQYNSTYRVVSVLTVLHQDWLNGKEYKCKVSNKGLPSSIEKTISKAKG
QPREPQVYTLPPSREEMTKNQVSLTCLVKGFYPSDIAVEWESNGQPENNYKTTPPVLDSDGSFFLYS
KLTVDKSRWQQGNVFSCSVMHEALHNHYTQKSLSLSPGK*** *EPKSADKTHT* EPSPGTLPRKAGVFSDLS
NQELKAVHSFLWSKKELRLQPSSTTTMAKNTVFLIEMLLPKKYHVLRFLDKGERHPVREARAVIFFGDQ
EHPNVTEFAVGPLPGPAYMRALSPRPGYQSSWASRPISTAEYALLYHTLQEATKPLHQFFLNTTGFSFQ
DCHDRCLAFTDVAPRGVASGQRRSWLIIQRYVEGYFLHPTGLELLVDHGSTDAGHWAVEQVWYNGKF
YGSPEELARKYADGEVDVVVLEDPLPGGKGHDSTEEPPLFSSHKPRGDFPSPIHVSGPRLVQPHGPRF
RLEGNAVLYGGWSFAFRLRSSSGLQVLNVHFGGERIAYEVSVQEAVALYGGHTPAGMQTKYLDVGWG
LGSVTHELAPGIDCPETATFLDTFHYYDADDPVHYPRALCLFEMPTGVPLRRHFNSNFKGGFNFYAGLK
GQVLVLRTTSTVYNYDYIWDFIFYPNGVMEAKMHATGYVHATFYTPEGLRHGTRLHTHLIGNIHTHLVHY
RVDLDVAGTKNSFQTLQMKLENITNPWSPRHRVVQPTLEQTQYSWERQAAFSFKTKLPKYLLFTSPQE
NPWGHKRSYRLQIHSMADQVLPPGWQEEQAITWARYPLAVTKYRESELCSSSIYHQNDPWHPPVVFE
QFLHNNENIENEDLVAWVTVGFLHIPHSEDIPNTATPGNSVGFLLRPFNFFPEDPSLASRDTVIVWPRDN
GPNYVQRWIPEDRDCSMPPPFSYNGTYRPV (SEQ ID NO:51)

Fc-hDAO-Hepmut5-Cysmut

MPALGWAVAAILMLQTAMA***ECPPCPAPPVAGPSVFLFPPKPKDTLMISRTPEVTCVVVDVSHEDPEVK
FNWYVDGVEVHNAKTKPREEQYNSTYRVVSVLTVLHQDWLNGKEYKCKVSNKGLPSSIEKTISKAKG
QPREPQVYTLPPSREEMTKNQVSLTCLVKGFYPSDIAVEWESNGQPENNYKTTPPVLDSDGSFFLYS
KLTVDKSRWQQGNVFSCSVMHEALHNHYTQKSLSLSPGK*** *EPKSADKTHT* EPSPGTLPRKAGVFSDLS
NQELKAVHSFLWSKKELRLQPSSTTTMAKNTVFLIEMLLPKKYHVLRFLDKGERHPVREARAVIFFGDQ
EHPNVTEFAVGPLPGPAYMRALSPRPGYQSSWASRPISTAEYALLYHTLQEATKPLHQFFLNTTGFSFQ
DCHDRCLAFTDVAPRGVASGQRRSWLIIQRYVEGYFLHPTGLELLVDHGSTDAGHWAVEQVWYNGKF
YGSPEELARKYADGEVDVVVLEDPLPGGKGHDSTEEPPLFSSHKPRGDFPSPIHVSGPRLVQPHGPRF
RLEGNAVLYGGWSFAFRLRSSSGLQVLNVHFGGERIAYEVSVQEAVALYGGHTPAGMQTKYLDVGWG
LGSVTHELAPGIDCPETATFLDTFHYYDADDPVHYPRALCLFEMPTGVPLRRHFNSNFKGGFNFYAGLK
GQVLVLRTTSTVYNYDYIWDFIFYPNGVMEAKMHATGYVHATFYTPEGLRHGTRLHTHLIGNIHTHLVHY
RVDLDVAGTKNSFQTLQMKLENITNPWSPRHRVVQPTLEQTQYSWERQAAFRFKTKLPTYLLFTSPQE
NPWGHKRSYRLQIHSMADQVLPPGWQEEQAITWARYPLAVTKYRESELCSSSIYHQNDPWHPPVVFE
QFLHNNENIENEDLVAWVTVGFLHIPHSEDIPNTATPGNSVGFLLRPFNFFPEDPSLASRDTVIVWPRDN
GPNYVQRWIPEDRDCSMPPPFSYNGTYRPV (SEQ ID NO:52)

Fc-hDAO-Hepmut6-Cysmut

MPALGWAVAAILMLQTAMA***ECPPCPAPPVAGPSVFLFPPKPKDTLMISRTPEVTCVVVDVSHEDPEVK
FNWYVDGVEVHNAKTKPREEQYNSTYRVVSVLTVLHQDWLNGKEYKCKVSNKGLPSSIEKTISKAKG
QPREPQVYTLPPSREEMTKNQVSLTCLVKGFYPSDIAVEWESNGQPENNYKTTPPVLDSDGSFFLYS
KLTVDKSRWQQGNVFSCSVMHEALHNHYTQKSLSLSPGK*** *EPKSADKTHT* EPSPGTLPRKAGVFSDLS
NQELKAVHSFLWSKKELRLQPSSTTTMAKNTVFLIEMLLPKKYHVLRFLDKGERHPVREARAVIFFGDQ
EHPNVTEFAVGPLPGPAYMRALSPRPGYQSSWASRPISTAEYALLYHTLQEATKPLHQFFLNTTGFSFQ
DCHDRCLAFTDVAPRGVASGQRRSWLIIQRYVEGYFLHPTGLELLVDHGSTDAGHWAVEQVWYNGKF
YGSPEELARKYADGEVDVVVLEDPLPGGKGHDSTEEPPLFSSHKPRGDFPSPIHVSGPRLVQPHGPRF
RLEGNAVLYGGWSFAFRLRSSSGLQVLNVHFGGERIAYEVSVQEAVALYGGHTPAGMQTKYLDVGWG
LGSVTHELAPGIDCPETATFLDTFHYYDADDPVHYPRALCLFEMPTGVPLRRHFNSNFKGGFNFYAGLK
GQVLVLRTTSTVYNYDYIWDFIFYPNGVMEAKMHATGYVHATFYTPEGLRHGTRLHTHLIGNIHTHLVHY
RVDLDVAGTKNSFQTLQMKLENITNPWSPRHRVVQPTLEQTQYSWERQAAFRFGQTLPKYLLFTSPQE
NPWGHKRSYRLQIHSMADQVLPPGWQEEQAITWARYPLAVTKYRESELCSSSIYHQNDPWHPPVVFE
QFLHNNENIENEDLVAWVTVGFLHIPHSEDIPNTATPGNSVGFLLRPFNFFPEDPSLASRDTVIVWPRDN
GPNYVQRWIPEDRDCSMPPPFSYNGTYRPV (SEQ ID NO:53)

Figure 1 continued

Fc-hDAO-Hepmut7-Cysmut

MPALGWAVAAILMLQTAMA*ECPPCPAPPVAGPSVFLFPPKPKDTLMISRTPEVTCVVVDVSHEDPEVK*
*FNWYVDGVEVHNAKTKPREEQYNSTYRVVSVLTVLHQDWLNGKEYKCKVSNKGLPSSIEKTISKAKG*
*QPREPQVYTLPPSREEMTKNQVSLTCLVKGFYPSDIAVEWESNGQPENNYKTTPPVLDSDGSFFLYS*
*KLTVDKSRWQQGNVFSCSVMHEALHNHYTQKSLSLSPGKEPKSADKTHT*EPSPGTLPRKAGVFSDLS
NQELKAVHSFLWSKKELRLQPSSTTTMAKNTVFLIEMLLPKKYHVLRFLDKGERHPVREARAVIFFGDQ
EHPNVTEFAVGPLPGPAYMRALSPRPGYQSSWASRPISTAEYALLYHTLQEATKPLHQFFLNTTGFSFQ
DCHDRCLAFTDVAPRGVASGQRRSWLIIQRYVEGYFLHPTGLELLVDHGSTDAGHWAVEQVWYNGKF
YGSPEELARKYADGEVDVVVLEDPLPGGKGHDSTEEPPLFSSHKPRGDFPSPIHVSGPRLVQPHGPRF
RLEGNAVLYGGWSFAFRLRSSSGLQVLNVHFGGERIAYEVSVQEAVALYGGHTPAGMQTKYLDVGWG
LGSVTHELAPGIDCPETATFLDTFHYYDADDPVHYPRALCLFEMPTGVPLRRHFNSNFKGGFNFYAGLK
GQVLVLRTTSTVYNYDYIWDFIFYPNGVMEAKMHATGYVHATFYTPEGLRHGTRLHTHLIGNIHTHLVHY
RVDLDVAGTKNSFQTLQMKLENITNPWSPRHRVVQPTLEQTQYSWERQAAFSFKRKLPTYLLFTSPQE
NPWGHKRSYRLQIHSMADQVLPPGWQEEQAITWARYPLAVTKYRESELCSSSIYHQNDPWHPPVVFE
QFLHNNENIENEDLVAWVTVGFLHIPHSEDIPNTATPGNSVGFLLRPFNFFPEDPSLASRDTVIVWPRDN
GPNYVQRWIPEDRDCSMPPPFSYNGTYRPV (SEQ ID NO:54)

hDAO-Fc

MPALGWAVAAILMLQTAMAEPSPGTLPRKAGVFSDLSNQELKAVHSFLWSKKELRLQPSSTTTMAKNT
VFLIEMLLPKKYHVLRFLDKGERHPVREARAVIFFGDQEHPNVTEFAVGPLPGPCYMRALSPRPGYQSS
WASRPISTAEYALLYHTLQEATKPLHQFFLNTTGFSFQDCHDRCLAFTDVAPRGVASGQRRSWLIIQRY
VEGYFLHPTGLELLVDHGSTDAGHWAVEQVWYNGKFYGSPEELARKYADGEVDVVVLEDPLPGGKGH
DSTEEPPLFSSHKPRGDFPSPIHVSGPRLVQPHGPRFRLEGNAVLYGGWSFAFRLRSSSGLQVLNVHF
GGERIAYEVSVQEAVALYGGHTPAGMQTKYLDVGWGLGSVTHELAPGIDCPETATFLDTFHYYDADDP
VHYPRALCLFEMPTGVPLRRHFNSNFKGGFNFYAGLKGQVLVLRTTSTVYNYDYIWDFIFYPNGVMEAK
MHATGYVHATFYTPEGLRHGTRLHTHLIGNIHTHLVHYRVDLDVAGTKNSFQTLQMKLENITNPWSPRH
RVVQPTLEQTQYSWERQAAFRFKRKLPKYLLFTSPQENPWGHKRSYRLQIHSMADQVLPPGWQEEQA
ITWARYPLAVTKYRESELCSSSIYHQNDPWHPPVVFEQFLHNNENIENEDLVAWVTVGFLHIPHSEDIPN
TATPGNSVGFLLRPFNFFPEDPSLASRDTVIVWPRDNGPNYVQRWIPEDRDCSMPPPFSYNGTYRPV*E*
*PKSADKTHTCPPCPAPPVAGPSVFLFPPKPKDTLMISRTPEVTCVVVDVSHEDPEVKFNWYVDGVEV*
*HNAKTKPREEQYNSTYRVVSVLTVLHQDWLNGKEYKCKVSNKGLPSSIEKTISKAKGQPREPQVYTL*
*PPSREEMTKNQVSLTCLVKGFYPSDIAVEWESNGQPENNYKTTPPVLDSDGSFFLYSKLTVDKSRWQ*
*QGNVFSCSVMHEALHNHYTQKSLSLSPGK* (SEQ ID NO:55)

hDAO-Fc-Hepmut1

MPALGWAVAAILMLQTAMAEPSPGTLPRKAGVFSDLSNQELKAVHSFLWSKKELRLQPSSTTTMAKNT
VFLIEMLLPKKYHVLRFLDKGERHPVREARAVIFFGDQEHPNVTEFAVGPLPGPCYMRALSPRPGYQSS
WASRPISTAEYALLYHTLQEATKPLHQFFLNTTGFSFQDCHDRCLAFTDVAPRGVASGQRRSWLIIQRY
VEGYFLHPTGLELLVDHGSTDAGHWAVEQVWYNGKFYGSPEELARKYADGEVDVVVLEDPLPGGKGH
DSTEEPPLFSSHKPRGDFPSPIHVSGPRLVQPHGPRFRLEGNAVLYGGWSFAFRLRSSSGLQVLNVHF
GGERIAYEVSVQEAVALYGGHTPAGMQTKYLDVGWGLGSVTHELAPGIDCPETATFLDTFHYYDADDP
VHYPRALCLFEMPTGVPLRRHFNSNFKGGFNFYAGLKGQVLVLRTTSTVYNYDYIWDFIFYPNGVMEAK
MHATGYVHATFYTPEGLRHGTRLHTHLIGNIHTHLVHYRVDLDVAGTKNSFQTLQMKLENITNPWSPRH
RVVQPTLEQTQYSWERQAAFSFKRKLPKYLLFTSPQENPWGHKRSYRLQIHSMADQVLPPGWQEEQA
ITWARYPLAVTKYRESELCSSSIYHQNDPWHPPVVFEQFLHNNENIENEDLVAWVTVGFLHIPHSEDIPN
TATPGNSVGFLLRPFNFFPEDPSLASRDTVIVWPRDNGPNYVQRWIPEDRDCSMPPPFSYNGTYRPV*E*
*PKSADKTHTCPPCPAPPVAGPSVFLFPPKPKDTLMISRTPEVTCVVVDVSHEDPEVKFNWYVDGVEV*
*HNAKTKPREEQYNSTYRVVSVLTVLHQDWLNGKEYKCKVSNKGLPSSIEKTISKAKGQPREPQVYTL*
*PPSREEMTKNQVSLTCLVKGFYPSDIAVEWESNGQPENNYKTTPPVLDSDGSFFLYSKLTVDKSRWQ*
*QGNVFSCSVMHEALHNHYTQKSLSLSPGK* (SEQ ID NO:56)

Figure 1 continued hDAO-Fc-Hepmut2

MPALGWAVAAILMLQTAMAEPSPGTLPRKAGVFSDLSNQELKAVHSFLWSKKELRLQPSSTTTMAKNT
VFLIEMLLPKKYHVLRFLDKGERHPVREARAVIFFGDQEHPNVTEFAVGPLPGPCYMRALSPRPGYQSS
WASRPISTAEYALLYHTLQEATKPLHQFFLNTTGFSFQDCHDRCLAFTDVAPRGVASGQRRSWLIIQRY
VEGYFLHPTGLELLVDHGSTDAGHWAVEQVWYNGKFYGSPEELARKYADGEVDVVVLEDPLPGGKGH
DSTEEPPLFSSHKPRGDFPSPIHVSGPRLVQPHGPRFRLEGNAVLYGGWSFAFRLRSSSGLQVLNVHF
GGERIAYEVSVQEAVALYGGHTPAGMQTKYLDVGWGLGSVTHELAPGIDCPETATFLDTFHYYDADDP
VHYPRALCLFEMPTGVPLRRHFNSNFKGGFNFYAGLKGQVLVLRTTSTVYNYDYIWDFIFYPNGVMEAK
MHATGYVHATFYTPEGLRHGTRLHTHLIGNIHTHLVHYRVDLDVAGTKNSFQTLQMKLENITNPWSPRH
RVVQPTLEQTQYSWERQAAFRFKRKLPTYLLFTSPQENPWGHKRSYRLQIHSMADQVLPPGWQEEQA
ITWARYPLAVTKYRESELCSSSIYHQNDPWHPPVVFEQFLHNNENIENEDLVAWVTVGFLHIPHSEDIPN
TATPGNSVGFLLRPFNFFPEDPSLASRDTVIVWPRDNGPNYVQRWIPEDRDCSMPPPFSYNGTYRPV*E*
*PKSADKTHTCPPCPAPPVAGPSVFLFPPKPKDTLMISRTPEVTCVVVDVSHEDPEVKFNWYVDGVEV*
*HNAKTKPREEQYNSTYRVVSVLTVLHQDWLNGKEYKCKVSNKGLPSSIEKTISKAKGQPREPQVYTL*
*PPSREEMTKNQVSLTCLVKGFYPSDIAVEWESNGQPENNYKTTPPVLDSDGSFFLYSKLTVDKSRWQ*
*QGNVFSCSVMHEALHNHYTQKSLSLSPGK* (SEQ ID NO:57)

hDAO-Fc-Hepmut3

MPALGWAVAAILMLQTAMAEPSPGTLPRKAGVFSDLSNQELKAVHSFLWSKKELRLQPSSTTTMAKNT
VFLIEMLLPKKYHVLRFLDKGERHPVREARAVIFFGDQEHPNVTEFAVGPLPGPCYMRALSPRPGYQSS
WASRPISTAEYALLYHTLQEATKPLHQFFLNTTGFSFQDCHDRCLAFTDVAPRGVASGQRRSWLIIQRY
VEGYFLHPTGLELLVDHGSTDAGHWAVEQVWYNGKFYGSPEELARKYADGEVDVVVLEDPLPGGKGH
DSTEEPPLFSSHKPRGDFPSPIHVSGPRLVQPHGPRFRLEGNAVLYGGWSFAFRLRSSSGLQVLNVHF
GGERIAYEVSVQEAVALYGGHTPAGMQTKYLDVGWGLGSVTHELAPGIDCPETATFLDTFHYYDADDP
VHYPRALCLFEMPTGVPLRRHFNSNFKGGFNFYAGLKGQVLVLRTTSTVYNYDYIWDFIFYPNGVMEAK
MHATGYVHATFYTPEGLRHGTRLHTHLIGNIHTHLVHYRVDLDVAGTKNSFQTLQMKLENITNPWSPRH
RVVQPTLEQTQYSWERQAAFRFKTKLPKYLLFTSPQENPWGHKRSYRLQIHSMADQVLPPGWQEEQA
ITWARYPLAVTKYRESELCSSSIYHQNDPWHPPVVFEQFLHNNENIENEDLVAWVTVGFLHIPHSEDIPN
TATPGNSVGFLLRPFNFFPEDPSLASRDTVIVWPRDNGPNYVQRWIPEDRDCSMPPPFSYNGTYRPV*E*
*PKSADKTHTCPPCPAPPVAGPSVFLFPPKPKDTLMISRTPEVTCVVVDVSHEDPEVKFNWYVDGVEV*
*HNAKTKPREEQYNSTYRVVSVLTVLHQDWLNGKEYKCKVSNKGLPSSIEKTISKAKGQPREPQVYTL*
*PPSREEMTKNQVSLTCLVKGFYPSDIAVEWESNGQPENNYKTTPPVLDSDGSFFLYSKLTVDKSRWQ*
*QGNVFSCSVMHEALHNHYTQKSLSLSPGK* (SEQ ID NO:58)

hDAO-Fc-Hepmut4

MPALGWAVAAILMLQTAMAEPSPGTLPRKAGVFSDLSNQELKAVHSFLWSKKELRLQPSSTTTMAKNT
VFLIEMLLPKKYHVLRFLDKGERHPVREARAVIFFGDQEHPNVTEFAVGPLPGPCYMRALSPRPGYQSS
WASRPISTAEYALLYHTLQEATKPLHQFFLNTTGFSFQDCHDRCLAFTDVAPRGVASGQRRSWLIIQRY
VEGYFLHPTGLELLVDHGSTDAGHWAVEQVWYNGKFYGSPEELARKYADGEVDVVVLEDPLPGGKGH
DSTEEPPLFSSHKPRGDFPSPIHVSGPRLVQPHGPRFRLEGNAVLYGGWSFAFRLRSSSGLQVLNVHF
GGERIAYEVSVQEAVALYGGHTPAGMQTKYLDVGWGLGSVTHELAPGIDCPETATFLDTFHYYDADDP
VHYPRALCLFEMPTGVPLRRHFNSNFKGGFNFYAGLKGQVLVLRTTSTVYNYDYIWDFIFYPNGVMEAK
MHATGYVHATFYTPEGLRHGTRLHTHLIGNIHTHLVHYRVDLDVAGTKNSFQTLQMKLENITNPWSPRH
RVVQPTLEQTQYSWERQAAFSFKTKLPKYLLFTSPQENPWGHKRSYRLQIHSMADQVLPPGWQEEQAI
TWARYPLAVTKYRESELCSSSIYHQNDPWHPPVVFEQFLHNNENIENEDLVAWVTVGFLHIPHSEDIPN
TATPGNSVGFLLRPFNFFPEDPSLASRDTVIVWPRDNGPNYVQRWIPEDRDCSMPPPFSYNGTYRPV*E*
*PKSADKTHTCPPCPAPPVAGPSVFLFPPKPKDTLMISRTPEVTCVVVDVSHEDPEVKFNWYVDGVEV*
*HNAKTKPREEQYNSTYRVVSVLTVLHQDWLNGKEYKCKVSNKGLPSSIEKTISKAKGQPREPQVYTL*
*PPSREEMTKNQVSLTCLVKGFYPSDIAVEWESNGQPENNYKTTPPVLDSDGSFFLYSKLTVDKSRWQ*
*QGNVFSCSVMHEALHNHYTQKSLSLSPGK* (SEQ ID NO:59)

Figure 1 continued hDAO-Fc-Hepmut5

MPALGWAVAAILMLQTAMAEPSPGTLPRKAGVFSDLSNQELKAVHSFLWSKKELRLQPSSTTTMAKNT
VFLIEMLLPKKYHVLRFLDKGERHPVREARAVIFFGDQEHPNVTEFAVGPLPGPCYMRALSPRPGYQSS
WASRPISTAEYALLYHTLQEATKPLHQFFLNTTGFSFQDCHDRCLAFTDVAPRGVASGQRRSWLIIQRY
VEGYFLHPTGLELLVDHGSTDAGHWAVEQVWYNGKFYGSPEELARKYADGEVDVVVLEDPLPGGKGH
DSTEEPPLFSSHKPRGDFPSPIHVSGPRLVQPHGPRFRLEGNAVLYGGWSFAFRLRSSSGLQVLNVHF
GGERIAYEVSVQEAVALYGGHTPAGMQTKYLDVGWGLGSVTHELAPGIDCPETATFLDTFHYYDADDP
VHYPRALCLFEMPTGVPLRRHFNSNFKGGFNYAGLKGQVLVLRTTSTVYNYDYIWDFIFYPNGVMEAK
MHATGYVHATFYTPEGLRHGTRLHTHLIGNIHTHLVHYRVDLDVAGTKNSFQTLQMKLENITNPWSPRH
RVVQPTLEQTQYSWERQAAFRFKTKLPTYLLFTSPQENPWGHKRSYRLQIHSMADQVLPPGWQEEQAI
TWARYPLAVTKYRESELCSSSIYHQNDPWHPPVVFEQFLHNNENIENEDLVAWVTVGFLHIPHSEDIPN
TATPGNSVGFLLRPFNFFPEDPSLASRDTVIVWPRDNGPNYVQRWIPEDRDCSMPPPFSYNGTYRPV*E*
*PKSADKTHT**CPPCPAPPVAGPSVFLFPPKPKDTLMISRTPEVTCVVVDVSHEDPEVKFNWYVDGVEV*
*HNAKTKPREEQYNSTYRVVSVLTVLHQDWLNGKEYKCKVSNKGLPSSIEKTISKAKGQPREPQVYTL*
*PPSREEMTKNQVSLTCLVKGFYPSDIAVEWESNGQPENNYKTTPPVLDSDGSFFLYSKLTVDKSRWQ*
*QGNVFSCSVMHEALHNHYTQKSLSLSPGK* (SEQ ID NO:60)

hDAO-Fc-Hepmut6

MPALGWAVAAILMLQTAMAEPSPGTLPRKAGVFSDLSNQELKAVHSFLWSKKELRLQPSSTTTMAKNT
VFLIEMLLPKKYHVLRFLDKGERHPVREARAVIFFGDQEHPNVTEFAVGPLPGPCYMRALSPRPGYQSS
WASRPISTAEYALLYHTLQEATKPLHQFFLNTTGFSFQDCHDRCLAFTDVAPRGVASGQRRSWLIIQRY
VEGYFLHPTGLELLVDHGSTDAGHWAVEQVWYNGKFYGSPEELARKYADGEVDVVVLEDPLPGGKGH
DSTEEPPLFSSHKPRGDFPSPIHVSGPRLVQPHGPRFRLEGNAVLYGGWSFAFRLRSSSGLQVLNVHF
GGERIAYEVSVQEAVALYGGHTPAGMQTKYLDVGWGLGSVTHELAPGIDCPETATFLDTFHYYDADDP
VHYPRALCLFEMPTGVPLRRHFNSNFKGGFNYAGLKGQVLVLRTTSTVYNYDYIWDFIFYPNGVMEAK
MHATGYVHATFYTPEGLRHGTRLHTHLIGNIHTHLVHYRVDLDVAGTKNSFQTLQMKLENITNPWSPRH
RVVQPTLEQTQYSWERQAAFRFGQTLPKYLLFTSPQENPWGHKRSYRLQIHSMADQVLPPGWQEEQA
ITWARYPLAVTKYRESELCSSSIYHQNDPWHPPVVFEQFLHNNENIENEDLVAWVTVGFLHIPHSEDIPN
TATPGNSVGFLLRPFNFFPEDPSLASRDTVIVWPRDNGPNYVQRWIPEDRDCSMPPPFSYNGTYRPV*E*
*PKSADKTHT**CPPCPAPPVAGPSVFLFPPKPKDTLMISRTPEVTCVVVDVSHEDPEVKFNWYVDGVEV*
*HNAKTKPREEQYNSTYRVVSVLTVLHQDWLNGKEYKCKVSNKGLPSSIEKTISKAKGQPREPQVYTL*
*PPSREEMTKNQVSLTCLVKGFYPSDIAVEWESNGQPENNYKTTPPVLDSDGSFFLYSKLTVDKSRWQ*
*QGNVFSCSVMHEALHNHYTQKSLSLSPGK* (SEQ ID NO:61)

hDAO-Fc-Hepmut7

MPALGWAVAAILMLQTAMAEPSPGTLPRKAGVFSDLSNQELKAVHSFLWSKKELRLQPSSTTTMAKNT
VFLIEMLLPKKYHVLRFLDKGERHPVREARAVIFFGDQEHPNVTEFAVGPLPGPCYMRALSPRPGYQSS
WASRPISTAEYALLYHTLQEATKPLHQFFLNTTGFSFQDCHDRCLAFTDVAPRGVASGQRRSWLIIQRY
VEGYFLHPTGLELLVDHGSTDAGHWAVEQVWYNGKFYGSPEELARKYADGEVDVVVLEDPLPGGKGH
DSTEEPPLFSSHKPRGDFPSPIHVSGPRLVQPHGPRFRLEGNAVLYGGWSFAFRLRSSSGLQVLNVHF
GGERIAYEVSVQEAVALYGGHTPAGMQTKYLDVGWGLGSVTHELAPGIDCPETATFLDTFHYYDADDP
VHYPRALCLFEMPTGVPLRRHFNSNFKGGFNYAGLKGQVLVLRTTSTVYNYDYIWDFIFYPNGVMEAK
MHATGYVHATFYTPEGLRHGTRLHTHLIGNIHTHLVHYRVDLDVAGTKNSFQTLQMKLENITNPWSPRH
RVVQPTLEQTQYSWERQAAFSFKRKLPTYLLFTSPQENPWGHKRSYRLQIHSMADQVLPPGWQEEQA
ITWARYPLAVTKYRESELCSSSIYHQNDPWHPPVVFEQFLHNNENIENEDLVAWVTVGFLHIPHSEDIPN
TATPGNSVGFLLRPFNFFPEDPSLASRDTVIVWPRDNGPNYVQRWIPEDRDCSMPPPFSYNGTYRPV*E*
*PKSADKTHT**CPPCPAPPVAGPSVFLFPPKPKDTLMISRTPEVTCVVVDVSHEDPEVKFNWYVDGVEV*
*HNAKTKPREEQYNSTYRVVSVLTVLHQDWLNGKEYKCKVSNKGLPSSIEKTISKAKGQPREPQVYTL*
*PPSREEMTKNQVSLTCLVKGFYPSDIAVEWESNGQPENNYKTTPPVLDSDGSFFLYSKLTVDKSRWQ*
*QGNVFSCSVMHEALHNHYTQKSLSLSPGK*(SEQ ID NO:62)

Figure 1 continued hDAO-Fc-Cysmut

MPALGWAVAAILMLQTAMAEPSPGTLPRKAGVFSDLSNQELKAVHSFLWSKKELRLQPSSTTTMAKNT
VFLIEMLLPKKYHVLRFLDKGERHPVREARAVIFFGDQEHPNVTEFAVGPLPGPAYMRALSPRPGYQSS
WASRPISTAEYALLYHTLQEATKPLHQFFLNTTGFSFQDCHDRCLAFTDVAPRGVASGQRRSWLIIQRY
VEGYFLHPTGLELLVDHGSTDAGHWAVEQVWYNGKFYGSPEELARKYADGEVDVVVLEDPLPGGKGH
DSTEEPPLFSSHKPRGDFPSPIHVSGPRLVQPHGPRFRLEGNAVLYGGWSFAFRLRSSSGLQVLNVHF
GGERIAYEVSVQEAVALYGGHTPAGMQTKYLDVGWGLGSVTHELAPGIDCPETATFLDTFHYYDADDP
VHYPRALCLFEMPTGVPLRRHFNSNFKGGFNFYAGLKGQVLVLRTTSTVYNYDYIWDFIFYPNGVMEAK
MHATGYVHATFYTPEGLRHGTRLHTHLIGNIHTHLVHYRVDLDVAGTKNSFQTLQMKLENITNPWSPRH
RVVQPTLEQTQYSWERQAAFRFKRKLPKYLLFTSPQENPWGHKRSYRLQIHSMADQVLPPGWQEEQA
ITWARYPLAVTKYRESELCSSSIYHQNDPWHPPVVFEQFLHNNENIENEDLVAWVTVGFLHIPHSEDIPN
TATPGNSVGFLLRPFNFFPEDPSLASRDTVIVWPRDNGPNYVQRWIPEDRDCSMPPPFSYNGTYRPV*E*
*PKSADKTHT**CPPCPAPPVAGPSVFLFPPKPKDTLMISRTPEVTCVVVDVSHEDPEVKFNWYVDGVEV*
*HNAKTKPREEQYNSTYRVVSVLTVLHQDWLNGKEYKCKVSNKGLPSSIEKTISKAKGQPREPQVYTL*
*PPSREEMTKNQVSLTCLVKGFYPSDIAVEWESNGQPENNYKTTPPVLDSDGSFFLYSKLTVDKSRWQ*
*QGNVFSCSVMHEALHNHYTQKSLSLSPGK* (SEQ ID NO:63)

hDAO-Fc-Hepmut1-Cysmut

MPALGWAVAAILMLQTAMAEPSPGTLPRKAGVFSDLSNQELKAVHSFLWSKKELRLQPSSTTTMAKNT
VFLIEMLLPKKYHVLRFLDKGERHPVREARAVIFFGDQEHPNVTEFAVGPLPGPAYMRALSPRPGYQSS
WASRPISTAEYALLYHTLQEATKPLHQFFLNTTGFSFQDCHDRCLAFTDVAPRGVASGQRRSWLIIQRY
VEGYFLHPTGLELLVDHGSTDAGHWAVEQVWYNGKFYGSPEELARKYADGEVDVVVLEDPLPGGKGH
DSTEEPPLFSSHKPRGDFPSPIHVSGPRLVQPHGPRFRLEGNAVLYGGWSFAFRLRSSSGLQVLNVHF
GGERIAYEVSVQEAVALYGGHTPAGMQTKYLDVGWGLGSVTHELAPGIDCPETATFLDTFHYYDADDP
VHYPRALCLFEMPTGVPLRRHFNSNFKGGFNFYAGLKGQVLVLRTTSTVYNYDYIWDFIFYPNGVMEAK
MHATGYVHATFYTPEGLRHGTRLHTHLIGNIHTHLVHYRVDLDVAGTKNSFQTLQMKLENITNPWSPRH
RVVQPTLEQTQYSWERQAAFSFKRKLPKYLLFTSPQENPWGHKRSYRLQIHSMADQVLPPGWQEEQA
ITWARYPLAVTKYRESELCSSSIYHQNDPWHPPVVFEQFLHNNENIENEDLVAWVTVGFLHIPHSEDIPN
TATPGNSVGFLLRPFNFFPEDPSLASRDTVIVWPRDNGPNYVQRWIPEDRDCSMPPPFSYNGTYRPV*E*
*PKSADKTHT**CPPCPAPPVAGPSVFLFPPKPKDTLMISRTPEVTCVVVDVSHEDPEVKFNWYVDGVEV*
*HNAKTKPREEQYNSTYRVVSVLTVLHQDWLNGKEYKCKVSNKGLPSSIEKTISKAKGQPREPQVYTL*
*PPSREEMTKNQVSLTCLVKGFYPSDIAVEWESNGQPENNYKTTPPVLDSDGSFFLYSKLTVDKSRWQ*
*QGNVFSCSVMHEALHNHYTQKSLSLSPGK* (SEQ ID NO:64)

hDAO-Fc-Hepmut2-Cysmut

MPALGWAVAAILMLQTAMAEPSPGTLPRKAGVFSDLSNQELKAVHSFLWSKKELRLQPSSTTTMAKNT
VFLIEMLLPKKYHVLRFLDKGERHPVREARAVIFFGDQEHPNVTEFAVGPLPGPAYMRALSPRPGYQSS
WASRPISTAEYALLYHTLQEATKPLHQFFLNTTGFSFQDCHDRCLAFTDVAPRGVASGQRRSWLIIQRY
VEGYFLHPTGLELLVDHGSTDAGHWAVEQVWYNGKFYGSPEELARKYADGEVDVVVLEDPLPGGKGH
DSTEEPPLFSSHKPRGDFPSPIHVSGPRLVQPHGPRFRLEGNAVLYGGWSFAFRLRSSSGLQVLNVHF
GGERIAYEVSVQEAVALYGGHTPAGMQTKYLDVGWGLGSVTHELAPGIDCPETATFLDTFHYYDADDP
VHYPRALCLFEMPTGVPLRRHFNSNFKGGFNFYAGLKGQVLVLRTTSTVYNYDYIWDFIFYPNGVMEAK
MHATGYVHATFYTPEGLRHGTRLHTHLIGNIHTHLVHYRVDLDVAGTKNSFQTLQMKLENITNPWSPRH
RVVQPTLEQTQYSWERQAAFRFKRKLPTYLLFTSPQENPWGHKRSYRLQIHSMADQVLPPGWQEEQA
ITWARYPLAVTKYRESELCSSSIYHQNDPWHPPVVFEQFLHNNENIENEDLVAWVTVGFLHIPHSEDIPN
TATPGNSVGFLLRPFNFFPEDPSLASRDTVIVWPRDNGPNYVQRWIPEDRDCSMPPPFSYNGTYRPV*E*
*PKSADKTHT**CPPCPAPPVAGPSVFLFPPKPKDTLMISRTPEVTCVVVDVSHEDPEVKFNWYVDGVEV*
*HNAKTKPREEQYNSTYRVVSVLTVLHQDWLNGKEYKCKVSNKGLPSSIEKTISKAKGQPREPQVYTL*
*PPSREEMTKNQVSLTCLVKGFYPSDIAVEWESNGQPENNYKTTPPVLDSDGSFFLYSKLTVDKSRWQ*
*QGNVFSCSVMHEALHNHYTQKSLSLSPGK* (SEQ ID NO:65)

Figure 1 continued hDAO-Fc-Hepmut3-Cysmut

MPALGWAVAAILMLQTAMAEPSPGTLPRKAGVFSDLSNQELKAVHSFLWSKKELRLQPSSTTTMAKNT
VFLIEMLLPKKYHVLRFLDKGERHPVREARAVIFFGDQEHPNVTEFAVGPLPGPAYMRALSPRPGYQSS
WASRPISTAEYALLYHTLQEATKPLHQFFLNTTGFSFQDCHDRCLAFTDVAPRGVASGQRRSWLIIQRY
VEGYFLHPTGLELLVDHGSTDAGHWAVEQVWYNGKFYGSPEELARKYADGEVDVVVLEDPLPGGKGH
DSTEEPPLFSSHKPRGDFPSPIHVSGPRLVQPHGPRFRLEGNAVLYGGWSFAFRLRSSSGLQVLNVHF
GGERIAYEVSVQEAVALYGGHTPAGMQTKYLDVGWGLGSVTHELAPGIDCPETATFLDTFHYYDADDP
VHYPRALCLFEMPTGVPLRRHFNSNFKGGFNYAGLKGQVLVLRTTSTVYNYDYIWDFIFYPNGVMEAK
MHATGYVHATFYTPEGLRHGTRLHTHLIGNIHTHLVHYRVDLDVAGTKNSFQTLQMKLENITNPWSPRH
RVVQPTLEQTQYSWERQAAFRFKTKLPKYLLFTSPQENPWGHKRSYRLQIHSMADQVLPPGWQEEQA
ITWARYPLAVTKYRESELCSSSIYHQNDPWHPPVVFEQFLHNNENIENEDLVAWVTVGFLHIPHSEDIPN
TATPGNSVGFLLRPFNFFPEDPSLASRDTVIVWPRDNGPNYVQRWIPEDRDCSMPPPFSYNGTYRPV*E*
***PKSADKTHT*CPPCPAPPVAGPSVFLFPPKPKDTLMISRTPEVTCVVVDVSHEDPEVKFNWYVDGVEV**
*HNAKTKPREEQYNSTYRVVSVLTVLHQDWLNGKEYKCKVSNKGLPSSIEKTISKAKGQPREPQVYTL*
*PPSREEMTKNQVSLTCLVKGFYPSDIAVEWESNGQPENNYKTTPPVLDSDGSFFLYSKLTVDKSRWQ*
*QGNVFSCSVMHEALHNHYTQKSLSLSPGK* (SEQ ID NO:66)

hDAO-Fc-Hepmut4-Cysmut

MPALGWAVAAILMLQTAMAEPSPGTLPRKAGVFSDLSNQELKAVHSFLWSKKELRLQPSSTTTMAKNT
VFLIEMLLPKKYHVLRFLDKGERHPVREARAVIFFGDQEHPNVTEFAVGPLPGPAYMRALSPRPGYQSS
WASRPISTAEYALLYHTLQEATKPLHQFFLNTTGFSFQDCHDRCLAFTDVAPRGVASGQRRSWLIIQRY
VEGYFLHPTGLELLVDHGSTDAGHWAVEQVWYNGKFYGSPEELARKYADGEVDVVVLEDPLPGGKGH
DSTEEPPLFSSHKPRGDFPSPIHVSGPRLVQPHGPRFRLEGNAVLYGGWSFAFRLRSSSGLQVLNVHF
GGERIAYEVSVQEAVALYGGHTPAGMQTKYLDVGWGLGSVTHELAPGIDCPETATFLDTFHYYDADDP
VHYPRALCLFEMPTGVPLRRHFNSNFKGGFNYAGLKGQVLVLRTTSTVYNYDYIWDFIFYPNGVMEAK
MHATGYVHATFYTPEGLRHGTRLHTHLIGNIHTHLVHYRVDLDVAGTKNSFQTLQMKLENITNPWSPRH
RVVQPTLEQTQYSWERQAAFSFKTKLPKYLLFTSPQENPWGHKRSYRLQIHSMADQVLPPGWQEEQAI
TWARYPLAVTKYRESELCSSSIYHQNDPWHPPVVFEQFLHNNENIENEDLVAWVTVGFLHIPHSEDIPN
TATPGNSVGFLLRPFNFFPEDPSLASRDTVIVWPRDNGPNYVQRWIPEDRDCSMPPPFSYNGTYRPV*E*
***PKSADKTHT*CPPCPAPPVAGPSVFLFPPKPKDTLMISRTPEVTCVVVDVSHEDPEVKFNWYVDGVEV**
*HNAKTKPREEQYNSTYRVVSVLTVLHQDWLNGKEYKCKVSNKGLPSSIEKTISKAKGQPREPQVYTL*
*PPSREEMTKNQVSLTCLVKGFYPSDIAVEWESNGQPENNYKTTPPVLDSDGSFFLYSKLTVDKSRWQ*
*QGNVFSCSVMHEALHNHYTQKSLSLSPGK* (SEQ ID NO:67)

hDAO-Fc-Hepmut5-Cysmut

MPALGWAVAAILMLQTAMAEPSPGTLPRKAGVFSDLSNQELKAVHSFLWSKKELRLQPSSTTTMAKNT
VFLIEMLLPKKYHVLRFLDKGERHPVREARAVIFFGDQEHPNVTEFAVGPLPGPAYMRALSPRPGYQSS
WASRPISTAEYALLYHTLQEATKPLHQFFLNTTGFSFQDCHDRCLAFTDVAPRGVASGQRRSWLIIQRY
VEGYFLHPTGLELLVDHGSTDAGHWAVEQVWYNGKFYGSPEELARKYADGEVDVVVLEDPLPGGKGH
DSTEEPPLFSSHKPRGDFPSPIHVSGPRLVQPHGPRFRLEGNAVLYGGWSFAFRLRSSSGLQVLNVHF
GGERIAYEVSVQEAVALYGGHTPAGMQTKYLDVGWGLGSVTHELAPGIDCPETATFLDTFHYYDADDP
VHYPRALCLFEMPTGVPLRRHFNSNFKGGFNYAGLKGQVLVLRTTSTVYNYDYIWDFIFYPNGVMEAK
MHATGYVHATFYTPEGLRHGTRLHTHLIGNIHTHLVHYRVDLDVAGTKNSFQTLQMKLENITNPWSPRH
RVVQPTLEQTQYSWERQAAFRFKTKLPTYLLFTSPQENPWGHKRSYRLQIHSMADQVLPPGWQEEQAI
TWARYPLAVTKYRESELCSSSIYHQNDPWHPPVVFEQFLHNNENIENEDLVAWVTVGFLHIPHSEDIPN
TATPGNSVGFLLRPFNFFPEDPSLASRDTVIVWPRDNGPNYVQRWIPEDRDCSMPPPFSYNGTYRPV*E*
***PKSADKTHT*CPPCPAPPVAGPSVFLFPPKPKDTLMISRTPEVTCVVVDVSHEDPEVKFNWYVDGVEV**
*HNAKTKPREEQYNSTYRVVSVLTVLHQDWLNGKEYKCKVSNKGLPSSIEKTISKAKGQPREPQVYTL*
*PPSREEMTKNQVSLTCLVKGFYPSDIAVEWESNGQPENNYKTTPPVLDSDGSFFLYSKLTVDKSRWQ*
*QGNVFSCSVMHEALHNHYTQKSLSLSPGK* (SEQ ID NO:68)

Figure 1 continued hDAO-Fc-Hepmut6-Cysmut

MPALGWAVAAILMLQTAMAEPSPGTLPRKAGVFSDLSNQELKAVHSFLWSKKELRLQPSSTTTMAKNT
VFLIEMLLPKKYHVLRFLDKGERHPVREARAVIFFGDQEHPNVTEFAVGPLPGPAYMRALSPRPGYQSS
WASRPISTAEYALLYHTLQEATKPLHQFFLNTTGFSFQDCHDRCLAFTDVAPRGVASGQRRSWLIIQRY
VEGYFLHPTGLELLVDHGSTDAGHWAVEQVWYNGKFYGSPEELARKYADGEVDVVVLEDPLPGGKGH
DSTEEPPLFSSHKPRGDFPSPIHVSGPRLVQPHGPRFRLEGNAVLYGGWSFAFRLRSSSGLQVLNVHF
GGERIAYEVSVQEAVALYGGHTPAGMQTKYLDVGWGLGSVTHELAPGIDCPETATFLDTFHYYDADDP
VHYPRALCLFEMPTGVPLRRHFNSNFKGGFNFYAGLKGQVLVLRTTSTVYNYDYIWDFIFYPNGVMEAK
MHATGYVHATFYTPEGLRHGTRLHTHLIGNIHTHLVHYRVDLDVAGTKNSFQTLQMKLENITNPWSPRH
RVVQPTLEQTQYSWERQAAFRFGQTLPKYLLFTSPQENPWGHKRSYRLQIHSMADQVLPPGWQEEQA
ITWARYPLAVTKYRESELCSSSIYHQNDPWHPPVVFEQFLHNNENIENEDLVAWVTVGFLHIPHSEDIPN
TATPGNSVGFLLRPFNFFPEDPSLASRDTVIVWPRDNGPNYVQRWIPEDRDCSMPPPFSYNGTYRPV
*EPKSADKTHTCPPCPAPPVAGPSVFLFPPKPKDTLMISRTPEVTCVVVDVSHEDPEVKFNWYVDGVEV*
*HNAKTKPREEQYNSTYRVVSVLTVLHQDWLNGKEYKCKVSNKGLPSSIEKTISKAKGQPREPQVYTL*
*PPSREEMTKNQVSLTCLVKGFYPSDIAVEWESNGQPENNYKTTPPVLDSDGSFFLYSKLTVDKSRWQ*
*QGNVFSCSVMHEALHNHYTQKSLSLSPGK* (SEQ ID NO:69)

hDAO-Fc-Hepmut7-Cysmut

MPALGWAVAAILMLQTAMAEPSPGTLPRKAGVFSDLSNQELKAVHSFLWSKKELRLQPSSTTTMAKNT
VFLIEMLLPKKYHVLRFLDKGERHPVREARAVIFFGDQEHPNVTEFAVGPLPGPAYMRALSPRPGYQSS
WASRPISTAEYALLYHTLQEATKPLHQFFLNTTGFSFQDCHDRCLAFTDVAPRGVASGQRRSWLIIQRY
VEGYFLHPTGLELLVDHGSTDAGHWAVEQVWYNGKFYGSPEELARKYADGEVDVVVLEDPLPGGKGH
DSTEEPPLFSSHKPRGDFPSPIHVSGPRLVQPHGPRFRLEGNAVLYGGWSFAFRLRSSSGLQVLNVHF
GGERIAYEVSVQEAVALYGGHTPAGMQTKYLDVGWGLGSVTHELAPGIDCPETATFLDTFHYYDADDP
VHYPRALCLFEMPTGVPLRRHFNSNFKGGFNFYAGLKGQVLVLRTTSTVYNYDYIWDFIFYPNGVMEAK
MHATGYVHATFYTPEGLRHGTRLHTHLIGNIHTHLVHYRVDLDVAGTKNSFQTLQMKLENITNPWSPRH
RVVQPTLEQTQYSWERQAAFSFKRKLPTYLLFTSPQENPWGHKRSYRLQIHSMADQVLPPGWQEEQA
ITWARYPLAVTKYRESELCSSSIYHQNDPWHPPVVFEQFLHNNENIENEDLVAWVTVGFLHIPHSEDIPN
TATPGNSVGFLLRPFNFFPEDPSLASRDTVIVWPRDNGPNYVQRWIPEDRDCSMPPPFSYNGTYRPV*E*
*PKSADKTHTCPPCPAPPVAGPSVFLFPPKPKDTLMISRTPEVTCVVVDVSHEDPEVKFNWYVDGVEV*
*HNAKTKPREEQYNSTYRVVSVLTVLHQDWLNGKEYKCKVSNKGLPSSIEKTISKAKGQPREPQVYTL*
*PPSREEMTKNQVSLTCLVKGFYPSDIAVEWESNGQPENNYKTTPPVLDSDGSFFLYSKLTVDKSRWQ*
*QGNVFSCSVMHEALHNHYTQKSLSLSPGK* (SEQ ID NO:70)

Fc-hDAO

ATGCCGGCCCTGGGCTGGGCCGTGGCTGCCATCCTGATGCTGCAGACGGCCATGGCG*GA*
*GTGCCCCCCCTGCCCCGCCCCCCCCGTGGCCGGCCCCTCCGTGTTCCTGTTCCCCCCCAAGCCC*
*AAGGACACCCTGATGATCTCCAGGACCCCCGAGGTGACCTGCGTGGTGGTGGACGTGTCCCACG*
*AGGACCCCGAGGTGAAGTTCAACTGGTACGTGGACGGCGTGGAGGTGCACAACGCCAAGACCA*
*AGCCCAGGGAGGAGCAGTACAACTCCACCTACAGGGTGGTGTCCGTGCTGACCGTGCTGCACC*
*AGGACTGGCTGAACGGCAAGGAGTACAAGTGCAAGGTGTCCAACAAGGGCCTGCCCTCCTCCAT*
*CGAGAAGACCATCTCCAAGGCCAAGGGCCAGCCCAGGGAGCCCCAGGTGTACACCCTGCCCCC*
*CTCCAGGGAGGAGATGACCAAGAACCAGGTGTCCCTGACCTGCCTGGTGAAGGGCTTCTACCCC*
*TCCGACATCGCCGTGGAGTGGGAGTCCAACGGCCAGCCCGAGAACAACTACAAGACCACCCCC*
*CCCGTGCTGGACTCCGACGGCTCCTTCTTCCTGTACTCCAAGCTGACCGTGGACAAGTCCAGGT*
*GGCAGCAGGGCAACGTGTTCTCCTGCTCCGTGATGCACGAGGCCCTGCACAACCACTACACCCA*
*GAAGTCCCTGTCCCTGTCCCCCGGCAAGGAGCCCAAGTCCGCCGACAAGACCCACACC*GAGCC
CTCCCCGGGGACTCTGCCCAGGAAGGCAGGGGTGTTTTCAGACCTAAGCAACCAAGAGCTGAAGG
CAGTGCACAGCTTCCTCTGGTCCAAGAAGGAGCTGAGGCTGCAGCCCTCCAGTACCACCACCATG
GCCAAGAACACCGTGTTTCTCATCGAGATGCTGCTGCCCAAGAAGTACCATGTGCTGAGGTTTCTG
GATAAAGGTGAAAGGCATCCTGTGCGGGAAGCCCGTGCCGTCATCTTCTTTGGTGACCAGGAGCA
TCCCAATGTCACCGAGTTTGCTGTGGGGCCCCTGCCAGGCCCCTGCTACATGCGAGCACTGTCCC
CCAGGCCTGGGTACCAGTCCTCCTGGGCATCGAGGCCCATCTCCACAGCAGAGTATGCCCTCCTC
TACCACACCCTGCAGGAAGCCACCAAGCCCCTGCATCAGTTCTTCCTCAATACCACAGGCTTCTCA
TTCCAAGACTGCCATGACAGATGCCTGGCCTTCACCGATGTGGCCCCCCGGGGTGTGGCTTCTGG
CCAGCGCCGCAGTTGGCTTATCATACAGCGCTATGTAGAAGGCTACTTTCTGCACCCCACTGGGCT
GGAGCTCCTCGTGGATCATGGGAGCACAGATGCTGGGCACTGGGCCGTGGAGCAGGTGTGGTAC
AACGGGAAGTTCTATGGGAGCCCAGAGGAACTGGCTCGGAAGTATGCAGATGGAGAGGTGGACGT

Figure 1 continued

GGTGGTCCTGGAGGACCCGCTGCCTGGGGGCAAGGGGCATGACAGCACAGAGGAGCCGCCCCT
CTTCTCCTCCCACAAGCCCCGCGGGGACTTCCCCAGCCCCATCCATGTGAGCGGCCCCCGCTTGG
TCCAGCCCCACGGCCCTCGCTTCAGGCTGGAGGGCAACGCTGTGCTCTACGGCGGCTGGAGCTT
TGCCTTCCGGCTGCGCTCCTCCTCCGGGCTGCAGGTCCTGAACGTGCACTTCGGCGGAGAGCGC
ATTGCCTATGAGGTCAGCGTGCAAGAGGCAGTGGCGCTGTATGGAGGACACACACCTGCAGGCAT
GCAGACCAAGTACCTCGATGTCGGCTGGGGCCTGGGCAGCGTCACTCATGAGTTAGCCCCCGGC
ATCGACTGCCCGGAGACCGCCACCTTCCTGGACACTTTCCACTACTATGATGCCGATGACCCGGTC
CATTATCCCCGAGCCCTCTGCCTCTTTGAAATGCCCACAGGGGTGCCCCTTCGGCGGCACTTTAAT
TCCAACTTTAAAGGTGGCTTCAACTTCTATGCGGGGCTGAAGGGCCAGGTGCTGGTGCTGCGGAC
AACTTCAACTGTCTACAATTATGATTACATTTGGGACTTTATCTTCTACCCCAACGGGGTGATGGAG
GCCAAGATGCATGCCACTGGCTACGTCCACGCCACCTTCTACACCCCCGAGGGGCTGCGCCACG
GCACTCGCCTGCACACCCACCTGATTGGCAACATACACACTCACTTGGTGCACTACCGCGTAGACC
TGGATGTGGCAGGCACCAAGAACAGCTTCCAGACACTGCAGATGAAGCTAGAAAACATCACCAACC
CCTGGAGCCCAAGACACCGCGTGGTCCAGCCAACTCTGGAGCAGACGCAGTACTCCTGGGAGCG
CCAGGCGGCCTTCCGCTTCAAAAGGAAGCTGCCCAAGTACCTGCTCTTTACCAGCCCCCAGGAGA
ACCCCTGGGGCCACAAGCGCAGCTACCGCCTGCAGATCCACTCCATGGCCGACCAGGTGCTGCC
CCCAGGCTGGCAGGAGGAGCAGGCCATCACCTGGGCAAGGTACCCCCTGGCAGTGACCAAGTAC
CGGGAGTCGGAGCTGTGCAGCAGCAGCATCTACCACCAGAACGACCCCTGGCACCCGCCCGTGG
TCTTTGAGCAGTTTCTTCACAACAACGAGAACATTGAAAATGAGGACCTGGTGGCCTGGGTGACGG
TGGGCTTCCTGCACATCCCCCACTCAGAGGACATTCCCAACACAGCCACACCTGGGAACTCCGTG
GGCTTCCTGCTCCGGCCATTCAACTTCTTCCCAGAGGACCCCTCCCTGGCATCCAGAGACACTGTG
ATCGTGTGGCCTCGGGACAACGGCCCCAACTACGTCCAGCGCTGGATCCCTGAGGACAGGGACT
GCTCGATGCCTCCCCCTTTTAGCTACAATGGGACCTATAGACCTGTGTGA (SEQ ID NO:71)

<u>Fc-hDAO-Hepmut1</u>

ATGCCGGCCCTGGGCTGGGCCGTGGCTGCCATCCTGATGCTGCAGACGGCCATGGCG*GA*
*GTGCCCCCCCTGCCCCGCCCCCCCCGTGGCCGGCCCCTCCGTGTTCCTGTTCCCCCCCAAGCCC*
*AAGGACACCCTGATGATCTCCAGGACCCCCGAGGTGACCTGCGTGGTGGTGGACGTGTCCCACG*
*AGGACCCCGAGGTGAAGTTCAACTGGTACGTGGACGGCGTGGAGGTGCACAACGCCAAGACCA*
*AGCCCAGGGAGGAGCAGTACAACTCCACCTACAGGGTGGTGTCCGTGCTGACCGTGCTGCACC*
*AGGACTGGCTGAACGGCAAGGAGTACAAGTGCAAGGTGTCCAACAAGGGCCTGCCCTCCTCCAT*
*CGAGAAGACCATCTCCAAGGCCAAGGGCCAGCCCAGGGAGCCCCAGGTGTACACCCTGCCCCC*
*CTCCAGGGAGGAGATGACCAAGAACCAGGTGTCCCTGACCTGCCTGGTGAAGGGCTTCTACCCC*
*TCCGACATCGCCGTGGAGTGGGAGTCCAACGGCCAGCCCGAGAACAACTACAAGACCACCCCC*
*CCCGTGCTGGACTCCGACGGCTCCTTCTTCCTGTACTCCAAGCTGACCGTGGACAAGTCCAGGT*
*GGCAGCAGGGCAACGTGTTCTCCTGCTCCGTGATGCACGAGGCCCTGCACAACCACTACACCCA*
*GAAGTCCCTGTCCCTGTCCCCCGGCAAGGAGCCCAAGTCCGCCGACAAGACCCACACC*GAGCC
CTCCCCGGGGACTCTGCCCAGGAAGGCAGGGGTGTTTTCAGACCTAAGCAACCAAGAGCTGAAGG
CAGTGCACAGCTTCCTCTGGTCCAAGAAGGAGCTGAGGCTGCAGCCCTCCAGTACCACCACCATG
GCCAAGAACACCGTGTTTCTCATCGAGATGCTGCTGCCCAAGAAGTACCATGTGCTGAGGTTTCTG
GATAAAGGTGAAAGGCATCCTGTGCGGGAAGCCCGTGCCGTCATCTTCTTTGGTGACCAGGAGCA
TCCCAATGTCACCGAGTTTGCTGTGGGGCCCCTGCCAGGCCCCTGCTACATGCGAGCACTGTCCC
CCAGGCCTGGGTACCAGTCCTCCTGGGCATCGAGGCCCATCTCCACAGCAGAGTATGCCCTCCTC
TACCACACCCTGCAGGAAGCCACCAAGCCCCTGCATCAGTTCTTCCTCAATACCACAGGCTTCTCA
TTCCAAGACTGCCATGACAGATGCCTGGCCTTCACCGATGTGGCCCCCCGGGGTGTGGCTTCTGG
CCAGCGCCGCAGTTGGCTTATCATACAGCGCTATGTAGAAGGCTACTTTCTGCACCCCACTGGGCT
GGAGCTCCTCGTGGATCATGGGAGCACAGATGCTGGGCACTGGGCCGTGGAGCAGGTGTGGTAC
AACGGGAAGTTCTATGGGAGCCCAGAGGAACTGGCTCGGAAGTATGCAGATGGAGAGGTGGACGT
GGTGGTCCTGGAGGACCCGCTGCCTGGGGGCAAGGGGCATGACAGCACAGAGGAGCCGCCCCT
CTTCTCCTCCCACAAGCCCCGCGGGGACTTCCCCAGCCCCATCCATGTGAGCGGCCCCCGCTTGG
TCCAGCCCCACGGCCCTCGCTTCAGGCTGGAGGGCAACGCTGTGCTCTACGGCGGCTGGAGCTT
TGCCTTCCGGCTGCGCTCCTCCTCCGGGCTGCAGGTCCTGAACGTGCACTTCGGCGGAGAGCGC
ATTGCCTATGAGGTCAGCGTGCAAGAGGCAGTGGCGCTGTATGGAGGACACACACCTGCAGGCAT
GCAGACCAAGTACCTCGATGTCGGCTGGGGCCTGGGCAGCGTCACTCATGAGTTAGCCCCCGGC
ATCGACTGCCCGGAGACCGCCACCTTCCTGGACACTTTCCACTACTATGATGCCGATGACCCGGTC
CATTATCCCCGAGCCCTCTGCCTCTTTGAAATGCCCACAGGGGTGCCCCTTCGGCGGCACTTTAAT
TCCAACTTTAAAGGTGGCTTCAACTTCTATGCGGGGCTGAAGGGCCAGGTGCTGGTGCTGCGGAC
AACTTCAACTGTCTACAATTATGATTACATTTGGGACTTTATCTTCTACCCCAACGGGGTGATGGAG
GCCAAGATGCATGCCACTGGCTACGTCCACGCCACCTTCTACACCCCCGAGGGGCTGCGCCACG
GCACTCGCCTGCACACCCACCTGATTGGCAACATACACACTCACTTGGTGCACTACCGCGTAGACC

Figure 1 continued

TGGATGTGGCAGGCACCAAGAACAGCTTCCAGACACTGCAGATGAAGCTAGAAAACATCACCAACC
CCTGGAGCCCAAGACACCGCGTGGTCCAGCCAACTCTGGAGCAGACGCAGTACTCCTGGGAGCG
CCAGGCGGCCTTCAGCTTCAAAAGGAAGCTGCCCAAGTACCTGCTCTTTACCAGCCCCCAGGAGA
ACCCCTGGGGCCACAAGCGCAGCTACCGCCTGCAGATCCACTCCATGGCCGACCAGGTGCTGCC
CCCAGGCTGGCAGGAGGAGCAGGCCATCACCTGGGCAAGGTACCCCCTGGCAGTGACCAAGTAC
CGGGAGTCGGAGCTGTGCAGCAGCAGCATCTACCACCAGAACGACCCCTGGCACCCGCCCGTGG
TCTTTGAGCAGTTTCTTCACAACAACGAGAACATTGAAAATGAGGACCTGGTGGCCTGGGTGACGG
TGGGCTTCCTGCACATCCCCCACTCAGAGGACATTCCCAACACAGCCACACCTGGGAACTCCGTG
GGCTTCCTGCTCCGGCCATTCAACTTCTTCCCAGAGGACCCCTCCCTGGCATCCAGAGACACTGTG
ATCGTGTGGCCTCGGGACAACGGCCCCAACTACGTCCAGCGCTGGATCCCTGAGGACAGGGACT
GCTCGATGCCTCCCCCTTTTAGCTACAATGGGACCTATAGACCTGTGTGA (SEQ ID NO:72)

<u>Fc-hDAO-Hepmut2</u>

ATGCCGGCCCTGGGCTGGGCCGTGGCTGCCATCCTGATGCTGCAGACGGCCATGGCG*GA*
*GTGCCCCCCCTGCCCCGCCCCCCCCGTGGCCGGCCCCTCCGTGTTCCTGTTCCCCCCCAAGCCC*
*AAGGACACCCTGATGATCTCCAGGACCCCCGAGGTGACCTGCGTGGTGGTGGACGTGTCCCACG*
*AGGACCCCGAGGTGAAGTTCAACTGGTACGTGGACGGCGTGGAGGTGCACAACGCCAAGACCA*
*AGCCCAGGGAGGAGCAGTACAACTCCACCTACAGGGTGGTGTCCGTGCTGACCGTGCTGCACC*
*AGGACTGGCTGAACGGCAAGGAGTACAAGTGCAAGGTGTCCAACAAGGGCCTGCCCTCCTCCAT*
*CGAGAAGACCATCTCCAAGGCCAAGGGCCAGCCCAGGGAGCCCCAGGTGTACACCCTGCCCCC*
*CTCCAGGGAGGAGATGACCAAGAACCAGGTGTCCCTGACCTGCCTGGTGAAGGGCTTCTACCCC*
*TCCGACATCGCCGTGGAGTGGGAGTCCAACGGCCAGCCCGAGAACAACTACAAGACCACCCCC*
*CCCGTGCTGGACTCCGACGGCTCCTTCTTCCTGTACTCCAAGCTGACCGTGGACAAGTCCAGGT*
*GGCAGCAGGGCAACGTGTTCTCCTGCTCCGTGATGCACGAGGCCCTGCACAACCACTACACCCA*
*GAAGTCCCTGTCCCTGTCCCCCGGCAAGGAGCCCAAGTCCGCCGACAAGACCCACACC*GAGCC
CTCCCCGGGGACTCTGCCCAGGAAGGCAGGGGTGTTTTCAGACCTAAGCAACCAAGAGCTGAAGG
CAGTGCACAGCTTCCTCTGGTCCAAGAAGGAGCTGAGGCTGCAGCCCTCCAGTACCACCACCATG
GCCAAGAACACCGTGTTTCTCATCGAGATGCTGCTGCCCAAGAAGTACCATGTGCTGAGGTTTCTG
GATAAAGGTGAAAGGCATCCTGTGCGGGAAGCCCGTGCCGTCATCTTCTTTGGTGACCAGGAGCA
TCCCAATGTCACCGAGTTTGCTGTGGGGCCCCTGCCAGGCCCCTGCTACATGCGAGCACTGTCCC
CCAGGCCTGGGTACCAGTCCTCCTGGGCATCGAGGCCCATCTCCACAGCAGAGTATGCCCTCCTC
TACCACACCCTGCAGGAAGCCACCAAGCCCCTGCATCAGTTCTTCCTCAATACCACAGGCTTCTCA
TTCCAAGACTGCCATGACAGATGCCTGGCCTTCACCGATGTGGCCCCCCGGGGTGTGGCTTCTGG
CCAGCGCCGCAGTTGGCTTATCATACAGCGCTATGTAGAAGGCTACTTTCTGCACCCCACTGGGCT
GGAGCTCCTCGTGGATCATGGGAGCACAGATGCTGGGCACTGGGCCGTGGAGCAGGTGTGGTAC
AACGGGAAGTTCTATGGGAGCCCAGAGGAACTGGCTCGGAAGTATGCAGATGGAGAGGTGGACGT
GGTGGTCCTGGAGGACCCGCTGCCTGGGGGCAAGGGGCATGACAGCACAGAGGAGCCGCCCCT
CTTCTCCTCCCACAAGCCCCGCGGGGACTTCCCCAGCCCCATCCATGTGAGCGGCCCCCGCTTGG
TCCAGCCCCACGGCCCTCGCTTCAGGCTGGAGGGCAACGCTGTGCTCTACGGCGGCTGGAGCTT
TGCCTTCCGGCTGCGCTCCTCCTCCGGGCTGCAGGTCCTGAACGTGCACTTCGGCGGAGAGCGC
ATTGCCTATGAGGTCAGCGTGCAAGAGGCAGTGGCGCTGTATGGAGGACACACACCTGCAGGCAT
GCAGACCAAGTACCTCGATGTCGGCTGGGGCCTGGGCAGCGTCACTCATGAGTTAGCCCCCGGC
ATCGACTGCCCGGAGACCGCCACCTTCCTGGACACTTTCCACTACTATGATGCCGATGACCCGGTC
CATTATCCCCGAGCCCTCTGCCTCTTTGAAATGCCCACAGGGGTGCCCCTTCGGCGGCACTTTAAT
TCCAACTTTAAAGGTGGCTTCAACTTCTATGCGGGGCTGAAGGGCCAGGTGCTGGTGCTGCGGAC
AACTTCAACTGTCTACAATTATGATTACATTTGGGACTTTATCTTCTACCCCAACGGGGTGATGGAG
GCCAAGATGCATGCCACTGGCTACGTCCACGCCACCTTCTACACCCCCGAGGGGCTGCGCCACG
GCACTCGCCTGCACACCCACCTGATTGGCAACATACACACTCACTTGGTGCACTACCGCGTAGACC
TGGATGTGGCAGGCACCAAGAACAGCTTCCAGACACTGCAGATGAAGCTAGAAAACATCACCAACC
CCTGGAGCCCAAGACACCGCGTGGTCCAGCCAACTCTGGAGCAGACGCAGTACTCCTGGGAGCG
CCAGGCGGCCTTCCGCTTCAAAAGGAAGCTGCCCACGTACCTGCTCTTTACCAGCCCCCAGGAGA
ACCCCTGGGGCCACAAGCGCAGCTACCGCCTGCAGATCCACTCCATGGCCGACCAGGTGCTGCC
CCCAGGCTGGCAGGAGGAGCAGGCCATCACCTGGGCAAGGTACCCCCTGGCAGTGACCAAGTAC
CGGGAGTCGGAGCTGTGCAGCAGCAGCATCTACCACCAGAACGACCCCTGGCACCCGCCCGTGG
TCTTTGAGCAGTTTCTTCACAACAACGAGAACATTGAAAATGAGGACCTGGTGGCCTGGGTGACGG
TGGGCTTCCTGCACATCCCCCACTCAGAGGACATTCCCAACACAGCCACACCTGGGAACTCCGTG
GGCTTCCTGCTCCGGCCATTCAACTTCTTCCCAGAGGACCCCTCCCTGGCATCCAGAGACACTGTG
ATCGTGTGGCCTCGGGACAACGGCCCCAACTACGTCCAGCGCTGGATCCCTGAGGACAGGGACT
GCTCGATGCCTCCCCCTTTTAGCTACAATGGGACCTATAGACCTGTGTGA (SEQ ID NO:73)

Figure 1 continued

Fc-hDAO-Hepmut3

ATGCCGGCCCTGGGCTGGGCCGTGGCTGCCATCCTGATGCTGCAGACGGCCATGGCG*GA*
*GTGCCCCCCCTGCCCCGCCCCCCCCGTGGCCGGCCCCTCCGTGTTCCTGTTCCCCCCCAAGCCC*
*AAGGACACCCTGATGATCTCCAGGACCCCCGAGGTGACCTGCGTGGTGGTGGACGTGTCCCACG*
*AGGACCCCGAGGTGAAGTTCAACTGGTACGTGGACGGCGTGGAGGTGCACAACGCCAAGACCA*
*AGCCCAGGGAGGAGCAGTACAACTCCACCTACAGGGTGGTGTCCGTGCTGACCGTGCTGCACC*
*AGGACTGGCTGAACGGCAAGGAGTACAAGTGCAAGGTGTCCAACAAGGGCCTGCCCTCCTCCAT*
*CGAGAAGACCATCTCCAAGGCCAAGGGCCAGCCCAGGGAGCCCCAGGTGTACACCCTGCCCCC*
*CTCCAGGGAGGAGATGACCAAGAACCAGGTGTCCCTGACCTGCCTGGTGAAGGGCTTCTACCCC*
*TCCGACATCGCCGTGGAGTGGGAGTCCAACGGCCAGCCCGAGAACAACTACAAGACCACCCCC*
*CCCGTGCTGGACTCCGACGGCTCCTTCTTCCTGTACTCCAAGCTGACCGTGGACAAGTCCAGGT*
*GGCAGCAGGGCAACGTGTTCTCCTGCTCCGTGATGCACGAGGCCCTGCACAACCACTACACCCA*
*GAAGTCCCTGTCCCTGTCCCCCGGCAAGGAGCCCAAGTCCGCCGACAAGACCCACACC*GAGCC
CTCCCCGGGGACTCTGCCCAGGAAGGCAGGGGTGTTTTCAGACCTAAGCAACCAAGAGCTGAAGG
CAGTGCACAGCTTCCTCTGGTCCAAGAAGGAGCTGAGGCTGCAGCCCTCCAGTACCACCACCATG
GCCAAGAACACCGTGTTTCTCATCGAGATGCTGCTGCCCAAGAAGTACCATGTGCTGAGGTTTCTG
GATAAAGGTGAAAGGCATCCTGTGCGGGAAGCCCGTGCCGTCATCTTCTTTGGTGACCAGGAGCA
TCCCAATGTCACCGAGTTTGCTGTGGGGCCCCTGCCAGGCCCCTGCTACATGCGAGCACTGTCCC
CCAGGCCTGGGTACCAGTCCTCCTGGGCATCGAGGCCCATCTCCACAGCAGAGTATGCCCTCCTC
TACCACACCCTGCAGGAAGCCACCAAGCCCCTGCATCAGTTCTTCCTCAATACCACAGGCTTCTCA
TTCCAAGACTGCCATGACAGATGCCTGGCCTTCACCGATGTGGCCCCCCGGGGTGTGGCTTCTGG
CCAGCGCCGCAGTTGGCTTATCATACAGCGCTATGTAGAAGGCTACTTTCTGCACCCCACTGGGCT
GGAGCTCCTCGTGGATCATGGGAGCACAGATGCTGGGCACTGGGCCGTGGAGCAGGTGTGGTAC
AACGGGAAGTTCTATGGGAGCCCAGAGGAACTGGCTCGGAAGTATGCAGATGGAGAGGTGGACGT
GGTGGTCCTGGAGGACCCGCTGCCTGGGGGCAAGGGGCATGACAGCACAGAGGAGCCGCCCCT
CTTCTCCTCCCACAAGCCCCGCGGGGACTTCCCCAGCCCCATCCATGTGAGCGGCCCCCGCTTGG
TCCAGCCCCACGGCCCTCGCTTCAGGCTGGAGGGCAACGCTGTGCTCTACGGCGGCTGGAGCTT
TGCCTTCCGGCTGCGCTCCTCCTCCGGGCTGCAGGTCCTGAACGTGCACTTCGGCGGAGAGCGC
ATTGCCTATGAGGTCAGCGTGCAAGAGGCAGTGGCGCTGTATGGAGGACACACACCTGCAGGCAT
GCAGACCAAGTACCTCGATGTCGGCTGGGGCCTGGGCAGCGTCACTCATGAGTTAGCCCCCGGC
ATCGACTGCCCGGAGACCGCCACCTTCCTGGACACTTTCCACTACTATGATGCCGATGACCCGGTC
CATTATCCCCGAGCCCTCTGCCTCTTTGAAATGCCCACAGGGGTGCCCCTTCGGCGGCACTTTAAT
TCCAACTTTAAAGGTGGCTTCAACTTCTATGCGGGGCTGAAGGGCCAGGTGCTGGTGCTGCGGAC
AACTTCAACTGTCTACAATTATGATTACATTTGGGACTTTATCTTCTACCCCAACGGGGTGATGGAG
GCCAAGATGCATGCCACTGGCTACGTCCACGCCACCTTCTACACCCCCGAGGGGCTGCGCCACG
GCACTCGCCTGCACACCCACCTGATTGGCAACATACACACTCACTTGGTGCACTACCGCGTAGACC
TGGATGTGGCAGGCACCAAGAACAGCTTCCAGACACTGCAGATGAAGCTAGAAAACATCACCAACC
CCTGGAGCCCAAGACACCGCGTGGTCCAGCCAACTCTGGAGCAGACGCAGTACTCCTGGGAGCG
CCAGGCGGCCTTCCGCTTCAAAACGAAGCTGCCCAAGTACCTGCTCTTTACCAGCCCCCAGGAGA
ACCCCTGGGGCCACAAGCGCAGCTACCGCCTGCAGATCCACTCCATGGCCGACCAGGTGCTGCC
CCCAGGCTGGCAGGAGGAGCAGGCCATCACCTGGGCAAGGTACCCCCTGGCAGTGACCAAGTAC
CGGGAGTCGGAGCTGTGCAGCAGCAGCATCTACCACCAGAACGACCCCTGGCACCCGCCCGTGG
TCTTTGAGCAGTTTCTTCACAACAACGAGAACATTGAAAATGAGGACCTGGTGGCCTGGGTGACGG
TGGGCTTCCTGCACATCCCCCACTCAGAGGACATTCCCAACACAGCCACACCTGGGAACTCCGTG
GGCTTCCTGCTCCGGCCATTCAACTTCTTCCCAGAGGACCCCTCCCTGGCATCCAGAGACACTGTG
ATCGTGTGGCCTCGGGACAACGGCCCCAACTACGTCCAGCGCTGGATCCCTGAGGACAGGGACT
GCTCGATGCCTCCCCCTTTTAGCTACAATGGGACCTATAGACCTGTGTGA (SEQ ID NO:74)

Fc-hDAO-Hepmut4

ATGCCGGCCCTGGGCTGGGCCGTGGCTGCCATCCTGATGCTGCAGACGGCCATGGCG*GA*
*GTGCCCCCCCTGCCCCGCCCCCCCCGTGGCCGGCCCCTCCGTGTTCCTGTTCCCCCCCAAGCCC*
*AAGGACACCCTGATGATCTCCAGGACCCCCGAGGTGACCTGCGTGGTGGTGGACGTGTCCCACG*
*AGGACCCCGAGGTGAAGTTCAACTGGTACGTGGACGGCGTGGAGGTGCACAACGCCAAGACCA*
*AGCCCAGGGAGGAGCAGTACAACTCCACCTACAGGGTGGTGTCCGTGCTGACCGTGCTGCACC*
*AGGACTGGCTGAACGGCAAGGAGTACAAGTGCAAGGTGTCCAACAAGGGCCTGCCCTCCTCCAT*
*CGAGAAGACCATCTCCAAGGCCAAGGGCCAGCCCAGGGAGCCCCAGGTGTACACCCTGCCCCC*
*CTCCAGGGAGGAGATGACCAAGAACCAGGTGTCCCTGACCTGCCTGGTGAAGGGCTTCTACCCC*
*TCCGACATCGCCGTGGAGTGGGAGTCCAACGGCCAGCCCGAGAACAACTACAAGACCACCCCC*

Figure 1 continued

*CCCGTGCTGGACTCCGACGGCTCCTTCTTCCTGTACTCCAAGCTGACCGTGGACAAGTCCAGGT*
*GGCAGCAGGGCAACGTGTTCTCCTGCTCCGTGATGCACGAGGCCCTGCACAACCACTACACCCA*
*GAAGTCCCTGTCCCTGTCCCCCGGCAAGGAGCCCAAGTCCGCCGACAAGACCCACACC*GAGCC
CTCCCCGGGGACTCTGCCCAGGAAGGCAGGGGTGTTTTCAGACCTAAGCAACCAAGAGCTGAAGG
CAGTGCACAGCTTCCTCTGGTCCAAGAAGGAGCTGAGGCTGCAGCCCTCCAGTACCACCACCATG
GCCAAGAACACCGTGTTTCTCATCGAGATGCTGCTGCCCAAGAAGTACCATGTGCTGAGGTTTCTG
GATAAAGGTGAAAGGCATCCTGTGCGGGAAGCCCGTGCCGTCATCTTCTTTGGTGACCAGGAGCA
TCCCAATGTCACCGAGTTTGCTGTGGGGCCCCTGCCAGGCCCCTGCTACATGCGAGCACTGTCCC
CCAGGCCTGGGTACCAGTCCTCCTGGGCATCGAGGCCCATCTCCACAGCAGAGTATGCCCTCCTC
TACCACACCCTGCAGGAAGCCACCAAGCCCCTGCATCAGTTCTTCCTCAATACCACAGGCTTCTCA
TTCCAAGACTGCCATGACAGATGCCTGGCCTTCACCGATGTGGCCCCCCGGGGTGTGGCTTCTGG
CCAGCGCCGCAGTTGGCTTATCATACAGCGCTATGTAGAAGGCTACTTTCTGCACCCCACTGGGCT
GGAGCTCCTCGTGGATCATGGGAGCACAGATGCTGGGCACTGGGCCGTGGAGCAGGTGTGGTAC
AACGGGAAGTTCTATGGGAGCCCAGAGGAACTGGCTCGGAAGTATGCAGATGGAGAGGTGGACGT
GGTGGTCCTGGAGGACCCGCTGCCTGGGGGCAAGGGGCATGACAGCACAGAGGAGCCGCCCCT
CTTCTCCTCCCACAAGCCCCGCGGGGACTTCCCCAGCCCCATCCATGTGAGCGGCCCCCGCTTGG
TCCAGCCCCACGGCCCTCGCTTCAGGCTGGAGGGCAACGCTGTGCTCTACGGCGGCTGGAGCTT
TGCCTTCCGGCTGCGCTCCTCCTCCGGGCTGCAGGTCCTGAACGTGCACTTCGGCGGAGAGCGC
ATTGCCTATGAGGTCAGCGTGCAAGAGGCAGTGGCGCTGTATGGAGGACACACACCTGCAGGCAT
GCAGACCAAGTACCTCGATGTCGGCTGGGGCCTGGGCAGCGTCACTCATGAGTTAGCCCCCGGC
ATCGACTGCCCGGAGACCGCCACCTTCCTGGACACTTTCCACTACTATGATGCCGATGACCCGGTC
CATTATCCCCGAGCCCTCTGCCTCTTTGAAATGCCCACAGGGGTGCCCCTTCGGCGGCACTTTAAT
TCCAACTTTAAAGGTGGCTTCAACTTCTATGCGGGGCTGAAGGGCCAGGTGCTGGTGCTGCGGAC
AACTTCAACTGTCTACAATTATGATTACATTTGGGACTTTATCTTCTACCCCAACGGGGTGATGGAG
GCCAAGATGCATGCCACTGGCTACGTCCACGCCACCTTCTACACCCCCGAGGGGCTGCGCCACG
GCACTCGCCTGCACACCCACCTGATTGGCAACATACACACTCACTTGGTGCACTACCGCGTAGACC
TGGATGTGGCAGGCACCAAGAACAGCTTCCAGACACTGCAGATGAAGCTAGAAAACATCACCAACC
CCTGGAGCCCAAGACACCGCGTGGTCCAGCCAACTCTGGAGCAGACGCAGTACTCCTGGGAGCG
CCAGGCGGCCTTCAGCTTCAAAACGAAGCTGCCCAAGTACCTGCTCTTTACCAGCCCCCAGGAGA
ACCCCTGGGGCCACAAGCGCAGCTACCGCCTGCAGATCCACTCCATGGCCGACCAGGTGCTGCC
CCCAGGCTGGCAGGAGGAGCAGGCCATCACCTGGGCAAGGTACCCCCTGGCAGTGACCAAGTAC
CGGGAGTCGGAGCTGTGCAGCAGCAGCATCTACCACCAGAACGACCCCTGGCACCCGCCCGTGG
TCTTTGAGCAGTTTCTTCACAACAACGAGAACATTGAAAATGAGGACCTGGTGGCCTGGGTGACGG
TGGGCTTCCTGCACATCCCCCACTCAGAGGACATTCCCAACACAGCCACACCTGGGAACTCCGTG
GGCTTCCTGCTCCGGCCATTCAACTTCTTCCCAGAGGACCCCTCCCTGGCATCCAGAGACACTGTG
ATCGTGTGGCCTCGGGACAACGGCCCCAACTACGTCCAGCGCTGGATCCCTGAGGACAGGGACT
GCTCGATGCCTCCCCCTTTTAGCTACAATGGGACCTATAGACCTGTGTGA (SEQ ID NO:75)

Fc-hDAO-Hepmut5

ATGCCGGCCCTGGGCTGGGCCGTGGCTGCCATCCTGATGCTGCAGACGGCCATGGCG*GA*
*GTGCCCCCCCTGCCCCGCCCCCCCCGTGGCCGGCCCCTCCGTGTTCCTGTTCCCCCCCAAGCCC*
*AAGGACACCCTGATGATCTCCAGGACCCCCGAGGTGACCTGCGTGGTGGTGGACGTGTCCCACG*
*AGGACCCCGAGGTGAAGTTCAACTGGTACGTGGACGGCGTGGAGGTGCACAACGCCAAGACCA*
*AGCCCAGGGAGGAGCAGTACAACTCCACCTACAGGGTGGTGTCCGTGCTGACCGTGCTGCACC*
*AGGACTGGCTGAACGGCAAGGAGTACAAGTGCAAGGTGTCCAACAAGGGCCTGCCCTCCTCCAT*
*CGAGAAGACCATCTCCAAGGCCAAGGGCCAGCCCAGGGAGCCCCAGGTGTACACCCTGCCCCC*
*CTCCAGGGAGGAGATGACCAAGAACCAGGTGTCCCTGACCTGCCTGGTGAAGGGCTTCTACCCC*
*TCCGACATCGCCGTGGAGTGGGAGTCCAACGGCCAGCCCGAGAACAACTACAAGACCACCCCC*
*CCCGTGCTGGACTCCGACGGCTCCTTCTTCCTGTACTCCAAGCTGACCGTGGACAAGTCCAGGT*
*GGCAGCAGGGCAACGTGTTCTCCTGCTCCGTGATGCACGAGGCCCTGCACAACCACTACACCCA*
*GAAGTCCCTGTCCCTGTCCCCCGGCAAGGAGCCCAAGTCCGCCGACAAGACCCACACC*GAGCC
CTCCCCGGGGACTCTGCCCAGGAAGGCAGGGGTGTTTTCAGACCTAAGCAACCAAGAGCTGAAGG
CAGTGCACAGCTTCCTCTGGTCCAAGAAGGAGCTGAGGCTGCAGCCCTCCAGTACCACCACCATG
GCCAAGAACACCGTGTTTCTCATCGAGATGCTGCTGCCCAAGAAGTACCATGTGCTGAGGTTTCTG
GATAAAGGTGAAAGGCATCCTGTGCGGGAAGCCCGTGCCGTCATCTTCTTTGGTGACCAGGAGCA
TCCCAATGTCACCGAGTTTGCTGTGGGGCCCCTGCCAGGCCCCTGCTACATGCGAGCACTGTCCC
CCAGGCCTGGGTACCAGTCCTCCTGGGCATCGAGGCCCATCTCCACAGCAGAGTATGCCCTCCTC
TACCACACCCTGCAGGAAGCCACCAAGCCCCTGCATCAGTTCTTCCTCAATACCACAGGCTTCTCA

Figure 1 continued

TTCCAAGACTGCCATGACAGATGCCTGGCCTTCACCGATGTGGCCCCCCGGGGTGTGGCTTCTGG
CCAGCGCCGCAGTTGGCTTATCATACAGCGCTATGTAGAAGGCTACTTTCTGCACCCCACTGGGCT
GGAGCTCCTCGTGGATCATGGGAGCACAGATGCTGGGCACTGGGCCGTGGAGCAGGTGTGGTAC
AACGGGAAGTTCTATGGGAGCCCAGAGGAACTGGCTCGGAAGTATGCAGATGGAGAGGTGGACGT
GGTGGTCCTGGAGGACCCGCTGCCTGGGGGCAAGGGGCATGACAGCACAGAGGAGCCGCCCCT
CTTCTCCTCCCACAAGCCCCGCGGGGACTTCCCCAGCCCCATCCATGTGAGCGGCCCCCGCTTGG
TCCAGCCCCACGGCCCTCGCTTCAGGCTGGAGGGCAACGCTGTGCTCTACGGCGGCTGGAGCTT
TGCCTTCCGGCTGCGCTCCTCCTCCGGGCTGCAGGTCCTGAACGTGCACTTCGGCGGAGAGCGC
ATTGCCTATGAGGTCAGCGTGCAAGAGGCAGTGGCGCTGTATGGAGGACACACACCTGCAGGCAT
GCAGACCAAGTACCTCGATGTCGGCTGGGGCCTGGGCAGCGTCACTCATGAGTTAGCCCCCGGC
ATCGACTGCCCGGAGACCGCCACCTTCCTGGACACTTTCCACTACTATGATGCCGATGACCCGGTC
CATTATCCCCGAGCCCTCTGCCTCTTTGAAATGCCCACAGGGGTGCCCCTTCGGCGGCACTTTAAT
TCCAACTTTAAAGGTGGCTTCAACTTCTATGCGGGGCTGAAGGGCCAGGTGCTGGTGCTGCGGAC
AACTTCAACTGTCTACAATTATGATTACATTTGGGACTTTATCTTCTACCCCAACGGGGTGATGGAG
GCCAAGATGCATGCCACTGGCTACGTCCACGCCACCTTCTACACCCCCGAGGGGCTGCGCCACG
GCACTCGCCTGCACACCCACCTGATTGGCAACATACACACTCACTTGGTGCACTACCGCGTAGACC
TGGATGTGGCAGGCACCAAGAACAGCTTCCAGACACTGCAGATGAAGCTAGAAAACATCACCAACC
CCTGGAGCCCAAGACACCGCGTGGTCCAGCCAACTCTGGAGCAGACGCAGTACTCCTGGGAGCG
CCAGGCGGCCTTCCGCTTCAAAACGAAGCTGCCCACGTACCTGCTCTTTACCAGCCCCCAGGAGA
ACCCCTGGGGCCACAAGCGCAGCTACCGCCTGCAGATCCACTCCATGGCCGACCAGGTGCTGCC
CCCAGGCTGGCAGGAGGAGCAGGCCATCACCTGGGCAAGGTACCCCCTGGCAGTGACCAAGTAC
CGGGAGTCGGAGCTGTGCAGCAGCAGCATCTACCACCAGAACGACCCCTGGCACCCGCCCGTGG
TCTTTGAGCAGTTTCTTCACAACAACGAGAACATTGAAAATGAGGACCTGGTGGCCTGGGTGACGG
TGGGCTTCCTGCACATCCCCCACTCAGAGGACATTCCCAACACAGCCACACCTGGGAACTCCGTG
GGCTTCCTGCTCCGGCCATTCAACTTCTTCCCAGAGGACCCCTCCCTGGCATCCAGAGACACTGTG
ATCGTGTGGCCTCGGGACAACGGCCCCAACTACGTCCAGCGCTGGATCCCTGAGGACAGGGACT
GCTCGATGCCTCCCCCTTTTAGCTACAATGGACCTATAGACCTGTGTGA (SEQ ID NO:76)

Fc-hDAO-Hepmut6

ATGCCGGCCCTGGGCTGGGCCGTGGCTGCCATCCTGATGCTGCAGACGGCCATGGCG***GA
GTGCCCCCCCTGCCCCGCCCCCCCCGTGGCCGGCCCCTCCGTGTTCCTGTTCCCCCCCAAGCCC
AAGGACACCCTGATGATCTCCAGGACCCCCGAGGTGACCTGCGTGGTGGTGGACGTGTCCCACG
AGGACCCCGAGGTGAAGTTCAACTGGTACGTGGACGGCGTGGAGGTGCACAACGCCAAGACCA
AGCCCAGGGAGGAGCAGTACAACTCCACCTACAGGGTGGTGTCCGTGCTGACCGTGCTGCACC
AGGACTGGCTGAACGGCAAGGAGTACAAGTGCAAGGTGTCCAACAAGGGCCTGCCCTCCTCCAT
CGAGAAGACCATCTCCAAGGCCAAGGGCCAGCCCAGGGAGCCCCAGGTGTACACCCTGCCCCC
CTCCAGGGAGGAGATGACCAAGAACCAGGTGTCCCTGACCTGCCTGGTGAAGGGCTTCTACCCC
TCCGACATCGCCGTGGAGTGGGAGTCCAACGGCCAGCCCGAGAACAACTACAAGACCACCCCC
CCCGTGCTGGACTCCGACGGCTCCTTCTTCCTGTACTCCAAGCTGACCGTGGACAAGTCCAGGT
GGCAGCAGGGCAACGTGTTCTCCTGCTCCGTGATGCACGAGGCCCTGCACAACCACTACACCCA
GAAGTCCCTGTCCCTGTCCCCCGGCAAGGAGCCCAAGTCCGCCGACAAGACCCACACC***GAGCC
CTCCCCGGGGACTCTGCCCAGGAAGGCAGGGGTGTTTTCAGACCTAAGCAACCAAGAGCTGAAGG
CAGTGCACAGCTTCCTCTGGTCCAAGAAGGAGCTGAGGCTGCAGCCCTCCAGTACCACCACCATG
GCCAAGAACACCGTGTTTCTCATCGAGATGCTGCTGCCCAAGAAGTACCATGTGCTGAGGTTTCTG
GATAAAGGTGAAAGGCATCCTGTGCGGGAAGCCCGTGCCGTCATCTTCTTTGGTGACCAGGAGCA
TCCCAATGTCACCGAGTTTGCTGTGGGGCCCCTGCCAGGCCCCTGCTACATGCGAGCACTGTCCC
CCAGGCCTGGGTACCAGTCCTCCTGGGCATCGAGGCCCATCTCCACAGCAGAGTATGCCCTCCTC
TACCACACCCTGCAGGAAGCCACCAAGCCCCTGCATCAGTTCTTCCTCAATACCACAGGCTTCTCA
TTCCAAGACTGCCATGACAGATGCCTGGCCTTCACCGATGTGGCCCCCCGGGGTGTGGCTTCTGG
CCAGCGCCGCAGTTGGCTTATCATACAGCGCTATGTAGAAGGCTACTTTCTGCACCCCACTGGGCT
GGAGCTCCTCGTGGATCATGGGAGCACAGATGCTGGGCACTGGGCCGTGGAGCAGGTGTGGTAC
AACGGGAAGTTCTATGGGAGCCCAGAGGAACTGGCTCGGAAGTATGCAGATGGAGAGGTGGACGT
GGTGGTCCTGGAGGACCCGCTGCCTGGGGGCAAGGGGCATGACAGCACAGAGGAGCCGCCCCT
CTTCTCCTCCCACAAGCCCCGCGGGGACTTCCCCAGCCCCATCCATGTGAGCGGCCCCCGCTTGG
TCCAGCCCCACGGCCCTCGCTTCAGGCTGGAGGGCAACGCTGTGCTCTACGGCGGCTGGAGCTT
TGCCTTCCGGCTGCGCTCCTCCTCCGGGCTGCAGGTCCTGAACGTGCACTTCGGCGGAGAGCGC
ATTGCCTATGAGGTCAGCGTGCAAGAGGCAGTGGCGCTGTATGGAGGACACACACCTGCAGGCAT
GCAGACCAAGTACCTCGATGTCGGCTGGGGCCTGGGCAGCGTCACTCATGAGTTAGCCCCCGGC

Figure 1 continued

ATCGACTGCCCGGAGACCGCCACCTTCCTGGACACTTTCCACTACTATGATGCCGATGACCCGGTC
CATTATCCCCGAGCCCTCTGCCTCTTTGAAATGCCCACAGGGGTGCCCCTTCGGCGGCACTTTAAT
TCCAACTTTAAAGGTGGCTTCAACTTCTATGCGGGGCTGAAGGGCCAGGTGCTGGTGCTGCGGAC
AACTTCAACTGTCTACAATTATGATTACATTTGGGACTTTATCTTCTACCCCAACGGGGTGATGGAG
GCCAAGATGCATGCCACTGGCTACGTCCACGCCACCTTCTACACCCCCGAGGGGCTGCGCCACG
GCACTCGCCTGCACACCCACCTGATTGGCAACATACACACTCACTTGGTGCACTACCGCGTAGACC
TGGATGTGGCAGGCACCAAGAACAGCTTCCAGACACTGCAGATGAAGCTAGAAAACATCACCAACC
CCTGGAGCCCAAGACACCGCGTGGTCCAGCCAACTCTGGAGCAGACGCAGTACTCCTGGGAGCG
CCAGGCGGCCTTCCGCTTCGGACAGACGCTGCCCAAGTACCTGCTCTTTACCAGCCCCCAGGAGA
ACCCCTGGGGCCACAAGCGCAGCTACCGCCTGCAGATCCACTCCATGGCCGACCAGGTGCTGCC
CCCAGGCTGGCAGGAGGAGCAGGCCATCACCTGGGCAAGGTACCCCCTGGCAGTGACCAAGTAC
CGGGAGTCGGAGCTGTGCAGCAGCAGCATCTACCACCAGAACGACCCCTGGCACCCGCCCGTGG
TCTTTGAGCAGTTTCTTCACAACAACGAGAACATTGAAAATGAGGACCTGGTGGCCTGGGTGACGG
TGGGCTTCCTGCACATCCCCCACTCAGAGGACATTCCCAACACAGCCACACCTGGGAACTCCGTG
GGCTTCCTGCTCCGGCCATTCAACTTCTTCCCAGAGGACCCCTCCCTGGCATCCAGAGACACTGTG
ATCGTGTGGCCTCGGGACAACGGCCCCAACTACGTCCAGCGCTGGATCCCTGAGGACAGGGACT
GCTCGATGCCTCCCCCTTTTAGCTACAATGGGACCTATAGACCTGTGTGA (SEQ ID NO:77)

<u>Fc-hDAO-Hepmut7</u>

ATGCCGGCCCTGGGCTGGGCCGTGGCTGCCATCCTGATGCTGCAGACGGCCATGGCG*GA*
*GTGCCCCCCCTGCCCCGCCCCCCCCGTGGCCGGCCCCTCCGTGTTCCTGTTCCCCCCCAAGCCC*
*AAGGACACCCTGATGATCTCCAGGACCCCCGAGGTGACCTGCGTGGTGGTGGACGTGTCCCACG*
*AGGACCCCGAGGTGAAGTTCAACTGGTACGTGGACGGCGTGGAGGTGCACAACGCCAAGACCA*
*AGCCCAGGGAGGAGCAGTACAACTCCACCTACAGGGTGGTGTCCGTGCTGACCGTGCTGCACC*
*AGGACTGGCTGAACGGCAAGGAGTACAAGTGCAAGGTGTCCAACAAGGGCCTGCCCTCCTCCAT*
*CGAGAAGACCATCTCCAAGGCCAAGGGCCAGCCCAGGGAGCCCCAGGTGTACACCCTGCCCCC*
*CTCCAGGGAGGAGATGACCAAGAACCAGGTGTCCCTGACCTGCCTGGTGAAGGGCTTCTACCCC*
*TCCGACATCGCCGTGGAGTGGGAGTCCAACGGCCAGCCCGAGAACAACTACAAGACCACCCCC*
*CCCGTGCTGGACTCCGACGGCTCCTTCTTCCTGTACTCCAAGCTGACCGTGGACAAGTCCAGGT*
*GGCAGCAGGGCAACGTGTTCTCCTGCTCCGTGATGCACGAGGCCCTGCACAACCACTACACCCA*
*GAAGTCCCTGTCCCTGTCCCCCGGCAAGGAGCCCAAGTCCGCCGACAAGACCCACACC*GAGCC
CTCCCCGGGGACTCTGCCCAGGAAGGCAGGGGTGTTTTCAGACCTAAGCAACCAAGAGCTGAAGG
CAGTGCACAGCTTCCTCTGGTCCAAGAAGGAGCTGAGGCTGCAGCCCTCCAGTACCACCACCATG
GCCAAGAACACCGTGTTTCTCATCGAGATGCTGCTGCCCAAGAAGTACCATGTGCTGAGGTTTCTG
GATAAAGGTGAAAGGCATCCTGTGCGGGAAGCCCGTGCCGTCATCTTCTTTGGTGACCAGGAGCA
TCCCAATGTCACCGAGTTTGCTGTGGGGCCCCTGCCAGGCCCCTGCTACATGCGAGCACTGTCCC
CCAGGCCTGGGTACCAGTCCTCCTGGGCATCGAGGCCCATCTCCACAGCAGAGTATGCCCTCCTC
TACCACACCCTGCAGGAAGCCACCAAGCCCCTGCATCAGTTCTTCCTCAATACCACAGGCTTCTCA
TTCCAAGACTGCCATGACAGATGCCTGGCCTTCACCGATGTGGCCCCCCGGGGTGTGGCTTCTGG
CCAGCGCCGCAGTTGGCTTATCATACAGCGCTATGTAGAAGGCTACTTTCTGCACCCCACTGGGCT
GGAGCTCCTCGTGGATCATGGGAGCACAGATGCTGGGCACTGGGCCGTGGAGCAGGTGTGGTAC
AACGGGAAGTTCTATGGGAGCCCAGAGGAACTGGCTCGGAAGTATGCAGATGGAGAGGTGGACGT
GGTGGTCCTGGAGGACCCGCTGCCTGGGGGCAAGGGGCATGACAGCACAGAGGAGCCGCCCCT
CTTCTCCTCCCACAAGCCCCGCGGGGACTTCCCCAGCCCCATCCATGTGAGCGGCCCCCGCTTGG
TCCAGCCCCACGGCCCTCGCTTCAGGCTGGAGGGCAACGCTGTGCTCTACGGCGGCTGGAGCTT
TGCCTTCCGGCTGCGCTCCTCCTCCGGGCTGCAGGTCCTGAACGTGCACTTCGGCGGAGAGCGC
ATTGCCTATGAGGTCAGCGTGCAAGAGGCAGTGGCGCTGTATGGAGGACACACACCTGCAGGCAT
GCAGACCAAGTACCTCGATGTCGGCTGGGGCCTGGGCAGCGTCACTCATGAGTTAGCCCCCGGC
ATCGACTGCCCGGAGACCGCCACCTTCCTGGACACTTTCCACTACTATGATGCCGATGACCCGGTC
CATTATCCCCGAGCCCTCTGCCTCTTTGAAATGCCCACAGGGGTGCCCCTTCGGCGGCACTTTAAT
TCCAACTTTAAAGGTGGCTTCAACTTCTATGCGGGGCTGAAGGGCCAGGTGCTGGTGCTGCGGAC
AACTTCAACTGTCTACAATTATGATTACATTTGGGACTTTATCTTCTACCCCAACGGGGTGATGGAG
GCCAAGATGCATGCCACTGGCTACGTCCACGCCACCTTCTACACCCCCGAGGGGCTGCGCCACG
GCACTCGCCTGCACACCCACCTGATTGGCAACATACACACTCACTTGGTGCACTACCGCGTAGACC
TGGATGTGGCAGGCACCAAGAACAGCTTCCAGACACTGCAGATGAAGCTAGAAAACATCACCAACC
CCTGGAGCCCAAGACACCGCGTGGTCCAGCCAACTCTGGAGCAGACGCAGTACTCCTGGGAGCG
CCAGGCGGCCTTCAGCTTCAAAAGGAAGCTGCCCACGTACCTGCTCTTTACCAGCCCCCAGGAGA
ACCCCTGGGGCCACAAGCGCAGCTACCGCCTGCAGATCCACTCCATGGCCGACCAGGTGCTGCC
CCCAGGCTGGCAGGAGGAGCAGGCCATCACCTGGGCAAGGTACCCCCTGGCAGTGACCAAGTAC

Figure 1 continued

CGGGAGTCGGAGCTGTGCAGCAGCAGCATCTACCACCAGAACGACCCCTGGCACCCGCCCGTGG
TCTTTGAGCAGTTTCTTCACAACAACGAGAACATTGAAAATGAGGACCTGGTGGCCTGGGTGACGG
TGGGCTTCCTGCACATCCCCCACTCAGAGGACATTCCCAACACAGCCACACCTGGGAACTCCGTG
GGCTTCCTGCTCCGGCCATTCAACTTCTTCCCAGAGGACCCCTCCCTGGCATCCAGAGACACTGTG
ATCGTGTGGCCTCGGGACAACGGCCCCAACTACGTCCAGCGCTGGATCCCTGAGGACAGGGACT
GCTCGATGCCTCCCCCTTTTAGCTACAATGGGACCTATAGACCTGTGTGA (SEQ ID NO:78)

<u>Fc-hDAO-Cysmut</u>

ATGCCGGCCCTGGGCTGGGCCGTGGCTGCCATCCTGATGCTGCAGACGGCCATGGCG*GA*
*GTGCCCCCCCTGCCCCGCCCCCCCCGTGGCCGGCCCCTCCGTGTTCCTGTTCCCCCCCAAGCCC*
*AAGGACACCCTGATGATCTCCAGGACCCCCGAGGTGACCTGCGTGGTGGTGGACGTGTCCCACG*
*AGGACCCCGAGGTGAAGTTCAACTGGTACGTGGACGGCGTGGAGGTGCACAACGCCAAGACCA*
*AGCCCAGGGAGGAGCAGTACAACTCCACCTACAGGGTGGTGTCCGTGCTGACCGTGCTGCACC*
*AGGACTGGCTGAACGGCAAGGAGTACAAGTGCAAGGTGTCCAACAAGGGCCTGCCCTCCTCCAT*
*CGAGAAGACCATCTCCAAGGCCAAGGGCCAGCCCAGGGAGCCCCAGGTGTACACCCTGCCCCC*
*CTCCAGGGAGGAGATGACCAAGAACCAGGTGTCCCTGACCTGCCTGGTGAAGGGCTTCTACCCC*
*TCCGACATCGCCGTGGAGTGGGAGTCCAACGGCCAGCCCGAGAACAACTACAAGACCACCCCC*
*CCCGTGCTGGACTCCGACGGCTCCTTCTTCCTGTACTCCAAGCTGACCGTGGACAAGTCCAGGT*
*GGCAGCAGGGCAACGTGTTCTCCTGCTCCGTGATGCACGAGGCCCTGCACAACCACTACACCCA*
*GAAGTCCCTGTCCCTGTCCCCCGGCAAGGAGCCCAAGTCCGCCGACAAGACCCACACC*GAGCC
CTCCCCGGGGACTCTGCCCAGGAAGGCAGGGGTGTTTTCAGACCTAAGCAACCAAGAGCTGAAGG
CAGTGCACAGCTTCCTCTGGTCCAAGAAGGAGCTGAGGCTGCAGCCCTCCAGTACCACCACCATG
GCCAAGAACACCGTGTTTCTCATCGAGATGCTGCTGCCCAAGAAGTACCATGTGCTGAGGTTTCTG
GATAAAGGTGAAAGGCATCCTGTGCGGGAAGCCCGTGCCGTCATCTTCTTTGGTGACCAGGAGCA
TCCCAATGTCACCGAGTTTGCTGTGGGGCCCCTGCCAGGCCCCGCCTACATGCGAGCACTGTCCC
CCAGGCCTGGGTACCAGTCCTCCTGGGCATCGAGGCCCATCTCCACAGCAGAGTATGCCCTCCTC
TACCACACCCTGCAGGAAGCCACCAAGCCCCTGCATCAGTTCTTCCTCAATACCACAGGCTTCTCA
TTCCAAGACTGCCATGACAGATGCCTGGCCTTCACCGATGTGGCCCCCCGGGGTGTGGCTTCTGG
CCAGCGCCGCAGTTGGCTTATCATACAGCGCTATGTAGAAGGCTACTTTCTGCACCCCACTGGGCT
GGAGCTCCTCGTGGATCATGGGAGCACAGATGCTGGGCACTGGGCCGTGGAGCAGGTGTGGTAC
AACGGGAAGTTCTATGGGAGCCCAGAGGAACTGGCTCGGAAGTATGCAGATGGAGAGGTGGACGT
GGTGGTCCTGGAGGACCCGCTGCCTGGGGGCAAGGGGCATGACAGCACAGAGGAGCCGCCCCT
CTTCTCCTCCCACAAGCCCCGCGGGGACTTCCCCAGCCCCATCCATGTGAGCGGCCCCCGCTTGG
TCCAGCCCCACGGCCCTCGCTTCAGGCTGGAGGGCAACGCTGTGCTCTACGGCGGCTGGAGCTT
TGCCTTCCGGCTGCGCTCCTCCTCCGGGCTGCAGGTCCTGAACGTGCACTTCGGCGGAGAGCGC
ATTGCCTATGAGGTCAGCGTGCAAGAGGCAGTGGCGCTGTATGGAGGACACACACCTGCAGGCAT
GCAGACCAAGTACCTCGATGTCGGCTGGGGCCTGGGCAGCGTCACTCATGAGTTAGCCCCCGGC
ATCGACTGCCCGGAGACCGCCACCTTCCTGGACACTTTCCACTACTATGATGCCGATGACCCGGTC
CATTATCCCCGAGCCCTCTGCCTCTTTGAAATGCCCACAGGGGTGCCCCTTCGGCGGCACTTTAAT
TCCAACTTTAAAGGTGGCTTCAACTTCTATGCGGGGCTGAAGGGCCAGGTGCTGGTGCTGCGGAC
AACTTCAACTGTCTACAATTATGATTACATTTGGGACTTTATCTTCTACCCCAACGGGGTGATGGAG
GCCAAGATGCATGCCACTGGCTACGTCCACGCCACCTTCTACACCCCCGAGGGGCTGCGCCACG
GCACTCGCCTGCACACCCACCTGATTGGCAACATACACACTCACTTGGTGCACTACCGCGTAGACC
TGGATGTGGCAGGCACCAAGAACAGCTTCCAGACACTGCAGATGAAGCTAGAAAACATCACCAACC
CCTGGAGCCCAAGACACCGCGTGGTCCAGCCAACTCTGGAGCAGACGCAGTACTCCTGGGAGCG
CCAGGCGGCCTTCCGCTTCAAAAGGAAGCTGCCCAAGTACCTGCTCTTTACCAGCCCCCAGGAGA
ACCCCTGGGGCCACAAGCGCAGCTACCGCCTGCAGATCCACTCCATGGCCGACCAGGTGCTGCC
CCCAGGCTGGCAGGAGGAGCAGGCCATCACCTGGGCAAGGTACCCCCTGGCAGTGACCAAGTAC
CGGGAGTCGGAGCTGTGCAGCAGCAGCATCTACCACCAGAACGACCCCTGGCACCCGCCCGTGG
TCTTTGAGCAGTTTCTTCACAACAACGAGAACATTGAAAATGAGGACCTGGTGGCCTGGGTGACGG
TGGGCTTCCTGCACATCCCCCACTCAGAGGACATTCCCAACACAGCCACACCTGGGAACTCCGTG
GGCTTCCTGCTCCGGCCATTCAACTTCTTCCCAGAGGACCCCTCCCTGGCATCCAGAGACACTGTG
ATCGTGTGGCCTCGGGACAACGGCCCCAACTACGTCCAGCGCTGGATCCCTGAGGACAGGGACT
GCTCGATGCCTCCCCCTTTTAGCTACAATGGGACCTATAGACCTGTGTGA (SEQ ID NO:79)

Figure 1 continued

<u>Fc-hDAO-Hepmut1-Cysmut</u>

ATGCCGGCCCTGGGCTGGGCCGTGGCTGCCATCCTGATGCTGCAGACGGCCATGGCG*GA*
*GTGCCCCCCCTGCCCCGCCCCCCCCGTGGCCGGCCCCTCCGTGTTCCTGTTCCCCCCCAAGCCC*
*AAGGACACCCTGATGATCTCCAGGACCCCCGAGGTGACCTGCGTGGTGGTGGACGTGTCCCACG*
*AGGACCCCGAGGTGAAGTTCAACTGGTACGTGGACGGCGTGGAGGTGCACAACGCCAAGACCA*
*AGCCCAGGGAGGAGCAGTACAACTCCACCTACAGGGTGGTGTCCGTGCTGACCGTGCTGCACC*
*AGGACTGGCTGAACGGCAAGGAGTACAAGTGCAAGGTGTCCAACAAGGGCCTGCCCTCCTCCAT*
*CGAGAAGACCATCTCCAAGGCCAAGGGCCAGCCCAGGGAGCCCCAGGTGTACACCCTGCCCCC*
*CTCCAGGGAGGAGATGACCAAGAACCAGGTGTCCCTGACCTGCCTGGTGAAGGGCTTCTACCCC*
*TCCGACATCGCCGTGGAGTGGGAGTCCAACGGCCAGCCCGAGAACAACTACAAGACCACCCCC*
*CCCGTGCTGGACTCCGACGGCTCCTTCTTCCTGTACTCCAAGCTGACCGTGGACAAGTCCAGGT*
*GGCAGCAGGGCAACGTGTTCTCCTGCTCCGTGATGCACGAGGCCCTGCACAACCACTACACCCA*
*GAAGTCCCTGTCCCTGTCCCCCGGCAAGGAGCCCAAGTCCGCCGACAAGACCCACACC*GAGCC
CTCCCCGGGGACTCTGCCCAGGAAGGCAGGGGTGTTTTCAGACCTAAGCAACCAAGAGCTGAAGG
CAGTGCACAGCTTCCTCTGGTCCAAGAAGGAGCTGAGGCTGCAGCCCTCCAGTACCACCACCATG
GCCAAGAACACCGTGTTTCTCATCGAGATGCTGCTGCCCAAGAAGTACCATGTGCTGAGGTTTCTG
GATAAAGGTGAAAGGCATCCTGTGCGGGAAGCCCGTGCCGTCATCTTCTTTGGTGACCAGGAGCA
TCCCAATGTCACCGAGTTTGCTGTGGGGCCCCTGCCAGGCCCCGCCTACATGCGAGCACTGTCCC
CCAGGCCTGGGTACCAGTCCTCCTGGGCATCGAGGCCCATCTCCACAGCAGAGTATGCCCTCCTC
TACCACACCCTGCAGGAAGCCACCAAGCCCCTGCATCAGTTCTTCCTCAATACCACAGGCTTCTCA
TTCCAAGACTGCCATGACAGATGCCTGGCCTTCACCGATGTGGCCCCCCGGGGTGTGGCTTCTGG
CCAGCGCCGCAGTTGGCTTATCATACAGCGCTATGTAGAAGGCTACTTTCTGCACCCCACTGGGCT
GGAGCTCCTCGTGGATCATGGGAGCACAGATGCTGGGCACTGGGCCGTGGAGCAGGTGTGGTAC
AACGGGAAGTTCTATGGGAGCCCAGAGGAACTGGCTCGGAAGTATGCAGATGGAGAGGTGGACGT
GGTGGTCCTGGAGGACCCGCTGCCTGGGGGCAAGGGGCATGACAGCACAGAGGAGCCGCCCCT
CTTCTCCTCCCACAAGCCCCGCGGGGACTTCCCCAGCCCCATCCATGTGAGCGGCCCCCGCTTGG
TCCAGCCCCACGGCCCTCGCTTCAGGCTGGAGGGCAACGCTGTGCTCTACGGCGGCTGGAGCTT
TGCCTTCCGGCTGCGCTCCTCCTCCGGGCTGCAGGTCCTGAACGTGCACTTCGGCGGAGAGCGC
ATTGCCTATGAGGTCAGCGTGCAAGAGGCAGTGGCGCTGTATGGAGGACACACACCTGCAGGCAT
GCAGACCAAGTACCTCGATGTCGGCTGGGGCCTGGGCAGCGTCACTCATGAGTTAGCCCCCGGC
ATCGACTGCCCGGAGACCGCCACCTTCCTGGACACTTTCCACTACTATGATGCCGATGACCCGGTC
CATTATCCCCGAGCCCTCTGCCTCTTTGAAATGCCCACAGGGGTGCCCCTTCGGCGGCACTTTAAT
TCCAACTTTAAAGGTGGCTTCAACTTCTATGCGGGGCTGAAGGGCCAGGTGCTGGTGCTGCGGAC
AACTTCAACTGTCTACAATTATGATTACATTTGGGACTTTATCTTCTACCCCAACGGGGTGATGGAG
GCCAAGATGCATGCCACTGGCTACGTCCACGCCACCTTCTACACCCCCGAGGGGCTGCGCCACG
GCACTCGCCTGCACACCCACCTGATTGGCAACATACACACTCACTTGGTGCACTACCGCGTAGACC
TGGATGTGGCAGGCACCAAGAACAGCTTCCAGACACTGCAGATGAAGCTAGAAAACATCACCAACC
CCTGGAGCCCAAGACACCGCGTGGTCCAGCCAACTCTGGAGCAGACGCAGTACTCCTGGGAGCG
CCAGGCGGCCTTCAGCTTCAAAAGGAAGCTGCCCAAGTACCTGCTCTTTACCAGCCCCCAGGAGA
ACCCCTGGGGCCACAAGCGCAGCTACCGCCTGCAGATCCACTCCATGGCCGACCAGGTGCTGCC
CCCAGGCTGGCAGGAGGAGCAGGCCATCACCTGGGCAAGGTACCCCCTGGCAGTGACCAAGTAC
CGGGAGTCGGAGCTGTGCAGCAGCAGCATCTACCACCAGAACGACCCCTGGCACCCGCCCGTGG
TCTTTGAGCAGTTTCTTCACAACAACGAGAACATTGAAAATGAGGACCTGGTGGCCTGGGTGACGG
TGGGCTTCCTGCACATCCCCCACTCAGAGGACATTCCCAACACAGCCACACCTGGGAACTCCGTG
GGCTTCCTGCTCCGGCCATTCAACTTCTTCCCAGAGGACCCCTCCCTGGCATCCAGAGACACTGTG
ATCGTGTGGCCTCGGGACAACGGCCCCAACTACGTCCAGCGCTGGATCCCTGAGGACAGGGACT
GCTCGATGCCTCCCCCTTTTAGCTACAATGGGACCTATAGACCTGTGTGA (SEQ ID NO:80)

<u>Fc-hDAO-Hepmut2-Cysmut</u>

ATGCCGGCCCTGGGCTGGGCCGTGGCTGCCATCCTGATGCTGCAGACGGCCATGGCG*GA*
*GTGCCCCCCCTGCCCCGCCCCCCCCGTGGCCGGCCCCTCCGTGTTCCTGTTCCCCCCCAAGCCC*
*AAGGACACCCTGATGATCTCCAGGACCCCCGAGGTGACCTGCGTGGTGGTGGACGTGTCCCACG*
*AGGACCCCGAGGTGAAGTTCAACTGGTACGTGGACGGCGTGGAGGTGCACAACGCCAAGACCA*
*AGCCCAGGGAGGAGCAGTACAACTCCACCTACAGGGTGGTGTCCGTGCTGACCGTGCTGCACC*
*AGGACTGGCTGAACGGCAAGGAGTACAAGTGCAAGGTGTCCAACAAGGGCCTGCCCTCCTCCAT*
*CGAGAAGACCATCTCCAAGGCCAAGGGCCAGCCCAGGGAGCCCCAGGTGTACACCCTGCCCCC*
*CTCCAGGGAGGAGATGACCAAGAACCAGGTGTCCCTGACCTGCCTGGTGAAGGGCTTCTACCCC*
*TCCGACATCGCCGTGGAGTGGGAGTCCAACGGCCAGCCCGAGAACAACTACAAGACCACCCCC*

Figure 1 continued

*CCCGTGCTGGACTCCGACGGCTCCTTCTTCCTGTACTCCAAGCTGACCGTGGACAAGTCCAGGT*
*GGCAGCAGGGCAACGTGTTCTCCTGCTCCGTGATGCACGAGGCCCTGCACAACCACTACACCCA*
*GAAGTCCCTGTCCCTGTCCCCCGGCAAGGAGCCCAAGTCCGCCGACAAGACCCACACC*GAGCC
CTCCCCGGGGACTCTGCCCAGGAAGGCAGGGGTGTTTTCAGACCTAAGCAACCAAGAGCTGAAGG
CAGTGCACAGCTTCCTCTGGTCCAAGAAGGAGCTGAGGCTGCAGCCCTCCAGTACCACCACCATG
GCCAAGAACACCGTGTTTCTCATCGAGATGCTGCTGCCCAAGAAGTACCATGTGCTGAGGTTTCTG
GATAAAGGTGAAAGGCATCCTGTGCGGGAAGCCCGTGCCGTCATCTTCTTTGGTGACCAGGAGCA
TCCCAATGTCACCGAGTTTGCTGTGGGGCCCCTGCCAGGCCCCGCCTACATGCGAGCACTGTCCC
CCAGGCCTGGGTACCAGTCCTCCTGGGCATCGAGGCCCATCTCCACAGCAGAGTATGCCCTCCTC
TACCACACCCTGCAGGAAGCCACCAAGCCCCTGCATCAGTTCTTCCTCAATACCACAGGCTTCTCA
TTCCAAGACTGCCATGACAGATGCCTGGCCTTCACCGATGTGGCCCCCCGGGGTGTGGCTTCTGG
CCAGCGCCGCAGTTGGCTTATCATACAGCGCTATGTAGAAGGCTACTTTCTGCACCCCACTGGGCT
GGAGCTCCTCGTGGATCATGGGAGCACAGATGCTGGGCACTGGGCCGTGGAGCAGGTGTGGTAC
AACGGGAAGTTCTATGGGAGCCCAGAGGAACTGGCTCGGAAGTATGCAGATGGAGAGGTGGACGT
GGTGGTCCTGGAGGACCCGCTGCCTGGGGGCAAGGGGCATGACAGCACAGAGGAGCCGCCCCT
CTTCTCCTCCCACAAGCCCCGCGGGGACTTCCCCAGCCCCATCCATGTGAGCGGCCCCCGCTTGG
TCCAGCCCCACGGCCCTCGCTTCAGGCTGGAGGGCAACGCTGTGCTCTACGGCGGCTGGAGCTT
TGCCTTCCGGCTGCGCTCCTCCTCCGGGCTGCAGGTCCTGAACGTGCACTTCGGCGGAGAGCGC
ATTGCCTATGAGGTCAGCGTGCAAGAGGCAGTGGCGCTGTATGGAGGACACACACCTGCAGGCAT
GCAGACCAAGTACCTCGATGTCGGCTGGGGCCTGGGCAGCGTCACTCATGAGTTAGCCCCCGGC
ATCGACTGCCCGGAGACCGCCACCTTCCTGGACACTTTCCACTACTATGATGCCGATGACCCGGTC
CATTATCCCCGAGCCCTCTGCCTCTTTGAAATGCCCACAGGGGTGCCCCTTCGGCGGCACTTTAAT
TCCAACTTTAAAGGTGGCTTCAACTTCTATGCGGGGCTGAAGGGCCAGGTGCTGGTGCTGCGGAC
AACTTCAACTGTCTACAATTATGATTACATTTGGGACTTTATCTTCTACCCCAACGGGGTGATGGAG
GCCAAGATGCATGCCACTGGCTACGTCCACGCCACCTTCTACACCCCCGAGGGGCTGCGCCACG
GCACTCGCCTGCACACCCACCTGATTGGCAACATACACACTCACTTGGTGCACTACCGCGTAGACC
TGGATGTGGCAGGCACCAAGAACAGCTTCCAGACACTGCAGATGAAGCTAGAAAACATCACCAACC
CCTGGAGCCCAAGACACCGCGTGGTCCAGCCAACTCTGGAGCAGACGCAGTACTCCTGGGAGCG
CCAGGCGGCCTTCCGCTTCAAAAGGAAGCTGCCCACGTACCTGCTCTTTACCAGCCCCCAGGAGA
ACCCCTGGGGCCACAAGCGCAGCTACCGCCTGCAGATCCACTCCATGGCCGACCAGGTGCTGCC
CCCAGGCTGGCAGGAGGAGCAGGCCATCACCTGGGCAAGGTACCCCCTGGCAGTGACCAAGTAC
CGGGAGTCGGAGCTGTGCAGCAGCAGCATCTACCACCAGAACGACCCCTGGCACCCGCCCGTGG
TCTTTGAGCAGTTTCTTCACAACAACGAGAACATTGAAAATGAGGACCTGGTGGCCTGGGTGACGG
TGGGCTTCCTGCACATCCCCCACTCAGAGGACATTCCCAACACAGCCACACCTGGGAACTCCGTG
GGCTTCCTGCTCCGGCCATTCAACTTCTTCCCAGAGGACCCCTCCCTGGCATCCAGAGACACTGTG
ATCGTGTGGCCTCGGGACAACGGCCCCAACTACGTCCAGCGCTGGATCCCTGAGGACAGGGACT
GCTCGATGCCTCCCCCTTTTAGCTACAATGGGACCTATAGACCTGTGTGA (SEQ ID NO:81)

Fc-hDAO-Hepmut3-Cysmut

ATGCCGGCCCTGGGCTGGGCCGTGGCTGCCATCCTGATGCTGCAGACGGCCATGGCG*GA*
*GTGCCCCCCCTGCCCCGCCCCCCCCGTGGCCGGCCCCTCCGTGTTCCTGTTCCCCCCCAAGCCC*
*AAGGACACCCTGATGATCTCCAGGACCCCCGAGGTGACCTGCGTGGTGGTGGACGTGTCCCACG*
*AGGACCCCGAGGTGAAGTTCAACTGGTACGTGGACGGCGTGGAGGTGCACAACGCCAAGACCA*
*AGCCCAGGGAGGAGCAGTACAACTCCACCTACAGGGTGGTGTCCGTGCTGACCGTGCTGCACC*
*AGGACTGGCTGAACGGCAAGGAGTACAAGTGCAAGGTGTCCAACAAGGGCCTGCCCTCCTCCAT*
*CGAGAAGACCATCTCCAAGGCCAAGGGCCAGCCCAGGGAGCCCCAGGTGTACACCCTGCCCCC*
*CTCCAGGGAGGAGATGACCAAGAACCAGGTGTCCCTGACCTGCCTGGTGAAGGGCTTCTACCCC*
*TCCGACATCGCCGTGGAGTGGGAGTCCAACGGCCAGCCCGAGAACAACTACAAGACCACCCCC*
*CCCGTGCTGGACTCCGACGGCTCCTTCTTCCTGTACTCCAAGCTGACCGTGGACAAGTCCAGGT*
*GGCAGCAGGGCAACGTGTTCTCCTGCTCCGTGATGCACGAGGCCCTGCACAACCACTACACCCA*
*GAAGTCCCTGTCCCTGTCCCCCGGCAAGGAGCCCAAGTCCGCCGACAAGACCCACACC*GAGCC
CTCCCCGGGGACTCTGCCCAGGAAGGCAGGGGTGTTTTCAGACCTAAGCAACCAAGAGCTGAAGG
CAGTGCACAGCTTCCTCTGGTCCAAGAAGGAGCTGAGGCTGCAGCCCTCCAGTACCACCACCATG
GCCAAGAACACCGTGTTTCTCATCGAGATGCTGCTGCCCAAGAAGTACCATGTGCTGAGGTTTCTG
GATAAAGGTGAAAGGCATCCTGTGCGGGAAGCCCGTGCCGTCATCTTCTTTGGTGACCAGGAGCA
TCCCAATGTCACCGAGTTTGCTGTGGGGCCCCTGCCAGGCCCCGCCTACATGCGAGCACTGTCCC
CCAGGCCTGGGTACCAGTCCTCCTGGGCATCGAGGCCCATCTCCACAGCAGAGTATGCCCTCCTC
TACCACACCCTGCAGGAAGCCACCAAGCCCCTGCATCAGTTCTTCCTCAATACCACAGGCTTCTCA
TTCCAAGACTGCCATGACAGATGCCTGGCCTTCACCGATGTGGCCCCCCGGGGTGTGGCTTCTGG

Figure 1 continued

CCAGCGCCGCAGTTGGCTTATCATACAGCGCTATGTAGAAGGCTACTTTCTGCACCCCACTGGGCT
GGAGCTCCTCGTGGATCATGGGAGCACAGATGCTGGGCACTGGGCCGTGGAGCAGGTGTGGTAC
AACGGGAAGTTCTATGGGAGCCCAGAGGAACTGGCTCGGAAGTATGCAGATGGAGAGGTGGACGT
GGTGGTCCTGGAGGACCCGCTGCCTGGGGGCAAGGGGCATGACAGCACAGAGGAGCCGCCCCT
CTTCTCCTCCCACAAGCCCCGCGGGGACTTCCCCAGCCCCATCCATGTGAGCGGCCCCCGCTTGG
TCCAGCCCCACGGCCCTCGCTTCAGGCTGGAGGGCAACGCTGTGCTCTACGGCGGCTGGAGCTT
TGCCTTCCGGCTGCGCTCCTCCTCCGGGCTGCAGGTCCTGAACGTGCACTTCGGCGGAGAGCGC
ATTGCCTATGAGGTCAGCGTGCAAGAGGCAGTGGCGCTGTATGGAGGACACACACCTGCAGGCAT
GCAGACCAAGTACCTCGATGTCGGCTGGGGCCTGGGCAGCGTCACTCATGAGTTAGCCCCCGGC
ATCGACTGCCCGGAGACCGCCACCTTCCTGGACACTTTCCACTACTATGATGCCGATGACCCGGTC
CATTATCCCCGAGCCCTCTGCCTCTTTGAAATGCCCACAGGGGTGCCCCTTCGGCGGCACTTTAAT
TCCAACTTTAAAGGTGGCTTCAACTTCTATGCGGGGCTGAAGGGCCAGGTGCTGGTGCTGCGGAC
AACTTCAACTGTCTACAATTATGATTACATTTGGGACTTTATCTTCTACCCCAACGGGGTGATGGAG
GCCAAGATGCATGCCACTGGCTACGTCCACGCCACCTTCTACACCCCCGAGGGGCTGCGCCACG
GCACTCGCCTGCACACCCACCTGATTGGCAACATACACACTCACTTGGTGCACTACCGCGTAGACC
TGGATGTGGCAGGCACCAAGAACAGCTTCCAGACACTGCAGATGAAGCTAGAAAACATCACCAACC
CCTGGAGCCCAAGACACCGCGTGGTCCAGCCAACTCTGGAGCAGACGCAGTACTCCTGGGAGCG
CCAGGCGGCCTTCCGCTTCAAAACGAAGCTGCCCAAGTACCTGCTCTTTACCAGCCCCCAGGAGA
ACCCCTGGGGCCACAAGCGCAGCTACCGCCTGCAGATCCACTCCATGGCCGACCAGGTGCTGCC
CCCAGGCTGGCAGGAGGAGCAGGCCATCACCTGGGCAAGGTACCCCCTGGCAGTGACCAAGTAC
CGGGAGTCGGAGCTGTGCAGCAGCAGCATCTACCACCAGAACGACCCCTGGCACCCGCCCGTGG
TCTTTGAGCAGTTTCTTCACAACAACGAGAACATTGAAAATGAGGACCTGGTGGCCTGGGTGACGG
TGGGCTTCCTGCACATCCCCCACTCAGAGGACATTCCCAACACAGCCACACCTGGGAACTCCGTG
GGCTTCCTGCTCCGGCCATTCAACTTCTTCCCAGAGGACCCCTCCCTGGCATCCAGAGACACTGTG
ATCGTGTGGCCTCGGGACAACGGCCCCAACTACGTCCAGCGCTGGATCCCTGAGGACAGGGACT
GCTCGATGCCTCCCCCTTTTAGCTACAATGGGACCTATAGACCTGTGTGA ((SEQ ID NO:82)

Fc-hDAO-Hepmut4-Cysmut

ATGCCGGCCCTGGGCTGGGCCGTGGCTGCCATCCTGATGCTGCAGACGGCCATGGCG*GA*
*GTGCCCCCCCTGCCCCGCCCCCCCCGTGGCCGGCCCCTCCGTGTTCCTGTTCCCCCCCAAGCCC*
*AAGGACACCCTGATGATCTCCAGGACCCCCGAGGTGACCTGCGTGGTGGTGGACGTGTCCCACG*
*AGGACCCCGAGGTGAAGTTCAACTGGTACGTGGACGGCGTGGAGGTGCACAACGCCAAGACCA*
*AGCCCAGGGAGGAGCAGTACAACTCCACCTACAGGGTGGTGTCCGTGCTGACCGTGCTGCACC*
*AGGACTGGCTGAACGGCAAGGAGTACAAGTGCAAGGTGTCCAACAAGGGCCTGCCCTCCTCCAT*
*CGAGAAGACCATCTCCAAGGCCAAGGGCCAGCCCAGGGAGCCCCAGGTGTACACCCTGCCCCC*
*CTCCAGGGAGGAGATGACCAAGAACCAGGTGTCCCTGACCTGCCTGGTGAAGGGCTTCTACCCC*
*TCCGACATCGCCGTGGAGTGGGAGTCCAACGGCCAGCCCGAGAACAACTACAAGACCACCCCC*
*CCCGTGCTGGACTCCGACGGCTCCTTCTTCCTGTACTCCAAGCTGACCGTGGACAAGTCCAGGT*
*GGCAGCAGGGCAACGTGTTCTCCTGCTCCGTGATGCACGAGGCCCTGCACAACCACTACACCCA*
*GAAGTCCCTGTCCCTGTCCCCCGGCAAGGAGCCCAAGTCCGCCGACAAGACCCACACC*GAGCC
CTCCCCGGGGACTCTGCCCAGGAAGGCAGGGGTGTTTTCAGACCTAAGCAACCAAGAGCTGAAGG
CAGTGCACAGCTTCCTCTGGTCCAAGAAGGAGCTGAGGCTGCAGCCCTCCAGTACCACCACCATG
GCCAAGAACACCGTGTTTCTCATCGAGATGCTGCTGCCCAAGAAGTACCATGTGCTGAGGTTTCTG
GATAAAGGTGAAAGGCATCCTGTGCGGGAAGCCCGTGCCGTCATCTTCTTTGGTGACCAGGAGCA
TCCCAATGTCACCGAGTTTGCTGTGGGGCCCCTGCCAGGCCCCGCCTACATGCGAGCACTGTCCC
CCAGGCCTGGGTACCAGTCCTCCTGGGCATCGAGGCCCATCTCCACAGCAGAGTATGCCCTCCTC
TACCACACCCTGCAGGAAGCCACCAAGCCCCTGCATCAGTTCTTCCTCAATACCACAGGCTTCTCA
TTCCAAGACTGCCATGACAGATGCCTGGCCTTCACCGATGTGGCCCCCCGGGGTGTGGCTTCTGG
CCAGCGCCGCAGTTGGCTTATCATACAGCGCTATGTAGAAGGCTACTTTCTGCACCCCACTGGGCT
GGAGCTCCTCGTGGATCATGGGAGCACAGATGCTGGGCACTGGGCCGTGGAGCAGGTGTGGTAC
AACGGGAAGTTCTATGGGAGCCCAGAGGAACTGGCTCGGAAGTATGCAGATGGAGAGGTGGACGT
GGTGGTCCTGGAGGACCCGCTGCCTGGGGGCAAGGGGCATGACAGCACAGAGGAGCCGCCCCT
CTTCTCCTCCCACAAGCCCCGCGGGGACTTCCCCAGCCCCATCCATGTGAGCGGCCCCCGCTTGG
TCCAGCCCCACGGCCCTCGCTTCAGGCTGGAGGGCAACGCTGTGCTCTACGGCGGCTGGAGCTT
TGCCTTCCGGCTGCGCTCCTCCTCCGGGCTGCAGGTCCTGAACGTGCACTTCGGCGGAGAGCGC
ATTGCCTATGAGGTCAGCGTGCAAGAGGCAGTGGCGCTGTATGGAGGACACACACCTGCAGGCAT
GCAGACCAAGTACCTCGATGTCGGCTGGGGCCTGGGCAGCGTCACTCATGAGTTAGCCCCCGGC
ATCGACTGCCCGGAGACCGCCACCTTCCTGGACACTTTCCACTACTATGATGCCGATGACCCGGTC
CATTATCCCCGAGCCCTCTGCCTCTTTGAAATGCCCACAGGGGTGCCCCTTCGGCGGCACTTTAAT

Figure 1 continued

TCCAACTTTAAAGGTGGCTTCAACTTCTATGCGGGGCTGAAGGGCCAGGTGCTGGTGCTGCGGAC
AACTTCAACTGTCTACAATTATGATTACATTTGGGACTTTATCTTCTACCCCAACGGGGTGATGGAG
GCCAAGATGCATGCCACTGGCTACGTCCACGCCACCTTCTACACCCCCGAGGGGCTGCGCCACG
GCACTCGCCTGCACACCCACCTGATTGGCAACATACACACTCACTTGGTGCACTACCGCGTAGACC
TGGATGTGGCAGGCACCAAGAACAGCTTCCAGACACTGCAGATGAAGCTAGAAAACATCACCAACC
CCTGGAGCCCAAGACACCGCGTGGTCCAGCCAACTCTGGAGCAGACGCAGTACTCCTGGGAGCG
CCAGGCGGCCTTCAGCTTCAAAACGAAGCTGCCCAAGTACCTGCTCTTTACCAGCCCCCAGGAGA
ACCCCTGGGGCCACAAGCGCAGCTACCGCCTGCAGATCCACTCCATGGCCGACCAGGTGCTGCC
CCCAGGCTGGCAGGAGGAGCAGGCCATCACCTGGGCAAGGTACCCCCTGGCAGTGACCAAGTAC
CGGGAGTCGGAGCTGTGCAGCAGCAGCATCTACCACCAGAACGACCCCTGGCACCCGCCCGTGG
TCTTTGAGCAGTTTCTTCACAACAACGAGAACATTGAAAATGAGGACCTGGTGGCCTGGGTGACGG
TGGGCTTCCTGCACATCCCCCACTCAGAGGACATTCCCAACACAGCCACACCTGGGAACTCCGTG
GGCTTCCTGCTCCGGCCATTCAACTTCTTCCCAGAGGACCCCTCCCTGGCATCCAGAGACACTGTG
ATCGTGTGGCCTCGGGACAACGGCCCCAACTACGTCCAGCGCTGGATCCCTGAGGACAGGGACT
GCTCGATGCCTCCCCCTTTTAGCTACAATGGGACCTATAGACCTGTGTGA ((SEQ ID NO:83)

Fc-hDAO-Hepmut5-Cysmut

ATGCCGGCCCTGGGCTGGGCCGTGGCTGCCATCCTGATGCTGCAGACGGCCATGGCG*GA*
*GTGCCCCCCCTGCCCCGCCCCCCCCGTGGCCGGCCCCTCCGTGTTCCTGTTCCCCCCCAAGCCC*
*AAGGACACCCTGATGATCTCCAGGACCCCCGAGGTGACCTGCGTGGTGGTGGACGTGTCCCACG*
*AGGACCCCGAGGTGAAGTTCAACTGGTACGTGGACGGCGTGGAGGTGCACAACGCCAAGACCA*
*AGCCCAGGGAGGAGCAGTACAACTCCACCTACAGGGTGGTGTCCGTGCTGACCGTGCTGCACC*
*AGGACTGGCTGAACGGCAAGGAGTACAAGTGCAAGGTGTCCAACAAGGGCCTGCCCTCCTCCAT*
*CGAGAAGACCATCTCCAAGGCCAAGGGCCAGCCCAGGGAGCCCCAGGTGTACACCCTGCCCCC*
*CTCCAGGGAGGAGATGACCAAGAACCAGGTGTCCCTGACCTGCCTGGTGAAGGGCTTCTACCCC*
*TCCGACATCGCCGTGGAGTGGGAGTCCAACGGCCAGCCCGAGAACAACTACAAGACCACCCCC*
*CCCGTGCTGGACTCCGACGGCTCCTTCTTCCTGTACTCCAAGCTGACCGTGGACAAGTCCAGGT*
*GGCAGCAGGGCAACGTGTTCTCCTGCTCCGTGATGCACGAGGCCCTGCACAACCACTACACCCA*
*GAAGTCCCTGTCCCTGTCCCCGGCAAGGAGCCCAAGTCCGCCGACAAGACCCACACC*GAGCC
CTCCCCGGGGACTCTGCCCAGGAAGGCAGGGGTGTTTTCAGACCTAAGCAACCAAGAGCTGAAGG
CAGTGCACAGCTTCCTCTGGTCCAAGAAGGAGCTGAGGCTGCAGCCCTCCAGTACCACCACCATG
GCCAAGAACACCGTGTTTCTCATCGAGATGCTGCTGCCCAAGAAGTACCATGTGCTGAGGTTTCTG
GATAAAGGTGAAAGGCATCCTGTGCGGGAAGCCCGTGCCGTCATCTTCTTTGGTGACCAGGAGCA
TCCCAATGTCACCGAGTTTGCTGTGGGGCCCCTGCCAGGCCCCGCCTACATGCGAGCACTGTCCC
CCAGGCCTGGGTACCAGTCCTCCTGGGCATCGAGGCCCATCTCCACAGCAGAGTATGCCCTCCTC
TACCACACCCTGCAGGAAGCCACCAAGCCCCTGCATCAGTTCTTCCTCAATACCACAGGCTTCTCA
TTCCAAGACTGCCATGACAGATGCCTGGCCTTCACCGATGTGGCCCCCCGGGGTGTGGCTTCTGG
CCAGCGCCGCAGTTGGCTTATCATACAGCGCTATGTAGAAGGCTACTTTCTGCACCCCACTGGGCT
GGAGCTCCTCGTGGATCATGGGAGCACAGATGCTGGGCACTGGGCCGTGGAGCAGGTGTGGTAC
AACGGGAAGTTCTATGGGAGCCCAGAGGAACTGGCTCGGAAGTATGCAGATGGAGAGGTGGACGT
GGTGGTCCTGGAGGACCCGCTGCCTGGGGGCAAGGGGCATGACAGCACAGAGGAGCCGCCCCT
CTTCTCCTCCCACAAGCCCCGCGGGGACTTCCCCAGCCCCATCCATGTGAGCGGCCCCCGCTTGG
TCCAGCCCCACGGCCCTCGCTTCAGGCTGGAGGGCAACGCTGTGCTCTACGGCGGCTGGAGCTT
TGCCTTCCGGCTGCGCTCCTCCTCCGGGCTGCAGGTCCTGAACGTGCACTTCGGCGGAGAGCGC
ATTGCCTATGAGGTCAGCGTGCAAGAGGCAGTGGCGCTGTATGGAGGACACACACCTGCAGGCAT
GCAGACCAAGTACCTCGATGTCGGCTGGGGCCTGGGCAGCGTCACTCATGAGTTAGCCCCCGGC
ATCGACTGCCCGGAGACCGCCACCTTCCTGGACACTTTCCACTACTATGATGCCGATGACCCGGTC
CATTATCCCCGAGCCCTCTGCCTCTTTGAAATGCCCACAGGGGTGCCCCTTCGGCGGCACTTTAAT
TCCAACTTTAAAGGTGGCTTCAACTTCTATGCGGGGCTGAAGGGCCAGGTGCTGGTGCTGCGGAC
AACTTCAACTGTCTACAATTATGATTACATTTGGGACTTTATCTTCTACCCCAACGGGGTGATGGAG
GCCAAGATGCATGCCACTGGCTACGTCCACGCCACCTTCTACACCCCCGAGGGGCTGCGCCACG
GCACTCGCCTGCACACCCACCTGATTGGCAACATACACACTCACTTGGTGCACTACCGCGTAGACC
TGGATGTGGCAGGCACCAAGAACAGCTTCCAGACACTGCAGATGAAGCTAGAAAACATCACCAACC
CCTGGAGCCCAAGACACCGCGTGGTCCAGCCAACTCTGGAGCAGACGCAGTACTCCTGGGAGCG
CCAGGCGGCCTTCCGCTTCAAAACGAAGCTGCCCACGTACCTGCTCTTTACCAGCCCCCAGGAGA
ACCCCTGGGGCCACAAGCGCAGCTACCGCCTGCAGATCCACTCCATGGCCGACCAGGTGCTGCC
CCCAGGCTGGCAGGAGGAGCAGGCCATCACCTGGGCAAGGTACCCCCTGGCAGTGACCAAGTAC
CGGGAGTCGGAGCTGTGCAGCAGCAGCATCTACCACCAGAACGACCCCTGGCACCCGCCCGTGG
TCTTTGAGCAGTTTCTTCACAACAACGAGAACATTGAAAATGAGGACCTGGTGGCCTGGGTGACGG

Figure 1 continued

TGGGCTTCCTGCACATCCCCCACTCAGAGGACATTCCCAACACAGCCACACCTGGGAACTCCGTG
GGCTTCCTGCTCCGGCCATTCAACTTCTTCCCAGAGGACCCCTCCCTGGCATCCAGAGACACTGTG
ATCGTGTGGCCTCGGGACAACGGCCCCAACTACGTCCAGCGCTGGATCCCTGAGGACAGGGACT
GCTCGATGCCTCCCCCTTTTAGCTACAATGGGACCTATAGACCTGTGTGA (SEQ ID NO:84)

<u>Fc-hDAO-Hepmut6-Cysmut</u>

ATGCCGGCCCTGGGCTGGGCCGTGGCTGCCATCCTGATGCTGCAGACGGCCATGGCG*GA*
*GTGCCCCCCCTGCCCCGCCCCCCCCGTGGCCGGCCCCTCCGTGTTCCTGTTCCCCCCCAAGCCC*
*AAGGACACCCTGATGATCTCCAGGACCCCCGAGGTGACCTGCGTGGTGGTGGACGTGTCCCACG*
*AGGACCCCGAGGTGAAGTTCAACTGGTACGTGGACGGCGTGGAGGTGCACAACGCCAAGACCA*
*AGCCCAGGGAGGAGCAGTACAACTCCACCTACAGGGTGGTGTCCGTGCTGACCGTGCTGCACC*
*AGGACTGGCTGAACGGCAAGGAGTACAAGTGCAAGGTGTCCAACAAGGGCCTGCCCTCCTCCAT*
*CGAGAAGACCATCTCCAAGGCCAAGGGCCAGCCCAGGGAGCCCCAGGTGTACACCCTGCCCCC*
*CTCCAGGGAGGAGATGACCAAGAACCAGGTGTCCCTGACCTGCCTGGTGAAGGGCTTCTACCCC*
*TCCGACATCGCCGTGGAGTGGGAGTCCAACGGCCAGCCCGAGAACAACTACAAGACCACCCCC*
*CCCGTGCTGGACTCCGACGGCTCCTTCTTCCTGTACTCCAAGCTGACCGTGGACAAGTCCAGGT*
*GGCAGCAGGGCAACGTGTTCTCCTGCTCCGTGATGCACGAGGCCCTGCACAACCACTACACCCA*
*GAAGTCCCTGTCCCTGTCCCCCGGCAAGGAGCCCAAGTCCGCCGACAAGACCCACACC*GAGCC
CTCCCCGGGGACTCTGCCCAGGAAGGCAGGGGTGTTTTCAGACCTAAGCAACCAAGAGCTGAAGG
CAGTGCACAGCTTCCTCTGGTCCAAGAAGGAGCTGAGGCTGCAGCCCTCCAGTACCACCACCATG
GCCAAGAACACCGTGTTTCTCATCGAGATGCTGCTGCCCAAGAAGTACCATGTGCTGAGGTTTCTG
GATAAAGGTGAAAGGCATCCTGTGCGGGAAGCCCGTGCCGTCATCTTCTTTGGTGACCAGGAGCA
TCCCAATGTCACCGAGTTTGCTGTGGGGCCCCTGCCAGGCCCCGCCTACATGCGAGCACTGTCCC
CCAGGCCTGGGTACCAGTCCTCCTGGGCATCGAGGCCCATCTCCACAGCAGAGTATGCCCTCCTC
TACCACACCCTGCAGGAAGCCACCAAGCCCCTGCATCAGTTCTTCCTCAATACCACAGGCTTCTCA
TTCCAAGACTGCCATGACAGATGCCTGGCCTTCACCGATGTGGCCCCCCGGGGTGTGGCTTCTGG
CCAGCGCCGCAGTTGGCTTATCATACAGCGCTATGTAGAAGGCTACTTTCTGCACCCCACTGGGCT
GGAGCTCCTCGTGGATCATGGGAGCACAGATGCTGGGCACTGGGCCGTGGAGCAGGTGTGGTAC
AACGGGAAGTTCTATGGGAGCCCAGAGGAACTGGCTCGGAAGTATGCAGATGGAGAGGTGGACGT
GGTGGTCCTGGAGGACCCGCTGCCTGGGGGCAAGGGGCATGACAGCACAGAGGAGCCGCCCCT
CTTCTCCTCCCACAAGCCCCGCGGGGACTTCCCCAGCCCCATCCATGTGAGCGGCCCCCGCTTGG
TCCAGCCCCACGGCCCTCGCTTCAGGCTGGAGGGCAACGCTGTGCTCTACGGCGGCTGGAGCTT
TGCCTTCCGGCTGCGCTCCTCCTCCGGGCTGCAGGTCCTGAACGTGCACTTCGGCGGAGAGCGC
ATTGCCTATGAGGTCAGCGTGCAAGAGGCAGTGGCGCTGTATGGAGGACACACACCTGCAGGCAT
GCAGACCAAGTACCTCGATGTCGGCTGGGGCCTGGGCAGCGTCACTCATGAGTTAGCCCCCGGC
ATCGACTGCCCGGAGACCGCCACCTTCCTGGACACTTTCCACTACTATGATGCCGATGACCCGGTC
CATTATCCCCGAGCCCTCTGCCTCTTTGAAATGCCCACAGGGGTGCCCCTTCGGCGGCACTTTAAT
TCCAACTTTAAAGGTGGCTTCAACTTCTATGCGGGGCTGAAGGGCCAGGTGCTGGTGCTGCGGAC
AACTTCAACTGTCTACAATTATGATTACATTTGGGACTTTATCTTCTACCCCAACGGGGTGATGGAG
GCCAAGATGCATGCCACTGGCTACGTCCACGCCACCTTCTACACCCCCGAGGGGCTGCGCCACG
GCACTCGCCTGCACACCCACCTGATTGGCAACATACACACTCACTTGGTGCACTACCGCGTAGACC
TGGATGTGGCAGGCACCAAGAACAGCTTCCAGACACTGCAGATGAAGCTAGAAAACATCACCAACC
CCTGGAGCCCAAGACACCGCGTGGTCCAGCCAACTCTGGAGCAGACGCAGTACTCCTGGGAGCG
CCAGGCGGCCTTCCGCTTCGGACAGACGCTGCCCAAGTACCTGCTCTTTACCAGCCCCCAGGAGA
ACCCCTGGGGCCACAAGCGCAGCTACCGCCTGCAGATCCACTCCATGGCCGACCAGGTGCTGCC
CCCAGGCTGGCAGGAGGAGCAGGCCATCACCTGGGCAAGGTACCCCCTGGCAGTGACCAAGTAC
CGGGAGTCGGAGCTGTGCAGCAGCAGCATCTACCACCAGAACGACCCCTGGCACCCGCCCGTGG
TCTTTGAGCAGTTTCTTCACAACAACGAGAACATTGAAAATGAGGACCTGGTGGCCTGGGTGACGG
TGGGCTTCCTGCACATCCCCCACTCAGAGGACATTCCCAACACAGCCACACCTGGGAACTCCGTG
GGCTTCCTGCTCCGGCCATTCAACTTCTTCCCAGAGGACCCCTCCCTGGCATCCAGAGACACTGTG
ATCGTGTGGCCTCGGGACAACGGCCCCAACTACGTCCAGCGCTGGATCCCTGAGGACAGGGACT
GCTCGATGCCTCCCCCTTTTAGCTACAATGGGACCTATAGACCTGTGTGA (SEQ ID NO:85)

<u>Fc-hDAO-Hepmut7-Cysmut</u>

ATGCCGGCCCTGGGCTGGGCCGTGGCTGCCATCCTGATGCTGCAGACGGCCATGGCG*GA*
*GTGCCCCCCCTGCCCCGCCCCCCCCGTGGCCGGCCCCTCCGTGTTCCTGTTCCCCCCCAAGCCC*
*AAGGACACCCTGATGATCTCCAGGACCCCCGAGGTGACCTGCGTGGTGGTGGACGTGTCCCACG*

Figure 1 continued

***AGGACCCCGAGGTGAAGTTCAACTGGTACGTGGACGGCGTGGAGGTGCACAACGCCAAGACCA
AGCCCAGGGAGGAGCAGTACAACTCCACCTACAGGGTGGTGTCCGTGCTGACCGTGCTGCACC
AGGACTGGCTGAACGGCAAGGAGTACAAGTGCAAGGTGTCCAACAAGGGCCTGCCCTCCTCCAT
CGAGAAGACCATCTCCAAGGCCAAGGGCCAGCCCAGGGAGCCCCAGGTGTACACCCTGCCCCC
CTCCAGGGAGGAGATGACCAAGAACCAGGTGTCCCTGACCTGCCTGGTGAAGGGCTTCTACCCC
TCCGACATCGCCGTGGAGTGGGAGTCCAACGGCCAGCCCGAGAACAACTACAAGACCACCCCC
CCCGTGCTGGACTCCGACGGCTCCTTCTTCCTGTACTCCAAGCTGACCGTGGACAAGTCCAGGT
GGCAGCAGGGCAACGTGTTCTCCTGCTCCGTGATGCACGAGGCCCTGCACAACCACTACACCCA
GAAGTCCCTGTCCCTGTCCCCCGGCAAGGAGCCCAAGTCCGCCGACAAGACCCACACC***GAGCC
CTCCCCGGGGACTCTGCCCAGGAAGGCAGGGGTGTTTTCAGACCTAAGCAACCAAGAGCTGAAGG
CAGTGCACAGCTTCCTCTGGTCCAAGAAGGAGCTGAGGCTGCAGCCCTCCAGTACCACCACCATG
GCCAAGAACACCGTGTTTCTCATCGAGATGCTGCTGCCCAAGAAGTACCATGTGCTGAGGTTTCTG
GATAAAGGTGAAAGGCATCCTGTGCGGGAAGCCCGTGCCGTCATCTTCTTTGGTGACCAGGAGCA
TCCCAATGTCACCGAGTTTGCTGTGGGGCCCCTGCCAGGCCCCGCCTACATGCGAGCACTGTCCC
CCAGGCCTGGGTACCAGTCCTCCTGGGCATCGAGGCCCATCTCCACAGCAGAGTATGCCCTCCTC
TACCACACCCTGCAGGAAGCCACCAAGCCCCTGCATCAGTTCTTCCTCAATACCACAGGCTTCTCA
TTCCAAGACTGCCATGACAGATGCCTGGCCTTCACCGATGTGGCCCCCCGGGGTGTGGCTTCTGG
CCAGCGCCGCAGTTGGCTTATCATACAGCGCTATGTAGAAGGCTACTTTCTGCACCCCACTGGGCT
GGAGCTCCTCGTGGATCATGGGAGCACAGATGCTGGGCACTGGGCCGTGGAGCAGGTGTGGTAC
AACGGGAAGTTCTATGGGAGCCCAGAGGAACTGGCTCGGAAGTATGCAGATGGAGAGGTGGACGT
GGTGGTCCTGGAGGACCCGCTGCCTGGGGGCAAGGGGCATGACAGCACAGAGGAGCCGCCCCT
CTTCTCCTCCCACAAGCCCCGCGGGGACTTCCCCAGCCCCATCCATGTGAGCGGCCCCCGCTTGG
TCCAGCCCCACGGCCCTCGCTTCAGGCTGGAGGGCAACGCTGTGCTCTACGGCGGCTGGAGCTT
TGCCTTCCGGCTGCGCTCCTCCTCCGGGCTGCAGGTCCTGAACGTGCACTTCGGCGGAGAGCGC
ATTGCCTATGAGGTCAGCGTGCAAGAGGCAGTGGCGCTGTATGGAGGACACACACCTGCAGGCAT
GCAGACCAAGTACCTCGATGTCGGCTGGGGCCTGGGCAGCGTCACTCATGAGTTAGCCCCCGGC
ATCGACTGCCCGGAGACCGCCACCTTCCTGGACACTTTCCACTACTATGATGCCGATGACCCGGTC
CATTATCCCCGAGCCCTCTGCCTCTTTGAAATGCCCACAGGGGTGCCCCTTCGGCGGCACTTTAAT
TCCAACTTTAAAGGTGGCTTCAACTTCTATGCGGGGCTGAAGGGCCAGGTGCTGGTGCTGCGGAC
AACTTCAACTGTCTACAATTATGATTACATTTGGGACTTTATCTTCTACCCCAACGGGGTGATGGAG
GCCAAGATGCATGCCACTGGCTACGTCCACGCCACCTTCTACACCCCCGAGGGGCTGCGCCACG
GCACTCGCCTGCACACCCACCTGATTGGCAACATACACACTCACTTGGTGCACTACCGCGTAGACC
TGGATGTGGCAGGCACCAAGAACAGCTTCCAGACACTGCAGATGAAGCTAGAAAACATCACCAACC
CCTGGAGCCCAAGACACCGCGTGGTCCAGCCAACTCTGGAGCAGACGCAGTACTCCTGGGAGCG
CCAGGCGGCCTTCAGCTTCAAAAGGAAGCTGCCCACGTACCTGCTCTTTACCAGCCCCCAGGAGA
ACCCCTGGGGCCACAAGCGCAGCTACCGCCTGCAGATCCACTCCATGGCCGACCAGGTGCTGCC
CCCAGGCTGGCAGGAGGAGCAGGCCATCACCTGGGCAAGGTACCCCCTGGCAGTGACCAAGTAC
CGGGAGTCGGAGCTGTGCAGCAGCAGCATCTACCACCAGAACGACCCCTGGCACCCGCCCGTGG
TCTTTGAGCAGTTTCTTCACAACAACGAGAACATTGAAAATGAGGACCTGGTGGCCTGGGTGACGG
TGGGCTTCCTGCACATCCCCCACTCAGAGGACATTCCCAACACAGCCACACCTGGGAACTCCGTG
GGCTTCCTGCTCCGGCCATTCAACTTCTTCCCAGAGGACCCCTCCCTGGCATCCAGAGACACTGTG
ATCGTGTGGCCTCGGGACAACGGCCCCAACTACGTCCAGCGCTGGATCCCTGAGGACAGGGACT
GCTCGATGCCTCCCCCTTTTAGCTACAATGGGACCTATAGACCTGTGTGA (SEQ ID NO:86)

<u>hDAO-Fc</u>

ATGCCGGCCCTGGGCTGGGCCGTGGCTGCCATCCTGATGCTGCAGACGGCCATGGCGGA
GCCCTCCCCGGGGACTCTGCCCAGGAAGGCAGGGGTGTTTTCAGACCTAAGCAACCAAGAGCTGA
AGGCAGTGCACAGCTTCCTCTGGTCCAAGAAGGAGCTGAGGCTGCAGCCCTCCAGTACCACCACC
ATGGCCAAGAACACCGTGTTTCTCATCGAGATGCTGCTGCCCAAGAAGTACCATGTGCTGAGGTTT
CTGGATAAAGGTGAAAGGCATCCTGTGCGGGAAGCCCGTGCCGTCATCTTCTTTGGTGACCAGGA
GCATCCCAATGTCACCGAGTTTGCTGTGGGGCCCCTGCCAGGGCCCTGCTACATGCGAGCACTGT
CCCCCAGGCCTGGGTACCAGTCCTCCTGGGCATCGAGGCCCATCTCCACAGCAGAGTATGCCCTC
CTCTACCACACCCTGCAGGAAGCCACCAAGCCCCTGCATCAGTTCTTCCTCAATACCACAGGCTTC
TCATTCCAAGACTGCCATGACAGATGCCTGGCCTTCACCGATGTGGCCCCCCGGGGTGTGGCTTC
TGGCCAGCGCCGCAGTTGGCTTATCATACAGCGCTATGTAGAAGGCTACTTTCTGCACCCCACTGG
GCTGGAGCTCCTCGTGGATCATGGGAGCACAGATGCTGGGCACTGGGCCGTGGAGCAGGTGTGG
TACAACGGGAAGTTCTATGGGAGCCCAGAGGAACTGGCTCGGAAGTATGCAGATGGAGAGGTGGA
CGTGGTGGTCCTGGAGGACCCGCTGCCTGGGGGCAAGGGGCATGACAGCACAGAGGAGCCGCC
CCTCTTCTCCTCCCACAAGCCCCGCGGGGACTTCCCCAGCCCCATCCATGTGAGCGGCCCCCGCT

Figure 1 continued

TGGTCCAGCCCCACGGCCCTCGCTTCAGGCTGGAGGGCAACGCTGTGCTCTACGGCGGCTGGAG
CTTTGCCTTCCGGCTGCGCTCCTCCTCCGGGCTGCAGGTCCTGAACGTGCACTTCGGCGGAGAGC
GCATTGCCTATGAGGTCAGCGTGCAAGAGGCAGTGGCGCTGTATGGAGGACACACACCTGCAGGC
ATGCAGACCAAGTACCTCGATGTCGGCTGGGGCCTGGGCAGCGTCACTCATGAGTTAGCCCCCGG
CATCGACTGCCCGGAGACCGCCACCTTCCTGGACACTTTCCACTACTATGATGCCGATGACCCGGT
CCATTATCCCCGAGCCCTCTGCCTCTTTGAAATGCCCACAGGGGTGCCCCTTCGGCGGCACTTTAA
TTCCAACTTTAAAGGTGGCTTCAACTTCTATGCGGGGCTGAAGGGCCAGGTGCTGGTGCTGCGGA
CAACTTCAACTGTCTACAATTATGATTACATTTGGGACTTTATCTTCTACCCCAACGGGGTGATGGA
GGCCAAGATGCATGCCACTGGCTACGTCCACGCCACCTTCTACACCCCCGAGGGGCTGCGCCAC
GGCACTCGCCTGCACACCCACCTGATTGGCAACATACACACTCACTTGGTGCACTACCGCGTAGAC
CTGGATGTGGCAGGCACCAAGAACAGCTTCCAGACACTGCAGATGAAGCTAGAAAACATCACCAAC
CCCTGGAGCCCAAGACACCGCGTGGTCCAGCCAACTCTGGAGCAGACGCAGTACTCCTGGGAGC
GCCAGGCGGCCTTCCGCTTCAAAAGGAAGCTGCCCAAGTACCTGCTCTTTACCAGCCCCCAGGAG
AACCCCTGGGGCCACAAGCGCAGCTACCGCCTGCAGATCCACTCCATGGCCGACCAGGTGCTGC
CCCCAGGCTGGCAGGAGGAGCAGGCCATCACCTGGGCAAGGTACCCCCTGGCAGTGACCAAGTA
CCGGGAGTCGGAGCTGTGCAGCAGCAGCATCTACCACCAGAACGACCCCTGGCACCCGCCCGTG
GTCTTTGAGCAGTTTCTTCACAACAACGAGAACATTGAAAATGAGGACCTGGTGGCCTGGGTGACG
GTGGGCTTCCTGCACATCCCCCACTCAGAGGACATTCCCAACACAGCCACACCTGGGAACTCCGT
GGGCTTCCTGCTCCGGCCATTCAACTTCTTCCCAGAGGACCCCTCCCTGGCATCCAGAGACACTGT
GATCGTGTGGCCTCGGGACAACGGCCCCAACTACGTCCAGCGCTGGATCCCTGAGGACAGGGAC
TGCTCGATGCCTCCCCCTTTTAGCTACAATGGGACCTATAGACCTGTG*GAGCCCAAGTCCGCCGA*
*CAAGACCCACACCTGCCCCCCCTGCCCCGCCCCCCCCGTGGCCGGCCCCTCCGTGTTCCTGTTC*
*CCCCCCAAGCCCAAGGACACCCTGATGATCTCCAGGACCCCCGAGGTGACCTGCGTGGTGGTG*
*GACGTGTCCCACGAGGACCCCGAGGTGAAGTTCAACTGGTACGTGGACGGCGTGGAGGTGCAC*
*AACGCCAAGACCAAGCCCAGGGAGGAGCAGTACAACTCCACCTACAGGGTGGTGTCCGTGCTG*
*ACCGTGCTGCACCAGGACTGGCTGAACGGCAAGGAGTACAAGTGCAAGGTGTCCAACAAGGGC*
*CTGCCCTCCTCCATCGAGAAGACCATCTCCAAGGCCAAGGGCCAGCCCAGGGAGCCCCAGGTG*
*TACACCCTGCCCCCCTCCAGGGAGGAGATGACCAAGAACCAGGTGTCCCTGACCTGCCTGGTGA*
*AGGGCTTCTACCCCTCCGACATCGCCGTGGAGTGGGAGTCCAACGGCCAGCCCGAGAACAACT*
*ACAAGACCACCCCCCCCGTGCTGGACTCCGACGGCTCCTTCTTCCTGTACTCCAAGCTGACCGT*
*GGACAAGTCCAGGTGGCAGCAGGGCAACGTGTTCTCCTGCTCCGTGATGCACGAGGCCCTGCAC*
*AACCACTACACCCAGAAGTCCCTGTCCCTGTCCCCCGGCAAGTGA*(SEQ ID NO:87)

hDAO-Fc-Hepmut1

ATGCCGGCCCTGGGCTGGGCCGTGGCTGCCATCCTGATGCTGCAGACGGCCATGGCGGA
GCCCTCCCCGGGGACTCTGCCCAGGAAGGCAGGGGTGTTTTCAGACCTAAGCAACCAAGAGCTGA
AGGCAGTGCACAGCTTCCTCTGGTCCAAGAAGGAGCTGAGGCTGCAGCCCTCCAGTACCACCACC
ATGGCCAAGAACACCGTGTTTCTCATCGAGATGCTGCTGCCCAAGAAGTACCATGTGCTGAGGTTT
CTGGATAAAGGTGAAAGGCATCCTGTGCGGGAAGCCCGTGCCGTCATCTTCTTTGGTGACCAGGA
GCATCCCAATGTCACCGAGTTTGCTGTGGGGCCCCTGCCAGGGCCCTGCTACATGCGAGCACTGT
CCCCCAGGCCTGGGTACCAGTCCTCCTGGGCATCGAGGCCCATCTCCACAGCAGAGTATGCCCTC
CTCTACCACACCCTGCAGGAAGCCACCAAGCCCCTGCATCAGTTCTTCCTCAATACCACAGGCTTC
TCATTCCAAGACTGCCATGACAGATGCCTGGCCTTCACCGATGTGGCCCCCCGGGGTGTGGCTTC
TGGCCAGCGCCGCAGTTGGCTTATCATACAGCGCTATGTAGAAGGCTACTTTCTGCACCCCACTGG
GCTGGAGCTCCTCGTGGATCATGGGAGCACAGATGCTGGGCACTGGGCCGTGGAGCAGGTGTGG
TACAACGGGAAGTTCTATGGGAGCCCAGAGGAACTGGCTCGGAAGTATGCAGATGGAGAGGTGGA
CGTGGTGGTCCTGGAGGACCCGCTGCCTGGGGGCAAGGGGCATGACAGCACAGAGGAGCCGCC
CCTCTTCTCCTCCCACAAGCCCCGCGGGGACTTCCCCAGCCCCATCCATGTGAGCGGCCCCCGCT
TGGTCCAGCCCCACGGCCCTCGCTTCAGGCTGGAGGGCAACGCTGTGCTCTACGGCGGCTGGAG
CTTTGCCTTCCGGCTGCGCTCCTCCTCCGGGCTGCAGGTCCTGAACGTGCACTTCGGCGGAGAGC
GCATTGCCTATGAGGTCAGCGTGCAAGAGGCAGTGGCGCTGTATGGAGGACACACACCTGCAGGC
ATGCAGACCAAGTACCTCGATGTCGGCTGGGGCCTGGGCAGCGTCACTCATGAGTTAGCCCCCGG
CATCGACTGCCCGGAGACCGCCACCTTCCTGGACACTTTCCACTACTATGATGCCGATGACCCGGT
CCATTATCCCCGAGCCCTCTGCCTCTTTGAAATGCCCACAGGGGTGCCCCTTCGGCGGCACTTTAA
TTCCAACTTTAAAGGTGGCTTCAACTTCTATGCGGGGCTGAAGGGCCAGGTGCTGGTGCTGCGGA
CAACTTCAACTGTCTACAATTATGATTACATTTGGGACTTTATCTTCTACCCCAACGGGGTGATGGA
GGCCAAGATGCATGCCACTGGCTACGTCCACGCCACCTTCTACACCCCCGAGGGGCTGCGCCAC
GGCACTCGCCTGCACACCCACCTGATTGGCAACATACACACTCACTTGGTGCACTACCGCGTAGAC
CTGGATGTGGCAGGCACCAAGAACAGCTTCCAGACACTGCAGATGAAGCTAGAAAACATCACCAAC

Figure 1 continued

CCCTGGAGCCCAAGACACCGCGTGGTCCAGCCAACTCTGGAGCAGACGCAGTACTCCTGGGAGC
GCCAGGCGGCCTTCAGCTTCAAAAGGAAGCTGCCCAAGTACCTGCTCTTTACCAGCCCCCAGGAG
AACCCCTGGGGCCACAAGCGCAGCTACCGCCTGCAGATCCACTCCATGGCCGACCAGGTGCTGC
CCCCAGGCTGGCAGGAGGAGCAGGCCATCACCTGGGCAAGGTACCCCCTGGCAGTGACCAAGTA
CCGGGAGTCGGAGCTGTGCAGCAGCAGCATCTACCACCAGAACGACCCCTGGCACCCGCCCGTG
GTCTTTGAGCAGTTTCTTCACAACAACGAGAACATTGAAAATGAGGACCTGGTGGCCTGGGTGACG
GTGGGCTTCCTGCACATCCCCCACTCAGAGGACATTCCCAACACAGCCACACCTGGGAACTCCGT
GGGCTTCCTGCTCCGGCCATTCAACTTCTTCCCAGAGGACCCCTCCCTGGCATCCAGAGACACTGT
GATCGTGTGGCCTCGGGACAACGGCCCCAACTACGTCCAGCGCTGGATCCCTGAGGACAGGGAC
TGCTCGATGCCTCCCCCTTTTAGCTACAATGGGACCTATAGACCTGTGGAGCCCAAGTCCGCCGA
CAAGACCCACACCTGCCCCCCCTGCCCCGCCCCCCCCGTGGCCGGCCCCTCCGTGTTCCTGTTC
CCCCCCAAGCCCAAGGACACCCTGATGATCTCCAGGACCCCCGAGGTGACCTGCGTGGTGGTG
GACGTGTCCCACGAGGACCCCGAGGTGAAGTTCAACTGGTACGTGGACGGCGTGGAGGTGCAC
AACGCCAAGACCAAGCCCAGGGAGGAGCAGTACAACTCCACCTACAGGGTGGTGTCCGTGCTG
ACCGTGCTGCACCAGGACTGGCTGAACGGCAAGGAGTACAAGTGCAAGGTGTCCAACAAGGGC
CTGCCCTCCTCCATCGAGAAGACCATCTCCAAGGCCAAGGGCCAGCCCAGGGAGCCCCAGGTG
TACACCCTGCCCCCCTCCAGGGAGGAGATGACCAAGAACCAGGTGTCCCTGACCTGCCTGGTGA
AGGGCTTCTACCCCTCCGACATCGCCGTGGAGTGGGAGTCCAACGGCCAGCCCGAGAACAACT
ACAAGACCACCCCCCCCGTGCTGGACTCCGACGGCTCCTTCTTCCTGTACTCCAAGCTGACCGT
GGACAAGTCCAGGTGGCAGCAGGGCAACGTGTTCTCCTGCTCCGTGATGCACGAGGCCCTGCAC
AACCACTACACCCAGAAGTCCCTGTCCCTGTCCCCCGGCAAGTGA(SEQ ID NO:88)

<u>hDAO-Fc-Hepmut2</u>

ATGCCGGCCCTGGGCTGGGCCGTGGCTGCCATCCTGATGCTGCAGACGGCCATGGCGGA
GCCCTCCCCGGGGACTCTGCCCAGGAAGGCAGGGGTGTTTTCAGACCTAAGCAACCAAGAGCTGA
AGGCAGTGCACAGCTTCCTCTGGTCCAAGAAGGAGCTGAGGCTGCAGCCCTCCAGTACCACCACC
ATGGCCAAGAACACCGTGTTTCTCATCGAGATGCTGCTGCCCAAGAAGTACCATGTGCTGAGGTTT
CTGGATAAAGGTGAAAGGCATCCTGTGCGGGAAGCCCGTGCCGTCATCTTCTTTGGTGACCAGGA
GCATCCCAATGTCACCGAGTTTGCTGTGGGGCCCCTGCCAGGGCCCTGCTACATGCGAGCACTGT
CCCCCAGGCCTGGGTACCAGTCCTCCTGGGCATCGAGGCCCATCTCCACAGCAGAGTATGCCCTC
CTCTACCACACCCTGCAGGAAGCCACCAAGCCCCTGCATCAGTTCTTCCTCAATACCACAGGCTTC
TCATTCCAAGACTGCCATGACAGATGCCTGGCCTTCACCGATGTGGCCCCCCGGGGTGTGGCTTC
TGGCCAGCGCCGCAGTTGGCTTATCATACAGCGCTATGTAGAAGGCTACTTTCTGCACCCCACTGG
GCTGGAGCTCCTCGTGGATCATGGGAGCACAGATGCTGGGCACTGGGCCGTGGAGCAGGTGTGG
TACAACGGGAAGTTCTATGGGAGCCCAGAGGAACTGGCTCGGAAGTATGCAGATGGAGAGGTGGA
CGTGGTGGTCCTGGAGGACCCGCTGCCTGGGGGCAAGGGGCATGACAGCACAGAGGAGCCGCC
CCTCTTCTCCTCCCACAAGCCCCGCGGGGACTTCCCCAGCCCCATCCATGTGAGCGGCCCCCGCT
TGGTCCAGCCCCACGGCCCTCGCTTCAGGCTGGAGGGCAACGCTGTGCTCTACGGCGGCTGGAG
CTTTGCCTTCCGGCTGCGCTCCTCCTCCGGGCTGCAGGTCCTGAACGTGCACTTCGGCGGAGAGC
GCATTGCCTATGAGGTCAGCGTGCAAGAGGCAGTGGCGCTGTATGGAGGACACACACCTGCAGGC
ATGCAGACCAAGTACCTCGATGTCGGCTGGGGCCTGGGCAGCGTCACTCATGAGTTAGCCCCCGG
CATCGACTGCCCGGAGACCGCCACCTTCCTGGACACTTTCCACTACTATGATGCCGATGACCCGGT
CCATTATCCCCGAGCCCTCTGCCTCTTTGAAATGCCCACAGGGGTGCCCCTTCGGCGGCACTTTAA
TTCCAACTTTAAAGGTGGCTTCAACTTCTATGCGGGGCTGAAGGGCCAGGTGCTGGTGCTGCGGA
CAACTTCAACTGTCTACAATTATGATTACATTTGGGACTTTATCTTCTACCCCAACGGGGTGATGGA
GGCCAAGATGCATGCCACTGGCTACGTCCACGCCACCTTCTACACCCCCGAGGGGCTGCGCCAC
GGCACTCGCCTGCACACCCACCTGATTGGCAACATACACACTCACTTGGTGCACTACCGCGTAGAC
CTGGATGTGGCAGGCACCAAGAACAGCTTCCAGACACTGCAGATGAAGCTAGAAAACATCACCAAC
CCCTGGAGCCCAAGACACCGCGTGGTCCAGCCAACTCTGGAGCAGACGCAGTACTCCTGGGAGC
GCCAGGCGGCCTTCCGCTTCAAAAGGAAGCTGCCCACGTACCTGCTCTTTACCAGCCCCCAGGAG
AACCCCTGGGGCCACAAGCGCAGCTACCGCCTGCAGATCCACTCCATGGCCGACCAGGTGCTGC
CCCCAGGCTGGCAGGAGGAGCAGGCCATCACCTGGGCAAGGTACCCCCTGGCAGTGACCAAGTA
CCGGGAGTCGGAGCTGTGCAGCAGCAGCATCTACCACCAGAACGACCCCTGGCACCCGCCCGTG
GTCTTTGAGCAGTTTCTTCACAACAACGAGAACATTGAAAATGAGGACCTGGTGGCCTGGGTGACG
GTGGGCTTCCTGCACATCCCCCACTCAGAGGACATTCCCAACACAGCCACACCTGGGAACTCCGT
GGGCTTCCTGCTCCGGCCATTCAACTTCTTCCCAGAGGACCCCTCCCTGGCATCCAGAGACACTGT
GATCGTGTGGCCTCGGGACAACGGCCCCAACTACGTCCAGCGCTGGATCCCTGAGGACAGGGAC
TGCTCGATGCCTCCCCCTTTTAGCTACAATGGGACCTATAGACCTGTGGAGCCCAAGTCCGCCGA
CAAGACCCACACCTGCCCCCCCTGCCCCGCCCCCCCCGTGGCCGGCCCCTCCGTGTTCCTGTTC

Figure 1 continued

CCCCCCAAGCCCAAGGACACCCTGATGATCTCCAGGACCCCCGAGGTGACCTGCGTGGTGGTG GACGTGTCCCACGAGGACCCCGAGGTGAAGTTCAACTGGTACGTGGACGGCGTGGAGGTGCAC AACGCCAAGACCAAGCCCAGGGAGGAGCAGTACAACTCCACCTACAGGGTGGTGTCCGTGCTG ACCGTGCTGCACCAGGACTGGCTGAACGGCAAGGAGTACAAGTGCAAGGTGTCCAACAAGGGC CTGCCCTCCTCCATCGAGAAGACCATCTCCAAGGCCAAGGGCCAGCCCAGGGAGCCCCAGGTG TACACCCTGCCCCCCTCCAGGGAGGAGATGACCAAGAACCAGGTGTCCCTGACCTGCCTGGTGA AGGGCTTCTACCCCTCCGACATCGCCGTGGAGTGGGAGTCCAACGGCCAGCCCGAGAACAACT ACAAGACCACCCCCCCCGTGCTGGACTCCGACGGCTCCTTCTTCCTGTACTCCAAGCTGACCGT GGACAAGTCCAGGTGGCAGCAGGGCAACGTGTTCTCCTGCTCCGTGATGCACGAGGCCCTGCAC AACCACTACACCCAGAAGTCCCTGTCCCTGTCCCCCGGCAAGTGA(SEQ ID NO:89)

hDAO-Fc-Hepmut3

ATGCCGGCCCTGGGCTGGGCCGTGGCTGCCATCCTGATGCTGCAGACGGCCATGGCGGA GCCCTCCCCGGGGACTCTGCCCAGGAAGGCAGGGGTGTTTTCAGACCTAAGCAACCAAGAGCTGA AGGCAGTGCACAGCTTCCTCTGGTCCAAGAAGGAGCTGAGGCTGCAGCCCTCCAGTACCACCACC ATGGCCAAGAACACCGTGTTTCTCATCGAGATGCTGCTGCCCAAGAAGTACCATGTGCTGAGGTTT CTGGATAAAGGTGAAAGGCATCCTGTGCGGGAAGCCCGTGCCGTCATCTTCTTTGGTGACCAGGA GCATCCCAATGTCACCGAGTTTGCTGTGGGGCCCCTGCCAGGGCCCTGCTACATGCGAGCACTGT CCCCCAGGCCTGGGTACCAGTCCTCCTGGGCATCGAGGCCCATCTCCACAGCAGAGTATGCCCTC CTCTACCACACCCTGCAGGAAGCCACCAAGCCCCTGCATCAGTTCTTCCTCAATACCACAGGCTTC TCATTCCAAGACTGCCATGACAGATGCCTGGCCTTCACCGATGTGGCCCCCCGGGGTGTGGCTTC TGGCCAGCGCCGCAGTTGGCTTATCATACAGCGCTATGTAGAAGGCTACTTTCTGCACCCCACTGG GCTGGAGCTCCTCGTGGATCATGGGAGCACAGATGCTGGGCACTGGGCCGTGGAGCAGGTGTGG TACAACGGGAAGTTCTATGGGAGCCCAGAGGAACTGGCTCGGAAGTATGCAGATGGAGAGGTGGA CGTGGTGGTCCTGGAGGACCCGCTGCCTGGGGGCAAGGGGCATGACAGCACAGAGGAGCCGCC CCTCTTCTCCTCCCACAAGCCCCGCGGGGACTTCCCCAGCCCCATCCATGTGAGCGGCCCCCGCT TGGTCCAGCCCCACGGCCCTCGCTTCAGGCTGGAGGGCAACGCTGTGCTCTACGGCGGCTGGAG CTTTGCCTTCCGGCTGCGCTCCTCCTCCGGGCTGCAGGTCCTGAACGTGCACTTCGGCGGAGAGC GCATTGCCTATGAGGTCAGCGTGCAAGAGGCAGTGGCGCTGTATGGAGGACACACACCTGCAGGC ATGCAGACCAAGTACCTCGATGTCGGCTGGGGCCTGGGCAGCGTCACTCATGAGTTAGCCCCCGG CATCGACTGCCCGGAGACCGCCACCTTCCTGGACACTTTCCACTACTATGATGCCGATGACCCGGT CCATTATCCCCGAGCCCTCTGCCTCTTTGAAATGCCCACAGGGGTGCCCCTTCGGCGGCACTTTAA TTCCAACTTTAAAGGTGGCTTCAACTTCTATGCGGGGCTGAAGGGCCAGGTGCTGGTGCTGCGGA CAACTTCAACTGTCTACAATTATGATTACATTTGGGACTTTATCTTCTACCCCAACGGGGTGATGGA GGCCAAGATGCATGCCACTGGCTACGTCCACGCCACCTTCTACACCCCCGAGGGGCTGCGCCAC GGCACTCGCCTGCACACCCACCTGATTGGCAACATACACACTCACTTGGTGCACTACCGCGTAGAC CTGGATGTGGCAGGCACCAAGAACAGCTTCCAGACACTGCAGATGAAGCTAGAAAACATCACCAAC CCCTGGAGCCCAAGACACCGCGTGGTCCAGCCAACTCTGGAGCAGACGCAGTACTCCTGGGAGC GCCAGGCGGCCTTCCGCTTCAAAACGAAGCTGCCCAAGTACCTGCTCTTTACCAGCCCCCAGGAG AACCCCTGGGGCCACAAGCGCAGCTACCGCCTGCAGATCCACTCCATGGCCGACCAGGTGCTGC CCCCAGGCTGGCAGGAGGAGCAGGCCATCACCTGGGCAAGGTACCCCCTGGCAGTGACCAAGTA CCGGGAGTCGGAGCTGTGCAGCAGCAGCATCTACCACCAGAACGACCCCTGGCACCCGCCCGTG GTCTTTGAGCAGTTTCTTCACAACAACGAGAACATTGAAAATGAGGACCTGGTGGCCTGGGTGACG GTGGGCTTCCTGCACATCCCCCACTCAGAGGACATTCCCAACACAGCCACACCTGGGAACTCCGT GGGCTTCCTGCTCCGGCCATTCAACTTCTTCCCAGAGGACCCCTCCCTGGCATCCAGAGACACTGT GATCGTGTGGCCTCGGGACAACGGCCCCAACTACGTCCAGCGCTGGATCCCTGAGGACAGGGAC TGCTCGATGCCTCCCCCTTTTAGCTACAATGGGACCTATAGACCTGTG*GAGCCCAAGTCCGCCGA CAAGACCCACACCTGCCCCCCCTGCCCCGCCCCCCCCGTGGCCGGCCCCTCCGTGTTCCTGTTC CCCCCCAAGCCCAAGGACACCCTGATGATCTCCAGGACCCCCGAGGTGACCTGCGTGGTGGTG GACGTGTCCCACGAGGACCCCGAGGTGAAGTTCAACTGGTACGTGGACGGCGTGGAGGTGCAC AACGCCAAGACCAAGCCCAGGGAGGAGCAGTACAACTCCACCTACAGGGTGGTGTCCGTGCTG ACCGTGCTGCACCAGGACTGGCTGAACGGCAAGGAGTACAAGTGCAAGGTGTCCAACAAGGGC CTGCCCTCCTCCATCGAGAAGACCATCTCCAAGGCCAAGGGCCAGCCCAGGGAGCCCCAGGTG TACACCCTGCCCCCCTCCAGGGAGGAGATGACCAAGAACCAGGTGTCCCTGACCTGCCTGGTGA AGGGCTTCTACCCCTCCGACATCGCCGTGGAGTGGGAGTCCAACGGCCAGCCCGAGAACAACT ACAAGACCACCCCCCCCGTGCTGGACTCCGACGGCTCCTTCTTCCTGTACTCCAAGCTGACCGT GGACAAGTCCAGGTGGCAGCAGGGCAACGTGTTCTCCTGCTCCGTGATGCACGAGGCCCTGCAC AACCACTACACCCAGAAGTCCCTGTCCCTGTCCCCCGGCAAGTGA* (SEQ ID NO:90)

Figure 1 continued hDAO-Fc-Hepmut4

ATGCCGGCCCTGGGCTGGGCCGTGGCTGCCATCCTGATGCTGCAGACGGCCATGGCGGA
GCCCTCCCCGGGGACTCTGCCCAGGAAGGCAGGGGTGTTTTCAGACCTAAGCAACCAAGAGCTGA
AGGCAGTGCACAGCTTCCTCTGGTCCAAGAAGGAGCTGAGGCTGCAGCCCTCCAGTACCACCACC
ATGGCCAAGAACACCGTGTTTCTCATCGAGATGCTGCTGCCCAAGAAGTACCATGTGCTGAGGTTT
CTGGATAAAGGTGAAAGGCATCCTGTGCGGGAAGCCCGTGCCGTCATCTTCTTTGGTGACCAGGA
GCATCCCAATGTCACCGAGTTTGCTGTGGGGCCCCTGCCAGGGCCCTGCTACATGCGAGCACTGT
CCCCCAGGCCTGGGTACCAGTCCTCCTGGGCATCGAGGCCCATCTCCACAGCAGAGTATGCCCTC
CTCTACCACACCCTGCAGGAAGCCACCAAGCCCCTGCATCAGTTCTTCCTCAATACCACAGGCTTC
TCATTCCAAGACTGCCATGACAGATGCCTGGCCTTCACCGATGTGGCCCCCCGGGGTGTGGCTTC
TGGCCAGCGCCGCAGTTGGCTTATCATACAGCGCTATGTAGAAGGCTACTTTCTGCACCCCACTGG
GCTGGAGCTCCTCGTGGATCATGGGAGCACAGATGCTGGGCACTGGGCCGTGGAGCAGGTGTGG
TACAACGGGAAGTTCTATGGGAGCCCAGAGGAACTGGCTCGGAAGTATGCAGATGGAGAGGTGGA
CGTGGTGGTCCTGGAGGACCCGCTGCCTGGGGGCAAGGGGCATGACAGCACAGAGGAGCCGCC
CCTCTTCTCCTCCCACAAGCCCCGCGGGGACTTCCCCAGCCCCATCCATGTGAGCGGCCCCCGCT
TGGTCCAGCCCCACGGCCCTCGCTTCAGGCTGGAGGGCAACGCTGTGCTCTACGGCGGCTGGAG
CTTTGCCTTCCGGCTGCGCTCCTCCTCCGGGCTGCAGGTCCTGAACGTGCACTTCGGCGGAGAGC
GCATTGCCTATGAGGTCAGCGTGCAAGAGGCAGTGGCGCTGTATGGAGGACACACACCTGCAGGC
ATGCAGACCAAGTACCTCGATGTCGGCTGGGGCCTGGGCAGCGTCACTCATGAGTTAGCCCCCGG
CATCGACTGCCCGGAGACCGCCACCTTCCTGGACACTTTCCACTACTATGATGCCGATGACCCGGT
CCATTATCCCCGAGCCCTCTGCCTCTTTGAAATGCCCACAGGGGTGCCCCTTCGGCGGCACTTTAA
TTCCAACTTTAAAGGTGGCTTCAACTTCTATGCGGGGCTGAAGGGCCAGGTGCTGGTGCTGCGGA
CAACTTCAACTGTCTACAATTATGATTACATTTGGGACTTTATCTTCTACCCCAACGGGGTGATGGA
GGCCAAGATGCATGCCACTGGCTACGTCCACGCCACCTTCTACACCCCCGAGGGGCTGCGCCAC
GGCACTCGCCTGCACACCCACCTGATTGGCAACATACACACTCACTTGGTGCACTACCGCGTAGAC
CTGGATGTGGCAGGCACCAAGAACAGCTTCCAGACACTGCAGATGAAGCTAGAAAACATCACCAAC
CCCTGGAGCCCAAGACACCGCGTGGTCCAGCCAACTCTGGAGCAGACGCAGTACTCCTGGGAGC
GCCAGGCGGCCTTCAGCTTCAAAACGAAGCTGCCCAAGTACCTGCTCTTTACCAGCCCCCAGGAG
AACCCCTGGGGCCACAAGCGCAGCTACCGCCTGCAGATCCACTCCATGGCCGACCAGGTGCTGC
CCCCAGGCTGGCAGGAGGAGCAGGCCATCACCTGGGCAAGGTACCCCCTGGCAGTGACCAAGTA
CCGGGAGTCGGAGCTGTGCAGCAGCAGCATCTACCACCAGAACGACCCCTGGCACCCGCCCGTG
GTCTTTGAGCAGTTTCTTCACAACAACGAGAACATTGAAAATGAGGACCTGGTGGCCTGGGTGACG
GTGGGCTTCCTGCACATCCCCCACTCAGAGGACATTCCCAACACAGCCACACCTGGGAACTCCGT
GGGCTTCCTGCTCCGGCCATTCAACTTCTTCCCAGAGGACCCCTCCCTGGCATCCAGAGACACTGT
GATCGTGTGGCCTCGGGACAACGGCCCCAACTACGTCCAGCGCTGGATCCCTGAGGACAGGGAC
TGCTCGATGCCTCCCCCTTTTAGCTACAATGGGACCTATAGACCTGTG*GAGCCCAAGTCCGCCGA*
*CAAGACCCACACCTGCCCCCCCTGCCCCGCCCCCCCCGTGGCCGGCCCCTCCGTGTTCCTGTTC*
*CCCCCCAAGCCCAAGGACACCCTGATGATCTCCAGGACCCCCGAGGTGACCTGCGTGGTGGTG*
*GACGTGTCCCACGAGGACCCCGAGGTGAAGTTCAACTGGTACGTGGACGGCGTGGAGGTGCAC*
*AACGCCAAGACCAAGCCCAGGGAGGAGCAGTACAACTCCACCTACAGGGTGGTGTCCGTGCTG*
*ACCGTGCTGCACCAGGACTGGCTGAACGGCAAGGAGTACAAGTGCAAGGTGTCCAACAAGGGC*
*CTGCCCTCCTCCATCGAGAAGACCATCTCCAAGGCCAAGGGCCAGCCCAGGGAGCCCCAGGTG*
*TACACCCTGCCCCCCTCCAGGGAGGAGATGACCAAGAACCAGGTGTCCCTGACCTGCCTGGTGA*
*AGGGCTTCTACCCCTCCGACATCGCCGTGGAGTGGGAGTCCAACGGCCAGCCCGAGAACAACT*
*ACAAGACCACCCCCCCCGTGCTGGACTCCGACGGCTCCTTCTTCCTGTACTCCAAGCTGACCGT*
*GGACAAGTCCAGGTGGCAGCAGGGCAACGTGTTCTCCTGCTCCGTGATGCACGAGGCCCTGCAC*
*AACCACTACACCCAGAAGTCCCTGTCCCTGTCCCCCGGCAAGTGA* (SEQ ID NO:91)

hDAO-Fc-Hepmut5

ATGCCGGCCCTGGGCTGGGCCGTGGCTGCCATCCTGATGCTGCAGACGGCCATGGCGGA
GCCCTCCCCGGGGACTCTGCCCAGGAAGGCAGGGGTGTTTTCAGACCTAAGCAACCAAGAGCTGA
AGGCAGTGCACAGCTTCCTCTGGTCCAAGAAGGAGCTGAGGCTGCAGCCCTCCAGTACCACCACC
ATGGCCAAGAACACCGTGTTTCTCATCGAGATGCTGCTGCCCAAGAAGTACCATGTGCTGAGGTTT
CTGGATAAAGGTGAAAGGCATCCTGTGCGGGAAGCCCGTGCCGTCATCTTCTTTGGTGACCAGGA
GCATCCCAATGTCACCGAGTTTGCTGTGGGGCCCCTGCCAGGGCCCTGCTACATGCGAGCACTGT
CCCCCAGGCCTGGGTACCAGTCCTCCTGGGCATCGAGGCCCATCTCCACAGCAGAGTATGCCCTC
CTCTACCACACCCTGCAGGAAGCCACCAAGCCCCTGCATCAGTTCTTCCTCAATACCACAGGCTTC
TCATTCCAAGACTGCCATGACAGATGCCTGGCCTTCACCGATGTGGCCCCCCGGGGTGTGGCTTC

Figure 1 continued

TGGCCAGCGCCGCAGTTGGCTTATCATACAGCGCTATGTAGAAGGCTACTTTCTGCACCCCACTGG
GCTGGAGCTCCTCGTGGATCATGGGAGCACAGATGCTGGGCACTGGGCCGTGGAGCAGGTGTGG
TACAACGGGAAGTTCTATGGGAGCCCAGAGGAACTGGCTCGGAAGTATGCAGATGGAGAGGTGGA
CGTGGTGGTCCTGGAGGACCCGCTGCCTGGGGGCAAGGGGCATGACAGCACAGAGGAGCCGCC
CCTCTTCTCCTCCCACAAGCCCCGCGGGGACTTCCCCAGCCCCATCCATGTGAGCGGCCCCCGCT
TGGTCCAGCCCCACGGCCCTCGCTTCAGGCTGGAGGGCAACGCTGTGCTCTACGGCGGCTGGAG
CTTTGCCTTCCGGCTGCGCTCCTCCTCCGGGCTGCAGGTCCTGAACGTGCACTTCGGCGGAGAGC
GCATTGCCTATGAGGTCAGCGTGCAAGAGGCAGTGGCGCTGTATGGAGGACACACACCTGCAGGC
ATGCAGACCAAGTACCTCGATGTCGGCTGGGGCCTGGGCAGCGTCACTCATGAGTTAGCCCCCGG
CATCGACTGCCCGGAGACCGCCACCTTCCTGGACACTTTCCACTACTATGATGCCGATGACCCGGT
CCATTATCCCCGAGCCCTCTGCCTCTTTGAAATGCCCACAGGGGTGCCCCTTCGGCGGCACTTTAA
TTCCAACTTTAAAGGTGGCTTCAACTTCTATGCGGGGCTGAAGGGCCAGGTGCTGGTGCTGCGGA
CAACTTCAACTGTCTACAATTATGATTACATTTGGGACTTTATCTTCTACCCCAACGGGGTGATGGA
GGCCAAGATGCATGCCACTGGCTACGTCCACGCCACCTTCTACACCCCCGAGGGGCTGCGCCAC
GGCACTCGCCTGCACACCCACCTGATTGGCAACATACACACTCACTTGGTGCACTACCGCGTAGAC
CTGGATGTGGCAGGCACCAAGAACAGCTTCCAGACACTGCAGATGAAGCTAGAAAACATCACCAAC
CCCTGGAGCCCAAGACACCGCGTGGTCCAGCCAACTCTGGAGCAGACGCAGTACTCCTGGGAGC
GCCAGGCGGCCTTCCGCTTCAAAACGAAGCTGCCCACGTACCTGCTCTTTACCAGCCCCCAGGAG
AACCCCTGGGGCCACAAGCGCAGCTACCGCCTGCAGATCCACTCCATGGCCGACCAGGTGCTGC
CCCCAGGCTGGCAGGAGGAGCAGGCCATCACCTGGGCAAGGTACCCCCTGGCAGTGACCAAGTA
CCGGGAGTCGGAGCTGTGCAGCAGCAGCATCTACCACCAGAACGACCCCTGGCACCCGCCCGTG
GTCTTTGAGCAGTTTCTTCACAACAACGAGAACATTGAAAATGAGGACCTGGTGGCCTGGGTGACG
GTGGGCTTCCTGCACATCCCCCACTCAGAGGACATTCCCAACACAGCCACACCTGGGAACTCCGT
GGGCTTCCTGCTCCGGCCATTCAACTTCTTCCCAGAGGACCCCTCCCTGGCATCCAGAGACACTGT
GATCGTGTGGCCTCGGGACAACGGCCCCAACTACGTCCAGCGCTGGATCCCTGAGGACAGGGAC
TGCTCGATGCCTCCCCCTTTTAGCTACAATGGACCTATAGACCTGTG*GAGCCCAAGTCCGCCGA*
*CAAGACCCACACCTGCCCCCCCTGCCCCGCCCCCCCCGTGGCCGGCCCCTCCGTGTTCCTGTTC*
*CCCCCCAAGCCCAAGGACACCCTGATGATCTCCAGGACCCCCGAGGTGACCTGCGTGGTGGTG*
*GACGTGTCCCACGAGGACCCCGAGGTGAAGTTCAACTGGTACGTGGACGGCGTGGAGGTGCAC*
*AACGCCAAGACCAAGCCCAGGGAGGAGCAGTACAACTCCACCTACAGGGTGGTGTCCGTGCTG*
*ACCGTGCTGCACCAGGACTGGCTGAACGGCAAGGAGTACAAGTGCAAGGTGTCCAACAAGGGC*
*CTGCCCTCCTCCATCGAGAAGACCATCTCCAAGGCCAAGGGCCAGCCCAGGGAGCCCCAGGTG*
*TACACCCTGCCCCCCTCCAGGGAGGAGATGACCAAGAACCAGGTGTCCCTGACCTGCCTGGTGA*
*AGGGCTTCTACCCCTCCGACATCGCCGTGGAGTGGGAGTCCAACGGCCAGCCCGAGAACAACT*
*ACAAGACCACCCCCCCCGTGCTGGACTCCGACGGCTCCTTCTTCCTGTACTCCAAGCTGACCGT*
*GGACAAGTCCAGGTGGCAGCAGGGCAACGTGTTCTCCTGCTCCGTGATGCACGAGGCCCTGCAC*
*AACCACTACACCCAGAAGTCCCTGTCCCTGTCCCCCGGCAAGTGA* (SEQ ID NO:92)

hDAO-Fc-Hepmut6

ATGCCGGCCCTGGGCTGGGCCGTGGCTGCCATCCTGATGCTGCAGACGGCCATGGCGGA
GCCCTCCCCGGGGACTCTGCCCAGGAAGGCAGGGGTGTTTTCAGACCTAAGCAACCAAGAGCTGA
AGGCAGTGCACAGCTTCCTCTGGTCCAAGAAGGAGCTGAGGCTGCAGCCCTCCAGTACCACCACC
ATGGCCAAGAACACCGTGTTTCTCATCGAGATGCTGCTGCCCAAGAAGTACCATGTGCTGAGGTTT
CTGGATAAAGGTGAAAGGCATCCTGTGCGGGAAGCCCGTGCCGTCATCTTCTTTGGTGACCAGGA
GCATCCCAATGTCACCGAGTTTGCTGTGGGGCCCCTGCCAGGGCCCTGCTACATGCGAGCACTGT
CCCCCAGGCCTGGGTACCAGTCCTCCTGGGCATCGAGGCCCATCTCCACAGCAGAGTATGCCCTC
CTCTACCACACCCTGCAGGAAGCCACCAAGCCCCTGCATCAGTTCTTCCTCAATACCACAGGCTTC
TCATTCCAAGACTGCCATGACAGATGCCTGGCCTTCACCGATGTGGCCCCCCGGGGTGTGGCTTC
TGGCCAGCGCCGCAGTTGGCTTATCATACAGCGCTATGTAGAAGGCTACTTTCTGCACCCCACTGG
GCTGGAGCTCCTCGTGGATCATGGGAGCACAGATGCTGGGCACTGGGCCGTGGAGCAGGTGTGG
TACAACGGGAAGTTCTATGGGAGCCCAGAGGAACTGGCTCGGAAGTATGCAGATGGAGAGGTGGA
CGTGGTGGTCCTGGAGGACCCGCTGCCTGGGGGCAAGGGGCATGACAGCACAGAGGAGCCGCC
CCTCTTCTCCTCCCACAAGCCCCGCGGGGACTTCCCCAGCCCCATCCATGTGAGCGGCCCCCGCT
TGGTCCAGCCCCACGGCCCTCGCTTCAGGCTGGAGGGCAACGCTGTGCTCTACGGCGGCTGGAG
CTTTGCCTTCCGGCTGCGCTCCTCCTCCGGGCTGCAGGTCCTGAACGTGCACTTCGGCGGAGAGC
GCATTGCCTATGAGGTCAGCGTGCAAGAGGCAGTGGCGCTGTATGGAGGACACACACCTGCAGGC
ATGCAGACCAAGTACCTCGATGTCGGCTGGGGCCTGGGCAGCGTCACTCATGAGTTAGCCCCCGG
CATCGACTGCCCGGAGACCGCCACCTTCCTGGACACTTTCCACTACTATGATGCCGATGACCCGGT
CCATTATCCCCGAGCCCTCTGCCTCTTTGAAATGCCCACAGGGGTGCCCCTTCGGCGGCACTTTAA

Figure 1 continued

TTCCAACTTTAAAGGTGGCTTCAACTTCTATGCGGGGCTGAAGGGCCAGGTGCTGGTGCTGCGGA
CAACTTCAACTGTCTACAATTATGATTACATTTGGGACTTTATCTTCTACCCCAACGGGGTGATGGA
GGCCAAGATGCATGCCACTGGCTACGTCCACGCCACCTTCTACACCCCCGAGGGGCTGCGCCAC
GGCACTCGCCTGCACACCCACCTGATTGGCAACATACACACTCACTTGGTGCACTACCGCGTAGAC
CTGGATGTGGCAGGCACCAAGAACAGCTTCCAGACACTGCAGATGAAGCTAGAAAACATCACCAAC
CCCTGGAGCCCAAGACACCGCGTGGTCCAGCCAACTCTGGAGCAGACGCAGTACTCCTGGGAGC
GCCAGGCGGCCTTCCGCTTCGGACAGACGCTGCCCAAGTACCTGCTCTTTACCAGCCCCCAGGA
GAACCCCTGGGGCCACAAGCGCAGCTACCGCCTGCAGATCCACTCCATGGCCGACCAGGTGCTG
CCCCCAGGCTGGCAGGAGGAGCAGGCCATCACCTGGGCAAGGTACCCCCTGGCAGTGACCAAGT
ACCGGGAGTCGGAGCTGTGCAGCAGCAGCATCTACCACCAGAACGACCCCTGGCACCCGCCCGT
GGTCTTTGAGCAGTTTCTTCACAACAACGAGAACATTGAAAATGAGGACCTGGTGGCCTGGGTGAC
GGTGGGCTTCCTGCACATCCCCCACTCAGAGGACATTCCCAACACAGCCACACCTGGGAACTCCG
TGGGCTTCCTGCTCCGGCCATTCAACTTCTTCCCAGAGGACCCCTCCCTGGCATCCAGAGACACTG
TGATCGTGTGGCCTCGGGACAACGGCCCCAACTACGTCCAGCGCTGGATCCCTGAGGACAGGGA
CTGCTCGATGCCTCCCCCTTTTAGCTACAATGGGACCTATAGACCTGTG*GAGCCCAAGTCCGCCG*
*ACAAGACCCACACCTGCCCCCCCTGCCCCGCCCCCCCCGTGGCCGGCCCCTCCGTGTTCCTGTT*
*CCCCCCCAAGCCCAAGGACACCCTGATGATCTCCAGGACCCCCGAGGTGACCTGCGTGGTGGT*
*GGACGTGTCCCACGAGGACCCCGAGGTGAAGTTCAACTGGTACGTGGACGGCGTGGAGGTGCA*
*CAACGCCAAGACCAAGCCCAGGGAGGAGCAGTACAACTCCACCTACAGGGTGGTGTCCGTGCT*
*GACCGTGCTGCACCAGGACTGGCTGAACGGCAAGGAGTACAAGTGCAAGGTGTCCAACAAGGG*
*CCTGCCCTCCTCCATCGAGAAGACCATCTCCAAGGCCAAGGGCCAGCCCAGGGAGCCCCAGGT*
*GTACACCCTGCCCCCCTCCAGGGAGGAGATGACCAAGAACCAGGTGTCCCTGACCTGCCTGGTG*
*AAGGGCTTCTACCCCTCCGACATCGCCGTGGAGTGGGAGTCCAACGGCCAGCCCGAGAACAAC*
*TACAAGACCACCCCCCCCGTGCTGGACTCCGACGGCTCCTTCTTCCTGTACTCCAAGCTGACCGT*
*GGACAAGTCCAGGTGGCAGCAGGGCAACGTGTTCTCCTGCTCCGTGATGCACGAGGCCCTGCAC*
*AACCACTACACCCAGAAGTCCCTGTCCCTGTCCCCCGGCAAGTGA* (SEQ ID NO:93)

hDAO-Fc-Hepmut7

ATGCCGGCCCTGGGCTGGGCCGTGGCTGCCATCCTGATGCTGCAGACGGCCATGGCGGA
GCCCTCCCCGGGGACTCTGCCCAGGAAGGCAGGGGTGTTTTCAGACCTAAGCAACCAAGAGCTGA
AGGCAGTGCACAGCTTCCTCTGGTCCAAGAAGGAGCTGAGGCTGCAGCCCTCCAGTACCACCACC
ATGGCCAAGAACACCGTGTTTCTCATCGAGATGCTGCTGCCCAAGAAGTACCATGTGCTGAGGTTT
CTGGATAAAGGTGAAAGGCATCCTGTGCGGGAAGCCCGTGCCGTCATCTTCTTTGGTGACCAGGA
GCATCCCAATGTCACCGAGTTTGCTGTGGGGCCCCTGCCAGGGCCCTGCTACATGCGAGCACTGT
CCCCCAGGCCTGGGTACCAGTCCTCCTGGGCATCGAGGCCCATCTCCACAGCAGAGTATGCCCTC
CTCTACCACACCCTGCAGGAAGCCACCAAGCCCCTGCATCAGTTCTTCCTCAATACCACAGGCTTC
TCATTCCAAGACTGCCATGACAGATGCCTGGCCTTCACCGATGTGGCCCCCCGGGGTGTGGCTTC
TGGCCAGCGCCGCAGTTGGCTTATCATACAGCGCTATGTAGAAGGCTACTTTCTGCACCCCACTGG
GCTGGAGCTCCTCGTGGATCATGGAGCACAGATGCTGGGCACTGGGCCGTGGAGCAGGTGTGG
TACAACGGGAAGTTCTATGGGAGCCCAGAGGAACTGGCTCGGAAGTATGCAGATGGAGAGGTGGA
CGTGGTGGTCCTGGAGGACCCGCTGCCTGGGGGCAAGGGGCATGACAGCACAGAGGAGCCGCC
CCTCTTCTCCTCCCACAAGCCCCGCGGGGACTTCCCCAGCCCCATCCATGTGAGCGGCCCCCGCT
TGGTCCAGCCCCACGGCCCTCGCTTCAGGCTGGAGGGCAACGCTGTGCTCTACGGCGGCTGGAG
CTTTGCCTTCCGGCTGCGCTCCTCCTCCGGGCTGCAGGTCCTGAACGTGCACTTCGGCGGAGAGC
GCATTGCCTATGAGGTCAGCGTGCAAGAGGCAGTGGCGCTGTATGGAGGACACACACCTGCAGGC
ATGCAGACCAAGTACCTCGATGTCGGCTGGGGCCTGGGCAGCGTCACTCATGAGTTAGCCCCCGG
CATCGACTGCCCGGAGACCGCCACCTTCCTGGACACTTTCCACTACTATGATGCCGATGACCCGGT
CCATTATCCCCGAGCCCTCTGCCTCTTTGAAATGCCCACAGGGGTGCCCCTTCGGCGGCACTTTAA
TTCCAACTTTAAAGGTGGCTTCAACTTCTATGCGGGGCTGAAGGGCCAGGTGCTGGTGCTGCGGA
CAACTTCAACTGTCTACAATTATGATTACATTTGGGACTTTATCTTCTACCCCAACGGGGTGATGGA
GGCCAAGATGCATGCCACTGGCTACGTCCACGCCACCTTCTACACCCCCGAGGGGCTGCGCCAC
GGCACTCGCCTGCACACCCACCTGATTGGCAACATACACACTCACTTGGTGCACTACCGCGTAGAC
CTGGATGTGGCAGGCACCAAGAACAGCTTCCAGACACTGCAGATGAAGCTAGAAAACATCACCAAC
CCCTGGAGCCCAAGACACCGCGTGGTCCAGCCAACTCTGGAGCAGACGCAGTACTCCTGGGAGC
GCCAGGCGGCCTTCAGCTTCAAAAGGAAGCTGCCCACGTACCTGCTCTTTACCAGCCCCCAGGAG
AACCCCTGGGGCCACAAGCGCAGCTACCGCCTGCAGATCCACTCCATGGCCGACCAGGTGCTGC
CCCCAGGCTGGCAGGAGGAGCAGGCCATCACCTGGGCAAGGTACCCCCTGGCAGTGACCAAGTA
CCGGGAGTCGGAGCTGTGCAGCAGCAGCATCTACCACCAGAACGACCCCTGGCACCCGCCCGTG

Figure 1 continued

GTCTTTGAGCAGTTTCTTCACAACAACGAGAACATTGAAAATGAGGACCTGGTGGCCTGGGTGACG
GTGGGCTTCCTGCACATCCCCCACTCAGAGGACATTCCCAACACAGCCACACCTGGGAACTCCGT
GGGCTTCCTGCTCCGGCCATTCAACTTCTTCCCAGAGGACCCCTCCCTGGCATCCAGAGACACTGT
GATCGTGTGGCCTCGGGACAACGGCCCCAACTACGTCCAGCGCTGGATCCCTGAGGACAGGGAC
TGCTCGATGCCTCCCCCTTTTAGCTACAATGGGACCTATAGACCTGTG*GAGCCCAAGTCCGCCGA*
*CAAGACCCACACCTGCCCCCCCTGCCCCGCCCCCCCCGTGGCCGGCCCCTCCGTGTTCCTGTTC*
*CCCCCCAAGCCCAAGGACACCCTGATGATCTCCAGGACCCCCGAGGTGACCTGCGTGGTGGTG*
*GACGTGTCCCACGAGGACCCCGAGGTGAAGTTCAACTGGTACGTGGACGGCGTGGAGGTGCAC*
*AACGCCAAGACCAAGCCCAGGGAGGAGCAGTACAACTCCACCTACAGGGTGGTGTCCGTGCTG*
*ACCGTGCTGCACCAGGACTGGCTGAACGGCAAGGAGTACAAGTGCAAGGTGTCCAACAAGGGC*
*CTGCCCTCCTCCATCGAGAAGACCATCTCCAAGGCCAAGGGCCAGCCCAGGGAGCCCCAGGTG*
*TACACCCTGCCCCCCTCCAGGGAGGAGATGACCAAGAACCAGGTGTCCCTGACCTGCCTGGTGA*
*AGGGCTTCTACCCCTCCGACATCGCCGTGGAGTGGGAGTCCAACGGCCAGCCCGAGAACAACT*
*ACAAGACCACCCCCCCCGTGCTGGACTCCGACGGCTCCTTCTTCCTGTACTCCAAGCTGACCGT*
*GGACAAGTCCAGGTGGCAGCAGGGCAACGTGTTCTCCTGCTCCGTGATGCACGAGGCCCTGCAC*
*AACCACTACACCCAGAAGTCCCTGTCCCTGTCCCCCGGCAAGTGA* (SEQ ID NO:94)

<u>hDAO-Fc-Cysmut</u>

ATGCCGGCCCTGGGCTGGGCCGTGGCTGCCATCCTGATGCTGCAGACGGCCATGGCGGA
GCCCTCCCCGGGGACTCTGCCCAGGAAGGCAGGGGTGTTTTCAGACCTAAGCAACCAAGAGCTGA
AGGCAGTGCACAGCTTCCTCTGGTCCAAGAAGGAGCTGAGGCTGCAGCCCTCCAGTACCACCACC
ATGGCCAAGAACACCGTGTTTCTCATCGAGATGCTGCTGCCCAAGAAGTACCATGTGCTGAGGTTT
CTGGATAAAGGTGAAAGGCATCCTGTGCGGGAAGCCCGTGCCGTCATCTTCTTTGGTGACCAGGA
GCATCCCAATGTCACCGAGTTTGCTGTGGGGCCCCTGCCAGGGCCCGCCTACATGCGAGCACTGT
CCCCCAGGCCTGGGTACCAGTCCTCCTGGGCATCGAGGCCCATCTCCACAGCAGAGTATGCCCTC
CTCTACCACACCCTGCAGGAAGCCACCAAGCCCCTGCATCAGTTCTTCCTCAATACCACAGGCTTC
TCATTCCAAGACTGCCATGACAGATGCCTGGCCTTCACCGATGTGGCCCCCCGGGGTGTGGCTTC
TGGCCAGCGCCGCAGTTGGCTTATCATACAGCGCTATGTAGAAGGCTACTTTCTGCACCCCACTGG
GCTGGAGCTCCTCGTGGATCATGGGAGCACAGATGCTGGGCACTGGGCCGTGGAGCAGGTGTGG
TACAACGGGAAGTTCTATGGGAGCCCAGAGGAACTGGCTCGGAAGTATGCAGATGGAGAGGTGGA
CGTGGTGGTCCTGGAGGACCCGCTGCCTGGGGGCAAGGGGCATGACAGCACAGAGGAGCCGCC
CCTCTTCTCCTCCCACAAGCCCCGCGGGGACTTCCCCAGCCCCATCCATGTGAGCGGCCCCCGCT
TGGTCCAGCCCCACGGCCCTCGCTTCAGGCTGGAGGGCAACGCTGTGCTCTACGGCGGCTGGAG
CTTTGCCTTCCGGCTGCGCTCCTCCTCCGGGCTGCAGGTCCTGAACGTGCACTTCGGCGGAGAGC
GCATTGCCTATGAGGTCAGCGTGCAAGAGGCAGTGGCGCTGTATGGAGGACACACACCTGCAGGC
ATGCAGACCAAGTACCTCGATGTCGGCTGGGGCCTGGGCAGCGTCACTCATGAGTTAGCCCCCGG
CATCGACTGCCCGGAGACCGCCACCTTCCTGGACACTTTCCACTACTATGATGCCGATGACCCGGT
CCATTATCCCCGAGCCCTCTGCCTCTTTGAAATGCCCACAGGGGTGCCCCTTCGGCGGCACTTTAA
TTCCAACTTTAAAGGTGGCTTCAACTTCTATGCGGGGCTGAAGGGCCAGGTGCTGGTGCTGCGGA
CAACTTCAACTGTCTACAATTATGATTACATTTGGGACTTTATCTTCTACCCCAACGGGGTGATGGA
GGCCAAGATGCATGCCACTGGCTACGTCCACGCCACCTTCTACACCCCCGAGGGGCTGCGCCAC
GGCACTCGCCTGCACACCCACCTGATTGGCAACATACACACTCACTTGGTGCACTACCGCGTAGAC
CTGGATGTGGCAGGCACCAAGAACAGCTTCCAGACACTGCAGATGAAGCTAGAAAACATCACCAAC
CCCTGGAGCCCAAGACACCGCGTGGTCCAGCCAACTCTGGAGCAGACGCAGTACTCCTGGGAGC
GCCAGGCGGCCTTCCGCTTCAAAAGGAAGCTGCCCAAGTACCTGCTCTTTACCAGCCCCCAGGAG
AACCCCTGGGGCCACAAGCGCAGCTACCGCCTGCAGATCCACTCCATGGCCGACCAGGTGCTGC
CCCCAGGCTGGCAGGAGGAGCAGGCCATCACCTGGGCAAGGTACCCCCTGGCAGTGACCAAGTA
CCGGGAGTCGGAGCTGTGCAGCAGCAGCATCTACCACCAGAACGACCCCTGGCACCCGCCCGTG
GTCTTTGAGCAGTTTCTTCACAACAACGAGAACATTGAAAATGAGGACCTGGTGGCCTGGGTGACG
GTGGGCTTCCTGCACATCCCCCACTCAGAGGACATTCCCAACACAGCCACACCTGGGAACTCCGT
GGGCTTCCTGCTCCGGCCATTCAACTTCTTCCCAGAGGACCCCTCCCTGGCATCCAGAGACACTGT
GATCGTGTGGCCTCGGGACAACGGCCCCAACTACGTCCAGCGCTGGATCCCTGAGGACAGGGAC
TGCTCGATGCCTCCCCCTTTTAGCTACAATGGGACCTATAGACCTGTG*GAGCCCAAGTCCGCCGA*
*CAAGACCCACACCTGCCCCCCCTGCCCCGCCCCCCCCGTGGCCGGCCCCTCCGTGTTCCTGTTC*
*CCCCCCAAGCCCAAGGACACCCTGATGATCTCCAGGACCCCCGAGGTGACCTGCGTGGTGGTG*
*GACGTGTCCCACGAGGACCCCGAGGTGAAGTTCAACTGGTACGTGGACGGCGTGGAGGTGCAC*
*AACGCCAAGACCAAGCCCAGGGAGGAGCAGTACAACTCCACCTACAGGGTGGTGTCCGTGCTG*
*ACCGTGCTGCACCAGGACTGGCTGAACGGCAAGGAGTACAAGTGCAAGGTGTCCAACAAGGGC*
*CTGCCCTCCTCCATCGAGAAGACCATCTCCAAGGCCAAGGGCCAGCCCAGGGAGCCCCAGGTG*

Figure 1 continued

*TACACCCTGCCCCCCTCCAGGGAGGAGATGACCAAGAACCAGGTGTCCCTGACCTGCCTGGTGA*
*AGGGCTTCTACCCCTCCGACATCGCCGTGGAGTGGGAGTCCAACGGCCAGCCCGAGAACAACT*
*ACAAGACCACCCCCCCCGTGCTGGACTCCGACGGCTCCTTCTTCCTGTACTCCAAGCTGACCGT*
*GGACAAGTCCAGGTGGCAGCAGGGCAACGTGTTCTCCTGCTCCGTGATGCACGAGGCCCTGCAC*
*AACCACTACACCCAGAAGTCCCTGTCCCTGTCCCCCGGCAAGTGA*(SEQ ID NO:95)

<u>hDAO-Fc-Hepmut1-Cysmut</u>

ATGCCGGCCCTGGGCTGGGCCGTGGCTGCCATCCTGATGCTGCAGACGGCCATGGCGGA
GCCCTCCCCGGGGACTCTGCCCAGGAAGGCAGGGGTGTTTTCAGACCTAAGCAACCAAGAGCTGA
AGGCAGTGCACAGCTTCCTCTGGTCCAAGAAGGAGCTGAGGCTGCAGCCCTCCAGTACCACCACC
ATGGCCAAGAACACCGTGTTTCTCATCGAGATGCTGCTGCCCAAGAAGTACCATGTGCTGAGGTTT
CTGGATAAAGGTGAAAGGCATCCTGTGCGGGAAGCCCGTGCCGTCATCTTCTTTGGTGACCAGGA
GCATCCCAATGTCACCGAGTTTGCTGTGGGGCCCCTGCCAGGGCCCGCCTACATGCGAGCACTGT
CCCCCAGGCCTGGGTACCAGTCCTCCTGGGCATCGAGGCCCATCTCCACAGCAGAGTATGCCCTC
CTCTACCACACCCTGCAGGAAGCCACCAAGCCCCTGCATCAGTTCTTCCTCAATACCACAGGCTTC
TCATTCCAAGACTGCCATGACAGATGCCTGGCCTTCACCGATGTGGCCCCCCGGGGTGTGGCTTC
TGGCCAGCGCCGCAGTTGGCTTATCATACAGCGCTATGTAGAAGGCTACTTTCTGCACCCCACTGG
GCTGGAGCTCCTCGTGGATCATGGGAGCACAGATGCTGGGCACTGGGCCGTGGAGCAGGTGTGG
TACAACGGGAAGTTCTATGGGAGCCCAGAGGAACTGGCTCGGAAGTATGCAGATGGAGAGGTGGA
CGTGGTGGTCCTGGAGGACCCGCTGCCTGGGGGCAAGGGGCATGACAGCACAGAGGAGCCGCC
CCTCTTCTCCTCCCACAAGCCCCGCGGGGACTTCCCCAGCCCCATCCATGTGAGCGGCCCCCGCT
TGGTCCAGCCCCACGGCCCTCGCTTCAGGCTGGAGGGCAACGCTGTGCTCTACGGCGGCTGGAG
CTTTGCCTTCCGGCTGCGCTCCTCCTCCGGGCTGCAGGTCCTGAACGTGCACTTCGGCGGAGAGC
GCATTGCCTATGAGGTCAGCGTGCAAGAGGCAGTGGCGCTGTATGGAGGACACACACCTGCAGGC
ATGCAGACCAAGTACCTCGATGTCGGCTGGGGCCTGGGCAGCGTCACTCATGAGTTAGCCCCCGG
CATCGACTGCCCGGAGACCGCCACCTTCCTGGACACTTTCCACTACTATGATGCCGATGACCCGGT
CCATTATCCCCGAGCCCTCTGCCTCTTTGAAATGCCCACAGGGGTGCCCCTTCGGCGGCACTTTAA
TTCCAACTTTAAAGGTGGCTTCAACTTCTATGCGGGGCTGAAGGGCCAGGTGCTGGTGCTGCGGA
CAACTTCAACTGTCTACAATTATGATTACATTTGGGACTTTATCTTCTACCCCAACGGGGTGATGGA
GGCCAAGATGCATGCCACTGGCTACGTCCACGCCACCTTCTACACCCCCGAGGGGCTGCGCCAC
GGCACTCGCCTGCACACCCACCTGATTGGCAACATACACACTCACTTGGTGCACTACCGCGTAGAC
CTGGATGTGGCAGGCACCAAGAACAGCTTCCAGACACTGCAGATGAAGCTAGAAAACATCACCAAC
CCCTGGAGCCCAAGACACCGCGTGGTCCAGCCAACTCTGGAGCAGACGCAGTACTCCTGGGAGC
GCCAGGCGGCCTTCAGCTTCAAAAGGAAGCTGCCCAAGTACCTGCTCTTTACCAGCCCCCAGGAG
AACCCCTGGGGCCACAAGCGCAGCTACCGCCTGCAGATCCACTCCATGGCCGACCAGGTGCTGC
CCCCAGGCTGGCAGGAGGAGCAGGCCATCACCTGGGCAAGGTACCCCCTGGCAGTGACCAAGTA
CCGGGAGTCGGAGCTGTGCAGCAGCAGCATCTACCACCAGAACGACCCCTGGCACCCGCCCGTG
GTCTTTGAGCAGTTTCTTCACAACAACGAGAACATTGAAAATGAGGACCTGGTGGCCTGGGTGACG
GTGGGCTTCCTGCACATCCCCCACTCAGAGGACATTCCCAACACAGCCACACCTGGGAACTCCGT
GGGCTTCCTGCTCCGGCCATTCAACTTCTTCCCAGAGGACCCCTCCCTGGCATCCAGAGACACTGT
GATCGTGTGGCCTCGGGACAACGGCCCCAACTACGTCCAGCGCTGGATCCCTGAGGACAGGGAC
TGCTCGATGCCTCCCCCTTTTAGCTACAATGGGACCTATAGACCTGTG*GAGCCCAAGTCCGCCGA*
*CAAGACCCACACCTGCCCCCCCTGCCCCGCCCCCCCCGTGGCCGGCCCCTCCGTGTTCCTGTTC*
*CCCCCCAAGCCCAAGGACACCCTGATGATCTCCAGGACCCCCGAGGTGACCTGCGTGGTGGTG*
*GACGTGTCCCACGAGGACCCCGAGGTGAAGTTCAACTGGTACGTGGACGGCGTGGAGGTGCAC*
*AACGCCAAGACCAAGCCCAGGGAGGAGCAGTACAACTCCACCTACAGGGTGGTGTCCGTGCTG*
*ACCGTGCTGCACCAGGACTGGCTGAACGGCAAGGAGTACAAGTGCAAGGTGTCCAACAAGGGC*
*CTGCCCTCCTCCATCGAGAAGACCATCTCCAAGGCCAAGGGCCAGCCCAGGGAGCCCCAGGTG*
*TACACCCTGCCCCCCTCCAGGGAGGAGATGACCAAGAACCAGGTGTCCCTGACCTGCCTGGTGA*
*AGGGCTTCTACCCCTCCGACATCGCCGTGGAGTGGGAGTCCAACGGCCAGCCCGAGAACAACT*
*ACAAGACCACCCCCCCCGTGCTGGACTCCGACGGCTCCTTCTTCCTGTACTCCAAGCTGACCGT*
*GGACAAGTCCAGGTGGCAGCAGGGCAACGTGTTCTCCTGCTCCGTGATGCACGAGGCCCTGCAC*
*AACCACTACACCCAGAAGTCCCTGTCCCTGTCCCCCGGCAAGTGA* (SEQ ID NO:96)

Figure 1 continued hDAO-Fc-Hepmut2-Cysmut

ATGCCGGCCCTGGGCTGGGCCGTGGCTGCCATCCTGATGCTGCAGACGGCCATGGCGGA
GCCCTCCCCGGGGACTCTGCCCAGGAAGGCAGGGGTGTTTTCAGACCTAAGCAACCAAGAGCTGA
AGGCAGTGCACAGCTTCCTCTGGTCCAAGAAGGAGCTGAGGCTGCAGCCCTCCAGTACCACCACC
ATGGCCAAGAACACCGTGTTTCTCATCGAGATGCTGCTGCCCAAGAAGTACCATGTGCTGAGGTTT
CTGGATAAAGGTGAAAGGCATCCTGTGCGGGAAGCCCGTGCCGTCATCTTCTTTGGTGACCAGGA
GCATCCCAATGTCACCGAGTTTGCTGTGGGGCCCCTGCCAGGGCCCGCCTACATGCGAGCACTGT
CCCCCAGGCCTGGGTACCAGTCCTCCTGGGCATCGAGGCCCATCTCCACAGCAGAGTATGCCCTC
CTCTACCACACCCTGCAGGAAGCCACCAAGCCCCTGCATCAGTTCTTCCTCAATACCACAGGCTTC
TCATTCCAAGACTGCCATGACAGATGCCTGGCCTTCACCGATGTGGCCCCCCGGGGTGTGGCTTC
TGGCCAGCGCCGCAGTTGGCTTATCATACAGCGCTATGTAGAAGGCTACTTTCTGCACCCCACTGG
GCTGGAGCTCCTCGTGGATCATGGGAGCACAGATGCTGGGCACTGGGCCGTGGAGCAGGTGTGG
TACAACGGGAAGTTCTATGGGAGCCCAGAGGAACTGGCTCGGAAGTATGCAGATGGAGAGGTGGA
CGTGGTGGTCCTGGAGGACCCGCTGCCTGGGGGCAAGGGGCATGACAGCACAGAGGAGCCGCC
CCTCTTCTCCTCCCACAAGCCCCGCGGGGACTTCCCCAGCCCCATCCATGTGAGCGGCCCCCGCT
TGGTCCAGCCCCACGGCCCTCGCTTCAGGCTGGAGGGCAACGCTGTGCTCTACGGCGGCTGGAG
CTTTGCCTTCCGGCTGCGCTCCTCCTCCGGGCTGCAGGTCCTGAACGTGCACTTCGGCGGAGAGC
GCATTGCCTATGAGGTCAGCGTGCAAGAGGCAGTGGCGCTGTATGGAGGACACACACCTGCAGGC
ATGCAGACCAAGTACCTCGATGTCGGCTGGGGCCTGGGCAGCGTCACTCATGAGTTAGCCCCCGG
CATCGACTGCCCGGAGACCGCCACCTTCCTGGACACTTTCCACTACTATGATGCCGATGACCCGGT
CCATTATCCCCGAGCCCTCTGCCTCTTTGAAATGCCCACAGGGGTGCCCCTTCGGCGGCACTTTAA
TTCCAACTTTAAAGGTGGCTTCAACTTCTATGCGGGGCTGAAGGGCCAGGTGCTGGTGCTGCGGA
CAACTTCAACTGTCTACAATTATGATTACATTTGGGACTTTATCTTCTACCCCAACGGGGTGATGGA
GGCCAAGATGCATGCCACTGGCTACGTCCACGCCACCTTCTACACCCCCGAGGGGCTGCGCCAC
GGCACTCGCCTGCACACCCACCTGATTGGCAACATACACACTCACTTGGTGCACTACCGCGTAGAC
CTGGATGTGGCAGGCACCAAGAACAGCTTCCAGACACTGCAGATGAAGCTAGAAAACATCACCAAC
CCCTGGAGCCCAAGACACCGCGTGGTCCAGCCAACTCTGGAGCAGACGCAGTACTCCTGGGAGC
GCCAGGCGGCCTTCCGCTTCAAAAGGAAGCTGCCCACGTACCTGCTCTTTACCAGCCCCCAGGAG
AACCCCTGGGGCCACAAGCGCAGCTACCGCCTGCAGATCCACTCCATGGCCGACCAGGTGCTGC
CCCCAGGCTGGCAGGAGGAGCAGGCCATCACCTGGGCAAGGTACCCCCTGGCAGTGACCAAGTA
CCGGGAGTCGGAGCTGTGCAGCAGCAGCATCTACCACCAGAACGACCCCTGGCACCCGCCCGTG
GTCTTTGAGCAGTTTCTTCACAACAACGAGAACATTGAAAATGAGGACCTGGTGGCCTGGGTGACG
GTGGGCTTCCTGCACATCCCCCACTCAGAGGACATTCCCAACACAGCCACACCTGGGAACTCCGT
GGGCTTCCTGCTCCGGCCATTCAACTTCTTCCCAGAGGACCCCTCCCTGGCATCCAGAGACACTGT
GATCGTGTGGCCTCGGGACAACGGCCCCAACTACGTCCAGCGCTGGATCCCTGAGGACAGGGAC
TGCTCGATGCCTCCCCCTTTTAGCTACAATGGGACCTATAGACCTGTG*GAGCCCAAGTCCGCCGA*
*CAAGACCCACACCTGCCCCCCCTGCCCCGCCCCCCCCGTGGCCGGCCCCTCCGTGTTCCTGTTC*
*CCCCCCAAGCCCAAGGACACCCTGATGATCTCCAGGACCCCCGAGGTGACCTGCGTGGTGGTG*
*GACGTGTCCCACGAGGACCCCGAGGTGAAGTTCAACTGGTACGTGGACGGCGTGGAGGTGCAC*
*AACGCCAAGACCAAGCCCAGGGAGGAGCAGTACAACTCCACCTACAGGGTGGTGTCCGTGCTG*
*ACCGTGCTGCACCAGGACTGGCTGAACGGCAAGGAGTACAAGTGCAAGGTGTCCAACAAGGGC*
*CTGCCCTCCTCCATCGAGAAGACCATCTCCAAGGCCAAGGGCCAGCCCAGGGAGCCCCAGGTG*
*TACACCCTGCCCCCCTCCAGGGAGGAGATGACCAAGAACCAGGTGTCCCTGACCTGCCTGGTGA*
*AGGGCTTCTACCCCTCCGACATCGCCGTGGAGTGGGAGTCCAACGGCCAGCCCGAGAACAACT*
*ACAAGACCACCCCCCCCGTGCTGGACTCCGACGGCTCCTTCTTCCTGTACTCCAAGCTGACCGT*
*GGACAAGTCCAGGTGGCAGCAGGGCAACGTGTTCTCCTGCTCCGTGATGCACGAGGCCCTGCAC*
*AACCACTACACCCAGAAGTCCCTGTCCCTGTCCCCCGGCAAGTGA* (SEQ ID NO:97)

hDAO-Fc-Hepmut3-Cysmut

ATGCCGGCCCTGGGCTGGGCCGTGGCTGCCATCCTGATGCTGCAGACGGCCATGGCGGA
GCCCTCCCCGGGGACTCTGCCCAGGAAGGCAGGGGTGTTTTCAGACCTAAGCAACCAAGAGCTGA
AGGCAGTGCACAGCTTCCTCTGGTCCAAGAAGGAGCTGAGGCTGCAGCCCTCCAGTACCACCACC
ATGGCCAAGAACACCGTGTTTCTCATCGAGATGCTGCTGCCCAAGAAGTACCATGTGCTGAGGTTT
CTGGATAAAGGTGAAAGGCATCCTGTGCGGGAAGCCCGTGCCGTCATCTTCTTTGGTGACCAGGA
GCATCCCAATGTCACCGAGTTTGCTGTGGGGCCCCTGCCAGGGCCCGCCTACATGCGAGCACTGT
CCCCCAGGCCTGGGTACCAGTCCTCCTGGGCATCGAGGCCCATCTCCACAGCAGAGTATGCCCTC
CTCTACCACACCCTGCAGGAAGCCACCAAGCCCCTGCATCAGTTCTTCCTCAATACCACAGGCTTC
TCATTCCAAGACTGCCATGACAGATGCCTGGCCTTCACCGATGTGGCCCCCCGGGGTGTGGCTTC

Figure 1 continued

TGGCCAGCGCCGCAGTTGGCTTATCATACAGCGCTATGTAGAAGGCTACTTTCTGCACCCCACTGG
GCTGGAGCTCCTCGTGGATCATGGGAGCACAGATGCTGGGCACTGGGCCGTGGAGCAGGTGTGG
TACAACGGGAAGTTCTATGGGAGCCCAGAGGAACTGGCTCGGAAGTATGCAGATGGAGAGGTGGA
CGTGGTGGTCCTGGAGGACCCGCTGCCTGGGGGCAAGGGGCATGACAGCACAGAGGAGCCGCC
CCTCTTCTCCTCCCACAAGCCCCGCGGGGACTTCCCCAGCCCCATCCATGTGAGCGGCCCCCGCT
TGGTCCAGCCCCACGGCCCTCGCTTCAGGCTGGAGGGCAACGCTGTGCTCTACGGCGGCTGGAG
CTTTGCCTTCCGGCTGCGCTCCTCCTCCGGGCTGCAGGTCCTGAACGTGCACTTCGGCGGAGAGC
GCATTGCCTATGAGGTCAGCGTGCAAGAGGCAGTGGCGCTGTATGGAGGACACACACCTGCAGGC
ATGCAGACCAAGTACCTCGATGTCGGCTGGGGCCTGGGCAGCGTCACTCATGAGTTAGCCCCCGG
CATCGACTGCCCGGAGACCGCCACCTTCCTGGACACTTTCCACTACTATGATGCCGATGACCCGGT
CCATTATCCCCGAGCCCTCTGCCTCTTTGAAATGCCCACAGGGGTGCCCCTTCGGCGGCACTTTAA
TTCCAACTTTAAAGGTGGCTTCAACTTCTATGCGGGGCTGAAGGGCCAGGTGCTGGTGCTGCGGA
CAACTTCAACTGTCTACAATTATGATTACATTTGGGACTTTATCTTCTACCCCAACGGGGTGATGGA
GGCCAAGATGCATGCCACTGGCTACGTCCACGCCACCTTCTACACCCCCGAGGGGCTGCGCCAC
GGCACTCGCCTGCACACCCACCTGATTGGCAACATACACACTCACTTGGTGCACTACCGCGTAGAC
CTGGATGTGGCAGGCACCAAGAACAGCTTCCAGACACTGCAGATGAAGCTAGAAAACATCACCAAC
CCCTGGAGCCCAAGACACCGCGTGGTCCAGCCAACTCTGGAGCAGACGCAGTACTCCTGGGAGC
GCCAGGCGGCCTTCCGCTTCAAAACGAAGCTGCCCAAGTACCTGCTCTTTACCAGCCCCCAGGAG
AACCCCTGGGGCCACAAGCGCAGCTACCGCCTGCAGATCCACTCCATGGCCGACCAGGTGCTGC
CCCCAGGCTGGCAGGAGGAGCAGGCCATCACCTGGGCAAGGTACCCCCTGGCAGTGACCAAGTA
CCGGGAGTCGGAGCTGTGCAGCAGCAGCATCTACCACCAGAACGACCCCTGGCACCCGCCCGTG
GTCTTTGAGCAGTTTCTTCACAACAACGAGAACATTGAAAATGAGGACCTGGTGGCCTGGGTGACG
GTGGGCTTCCTGCACATCCCCCACTCAGAGGACATTCCCAACACAGCCACACCTGGGAACTCCGT
GGGCTTCCTGCTCCGGCCATTCAACTTCTTCCCAGAGGACCCCTCCCTGGCATCCAGAGACACTGT
GATCGTGTGGCCTCGGGACAACGGCCCCAACTACGTCCAGCGCTGGATCCCTGAGGACAGGGAC
TGCTCGATGCCTCCCCCTTTTAGCTACAATGGGACCTATAGACCTGTG*GAGCCCAAGTCCGCCGA*
*CAAGACCCACACCTGCCCCCCCTGCCCCGCCCCCCCCGTGGCCGGCCCCTCCGTGTTCCTGTTC*
*CCCCCCAAGCCCAAGGACACCCTGATGATCTCCAGGACCCCCGAGGTGACCTGCGTGGTGGTG*
*GACGTGTCCCACGAGGACCCCGAGGTGAAGTTCAACTGGTACGTGGACGGCGTGGAGGTGCAC*
*AACGCCAAGACCAAGCCCAGGGAGGAGCAGTACAACTCCACCTACAGGGTGGTGTCCGTGCTG*
*ACCGTGCTGCACCAGGACTGGCTGAACGGCAAGGAGTACAAGTGCAAGGTGTCCAACAAGGGC*
*CTGCCCTCCTCCATCGAGAAGACCATCTCCAAGGCCAAGGGCCAGCCCAGGGAGCCCCAGGTG*
*TACACCCTGCCCCCCTCCAGGGAGGAGATGACCAAGAACCAGGTGTCCCTGACCTGCCTGGTGA*
*AGGGCTTCTACCCCTCCGACATCGCCGTGGAGTGGGAGTCCAACGGCCAGCCCGAGAACAACT*
*ACAAGACCACCCCCCCCGTGCTGGACTCCGACGGCTCCTTCTTCCTGTACTCCAAGCTGACCGT*
*GGACAAGTCCAGGTGGCAGCAGGGCAACGTGTTCTCCTGCTCCGTGATGCACGAGGCCCTGCAC*
*AACCACTACACCCAGAAGTCCCTGTCCCTGTCCCCCGGCAAGTGA*(SEQ ID NO:98)

hDAO-Fc-Hepmut4-Cysmut

ATGCCGGCCCTGGGCTGGGCCGTGGCTGCCATCCTGATGCTGCAGACGGCCATGGCGGA
GCCCTCCCCGGGGACTCTGCCCAGGAAGGCAGGGGTGTTTTCAGACCTAAGCAACCAAGAGCTGA
AGGCAGTGCACAGCTTCCTCTGGTCCAAGAAGGAGCTGAGGCTGCAGCCCTCCAGTACCACCACC
ATGGCCAAGAACACCGTGTTTCTCATCGAGATGCTGCTGCCCAAGAAGTACCATGTGCTGAGGTTT
CTGGATAAAGGTGAAAGGCATCCTGTGCGGGAAGCCCGTGCCGTCATCTTCTTTGGTGACCAGGA
GCATCCCAATGTCACCGAGTTTGCTGTGGGGCCCCTGCCAGGGCCCGCCTACATGCGAGCACTGT
CCCCCAGGCCTGGGTACCAGTCCTCCTGGGCATCGAGGCCCATCTCCACAGCAGAGTATGCCCTC
CTCTACCACACCCTGCAGGAAGCCACCAAGCCCCTGCATCAGTTCTTCCTCAATACCACAGGCTTC
TCATTCCAAGACTGCCATGACAGATGCCTGGCCTTCACCGATGTGGCCCCCCGGGGTGTGGCTTC
TGGCCAGCGCCGCAGTTGGCTTATCATACAGCGCTATGTAGAAGGCTACTTTCTGCACCCCACTGG
GCTGGAGCTCCTCGTGGATCATGGGAGCACAGATGCTGGGCACTGGGCCGTGGAGCAGGTGTGG
TACAACGGGAAGTTCTATGGGAGCCCAGAGGAACTGGCTCGGAAGTATGCAGATGGAGAGGTGGA
CGTGGTGGTCCTGGAGGACCCGCTGCCTGGGGGCAAGGGGCATGACAGCACAGAGGAGCCGCC
CCTCTTCTCCTCCCACAAGCCCCGCGGGGACTTCCCCAGCCCCATCCATGTGAGCGGCCCCCGCT
TGGTCCAGCCCCACGGCCCTCGCTTCAGGCTGGAGGGCAACGCTGTGCTCTACGGCGGCTGGAG
CTTTGCCTTCCGGCTGCGCTCCTCCTCCGGGCTGCAGGTCCTGAACGTGCACTTCGGCGGAGAGC
GCATTGCCTATGAGGTCAGCGTGCAAGAGGCAGTGGCGCTGTATGGAGGACACACACCTGCAGGC
ATGCAGACCAAGTACCTCGATGTCGGCTGGGGCCTGGGCAGCGTCACTCATGAGTTAGCCCCCGG
CATCGACTGCCCGGAGACCGCCACCTTCCTGGACACTTTCCACTACTATGATGCCGATGACCCGGT
CCATTATCCCCGAGCCCTCTGCCTCTTTGAAATGCCCACAGGGGTGCCCCTTCGGCGGCACTTTAA

Figure 1 continued

TTCCAACTTTAAAGGTGGCTTCAACTTCTATGCGGGGCTGAAGGGCCAGGTGCTGGTGCTGCGGA
CAACTTCAACTGTCTACAATTATGATTACATTTGGGACTTTATCTTCTACCCCAACGGGGTGATGGA
GGCCAAGATGCATGCCACTGGCTACGTCCACGCCACCTTCTACACCCCCGAGGGGCTGCGCCAC
GGCACTCGCCTGCACACCCACCTGATTGGCAACATACACACTCACTTGGTGCACTACCGCGTAGAC
CTGGATGTGGCAGGCACCAAGAACAGCTTCCAGACACTGCAGATGAAGCTAGAAAACATCACCAAC
CCCTGGAGCCCAAGACACCGCGTGGTCCAGCCAACTCTGGAGCAGACGCAGTACTCCTGGGAGC
GCCAGGCGGCCTTCAGCTTCAAAACGAAGCTGCCCAAGTACCTGCTCTTTACCAGCCCCCAGGAG
AACCCCTGGGGCCACAAGCGCAGCTACCGCCTGCAGATCCACTCCATGGCCGACCAGGTGCTGC
CCCCAGGCTGGCAGGAGGAGCAGGCCATCACCTGGGCAAGGTACCCCCTGGCAGTGACCAAGTA
CCGGGAGTCGGAGCTGTGCAGCAGCAGCATCTACCACCAGAACGACCCCTGGCACCCGCCCGTG
GTCTTTGAGCAGTTTCTTCACAACAACGAGAACATTGAAAATGAGGACCTGGTGGCCTGGGTGACG
GTGGGCTTCCTGCACATCCCCCACTCAGAGGACATTCCCAACACAGCCACACCTGGGAACTCCGT
GGGCTTCCTGCTCCGGCCATTCAACTTCTTCCCAGAGGACCCCTCCCTGGCATCCAGAGACACTGT
GATCGTGTGGCCTCGGGACAACGGCCCCAACTACGTCCAGCGCTGGATCCCTGAGGACAGGGAC
TGCTCGATGCCTCCCCCTTTTAGCTACAATGGGACCTATAGACCTGTG*GAGCCCAAGTCCGCCGA*
*CAAGACCCACACCTGCCCCCCCTGCCCCGCCCCCCCCGTGGCCGGCCCCTCCGTGTTCCTGTTC*
*CCCCCCAAGCCCAAGGACACCCTGATGATCTCCAGGACCCCCGAGGTGACCTGCGTGGTGGTG*
*GACGTGTCCCACGAGGACCCCGAGGTGAAGTTCAACTGGTACGTGGACGGCGTGGAGGTGCAC*
*AACGCCAAGACCAAGCCCAGGGAGGAGCAGTACAACTCCACCTACAGGGTGGTGTCCGTGCTG*
*ACCGTGCTGCACCAGGACTGGCTGAACGGCAAGGAGTACAAGTGCAAGGTGTCCAACAAGGGC*
*CTGCCCTCCTCCATCGAGAAGACCATCTCCAAGGCCAAGGGCCAGCCCAGGGAGCCCCAGGTG*
*TACACCCTGCCCCCCTCCAGGGAGGAGATGACCAAGAACCAGGTGTCCCTGACCTGCCTGGTGA*
*AGGGCTTCTACCCCTCCGACATCGCCGTGGAGTGGGAGTCCAACGGCCAGCCCGAGAACAACT*
*ACAAGACCACCCCCCCCGTGCTGGACTCCGACGGCTCCTTCTTCCTGTACTCCAAGCTGACCGT*
*GGACAAGTCCAGGTGGCAGCAGGGCAACGTGTTCTCCTGCTCCGTGATGCACGAGGCCCTGCAC*
*AACCACTACACCCAGAAGTCCCTGTCCCTGTCCCCCGGCAAGTGA* (SEQ ID NO:99)

hDAO-Fc-Hepmut5-Cysmut

ATGCCGGCCCTGGGCTGGGCCGTGGCTGCCATCCTGATGCTGCAGACGGCCATGGCGGA
GCCCTCCCCGGGGACTCTGCCCAGGAAGGCAGGGGTGTTTTCAGACCTAAGCAACCAAGAGCTGA
AGGCAGTGCACAGCTTCCTCTGGTCCAAGAAGGAGCTGAGGCTGCAGCCCTCCAGTACCACCACC
ATGGCCAAGAACACCGTGTTTCTCATCGAGATGCTGCTGCCCAAGAAGTACCATGTGCTGAGGTTT
CTGGATAAAGGTGAAAGGCATCCTGTGCGGGAAGCCCGTGCCGTCATCTTCTTTGGTGACCAGGA
GCATCCCAATGTCACCGAGTTTGCTGTGGGGCCCCTGCCAGGGCCCGCCTACATGCGAGCACTGT
CCCCCAGGCCTGGGTACCAGTCCTCCTGGGCATCGAGGCCCATCTCCACAGCAGAGTATGCCCTC
CTCTACCACACCCTGCAGGAAGCCACCAAGCCCCTGCATCAGTTCTTCCTCAATACCACAGGCTTC
TCATTCCAAGACTGCCATGACAGATGCCTGGCCTTCACCGATGTGGCCCCCCGGGGTGTGGCTTC
TGGCCAGCGCCGCAGTTGGCTTATCATACAGCGCTATGTAGAAGGCTACTTTCTGCACCCCACTGG
GCTGGAGCTCCTCGTGGATCATGGGAGCACAGATGCTGGGCACTGGGCCGTGGAGCAGGTGTGG
TACAACGGGAAGTTCTATGGGAGCCCAGAGGAACTGGCTCGGAAGTATGCAGATGGAGAGGTGGA
CGTGGTGGTCCTGGAGGACCCGCTGCCTGGGGGCAAGGGGCATGACAGCACAGAGGAGCCGCC
CCTCTTCTCCTCCCACAAGCCCCGCGGGGACTTCCCCAGCCCCATCCATGTGAGCGGCCCCCGCT
TGGTCCAGCCCCACGGCCCTCGCTTCAGGCTGGAGGGCAACGCTGTGCTCTACGGCGGCTGGAG
CTTTGCCTTCCGGCTGCGCTCCTCCTCCGGGCTGCAGGTCCTGAACGTGCACTTCGGCGGAGAGC
GCATTGCCTATGAGGTCAGCGTGCAAGAGGCAGTGGCGCTGTATGGAGGACACACACCTGCAGGC
ATGCAGACCAAGTACCTCGATGTCGGCTGGGGCCTGGGCAGCGTCACTCATGAGTTAGCCCCCGG
CATCGACTGCCCGGAGACCGCCACCTTCCTGGACACTTTCCACTACTATGATGCCGATGACCCGGT
CCATTATCCCCGAGCCCTCTGCCTCTTTGAAATGCCCACAGGGGTGCCCCTTCGGCGGCACTTTAA
TTCCAACTTTAAAGGTGGCTTCAACTTCTATGCGGGGCTGAAGGGCCAGGTGCTGGTGCTGCGGA
CAACTTCAACTGTCTACAATTATGATTACATTTGGGACTTTATCTTCTACCCCAACGGGGTGATGGA
GGCCAAGATGCATGCCACTGGCTACGTCCACGCCACCTTCTACACCCCCGAGGGGCTGCGCCAC
GGCACTCGCCTGCACACCCACCTGATTGGCAACATACACACTCACTTGGTGCACTACCGCGTAGAC
CTGGATGTGGCAGGCACCAAGAACAGCTTCCAGACACTGCAGATGAAGCTAGAAAACATCACCAAC
CCCTGGAGCCCAAGACACCGCGTGGTCCAGCCAACTCTGGAGCAGACGCAGTACTCCTGGGAGC
GCCAGGCGGCCTTCCGCTTCAAAACGAAGCTGCCCACGTACCTGCTCTTTACCAGCCCCCAGGAG
AACCCCTGGGGCCACAAGCGCAGCTACCGCCTGCAGATCCACTCCATGGCCGACCAGGTGCTGC
CCCCAGGCTGGCAGGAGGAGCAGGCCATCACCTGGGCAAGGTACCCCCTGGCAGTGACCAAGTA
CCGGGAGTCGGAGCTGTGCAGCAGCAGCATCTACCACCAGAACGACCCCTGGCACCCGCCCGTG
GTCTTTGAGCAGTTTCTTCACAACAACGAGAACATTGAAAATGAGGACCTGGTGGCCTGGGTGACG

Figure 1 continued

GTGGGCTTCCTGCACATCCCCCACTCAGAGGACATTCCCAACACAGCCACACCTGGGAACTCCGT
GGGCTTCCTGCTCCGGCCATTCAACTTCTTCCCAGAGGACCCCTCCCTGGCATCCAGAGACACTGT
GATCGTGTGGCCTCGGGACAACGGCCCCAACTACGTCCAGCGCTGGATCCCTGAGGACAGGGAC
TGCTCGATGCCTCCCCCTTTTAGCTACAATGGGACCTATAGACCTGTG*GAGCCCAAGTCCGCCGA*
*CAAGACCCACACCTGCCCCCCCTGCCCCGCCCCCCCCGTGGCCGGCCCCTCCGTGTTCCTGTTC*
*CCCCCCAAGCCCAAGGACACCCTGATGATCTCCAGGACCCCCGAGGTGACCTGCGTGGTGGTG*
*GACGTGTCCCACGAGGACCCCGAGGTGAAGTTCAACTGGTACGTGGACGGCGTGGAGGTGCAC*
*AACGCCAAGACCAAGCCCAGGGAGGAGCAGTACAACTCCACCTACAGGGTGGTGTCCGTGCTG*
*ACCGTGCTGCACCAGGACTGGCTGAACGGCAAGGAGTACAAGTGCAAGGTGTCCAACAAGGGC*
*CTGCCCTCCTCCATCGAGAAGACCATCTCCAAGGCCAAGGGCCAGCCCAGGGAGCCCCAGGTG*
*TACACCCTGCCCCCCTCCAGGGAGGAGATGACCAAGAACCAGGTGTCCCTGACCTGCCTGGTGA*
*AGGGCTTCTACCCCTCCGACATCGCCGTGGAGTGGGAGTCCAACGGCCAGCCCGAGAACAACT*
*ACAAGACCACCCCCCCCGTGCTGGACTCCGACGGCTCCTTCTTCCTGTACTCCAAGCTGACCGT*
*GGACAAGTCCAGGTGGCAGCAGGGCAACGTGTTCTCCTGCTCCGTGATGCACGAGGCCCTGCAC*
*AACCACTACACCCAGAAGTCCCTGTCCCTGTCCCCCGGCAAGTGA* (SEQ ID NO:100)

hDAO-Fc-Hepmut6-Cysmut

ATGCCGGCCCTGGGCTGGGCCGTGGCTGCCATCCTGATGCTGCAGACGGCCATGGCGGA
GCCCTCCCCGGGGACTCTGCCCAGGAAGGCAGGGGTGTTTTCAGACCTAAGCAACCAAGAGCTGA
AGGCAGTGCACAGCTTCCTCTGGTCCAAGAAGGAGCTGAGGCTGCAGCCCTCCAGTACCACCACC
ATGGCCAAGAACACCGTGTTTCTCATCGAGATGCTGCTGCCCAAGAAGTACCATGTGCTGAGGTTT
CTGGATAAAGGTGAAAGGCATCCTGTGCGGGAAGCCCGTGCCGTCATCTTCTTTGGTGACCAGGA
GCATCCCAATGTCACCGAGTTTGCTGTGGGGCCCCTGCCAGGGCCCGCCTACATGCGAGCACTGT
CCCCCAGGCCTGGGTACCAGTCCTCCTGGGCATCGAGGCCCATCTCCACAGCAGAGTATGCCCTC
CTCTACCACACCCTGCAGGAAGCCACCAAGCCCCTGCATCAGTTCTTCCTCAATACCACAGGCTTC
TCATTCCAAGACTGCCATGACAGATGCCTGGCCTTCACCGATGTGGCCCCCCGGGGTGTGGCTTC
TGGCCAGCGCCGCAGTTGGCTTATCATACAGCGCTATGTAGAAGGCTACTTTCTGCACCCCACTGG
GCTGGAGCTCCTCGTGGATCATGGGAGCACAGATGCTGGGCACTGGGCCGTGGAGCAGGTGTGG
TACAACGGGAAGTTCTATGGAGCCCAGAGGAACTGGCTCGGAAGTATGCAGATGGAGAGGTGGA
CGTGGTGGTCCTGGAGGACCCGCTGCCTGGGGGCAAGGGGCATGACAGCACAGAGGAGCCGCC
CCTCTTCTCCTCCCACAAGCCCCGCGGGGACTTCCCCAGCCCCATCCATGTGAGCGGCCCCCGCT
TGGTCCAGCCCCACGGCCCTCGCTTCAGGCTGGAGGGCAACGCTGTGCTCTACGGCGGCTGGAG
CTTTGCCTTCCGGCTGCGCTCCTCCTCCGGGCTGCAGGTCCTGAACGTGCACTTCGGCGGAGAGC
GCATTGCCTATGAGGTCAGCGTGCAAGAGGCAGTGGCGCTGTATGGAGGACACACACCTGCAGGC
ATGCAGACCAAGTACCTCGATGTCGGCTGGGGCCTGGGCAGCGTCACTCATGAGTTAGCCCCCGG
CATCGACTGCCCGGAGACCGCCACCTTCCTGGACACTTTCCACTACTATGATGCCGATGACCCGGT
CCATTATCCCCGAGCCCTCTGCCTCTTTGAAATGCCCACAGGGGTGCCCCTTCGGCGGCACTTTAA
TTCCAACTTTAAAGGTGGCTTCAACTTCTATGCGGGGCTGAAGGGCCAGGTGCTGGTGCTGCGGA
CAACTTCAACTGTCTACAATTATGATTACATTTGGGACTTTATCTTCTACCCCAACGGGGTGATGGA
GGCCAAGATGCATGCCACTGGCTACGTCCACGCCACCTTCTACACCCCCGAGGGGCTGCGCCAC
GGCACTCGCCTGCACACCCACCTGATTGGCAACATACACACTCACTTGGTGCACTACCGCGTAGAC
CTGGATGTGGCAGGCACCAAGAACAGCTTCCAGACACTGCAGATGAAGCTAGAAAACATCACCAAC
CCCTGGAGCCCAAGACACCGCGTGGTCCAGCCAACTCTGGAGCAGACGCAGTACTCCTGGGAGC
GCCAGGCGGCCTTCCGCTTCGGACAGACGCTGCCCAAGTACCTGCTCTTTACCAGCCCCCAGGA
GAACCCCTGGGGCCACAAGCGCAGCTACCGCCTGCAGATCCACTCCATGGCCGACCAGGTGCTG
CCCCCAGGCTGGCAGGAGGAGCAGGCCATCACCTGGGCAAGGTACCCCCTGGCAGTGACCAAGT
ACCGGGAGTCGGAGCTGTGCAGCAGCAGCATCTACCACCAGAACGACCCCTGGCACCCGCCCGT
GGTCTTTGAGCAGTTTCTTCACAACAACGAGAACATTGAAAATGAGGACCTGGTGGCCTGGGTGAC
GGTGGGCTTCCTGCACATCCCCCACTCAGAGGACATTCCCAACACAGCCACACCTGGGAACTCCG
TGGGCTTCCTGCTCCGGCCATTCAACTTCTTCCCAGAGGACCCCTCCCTGGCATCCAGAGACACTG
TGATCGTGTGGCCTCGGGACAACGGCCCCAACTACGTCCAGCGCTGGATCCCTGAGGACAGGGA
CTGCTCGATGCCTCCCCCTTTTAGCTACAATGGGACCTATAGACCTGTG*GAGCCCAAGTCCGCCG*
*ACAAGACCCACACCTGCCCCCCCTGCCCCGCCCCCCCCGTGGCCGGCCCCTCCGTGTTCCTGTT*
*CCCCCCCAAGCCCAAGGACACCCTGATGATCTCCAGGACCCCCGAGGTGACCTGCGTGGTGGT*
*GGACGTGTCCCACGAGGACCCCGAGGTGAAGTTCAACTGGTACGTGGACGGCGTGGAGGTGCA*
*CAACGCCAAGACCAAGCCCAGGGAGGAGCAGTACAACTCCACCTACAGGGTGGTGTCCGTGCT*
*GACCGTGCTGCACCAGGACTGGCTGAACGGCAAGGAGTACAAGTGCAAGGTGTCCAACAAGGG*
*CCTGCCCTCCTCCATCGAGAAGACCATCTCCAAGGCCAAGGGCCAGCCCAGGGAGCCCCAGGT*

Figure 1 continued

*GTACACCCTGCCCCCCTCCAGGGAGGAGATGACCAAGAACCAGGTGTCCCTGACCTGCCTGGT*
*GAAGGGCTTCTACCCCTCCGACATCGCCGTGGAGTGGGAGTCCAACGGCCAGCCCGAGAACAA*
*CTACAAGACCACCCCCCCCGTGCTGGACTCCGACGGCTCCTTCTTCCTGTACTCCAAGCTGACCG*
*TGGACAAGTCCAGGTGGCAGCAGGGCAACGTGTTCTCCTGCTCCGTGATGCACGAGGCCCTGCA*
*CAACCACTACACCCAGAAGTCCCTGTCCCTGTCCCCCGGCAAGTGA* (SEQ ID NO:101)

hDAO-Fc-Hepmut7-Cysmut

ATGCCGGCCCTGGGCTGGGCCGTGGCTGCCATCCTGATGCTGCAGACGGCCATGGCGGA
GCCCTCCCCGGGGACTCTGCCCAGGAAGGCAGGGGTGTTTTCAGACCTAAGCAACCAAGAGCTGA
AGGCAGTGCACAGCTTCCTCTGGTCCAAGAAGGAGCTGAGGCTGCAGCCCTCCAGTACCACCACC
ATGGCCAAGAACACCGTGTTTCTCATCGAGATGCTGCTGCCCAAGAAGTACCATGTGCTGAGGTTT
CTGGATAAAGGTGAAAGGCATCCTGTGCGGGAAGCCCGTGCCGTCATCTTCTTTGGTGACCAGGA
GCATCCCAATGTCACCGAGTTTGCTGTGGGGCCCCTGCCAGGGCCCGCCTACATGCGAGCACTGT
CCCCCAGGCCTGGGTACCAGTCCTCCTGGGCATCGAGGCCCATCTCCACAGCAGAGTATGCCCTC
CTCTACCACACCCTGCAGGAAGCCACCAAGCCCCTGCATCAGTTCTTCCTCAATACCACAGGCTTC
TCATTCCAAGACTGCCATGACAGATGCCTGGCCTTCACCGATGTGGCCCCCCGGGGTGTGGCTTC
TGGCCAGCGCCGCAGTTGGCTTATCATACAGCGCTATGTAGAAGGCTACTTTCTGCACCCCACTGG
GCTGGAGCTCCTCGTGGATCATGGGAGCACAGATGCTGGGCACTGGGCCGTGGAGCAGGTGTGG
TACAACGGGAAGTTCTATGGGAGCCCAGAGGAACTGGCTCGGAAGTATGCAGATGGAGAGGTGGA
CGTGGTGGTCCTGGAGGACCCGCTGCCTGGGGGCAAGGGGCATGACAGCACAGAGGAGCCGCC
CCTCTTCTCCTCCCACAAGCCCCGCGGGGACTTCCCCAGCCCCATCCATGTGAGCGGCCCCCGCT
TGGTCCAGCCCCACGGCCCTCGCTTCAGGCTGGAGGGCAACGCTGTGCTCTACGGCGGCTGGAG
CTTTGCCTTCCGGCTGCGCTCCTCCTCCGGGCTGCAGGTCCTGAACGTGCACTTCGGCGGAGAGC
GCATTGCCTATGAGGTCAGCGTGCAAGAGGCAGTGGCGCTGTATGGAGGACACACACCTGCAGGC
ATGCAGACCAAGTACCTCGATGTCGGCTGGGGCCTGGGCAGCGTCACTCATGAGTTAGCCCCCGG
CATCGACTGCCCGGAGACCGCCACCTTCCTGGACACTTTCCACTACTATGATGCCGATGACCCGGT
CCATTATCCCCGAGCCCTCTGCCTCTTTGAAATGCCCACAGGGGTGCCCCTTCGGCGGCACTTTAA
TTCCAACTTTAAAGGTGGCTTCAACTTCTATGCGGGGCTGAAGGGCCAGGTGCTGGTGCTGCGGA
CAACTTCAACTGTCTACAATTATGATTACATTTGGGACTTTATCTTCTACCCCAACGGGGTGATGGA
GGCCAAGATGCATGCCACTGGCTACGTCCACGCCACCTTCTACACCCCCGAGGGGCTGCGCCAC
GGCACTCGCCTGCACACCCACCTGATTGGCAACATACACACTCACTTGGTGCACTACCGCGTAGAC
CTGGATGTGGCAGGCACCAAGAACAGCTTCCAGACACTGCAGATGAAGCTAGAAAACATCACCAAC
CCCTGGAGCCCAAGACACCGCGTGGTCCAGCCAACTCTGGAGCAGACGCAGTACTCCTGGGAGC
GCCAGGCGGCCTTCAGCTTCAAAAGGAAGCTGCCCACGTACCTGCTCTTTACCAGCCCCCAGGAG
AACCCCTGGGGCCACAAGCGCAGCTACCGCCTGCAGATCCACTCCATGGCCGACCAGGTGCTGC
CCCCAGGCTGGCAGGAGGAGCAGGCCATCACCTGGGCAAGGTACCCCCTGGCAGTGACCAAGTA
CCGGGAGTCGGAGCTGTGCAGCAGCAGCATCTACCACCAGAACGACCCCTGGCACCCGCCCGTG
GTCTTTGAGCAGTTTCTTCACAACAACGAGAACATTGAAAATGAGGACCTGGTGGCCTGGGTGACG
GTGGGCTTCCTGCACATCCCCCACTCAGAGGACATTCCCAACACAGCCACACCTGGGAACTCCGT
GGGCTTCCTGCTCCGGCCATTCAACTTCTTCCCAGAGGACCCCTCCCTGGCATCCAGAGACACTGT
GATCGTGTGGCCTCGGGACAACGGCCCCAACTACGTCCAGCGCTGGATCCCTGAGGACAGGGAC
TGCTCGATGCCTCCCCCTTTTAGCTACAATGGGACCTATAGACCTGTG*GAGCCCAAGTCCGCCGA*
*CAAGACCCACACCTGCCCCCCCTGCCCCGCCCCCCCCGTGGCCGGCCCCTCCGTGTTCCTGTTC*
*CCCCCCAAGCCCAAGGACACCCTGATGATCTCCAGGACCCCCGAGGTGACCTGCGTGGTGGTG*
*GACGTGTCCCACGAGGACCCCGAGGTGAAGTTCAACTGGTACGTGGACGGCGTGGAGGTGCAC*
*AACGCCAAGACCAAGCCCAGGGAGGAGCAGTACAACTCCACCTACAGGGTGGTGTCCGTGCTG*
*ACCGTGCTGCACCAGGACTGGCTGAACGGCAAGGAGTACAAGTGCAAGGTGTCCAACAAGGGC*
*CTGCCCTCCTCCATCGAGAAGACCATCTCCAAGGCCAAGGGCCAGCCCAGGGAGCCCCAGGTG*
*TACACCCTGCCCCCCTCCAGGGAGGAGATGACCAAGAACCAGGTGTCCCTGACCTGCCTGGTGA*
*AGGGCTTCTACCCCTCCGACATCGCCGTGGAGTGGGAGTCCAACGGCCAGCCCGAGAACAACT*
*ACAAGACCACCCCCCCCGTGCTGGACTCCGACGGCTCCTTCTTCCTGTACTCCAAGCTGACCGT*
*GGACAAGTCCAGGTGGCAGCAGGGCAACGTGTTCTCCTGCTCCGTGATGCACGAGGCCCTGCAC*
*AACCACTACACCCAGAAGTCCCTGTCCCTGTCCCCCGGCAAGTGA* (SEQ ID NO:102)

Figure 1 continued

Human serum albumin (HSA), wild type sequence

DAHKSEVAHRFKDLGEENFKALVLIAFAQYLQQCPFEDHVKLVNEVTEFAKTCVADESAENCDKSLHTL
FGDKLCTVATLRETYGEMADCCAKQEPERNECFLQHKDDNPNLPRLVRPEVDVMCTAFHDNEETFLKK
YLYEIARRHPYFYAPELLFFAKRYKAAFTECCQAADKAACLLPKLDELRDEGKASSAKQRLKCASLQKF
GERAFKAWAVARLSQRFPKAEFAEVSKLVTDLTKVHTECCHGDLLECADDRADLAKYICENQDSISSKL
KECCEKPLLEKSHCIAEVENDEMPADLPSLAADFVESKDVCKNYAEAKDVFLGMFLYEYARRHPDYSVV
LLLRLAKTYETTLEKCCAAADPHECYAKVFDEFKPLVEEPQNLIKQNCELFEQLGEYKFQNALLVRYTKK
VPQVSTPTLVEVSRNLGKVGSKCCKHPEAKRMPCAEDYLSVVLNQLCVLHEKTPVSDRVTKCCTESLV
NRRPCFSALEVDETYVPKEFNAETFTFHADICTLSEKERQIKKQTALVELVKHKPKATKEQLKAVMDDFA
AFVEKCCKADDKETCFAEEGKKLVAASQAALGL (SEQ ID NO:103)

hDAO-Hepmut4 Asn168Gln

MPALGWAVAAILMLQTAMAEPSPGTLPRKAGVFSDLSNQELKAVHSFLWSKKELRLQPSSTTTMAKNT
VFLIEMLLPKKYHVLRFLDKGERHPVREARAVIFFGDQEHPNVTEFAVGPLPGPCYMRALSPRPGYQSS
WASRPISTAEYALLYHTLQEATKPLHQFFLQTTGFSFQDCHDRCLAFTDVAPRGVASGQRRSWLIIQRY
VEGYFLHPTGLELLVDHGSTDAGHWAVEQVWYNGKFYGSPEELARKYADGEVDVVLEDPLPGGKGH
DSTEEPPLFSSHKPRGDFPSPIHVSGPRLVQPHGPRFRLEGNAVLYGGWSFAFRLRSSSGLQVLNVHF
GGERIAYEVSVQEAVALYGGHTPAGMQTKYLDVGWGLGSVTHELAPGIDCPETATFLDTFHYYDADDP
VHYPRALCLFEMPTGVPLRRHFNSNFKGGFNFYAGLKGQVLVLRTTSTVYNYDYIWDFIFYPNGVMEAK
MHATGYVHATFYTPEGLRHGTRLHTHLIGNIHTHLVHYRVDLDVAGTKNSFQTLQMKLENITNPWSPRH
RVVQPTLEQTQYSWERQAAFSFKTKLPKYLLFTSPQENPWGHKRSYRLQIHSMADQVLPPGWQEEQAI
TWARYPLAVTKYRESELCSSSIYHQNDPWHPPVVFEQFLHNNENIENEDLVAWVTVGFLHIPHSEDIPN
TATPGNSVGFLLRPFNFFPEDPSLASRDTVIVWPRDNGPNYVQRWIPEDRDCSMPPPFSYNGTYRPV
(SEQ ID NO:106)

Figure 7
a)
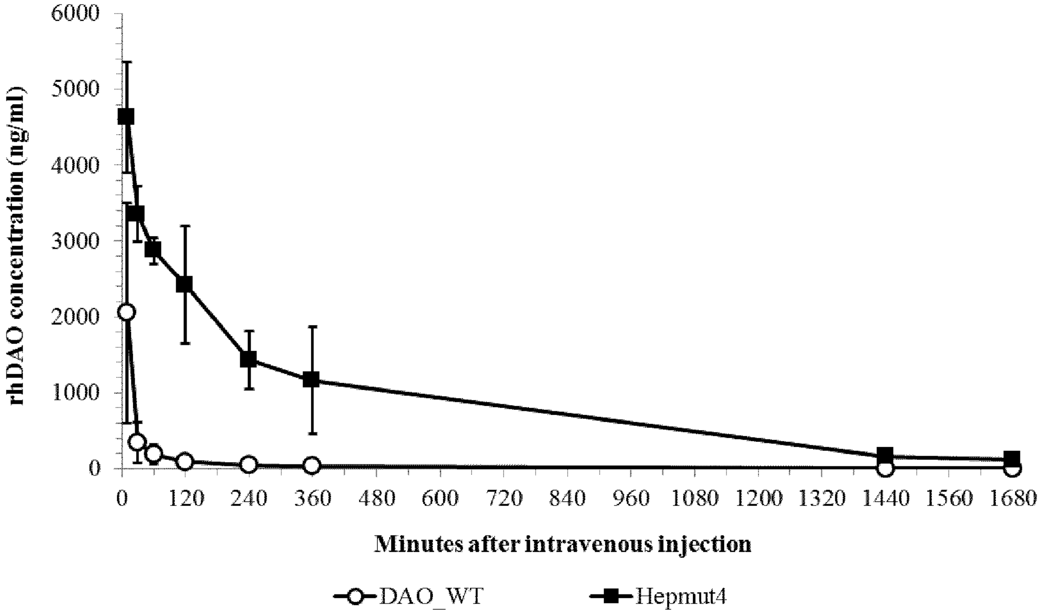
b)
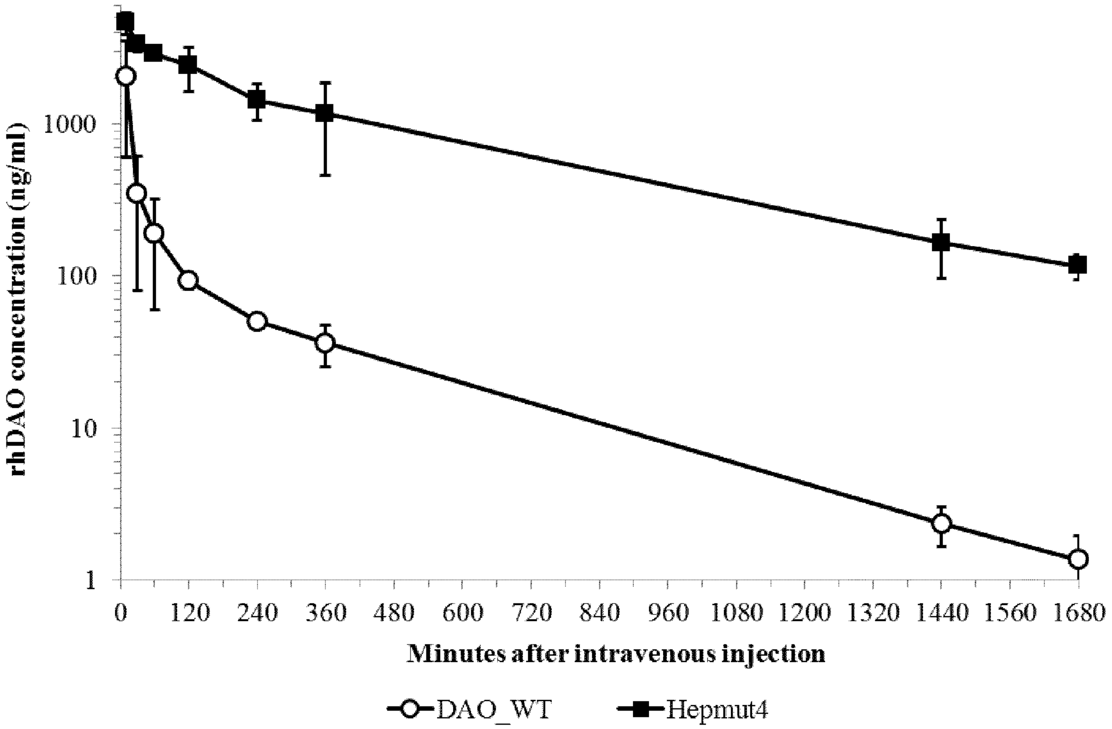

RECOMBINANT HUMAN DIAMINE OXIDASE AND METHODS FOR TREATMENT OF EXCESS HISTAMINE CONDITIONS USING THE SAME

CROSS-REFERENCE TO RELATED APPLICATIONS

This application is the U.S. national stage of International Patent Application No. PCT/EP2020/054197, filed on Feb. 18, 2020 and entitled NEW RECOMBINANT DIAMINE OXIDASE AND ITS USE FOR THE TREATMENT OF DISEASES CHARACTERIZED BY EXCESS HISTAMINE, which claims the benefit of priority under 35 U.S.C. § 119 from European Patent Application No. 19157932.5, filed on Feb. 19, 2019. The disclosures of the foregoing applications are incorporated herein by reference in their entirety.

SEQUENCE LISTING

The entire content of a sequence listing titled "Sequence_Listing.txt," created on Jul. 7, 2021 and having a size of 553 kilobytes, which has been submitted in electronic form in connection with the present application, is hereby incorporated by reference herein in its entirety.

FIELD OF THE INVENTION

The present invention refers to a recombinant diamine oxidase (DAO) with decreased glycosaminoglycan binding affinity, wherein said DAO comprises at least one amino acid modification in the glycosaminoglycan (GAG) binding domain.

The present invention also refers to the use of the DAO in the treatment of a condition associated with excess histamine, specifically in the treatment of chronic allergic diseases and/or in the treatment of high risk pregnancy, more specifically in the treatment of anaphylaxis, anaphylactic shock, chronic urticaria, acute urticaria, asthma, hay fever, allergic rhinitis, allergic conjunctivitis, histamine intoxication, headache, atopic dermatitis inflammatory diseases, mastocytosis, mast cell activation syndrome (MCAS), preeclampsia, hyperemesis gravidarum, pre-term labor, peptic ulcers, acid reflux, pruritus, and sepsis.

BACKGROUND OF THE INVENTION

Histamine (2-(1H-Imidazol-4-yl)ethanamine) is an organic nitrogenous compound involved in local immune responses, regulating physiological function in the gut and acting as a neurotransmitter for the brain, spinal cord, and uterus. Histamine is involved in the inflammatory response and has a central role as a mediator of itching. As part of an immune response to foreign pathogens, histamine is produced by basophils and by mast cells found in nearby connective tissues. It is stored in inactive form in the metachromatic granules of the mast cells and basophilic leukocytes, where it is available for an immediate release. Histamine can also be freshly synthesized by neutrophils and macrophages during inflammation. After its release, histamine is a powerful physiological and pathological mediator binding to four receptors ($H_1$-$H_4$) expressed on many different cells in the body. Binding of histamine to its receptors is very specific. After binding many downstream activities are induced. Acute allergic reactions such as hay fever, runny nose, itchy eyes or in more severe cases asthma with breathing problems; acute and chronic urticaria and hypersensitivity reactions, also called anaphylaxis for example caused by medications especially antibiotics or radio contrast agents, by a peanut or wasp allergy etc., are mediated by tissue mast cells and basophils in the blood releasing several mediators of which histamine is one of the most active ones. Histamine-induced symptoms include anaphylaxis, a hypersensitivity reaction with drop in blood pressure, fainting and breathing problems among other symptoms, bronchospasm, flushing (reddening of the skin), pruritus (itchiness), tachycardia (high pulse rate), syncope (fainting), hypotension (low blood pressure), epigastric and abdominal pain, nausea, vomiting, diarrhea, fatigue, memory loss, depression and headache among others. Excess histamine (>10 ng/ml; symptoms start at 1 to 3 ng/ml) in the blood is life-threatening. Histamine concentration in blood of approximately 100 ng/ml can result in cardiac arrest. Specifically during pregnancy, hyperhistaminemia can lead to specific gestational complications such as preeclampsia, spontaneous abortion, preterm labour and hyperemesis gravidarum (Brew 0. and Sullivan M. H. F., J. Reprod. Immunol., 72(2006), 94-107, Maintz L. et al., Human Reproduction Update, 14, 5, 2008, 485-495).

Mast cells and basophils are cells of the immune system with many different functions. Nevertheless, mast cells and histamine play an important role in many diseases like mast cell activation syndromes, MCAS, i.e. inability to tolerate histamine in red wine or cheese or other foods; in literature often described as histamine intolerance, atopic dermatitis (also called neurodermitis, a skin disease), mastocytosis (increased number of mast cells in the skin and/or internal organs like the bone marrow or liver or spleen), peptic ulcers (damage of the mucosa in the stomach or duodenum caused by excessive histamine followed by acid release), acid reflux, headache, pruritus and possibly even sepsis among other diseases. Histamine can be also newly synthesized by histidine decarboxylase induced in for example neutrophils and macrophages under certain disease conditions.

Moreover, histamine may also get into the body from the outside, by inhaling, or orally, e.g. by ingesting histamine-containing foodstuffs, such as cheese, wine, canned fish and sauerkraut. Histamine can also be produced by bacteria of the microbiome.

Anti-histamines opposing the activity of histamine receptors $H_1$ and $H_2$ have been available for several decades and they are assumed to be efficacious in treating symptoms such as runny nose and itching skin and eyes. Anti-histamines are one of the most frequently prescribed medications worldwide. Nevertheless, thorough data analysis has clearly shown that the efficacy of anti-histamines is limited under several pathological conditions. For example, about 25% of chronic urticaria patients are anti-histamine resistant and suffer from a low quality of life. Treatment of hypersensitivity reactions with anti-histamines is widely practiced but high quality efficacy data are missing and in some documents a lack of efficacy is stated. Anaphylaxis guidelines do not necessarily recommend the use of histamine $H_1$ receptor blocker for the treatment because the evidence of benefit is not clear. The use of histamine $H_2$ receptors antagonists in anaphylaxis is discouraged because it can worsen the symptoms.

This limited efficacy of anti-histamines is not surprising. Several studies have shown that anti-histamines can only block the effects of 2- to 3-fold increased histamine concentrations, but are much less efficacious when histamine concentrations increase beyond that. During anaphylaxis or hypersensitivity reactions histamine concentrations in the circulation can be increased more than 100-fold in normal people and even more in mastocytosis patients. Mastocytosis patients have continuously 5- to 15-fold increased levels of histamine and its metabolites under steady-state, non-anaphylactic conditions. The body cannot degrade the excessive histamine fast enough and the development of various symptoms is a logical consequence.

In the mammalian organism, histamine is degraded by two enzymes: diamine oxidase (diamine oxidase, DAO, EC 1.4.3.6) and histamine-N-methyltransferase (HNMT or short NMT, EC 2.1.1.8). NMT catalyzes the N-methylation to N-methyl-histamine.

The structure and inhibition of human DAO is reviewed in McGrath A P et al. (Biochemistry, 2009, 48(41), 9810-9822). DAO catalyzes the oxidative deamination of histamine to imidazole acetaldehyde. DAO was originally identified as the enzyme that cleared exogenous histamine from minced lung and liver samples and was therefore termed histaminase (Best C H., J. Physiol., 1929, 67, 256-263). Subsequently, a protein identified as diamine oxidase was termed amiloride-binding protein, and was incorrectly implicated with the amiloride-sensitive $Na^+$ channel. Some databases still designate AOC1 as ABP1. That DAO and ABP1 were in fact the same protein was later noted by the original authors (Novotny W F et al., J. Biol. Chem., 1994, 269, 9921-9925) who also reported the cloning of the human gene, corresponding to a 751 amino acid residues protein. Over-expression of recombinant human DAO (hDAO) has been achieved in insect cells (Elmore B O. et al., J. Biol. Inorg. Chem., 2002, 7, 565-579). Whilst it is further reported by Elmore et al. that DAO contains a heparin binding consensus sequence (residues 568-575), it could not be derived from this structure that the heparin-binding domain really binds heparin. A 12-mer heparin molecule is ~5 nm (50 Å) long and the diameter of the circular heparin binding domain in DAO is about 25 Å. The molecular weight of a heparin 12-mer=284*12=3408 Da. LMWH does not strongly bind to DAO but has an average molecular weight of 5000 Da (18 sugar units). Only HMWH binds to DAO with an average molecular weight of 15000 Da but this corresponds to 15000/284=52 sugar units in a row.

The availability of large amounts of recombinant hDAO enabled the identification of its preferred substrates in vitro, showing a distinct preference for diamines. In particular two atypical diamines, histamine and 1-methyl histamine are excellent substrates. Each contains an imidazole group in place of one of the primary amines present in typical diamine substrates like spermidine, putrescine or cadaverine. hDAO is the frontline enzyme for degradation of exogenous histamine and reduced levels of DAO have been shown to be directly correlated with histamine intolerance (Maintz L. et al., Am. J. Clin. Nutr., 2007, 85, 1185-1196). Reduced DAO activities have been found in multiple heterogenous complications of pregnancy such as diabetes, threatened and missed abortion and trophoblastic disorders (Maintz L., et al., 2008).

In the gastro-intestinal tract DAO degrades histamine from the diet to avoid and to protect the body from increased concentrations in the blood. Nevertheless, except during pregnancy, DAO antigen and consequently activity is low or even absent in plasma (Boehm T. et al., Clinical Biochemistry 50, 2017, 444-451). During pregnancy DAO activity is increased more than 100-fold.

In WO 02/43745 the systemic use of DAO of plant origin for the treatment of histamine-mediate diseases is disclosed. The administration of enzymes directly isolated from plants, however, is a great problem because of the frequent occurrence of allergens in plants, primarily in view of the fact that the leguminous plants disclosed in WO 02/43745 have a high allergenic potential.

WO2006/003213A1 describes specific administration formulations of animal derived or recombinantly produced DAO.

The expression and purification of recombinant wild-type (wt) human (rh) DAO in CHO cells was published by Gludovacz E. et al. (J Biotechnol. 2016, 227:120-130). Nevertheless, in rats the alpha-distribution half-life of wt rhDAO was less than 10 minutes and comprised more than 80% of the injected protein amount. The beta-elimination half-life was about 3 hours. The scaling factor for biologics to extrapolate from rat to human is about 4 to 8 and therefore the PK profile of recombinant wt DAO is not suitable for preclinical and clinical development. Three glycosylation sites of DAO had been mutated, but glycan mutations did not improve the PK profile. The effects of glycan mutations on expression and activity of DAO have been published by Gludovacz E. et al. (J. Biol. Chem. 2018, 293(3), 1070-1087).

DATABASE UniProt Accession No. G3QJ02, 2011, XP-002792064 discloses diamine oxidase sequence from Gorilla gorilla.

DATABASE UniProt Accession No. Q9SXW5, 2000 discloses diamine oxidase sequence from *Pisum sativum.*

WO 2012/028891A1 reports histaminase from vegetable origin. Because released histamine cannot be blocked or inactivated efficiently by anti-histamines, new treatment and prophylaxis approaches for rapid inactivation of excess histamine would be of significant benefit to patients suffering from high circulatory histamine concentrations. Many patients suffer for hours from increased histamine concentrations. The half-life of histamine is even increased during anaphylaxis and hypotension due to reduced kidney filtration and blood flow.

Thus there is a high and unmet demand for improved treatment of conditions associated with excess histamine.

SUMMARY OF THE INVENTION

Under pathological conditions excess histamine cannot be efficiently antagonized by currently available anti-histamines. The increased histamine levels cause annoying, severe, debilitating, life-threatening symptoms and occasionally death.

It is an objective of the present invention to provide an improved regimen for removal of excess histamine and treatment and prevention of histamine-induced diseases and conditions.

The objective is solved by the present invention by the provision of a recombinant modified DAO to increase the concentration of active DAO within the body of an individual to thereby assist in, or enable, respectively, the degradation of histamine.

Administration of recombinant human DAO as described herein can degrade excess histamine under acute, subacute, subchronic, chronic and prophylactic conditions, thereby significantly benefiting patients suffering or going to suffer from several diseases, where anti-histamines are not efficacious enough to degrade the excess histamine concentrations. This establishes an entirely new treatment option for subjects suffering from excess histamine.

According to the invention, a recombinant human diamine oxidase (DAO) with decreased glycosaminoglycan (GAG) binding affinity compared to the GAG binding affinity of the respective wild type human DAO is provided, wherein said DAO comprises at least one amino acid modification in the glycosaminoglycan (GAG) binding domain, specifically the GAG binding domain comprises the amino acids at positions 568-575 with reference to the numbering of SEQ ID NO:1.

Specifically, the GAG binding domain is a heparin/heparan sulfate binding domain.

Specifically, the amino acid modification results in decreased GAG binding affinity of the DAO while its enzymatic activity towards histamine is preserved.

According to a specific embodiment, the at least one amino acid modification in the GAG binding domain of the DAO is an amino acid substitution, deletion, insertion or coupling with a chemical moiety.

According to a specific embodiment of the invention, the recombinant DAO of the invention comprises 2, 3, 4, 5, 6, 7, or 8 amino acid modifications in the GAG binding domain. Specifically, said amino acid residues are substituted by other amino acid residues, specifically arginine or lysine is substituted by serine or threonine.

According to an alternative embodiment, the recombinant DAO comprises a GAG binding domain of amino acid sequence X1FX2X3X4LPX5, wherein X1 can be by any amino acid, specifically it is A or S, more specifically it is S;

X2 can be by any amino acid, specifically it is K;

X3 can be by any amino acid, specifically it is A or T, more specifically it is T, X4 can be by any amino acid, specifically it is K, and X5 can be by any amino acid, specifically it is K or T, more specifically it is T.

In a further specific embodiment, the recombinant DAO comprises the amino acid sequence selected from the group consisting of SFKAKLPK (SEQ ID NO:33), AFKAKLPT (SEQ ID NO:34), AFKTKLPK (SEQ ID NO:35), SFKTKLPK (SEQ ID NO:36), AFKTKLPT (SEQ ID NO:37), SFKAKLPK (SEQ ID NO:38).

According to a specific embodiment, the recombinant DAO as disclosed herein, further comprises at least one modification of the solvent accessible cysteine at amino acid position 123 (cys123) with reference to the numbering of SEQ ID NO: 1, specifically the modification of the cysteine is an amino acid substitution, deletion or conjugation with a chemical moiety.

In a preferred embodiment, cys123, according to the numbering of SEQ ID 1 of DAO is substituted by alanine (cys123ala, C123A).

The DAO of the invention specifically shows reduced clearance from plasma. The invention specifically provides a recombinant DAO which has significantly increased plasma half-life compared to wild type DAO, specifically said half-life is increased at least 1.5 fold, specifically at least 2 fold compared to wild type DAO.

In an alternative or further embodiment, the DAO has an at least 10-fold increased AUC compared to wild type DAO.

According to an embodiment provided herein, internalization of the recombinant DAO by endothelial cells is at least 10%, 25%, 50%, 60%, 70%, 80%, specifically 90% reduced compared to wild type DAO.

According to a further embodiment, the GAG binding affinity of the DAO as described herein, specifically the heparin/heparan sulfate binding affinity is at least 10%, 25%, 50%, 60%, 70%, 80%, specifically 90% reduced compared to wild type DAO.

Herein provided is also a recombinant DAO or functional derivative or analogue thereof comprising the amino acid sequences of SEQ ID NOs:2, 3, 4, 5, 6, 7, 8, 9, 10, 11, 12, 13, 14, 15 or 16 or having at least 90% sequence identity with any one of SEQ ID NOs:2, 3, 4, 5, 6, 7, 8, 9, 10, 11, 12, 13, 14, 15 or 16.

Human DAO also has multiple N-glycosylation sites playing a role in secretion and retention in the endoplasmatic reticulum. Specifically, glycans at Asn-168 are predominantly sialylated with bi- to tetra-antennary branches.

According to an embodiment, the recombinant DAO described herein further comprises a modification, specifically an amino acid substitution at position 168 with reference to SEQ ID NO 1. Specifically, the modification is a single modification at position 168. More specifically, Asn is replaced by Gln. Specifically, said modification increases the PK of the DAO described herein. More specifically, the DAO comprises the amino acid sequence of SEQ ID NO:106.

Herein provided is also a recombinant DAO or a functional derivative or analogue thereof encoded by any one of SEQ ID NOs: 17, 18, 19, 20, 21, 22, 23, 24, 25, 26, 27, 28, 29, 30, 31 or 32 or having at least 90% sequence identity with any one of SEQ ID NOs: 17, 18, 19, 20, 21, 22, 23, 24, 25, 26, 27, 28, 29, 30, 31 or 32.

Herein provided is also an isolated nucleotide sequence encoding the DAO or a functional analogue or derivative thereof as described herein, specifically comprising sequences SEQ ID NOs: 17, 18, 19, 20, 21, 22, 23, 24, 25, 26, 27, 28, 29, 30, 31 or 32 or fragments thereof.

According to a specific embodiment of the invention, herein provided is a fusion polypeptide comprising the recombinant DAO described herein and an Fc domain of human IgG or human serum albumin (HSA) or a fragment thereof, wherein the fusion polypeptide retains the functional activity of the recombinant DAO.

Herein provided is also a fusion polypeptide comprising the recombinant DAO described herein and an Fc domain of human IgG comprising the sequences of any one of SEQ ID Nos:56 to 70 or having at least 90% sequence identity with any one of SEQ ID NOs: 56 to 70.

Herein provided is also a fusion polypeptide comprising the recombinant DAO described herein and an Fc domain of human IgG or a functional derivative or analogue thereof encoded by any one of SEQ ID NOs: 72 to 102 or having at least 90% sequence identity with any one of SEQ ID NOs: 72 to 102.

Further provided herein is a recombinant vector comprising the nucleotide sequence described herein, specifically the vector is a bacterial, yeast, baculoviral, plant or mammalian expression vector.

According to an embodiment, herein provided is an expression cassette comprising the nucleotide sequence, operably linked to regulatory elements.

According to an embodiment, herein provided is a recombinant host cell or a host cell line of bacterial, yeast, baculoviral, plant or mammalian origin, comprising the recombinant DAO described herein, wherein the host cells are specifically selected from the group consisting of CHO cells, Vero cells, MDCK cells, *Pichia pastoris* cells, and SF9 cells.

Further provided herein is an expression system comprising the vector, or the expression cassette and a host cell, or host cell line described herein.

According to an embodiment, herein provided is also a method for producing the recombinant DAO described herein, said method comprising the steps of i. cloning a nucleotide sequence encoding the DAO into an expression vector, ii. transforming a host cell with said vector, iii. cultivating the transformed host cell under conditions wherein the DAO is expressed,
iv. isolating the DAO from the host cell culture, optionally by disintegrating the host cells, and optionally
v. purifying the DAO.

According to an embodiment, a pharmaceutical composition is provided comprising the recombinant DAO and optionally one or more excipients.

Specifically, the pharmaceutical composition can be applied intravenously, intramuscularly and subcutaneously or via other parenteral routes of administration like intraperitoneally or intrathecally.

In a further embodiment, the use of the recombinant DAO for preparing a pharmaceutical composition is provided.

Specifically, the recombinant DAO is provided for use in the treatment of a condition associated with excess histamine, specifically for the treatment of chronic allergic diseases or diseases associated with increase of histamine or decreased DAO activity, more specifically for the treatment of anaphylaxis, anaphylactic shock, chronic urticaria, acute urticaria, asthma, hay fever, allergic rhinitis, allergic conjunctivitis, histamine intoxication, headache, atopic dermatitis inflammatory diseases, mastocytosis, mast cell activation syndrome (MCAS), pre-eclampsia, hyperemesis gravidarum, pre-term labor, peptic ulcers, acid reflux, pruritus, and sepsis.

In an embodiment of the invention, the use of the recombinant DAO is encompassed for the manufacture of a medicament for the treatment of a condition associated with excess histamine, specifically for the treatment of chronic allergic diseases, or diseases associated with increase of histamine or decreased DAO activity, more specifically for the treatment of anaphylaxis, anaphylactic shock, chronic urticaria, acute urticaria, asthma, hay fever, allergic rhinitis, allergic conjunctivitis, histamine intoxication, headache, atopic dermatitis inflammatory diseases, mastocytosis, mast cell activation syndrome (MCAS), pre-eclampsia, hyperemesis gravidarum, pre-term labor, peptic ulcers, acid reflux, pruritus, and sepsis.

In an alternative embodiment, herein provided is a target-specific ligand specifically binding to the GAG binding domain of DAO, specifically binding to one or more of amino acids at position 568-575 with reference to the numbering of SEQ ID NO: 1.

Alternatively, herein provided is a target-specific ligand specifically inhibiting heparin/heparan sulfate binding to the GAG binding domain of DAO, specifically to any one or more of amino acids at position 568-575 with reference to the numbering of SEQ ID NO: 1.

Specifically, the ligand is selected from the group consisting of nucleic acid, small molecule inhibitor or antigen binding protein.

In an alternative embodiment, the ligand is an antigen binding protein, specifically selected from the group consisting of antibodies or antibody fragments, such as any of Fab, Fd, scFv, diabodies, triabodies, Fv tetramers, minibodies, nanobodies, single-domain antibodies like VH, VHH, IgNARs, or V-NAR, antibody mimetics, such as Adnectins™, Affibodies®, Affilins®, Affimers®, Affitins, Alphabodies, Aptamers, Anticalins, Avimers, DARPins®, Fynomers®, Kunitz domain peptides, Monobodies, or NanoCLAMPS; or fusion proteins comprising one or more immunoglobulin-fold domains, antibody domains or antibody mimetics.

According to an embodiment, herein provided is a method for identifying compounds which modulate the heparin binding of the DAO, comprising the steps of (a) constructing a computer model of the GAG binding domain defined by the structure coordinates of the amino acids of the DAO sequence of SEQ ID NO: 1,
(b) selecting a potential modulating compound by a method selected from the group consisting of:
(i) assembling molecular fragments into said compound,
(ii) selecting a compound from a small molecule database, and
(iii) de novo ligand design of said compound;
(c) employing computational means to perform a fitting program operation between computer models of the said compound and the GAG binding domain in order to provide an energy-minimized configuration of the said compound in the heparin binding domain; and
(d) evaluating the results of said fitting operation to quantify the association between the said compound and the heparin/heparan sulfate binding domain, thereby evaluating the ability of said compound to associate with the said heparin binding domain.

FIGURES

FIG. 1: Amino acid and nucleotide sequences of wild type DAO and modified DAO. With reference to amino acid sequences: Bold letters refer to substitutions compared to wt sequences; underlined letter refer to secretion signal; bold, italic letters refer to Fc, bold, italic and underlined letters refer to linker sequences from IgG1 hinge region.

FIG. 2: Heparin-sepharose elution profiles of recombinant human DAO wild type and heparin/heparan sulfate mutants.

Figure 3:
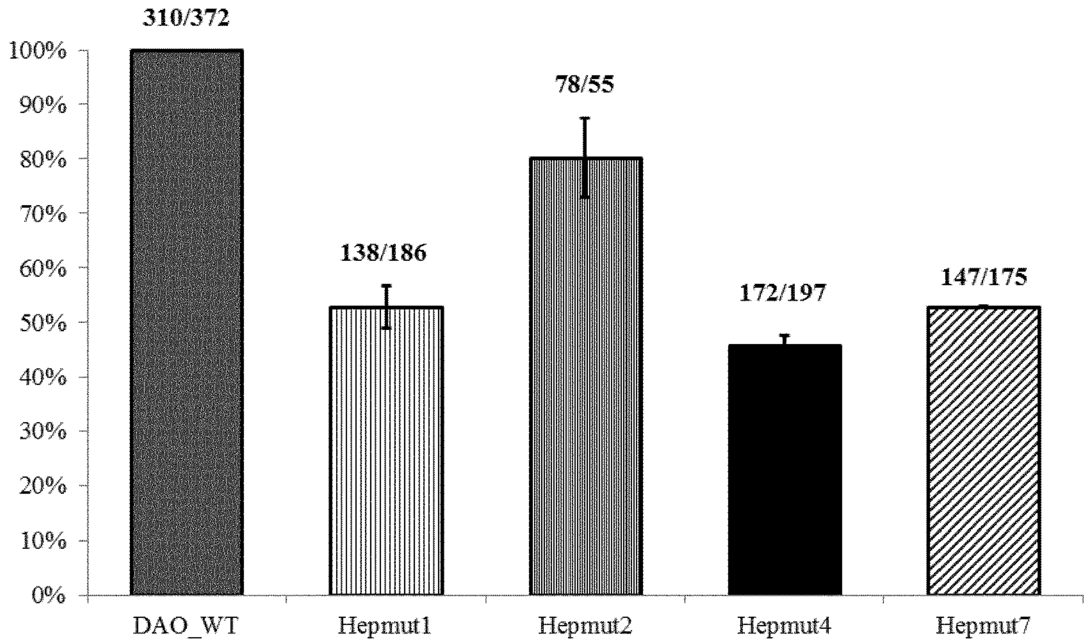

FIG. 3: Hepmut 1, 4 and 7 variants are eluted from heparin-sepharose at 50% lower salt concentrations compared to DAO_WT.

Figure 4:
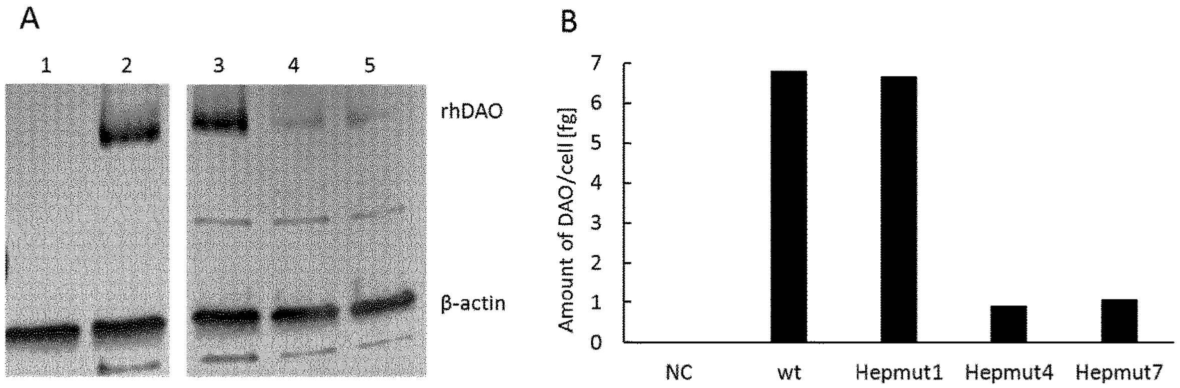

FIG. 4: Western blot of SK-Hep1 cell lysates after incubation with DAO_WT and Hepmut variants FIG. 5: Hepmut4 variant shows reduced binding to SK-Hep1 cells compared to DAO_WT.

Figure 6:
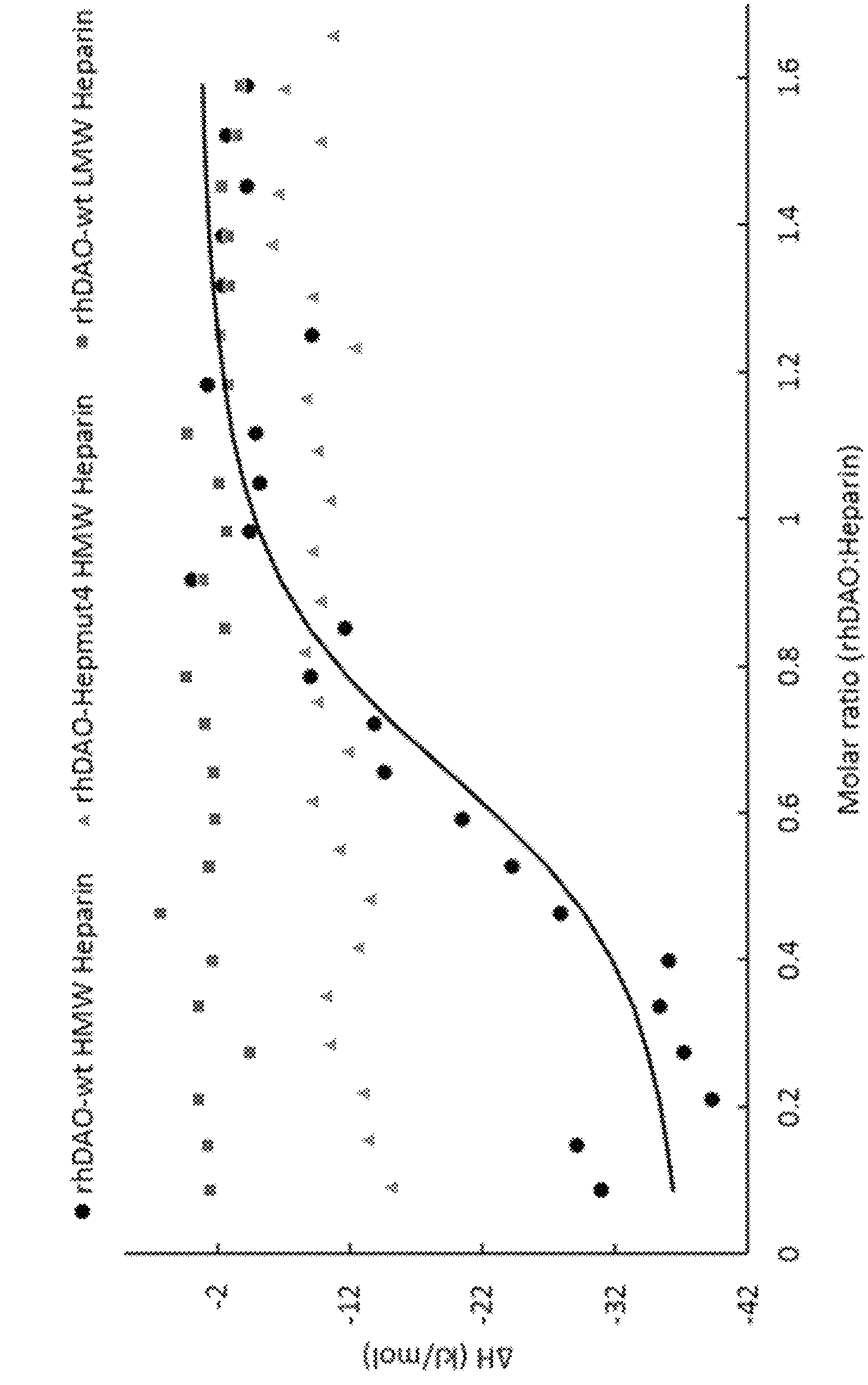

FIG. 6: Isothermal titration calorimetry of DAO_WT and Hepmut4.

FIG. 7: Linear (a) and log y-scales (b) are shown. Hepmut4 increases the AUC (Area Under the Curve) more than 19-fold compared to wild type DAO protein after intravenous injection of 1 mg/kg DAO variants.

Figure 8:
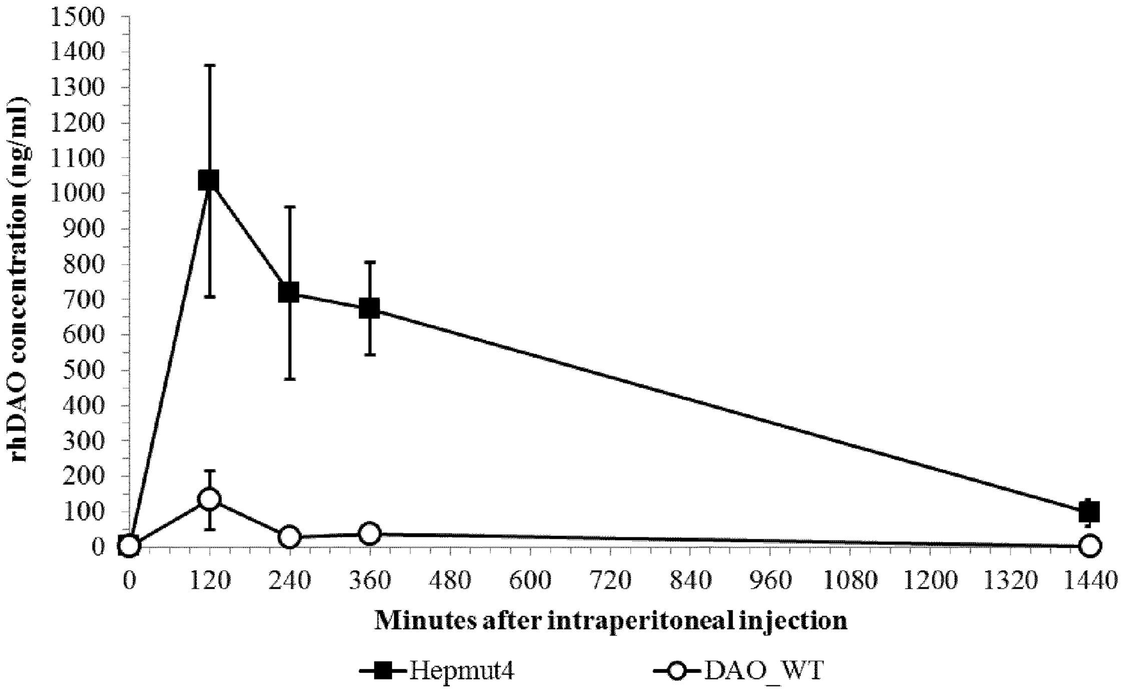

FIG. 8: Hepmut4 increases the AUC more than 16-fold compared to DAO_WT protein after intraperitoneal injection.

Figure 9:
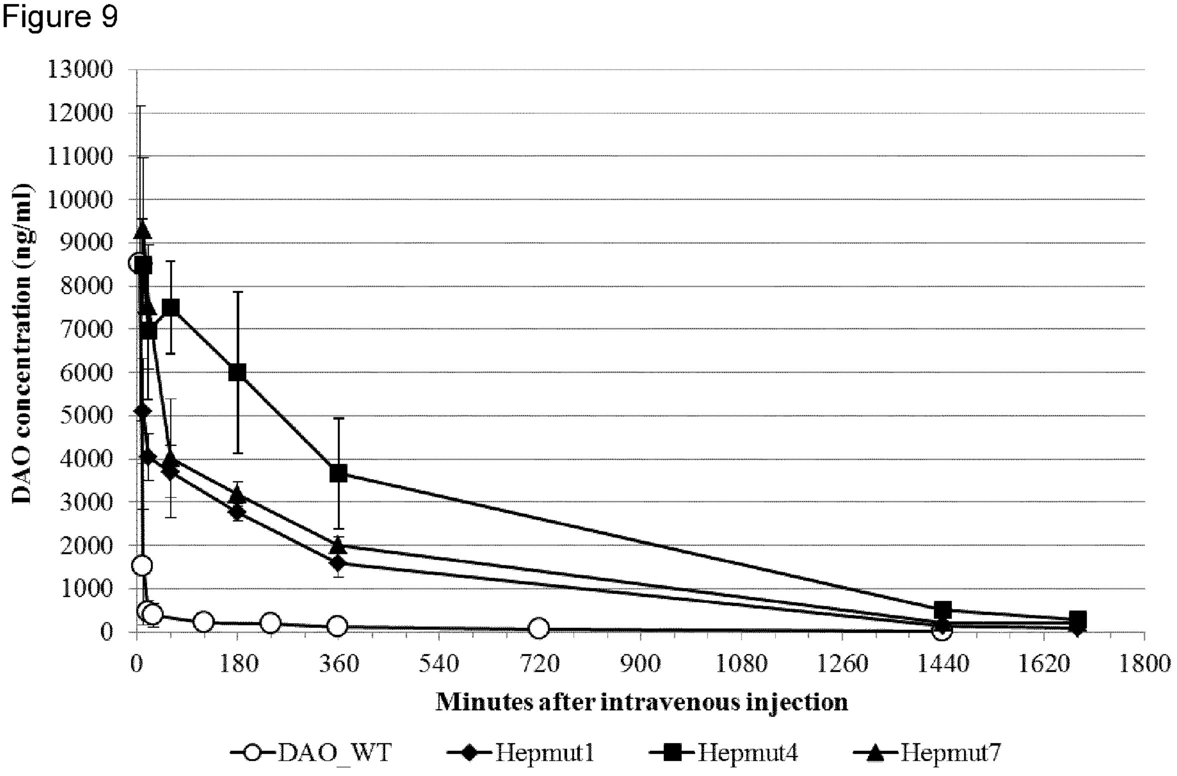

FIG. 9: Means of the measured values using 1 mg/kg DAO wild-type and different Hepmut variants.

Figure 10:
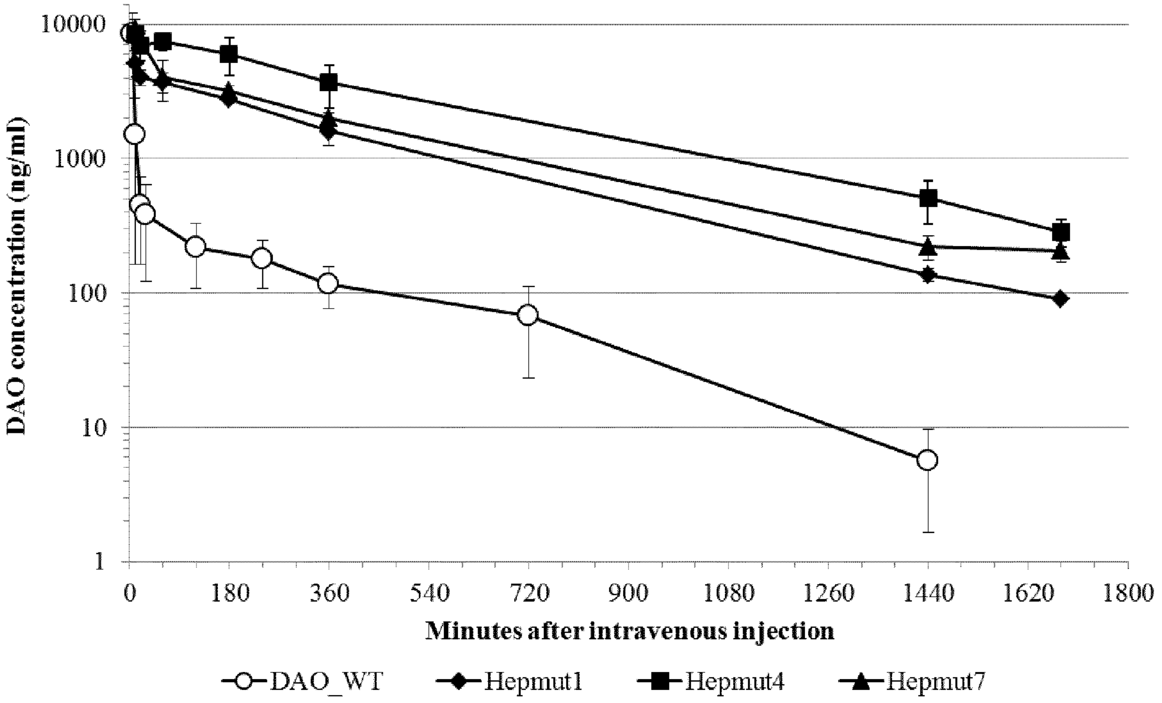

FIG. 10: Slow clearance of heparin/heparan sulfate-binding domain mutants compared to DAO wild type protein administered at 1 mg/kg.

Figure 11:
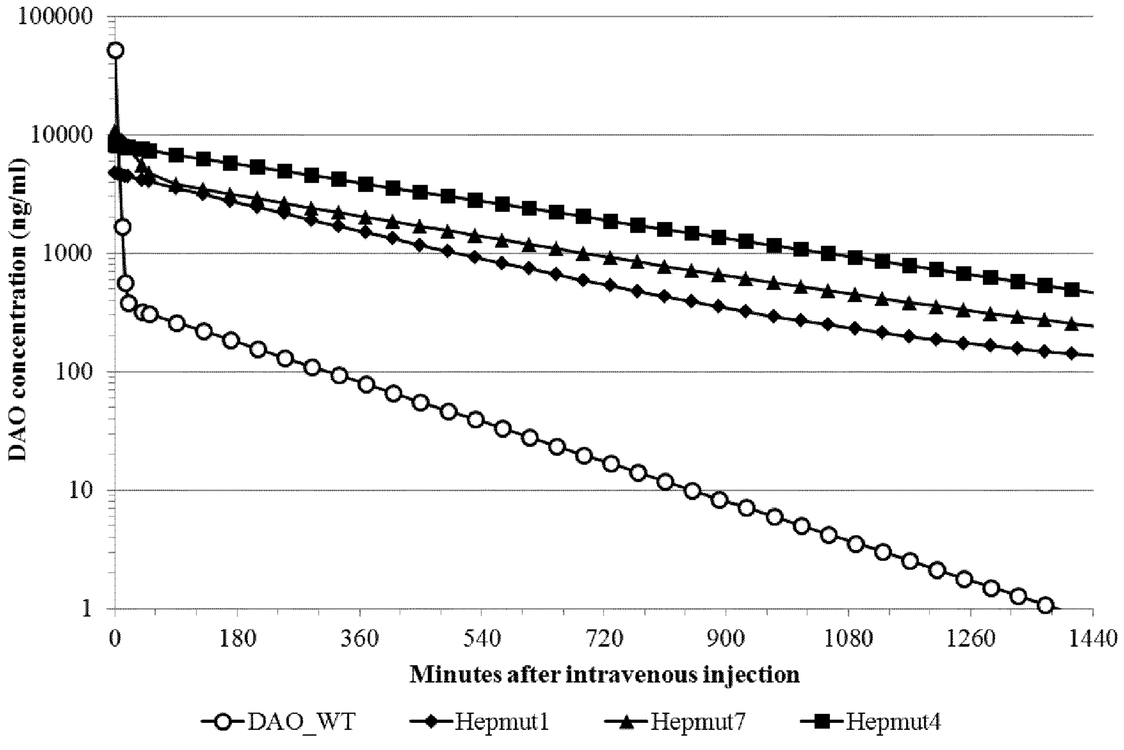

FIG. 11: Slow clearance of heparin-binding domain mutants compared to DAO wild type protein.

Figure 12:
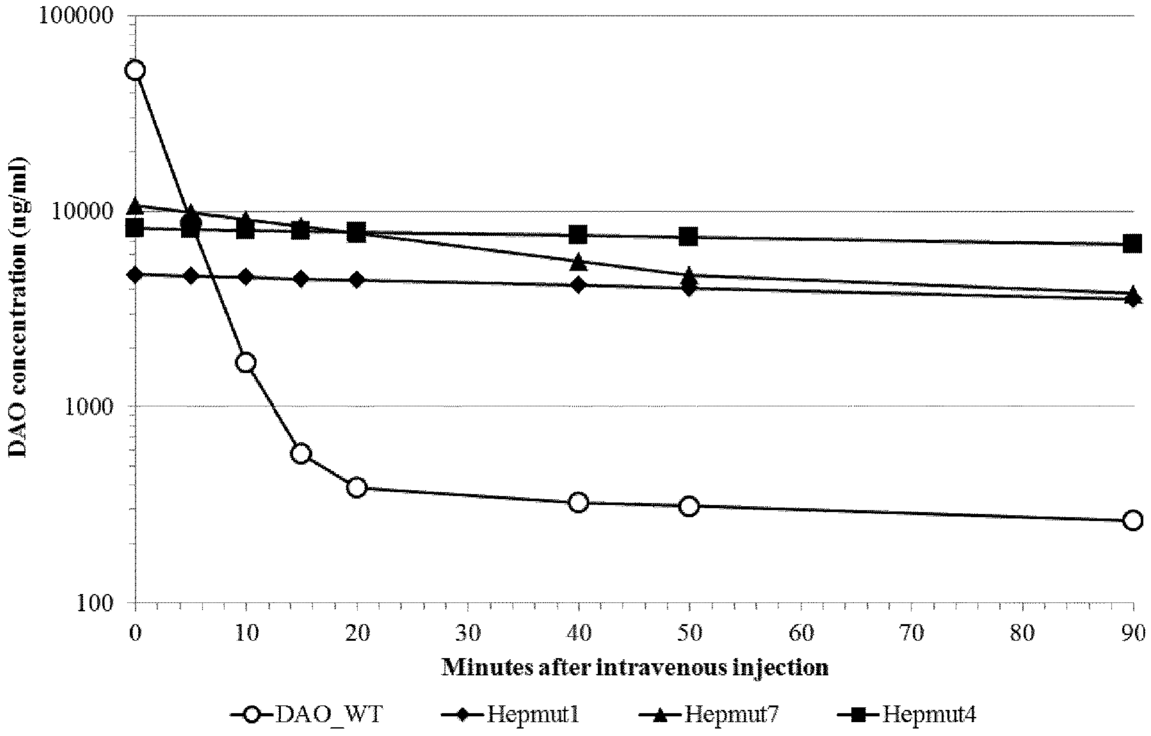

FIG. 12: Slow clearance of heparin-binding domain mutants compared to DAO wild type protein administered at 1 mg/kg.

Figure 13:
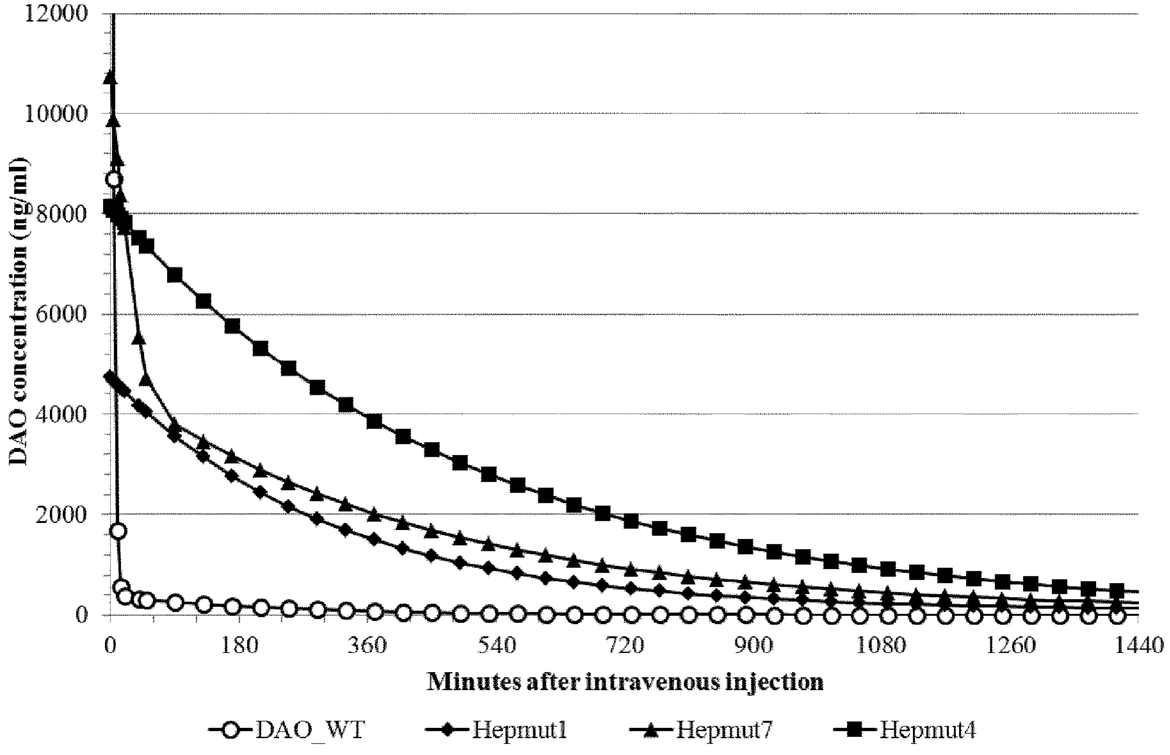

FIG. 13: Slow clearance of heparin-binding domain mutants compared to DAO wild type protein administered at 1 mg/kg. Linear y-axis scale.

Figure 14:
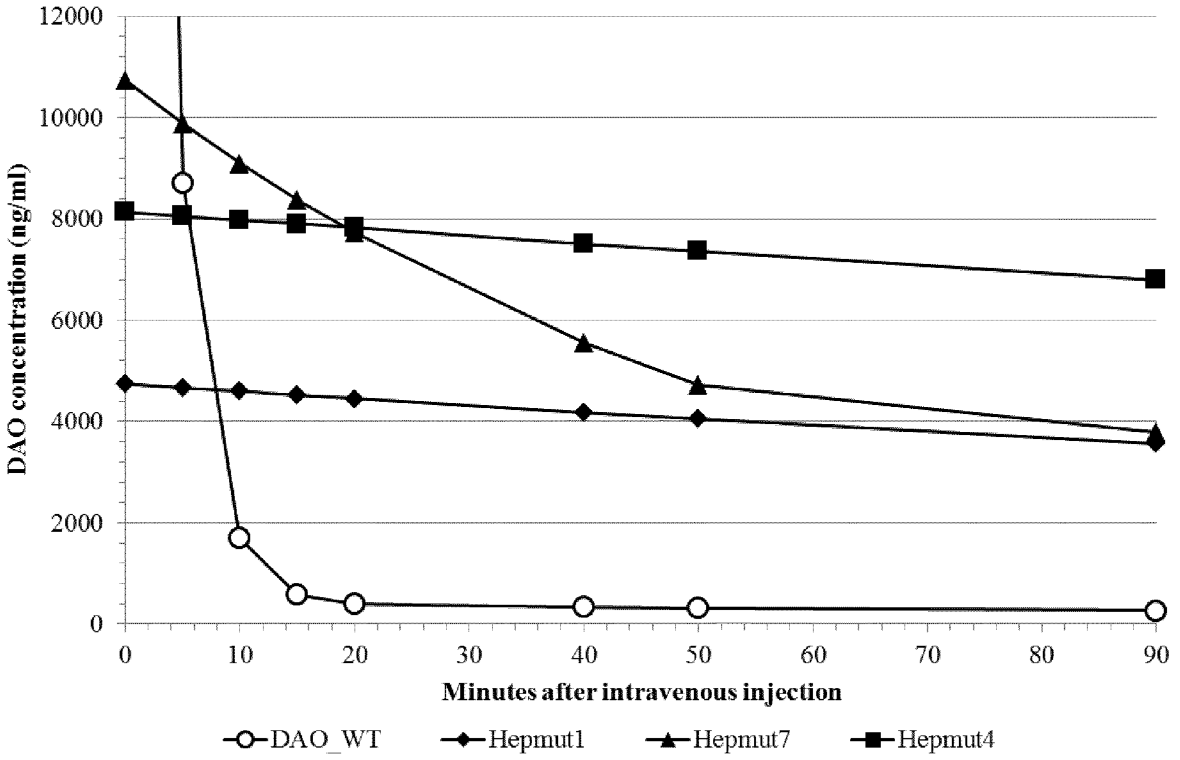

FIG. 14: Slow clearance of heparin-binding domain mutants compared to DAO wild type protein administered at 1 mg/kg. The first 90 minutes are shown; Linear y-axis scale.

Figure 15:
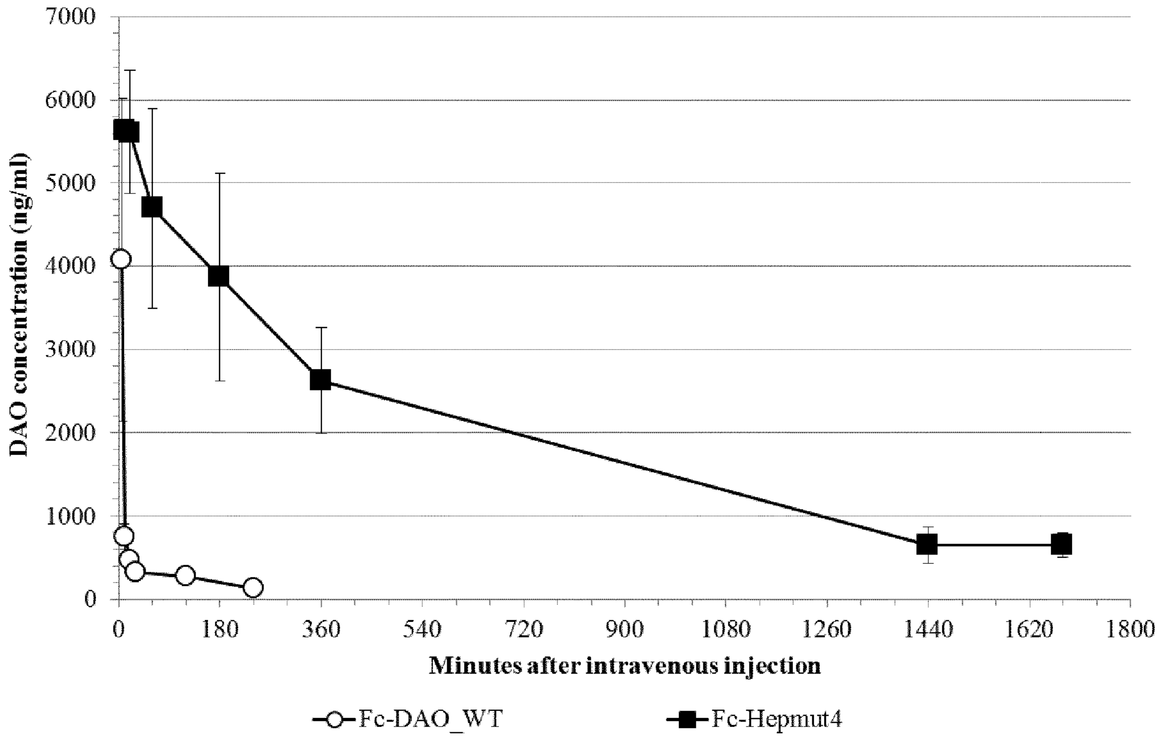

FIG. 15: Rapid clearance of Fc-DAO wild-type compared to Fc-Hepmut4 administered at 1 mg/kg in 6 or 4 rats respectively. The means with the standard deviations are shown; Linear y-axis scale.

Figure 16:
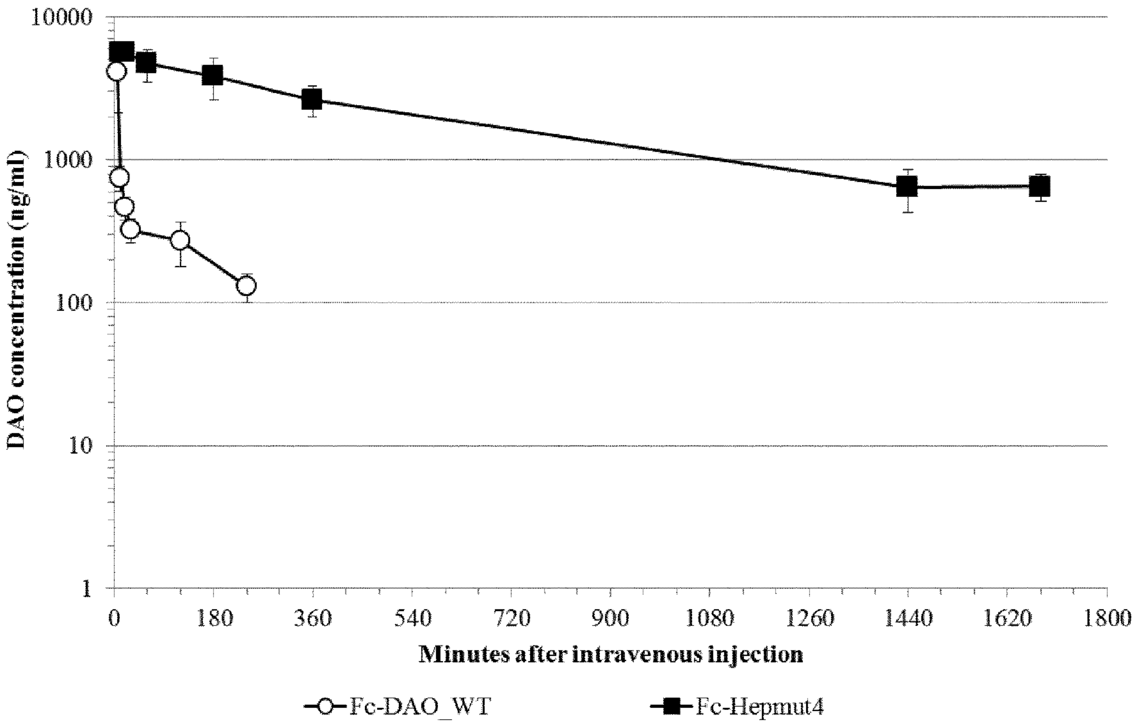

FIG. 16: Rapid clearance of Fc-DAO wild type compared to Fc-Hepmut4 administered at 1 mg/kg in 6 or 4 rats respectively. The means with the standard deviations are shown; Log y-axis scale.

Figure 17:
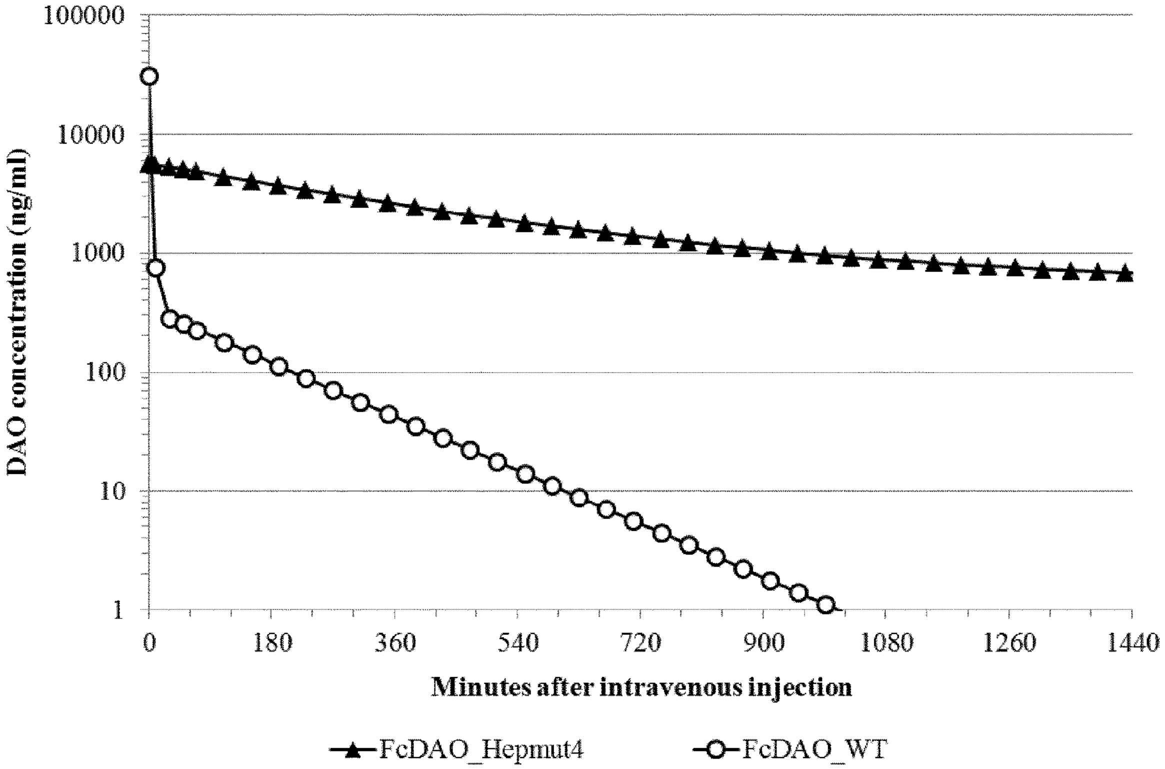

FIG. 17: Fc-DAO-Hepmut4 shows a strong increase in the AUC after intravenous administration of 1 mg/kg; Log y-axis scale.

Figure 18:
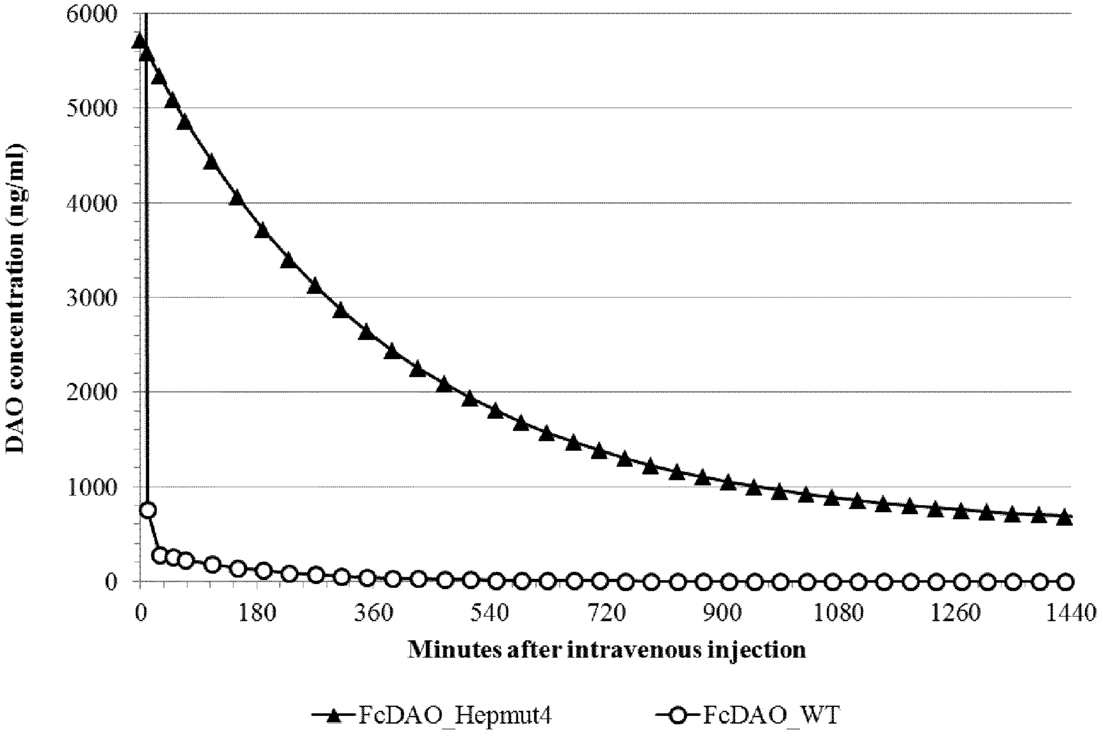

FIG. 18: Fc-DAO-Hepmut4 shows a strong increase in the AUC after intravenous administration of 1 mg/kg; Linear y-axis scale.

Figure 19:
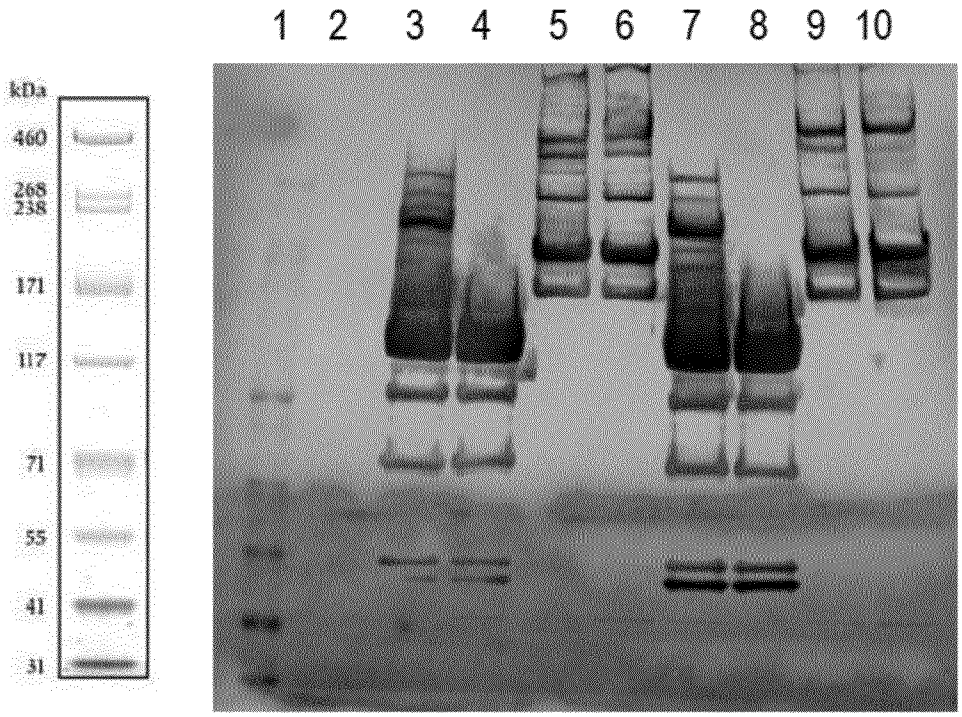

FIG. 19: Western blot of DAO mutants.

Figure 20:
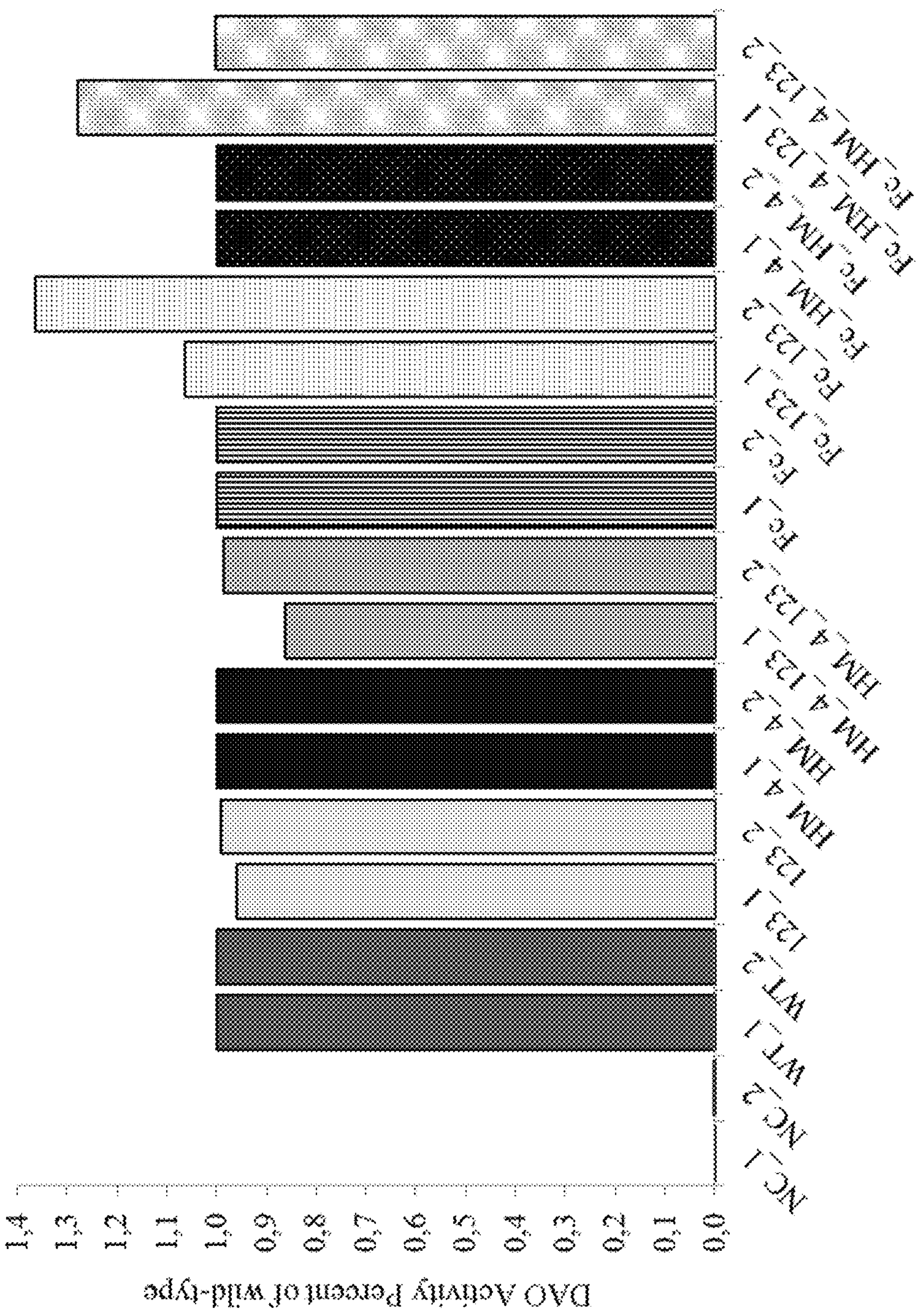

FIG. 20: No relevant difference in the DAO activity between DAO_WT and cys123 mutations.

DETAILED DESCRIPTION

Unless indicated or defined otherwise, all terms used herein have their usual meaning in the art, which will be clear to the skilled person. Reference is for example made to standard handbooks, such as Sambrook et al, "Molecular Cloning: A Laboratory Manual" (2nd Ed.), Vols. 1-3, Cold Spring Harbor Laboratory Press (1989); Lewin, "Genes IV", Oxford University Press, New York, (1990), and Janeway et al, "Immunobiology" (5th Ed., or more recent editions, Garland Science, New York, 2001).

The subject matter of the claims specifically refers to artificial products or methods employing or producing such artificial products, which may be variants of native (wild-type) products. Though there can be a certain degree of sequence identity to the native structure, it is well understood that the materials, methods and uses of the invention, e.g., specifically referring to isolated nucleic acid sequences, amino acid sequences, fusion constructs, expression constructs, transformed host cells and modified proteins, are "man-made" or synthetic, and are therefore not considered as a result of "laws of nature".

The terms "comprise", "contain", "have" and "include" as used herein can be used synonymously and shall be understood as an open definition, allowing further members or parts or elements. "Consisting" is considered as a closest definition without further elements of the consisting definition feature. Thus "comprising" is broader and contains the "consisting" definition.

The term "about" as used herein refers to the same value or a value differing by +/−5% of the given value.

Human DAO monomer comprises about 751 amino acids and forms dimers which are enzymatically active. Of 14 cysteines in the DAO dimer, 10 of them are involved in S-S formation and 4 are not. Specifically, cysteine 123 and 633 are not involved in disulfide bond formation.

As used herein, amino acids refer to twenty naturally occurring amino acids encoded by sixty-four triplet codons. These 20 amino acids can be split into those that have neutral charges, positive charges, and negative charges:

The "neutral" amino acids are shown below along with their respective three-letter and single-letter code and polarity:

Alanine: (Ala, A) nonpolar, neutral;
Asparagine: (Asn, N) polar, neutral;
Cysteine: (Cys, C) nonpolar, neutral;
Glutamine: (Gln, Q) polar, neutral;
Glycine: (Gly, G) nonpolar, neutral;
Isoleucine: (Ile, I) nonpolar, neutral;
Leucine: (Leu, L) nonpolar, neutral;
Methionine: (Met, M) nonpolar, neutral;
Phenylalanine: (Phe, F) nonpolar, neutral;
Proline: (Pro, P) nonpolar, neutral;
Serine: (Ser, S) polar, neutral;
Threonine: (Thr, T) polar, neutral;
Tryptophan: (Trp, W) nonpolar, neutral;
Tyrosine: (Tyr, Y) polar, neutral;
Valine: (Val, V) nonpolar, neutral; and
Histidine: (His, H) polar, positive (10%) neutral (90%).

The "positively" charged amino acids are:
Arginine: (Arg, R) polar, positive; and
Lysine: (Lys, K) polar, positive.

The "negatively" charged amino acids are:
Aspartic acid: (Asp, D) polar, negative; and
Glutamic acid: (Glu, E) polar, negative.

The term "modification" of the inventive DAO refers to any amino acid sequence alteration including, but not limited to, amino acid substitutions, additions, deletions, mutations, and insertions. Modifications can also be chemoselective modifications. Such modification can be a conjugation or coupling with a chemical moiety wherein a stable covalent link is formed between two molecules, at least one of which is a biomolecule. Such conjugation can be formed with one or more amino acid residues, such as, but not limited to, conjugation with maleimides, iodoacetamides, isoacetoamides, 2-thiopyridine, 3-arylpropiolonitrile, benzoyl fluorides, isothyocyanates, isocyanates, diazonium salts, PTAD, NaIO4, or PLP.

Free cysteine rarely occurs on protein surfaces and is an excellent choice for chemoselective modification. Specifically, Cys at amino acid positions 123 and 633 of the modified DAO as described herein are solvent accessible. By specifically substituting the solvent accessible cys123, specifically by exchanging cys123 to ala123, the so produced DAO becomes unable to form disulfide bonds or other molecular interactions leading to higher order aggregates. Upon expression of recombinant DAO in CHO cells certain percentages of DAO molecules (~20% to 30%) form not only dimers but also tetramers, hexamers and even octamers. These higher order oligomers have been described and can be considered to be natural variants with unknown function. It is not clear, whether they form during folding and transport from ER to Golgi and secretion into the extracellular environment or in general only in the extracellular environment. Nevertheless, these tetramers and larger oligomers complicate expression, purification, characterization, standardization and the selection of the optimal formulation of the recombinant DAO described herein. By mutating a relatively solvent accessible cysteine on the surface of DAO, specifically by mutating Cys123, only DAO dimers are found in the supernatant of the host cells, specifically of CHO cells.

In addition, according to a further specific embodiment, cysteine at amino acid position 633 may also be modified as described herein for cys123. Cys633 is also not involved in disulfide bond formation.

Under basic condition, cysteine residues can be deprotonated to generate a thiolate nucleophile, which will react with soft electrophiles, such as maleimides and iodoacetamides. As a result, a carbon-sulfur bond is formed. Another modification of cysteine residues involves the formation of disulfide bond. The reduced cysteine residues react with exogenous disulfides, generating new disulfides bond on protein. An excess of disulfides is often used to drive the reaction, such as 2-thiopyridone and 3-carboxy-4-nitrothiophenol. Electron-deficient alkynes were demonstrated to selectively react with cysteine residues of proteins in the presence of other nucleophilic amino acid residues. Depending on the alkyne substitution, these reactions can produce either cleavable (when alkynone derivatives are used), or hydrolytically stable bioconjugates (when 3-arylpropiolonitriles are used).

Within the term modification also the substitution of natural amino acids with unnatural amino acids is encompassed. Unnatural amino acids are not encoded by the Universal Genetic Code. Usually they can be found in nature as metabolic products, especially in plants and bacteria. Such unnatural amino acids can be selected from, but are not limited to D-amino acids, homo amino acids, N-methyl amino acids, alpha methyl amino acids, $beta^2$ amino acids, $beta^3$ amino acids, $beta^3$ homo amino acids, ACHC, peptoids or heavy amino acids, specifically substituted with 13C and/or 15N atoms, specifically E-acetyl-lysine, alanine(3-amino-proprionic acid), 6-aminocaproic acid, ?-aminobutyric acid, citrulline, cysteine acetamidomethyl protected, dimethyl-lysine, hydroxyl-proline, mercaptoproprionic acid, methyl-lysine, 3-notro-tyrosine, norleucines, pyro glutamic acid, carbobenzoxyl.

The term "GAG binding domain" as used herein refers to the region with the DAO which is involved in binding to or interaction with all four classes of glycosaminoglycans, including heparin/heparan sulfate, chondroitin/dermatan sulfate, keratin sulfate, and hyaluronan. Binding to heparin/heparan sulfate is preferred. Heparin is present in mast cells. Heparan sulfate is present on almost all cells such as endothelial cells.

The term "GAG binding" refers to the interaction/binding of DAO with glycosaminoglycan, specifically with heparin or heparan sulfate. GAGs bind to many different classes of proteins mostly through electrostatic interactions between negatively charged sulfate groups and uronic acids and positively charged amino acids in the protein. Heparin binding affinity can be determined by any method known to the skilled person. Numerous methods are available for analyzing GAG-protein interactions, and some provide a direct measurement of $K_d$ values. A common method involves affinity fractionation of proteins on sepharose columns containing covalently linked GAG chains, usually heparin. The bound proteins are eluted with different concentrations of sodium chloride, and the concentration required for elution is generally proportional to the $K_d$. High-affinity interactions require at least 1 M NaCl to displace bound ligand, which translates into $K_d$ values of $10^{-7}$-$10^{-9}$ M (determined under physiological salt concentrations by equilibrium binding). Proteins with low affinity ($10^{-4}$-$10^{-6}$ M) either do not bind under "normal" conditions (0.15 M NaCl) or require only 0.3-0.5 M NaCl to elute. This method is based on the assumption that GAG-protein interaction is entirely ionic and can provide an assessment of relative affinity, when comparing different GAG-binding proteins. Alternative methods can be, but are not limited to affinity co-electrophoresis, analytical ultracentrifugation, circular dichroism, competition ELISA, fluorescence microscopy, ion mobility mass spectrometry, isothermal titration calorimetry, laser light scattering, NMR, surface plasmon resonance, and X-ray and thereby provide detailed thermodynamic data (ΔH [change in enthalpy], ΔS [change in entropy], ΔCp [change in molar heat capacity], etc.), kinetic data (association and dissociation rates), and high-resolution data on atomic contacts in GAG-protein interactions (Esko J D. et al., Essentials of Glycobiology, 3rd edition, Chapter 38, 2017).

Specifically, the DAO mutants as described herein have diminished or show reduced binding to heparin and/or heparan sulfate. Specifically, heparin/heparan sulfate binding affinity of the recombinant DAO is at least 10%, 25%, 50%, 60%, 70%, 80%, specifically 90% reduced compared to wild type DAO. According to a specific method, binding affinity is determined using heparin-sepharose chromatography, wherein the DAO variants are incubated at low salt concentrations and eluted with increasing salt concentrations. The salt concentrations with the peak in DAO protein (measured using absorbance at 280 nm) is used as the mM salt concentration at which DAO is eluted.

The DAO of the invention further show decreased internalization into endothelial cells compared to wild type DAO which is internalized. Specifically, internalization by endothelial cells is at least 10%, 25%, 50%, 60%, 70%, 80%, specifically 90% reduced compared to wild type DAO.

Specifically, the GAG binding domain comprises amino acids at positions 568-575 with reference to the numbering of SEQ ID NO:1. Within said domain, 1, 2, 3, 4, 5, 6, 7, or all amino acids can be modified.

A DAO monomer contains 24 lysines and 44 arginines in the primary amino acid sequence, most of them being on the surface of the molecule. It is likely that other lysines and arginines are involved in heparin binding. Besides the GAG binding domain encompassing amino acids at positions 568-575 further lysines or arginines on the surface of DAO may be involved in heparin/heparan sulfate binding.

Modification of one or more of these lysines and/or arginines may further decrease heparin/heparan sulfate binding of the recombinant DAO.

The term "enzymatic activity" of DAO refers to the polypeptide's ability to catalyze the oxidative deamination of an appropriate substrate like putrescine or histamine to aminobutyraldehyde or imidazole acetaldehyde. Preservation of enzymatic activity means that the DAO of the invention has the same or similar enzymatic activity as the respective wild type DAO. Enzymatic activity that is at least 80%, specifically at least 90% of the wild type activity is interpreted to be the similar enzymatic activity as a wild type DAO.

For determining enzymatic activity of DAO, any methods can be used known in the art. These methods can be, but are not limited to assays using horseradish peroxidase (HRP)-mediated luminol oxidation (Bartko J. et al., Alcohol. 2016 August; 54:51-9), spectrophotometric methods as described by Holmstedt B. O. and Tham R. (Acta Physiol. Scand., 1959, 45, 152-163) and Bardsley W. G. et al., (Biochem. J. 1972, 127, 875-879), mass spectrometry (Gludovacz E. et al., 2016), liquid scintillation counting (Okuyama T. and Kobayashi Y., Archives Biochem. Biophys., 19661, 95, 242-250), titrimetric, manometric, fluorometric, biological or radioactive assay methods (Zeller E A., The enzymes, (J. B. Sumner and K Maybäck, eds.) Vol II, Part A, p. 536, Academic Press, New York 1951; Shore P. A. et al., J. Pharmacol., Exptl. Therap. 127, 1959, 182; Ahlark A., Acta Physiol. Scand. Suppl., 1944, 28, 9)

The term "functional variant" or "functionally active variant" also includes naturally occurring allelic variants, as well as mutants or any other non-naturally occurring variants. As is known in the art, an allelic variant is an alternate form of a nucleic acid or peptide that is characterized as having a substitution, deletion, or addition of one or more nucleotides or one or more amino acids that does essentially not alter the biological function of the nucleic acid or polypeptide.

Functional variants may be obtained by sequence alterations in the polypeptide or the nucleotide sequence, e.g. by one or more point mutations, wherein the sequence alterations retain or improve a function of the unaltered polypeptide or the nucleotide sequence, when used in combination of the invention. Such sequence alterations can include, but are not limited to, (conservative) substitutions, additions, deletions, mutations and insertions. Conservative substitutions are those that take place within a family of amino acids that are related in their side chains and chemical properties. Examples of such families are amino acids with basic side chains, with acidic side chains, with non-polar aliphatic side chains, with non-polar aromatic side chains, with uncharged polar side chains, with small side chains, with large side chains etc.

A point mutation is particularly understood as the engineering of a poly-nucleotide that results in the expression of an amino acid sequence that differs from the non-engineered amino acid sequence in the substitution or exchange, deletion or insertion of one or more single (non-consecutive) or doublets of amino acids for different amino acids.

In an alternative embodiment, a GAG binding domain can be introduced into DAO at any position within the polypeptide by recombinant means. The respective domain can be comprised of amino acid sequence X1FX2X3X4LPX5, X1 being any amino acid, specifically being A or S, more specifically being S; X2 being any amino acid, specifically being K; X3 being any amino acid, specifically A or T, more specifically T, X4 being any amino acid, specifically K, and X5 being any amino acid, specifically K or T, more specifically T. In a specific embodiment one or more of the amino acid sequences SFKAKLPK (SEQ ID NO:33), AFKAKLPT (SEQ ID NO:34), AFKTKLPK (SEQ ID NO:35), SFKTKLPK (SEQ ID NO:36), AFKTKLPT (SEQ ID NO:37), SFKAKLPK (SEQ ID NO:38) are introduced into the DAO polypeptide described herein.

The term "sequence identity" as used herein is understood as the relatedness between two amino acid sequences or between two nucleotide sequences and described by the degree of sequence identity or sequence complementarity. The sequence identity of a variant, homologue or orthologue as compared to a parent nucleotide or amino acid sequence indicates the degree of identity of two or more sequences. Two or more amino acid sequences may have the same or conserved amino acid residues at a corresponding position, to a certain degree, up to 100%. Two or more nucleotide sequences may have the same or conserved base pairs at a corresponding position, to a certain degree, up to 100%.

Sequence similarity searching is an effective and reliable strategy for identifying homologs with excess (e.g., at least 50%) sequence identity. Sequence similarity search tools frequently used are e.g., BLAST, FASTA, and HMMER.

Sequence similarity searches can identify such homologous proteins or polynucleotides by detecting excess similarity, and statistically significant similarity that reflects common ancestry. Homologues may encompass orthologues, which are herein understood as the same protein in different organisms, e.g., variants of such protein in different organisms or species.

To determine the % complementarity of two complementary sequences, one of the two sequences needs to be converted to its complementary sequence before the % complementarity can then be calculated as the % identity between the first sequence and the second converted sequences using the above-mentioned algorithm.

"Percent (%) identity" with respect to an amino acid sequence, homologs and orthologues described herein is defined as the percentage of amino acid residues in a candidate sequence that are identical with the amino acid residues in the specific polypeptide sequence, after aligning the sequence and introducing gaps, if necessary, to achieve the maximum percent sequence identity, and not considering any conservative substitutions as part of the sequence identity. Those skilled in the art can determine appropriate parameters for measuring alignment, including any algorithms needed to achieve maximal alignment over the full length of the sequences being compared.

For purposes described herein, the sequence identity between two amino acid sequences is determined using the NCBI BLAST program version 2.2.29 (Jan.-06-2014) with blastp set at the following exemplary parameters: Program: blastp, Word size: 6, Expect value: 10, Hitlist size: 100, Gapcosts: 11.1, Matrix: BLOSUM62, Filter string: F, Genetic Code: 1, Window Size: 40, Threshold: 21, Composition-based stats: 2.

"Percent (%) identity" with respect to a nucleotide sequence e.g., of a nucleic acid molecule or a part thereof, in particular a coding DNA sequence, is defined as the percentage of nucleotides in a candidate DNA sequence that is identical with the nucleotides in the DNA sequence, after aligning the sequence and introducing gaps, if necessary, to achieve the maximum percent sequence identity, and not considering any conservative substitutions as part of the sequence identity. Alignment for purposes of determining percent nucleotide sequence identity can be achieved in various ways that are within the skill in the art, for instance, using publicly available computer software. Those skilled in the art can determine appropriate parameters for measuring alignment, including any algorithms needed to achieve maximal alignment over the full length of the sequences being compared.

Optimal alignment may be determined with the use of any suitable algorithm tor aligning sequences, non-limiting examples of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at novocraft.com), ELAND (Illumina, San Diego, CA), SOAP (available at soap.genomies.org.cn), and Maq (available at maq.sourceforge.net).

The DAO as described herein can comprise the amino acid sequences of SEQ ID NOs:2 to 16 and any functional variants thereof having 90%, 95%, 99% sequence identity with any of SEQ ID NOs:2 to 16.

The recombinant DAO has increased plasma half-life compared to wild type DAO, specifically said half-life is increased at least 1.5 fold, specifically at least 2 fold compared to wild type DAO.

The duration of action or physical presence of a drug is known as its half-life. This is the period of time required for the concentration or amount of drug in the body or whole blood or plasma to be reduced by one-half. Half-life of a drug is usually considered in relation to the amount of the drug in plasma or serum. A drug's plasma or serum half-life depends on how quickly the drug is eliminated from the plasma or serum. A drug molecule may be eliminated from the body, or it can be translocated to another body fluid compartment such as the intracellular fluid or it can be destroyed in the blood. The removal of a drug from the plasma is known as clearance and the distribution of the drug in the various body tissues is known as the volume of distribution.

The area under the plasma drug concentration-time curve (AUC) reflects the actual body exposure to drug, i.e. the recombinant DAO described herein, after administration of a dose of the drug and is expressed in µg/min/ml. This area under the curve is dependent on the rate of elimination of the drug from the body and the dose administered. The total amount of drug eliminated by the body may be assessed by adding up or integrating the amounts eliminated in each time interval, from time zero (time of the administration of the drug) to infinite time. This total amount corresponds to the fraction of the dose administered that reaches the systemic circulation. The AUC is directly proportional to the dose when the drug follows linear kinetics. The AUC is inversely proportional to the clearance of the drug. That is, the higher the clearance, the less time the drug spends in the systemic circulation and the faster the decline in the plasma drug concentration. Therefore, in such situations, the body exposure to the drug and the area under the concentration-time curve are smaller.

The recombinant DAO as described herein has an at least 2-fold, at least 5-fold, 10-fold, at least 15-fold, at least 20-fold, at least 25-fold, at least 30-fold increased AUC compared to wild type DAO.

The term "expression" is understood in the following way. Nucleic acid molecules containing a desired coding sequence of an expression product such as e.g., a fusion protein as described herein may be used for expression purposes. Hosts transformed or transfected with these sequences are capable of producing the encoded proteins. In order to effect transformation, the expression system may be included in a vector; however, the relevant DNA may also be integrated into the host chromosome. Specifically, the term refers to a host cell and compatible vector under suitable conditions, e.g., for the expression of a protein coded for by foreign DNA carried by the vector and introduced to the host cell.

Coding DNA is a DNA sequence that encodes a particular amino acid sequence for a particular polypeptide or protein. Promoter DNA is a DNA sequence which initiates, regulates, or otherwise mediates or controls the expression of the coding DNA. Promoter DNA and coding DNA may be from the same gene or from different genes, and may be from the same or different organisms. Recombinant cloning vectors often include one or more replication systems for cloning or expression, one or more markers for selection in the host, e.g., antibiotic resistance, one or more nuclear localization signals (NLS) and one or more expression cassettes.

"Expression vector" as used herein is defined as DNA sequences that are required for the transcription of cloned recombinant nucleotide sequences, i.e. of recombinant genes and the translation of their mRNA in a suitable host organism. To obtain expression, a sequence encoding a desired expression product, such as the DAO described herein, is typically cloned into an expression vector that contains a promoter to direct transcription. Suitable bacterial and eukaryotic promoters are well known in the art. The promoter used to direct expression of a nucleic acid depends on the particular application. For example, a strong constitutive promoter is typically used for expression and purification of fusion proteins. In contrast, when the expression product is to be administered in vivo for gene regulation, either a constitutive or an inducible promoter can be used, depending on the particular use of the expression product. In addition, a preferred promoter for administration can be a weak promoter. The promoter can also include elements that are responsive to transactivation, e.g., hypoxia response elements, Gal4 response elements and lac repressor response elements. Expression vectors comprise the expression cassette and additionally usually comprise an origin for autonomous replication in the host cells or a genome integration site, one or more selectable markers (e.g., an amino acid synthesis gene or a gene conferring resistance to antibiotics such as zeocin, kanamycin, G418 or hygromycin), a number of restriction enzyme cleavage sites, a suitable promoter sequence and a transcription terminator, which components are operably linked together.

An "expression cassette" refers to a DNA coding sequence or segment of DNA coding for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct".

Any suitable host cell or cell line can be used for expressing the recombinant DAO which allows proper folding, post-translational modifications, and enzymatic activity. Specifically, recombinant host cells may be selected from CHO cells, COS cells, Vero cells, MDCK cells, *Pichia pastoris* cells, SF9 cells, human cell lines such as HEK and HeLa.

The term "vector" as used herein includes autonomously replicating nucleotide sequences as well as genome integrating nucleotide sequences. A common type of vector is a "plasmid", which generally is a self-contained molecule of double-stranded DNA that can readily accept additional (foreign) DNA and which can readily be introduced into a suitable host cell. A plasmid vector often contains coding DNA and promoter DNA and has one or more restriction sites suitable for inserting foreign DNA. Specifically, the term "vector" or "plasmid" refers to a vehicle by which a DNA or RNA sequence (e.g., a foreign gene) can be introduced into a host cell, so as to transform the host and promote expression (e.g., transcription and translation) of the introduced sequence. Vectors are transfected into the cells and the DNA may be integrated into the genome by homologous recombination in the case of stable transfection, or the cells may be transiently transfected. Specifically the vector is a bacterial, yeast, baculoviral, plant or mammalian expression vector.

Any of the known procedures for introducing foreign nucleotide sequences into host cells may be used. These include the use of calcium phosphate transfection, polybrene, protoplast fusion, electroporation, nucleofection, liposomes, microinjection, naked DNA, plasmid vectors, viral vectors, both episomal and integrative, and any of the other well-known methods for introducing cloned genomic DNA, cDNA, synthetic DNA or other foreign genetic material into a host cell (see, e.g., Sambrook et al.).

Examples of mammalian expression vectors include the adenoviral vectors, the pSV and the pCMV series of plasmid vectors, vaccinia and retroviral vectors, as well as baculovirus. The promoters for cytomegalovirus (CMV) and SV40 are commonly used in mammalian expression vectors to drive gene expression. Non-viral promoter, such as the elongation factor (EF)-1 promoter, is also known.

Using above described vectors and host cells, the present invention provides a method for producing the recombinant DAO comprising the sequential steps of cloning a nucleotide sequence encoding the DAO into an expression vector, transforming a host cell, specifically a mammalian cell with said vector, cultivating the transformed host cell under conditions wherein the DAO is expressed, isolating the DAO from the host cell culture, optionally by disintegrating the host cells or isolating the DAO from cell culture supernatant, and optionally purifying the DAO.

Further described is a pharmaceutical composition, comprising the recombinant DAO provided herein. According to a specific embodiment, such pharmaceutical composition comprising the DAO or its functional variants as described herein is used for the treatment of any condition associated with excess histamine, specifically of excess histamine of >1 ng/ml plasma concentration, specifically for the treatment of chronic allergic diseases, more specifically for the treatment of anaphylaxis, anaphylactic shock, chronic urticaria, acute urticaria, asthma, hay fever, allergic rhinitis, allergic conjunctivitis, histamine intoxication, headache, itching, vomiting, tachycardia, hypotension, cardiac arrest, atopic dermatitis inflammatory diseases, mastocytosis, mast cell activation syndrome (MCAS), pre-eclampsia, hyperemesis gravidarum, pre-term labor, peptic ulcers, acid reflux, pruritus, and sepsis.

Specifically, the pharmaceutical composition described herein further comprises pharmaceutically acceptable carriers or excipients, such as for example bulking agents, when used for diagnosis or therapy. These pharmaceutical compositions can be administered in accordance with the present invention as a bolus injection or infusion or by continuous infusion. Pharmaceutical carriers suitable for facilitating such means of administration are well-known in the art.

Pharmaceutically acceptable carriers generally include any and all suitable solvents, dispersion media, coatings, isotonic and absorption delaying agents, and the like that are physiologically compatible with the DAO provided by the invention. Further examples of pharmaceutically acceptable carriers include sterile water, saline, phosphate buffered saline, dextrose, glycerol, ethanol, and the like, as well as combinations of any thereof.

Additional pharmaceutically acceptable carriers are known in the art and described in, e.g., Remington's Pharmaceutical Sciences (Gennaro, AR, ed., Mack Publishing Co, 1985). Liquid formulations can be solutions, emulsions or suspensions and can include excipients such as suspending agents, solubilizers, surfactants, preservatives, and chelating agents.

Exemplary formulations as used for parenteral administration include those suitable for subcutaneous, intramuscular or intravenous injection as, for example, a solution, emulsion or suspension.

The DAO described herein is specifically administered at a therapeutically effective amount, meaning a quantity or activity sufficient to effect beneficial or desired results, including clinical results, when administered to a subject, e.g. a patient suffering from cancer. As such, an effective amount or synonymous quantity thereof depends upon the context in which it is being applied. An effective amount is intended to mean that amount of a compound that is sufficient to treat, prevent or inhibit such diseases or disorders.

The amount of the compound, i.e. the recombinant DAO described herein, that will correspond to such an effective amount will vary depending on various factors, such as the given drug or compound, the pharmaceutical formulation, the route of administration, the type of disease or disorder, the identity of the subject or host being treated, and the like, but can nevertheless be routinely determined by one skilled in the art.

According to a specific embodiment of the invention, a fusion polypeptide is provided wherein the recombinant DAO is conjugated to a second moiety, which can be, but is not limited to Fc or human serum albumin (HSA).

According to a specific embodiment, the DAO conjugated to and Fc comprises any one of SEQ ID NOs: 40 to 70 or a functional fragment thereof having at least 80%, specifically at least 85%, 90%, 95%, 99% sequence identity with any one of SEQ ID NOs:40 to 70.

According to a specific embodiment, the DAO conjugated to and Fc is encoded by any one of SEQ ID NOs: 72 to 102 or by a fragment thereof having at least 80%, specifically at least 85%, 90%, 95%, 99% sequence identity with any one of SEQ ID NOs:72 to 102.

The term "fusion polypeptide" in the context of the present invention concerns a sequence of amino acids, predominantly (but not necessarily) connected to each other by peptide bonds. The term "fused" in accordance with the fusion polypeptide of the present invention refers to the fact that the amino acid sequences of at least two different origins, namely, the modified DAO as herein defined and the second moiety, specifically the Fc domain of human IgG or albumin, are linked to each other by covalent bonds either directly or via an amino acid linker or spacer, joining (bridging, conjugating, covalently binding) the amino acid sequences. The fusion may be performed by chemical conjugation or by genetic engineering methods that are well known in the art.

In some embodiments the DAO polypeptide as herein defined is covalently linked through its C-terminus to either the Fc domain of human IgG or to HSA. Namely, in some embodiments, in the N- to C-terminal direction, the fusion polypeptide according to the invention comprises the DAO polypeptide and either the Fc domain component or HSA.

In other embodiments the DAO polypeptide as herein defined is covalently linked through its N-terminus to either the Fc domain of human IgG or to HSA. Namely, in some embodiments, in the N- to C-terminal direction, the fusion polypeptide of the invention comprises the Fc domain component or HSA and the DAO polypeptide.

The term "polypeptide" as used herein refers to amino acid residues, connected by peptide bonds. A polypeptide sequence is generally reported from the N-terminal end containing free amino group to the C-terminal end containing free carboxyl group. A polypeptide may also be termed amino acid sequence, peptide, or protein and can be modified, for example, by manosylation, glycosylation, amidation, carboxylation or phosphorylation.

By the term "covalently linked" or "covalently linking" it is meant that the indicated domains are connected or linked by covalent bonds.

Specifically, as used herein, the term "Fc fusion polypeptide" encompasses the DAO of the present disclosure comprising a full length Fc domain as well as proteins comprising Fc domain fragments (e.g., a full CH2 domain, a full CH3 domain, a CH2 fragment, a CH3 fragment, or combinations thereof). An Fc fusion protein may also comprise all or a portion of the hinge region.

As used herein the Fc region includes the polypeptides comprising the constant region of an antibody excluding the first constant region immunoglobulin domain, and fragments thereof. Thus Fc refers to the last two constant region immunoglobulin domains of IgA, IgD, and IgG, and the last three constant region immunoglobulin domains of IgE and IgM, and optionally the flexible hinge region N-terminal to these domains. For IgA and IgM the Fc region can include the J chain. For IgG, Fc comprises immunoglobulin domains Cgamma2 and Cgamma3 (Cγ2 and Cγ3) and optionally the hinge region between Cgamma1 (Cγ1) and Cgamma2 (Cγ2). Although the boundaries of the Fc region can vary, the human IgG heavy chain Fc region is usually defined to comprise residues C226 or P230 to its carboxyl-terminus, wherein the numbering is according to the EU index as set forth in Kabat (Kabat et al., Sequences of Proteins of Immunological Interest, 5th Ed. Public Health Service, National Institutes of Health, Bethesda, Md. (1991)). Fc can refer to this region in isolation, or this region in the context of an antibody, antibody fragment, or Fc fusion protein.

The HSA sequence fused to the DAO polypeptide described herein can comprise the wild type sequence or 90%, specifically at least 95%, more specifically at least 99%, more specifically at least 99.9% sequence identity with the wild type sequence (SEQ ID NO: 103). Optionally a linker sequence is contained between DAO and HSA, specifically comprising 2 to about 10 amino acid residues.

According to a specific embodiment, GAG binding of DAO, specifically heparin/heparan sulfate binding is inhibited thus leading to decreased internalization of DAO and increased amount of DAO in the body's circularization which can be determined by AUC. By modifying the DAO as described herein, the DAO indeed shows significantly decreased heparin/heparan sulfate binding.

A further option to increase DAO in the body's circularization is to provide a target-specific ligand specifically binding to the heparin/heparan sulfate binding domain. Specifically, an antibody or antibody fragment or any ligand may bind to DAO close to the heparin binding domain and thereby blocks access to the heparin binding domain. Alternatively it is a fusion protein where parts of the fusion protein cover and block the function of the heparin binding domain and therefore have the same effect as mutations or antibody binding directly to the heparin binding domain.

As an alternative, heparin/heparan sulfate binding to the GAG binding domain of DAO is inhibited. The ligand can be an antigen binding protein, specifically selected from the group consisting of antibodies or antibody fragments, such as any of Fab, Fd, scFv, diabodies, triabodies, Fv tetramers, minibodies, nanobodies, single-domain antibodies like VH, VHH, IgNARs, or V-NAR; antibody mimetics, such as Adnectins™ (sharing with antibody variable domains a beta-sheet sandwich fold with diversified loops, but differing from antibodies in primary sequence and having a single-domain structure without disulfide bonds), Affibodies® (small, simple proteins composed of a three-helix bundle based on the scaffold of one of the IgG-binding domains of Protein A), Affilins® (structurally derived from human ubiquitin, constructed by modification of surface-exposed amino acids of these proteins and isolated by display techniques such as phage display and screening. Affilins resemble antibodies in their affinity and specificity to antigens but not in structure, which makes them a type of antibody mimetic), Affimers® (small proteins that bind to target molecules with similar specificity and affinity to that of antibodies), Affitins (artificial proteins with the ability to selectively bind antigens), Alphabodies, Aptamers, Anticalins, Avimers, DARPins® (genetically engineered antibody mimetic proteins typically exhibiting highly specific and high-affinity target protein binding), Fynomers® (small binding proteins (7 kDa) derived from the human SH3 domain of Fyn kinase which can be engineered to yield specific and high-affinity binding domains to target the specific proteins), Kunitz domain peptides, monobodies, or NanoCLAMPS (CLostridal Antibody Mimetic Proteins); or fusion proteins comprising one or more immunoglobulin-fold domains, antibody domains or antibody mimetics.

Further provided is a method for identifying compounds which modulate the heparin binding of the DAO, comprising the steps of (a) constructing a computer model of the GAG binding domain defined by the structure coordinates of the amino acids of the DAO sequence of SEQ ID NO: 1,
(b) selecting a potential modulating compound by a method selected from the group consisting of:
   (i) assembling molecular fragments into said compound,
   (ii) selecting a compound from a small molecule database, and
   (iii) de novo ligand design of said compound;
(c) employing computational means to perform a fitting program operation between computer models of the said compound and the GAG binding domain in order to provide an energy-minimized configuration of the said compound in the heparin binding domain; and
(d) evaluating the results of said fitting operation to quantify the association between the said compound and the heparin/heparan sulfate binding domain, thereby evaluating the ability of said compound to associate with the said heparin/heparin sulfate binding domain.

The term "structure coordinates" refers to a set of values that define the position of one or more amino acid residues with reference to a system of axes. The term refers to a data set that defines the three-dimensional structure of a molecule or molecules (e.g., Cartesian coordinates, temperature factors, and occupancies). Structural coordinates can be slightly modified and still render nearly identical three-dimensional structures. A measure of a unique set of structural coordinates is the root mean square deviation of the resulting structure. Structural coordinates that render three-dimensional structures (in particular, a three-dimensional structure of a heparin/heparin sulfate binding domain) that deviate from one another by a root mean square deviation of less than 3 Å, 2 Å, 1.5 Å, 1.0 Å, or 0.5 Å may be viewed by a person of ordinary skill in the art as very similar.

As used herein, the term "constructing a computer model" includes the quantitative and qualitative analysis of molecular structure and/or function based on atomic structural information and interaction models. The term "modeling" includes conventional numeric-based molecular dynamic and energy minimization models, interactive computer graphic models, modified molecular mechanics models, distance geometry, and other structure-based constraint models.

The term "fitting program operation" refers to an operation that utilizes the structure coordinates of a chemical entity, an enzymatically active center, a binding pocket, molecule or molecular complex, or portion thereof, to associate the chemical entity with the enzymatically active center, the binding pocket, molecule or molecular complex, or portion thereof. This may be achieved by positioning, rotating or translating the chemical entity in the enzymatically active center to match the shape and electrostatic complementarity of the enzymatically active center. Covalent interactions, non-covalent interactions such as hydrogen bond, electrostatic, hydrophobic, van der Waals interactions, and non-complementary electrostatic interactions such as repulsive charge-charge, dipole-dipole and charge-dipole interactions may be optimized. Alternatively, one may minimize the deformation energy of binding of the chemical entity to the enzymatically active center.

The following items are particular embodiments of the invention provided herein.

1. A recombinant diamine oxidase (DAO) with decreased glycosaminoglycan binding affinity, wherein said DAO comprises at least one amino acid modification in the glycosaminoglycan (GAG) binding domain.

2. The recombinant DAO of item 1, further comprising at least one modification of solvent accessible cysteine at amino acid position 123 with reference to the numbering of SEQ ID NO: 1, specifically the modification of the cysteine is an amino acid substitution, deletion or coupling with a chemical moiety.
3. The recombinant DAO of item 1 or 2, wherein the cysteine at position 123, according to the numbering of SEQ ID 1 is substituted by alanine.
4. The recombinant DAO of any one of items 1 to 3, wherein the GAG binding domain is a heparin/heparan sulfate binding domain.
5. The recombinant DAO of any one of items 1 to 4, wherein the at least one amino acid modification in the GAG binding domain is an amino acid substitution, deletion, insertion or coupling with a chemical moiety.
6. The recombinant DAO of any one of items 1 to 5, comprising 2, 3, 4, 5, 6, 7, or 8 amino acid substitutions in the GAG binding domain.
7. The recombinant DAO of any one of items 1 to 6, wherein the GAG binding domain comprises the amino acids at positions 568-575 with reference to the numbering of SEQ ID NO:1.
8. The recombinant DAO of any one of items 1 to 7, comprising a GAG binding domain of amino acid sequence X1FX2X3X4LPX5, wherein X1 can be by any amino acid, specifically it is A or S, more specifically it is S, X2 can be by any amino acid, specifically it is K;

X3 can be by any amino acid, specifically it is A or T, more specifically it is T, X4 can be by any amino acid, specifically it is K, and X5 can be by any amino acid, specifically it is K or T, more specifically it is T.

9. The recombinant DAO of item 7 or 8, comprising the amino acid sequence selected from the group consisting of SFKAKLPK (SEQ ID NO:33), AFKAKLPT (SEQ ID NO:34), AFKTKLPK (SEQ ID NO:35), SFKTKLPK (SEQ ID NO:36), AFKTKLPT (SEQ ID NO:37), SFKAKLPK (SEQ ID NO:38).
10. The recombinant DAO of any one of items 1 to 9, wherein said DAO has increased plasma half-life compared to wild type DAO, specifically said half-life is increased at least 1.5 fold, specifically at least 2 fold compared to wild type DAO.
11. The recombinant DAO of any one of items 1 to 10, wherein said DAO has an at least 10-fold increased AUC compared to wild type DAO.
12. The recombinant DAO of any one of items 1 to 11, wherein internalization by endothelial cells is at least 10%, 25%, 50%, 60%, 70%, 80%, specifically 90% reduced compared to wild type DAO.
13. The recombinant DAO of any one of items 1 to 12, wherein GAG binding affinity, specifically heparin/heparan sulfate binding affinity is at least 10%, 25%, 50%, 60%, 70%, 80%, specifically 90% reduced compared to wild type DAO.
14. The recombinant DAO of any one of items 1 to 13, comprising the amino acid sequences of SEQ ID NOs:2 to 16.
15. A fusion polypeptide comprising the recombinant DAO of any one of items 1 to 14 and an Fc domain of human IgG or human serum albumin (HSA), wherein the fusion polypeptide retains the functional activity of the recombinant DAO.
16. An isolated nucleotide sequence encoding the DAO of any one of items 1 to 15, specifically comprising sequences SEQ ID NOs:17 to 32.
17. A recombinant vector comprising the nucleotide sequence of item 16, specifically the vector is a bacterial, yeast, baculoviral, plant or mammalian expression vector.
18. An expression cassette comprising the nucleotide sequence of item 17, operably linked to regulatory elements.
19. A recombinant host cell or a host cell line comprising the recombinant DAO of any one of items 1 to 15, wherein the host cells are selected from the group consisting of CHO cells, Vero cells, MDCK cells, *Pichia pastoris* cells, SF9 cells.
20. An expression system comprising the vector of item 17 or the expression cassette of item 18 and a host cell or host cell line of item 19.
21. A method for producing the recombinant DAO according to items 1 to 15, said method comprising the steps of i. cloning a nucleotide sequence encoding the DAO of any one of items 1 to 15 into an expression vector, ii. transforming a host cell with said vector, iii. cultivating the transformed host cell under conditions wherein the DAO is expressed, iv. isolating the DAO from the host cell culture, optionally by disintegrating the host cells, and optionally v. purifying the DAO.

22. Pharmaceutical composition comprising the recombinant DAO of any one of items 1 to 15 and optionally one or more excipients.
23. Use of the recombinant DAO of any one of items 1 to 15 for preparing a pharmaceutical composition.
24. The recombinant DAO of any one of items 1 to 15 for use in the treatment of a condition associated with excess histamine, specifically for the treatment of chronic allergic diseases, more specifically for the treatment of anaphylaxis, anaphylactic shock, chronic urticaria, acute urticaria, asthma, hay fever, allergic rhinitis, allergic conjunctivitis, histamine intoxication, headache, atopic dermatitis inflammatory diseases, mastocytosis, mast cell activation syndrome (MCAS), pre-eclampsia, hyperemesis gravidarum, pre-term labor, peptic ulcers, acid reflux, pruritus, and sepsis.
25. The use of the recombinant DAO of any one of items 1 to 15 for the manufacture of a medicament for the treatment of a condition associated with excess histamine, specifically for the treatment of chronic allergic diseases, more specifically for the treatment of anaphylaxis, anaphylactic shock, chronic urticaria, acute urticaria, asthma, hay fever, allergic rhinitis, allergic conjunctivitis, histamine intoxication, headache, atopic dermatitis inflammatory diseases, mastocytosis, peptic ulcers, acid reflux, pruritus, and sepsis.
26. A target-specific ligand specifically binding to the GAG binding domain of DAO, specifically binding to one or more of amino acids at position 568-575 with reference to the numbering of SEQ ID NO: 1.
27. A target-specific ligand specifically inhibiting heparin/heparan sulfate binding to the GAG binding domain of DAO, specifically to any one or more of amino acids at position 568-575 with reference to the numbering of SEQ ID NO: 1.

28. The target-specific ligand of item 26 or 27 wherein said ligand is selected from the group consisting of nucleic acid, small molecule inhibitor or antigen binding protein.
29. The target-specific ligand of item 28 wherein said ligand is an antigen binding protein, specifically selected from the group consisting of
   antibodies or antibody fragments, such as any of Fab, Fd, scFv, diabodies, triabodies, Fv tetramers, minibodies, nanobodies, single-domain antibodies like VH, VHH, IgNARs, or V-NAR,
   antibody mimetics, such as Adnectins™, Affibodies®, Affilins®, Affimers®, Affitins, Alphabodies, Aptamers, Anticalins, Avimers, DARPins®, Fynomers®, Kunitz domain peptides, Monobodies, or NanoCLAMPS; or
   fusion proteins comprising one or more immunoglobulin-fold domains, antibody domains or antibody mimetics.
30. A method for identifying compounds which modulate the heparin binding of the DAO, comprising the steps of
(a) constructing a computer model of the GAG binding domain defined by the structure coordinates of the amino acids of the DAO sequence of SEQ ID NO: 1,
(b) selecting a potential modulating compound by a method selected from the group consisting of:
   (i) assembling molecular fragments into said compound,
   (ii) selecting a compound from a small molecule database, and
   (iii) de novo ligand design of said compound;
(c) employing computational means to perform a fitting program operation between computer models of the said compound and the GAG binding domain in order to provide an energy-minimized configuration of the said compound in the heparin binding domain; and
(d) evaluating the results of said fitting operation to quantify the association between the said compound and the heparin/heparan sulfate binding domain, thereby evaluating the ability of said compound to associate with the said heparin binding domain.

The examples described herein are illustrative of the present invention and are not intended to be limitations thereon. Different embodiments of the present invention have been described according to the present invention. Many modifications and variations may be made to the techniques described and illustrated herein without departing from the spirit and scope of the invention. Accordingly, it should be understood that the examples are illustrative only and are not limiting upon the scope of the invention.

EXAMPLES

Example 1

DAO with Modified GAG Binding Domain:

Summary: Amino acids in the GAG binding (heparin/heparan sulfate-binding domain) of DAO were mutated. After mutations in the heparin-binding domain of DAO, animal studies were performed with these mutants. The short alpha half-life could be almost eliminated and the beta half-life increased to 6 hours in rats. The alpha half-life refers to the rate of decline in plasma concentrations due to the process of drug redistribution from the central to the peripheral compartment, the beta half-life refers to the rate of decline due to the process of drug elimination due to metabolism or excretion. The area under curve (AUC) increased more than 20-fold. A half-life of 6 hours in rats extrapolates to 24 to 48 hours in humans and this is certainly sufficient for the treatment of acute and subacute conditions with excess histamine. For example, anaphylaxis or MCAS events last a few hours to 1 to 2 days, and anaphylaxis may be biphasic in 10-20% of patients meaning that a second episode may occur within 24 hours. Several mutations have been tested, and a distinct double mutant in the heparin-binding domain showed the most pronounced improvements in the pharmacokinetic (PK) parameters. Because DAO is a dimer and the heparin-binding domain forms a ring structure composed of both monomers, four mutations are located closely to each other. Nevertheless, expression, stability and activity of DAO wild type and DAO mutants are identical.

DAO with Modified Cysteine

When DAO were expressed in CHO cells, certain percentages of DAO molecules (~20% to 30%) formed not only dimers but also tetramers, hexamers and even octamers. These higher order oligomers can be considered to be natural variants with unknown function. It is not clear, whether they form during folding and transport from ER to Golgi and secretion into the extracellular environment or in general only in the extracellular environment. Nevertheless, these tetramers and larger oligomers complicate expression, purification, characterization, standardization and the selection of the optimal formulation of rhDAO. Therefore a relatively solvent accessible cysteine on the surface of DAO was mutated and in this mutant only DAO dimers are found in the supernatant of CHO cells.

DAO constructs, having 2 point mutations in the heparin/heparan sulfate-binding domain and a single mutation in a distinct cysteine are specific embodiments.

The following table shows recombinant DAO. Threonine and serine mutations were preferred over alanine and glycine to exchange lysine and arginine with polar amino acids. This helped to keep the confirmation unaltered.

TABLE 1

DAO Mutations in the GAG binding domain with exchange of arginine and lysine to serine and threonine

| DAO Variant | | Amino Acid 568 | 570 | 571 | 572 | 575 |
|---|---|---|---|---|---|---|
| WT | | Arginine | Lysine | Arginine | Lysine | Lysine |
| Hepmut1 | Arg_568_Ser | Serine | Lysine | Arginine | Lysine | Lysine |
| Hepmut2 | Lys_575_Thr | Arginine | Lysine | Arginine | Lysine | Threonine |
| Hepmut3 | | Arginine | Lysine | Threonine | Lysine | Lysine |
| Hepmut4 | Arg_568_Ser; Arg_571_Thr | Serine | Lysine | Threonine | Lysine | Lysine |

TABLE 1-continued

DAO Mutations in the GAG binding domain with exchange of arginine and lysine to serine and threonine

| DAO Variant | | Amino Acid 568 | 570 | 571 | 572 | 575 |
|---|---|---|---|---|---|---|
| Hepmut5 | | Arginine | Lysine | Threonine | Lysine | Threonine |
| Hepmut7 | Arg_568_Ser; Lys_575_Thr | Serine | Lysine | Arginine | Lysine | Threonine |

The Hepmut4 mutation showed the strongest loss of binding to heparin. Hepmut6 is a triple mutation replacing 570/571/572 with Gly/Gln/Thr, which is present in rodents. The glutamine in the rodent sequence can also bind negatively charged sulfate and can sometimes replace arginine or lysine. All animal experiments were done in rodents so far (mice and rats).

Below are data from heparin-sepharose experiments using KCl and NaCl to elute purified DAO wild type and Hepmut variants from heparin-sepharose. Heparin is irreversibly coupled to sepharose and purified DAO is incubated at low salt concentrations followed by a linear gradient of increasing concentrations of KCl or NaCl. The salt concentrations with the peak in DAO protein (measured using absorbance at 280 nm) is used as the mM salt concentration at which DAO is eluted.

FIG. 2 shows the Heparin-sepharose elution profiles of recombinant human DAO wild type (WT) and heparin mutants. Hepmut variants are eluted earlier compared to DAO_WT, Purified DAO_WT and hepmut variants were loaded onto a HiTrap Heparin HP (High Performance) 1 ml column using a 50 mM HEPES buffer, pH 7.4 and a flow rate of 0.2 ml/min. Elution was performed using a linear gradient of 0% to 70% 50 mM HEPES with 1 M sodium chloride, pH 7.4 with a gradient time of 60 minutes; rh=recombinant human. For KCl elution purified rhDAO variants were loaded onto a HiTrap Heparin HP 1 ml column using a 10 mM potassium phosphate buffer, pH 7.2 and a flow rate of 0.2 ml/min. Elution was performed using a linear gradient of 0% to 100% 10 mM potassium phosphate buffer with 1M potassium chloride, pH 7.2 with a gradient time of 60 minutes. The elution profiles are not shown but the salt concentrations at peak elution are shown below.

Table 2 and FIG. 3 show the raw results but also normalized based on data using the DAO wild-type protein. The mean and the standard deviation (SD) from the two salt experiments were calculated and presented as bar graph. The numbers above the bars correspond to the numbers in the table. For DAO_WT they represent the salt concentration of elution. For the mutations the difference to the DAO_WT salt concentration is shown.

DAO_WT was eluted from the heparin sepharose at 372 mM NaCl or 310 mM KCl salt concentration. Hepmuts were eluted at significantly lower salt concentrations. The correlation coefficient R between the NaCl and KCl elution profiles is 97% with a p-value of 0.0056. Therefore, it seemed justified to combine both profiles and calculate a mean with SD. The mean plus/minus SD are represented by the bar height (mean) and by the error bars (plus/minus SD).

TABLE 2

Elution of DAO_WT and hepmut variants from heparin-sepharose at different NaCl or KCl concentrations

| | KCl Conc. [mM] | NaCl Conc. [mM] | DAO_WT binding KCl % | DAO_WT binding NaCl % | Mean % | SD % |
|---|---|---|---|---|---|---|
| DAO_WT | 310 | 372 | 100% | 100% | 100% | 0.0% |
| Hepmut1 | 172 | 186 | 56% | 50% | 53% | 3.9% |
| Hepmut2 | 233 | 317 | 75% | 85% | 80% | 7.3% |
| Hepmut4 | 138 | 175 | 44% | 47% | 46% | 1.8% |
| Hepmut7 | 164 | 197 | 53% | 53% | 53% | 0.1% |

WT = Wild-Type; Conc. = Concentration; SD = Standard Deviation

FIG. 3 shows Hepmut 1, 4 and 7 variants that are eluted from heparin-sepharose at 50% lower salt concentrations compared to DAO_WT. The data are from Table 2.

Table 3 shows the delta salt concentration from DAO_WT versus mutants for NaCl and KCl. For example 200 mM means that 200 mM less NaCl were necessary to elute the mutant from the heparin-sepharose compared to DAO_WT.

TABLE 3

Hepmut variants are eluted at significantly lower NaCl or KCl concentrations compared to DAO wild-type protein from heparin-sepharose

| | Delta mM KCl DAO | Delta mM NaCl DAO |
|---|---|---|
| DAO_WT | 0 | 0 |
| Hepmut1 | 138 | 186 |
| Hepmut2 | 78 | 55 |
| Hepmut4 | 172 | 197 |
| Hepmut7 | 147 | 175 |

Based on these data Hepmut4 might be the weakest heparin-binding mutant but the difference to Hepmut1 and Hepmut7 is not significant. Mutating a single lysine residue in Hepmut2 reduces the affinity to heparin-sepharose.

Serum and plasma contain about 145 to 150 mM Na+ and K+ combined and 100 mM Cl− ions. Elution of Hepmut1, 4 and 7 variants from the heparin-sepharose is close to the physiological concentration of ions in serum and therefore these mutants should be minimally active in vivo and this is the case as shown below in vitro using cells and in vivo in rats and in mice.

These data clearly show that DAO binds heparin via the heparin/heparan sulfate binding domain. To place these results in a bigger context, mutation of 1 to 2 arginine/lysine residues among 48 lysine and 88 arginine amino acids in the DAO sequence (and most of them are surface exposed) almost abolish heparin binding, although using Hepmut4 with two arginine mutations only 2/88=2.3% of arginine residues have been mutated.

The clearance of DAO_WT in mice and rats is significantly faster compared to Hepmut variants. It was assumed that the heparin-binding domain is involved in the reduced Area Under the Curve (AUC) values. Heparin-binding mutants show elution from the heparin-sepharose at lower salt concentrations implying the heparin or heparan sulfate binding is reduced.

In the next set of experiments it was discovered that DAO does not only bind to but is actually internalized into endothelial cells and shows vesicular staining inside cells. Hepmut variants are not internalized anymore by endothelial cells. Endothelial cells are the first cells (except blood cells) exposed to DAO after intravenous administration. They are in direct contact with blood. They also exposed to DAO after subcutaneous administration because DAO will be transported via the lymph system into the blood compartment.

Immunofluorescence microscopy of SK-Hep1 cells, an endothelial cell-like immortal cell line from a patient with liver cancer, after incubation with DAO_WT and Hepmut variants showed that internalization of Hepmut variants was inhibited. SK-Hep1 cells were incubated for 60 minutes with 20 μg/ml of the purified recombinant human DAO and Hepmut variants (negative control=no rhDAO added) were incubated at 37° C., washed twice with 150 mM glycine buffer with 150 mM sodium chloride, pH 3.0 and once with PBS to remove membrane-bound DAO. After fixation and permeabilization the cells were incubated with a 1:500 dilution of anti-ABP1 (ABP1=amiloride binding protein 1, alternative name for DAO) antibody produced in rabbits (Sigma Aldrich). A 1:500 dilution of Alexa Fluor 488 donkey anti-rabbit (H+L) (Jackson Research, 711-545-152) was used as the secondary antibody. DAPI was used for counter-staining of the nuclei. The cells were analyzed by fluorescence microscopy on an inverted DMI-6000B microscope equipped with a HCX PL APO 63x/1.30 glycerol immersion objective and filter sets A4 (for DAPI) and L5 (for Alexa Fluor 488) (Leica Microsystems). Analogous results were obtained using HUVEC=human umbilical vein endothelial cells, the prototypical endothelial cells (EC) used for EC research.

Hepmut4 and Hepmut7 variants showed strongly reduced uptake into the SK-Hep1 cells, whereas Hepmut1 caused some staining similar to the vesicular-like staining of DAO_WT. These results not only demonstrated that Hepmut DAO variants block uptake into EC, but also for the first time that DAO is internalized by cells. It has been shown that DAO binds to the surface of EC, and DAO has been localized inside cells, but incubation of cells with DAO and proof that DAO_WT is internalized implying the existence of a DAO receptor. It was confirmed that DAO binds to heparan sulfate glycosaminoglycans present on ECs (heparin is only present in mast cells in the human body) and Hepmut variants are not able anymore to efficiently bind and are therefore not internalized. This is also reflected in the in vivo rat and mouse data described herein.

The immunofluorescence data discussed above were also reflected in Western blotting data. There is a more than a 6-fold difference in Western blotting signal of Hepmut4 and Hepmut7 versus DAO_WT and Hepmut1. These data are in agreement with the immunofluorescence data. Hepmut4 and Hepmut7 were not internalized by SK-Hep1 cells.

FIG. 4 shows a Western blot of SK-Hep1 cell lysates after incubation with DAO_WT and Hepmut variants A. Lane 1: Negative control, 2: rhDAO_WT, 3: rhDAO-Hepmut1, 4: rhDAO-Hepmut4, 5: rhDAO-Hepmut7. SK-Hep1 cells were incubated for 60 minutes with 20 μg/ml of the respective purified DAO variants (negative control=no rhDAO added) at 37° C., washed twice with 150 mM glycine buffer with 150 mM sodium chloride, pH 3.0 and once with PBS to remove membrane-bound DAO. The cells were then lysed with RIPA buffer and sonication. The cell lysates were loaded onto a SDS-PAGE gel, followed by blotting onto a PVDF membrane. The membrane was incubated after blocking with a 1:1000 dilution of a serum IgG fraction from rabbits immunized with purified rhDAO. This step was followed by incubation with a 1:5000 dilution of β-actin mABAC-15 (Invitrogen). 1:5000 dilutions of IRDye®800CW goat anti-rabbit IgG (H+L) secondary antibody and IRDye®680RD goat anti-mouse IgG (H+L) (Li-Cor) were used as secondary antibodies. The membrane was scanned at 700 and 800 nm using the Odyssey Infrared Imaging System (Li-Cor). B. Band intensities were determined in reference to purified rhDAO_WT (not shown) and used to calculate the amount of internalized rh DAO.

Binding of DAO_WT and Hepmut4 variants to SK-Hep1 cells in an in vitro assay is about 5-times lower. DAO was labelled with Alexa488 fluorescent dye on the glycosaminoglycans and incubated with SK-HEP1 cells. This assay is performed in microtiter plates. The fluorescent signal is measured after washing and cell lysis.

Figure 5:
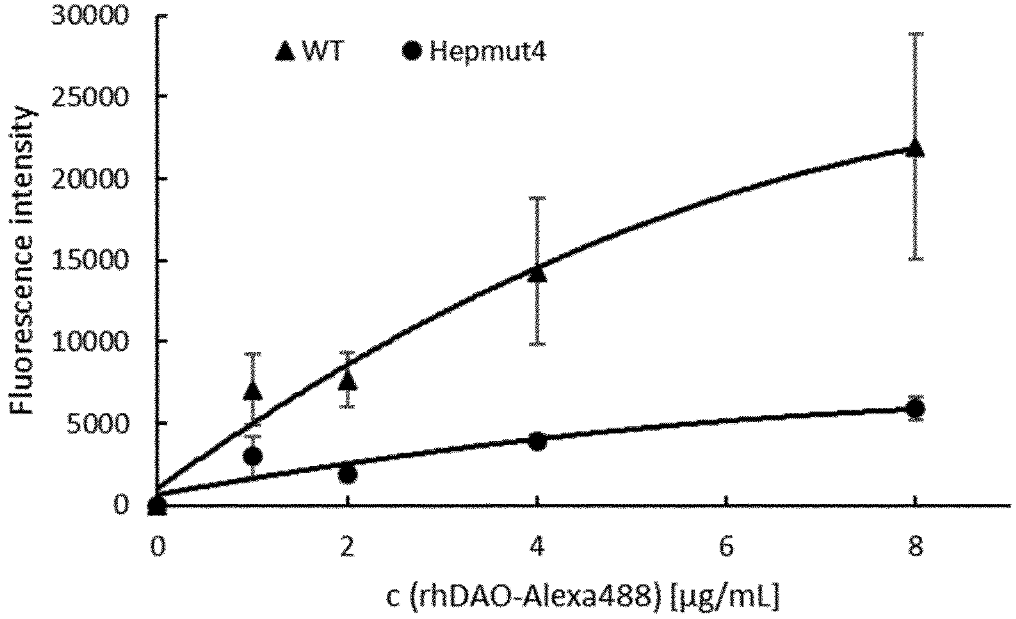

In FIG. 5, Hepmut4 variant shows reduced binding to SK-Hep1 cells compared to DAO_WT.

SK-Hep1 cells were grown in a 96-well plate and incubated with 0 to 8 μg/ml Alexa488-labelled rhDAO_WT and rhDAO-Hepmut4 for 60 minutes at 37° C. The cells were washed twice with 150 mM glycine buffer with 150 mM sodium chloride, pH 3.0 and once with PBS to remove membrane-bound DAO. After cell lysis using RIPA buffer the fluorescence intensities were determined using a Tecan plate reader. The means of triplicates with the standard errors of the mean (SEM) are shown.

The binding of DAO_WT and Hepmut4 to high and low molecular weight heparin (HMWH, LMWH) using Isothermal Titration calorimetry (ITC), the state of the art instrument for the determination of label-free binding affinities, was also tested.

FIG. 6 provides the ITC data of DAO_WT and Hepmut4. 12.5 μM purified rhDAO_WT and 12.0 μM purified rhDAO-Hepmut4 were subjected to isothermal titration calorimetry (MicroCal PEAQ-ITC, Malvern) using 25×1 μl injections of 160 μM high molecular weight (HMWH, Gilvasan, average molecular weight=15 kDa) and low molecular weight heparin (LMWH, Lovenox, average molecular weight=4.5 kDa). The buffer was 50 mM HEPES with 150 mM KCl pH 7.3. Binding was only observed for rhDAO_WT and HMWH with a $K_D$ value of 423 nM.

Both components, DAO protein and the two heparin molecules, are unaltered and not immobilized. This allowed the determination of true binding affinities. Heparin-sepharose represents a multivalent matrix, where molecules are gliding from one heparin molecule to the next. DAO_WT was binding to HMWH with a $K_d$ of 423 nM, whereas Hepmut4 did not bind to HMWH. DAO_WT was also not binding to LMWH.

Intravenous Injection of DAO_WT and Hepmut4 into C57BL6 Mice

DAO_WT and Hepmut4 protein were injected at 1 mg/kg into the tail vein of C57BL6 mice with a body weight of about 20 gram. Protein concentrations and enzymatic activity of the two purified DAO variantes were comparable. Protein purification was performed as published recently (Gludovacz 2016). Linear and log y-axis scales are shown.

In FIG. 7 linear (a) and log y-scales (b) are shown. Hepmut4 increases the AUC (Area Under the Curve) more than 19-fold compared to wild-type DAO protein after intravenous injection of 1 mg/kg DAO variants. The measured values (n=3 to 4 mice per time point) plus/minus standard deviations are shown. DAO concentrations were measured using our in-house developed human DAO ELISA, which does not recognize mouse or rat DAO (Boehm 2017). Half-life and AUC data are summarized in the following table.

TABLE 4

The AUC increases 19-fold in Hepmut4 versus DAO_WT treated mice after intravenous administration

| | Half-life minutes* | AUC µg*min/ml§ |
|---|---|---|
| DAO_WT | 76.1 | 76 |
| Hepmut4 | 192.1 | 1468 |
| Ratio Hepmut4 to DAO_WT | 2.5 | 19.4 |

*Calculated from 60 to 1680 minutes
§AUC = Area Under the Curve; Calculated from 10 to 1680 minutes The half-life was calculated from 60 to 1680 minutes to exclude the fast alpha distribution half-life using DAO_WT, which is about 10 minutes. Using the Hepmut4 variant this very rapid elimination of DAO from the circulation is more or less not present anymore. There is a high curve fit using a mono-exponential decay function from 60 to 1680.

Intraperitoneal Injection of DAO_WT and Hepmut4 into C57BL6 Mice

DAO_WT and Hepmut4 protein was injected intraperitoneally at 1 mg/kg in mice with a body weight of 21 gram. As shown in FIG. 8, Hepmut4 increases the AUC (Area Under the Curve) more than 16-fold compared to DAO_WT protein after intraperitoneal injection. Each time point represents the mean of 3 mice and therefore in total 15 mice DAO_WT and 15 mice Hepmut4 were used. The means with the standard deviations are shown. DAO concentrations were measured using a recently published human DAO ELISA (Boehm 2017). AUC data are summarized in the following table. Half-life data are not included because we would need to assume that the absorption of DAO_WT and Hepmut4 from the intraperitoneal space is the same and this might not be the case.

TABLE 5

The AUC is increased 16-fold in Hepmut4 versus DAO_WT treated mice.

| | AUC µg*min/ml§ |
|---|---|
| DAO_WT | 41.2 |
| Hepmut4 | 666.3 |
| Ratio Hepmut4 to DAO_WT | 16.2 |

§AUC = Area Under the Curve; Calculated from 0 to 1440 minutes

Intravenous Injection of DAO_WT and Hepmut1, 4 and 7 into Rats

FIG. 9 shows means of the measured values plus/minus the standard deviation (SD) using 1 mg/kg DAO wild-type and different Hepmut variants. Slow clearance of Heparin-binding domain mutants compared to DAO wild-type protein administered at 1 mg/kg. DAO_WT n=9; Hepmut1 n=4; Hepmut4 n=5; Hepmut7 n=4; Linear y-axis scale. The means with the SD are shown.

FIG. 10 exhibits the slow clearance of Heparin-binding domain mutants compared to DAO wild-type protein administered at 1 mg/kg. DAO_WT n=9; Hepmut1 n=4; Hepmut4 n=5; Hepmut7 n=4; Log y-axis scale. The means with the SD are shown.

DAO_WT and Hepmut7 show a fast alpha half-life and two equations are used to derive the best fit curve. Nevertheless, the alpha half-life for Hepmut7 is significantly longer compared to DAO_WT. The half-lives are shown below. For Hepmut1 and Hepmut4 mono-exponential decay shows the best fit with the highest adjusted R square and lowest p-value. This can be also seen in the figure with the original data.

In FIG. 11, the curves using the different derived exponential equations are shown. These curves have been used to calculate the AUCs and half-lives shown later.

FIG. 11: Slow clearance of Heparin-binding domain mutants compared to DAO wild-type protein administered at 1 mg/kg. DAO_WT n=9; Hepmut1 n=4; Hepmut4 n=5; Hepmut7 n=4; Log y-axis scale; These curves have been generated using the best fit exponential equations.

FIGS. 12, 13, and 14 show the first 90 minutes to see the fast clearance using DAO wild-type protein.

FIG. 12 shows slow clearance of Heparin-binding domain mutants compared to DAO wild-type protein administered at 1 mg/kg. DAO_WT n=9; Hepmut1 n=4; Hepmut4 n=5; Hepmut7 n=4; Log y-axis scale; Only the first 90 minutes are shown.

Below are the linear y-axis versions of these figures.

FIG. 13 shows slow clearance of Heparin-binding domain mutants compared to DAO wild-type protein administered at 1 mg/kg. DAO_WT n=9; Hepmut1 n=4; Hepmut4 n=5; Hepmut7 n=4. The curves have been generated using the best fit exponential equations; Linear y-axis scale.

FIG. 14 shows slow clearance of Heparin-binding domain mutants compared to DAO wild-type protein administered at 1 mg/kg. DAO_WT n=9; Hepmut1 n=4; Hepmut4 n=5; Hepmut7 n=4; only the first 90 minutes are shown; Linear y-axis scale.

Because of the fast alpha half-life in DAO_WT treated rats we calculated the AUCs from 0 but also 5 minutes to 240 and 1440 minutes. The data points within 10 minutes are likely quite variable. The data are summarized in the following tables.

TABLE 6

The AUC is increased in Heparin-binding mutants versus DAO_WT treated rats

| | DAO Wild-type (n = 9) | Hepmut1 (n = 4) | Hepmut4 (n = 5) | Hepmut7 (n = 4) | |
|---|---|---|---|---|---|
| AUC_0-1440 | 270 | 1554 | 3829 | 2165 | µg/ml/min |
| AUC_0-240 | 238 | 797 | 1550 | 1010 | µg/ml/min |
| AUC_5-1440 | 116 | 1531 | 3788 | 2113 | µg/ml/min |
| AUC_5-240 | 84 | 774 | 1509 | 958 | µg/ml/min |

For Hepmut variants 0 to 1440 or 5 to 1440 minutes do not make any relevant difference but for DAO wild-type protein starting at 5 minutes significantly reduced the AUC. The calculated DAO concentrations using the best fit exponential equations are above the theoretical DAO concentrations and therefore not possible. The strong increase in the AUCs is also clearly seen using the time window from 0 to 1440 minutes.

Also in this set of experiment the Hepmut4 variant shows the strongest effect. This is also reflected in the half-life data.

TABLE 7

The AUC is increased between 3 and 33-fold in Heparin-binding mutants versus DAO_WT treated rats with Hepmut4 showing the largest increase.

| | DAO Wild-type (n = 9) | Hepmut1 (n = 4) | Hepmut4 (n = 5) | Hepmut7 (n = 4) |
|---|---|---|---|---|
| AUC_0-1440 | 1.0 | 5.8 | 14.2 | 8.0 |
| AUC_0-240 | 1.0 | 3.4 | 6.5 | 4.2 |
| AUC_5-1440 | 1.0 | 13.2 | 32.6 | 18.2 |
| AUC_5-240 | 1.0 | 9.2 | 17.9 | 11.4 |

FIG. 15 shows the rapid clearance of Fc-DAO wild-type compared to Fc-Hepmut4 administered at 1 mg/kg in 6 or 4 rats respectively. The means with the standard deviations are shown; Linear y-axis scale.

TABLE 8

Elimination of the very fast alpha half-life in DAO wild-type and increase in the beta half-life in heparin-binding mutants.

| | $t_{1/2}$ alpha minutes | $t_{1/2}$ beta minutes |
|---|---|---|
| DAO_WT | 1.9 | 162 |
| Hepmut1 | na | 214 |
| Hepmut4 | na | 343 |
| Hepmut7 | 42 | 297 |

na = not applicable

In conclusion mutations in the putative Heparin-binding domain of DAO strongly increase the AUC in rats after intravenous injection of 1 mg/kg body weight. The best performing mutant is the double mutant Hepmut4 with 2 arginines removed. This fits well to prediction and heparin-sepharose elution data.

Example 2

Fc-DAO with Modified GAG Binding Domain:

Also Fc-DAO fusion variants were tested with the heparin-binding mutations and the PK parameters further improved with a beta half live of 9 hours and increased AUC. Amino acids involved in the high affinity interaction with Fc_gamma receptor were removed and amino acids involved in the interaction with FcRN have not been altered.

Intravenous Injection of Fc-DAO_WT and Fc-DAO-Hepmut4 into Rats

Below are the results from 6 and 4 rats after intravenous injection of 1 mg/kg Fc-DAO wild-type and Fc-Hepmut4 protein using linear and log scales. We only measured for 4 hours using Fc-DAO wild-type. Nevertheless, the derived exponential function can be used to extrapolate to 1680 minutes like it was measured using the Fc-Hepmut4 variant (see below). The Fc-DAO fusion protein shows similarly to the DAO wild-type protein a very fast alpha distribution half-life. Most of the fusion variant is removed from plasma within 20 minutes. Afterwards the half-life is about 120 minutes calculated using the 30, 120 and 240 time point values.

Fc-Hepmut4 is much more stable in plasma. The DAO clearance mechanism is clearly dominant over the Fc part. The half-life of human IgGs in rats is several days and this half-life is mainly determined by binding of the Fc part to the FcRN receptor.

FIG. 16 shows the rapid clearance of Fc-DAO wild-type compared to Fc-Hepmut4 administered at 1 mg/kg in 6 or 4 rats respectively. The means with the standard deviations are shown; Log y-axis scale.

Both data sets can be best fit to a mono-exponential decay function with p-values of less than 0.001 and adjusted R square values of >97%. For Fc-DAO-wild-type protein the half-life after 30 minutes was calculated to be 120 minutes based on the data from time points 30, 120 and 240 minutes. A two factor decay exponential curve fitting did not converge. The best fit equations are used to extrapolate the Fc-DAO data to 24 hours. The curves are shown below.

In FIG. 17, Fc-DAO-Hepmut4 shows a strong increase in the AUC after intravenous administration of 1 mg/kg; Log y-axis scale.

In FIG. 18, Fc-DAO-Hepmut4 shows a strong increase in the AUC after intravenous administration of 1 mg/kg; Linear y-axis scale.

Areas under the curves were calculated from 0 and 5 minutes to 240 or 1440 minutes after intravenous injection. Curve fitting in the first minutes resulted in very high values at 0 minutes in the Fc-DAO data and therefore we also calculated the AUC starting at 5 minutes.

TABLE 9

The AUC is strongly increased in Fc-Hepmut4 versus Fc-DAO_WT treated rats

| | Fc-DAO Wild-type (n = 6) | Fc-Hepmut4 (n = 4) | |
|---|---|---|---|
| AUC_0-1440 | 157 | 2751 | μg/ml/min |
| AUC_0-240 | 142 | 1057 | μg/ml/min |
| AUC_5-1440 | 69 | 2723 | μg/ml/min |
| AUC_5-240 | 54 | 1028 | μg/ml/min |

The ratios of the AUCs are shown in the next tables followed by a table with the calculated half-lives.

TABLE 10

The AUCs of Fc-Hepmut4 versus Fc-DAO_WT are 7 to 40-fold larger

| | Fc_DAO Wild-type (n = 6) | Fc_Hepmut4 (n = 4) |
|---|---|---|
| AUC_0-1440 | 1.0 | 17.6 |
| AUC_0-240 | 1.0 | 7.4 |
| AUC_5-1440 | 1.0 | 39.5 |
| AUC_5-240 | 1.0 | 19.0 |

TABLE 11

The fast alpha half-live of Fc-DAO_WT is eliminated in Fc-Hepmut rats

| | $t_{1/2}$ alpha minutes | $t_{1/2}$ beta minutes* |
|---|---|---|
| Fc_DAO_WT | 1.7 | 120 |
| Fc_Hepmut4 | na | 268 |

*Starting at 30 minutes after intravenous injection

Fc-Hepmut4 variants are more stable in plasma compared to Fc-DAO. This is in agreement with mice and rat data using non-fusion DAO variants. Nevertheless, the half-life of Fc-Hepmut4 is still rather short compared to IgG antibodies. DAO clearance seems still dominant over slower Fc clearance mechanisms.

Example 3

DAO with Modified GAG Binding Domain and Modified Cys123:

Cysteine 123 and 633 are not involved in disulfide bond formation of the DAO dimer.

Relative accessible surface area or relative solvent accessibility (RSA) of a protein residue is a measure of residue solvent exposure. It can be calculated by the formula: RSA=ASA/MaxASA, wherein ASA is the solvent accessible surface area and MaxASA is the maximum possible solvent accessible surface area or the residue. Both ASA and MaxASA are commonly measured in Å$^2$.

RSA Cys123

Cys123=93.84 Å$^2$ accessible of 148 Å$^2$=63.4% (monomer B)

Cys123=90.72 Å$^2$ accessible of 148 Å$^2$=61.3% (monomer A) Mean=62.4%

RSA Cys633

Cys633=34.62 accessible of 148=23.4% (monomer B)

Cys633=33.49 accessible of 148=22.6% (monomer A) Mean=23%

Cys123 is on the surface and this is unusual. The amino acid cysteine is the rarest and the "least and highest" conserved amino acid in proteins (Marino SM and Gladyshev VN, J Mol Biol. 2010 Dec. 17; 404(5):902-16), likely because it is available for oxidation. DAO produces hydrogen peroxide, which might cause exactly this oxidation of cys123 and consequently it can form a disulfide bond which might severely disturb function. It is highly conserved in enzymes as catalytic amino acid and if involved in disulfide bond formation, as it is also the case in DAO. Cys633 is deeper inside the structure and less accessible and may not play a role in aggregate formation. It might play a role at high DAO concentrations.

Because a DAO dimer possesses two accessible Cys123 amino acids, one dimer can form a disulfide bridge with another dimer resulting in a tetramer, but it can also interact with two dimers forming a hexamers, etc. The molecular weight of DAO lacking the secretion signal purely based on amino acids (732) would be 166872 Da for the dimer. The tetramer would be 333744 Da, the hexamer 500617 Da and the octamer 667489 Da but the glycans will increase this by probably about 25% (Elmore, 2002). The height of a DAO monomer or dimer is about 65 Å but increases to 130 Å in the tetramer, 195 Å and 260 Å in the hexamer and octamer respectively. We have no data about the structure of multimeric stack of DAO. The aggregate might be rigid or flexible. These aggregates are certainly more immunogenic because neo-epitopes might be created between two dimers and repeated 2 or 3 times with potential and likely negative consequences for efficacy and safety (see below).

TABLE 12

Molecular weight of DAO monomer to octamer using 25% glycan weight

| | 732 amino acids (aa) | 732 aa plus Glycans 25% | DAO height nm | DAO length nm |
|---|---|---|---|---|
| Monomer | 83436 | 104295 | 6.5 | 10.0 |
| Dimer | 166872 | 208590 | 6.5 | 10.0 |
| Tetramer | 333744 | 417180 | 13.0 | 10.0 |
| Hexamer | 500616 | 625770 | 19.5 | 10.0 |
| Octamer | 667488 | 834360 | 26.0 | 10.0 |

Higher order aggregates of DAO have been described. Paolucci et al (Biochimie. 1971; 53(6):735-49) published that the molecular weight of human placenta DAO is comprised of 1-4 multiples of 125 kDa+/−5 or in other words 125, 250, 375 and 500 kDa. Tufvesson (Scand J Clin Lab Invest. 1978 September; 38(5):463-72) published a DAO molecular weight of 245 and 485 kDa again after purification from human amniotic fluid corresponding to dimer and tetramer. Wilfingseder et al. (Inflamm Res. 2002 April; 51 Suppl 1:S89-90) showed "complex formation" of human placental DAO using Western blotting.

Different DAO-expressing plasmids were transfected into ExpiCHO cells for transient expression. Western blotting was performed directly on the supernatants after 7 days of culture. The results are shown in FIG. 19.

FIG. 19: lane 1: HiMark Standard; lane 2: Negative Control (empty plasmid); lane 3: rhDAO_WT, lane 4: rhDAOΔ123; lane 5: rhFc-DAO; lane 6: rhFc-DAOΔ123; lane 7: rhDAO-Hepmut4; lane 8: rhDAO-Hepmut4Δ123; lane 9: rhFc-DAO-Hepmut4; lane 10: rhFc-DAO-Hepmut4Δ123. rhFc=recombinant human Fc fusion protein with DAO; 15 μl of each culture supernatant were loaded. SDS-PAGE was performed under non-reducing conditions. Antibody: MUV rabbit serum #408, 1:5000.

Cys123 to Ala123 mutation completely prevented tetramerization and higher order aggregate formation of recombinant human wild-type DAO and Hepmut4 variants. There is no effect in the rhFc-DAO fusion constructs. This implies that aggregate formation in these Fc fusion variants is not caused by Cys123 but more likely by the Fc part, which contains also cysteines.

Under reducing conditions using mercaptoethanol, the disulfide bonds are opened and no tetramer or higher order aggregates are seen neither in wild-type DAO and Hepmuts or fusion variants. The molecular weight is between 71 and 117 and would be predicted based just on amino acids to be 83.436 Da. These data clearly proof that the cys123 to ala123 mutation completely prevents tetramerization and higher order n-meric variants of DAO. Cys633 is not involved.

The signal intensity of each lane was determined using ImageJ software to roughly quantify the percent of higher n-meric variants. To compare the WT and the corresponding cys123 mutant lanes, equally sized areas were selected (as indicated) and a signal profile was generated. The area under the curve (AUC) for each lane was calculated.

TABLE 13

Quantification of the effect of the ala123 mutation on aggregate formation in two replicates

| | Replicate 1 | | Replicate 2 | |
|---|---|---|---|---|
| | Signal | Percent | Signal | Percent |
| rhDAO_WT | 77693 | 100% | 68048 | 100% |
| rhDAO_Ala123 | 66523 | 86% | 57007 | 84% |
| rhDAO_Hepmut4 | 76456 | 100% | 67066 | 100% |
| rhDAO_Hepmut4_Ala123 | 56045 | 73% | 55377 | 83% |
| rhDAO WT minus Ala123 | 11170 | 14% | 11041 | 16% |
| Hepmut4 WT minus Ala123 | 20411 | 27% | 11689 | 17% |
| Mean | 19% | | | |
| SD | 5.5% | | | |
| rhFc-DAO | 70709 | 100% | 64270 | 100% |
| rhFc-DAO_Ala123 | 61878 | 88% | 69892 | 109% |
| rhFc-DAO-Hepmut4 | 56134 | 100% | 66383 | 100% |
| rhFc-DAO-Hepmut4_Ala123 | 57673 | 103% | 82826 | 125% |
| rhFc-DAO WT minus Ala123 | 8831 | 12% | −5622 | −9% |
| rhFc-Hepmut4 WT minus Ala123 | −1538 | −3% | −16443 | −25% |
| Mean | −6% | | | |
| SD | 15.4% | | | |

The mean (SD) difference between Cys123 and Ala123 mutation is on average combining data from replicate 1 and 2 about 19% (5.5%) for WT and Hepmut4 mutant. For the Fc-DAO variants the mean (SD) difference is −6% (15.4%) or in other words cys123 to ala123 mutation are not different.

Therefore, the ala123 mutation has a significant advantage for manufacturing and quality control in general but also for reduction of immunogenicity and therefore this mutation is also clinically highly relevant. It is well known that aggregates are more immunogenic and therefore using this mutation the immunogenicity of rhDAO will be reduced.

The supernatants were tested for DAO activity using a standard DAO activity assay as described in Bartko (Alcohol. 2016 August; 54:51-9.) or Gludovacz 2016. It was confirmed that here is no effect of the cys123 to ala123 mutation on DAO activity. In FIG. 20, DAO activity is presented. WT DAO, Hepmut4 or Fc variants are set to 100% and compared to cys123 to ala123 mutants. It is shown that there is no significant difference in the DAO activity between DAO_WT and cys123 mutations.

Example 4

Generation of Asn168 Glycosylation Mutants

Site Directed Mutagenesis of Asn-168

To replace asparagine at N-glycosylation site Asn-168 (AAT) with glutamine (CAG), the respective codon in the DAO expression plasmid (Gludovacz E. et al., 2016, J. Biotechnol., 227, 120-130) was mutated using site-directed mutagenesis. Therefore, a PCR was conducted using the following 5-phosphorylated primers: Asn-168, CAGaccacaggcttctcattc (forward, SEQ ID NO:104) and gaggaagaactgatgcag (reverse, SEQ ID NO:105). Phusion polymerase (Thermo Fisher Scientific) was used: annealing temperature: 56.3° C.; elongation times, 4 min for 30 cycles. Ligation (T4 DNA ligase, New England Biolabs) and amplification of the final plasmids were performed. Correctness of sequence was verified by DNA sequencing (Eurofins MWG Operon). All cloning techniques were conducted according to Green M. R. and Sambrook, J. (2012), Molecular Cloning: A Laboratory Manual 4th Ed. Cold Spring Harbor Laboratory Press, Cold Spring Harbor, NY; and according to the manufacturer's instructions.

Intravenous Administration of rhDAO, Competing Proteins and Glycosylation Mutants in Rats and Mice The experimental protocols for the treatment of rats and mice were approved by the local Animal Welfare Committee and the Federal Ministry of Science, Research and Economy (GZ 66.009/0152-WFN/3b/2014) and conducted in full accordance with the ARRIVE guidelines (Kilkenny, C et al., Br. J. Pharmacol. (2010) 160, 1577-1579). For implanting a vascular access port into the Vena jugularis (Rodent Vascular Access Port with Detachable Silastic Catheter, Hugo-Sachs Elektronic-Harvard Apparatus) rats are anesthetized via intraperitoneal injection of ketamine (100 mg/kg) and xylazine (5 mg/kg). After intubation anesthesia is maintained through continuous volume-controlled ventilation ($O_2$-air-mixture+1.5% isoflurane). The fur is depilated at the area of surgery and subsequently disinfected with iodine solution (Betaisodona, Mundipharma). Metamizol (100 mg/kg) is administered subcutaneously for analgesia. A skin incision of approximately 1 cm is made at the dorsum of the animals to place the balloon of the vascular access port subcutaneously. The port is flushed with saline before the balloon is fixated with sutures between the scapulae. A second skin incision is made at the site of the V. jugularis sinistra to dissect the V. jugularis for catheterization. A small incision is placed at the exposed V. jugularis sinistra and the catheter is inserted and fixated with silk threats (7-0). Subcutaneous tissue and skin is closed with simple interrupted sutures (4-0). The surgery is performed aseptically. The average surgery time is approximately 2 hours. Post-operative analgesia is provided by ad libitum drinking water with piritramid and glucose (30 mg piritramid and 10 mL 10% glucose in 250 mL drinking water). During the experiments the vascular access port is filled with a solution containing 10 µg/mL argatroban (Argatra 100 mg/mL; Mitsubishi Pharma), 0.3 µg/mL tissue plasminogen activator (Alteplase, Actilyse, Boehringer Ingelheim) and 0.38% sodium citrate in 0.9% NaCl to prevent coagulation.

Venous blood withdrawals (0.5 mL) are conducted at pre-defined time points under short isoflurane anesthesia into tubes containing sodium citrate for anticoagulation. Plasma is prepared within 4 hours and stored at −32° C. until analysis. Fluid substitution (0.5 mL) using physiological saline solution (0.9% NaCl) is provided to the animals. Animals are sacrificed after the last blood withdrawal time point under deep ketamine-xylazine (35 mg and 5 mg/kg) anesthesia by an overdose of pentobarbital (300 mg/kg). Male rats (Sprague-Dawley) with approximately 400 gram and female mice (C57BL/6N) with approximately 20 g body weight are included.

Male Sprague Dawley rats are purchased from commercial vendors (Janvier Labs, Le Genest-Saint-Isle, France and Division Laboratory Animal Science and Genetics, Medical University of Vienna, Himberg, Austria). The animals are housed under controlled and standardized conditions (artificial L/D cycle 12:12, room temperature 22±2° C., humidity 45±10%). The animals are kept in groups of two (Makrolon 3 cages) and are provided with environment enrichment. The animals have ad libitum access to water and to complete feed for rats (Alleinfutter für Ratten and Mäuse sniff R/M-H; sniff Spezialdiäten GmbH).

Female mice (C57BL/6N) are obtained from a commercial vendor (Charles River Laboratories, Sulzfeld, Germany and Division Laboratory Animal Science and Genetics, Medical University of Vienna, Himberg, Austria). The animals are housed under controlled and standardized conditions (artificial L/D cycle 12:12, room temperature 22±2° C., humidity 45±10%). The animals are kept in groups of five (Makrolon 2 long cages) and have ad libitum access to water and to complete feed for mice as described above for rats.

Rapid Plasma Clearance of rhDAO in Rats and Mice after Intravenous Administration Purified rhDAO, wild type rhDAO and rhDAO containing any one of mutations HepMut 1 to HepMut 7 or any of HepMut1 to HepMut4 further comprising Cys123 and/or Asn168Gln mutations, is intravenously administered at 1 mg/kg into rats and mice and blood samples are drawn at the indicated time points. DAO antigen concentrations are measured using a recently published human DAO ELISA (Boehm T. et al., 2017, Clin. Biochem., 50, 444-451). The distribution (alpha) and elimination (beta) half-lives are approximately 3 and 230 minutes respectively in rats and approximately 11 and 110 minutes respectively in mice. In rats more than 90% of the injected dose is removed from the plasma pool within 10 minutes. The rapid clearance in mice is somewhat slower.

The invention claimed is:

1. A recombinant human diamine oxidase (DAO) for degrading histamine with decreased glycosaminoglycan (GAG) binding affinity and increased plasma half-life compared to a wild type human DAO having the sequence of SEQ ID NO:1, wherein the recombinant human DAO has the sequence of SEQ ID NO:1 with at least one amino acid modification at positions 568-575 of SEQ ID NO: 1 selected from the group consisting of R568S, K575T, R571T, R568S+R571T, R571T+K575T, K570G+R571Q+K572T, and R568S+K575T, or a sequence having at least 99% sequence identity to SEQ ID NO: 1 with at least one amino acid modification selected from the group consisting of R568S, K575T, R571T, R568S+R571T, R571T+K575T, K570G+R571Q+K572T, and R568S+K575T.

2. The recombinant human DAO of claim 1, further comprising at least one modification of solvent accessible cysteine at amino acid position 123 (cys123) corresponding to the numbering of SEQ ID NO:1.

3. The recombinant human DAO of claim 1, wherein positions 568-575 comprise a heparin/heparan sulfate binding domain.

4. The recombinant human DAO of claim 1, consisting of 2, 3, 4, 5, 6, or 7 amino acid substitutions at positions 568-575 of SEQ ID NO:1.

5. The recombinant human DAO of claim 1, comprising a GAG binding domain of amino acid sequence X1FX2X3X4LPX5 (SEQ ID NO:107), wherein:

X1 is S;
X2 is K;
X3 is T;
X4 is K; and
X5 is K or T.

6. The recombinant human DAO of claim 1, comprising a GAG binding domain of an amino acid sequence selected from the group consisting of SFKAKLPK (SEQ ID NO:33), AFKAKLPT (SEQ ID NO:34), AFKTKLPK (SEQ ID NO: 35), SFKTKLPK (SEQ ID NO:36), and AFKTKLPT (SEQ ID NO:37).

7. The recombinant human DAO of claim 1, further comprising an amino acid substitution of Asn at position 168 of SEQ ID NO:1.

8. The recombinant human DAO of claim 1, wherein the DAO has a 1.5 fold increased plasma half-life compared to the human wild type DAO.

9. The recombinant human DAO of claim 1, wherein the DAO has an at least 10-fold increased area under the curve (AUC) compared to the human wild type DAO.

10. The recombinant human DAO of claim 1, wherein the DAO is internalized and internalization by endothelial cells is at least 10%, 25%, 50%, 60%, 70%, 80%, or 90% reduced compared to the human wild type DAO.

11. The recombinant human DAO of claim 3, wherein when binding to heparin, heparin/heparan sulfate binding affinity is at least 10%, 25%, 50%, 60%, 70%, 80%, or 90% reduced compared to the human wild type DAO.

12. The recombinant human DAO of claim 1, wherein the recombinant human DAO is a fusion polypeptide comprising the recombinant DAO and an Fc domain of human IgG or human serum albumin (HSA), and wherein the fusion polypeptide retains the functional activity of the recombinant DAO.

13. The recombinant human DAO of claim 1, wherein the recombinant DAO is expressed in a recombinant host cell selected from the group consisting of a Chinese Hamster Ovary (CHO) cell, a Vero cell, Madin-Darby Canine Kidney (MDCK) cell, a *Pichia pastoris* cell, and a *Spodoptera frugiperda* (SF9) cell.

14. The recombinant human DAO of claim 1, wherein the recombinant DAO is a pharmaceutical composition comprising the recombinant human DAO and one or more pharmaceutically acceptable carriers or excipients.

15. The recombinant human DAO of claim 2, wherein the cys123 is substituted by alanine.

16. The recombinant human DAO of claim 5, wherein X5 is T.

17. The recombinant human DAO of claim 7, wherein the Asn is replaced by Gln.

18. The recombinant human DAO of claim 1, wherein the recombinant human DAO has a 2 fold increased plasma half-life compared to the human wild type DAO.

19. A method of treating chronic allergic conditions in a subject by removing excess histamine, comprising:

administering an effective amount of the recombinant human DAO of claim 1 to the subject, wherein the chronic allergic conditions are selected from the group consisting of acute urticaria, asthma, hay fever, allergic rhinitis, allergic conjunctivitis, anaphylaxis, anaphylactic shock, and itching, and wherein administering the recombinant human DAO reduces histamine to treat chronic allergic conditions.

20. A method of treating a medical condition in a subject by removing excess histamine, comprising:

administering an effective amount of the recombinant human DAO of claim 1 to the subject, wherein the medical condition is selected from the group consisting of mastocytosis and mast cell activation syndrome (MCAS), and wherein administering the recombinant human DAO reduces histamine to treat the mastocytosis or MCAS.

* * * * *

SEQUENCE LISTING

```
<160> NUMBER OF SEQ ID NOS: 106

<210> SEQ ID NO 1
<211> LENGTH: 751
<212> TYPE: PRT
<213> ORGANISM: Homo sapiens

<400> SEQUENCE: 1

Met Pro Ala Leu Gly Trp Ala Val Ala Ala Ile Leu Met Leu Gln Thr
1               5                   10                  15

Ala Met Ala Glu Pro Ser Pro Gly Thr Leu Pro Arg Lys Ala Gly Val
            20                  25                  30

Phe Ser Asp Leu Ser Asn Gln Glu Leu Lys Ala Val His Ser Phe Leu
        35                  40                  45

Trp Ser Lys Lys Glu Leu Arg Leu Gln Pro Ser Ser Thr Thr Thr Met
    50                  55                  60

Ala Lys Asn Thr Val Phe Leu Ile Glu Met Leu Leu Pro Lys Lys Tyr
65                  70                  75                  80

His Val Leu Arg Phe Leu Asp Lys Gly Glu Arg His Pro Val Arg Glu
                85                  90                  95

Ala Arg Ala Val Ile Phe Phe Gly Asp Gln Glu His Pro Asn Val Thr
            100                 105                 110

Glu Phe Ala Val Gly Pro Leu Pro Gly Pro Cys Tyr Met Arg Ala Leu
        115                 120                 125

Ser Pro Arg Pro Gly Tyr Gln Ser Ser Trp Ala Ser Arg Pro Ile Ser
    130                 135                 140

Thr Ala Glu Tyr Ala Leu Leu Tyr His Thr Leu Gln Glu Ala Thr Lys
145                 150                 155                 160

Pro Leu His Gln Phe Phe Leu Asn Thr Thr Gly Phe Ser Phe Gln Asp
                165                 170                 175

Cys His Asp Arg Cys Leu Ala Phe Thr Asp Val Ala Pro Arg Gly Val
            180                 185                 190

Ala Ser Gly Gln Arg Arg Ser Trp Leu Ile Ile Gln Arg Tyr Val Glu
        195                 200                 205

Gly Tyr Phe Leu His Pro Thr Gly Leu Glu Leu Leu Val Asp His Gly
    210                 215                 220

Ser Thr Asp Ala Gly His Trp Ala Val Glu Gln Val Trp Tyr Asn Gly
225                 230                 235                 240

Lys Phe Tyr Gly Ser Pro Glu Glu Leu Ala Arg Lys Tyr Ala Asp Gly
                245                 250                 255

Glu Val Asp Val Val Val Leu Glu Asp Pro Leu Pro Gly Gly Lys Gly
            260                 265                 270
```

-continued

```
His Asp Ser Thr Glu Glu Pro Pro Leu Phe Ser Ser His Lys Pro Arg
        275                 280                 285

Gly Asp Phe Pro Ser Pro Ile His Val Ser Gly Pro Arg Leu Val Gln
    290                 295                 300

Pro His Gly Pro Arg Phe Arg Leu Glu Gly Asn Ala Val Leu Tyr Gly
305                 310                 315                 320

Gly Trp Ser Phe Ala Phe Arg Leu Arg Ser Ser Ser Gly Leu Gln Val
                325                 330                 335

Leu Asn Val His Phe Gly Gly Glu Arg Ile Ala Tyr Glu Val Ser Val
            340                 345                 350

Gln Glu Ala Val Ala Leu Tyr Gly Gly His Thr Pro Ala Gly Met Gln
        355                 360                 365

Thr Lys Tyr Leu Asp Val Gly Trp Gly Leu Gly Ser Val Thr His Glu
    370                 375                 380

Leu Ala Pro Gly Ile Asp Cys Pro Glu Thr Ala Thr Phe Leu Asp Thr
385                 390                 395                 400

Phe His Tyr Tyr Asp Ala Asp Asp Pro Val His Tyr Pro Arg Ala Leu
                405                 410                 415

Cys Leu Phe Glu Met Pro Thr Gly Val Pro Leu Arg Arg His Phe Asn
            420                 425                 430

Ser Asn Phe Lys Gly Gly Phe Asn Phe Tyr Ala Gly Leu Lys Gly Gln
        435                 440                 445

Val Leu Val Leu Arg Thr Thr Ser Thr Val Tyr Asn Tyr Asp Tyr Ile
    450                 455                 460

Trp Asp Phe Ile Phe Tyr Pro Asn Gly Val Met Glu Ala Lys Met His
465                 470                 475                 480

Ala Thr Gly Tyr Val His Ala Thr Phe Tyr Thr Pro Glu Gly Leu Arg
                485                 490                 495

His Gly Thr Arg Leu His Thr His Leu Ile Gly Asn Ile His Thr His
            500                 505                 510

Leu Val His Tyr Arg Val Asp Leu Asp Val Ala Gly Thr Lys Asn Ser
        515                 520                 525

Phe Gln Thr Leu Gln Met Lys Leu Glu Asn Ile Thr Asn Pro Trp Ser
    530                 535                 540

Pro Arg His Arg Val Val Gln Pro Thr Leu Glu Gln Thr Gln Tyr Ser
545                 550                 555                 560

Trp Glu Arg Gln Ala Ala Phe Arg Phe Lys Arg Lys Leu Pro Lys Tyr
                565                 570                 575

Leu Leu Phe Thr Ser Pro Gln Glu Asn Pro Trp Gly His Lys Arg Ser
            580                 585                 590

Tyr Arg Leu Gln Ile His Ser Met Ala Asp Gln Val Leu Pro Pro Gly
        595                 600                 605

Trp Gln Glu Glu Gln Ala Ile Thr Trp Ala Arg Tyr Pro Leu Ala Val
    610                 615                 620

Thr Lys Tyr Arg Glu Ser Glu Leu Cys Ser Ser Ser Ile Tyr His Gln
625                 630                 635                 640

Asn Asp Pro Trp His Pro Pro Val Val Phe Glu Gln Phe Leu His Asn
                645                 650                 655

Asn Glu Asn Ile Glu Asn Glu Asp Leu Val Ala Trp Val Thr Val Gly
            660                 665                 670

Phe Leu His Ile Pro His Ser Glu Asp Ile Pro Asn Thr Ala Thr Pro
        675                 680                 685

Gly Asn Ser Val Gly Phe Leu Leu Arg Pro Phe Asn Phe Phe Pro Glu
```

```
    690                 695                 700

Asp Pro Ser Leu Ala Ser Arg Asp Thr Val Ile Val Trp Pro Arg Asp
705                 710                 715                 720

Asn Gly Pro Asn Tyr Val Gln Arg Trp Ile Pro Glu Asp Arg Asp Cys
                725                 730                 735

Ser Met Pro Pro Pro Phe Ser Tyr Asn Gly Thr Tyr Arg Pro Val
            740                 745                 750


<210> SEQ ID NO 2
<211> LENGTH: 751
<212> TYPE: PRT
<213> ORGANISM: Artificial Sequence
<220> FEATURE:
<223> OTHER INFORMATION: hDAO-Hepmut1

<400> SEQUENCE: 2

Met Pro Ala Leu Gly Trp Ala Val Ala Ala Ile Leu Met Leu Gln Thr
1               5                   10                  15

Ala Met Ala Glu Pro Ser Pro Gly Thr Leu Pro Arg Lys Ala Gly Val
            20                  25                  30

Phe Ser Asp Leu Ser Asn Gln Glu Leu Lys Ala Val His Ser Phe Leu
        35                  40                  45

Trp Ser Lys Lys Glu Leu Arg Leu Gln Pro Ser Ser Thr Thr Thr Met
    50                  55                  60

Ala Lys Asn Thr Val Phe Leu Ile Glu Met Leu Leu Pro Lys Lys Tyr
65                  70                  75                  80

His Val Leu Arg Phe Leu Asp Lys Gly Glu Arg His Pro Val Arg Glu
                85                  90                  95

Ala Arg Ala Val Ile Phe Phe Gly Asp Gln Glu His Pro Asn Val Thr
            100                 105                 110

Glu Phe Ala Val Gly Pro Leu Pro Gly Pro Cys Tyr Met Arg Ala Leu
        115                 120                 125

Ser Pro Arg Pro Gly Tyr Gln Ser Ser Trp Ala Ser Arg Pro Ile Ser
    130                 135                 140

Thr Ala Glu Tyr Ala Leu Leu Tyr His Thr Leu Gln Glu Ala Thr Lys
145                 150                 155                 160

Pro Leu His Gln Phe Phe Leu Asn Thr Thr Gly Phe Ser Phe Gln Asp
                165                 170                 175

Cys His Asp Arg Cys Leu Ala Phe Thr Asp Val Ala Pro Arg Gly Val
            180                 185                 190

Ala Ser Gly Gln Arg Arg Ser Trp Leu Ile Ile Gln Arg Tyr Val Glu
        195                 200                 205

Gly Tyr Phe Leu His Pro Thr Gly Leu Glu Leu Leu Val Asp His Gly
    210                 215                 220

Ser Thr Asp Ala Gly His Trp Ala Val Glu Gln Val Trp Tyr Asn Gly
225                 230                 235                 240

Lys Phe Tyr Gly Ser Pro Glu Glu Leu Ala Arg Lys Tyr Ala Asp Gly
                245                 250                 255

Glu Val Asp Val Val Val Leu Glu Asp Pro Leu Pro Gly Gly Lys Gly
            260                 265                 270

His Asp Ser Thr Glu Glu Pro Pro Leu Phe Ser Ser His Lys Pro Arg
        275                 280                 285

Gly Asp Phe Pro Ser Pro Ile His Val Ser Gly Pro Arg Leu Val Gln
    290                 295                 300

Pro His Gly Pro Arg Phe Arg Leu Glu Gly Asn Ala Val Leu Tyr Gly
```

```
305                 310                 315                 320

Gly Trp Ser Phe Ala Phe Arg Leu Arg Ser Ser Ser Gly Leu Gln Val
                325                 330                 335

Leu Asn Val His Phe Gly Gly Glu Arg Ile Ala Tyr Glu Val Ser Val
            340                 345                 350

Gln Glu Ala Val Ala Leu Tyr Gly Gly His Thr Pro Ala Gly Met Gln
        355                 360                 365

Thr Lys Tyr Leu Asp Val Gly Trp Gly Leu Gly Ser Val Thr His Glu
    370                 375                 380

Leu Ala Pro Gly Ile Asp Cys Pro Glu Thr Ala Thr Phe Leu Asp Thr
385                 390                 395                 400

Phe His Tyr Tyr Asp Ala Asp Asp Pro Val His Tyr Pro Arg Ala Leu
                405                 410                 415

Cys Leu Phe Glu Met Pro Thr Gly Val Pro Leu Arg Arg His Phe Asn
            420                 425                 430

Ser Asn Phe Lys Gly Gly Phe Asn Phe Tyr Ala Gly Leu Lys Gly Gln
        435                 440                 445

Val Leu Val Leu Arg Thr Thr Ser Thr Val Tyr Asn Tyr Asp Tyr Ile
    450                 455                 460

Trp Asp Phe Ile Phe Tyr Pro Asn Gly Val Met Glu Ala Lys Met His
465                 470                 475                 480

Ala Thr Gly Tyr Val His Ala Thr Phe Tyr Thr Pro Glu Gly Leu Arg
                485                 490                 495

His Gly Thr Arg Leu His Thr His Leu Ile Gly Asn Ile His Thr His
            500                 505                 510

Leu Val His Tyr Arg Val Asp Leu Asp Val Ala Gly Thr Lys Asn Ser
        515                 520                 525

Phe Gln Thr Leu Gln Met Lys Leu Glu Asn Ile Thr Asn Pro Trp Ser
    530                 535                 540

Pro Arg His Arg Val Val Gln Pro Thr Leu Glu Gln Thr Gln Tyr Ser
545                 550                 555                 560

Trp Glu Arg Gln Ala Ala Phe Ser Phe Lys Arg Lys Leu Pro Lys Tyr
                565                 570                 575

Leu Leu Phe Thr Ser Pro Gln Glu Asn Pro Trp Gly His Lys Arg Ser
            580                 585                 590

Tyr Arg Leu Gln Ile His Ser Met Ala Asp Gln Val Leu Pro Pro Gly
        595                 600                 605

Trp Gln Glu Glu Gln Ala Ile Thr Trp Ala Arg Tyr Pro Leu Ala Val
    610                 615                 620

Thr Lys Tyr Arg Glu Ser Glu Leu Cys Ser Ser Ser Ile Tyr His Gln
625                 630                 635                 640

Asn Asp Pro Trp His Pro Pro Val Val Phe Glu Gln Phe Leu His Asn
                645                 650                 655

Asn Glu Asn Ile Glu Asn Glu Asp Leu Val Ala Trp Val Thr Val Gly
            660                 665                 670

Phe Leu His Ile Pro His Ser Glu Asp Ile Pro Asn Thr Ala Thr Pro
        675                 680                 685

Gly Asn Ser Val Gly Phe Leu Leu Arg Pro Phe Asn Phe Phe Pro Glu
    690                 695                 700

Asp Pro Ser Leu Ala Ser Arg Asp Thr Val Ile Val Trp Pro Arg Asp
705                 710                 715                 720

Asn Gly Pro Asn Tyr Val Gln Arg Trp Ile Pro Glu Asp Arg Asp Cys
                725                 730                 735
```

Ser Met Pro Pro Pro Phe Ser Tyr Asn Gly Thr Tyr Arg Pro Val
740 745 750

<210> SEQ ID NO 3
<211> LENGTH: 751
<212> TYPE: PRT
<213> ORGANISM: Artificial Sequence
<220> FEATURE:
<223> OTHER INFORMATION: hDAO-Hepmut2

<400> SEQUENCE: 3

Met Pro Ala Leu Gly Trp Ala Val Ala Ala Ile Leu Met Leu Gln Thr
1 5 10 15

Ala Met Ala Glu Pro Ser Pro Gly Thr Leu Pro Arg Lys Ala Gly Val
20 25 30

Phe Ser Asp Leu Ser Asn Gln Glu Leu Lys Ala Val His Ser Phe Leu
35 40 45

Trp Ser Lys Lys Glu Leu Arg Leu Gln Pro Ser Ser Thr Thr Thr Met
50 55 60

Ala Lys Asn Thr Val Phe Leu Ile Glu Met Leu Leu Pro Lys Lys Tyr
65 70 75 80

His Val Leu Arg Phe Leu Asp Lys Gly Glu Arg His Pro Val Arg Glu
85 90 95

Ala Arg Ala Val Ile Phe Phe Gly Asp Gln Glu His Pro Asn Val Thr
100 105 110

Glu Phe Ala Val Gly Pro Leu Pro Gly Pro Cys Tyr Met Arg Ala Leu
115 120 125

Ser Pro Arg Pro Gly Tyr Gln Ser Ser Trp Ala Ser Arg Pro Ile Ser
130 135 140

Thr Ala Glu Tyr Ala Leu Leu Tyr His Thr Leu Gln Glu Ala Thr Lys
145 150 155 160

Pro Leu His Gln Phe Phe Leu Asn Thr Thr Gly Phe Ser Phe Gln Asp
165 170 175

Cys His Asp Arg Cys Leu Ala Phe Thr Asp Val Ala Pro Arg Gly Val
180 185 190

Ala Ser Gly Gln Arg Arg Ser Trp Leu Ile Ile Gln Arg Tyr Val Glu
195 200 205

Gly Tyr Phe Leu His Pro Thr Gly Leu Glu Leu Leu Val Asp His Gly
210 215 220

Ser Thr Asp Ala Gly His Trp Ala Val Glu Gln Val Trp Tyr Asn Gly
225 230 235 240

Lys Phe Tyr Gly Ser Pro Glu Glu Leu Ala Arg Lys Tyr Ala Asp Gly
245 250 255

Glu Val Asp Val Val Val Leu Glu Asp Pro Leu Pro Gly Gly Lys Gly
260 265 270

His Asp Ser Thr Glu Glu Pro Pro Leu Phe Ser Ser His Lys Pro Arg
275 280 285

Gly Asp Phe Pro Ser Pro Ile His Val Ser Gly Pro Arg Leu Val Gln
290 295 300

Pro His Gly Pro Arg Phe Arg Leu Glu Gly Asn Ala Val Leu Tyr Gly
305 310 315 320

Gly Trp Ser Phe Ala Phe Arg Leu Arg Ser Ser Ser Gly Leu Gln Val
325 330 335

Leu Asn Val His Phe Gly Gly Glu Arg Ile Ala Tyr Glu Val Ser Val
340 345 350

```
Gln Glu Ala Val Ala Leu Tyr Gly Gly His Thr Pro Ala Gly Met Gln
        355                 360                 365

Thr Lys Tyr Leu Asp Val Gly Trp Gly Leu Gly Ser Val Thr His Glu
    370                 375                 380

Leu Ala Pro Gly Ile Asp Cys Pro Glu Thr Ala Thr Phe Leu Asp Thr
385                 390                 395                 400

Phe His Tyr Tyr Asp Ala Asp Asp Pro Val His Tyr Pro Arg Ala Leu
                405                 410                 415

Cys Leu Phe Glu Met Pro Thr Gly Val Pro Leu Arg Arg His Phe Asn
            420                 425                 430

Ser Asn Phe Lys Gly Gly Phe Asn Phe Tyr Ala Gly Leu Lys Gly Gln
        435                 440                 445

Val Leu Val Leu Arg Thr Thr Ser Thr Val Tyr Asn Tyr Asp Tyr Ile
    450                 455                 460

Trp Asp Phe Ile Phe Tyr Pro Asn Gly Val Met Glu Ala Lys Met His
465                 470                 475                 480

Ala Thr Gly Tyr Val His Ala Thr Phe Tyr Thr Pro Glu Gly Leu Arg
                485                 490                 495

His Gly Thr Arg Leu His Thr His Leu Ile Gly Asn Ile His Thr His
            500                 505                 510

Leu Val His Tyr Arg Val Asp Leu Asp Val Ala Gly Thr Lys Asn Ser
        515                 520                 525

Phe Gln Thr Leu Gln Met Lys Leu Glu Asn Ile Thr Asn Pro Trp Ser
    530                 535                 540

Pro Arg His Arg Val Val Gln Pro Thr Leu Glu Gln Thr Gln Tyr Ser
545                 550                 555                 560

Trp Glu Arg Gln Ala Ala Phe Arg Phe Lys Arg Lys Leu Pro Thr Tyr
                565                 570                 575

Leu Leu Phe Thr Ser Pro Gln Glu Asn Pro Trp Gly His Lys Arg Ser
            580                 585                 590

Tyr Arg Leu Gln Ile His Ser Met Ala Asp Gln Val Leu Pro Pro Gly
        595                 600                 605

Trp Gln Glu Glu Gln Ala Ile Thr Trp Ala Arg Tyr Pro Leu Ala Val
    610                 615                 620

Thr Lys Tyr Arg Glu Ser Glu Leu Cys Ser Ser Ser Ile Tyr His Gln
625                 630                 635                 640

Asn Asp Pro Trp His Pro Pro Val Val Phe Glu Gln Phe Leu His Asn
                645                 650                 655

Asn Glu Asn Ile Glu Asn Glu Asp Leu Val Ala Trp Val Thr Val Gly
            660                 665                 670

Phe Leu His Ile Pro His Ser Glu Asp Ile Pro Asn Thr Ala Thr Pro
        675                 680                 685

Gly Asn Ser Val Gly Phe Leu Leu Arg Pro Phe Asn Phe Phe Pro Glu
    690                 695                 700

Asp Pro Ser Leu Ala Ser Arg Asp Thr Val Ile Val Trp Pro Arg Asp
705                 710                 715                 720

Asn Gly Pro Asn Tyr Val Gln Arg Trp Ile Pro Glu Asp Arg Asp Cys
                725                 730                 735

Ser Met Pro Pro Pro Phe Ser Tyr Asn Gly Thr Tyr Arg Pro Val
            740                 745                 750
```

<210> SEQ ID NO 4
<211> LENGTH: 751

```
<212> TYPE: PRT
<213> ORGANISM: Artificial Sequence
<220> FEATURE:
<223> OTHER INFORMATION: hDAO-Hepmut3

<400> SEQUENCE: 4

Met Pro Ala Leu Gly Trp Ala Val Ala Ala Ile Leu Met Leu Gln Thr
1               5                   10                  15

Ala Met Ala Glu Pro Ser Pro Gly Thr Leu Pro Arg Lys Ala Gly Val
            20                  25                  30

Phe Ser Asp Leu Ser Asn Gln Glu Leu Lys Ala Val His Ser Phe Leu
        35                  40                  45

Trp Ser Lys Lys Glu Leu Arg Leu Gln Pro Ser Ser Thr Thr Thr Met
    50                  55                  60

Ala Lys Asn Thr Val Phe Leu Ile Glu Met Leu Leu Pro Lys Lys Tyr
65                  70                  75                  80

His Val Leu Arg Phe Leu Asp Lys Gly Glu Arg His Pro Val Arg Glu
                85                  90                  95

Ala Arg Ala Val Ile Phe Phe Gly Asp Gln Glu His Pro Asn Val Thr
            100                 105                 110

Glu Phe Ala Val Gly Pro Leu Pro Gly Pro Cys Tyr Met Arg Ala Leu
        115                 120                 125

Ser Pro Arg Pro Gly Tyr Gln Ser Ser Trp Ala Ser Arg Pro Ile Ser
    130                 135                 140

Thr Ala Glu Tyr Ala Leu Leu Tyr His Thr Leu Gln Glu Ala Thr Lys
145                 150                 155                 160

Pro Leu His Gln Phe Phe Leu Asn Thr Thr Gly Phe Ser Phe Gln Asp
                165                 170                 175

Cys His Asp Arg Cys Leu Ala Phe Thr Asp Val Ala Pro Arg Gly Val
            180                 185                 190

Ala Ser Gly Gln Arg Arg Ser Trp Leu Ile Ile Gln Arg Tyr Val Glu
        195                 200                 205

Gly Tyr Phe Leu His Pro Thr Gly Leu Glu Leu Leu Val Asp His Gly
    210                 215                 220

Ser Thr Asp Ala Gly His Trp Ala Val Glu Gln Val Trp Tyr Asn Gly
225                 230                 235                 240

Lys Phe Tyr Gly Ser Pro Glu Glu Leu Ala Arg Lys Tyr Ala Asp Gly
                245                 250                 255

Glu Val Asp Val Val Val Leu Glu Asp Pro Leu Pro Gly Gly Lys Gly
            260                 265                 270

His Asp Ser Thr Glu Glu Pro Pro Leu Phe Ser Ser His Lys Pro Arg
        275                 280                 285

Gly Asp Phe Pro Ser Pro Ile His Val Ser Gly Pro Arg Leu Val Gln
    290                 295                 300

Pro His Gly Pro Arg Phe Arg Leu Glu Gly Asn Ala Val Leu Tyr Gly
305                 310                 315                 320

Gly Trp Ser Phe Ala Phe Arg Leu Arg Ser Ser Ser Gly Leu Gln Val
                325                 330                 335

Leu Asn Val His Phe Gly Gly Glu Arg Ile Ala Tyr Glu Val Ser Val
            340                 345                 350

Gln Glu Ala Val Ala Leu Tyr Gly Gly His Thr Pro Ala Gly Met Gln
        355                 360                 365

Thr Lys Tyr Leu Asp Val Gly Trp Gly Leu Gly Ser Val Thr His Glu
    370                 375                 380
```

Leu Ala Pro Gly Ile Asp Cys Pro Glu Thr Ala Thr Phe Leu Asp Thr
385 390 395 400

Phe His Tyr Tyr Asp Ala Asp Asp Pro Val His Tyr Pro Arg Ala Leu
405 410 415

Cys Leu Phe Glu Met Pro Thr Gly Val Pro Leu Arg Arg His Phe Asn
420 425 430

Ser Asn Phe Lys Gly Gly Phe Asn Phe Tyr Ala Gly Leu Lys Gly Gln
435 440 445

Val Leu Val Leu Arg Thr Thr Ser Thr Val Tyr Asn Tyr Asp Tyr Ile
450 455 460

Trp Asp Phe Ile Phe Tyr Pro Asn Gly Val Met Glu Ala Lys Met His
465 470 475 480

Ala Thr Gly Tyr Val His Ala Thr Phe Tyr Thr Pro Glu Gly Leu Arg
485 490 495

His Gly Thr Arg Leu His Thr His Leu Ile Gly Asn Ile His Thr His
500 505 510

Leu Val His Tyr Arg Val Asp Leu Asp Val Ala Gly Thr Lys Asn Ser
515 520 525

Phe Gln Thr Leu Gln Met Lys Leu Glu Asn Ile Thr Asn Pro Trp Ser
530 535 540

Pro Arg His Arg Val Val Gln Pro Thr Leu Glu Gln Thr Gln Tyr Ser
545 550 555 560

Trp Glu Arg Gln Ala Ala Phe Arg Phe Lys Thr Lys Leu Pro Lys Tyr
565 570 575

Leu Leu Phe Thr Ser Pro Gln Glu Asn Pro Trp Gly His Lys Arg Ser
580 585 590

Tyr Arg Leu Gln Ile His Ser Met Ala Asp Gln Val Leu Pro Pro Gly
595 600 605

Trp Gln Glu Glu Gln Ala Ile Thr Trp Ala Arg Tyr Pro Leu Ala Val
610 615 620

Thr Lys Tyr Arg Glu Ser Glu Leu Cys Ser Ser Ser Ile Tyr His Gln
625 630 635 640

Asn Asp Pro Trp His Pro Pro Val Val Phe Glu Gln Phe Leu His Asn
645 650 655

Asn Glu Asn Ile Glu Asn Glu Asp Leu Val Ala Trp Val Thr Val Gly
660 665 670

Phe Leu His Ile Pro His Ser Glu Asp Ile Pro Asn Thr Ala Thr Pro
675 680 685

Gly Asn Ser Val Gly Phe Leu Leu Arg Pro Phe Asn Phe Phe Pro Glu
690 695 700

Asp Pro Ser Leu Ala Ser Arg Asp Thr Val Ile Val Trp Pro Arg Asp
705 710 715 720

Asn Gly Pro Asn Tyr Val Gln Arg Trp Ile Pro Glu Asp Arg Asp Cys
725 730 735

Ser Met Pro Pro Pro Phe Ser Tyr Asn Gly Thr Tyr Arg Pro Val
740 745 750

<210> SEQ ID NO 5
<211> LENGTH: 751
<212> TYPE: PRT
<213> ORGANISM: Artificial Sequence
<220> FEATURE:
<223> OTHER INFORMATION: hDAO-Hepmut4

<400> SEQUENCE: 5

-continued

```
Met Pro Ala Leu Gly Trp Ala Val Ala Ala Ile Leu Met Leu Gln Thr
1               5                   10                  15

Ala Met Ala Glu Pro Ser Pro Gly Thr Leu Pro Arg Lys Ala Gly Val
            20                  25                  30

Phe Ser Asp Leu Ser Asn Gln Glu Leu Lys Ala Val His Ser Phe Leu
        35                  40                  45

Trp Ser Lys Lys Glu Leu Arg Leu Gln Pro Ser Ser Thr Thr Thr Met
    50                  55                  60

Ala Lys Asn Thr Val Phe Leu Ile Glu Met Leu Leu Pro Lys Lys Tyr
65                  70                  75                  80

His Val Leu Arg Phe Leu Asp Lys Gly Glu Arg His Pro Val Arg Glu
                85                  90                  95

Ala Arg Ala Val Ile Phe Phe Gly Asp Gln Glu His Pro Asn Val Thr
            100                 105                 110

Glu Phe Ala Val Gly Pro Leu Pro Gly Pro Cys Tyr Met Arg Ala Leu
        115                 120                 125

Ser Pro Arg Pro Gly Tyr Gln Ser Ser Trp Ala Ser Arg Pro Ile Ser
    130                 135                 140

Thr Ala Glu Tyr Ala Leu Leu Tyr His Thr Leu Gln Glu Ala Thr Lys
145                 150                 155                 160

Pro Leu His Gln Phe Phe Leu Asn Thr Thr Gly Phe Ser Phe Gln Asp
                165                 170                 175

Cys His Asp Arg Cys Leu Ala Phe Thr Asp Val Ala Pro Arg Gly Val
            180                 185                 190

Ala Ser Gly Gln Arg Arg Ser Trp Leu Ile Ile Gln Arg Tyr Val Glu
        195                 200                 205

Gly Tyr Phe Leu His Pro Thr Gly Leu Glu Leu Leu Val Asp His Gly
    210                 215                 220

Ser Thr Asp Ala Gly His Trp Ala Val Glu Gln Val Trp Tyr Asn Gly
225                 230                 235                 240

Lys Phe Tyr Gly Ser Pro Glu Glu Leu Ala Arg Lys Tyr Ala Asp Gly
                245                 250                 255

Glu Val Asp Val Val Val Leu Glu Asp Pro Leu Pro Gly Gly Lys Gly
            260                 265                 270

His Asp Ser Thr Glu Glu Pro Pro Leu Phe Ser Ser His Lys Pro Arg
        275                 280                 285

Gly Asp Phe Pro Ser Pro Ile His Val Ser Gly Pro Arg Leu Val Gln
    290                 295                 300

Pro His Gly Pro Arg Phe Arg Leu Glu Gly Asn Ala Val Leu Tyr Gly
305                 310                 315                 320

Gly Trp Ser Phe Ala Phe Arg Leu Arg Ser Ser Ser Gly Leu Gln Val
                325                 330                 335

Leu Asn Val His Phe Gly Gly Glu Arg Ile Ala Tyr Glu Val Ser Val
            340                 345                 350

Gln Glu Ala Val Ala Leu Tyr Gly Gly His Thr Pro Ala Gly Met Gln
        355                 360                 365

Thr Lys Tyr Leu Asp Val Gly Trp Gly Leu Gly Ser Val Thr His Glu
    370                 375                 380

Leu Ala Pro Gly Ile Asp Cys Pro Glu Thr Ala Thr Phe Leu Asp Thr
385                 390                 395                 400

Phe His Tyr Tyr Asp Ala Asp Asp Pro Val His Tyr Pro Arg Ala Leu
                405                 410                 415

Cys Leu Phe Glu Met Pro Thr Gly Val Pro Leu Arg Arg His Phe Asn
```

```
            420                 425                 430

Ser Asn Phe Lys Gly Gly Phe Asn Phe Tyr Ala Gly Leu Lys Gly Gln
        435                 440                 445

Val Leu Val Leu Arg Thr Thr Ser Thr Val Tyr Asn Tyr Asp Tyr Ile
    450                 455                 460

Trp Asp Phe Ile Phe Tyr Pro Asn Gly Val Met Glu Ala Lys Met His
465                 470                 475                 480

Ala Thr Gly Tyr Val His Ala Thr Phe Tyr Thr Pro Glu Gly Leu Arg
                485                 490                 495

His Gly Thr Arg Leu His Thr His Leu Ile Gly Asn Ile His Thr His
            500                 505                 510

Leu Val His Tyr Arg Val Asp Leu Asp Val Ala Gly Thr Lys Asn Ser
        515                 520                 525

Phe Gln Thr Leu Gln Met Lys Leu Glu Asn Ile Thr Asn Pro Trp Ser
    530                 535                 540

Pro Arg His Arg Val Val Gln Pro Thr Leu Glu Gln Thr Gln Tyr Ser
545                 550                 555                 560

Trp Glu Arg Gln Ala Ala Phe Ser Phe Lys Thr Lys Leu Pro Lys Tyr
                565                 570                 575

Leu Leu Phe Thr Ser Pro Gln Glu Asn Pro Trp Gly His Lys Arg Ser
            580                 585                 590

Tyr Arg Leu Gln Ile His Ser Met Ala Asp Gln Val Leu Pro Pro Gly
        595                 600                 605

Trp Gln Glu Glu Gln Ala Ile Thr Trp Ala Arg Tyr Pro Leu Ala Val
    610                 615                 620

Thr Lys Tyr Arg Glu Ser Glu Leu Cys Ser Ser Ser Ile Tyr His Gln
625                 630                 635                 640

Asn Asp Pro Trp His Pro Pro Val Val Phe Glu Gln Phe Leu His Asn
                645                 650                 655

Asn Glu Asn Ile Glu Asn Glu Asp Leu Val Ala Trp Val Thr Val Gly
            660                 665                 670

Phe Leu His Ile Pro His Ser Glu Asp Ile Pro Asn Thr Ala Thr Pro
        675                 680                 685

Gly Asn Ser Val Gly Phe Leu Leu Arg Pro Phe Asn Phe Phe Pro Glu
    690                 695                 700

Asp Pro Ser Leu Ala Ser Arg Asp Thr Val Ile Val Trp Pro Arg Asp
705                 710                 715                 720

Asn Gly Pro Asn Tyr Val Gln Arg Trp Ile Pro Glu Asp Arg Asp Cys
                725                 730                 735

Ser Met Pro Pro Pro Phe Ser Tyr Asn Gly Thr Tyr Arg Pro Val
            740                 745                 750


<210> SEQ ID NO 6
<211> LENGTH: 751
<212> TYPE: PRT
<213> ORGANISM: Artificial Sequence
<220> FEATURE:
<223> OTHER INFORMATION: hDAO-Hepmut5

<400> SEQUENCE: 6

Met Pro Ala Leu Gly Trp Ala Val Ala Ala Ile Leu Met Leu Gln Thr
1               5                   10                  15

Ala Met Ala Glu Pro Ser Pro Gly Thr Leu Pro Arg Lys Ala Gly Val
            20                  25                  30

Phe Ser Asp Leu Ser Asn Gln Glu Leu Lys Ala Val His Ser Phe Leu
```

```
        35                  40                  45

Trp Ser Lys Lys Glu Leu Arg Leu Gln Pro Ser Ser Thr Thr Thr Met
    50                  55                  60

Ala Lys Asn Thr Val Phe Leu Ile Glu Met Leu Leu Pro Lys Lys Tyr
65                  70                  75                  80

His Val Leu Arg Phe Leu Asp Lys Gly Glu Arg His Pro Val Arg Glu
                85                  90                  95

Ala Arg Ala Val Ile Phe Phe Gly Asp Gln Glu His Pro Asn Val Thr
            100                 105                 110

Glu Phe Ala Val Gly Pro Leu Pro Gly Pro Cys Tyr Met Arg Ala Leu
        115                 120                 125

Ser Pro Arg Pro Gly Tyr Gln Ser Ser Trp Ala Ser Arg Pro Ile Ser
    130                 135                 140

Thr Ala Glu Tyr Ala Leu Leu Tyr His Thr Leu Gln Glu Ala Thr Lys
145                 150                 155                 160

Pro Leu His Gln Phe Phe Leu Asn Thr Thr Gly Phe Ser Phe Gln Asp
                165                 170                 175

Cys His Asp Arg Cys Leu Ala Phe Thr Asp Val Ala Pro Arg Gly Val
            180                 185                 190

Ala Ser Gly Gln Arg Arg Ser Trp Leu Ile Ile Gln Arg Tyr Val Glu
        195                 200                 205

Gly Tyr Phe Leu His Pro Thr Gly Leu Glu Leu Leu Val Asp His Gly
    210                 215                 220

Ser Thr Asp Ala Gly His Trp Ala Val Glu Gln Val Trp Tyr Asn Gly
225                 230                 235                 240

Lys Phe Tyr Gly Ser Pro Glu Glu Leu Ala Arg Lys Tyr Ala Asp Gly
                245                 250                 255

Glu Val Asp Val Val Val Leu Glu Asp Pro Leu Pro Gly Gly Lys Gly
            260                 265                 270

His Asp Ser Thr Glu Glu Pro Pro Leu Phe Ser Ser His Lys Pro Arg
        275                 280                 285

Gly Asp Phe Pro Ser Pro Ile His Val Ser Gly Pro Arg Leu Val Gln
    290                 295                 300

Pro His Gly Pro Arg Phe Arg Leu Glu Gly Asn Ala Val Leu Tyr Gly
305                 310                 315                 320

Gly Trp Ser Phe Ala Phe Arg Leu Arg Ser Ser Ser Gly Leu Gln Val
                325                 330                 335

Leu Asn Val His Phe Gly Gly Glu Arg Ile Ala Tyr Glu Val Ser Val
            340                 345                 350

Gln Glu Ala Val Ala Leu Tyr Gly Gly His Thr Pro Ala Gly Met Gln
        355                 360                 365

Thr Lys Tyr Leu Asp Val Gly Trp Gly Leu Gly Ser Val Thr His Glu
    370                 375                 380

Leu Ala Pro Gly Ile Asp Cys Pro Glu Thr Ala Thr Phe Leu Asp Thr
385                 390                 395                 400

Phe His Tyr Tyr Asp Ala Asp Asp Pro Val His Tyr Pro Arg Ala Leu
                405                 410                 415

Cys Leu Phe Glu Met Pro Thr Gly Val Pro Leu Arg Arg His Phe Asn
            420                 425                 430

Ser Asn Phe Lys Gly Gly Phe Asn Phe Tyr Ala Gly Leu Lys Gly Gln
        435                 440                 445

Val Leu Val Leu Arg Thr Thr Ser Thr Val Tyr Asn Tyr Asp Tyr Ile
    450                 455                 460
```

Trp Asp Phe Ile Phe Tyr Pro Asn Gly Val Met Glu Ala Lys Met His
465 470 475 480

Ala Thr Gly Tyr Val His Ala Thr Phe Tyr Thr Pro Glu Gly Leu Arg
485 490 495

His Gly Thr Arg Leu His Thr His Leu Ile Gly Asn Ile His Thr His
500 505 510

Leu Val His Tyr Arg Val Asp Leu Asp Val Ala Gly Thr Lys Asn Ser
515 520 525

Phe Gln Thr Leu Gln Met Lys Leu Glu Asn Ile Thr Asn Pro Trp Ser
530 535 540

Pro Arg His Arg Val Val Gln Pro Thr Leu Glu Gln Thr Gln Tyr Ser
545 550 555 560

Trp Glu Arg Gln Ala Ala Phe Arg Phe Lys Thr Lys Leu Pro Thr Tyr
565 570 575

Leu Leu Phe Thr Ser Pro Gln Glu Asn Pro Trp Gly His Lys Arg Ser
580 585 590

Tyr Arg Leu Gln Ile His Ser Met Ala Asp Gln Val Leu Pro Pro Gly
595 600 605

Trp Gln Glu Glu Gln Ala Ile Thr Trp Ala Arg Tyr Pro Leu Ala Val
610 615 620

Thr Lys Tyr Arg Glu Ser Glu Leu Cys Ser Ser Ser Ile Tyr His Gln
625 630 635 640

Asn Asp Pro Trp His Pro Pro Val Val Phe Glu Gln Phe Leu His Asn
645 650 655

Asn Glu Asn Ile Glu Asn Glu Asp Leu Val Ala Trp Val Thr Val Gly
660 665 670

Phe Leu His Ile Pro His Ser Glu Asp Ile Pro Asn Thr Ala Thr Pro
675 680 685

Gly Asn Ser Val Gly Phe Leu Leu Arg Pro Phe Asn Phe Phe Pro Glu
690 695 700

Asp Pro Ser Leu Ala Ser Arg Asp Thr Val Ile Val Trp Pro Arg Asp
705 710 715 720

Asn Gly Pro Asn Tyr Val Gln Arg Trp Ile Pro Glu Asp Arg Asp Cys
725 730 735

Ser Met Pro Pro Pro Phe Ser Tyr Asn Gly Thr Tyr Arg Pro Val
740 745 750

<210> SEQ ID NO 7
<211> LENGTH: 751
<212> TYPE: PRT
<213> ORGANISM: Artificial Sequence
<220> FEATURE:
<223> OTHER INFORMATION: hDAO-Hepmut6

<400> SEQUENCE: 7

Met Pro Ala Leu Gly Trp Ala Val Ala Ala Ile Leu Met Leu Gln Thr
1 5 10 15

Ala Met Ala Glu Pro Ser Pro Gly Thr Leu Pro Arg Lys Ala Gly Val
20 25 30

Phe Ser Asp Leu Ser Asn Gln Glu Leu Lys Ala Val His Ser Phe Leu
35 40 45

Trp Ser Lys Lys Glu Leu Arg Leu Gln Pro Ser Ser Thr Thr Thr Met
50 55 60

Ala Lys Asn Thr Val Phe Leu Ile Glu Met Leu Leu Pro Lys Lys Tyr
65 70 75 80

-continued

```
His Val Leu Arg Phe Leu Asp Lys Gly Glu Arg His Pro Val Arg Glu
                85                  90                  95

Ala Arg Ala Val Ile Phe Phe Gly Asp Gln Glu His Pro Asn Val Thr
            100                 105                 110

Glu Phe Ala Val Gly Pro Leu Pro Gly Pro Cys Tyr Met Arg Ala Leu
        115                 120                 125

Ser Pro Arg Pro Gly Tyr Gln Ser Ser Trp Ala Ser Arg Pro Ile Ser
    130                 135                 140

Thr Ala Glu Tyr Ala Leu Leu Tyr His Thr Leu Gln Glu Ala Thr Lys
145                 150                 155                 160

Pro Leu His Gln Phe Phe Leu Asn Thr Thr Gly Phe Ser Phe Gln Asp
                165                 170                 175

Cys His Asp Arg Cys Leu Ala Phe Thr Asp Val Ala Pro Arg Gly Val
            180                 185                 190

Ala Ser Gly Gln Arg Arg Ser Trp Leu Ile Ile Gln Arg Tyr Val Glu
        195                 200                 205

Gly Tyr Phe Leu His Pro Thr Gly Leu Glu Leu Leu Val Asp His Gly
    210                 215                 220

Ser Thr Asp Ala Gly His Trp Ala Val Glu Gln Val Trp Tyr Asn Gly
225                 230                 235                 240

Lys Phe Tyr Gly Ser Pro Glu Glu Leu Ala Arg Lys Tyr Ala Asp Gly
                245                 250                 255

Glu Val Asp Val Val Val Leu Glu Asp Pro Leu Pro Gly Gly Lys Gly
            260                 265                 270

His Asp Ser Thr Glu Glu Pro Pro Leu Phe Ser Ser His Lys Pro Arg
        275                 280                 285

Gly Asp Phe Pro Ser Pro Ile His Val Ser Gly Pro Arg Leu Val Gln
    290                 295                 300

Pro His Gly Pro Arg Phe Arg Leu Glu Gly Asn Ala Val Leu Tyr Gly
305                 310                 315                 320

Gly Trp Ser Phe Ala Phe Arg Leu Arg Ser Ser Ser Gly Leu Gln Val
                325                 330                 335

Leu Asn Val His Phe Gly Gly Glu Arg Ile Ala Tyr Glu Val Ser Val
            340                 345                 350

Gln Glu Ala Val Ala Leu Tyr Gly Gly His Thr Pro Ala Gly Met Gln
        355                 360                 365

Thr Lys Tyr Leu Asp Val Gly Trp Gly Leu Gly Ser Val Thr His Glu
    370                 375                 380

Leu Ala Pro Gly Ile Asp Cys Pro Glu Thr Ala Thr Phe Leu Asp Thr
385                 390                 395                 400

Phe His Tyr Tyr Asp Ala Asp Asp Pro Val His Tyr Pro Arg Ala Leu
                405                 410                 415

Cys Leu Phe Glu Met Pro Thr Gly Val Pro Leu Arg Arg His Phe Asn
            420                 425                 430

Ser Asn Phe Lys Gly Gly Phe Asn Phe Tyr Ala Gly Leu Lys Gly Gln
        435                 440                 445

Val Leu Val Leu Arg Thr Thr Ser Thr Val Tyr Asn Tyr Asp Tyr Ile
    450                 455                 460

Trp Asp Phe Ile Phe Tyr Pro Asn Gly Val Met Glu Ala Lys Met His
465                 470                 475                 480

Ala Thr Gly Tyr Val His Ala Thr Phe Tyr Thr Pro Glu Gly Leu Arg
                485                 490                 495
```

His Gly Thr Arg Leu His Thr His Leu Ile Gly Asn Ile His Thr His
500 505 510

Leu Val His Tyr Arg Val Asp Leu Asp Val Ala Gly Thr Lys Asn Ser
515 520 525

Phe Gln Thr Leu Gln Met Lys Leu Glu Asn Ile Thr Asn Pro Trp Ser
530 535 540

Pro Arg His Arg Val Val Gln Pro Thr Leu Glu Gln Thr Gln Tyr Ser
545 550 555 560

Trp Glu Arg Gln Ala Ala Phe Arg Phe Gly Gln Thr Leu Pro Lys Tyr
565 570 575

Leu Leu Phe Thr Ser Pro Gln Glu Asn Pro Trp Gly His Lys Arg Ser
580 585 590

Tyr Arg Leu Gln Ile His Ser Met Ala Asp Gln Val Leu Pro Pro Gly
595 600 605

Trp Gln Glu Glu Gln Ala Ile Thr Trp Ala Arg Tyr Pro Leu Ala Val
610 615 620

Thr Lys Tyr Arg Glu Ser Glu Leu Cys Ser Ser Ser Ile Tyr His Gln
625 630 635 640

Asn Asp Pro Trp His Pro Pro Val Val Phe Glu Gln Phe Leu His Asn
645 650 655

Asn Glu Asn Ile Glu Asn Glu Asp Leu Val Ala Trp Val Thr Val Gly
660 665 670

Phe Leu His Ile Pro His Ser Glu Asp Ile Pro Asn Thr Ala Thr Pro
675 680 685

Gly Asn Ser Val Gly Phe Leu Leu Arg Pro Phe Asn Phe Phe Pro Glu
690 695 700

Asp Pro Ser Leu Ala Ser Arg Asp Thr Val Ile Val Trp Pro Arg Asp
705 710 715 720

Asn Gly Pro Asn Tyr Val Gln Arg Trp Ile Pro Glu Asp Arg Asp Cys
725 730 735

Ser Met Pro Pro Pro Phe Ser Tyr Asn Gly Thr Tyr Arg Pro Val
740 745 750

<210> SEQ ID NO 8
<211> LENGTH: 751
<212> TYPE: PRT
<213> ORGANISM: Artificial Sequence
<220> FEATURE:
<223> OTHER INFORMATION: hDAO-Hepmut7

<400> SEQUENCE: 8

Met Pro Ala Leu Gly Trp Ala Val Ala Ala Ile Leu Met Leu Gln Thr
1 5 10 15

Ala Met Ala Glu Pro Ser Pro Gly Thr Leu Pro Arg Lys Ala Gly Val
20 25 30

Phe Ser Asp Leu Ser Asn Gln Glu Leu Lys Ala Val His Ser Phe Leu
35 40 45

Trp Ser Lys Lys Glu Leu Arg Leu Gln Pro Ser Ser Thr Thr Thr Met
50 55 60

Ala Lys Asn Thr Val Phe Leu Ile Glu Met Leu Leu Pro Lys Lys Tyr
65 70 75 80

His Val Leu Arg Phe Leu Asp Lys Gly Glu Arg His Pro Val Arg Glu
85 90 95

Ala Arg Ala Val Ile Phe Phe Gly Asp Gln Glu His Pro Asn Val Thr
100 105 110

-continued

```
Glu Phe Ala Val Gly Pro Leu Pro Gly Pro Cys Tyr Met Arg Ala Leu
        115                 120                 125

Ser Pro Arg Pro Gly Tyr Gln Ser Ser Trp Ala Ser Arg Pro Ile Ser
    130                 135                 140

Thr Ala Glu Tyr Ala Leu Leu Tyr His Thr Leu Gln Glu Ala Thr Lys
145                 150                 155                 160

Pro Leu His Gln Phe Phe Leu Asn Thr Thr Gly Phe Ser Phe Gln Asp
                165                 170                 175

Cys His Asp Arg Cys Leu Ala Phe Thr Asp Val Ala Pro Arg Gly Val
            180                 185                 190

Ala Ser Gly Gln Arg Arg Ser Trp Leu Ile Ile Gln Arg Tyr Val Glu
        195                 200                 205

Gly Tyr Phe Leu His Pro Thr Gly Leu Glu Leu Leu Val Asp His Gly
    210                 215                 220

Ser Thr Asp Ala Gly His Trp Ala Val Glu Gln Val Trp Tyr Asn Gly
225                 230                 235                 240

Lys Phe Tyr Gly Ser Pro Glu Glu Leu Ala Arg Lys Tyr Ala Asp Gly
                245                 250                 255

Glu Val Asp Val Val Val Leu Glu Asp Pro Leu Pro Gly Gly Lys Gly
            260                 265                 270

His Asp Ser Thr Glu Glu Pro Pro Leu Phe Ser Ser His Lys Pro Arg
        275                 280                 285

Gly Asp Phe Pro Ser Pro Ile His Val Ser Gly Pro Arg Leu Val Gln
    290                 295                 300

Pro His Gly Pro Arg Phe Arg Leu Glu Gly Asn Ala Val Leu Tyr Gly
305                 310                 315                 320

Gly Trp Ser Phe Ala Phe Arg Leu Arg Ser Ser Ser Gly Leu Gln Val
                325                 330                 335

Leu Asn Val His Phe Gly Gly Glu Arg Ile Ala Tyr Glu Val Ser Val
            340                 345                 350

Gln Glu Ala Val Ala Leu Tyr Gly Gly His Thr Pro Ala Gly Met Gln
        355                 360                 365

Thr Lys Tyr Leu Asp Val Gly Trp Gly Leu Gly Ser Val Thr His Glu
    370                 375                 380

Leu Ala Pro Gly Ile Asp Cys Pro Glu Thr Ala Thr Phe Leu Asp Thr
385                 390                 395                 400

Phe His Tyr Tyr Asp Ala Asp Asp Pro Val His Tyr Pro Arg Ala Leu
                405                 410                 415

Cys Leu Phe Glu Met Pro Thr Gly Val Pro Leu Arg Arg His Phe Asn
            420                 425                 430

Ser Asn Phe Lys Gly Gly Phe Asn Phe Tyr Ala Gly Leu Lys Gly Gln
        435                 440                 445

Val Leu Val Leu Arg Thr Thr Ser Thr Val Tyr Asn Tyr Asp Tyr Ile
    450                 455                 460

Trp Asp Phe Ile Phe Tyr Pro Asn Gly Val Met Glu Ala Lys Met His
465                 470                 475                 480

Ala Thr Gly Tyr Val His Ala Thr Phe Tyr Thr Pro Glu Gly Leu Arg
                485                 490                 495

His Gly Thr Arg Leu His Thr His Leu Ile Gly Asn Ile His Thr His
            500                 505                 510

Leu Val His Tyr Arg Val Asp Leu Asp Val Ala Gly Thr Lys Asn Ser
        515                 520                 525

Phe Gln Thr Leu Gln Met Lys Leu Glu Asn Ile Thr Asn Pro Trp Ser
```

```
    530                 535                 540

Pro Arg His Arg Val Val Gln Pro Thr Leu Glu Gln Thr Gln Tyr Ser
545                 550                 555                 560

Trp Glu Arg Gln Ala Ala Phe Ser Phe Lys Arg Lys Leu Pro Thr Tyr
                565                 570                 575

Leu Leu Phe Thr Ser Pro Gln Glu Asn Pro Trp Gly His Lys Arg Ser
            580                 585                 590

Tyr Arg Leu Gln Ile His Ser Met Ala Asp Gln Val Leu Pro Pro Gly
        595                 600                 605

Trp Gln Glu Glu Gln Ala Ile Thr Trp Ala Arg Tyr Pro Leu Ala Val
    610                 615                 620

Thr Lys Tyr Arg Glu Ser Glu Leu Cys Ser Ser Ser Ile Tyr His Gln
625                 630                 635                 640

Asn Asp Pro Trp His Pro Pro Val Val Phe Glu Gln Phe Leu His Asn
                645                 650                 655

Asn Glu Asn Ile Glu Asn Glu Asp Leu Val Ala Trp Val Thr Val Gly
            660                 665                 670

Phe Leu His Ile Pro His Ser Glu Asp Ile Pro Asn Thr Ala Thr Pro
        675                 680                 685

Gly Asn Ser Val Gly Phe Leu Leu Arg Pro Phe Asn Phe Phe Pro Glu
    690                 695                 700

Asp Pro Ser Leu Ala Ser Arg Asp Thr Val Ile Val Trp Pro Arg Asp
705                 710                 715                 720

Asn Gly Pro Asn Tyr Val Gln Arg Trp Ile Pro Glu Asp Arg Asp Cys
                725                 730                 735

Ser Met Pro Pro Pro Phe Ser Tyr Asn Gly Thr Tyr Arg Pro Val
            740                 745                 750


<210> SEQ ID NO 9
<211> LENGTH: 751
<212> TYPE: PRT
<213> ORGANISM: Artificial Sequence
<220> FEATURE:
<223> OTHER INFORMATION: hDAO-Cysmut

<400> SEQUENCE: 9

Met Pro Ala Leu Gly Trp Ala Val Ala Ala Ile Leu Met Leu Gln Thr
1               5                   10                  15

Ala Met Ala Glu Pro Ser Pro Gly Thr Leu Pro Arg Lys Ala Gly Val
            20                  25                  30

Phe Ser Asp Leu Ser Asn Gln Glu Leu Lys Ala Val His Ser Phe Leu
        35                  40                  45

Trp Ser Lys Lys Glu Leu Arg Leu Gln Pro Ser Ser Thr Thr Thr Met
    50                  55                  60

Ala Lys Asn Thr Val Phe Leu Ile Glu Met Leu Leu Pro Lys Lys Tyr
65                  70                  75                  80

His Val Leu Arg Phe Leu Asp Lys Gly Glu Arg His Pro Val Arg Glu
                85                  90                  95

Ala Arg Ala Val Ile Phe Phe Gly Asp Gln Glu His Pro Asn Val Thr
            100                 105                 110

Glu Phe Ala Val Gly Pro Leu Pro Gly Pro Ala Tyr Met Arg Ala Leu
        115                 120                 125

Ser Pro Arg Pro Gly Tyr Gln Ser Ser Trp Ala Ser Arg Pro Ile Ser
    130                 135                 140

Thr Ala Glu Tyr Ala Leu Leu Tyr His Thr Leu Gln Glu Ala Thr Lys
```

-continued

```
145                 150                 155                 160

Pro Leu His Gln Phe Phe Leu Asn Thr Thr Gly Phe Ser Phe Gln Asp
                165                 170                 175

Cys His Asp Arg Cys Leu Ala Phe Thr Asp Val Ala Pro Arg Gly Val
            180                 185                 190

Ala Ser Gly Gln Arg Arg Ser Trp Leu Ile Ile Gln Arg Tyr Val Glu
        195                 200                 205

Gly Tyr Phe Leu His Pro Thr Gly Leu Glu Leu Leu Val Asp His Gly
    210                 215                 220

Ser Thr Asp Ala Gly His Trp Ala Val Glu Gln Val Trp Tyr Asn Gly
225                 230                 235                 240

Lys Phe Tyr Gly Ser Pro Glu Glu Leu Ala Arg Lys Tyr Ala Asp Gly
                245                 250                 255

Glu Val Asp Val Val Val Leu Glu Asp Pro Leu Pro Gly Gly Lys Gly
            260                 265                 270

His Asp Ser Thr Glu Glu Pro Pro Leu Phe Ser Ser His Lys Pro Arg
        275                 280                 285

Gly Asp Phe Pro Ser Pro Ile His Val Ser Gly Pro Arg Leu Val Gln
    290                 295                 300

Pro His Gly Pro Arg Phe Arg Leu Glu Gly Asn Ala Val Leu Tyr Gly
305                 310                 315                 320

Gly Trp Ser Phe Ala Phe Arg Leu Arg Ser Ser Ser Gly Leu Gln Val
                325                 330                 335

Leu Asn Val His Phe Gly Gly Glu Arg Ile Ala Tyr Glu Val Ser Val
            340                 345                 350

Gln Glu Ala Val Ala Leu Tyr Gly Gly His Thr Pro Ala Gly Met Gln
        355                 360                 365

Thr Lys Tyr Leu Asp Val Gly Trp Gly Leu Gly Ser Val Thr His Glu
    370                 375                 380

Leu Ala Pro Gly Ile Asp Cys Pro Glu Thr Ala Thr Phe Leu Asp Thr
385                 390                 395                 400

Phe His Tyr Tyr Asp Ala Asp Asp Pro Val His Tyr Pro Arg Ala Leu
                405                 410                 415

Cys Leu Phe Glu Met Pro Thr Gly Val Pro Leu Arg Arg His Phe Asn
            420                 425                 430

Ser Asn Phe Lys Gly Gly Phe Asn Phe Tyr Ala Gly Leu Lys Gly Gln
        435                 440                 445

Val Leu Val Leu Arg Thr Thr Ser Thr Val Tyr Asn Tyr Asp Tyr Ile
    450                 455                 460

Trp Asp Phe Ile Phe Tyr Pro Asn Gly Val Met Glu Ala Lys Met His
465                 470                 475                 480

Ala Thr Gly Tyr Val His Ala Thr Phe Tyr Thr Pro Glu Gly Leu Arg
                485                 490                 495

His Gly Thr Arg Leu His Thr His Leu Ile Gly Asn Ile His Thr His
            500                 505                 510

Leu Val His Tyr Arg Val Asp Leu Asp Val Ala Gly Thr Lys Asn Ser
        515                 520                 525

Phe Gln Thr Leu Gln Met Lys Leu Glu Asn Ile Thr Asn Pro Trp Ser
    530                 535                 540

Pro Arg His Arg Val Val Gln Pro Thr Leu Glu Gln Thr Gln Tyr Ser
545                 550                 555                 560

Trp Glu Arg Gln Ala Ala Phe Arg Phe Lys Arg Lys Leu Pro Lys Tyr
                565                 570                 575
```

```
Leu Leu Phe Thr Ser Pro Gln Glu Asn Pro Trp Gly His Lys Arg Ser
            580                 585                 590

Tyr Arg Leu Gln Ile His Ser Met Ala Asp Gln Val Leu Pro Pro Gly
        595                 600                 605

Trp Gln Glu Glu Gln Ala Ile Thr Trp Ala Arg Tyr Pro Leu Ala Val
    610                 615                 620

Thr Lys Tyr Arg Glu Ser Glu Leu Cys Ser Ser Ser Ile Tyr His Gln
625                 630                 635                 640

Asn Asp Pro Trp His Pro Pro Val Val Phe Glu Gln Phe Leu His Asn
                645                 650                 655

Asn Glu Asn Ile Glu Asn Glu Asp Leu Val Ala Trp Val Thr Val Gly
            660                 665                 670

Phe Leu His Ile Pro His Ser Glu Asp Ile Pro Asn Thr Ala Thr Pro
        675                 680                 685

Gly Asn Ser Val Gly Phe Leu Leu Arg Pro Phe Asn Phe Phe Pro Glu
    690                 695                 700

Asp Pro Ser Leu Ala Ser Arg Asp Thr Val Ile Val Trp Pro Arg Asp
705                 710                 715                 720

Asn Gly Pro Asn Tyr Val Gln Arg Trp Ile Pro Glu Asp Arg Asp Cys
                725                 730                 735

Ser Met Pro Pro Pro Phe Ser Tyr Asn Gly Thr Tyr Arg Pro Val
            740                 745                 750


<210> SEQ ID NO 10
<211> LENGTH: 751
<212> TYPE: PRT
<213> ORGANISM: Artificial Sequence
<220> FEATURE:
<223> OTHER INFORMATION: hDAO-Hepmut1-Cysmut

<400> SEQUENCE: 10

Met Pro Ala Leu Gly Trp Ala Val Ala Ala Ile Leu Met Leu Gln Thr
1               5                   10                  15

Ala Met Ala Glu Pro Ser Pro Gly Thr Leu Pro Arg Lys Ala Gly Val
            20                  25                  30

Phe Ser Asp Leu Ser Asn Gln Glu Leu Lys Ala Val His Ser Phe Leu
        35                  40                  45

Trp Ser Lys Lys Glu Leu Arg Leu Gln Pro Ser Ser Thr Thr Thr Met
    50                  55                  60

Ala Lys Asn Thr Val Phe Leu Ile Glu Met Leu Leu Pro Lys Lys Tyr
65                  70                  75                  80

His Val Leu Arg Phe Leu Asp Lys Gly Glu Arg His Pro Val Arg Glu
                85                  90                  95

Ala Arg Ala Val Ile Phe Phe Gly Asp Gln Glu His Pro Asn Val Thr
            100                 105                 110

Glu Phe Ala Val Gly Pro Leu Pro Gly Pro Ala Tyr Met Arg Ala Leu
        115                 120                 125

Ser Pro Arg Pro Gly Tyr Gln Ser Ser Trp Ala Ser Arg Pro Ile Ser
    130                 135                 140

Thr Ala Glu Tyr Ala Leu Leu Tyr His Thr Leu Gln Glu Ala Thr Lys
145                 150                 155                 160

Pro Leu His Gln Phe Phe Leu Asn Thr Thr Gly Phe Ser Phe Gln Asp
                165                 170                 175

Cys His Asp Arg Cys Leu Ala Phe Thr Asp Val Ala Pro Arg Gly Val
            180                 185                 190
```

```
Ala Ser Gly Gln Arg Arg Ser Trp Leu Ile Ile Gln Arg Tyr Val Glu
        195                 200                 205

Gly Tyr Phe Leu His Pro Thr Gly Leu Glu Leu Leu Val Asp His Gly
    210                 215                 220

Ser Thr Asp Ala Gly His Trp Ala Val Glu Gln Val Trp Tyr Asn Gly
225                 230                 235                 240

Lys Phe Tyr Gly Ser Pro Glu Glu Leu Ala Arg Lys Tyr Ala Asp Gly
                245                 250                 255

Glu Val Asp Val Val Val Leu Glu Asp Pro Leu Pro Gly Gly Lys Gly
            260                 265                 270

His Asp Ser Thr Glu Glu Pro Pro Leu Phe Ser Ser His Lys Pro Arg
        275                 280                 285

Gly Asp Phe Pro Ser Pro Ile His Val Ser Gly Pro Arg Leu Val Gln
    290                 295                 300

Pro His Gly Pro Arg Phe Arg Leu Glu Gly Asn Ala Val Leu Tyr Gly
305                 310                 315                 320

Gly Trp Ser Phe Ala Phe Arg Leu Arg Ser Ser Ser Gly Leu Gln Val
                325                 330                 335

Leu Asn Val His Phe Gly Gly Glu Arg Ile Ala Tyr Glu Val Ser Val
            340                 345                 350

Gln Glu Ala Val Ala Leu Tyr Gly Gly His Thr Pro Ala Gly Met Gln
        355                 360                 365

Thr Lys Tyr Leu Asp Val Gly Trp Gly Leu Gly Ser Val Thr His Glu
    370                 375                 380

Leu Ala Pro Gly Ile Asp Cys Pro Glu Thr Ala Thr Phe Leu Asp Thr
385                 390                 395                 400

Phe His Tyr Tyr Asp Ala Asp Asp Pro Val His Tyr Pro Arg Ala Leu
                405                 410                 415

Cys Leu Phe Glu Met Pro Thr Gly Val Pro Leu Arg Arg His Phe Asn
            420                 425                 430

Ser Asn Phe Lys Gly Gly Phe Asn Phe Tyr Ala Gly Leu Lys Gly Gln
        435                 440                 445

Val Leu Val Leu Arg Thr Thr Ser Thr Val Tyr Asn Tyr Asp Tyr Ile
    450                 455                 460

Trp Asp Phe Ile Phe Tyr Pro Asn Gly Val Met Glu Ala Lys Met His
465                 470                 475                 480

Ala Thr Gly Tyr Val His Ala Thr Phe Tyr Thr Pro Glu Gly Leu Arg
                485                 490                 495

His Gly Thr Arg Leu His Thr His Leu Ile Gly Asn Ile His Thr His
            500                 505                 510

Leu Val His Tyr Arg Val Asp Leu Asp Val Ala Gly Thr Lys Asn Ser
        515                 520                 525

Phe Gln Thr Leu Gln Met Lys Leu Glu Asn Ile Thr Asn Pro Trp Ser
    530                 535                 540

Pro Arg His Arg Val Val Gln Pro Thr Leu Glu Gln Thr Gln Tyr Ser
545                 550                 555                 560

Trp Glu Arg Gln Ala Ala Phe Ser Phe Lys Arg Lys Leu Pro Lys Tyr
                565                 570                 575

Leu Leu Phe Thr Ser Pro Gln Glu Asn Pro Trp Gly His Lys Arg Ser
            580                 585                 590

Tyr Arg Leu Gln Ile His Ser Met Ala Asp Gln Val Leu Pro Pro Gly
        595                 600                 605
```

```
Trp Gln Glu Glu Gln Ala Ile Thr Trp Ala Arg Tyr Pro Leu Ala Val
    610                 615                 620

Thr Lys Tyr Arg Glu Ser Glu Leu Cys Ser Ser Ser Ile Tyr His Gln
625                 630                 635                 640

Asn Asp Pro Trp His Pro Pro Val Val Phe Glu Gln Phe Leu His Asn
                645                 650                 655

Asn Glu Asn Ile Glu Asn Glu Asp Leu Val Ala Trp Val Thr Val Gly
            660                 665                 670

Phe Leu His Ile Pro His Ser Glu Asp Ile Pro Asn Thr Ala Thr Pro
        675                 680                 685

Gly Asn Ser Val Gly Phe Leu Leu Arg Pro Phe Asn Phe Phe Pro Glu
    690                 695                 700

Asp Pro Ser Leu Ala Ser Arg Asp Thr Val Ile Val Trp Pro Arg Asp
705                 710                 715                 720

Asn Gly Pro Asn Tyr Val Gln Arg Trp Ile Pro Glu Asp Arg Asp Cys
                725                 730                 735

Ser Met Pro Pro Pro Phe Ser Tyr Asn Gly Thr Tyr Arg Pro Val
            740                 745                 750


<210> SEQ ID NO 11
<211> LENGTH: 751
<212> TYPE: PRT
<213> ORGANISM: Artificial Sequence
<220> FEATURE:
<223> OTHER INFORMATION: hDAO-Hepmut2-Cysmut

<400> SEQUENCE: 11

Met Pro Ala Leu Gly Trp Ala Val Ala Ala Ile Leu Met Leu Gln Thr
1               5                   10                  15

Ala Met Ala Glu Pro Ser Pro Gly Thr Leu Pro Arg Lys Ala Gly Val
            20                  25                  30

Phe Ser Asp Leu Ser Asn Gln Glu Leu Lys Ala Val His Ser Phe Leu
        35                  40                  45

Trp Ser Lys Lys Glu Leu Arg Leu Gln Pro Ser Ser Thr Thr Thr Met
    50                  55                  60

Ala Lys Asn Thr Val Phe Leu Ile Glu Met Leu Leu Pro Lys Lys Tyr
65                  70                  75                  80

His Val Leu Arg Phe Leu Asp Lys Gly Glu Arg His Pro Val Arg Glu
                85                  90                  95

Ala Arg Ala Val Ile Phe Phe Gly Asp Gln Glu His Pro Asn Val Thr
            100                 105                 110

Glu Phe Ala Val Gly Pro Leu Pro Gly Pro Ala Tyr Met Arg Ala Leu
        115                 120                 125

Ser Pro Arg Pro Gly Tyr Gln Ser Ser Trp Ala Ser Arg Pro Ile Ser
    130                 135                 140

Thr Ala Glu Tyr Ala Leu Leu Tyr His Thr Leu Gln Glu Ala Thr Lys
145                 150                 155                 160

Pro Leu His Gln Phe Phe Leu Asn Thr Thr Gly Phe Ser Phe Gln Asp
                165                 170                 175

Cys His Asp Arg Cys Leu Ala Phe Thr Asp Val Ala Pro Arg Gly Val
            180                 185                 190

Ala Ser Gly Gln Arg Arg Ser Trp Leu Ile Ile Gln Arg Tyr Val Glu
        195                 200                 205

Gly Tyr Phe Leu His Pro Thr Gly Leu Glu Leu Leu Val Asp His Gly
    210                 215                 220
```

```
Ser Thr Asp Ala Gly His Trp Ala Val Glu Gln Val Trp Tyr Asn Gly
225                 230                 235                 240

Lys Phe Tyr Gly Ser Pro Glu Glu Leu Ala Arg Lys Tyr Ala Asp Gly
                245                 250                 255

Glu Val Asp Val Val Val Leu Glu Asp Pro Leu Pro Gly Gly Lys Gly
            260                 265                 270

His Asp Ser Thr Glu Glu Pro Pro Leu Phe Ser Ser His Lys Pro Arg
        275                 280                 285

Gly Asp Phe Pro Ser Pro Ile His Val Ser Gly Pro Arg Leu Val Gln
    290                 295                 300

Pro His Gly Pro Arg Phe Arg Leu Glu Gly Asn Ala Val Leu Tyr Gly
305                 310                 315                 320

Gly Trp Ser Phe Ala Phe Arg Leu Arg Ser Ser Ser Gly Leu Gln Val
                325                 330                 335

Leu Asn Val His Phe Gly Gly Glu Arg Ile Ala Tyr Glu Val Ser Val
            340                 345                 350

Gln Glu Ala Val Ala Leu Tyr Gly Gly His Thr Pro Ala Gly Met Gln
        355                 360                 365

Thr Lys Tyr Leu Asp Val Gly Trp Gly Leu Gly Ser Val Thr His Glu
    370                 375                 380

Leu Ala Pro Gly Ile Asp Cys Pro Glu Thr Ala Thr Phe Leu Asp Thr
385                 390                 395                 400

Phe His Tyr Tyr Asp Ala Asp Asp Pro Val His Tyr Pro Arg Ala Leu
                405                 410                 415

Cys Leu Phe Glu Met Pro Thr Gly Val Pro Leu Arg Arg His Phe Asn
            420                 425                 430

Ser Asn Phe Lys Gly Gly Phe Asn Phe Tyr Ala Gly Leu Lys Gly Gln
        435                 440                 445

Val Leu Val Leu Arg Thr Thr Ser Thr Val Tyr Asn Tyr Asp Tyr Ile
    450                 455                 460

Trp Asp Phe Ile Phe Tyr Pro Asn Gly Val Met Glu Ala Lys Met His
465                 470                 475                 480

Ala Thr Gly Tyr Val His Ala Thr Phe Tyr Thr Pro Glu Gly Leu Arg
                485                 490                 495

His Gly Thr Arg Leu His Thr His Leu Ile Gly Asn Ile His Thr His
            500                 505                 510

Leu Val His Tyr Arg Val Asp Leu Asp Val Ala Gly Thr Lys Asn Ser
        515                 520                 525

Phe Gln Thr Leu Gln Met Lys Leu Glu Asn Ile Thr Asn Pro Trp Ser
    530                 535                 540

Pro Arg His Arg Val Val Gln Pro Thr Leu Glu Gln Thr Gln Tyr Ser
545                 550                 555                 560

Trp Glu Arg Gln Ala Ala Phe Arg Phe Lys Arg Lys Leu Pro Thr Tyr
                565                 570                 575

Leu Leu Phe Thr Ser Pro Gln Glu Asn Pro Trp Gly His Lys Arg Ser
            580                 585                 590

Tyr Arg Leu Gln Ile His Ser Met Ala Asp Gln Val Leu Pro Pro Gly
        595                 600                 605

Trp Gln Glu Glu Gln Ala Ile Thr Trp Ala Arg Tyr Pro Leu Ala Val
    610                 615                 620

Thr Lys Tyr Arg Glu Ser Glu Leu Cys Ser Ser Ser Ile Tyr His Gln
625                 630                 635                 640

Asn Asp Pro Trp His Pro Pro Val Val Phe Glu Gln Phe Leu His Asn
```

645 650 655

Asn Glu Asn Ile Glu Asn Glu Asp Leu Val Ala Trp Val Thr Val Gly
660 665 670

Phe Leu His Ile Pro His Ser Glu Asp Ile Pro Asn Thr Ala Thr Pro
675 680 685

Gly Asn Ser Val Gly Phe Leu Leu Arg Pro Phe Asn Phe Phe Pro Glu
690 695 700

Asp Pro Ser Leu Ala Ser Arg Asp Thr Val Ile Val Trp Pro Arg Asp
705 710 715 720

Asn Gly Pro Asn Tyr Val Gln Arg Trp Ile Pro Glu Asp Arg Asp Cys
725 730 735

Ser Met Pro Pro Pro Phe Ser Tyr Asn Gly Thr Tyr Arg Pro Val
740 745 750

<210> SEQ ID NO 12
<211> LENGTH: 751
<212> TYPE: PRT
<213> ORGANISM: Artificial Sequence
<220> FEATURE:
<223> OTHER INFORMATION: hDAO-Hepmut3-Cysmut

<400> SEQUENCE: 12

Met Pro Ala Leu Gly Trp Ala Val Ala Ala Ile Leu Met Leu Gln Thr
1 5 10 15

Ala Met Ala Glu Pro Ser Pro Gly Thr Leu Pro Arg Lys Ala Gly Val
20 25 30

Phe Ser Asp Leu Ser Asn Gln Glu Leu Lys Ala Val His Ser Phe Leu
35 40 45

Trp Ser Lys Lys Glu Leu Arg Leu Gln Pro Ser Ser Thr Thr Thr Met
50 55 60

Ala Lys Asn Thr Val Phe Leu Ile Glu Met Leu Leu Pro Lys Lys Tyr
65 70 75 80

His Val Leu Arg Phe Leu Asp Lys Gly Glu Arg His Pro Val Arg Glu
85 90 95

Ala Arg Ala Val Ile Phe Phe Gly Asp Gln Glu His Pro Asn Val Thr
100 105 110

Glu Phe Ala Val Gly Pro Leu Pro Gly Pro Ala Tyr Met Arg Ala Leu
115 120 125

Ser Pro Arg Pro Gly Tyr Gln Ser Ser Trp Ala Ser Arg Pro Ile Ser
130 135 140

Thr Ala Glu Tyr Ala Leu Leu Tyr His Thr Leu Gln Glu Ala Thr Lys
145 150 155 160

Pro Leu His Gln Phe Phe Leu Asn Thr Thr Gly Phe Ser Phe Gln Asp
165 170 175

Cys His Asp Arg Cys Leu Ala Phe Thr Asp Val Ala Pro Arg Gly Val
180 185 190

Ala Ser Gly Gln Arg Arg Ser Trp Leu Ile Ile Gln Arg Tyr Val Glu
195 200 205

Gly Tyr Phe Leu His Pro Thr Gly Leu Glu Leu Leu Val Asp His Gly
210 215 220

Ser Thr Asp Ala Gly His Trp Ala Val Glu Gln Val Trp Tyr Asn Gly
225 230 235 240

Lys Phe Tyr Gly Ser Pro Glu Glu Leu Ala Arg Lys Tyr Ala Asp Gly
245 250 255

Glu Val Asp Val Val Val Leu Glu Asp Pro Leu Pro Gly Gly Lys Gly

```
            260                 265                 270

His Asp Ser Thr Glu Glu Pro Pro Leu Phe Ser Ser His Lys Pro Arg
        275                 280                 285

Gly Asp Phe Pro Ser Pro Ile His Val Ser Gly Pro Arg Leu Val Gln
    290                 295                 300

Pro His Gly Pro Arg Phe Arg Leu Glu Gly Asn Ala Val Leu Tyr Gly
305                 310                 315                 320

Gly Trp Ser Phe Ala Phe Arg Leu Arg Ser Ser Ser Gly Leu Gln Val
                325                 330                 335

Leu Asn Val His Phe Gly Gly Glu Arg Ile Ala Tyr Glu Val Ser Val
            340                 345                 350

Gln Glu Ala Val Ala Leu Tyr Gly Gly His Thr Pro Ala Gly Met Gln
        355                 360                 365

Thr Lys Tyr Leu Asp Val Gly Trp Gly Leu Gly Ser Val Thr His Glu
    370                 375                 380

Leu Ala Pro Gly Ile Asp Cys Pro Glu Thr Ala Thr Phe Leu Asp Thr
385                 390                 395                 400

Phe His Tyr Tyr Asp Ala Asp Asp Pro Val His Tyr Pro Arg Ala Leu
                405                 410                 415

Cys Leu Phe Glu Met Pro Thr Gly Val Pro Leu Arg Arg His Phe Asn
            420                 425                 430

Ser Asn Phe Lys Gly Gly Phe Asn Phe Tyr Ala Gly Leu Lys Gly Gln
        435                 440                 445

Val Leu Val Leu Arg Thr Thr Ser Thr Val Tyr Asn Tyr Asp Tyr Ile
    450                 455                 460

Trp Asp Phe Ile Phe Tyr Pro Asn Gly Val Met Glu Ala Lys Met His
465                 470                 475                 480

Ala Thr Gly Tyr Val His Ala Thr Phe Tyr Thr Pro Glu Gly Leu Arg
                485                 490                 495

His Gly Thr Arg Leu His Thr His Leu Ile Gly Asn Ile His Thr His
            500                 505                 510

Leu Val His Tyr Arg Val Asp Leu Asp Val Ala Gly Thr Lys Asn Ser
        515                 520                 525

Phe Gln Thr Leu Gln Met Lys Leu Glu Asn Ile Thr Asn Pro Trp Ser
    530                 535                 540

Pro Arg His Arg Val Val Gln Pro Thr Leu Glu Gln Thr Gln Tyr Ser
545                 550                 555                 560

Trp Glu Arg Gln Ala Ala Phe Arg Phe Lys Thr Lys Leu Pro Lys Tyr
                565                 570                 575

Leu Leu Phe Thr Ser Pro Gln Glu Asn Pro Trp Gly His Lys Arg Ser
            580                 585                 590

Tyr Arg Leu Gln Ile His Ser Met Ala Asp Gln Val Leu Pro Pro Gly
        595                 600                 605

Trp Gln Glu Glu Gln Ala Ile Thr Trp Ala Arg Tyr Pro Leu Ala Val
    610                 615                 620

Thr Lys Tyr Arg Glu Ser Glu Leu Cys Ser Ser Ser Ile Tyr His Gln
625                 630                 635                 640

Asn Asp Pro Trp His Pro Pro Val Val Phe Glu Gln Phe Leu His Asn
                645                 650                 655

Asn Glu Asn Ile Glu Asn Glu Asp Leu Val Ala Trp Val Thr Val Gly
            660                 665                 670

Phe Leu His Ile Pro His Ser Glu Asp Ile Pro Asn Thr Ala Thr Pro
        675                 680                 685
```

```
Gly Asn Ser Val Gly Phe Leu Leu Arg Pro Phe Asn Phe Phe Pro Glu
    690                 695                 700

Asp Pro Ser Leu Ala Ser Arg Asp Thr Val Ile Val Trp Pro Arg Asp
705                 710                 715                 720

Asn Gly Pro Asn Tyr Val Gln Arg Trp Ile Pro Glu Asp Arg Asp Cys
                725                 730                 735

Ser Met Pro Pro Pro Phe Ser Tyr Asn Gly Thr Tyr Arg Pro Val
            740                 745                 750


<210> SEQ ID NO 13
<211> LENGTH: 751
<212> TYPE: PRT
<213> ORGANISM: Artificial Sequence
<220> FEATURE:
<223> OTHER INFORMATION: hDAO-Hepmut4-Cysmut

<400> SEQUENCE: 13

Met Pro Ala Leu Gly Trp Ala Val Ala Ala Ile Leu Met Leu Gln Thr
1               5                   10                  15

Ala Met Ala Glu Pro Ser Pro Gly Thr Leu Pro Arg Lys Ala Gly Val
            20                  25                  30

Phe Ser Asp Leu Ser Asn Gln Glu Leu Lys Ala Val His Ser Phe Leu
        35                  40                  45

Trp Ser Lys Lys Glu Leu Arg Leu Gln Pro Ser Ser Thr Thr Thr Met
    50                  55                  60

Ala Lys Asn Thr Val Phe Leu Ile Glu Met Leu Leu Pro Lys Lys Tyr
65                  70                  75                  80

His Val Leu Arg Phe Leu Asp Lys Gly Glu Arg His Pro Val Arg Glu
                85                  90                  95

Ala Arg Ala Val Ile Phe Phe Gly Asp Gln Glu His Pro Asn Val Thr
            100                 105                 110

Glu Phe Ala Val Gly Pro Leu Pro Gly Pro Ala Tyr Met Arg Ala Leu
        115                 120                 125

Ser Pro Arg Pro Gly Tyr Gln Ser Ser Trp Ala Ser Arg Pro Ile Ser
    130                 135                 140

Thr Ala Glu Tyr Ala Leu Leu Tyr His Thr Leu Gln Glu Ala Thr Lys
145                 150                 155                 160

Pro Leu His Gln Phe Phe Leu Asn Thr Thr Gly Phe Ser Phe Gln Asp
                165                 170                 175

Cys His Asp Arg Cys Leu Ala Phe Thr Asp Val Ala Pro Arg Gly Val
            180                 185                 190

Ala Ser Gly Gln Arg Arg Ser Trp Leu Ile Ile Gln Arg Tyr Val Glu
        195                 200                 205

Gly Tyr Phe Leu His Pro Thr Gly Leu Glu Leu Leu Val Asp His Gly
    210                 215                 220

Ser Thr Asp Ala Gly His Trp Ala Val Glu Gln Val Trp Tyr Asn Gly
225                 230                 235                 240

Lys Phe Tyr Gly Ser Pro Glu Glu Leu Ala Arg Lys Tyr Ala Asp Gly
                245                 250                 255

Glu Val Asp Val Val Val Leu Glu Asp Pro Leu Pro Gly Gly Lys Gly
            260                 265                 270

His Asp Ser Thr Glu Glu Pro Pro Leu Phe Ser Ser His Lys Pro Arg
        275                 280                 285

Gly Asp Phe Pro Ser Pro Ile His Val Ser Gly Pro Arg Leu Val Gln
    290                 295                 300
```

```
Pro His Gly Pro Arg Phe Arg Leu Glu Gly Asn Ala Val Leu Tyr Gly
305                 310                 315                 320

Gly Trp Ser Phe Ala Phe Arg Leu Arg Ser Ser Ser Gly Leu Gln Val
                325                 330                 335

Leu Asn Val His Phe Gly Gly Glu Arg Ile Ala Tyr Glu Val Ser Val
            340                 345                 350

Gln Glu Ala Val Ala Leu Tyr Gly Gly His Thr Pro Ala Gly Met Gln
        355                 360                 365

Thr Lys Tyr Leu Asp Val Gly Trp Gly Leu Gly Ser Val Thr His Glu
    370                 375                 380

Leu Ala Pro Gly Ile Asp Cys Pro Glu Thr Ala Thr Phe Leu Asp Thr
385                 390                 395                 400

Phe His Tyr Tyr Asp Ala Asp Asp Pro Val His Tyr Pro Arg Ala Leu
                405                 410                 415

Cys Leu Phe Glu Met Pro Thr Gly Val Pro Leu Arg Arg His Phe Asn
            420                 425                 430

Ser Asn Phe Lys Gly Gly Phe Asn Phe Tyr Ala Gly Leu Lys Gly Gln
        435                 440                 445

Val Leu Val Leu Arg Thr Thr Ser Thr Val Tyr Asn Tyr Asp Tyr Ile
    450                 455                 460

Trp Asp Phe Ile Phe Tyr Pro Asn Gly Val Met Glu Ala Lys Met His
465                 470                 475                 480

Ala Thr Gly Tyr Val His Ala Thr Phe Tyr Thr Pro Glu Gly Leu Arg
                485                 490                 495

His Gly Thr Arg Leu His Thr His Leu Ile Gly Asn Ile His Thr His
            500                 505                 510

Leu Val His Tyr Arg Val Asp Leu Asp Val Ala Gly Thr Lys Asn Ser
        515                 520                 525

Phe Gln Thr Leu Gln Met Lys Leu Glu Asn Ile Thr Asn Pro Trp Ser
    530                 535                 540

Pro Arg His Arg Val Val Gln Pro Thr Leu Glu Gln Thr Gln Tyr Ser
545                 550                 555                 560

Trp Glu Arg Gln Ala Ala Phe Ser Phe Lys Thr Lys Leu Pro Lys Tyr
                565                 570                 575

Leu Leu Phe Thr Ser Pro Gln Glu Asn Pro Trp Gly His Lys Arg Ser
            580                 585                 590

Tyr Arg Leu Gln Ile His Ser Met Ala Asp Gln Val Leu Pro Pro Gly
        595                 600                 605

Trp Gln Glu Glu Gln Ala Ile Thr Trp Ala Arg Tyr Pro Leu Ala Val
    610                 615                 620

Thr Lys Tyr Arg Glu Ser Glu Leu Cys Ser Ser Ser Ile Tyr His Gln
625                 630                 635                 640

Asn Asp Pro Trp His Pro Pro Val Val Phe Glu Gln Phe Leu His Asn
                645                 650                 655

Asn Glu Asn Ile Glu Asn Glu Asp Leu Val Ala Trp Val Thr Val Gly
            660                 665                 670

Phe Leu His Ile Pro His Ser Glu Asp Ile Pro Asn Thr Ala Thr Pro
        675                 680                 685

Gly Asn Ser Val Gly Phe Leu Leu Arg Pro Phe Asn Phe Phe Pro Glu
    690                 695                 700

Asp Pro Ser Leu Ala Ser Arg Asp Thr Val Ile Val Trp Pro Arg Asp
705                 710                 715                 720
```

Asn Gly Pro Asn Tyr Val Gln Arg Trp Ile Pro Glu Asp Arg Asp Cys
725 730 735

Ser Met Pro Pro Pro Phe Ser Tyr Asn Gly Thr Tyr Arg Pro Val
740 745 750

<210> SEQ ID NO 14
<211> LENGTH: 751
<212> TYPE: PRT
<213> ORGANISM: Artificial Sequence
<220> FEATURE:
<223> OTHER INFORMATION: hDAO-Hepmut5-Cysmut

<400> SEQUENCE: 14

Met Pro Ala Leu Gly Trp Ala Val Ala Ala Ile Leu Met Leu Gln Thr
1 5 10 15

Ala Met Ala Glu Pro Ser Pro Gly Thr Leu Pro Arg Lys Ala Gly Val
20 25 30

Phe Ser Asp Leu Ser Asn Gln Glu Leu Lys Ala Val His Ser Phe Leu
35 40 45

Trp Ser Lys Lys Glu Leu Arg Leu Gln Pro Ser Ser Thr Thr Thr Met
50 55 60

Ala Lys Asn Thr Val Phe Leu Ile Glu Met Leu Leu Pro Lys Lys Tyr
65 70 75 80

His Val Leu Arg Phe Leu Asp Lys Gly Glu Arg His Pro Val Arg Glu
85 90 95

Ala Arg Ala Val Ile Phe Phe Gly Asp Gln Glu His Pro Asn Val Thr
100 105 110

Glu Phe Ala Val Gly Pro Leu Pro Gly Pro Ala Tyr Met Arg Ala Leu
115 120 125

Ser Pro Arg Pro Gly Tyr Gln Ser Ser Trp Ala Ser Arg Pro Ile Ser
130 135 140

Thr Ala Glu Tyr Ala Leu Leu Tyr His Thr Leu Gln Glu Ala Thr Lys
145 150 155 160

Pro Leu His Gln Phe Phe Leu Asn Thr Thr Gly Phe Ser Phe Gln Asp
165 170 175

Cys His Asp Arg Cys Leu Ala Phe Thr Asp Val Ala Pro Arg Gly Val
180 185 190

Ala Ser Gly Gln Arg Arg Ser Trp Leu Ile Ile Gln Arg Tyr Val Glu
195 200 205

Gly Tyr Phe Leu His Pro Thr Gly Leu Glu Leu Leu Val Asp His Gly
210 215 220

Ser Thr Asp Ala Gly His Trp Ala Val Glu Gln Val Trp Tyr Asn Gly
225 230 235 240

Lys Phe Tyr Gly Ser Pro Glu Glu Leu Ala Arg Lys Tyr Ala Asp Gly
245 250 255

Glu Val Asp Val Val Val Leu Glu Asp Pro Leu Pro Gly Gly Lys Gly
260 265 270

His Asp Ser Thr Glu Glu Pro Pro Leu Phe Ser Ser His Lys Pro Arg
275 280 285

Gly Asp Phe Pro Ser Pro Ile His Val Ser Gly Pro Arg Leu Val Gln
290 295 300

Pro His Gly Pro Arg Phe Arg Leu Glu Gly Asn Ala Val Leu Tyr Gly
305 310 315 320

Gly Trp Ser Phe Ala Phe Arg Leu Arg Ser Ser Ser Gly Leu Gln Val
325 330 335

```
Leu Asn Val His Phe Gly Gly Glu Arg Ile Ala Tyr Glu Val Ser Val
            340                 345                 350

Gln Glu Ala Val Ala Leu Tyr Gly Gly His Thr Pro Ala Gly Met Gln
        355                 360                 365

Thr Lys Tyr Leu Asp Val Gly Trp Gly Leu Gly Ser Val Thr His Glu
    370                 375                 380

Leu Ala Pro Gly Ile Asp Cys Pro Glu Thr Ala Thr Phe Leu Asp Thr
385                 390                 395                 400

Phe His Tyr Tyr Asp Ala Asp Asp Pro Val His Tyr Pro Arg Ala Leu
                405                 410                 415

Cys Leu Phe Glu Met Pro Thr Gly Val Pro Leu Arg Arg His Phe Asn
            420                 425                 430

Ser Asn Phe Lys Gly Gly Phe Asn Phe Tyr Ala Gly Leu Lys Gly Gln
        435                 440                 445

Val Leu Val Leu Arg Thr Thr Ser Thr Val Tyr Asn Tyr Asp Tyr Ile
    450                 455                 460

Trp Asp Phe Ile Phe Tyr Pro Asn Gly Val Met Glu Ala Lys Met His
465                 470                 475                 480

Ala Thr Gly Tyr Val His Ala Thr Phe Tyr Thr Pro Glu Gly Leu Arg
                485                 490                 495

His Gly Thr Arg Leu His Thr His Leu Ile Gly Asn Ile His Thr His
            500                 505                 510

Leu Val His Tyr Arg Val Asp Leu Asp Val Ala Gly Thr Lys Asn Ser
        515                 520                 525

Phe Gln Thr Leu Gln Met Lys Leu Glu Asn Ile Thr Asn Pro Trp Ser
    530                 535                 540

Pro Arg His Arg Val Val Gln Pro Thr Leu Glu Gln Thr Gln Tyr Ser
545                 550                 555                 560

Trp Glu Arg Gln Ala Ala Phe Arg Phe Lys Thr Lys Leu Pro Thr Tyr
                565                 570                 575

Leu Leu Phe Thr Ser Pro Gln Glu Asn Pro Trp Gly His Lys Arg Ser
            580                 585                 590

Tyr Arg Leu Gln Ile His Ser Met Ala Asp Gln Val Leu Pro Pro Gly
        595                 600                 605

Trp Gln Glu Glu Gln Ala Ile Thr Trp Ala Arg Tyr Pro Leu Ala Val
    610                 615                 620

Thr Lys Tyr Arg Glu Ser Glu Leu Cys Ser Ser Ser Ile Tyr His Gln
625                 630                 635                 640

Asn Asp Pro Trp His Pro Pro Val Val Phe Glu Gln Phe Leu His Asn
                645                 650                 655

Asn Glu Asn Ile Glu Asn Glu Asp Leu Val Ala Trp Val Thr Val Gly
            660                 665                 670

Phe Leu His Ile Pro His Ser Glu Asp Ile Pro Asn Thr Ala Thr Pro
        675                 680                 685

Gly Asn Ser Val Gly Phe Leu Leu Arg Pro Phe Asn Phe Phe Pro Glu
    690                 695                 700

Asp Pro Ser Leu Ala Ser Arg Asp Thr Val Ile Val Trp Pro Arg Asp
705                 710                 715                 720

Asn Gly Pro Asn Tyr Val Gln Arg Trp Ile Pro Glu Asp Arg Asp Cys
                725                 730                 735

Ser Met Pro Pro Pro Phe Ser Tyr Asn Gly Thr Tyr Arg Pro Val
            740                 745                 750
```

<210> SEQ ID NO 15
<211> LENGTH: 751
<212> TYPE: PRT
<213> ORGANISM: Artificial Sequence
<220> FEATURE:
<223> OTHER INFORMATION: hDAO-Hepmut6-Cysmut

<400> SEQUENCE: 15

```
Met Pro Ala Leu Gly Trp Ala Val Ala Ala Ile Leu Met Leu Gln Thr
1               5                   10                  15

Ala Met Ala Glu Pro Ser Pro Gly Thr Leu Pro Arg Lys Ala Gly Val
            20                  25                  30

Phe Ser Asp Leu Ser Asn Gln Glu Leu Lys Ala Val His Ser Phe Leu
        35                  40                  45

Trp Ser Lys Lys Glu Leu Arg Leu Gln Pro Ser Ser Thr Thr Thr Met
    50                  55                  60

Ala Lys Asn Thr Val Phe Leu Ile Glu Met Leu Leu Pro Lys Lys Tyr
65                  70                  75                  80

His Val Leu Arg Phe Leu Asp Lys Gly Glu Arg His Pro Val Arg Glu
                85                  90                  95

Ala Arg Ala Val Ile Phe Phe Gly Asp Gln Glu His Pro Asn Val Thr
            100                 105                 110

Glu Phe Ala Val Gly Pro Leu Pro Gly Pro Ala Tyr Met Arg Ala Leu
        115                 120                 125

Ser Pro Arg Pro Gly Tyr Gln Ser Ser Trp Ala Ser Arg Pro Ile Ser
    130                 135                 140

Thr Ala Glu Tyr Ala Leu Leu Tyr His Thr Leu Gln Glu Ala Thr Lys
145                 150                 155                 160

Pro Leu His Gln Phe Phe Leu Asn Thr Thr Gly Phe Ser Phe Gln Asp
                165                 170                 175

Cys His Asp Arg Cys Leu Ala Phe Thr Asp Val Ala Pro Arg Gly Val
            180                 185                 190

Ala Ser Gly Gln Arg Arg Ser Trp Leu Ile Ile Gln Arg Tyr Val Glu
        195                 200                 205

Gly Tyr Phe Leu His Pro Thr Gly Leu Glu Leu Leu Val Asp His Gly
    210                 215                 220

Ser Thr Asp Ala Gly His Trp Ala Val Glu Gln Val Trp Tyr Asn Gly
225                 230                 235                 240

Lys Phe Tyr Gly Ser Pro Glu Glu Leu Ala Arg Lys Tyr Ala Asp Gly
                245                 250                 255

Glu Val Asp Val Val Val Leu Glu Asp Pro Leu Pro Gly Gly Lys Gly
            260                 265                 270

His Asp Ser Thr Glu Glu Pro Pro Leu Phe Ser Ser His Lys Pro Arg
        275                 280                 285

Gly Asp Phe Pro Ser Pro Ile His Val Ser Gly Pro Arg Leu Val Gln
    290                 295                 300

Pro His Gly Pro Arg Phe Arg Leu Glu Gly Asn Ala Val Leu Tyr Gly
305                 310                 315                 320

Gly Trp Ser Phe Ala Phe Arg Leu Arg Ser Ser Ser Gly Leu Gln Val
                325                 330                 335

Leu Asn Val His Phe Gly Gly Glu Arg Ile Ala Tyr Glu Val Ser Val
            340                 345                 350

Gln Glu Ala Val Ala Leu Tyr Gly Gly His Thr Pro Ala Gly Met Gln
        355                 360                 365

Thr Lys Tyr Leu Asp Val Gly Trp Gly Leu Gly Ser Val Thr His Glu
```

```
    370                 375                 380

Leu Ala Pro Gly Ile Asp Cys Pro Glu Thr Ala Thr Phe Leu Asp Thr
385                 390                 395                 400

Phe His Tyr Tyr Asp Ala Asp Asp Pro Val His Tyr Pro Arg Ala Leu
                405                 410                 415

Cys Leu Phe Glu Met Pro Thr Gly Val Pro Leu Arg Arg His Phe Asn
            420                 425                 430

Ser Asn Phe Lys Gly Gly Phe Asn Phe Tyr Ala Gly Leu Lys Gly Gln
        435                 440                 445

Val Leu Val Leu Arg Thr Thr Ser Thr Val Tyr Asn Tyr Asp Tyr Ile
    450                 455                 460

Trp Asp Phe Ile Phe Tyr Pro Asn Gly Val Met Glu Ala Lys Met His
465                 470                 475                 480

Ala Thr Gly Tyr Val His Ala Thr Phe Tyr Thr Pro Glu Gly Leu Arg
                485                 490                 495

His Gly Thr Arg Leu His Thr His Leu Ile Gly Asn Ile His Thr His
            500                 505                 510

Leu Val His Tyr Arg Val Asp Leu Asp Val Ala Gly Thr Lys Asn Ser
        515                 520                 525

Phe Gln Thr Leu Gln Met Lys Leu Glu Asn Ile Thr Asn Pro Trp Ser
    530                 535                 540

Pro Arg His Arg Val Val Gln Pro Thr Leu Glu Gln Thr Gln Tyr Ser
545                 550                 555                 560

Trp Glu Arg Gln Ala Ala Phe Arg Phe Gly Gln Thr Leu Pro Lys Tyr
                565                 570                 575

Leu Leu Phe Thr Ser Pro Gln Glu Asn Pro Trp Gly His Lys Arg Ser
            580                 585                 590

Tyr Arg Leu Gln Ile His Ser Met Ala Asp Gln Val Leu Pro Pro Gly
        595                 600                 605

Trp Gln Glu Glu Gln Ala Ile Thr Trp Ala Arg Tyr Pro Leu Ala Val
    610                 615                 620

Thr Lys Tyr Arg Glu Ser Glu Leu Cys Ser Ser Ser Ile Tyr His Gln
625                 630                 635                 640

Asn Asp Pro Trp His Pro Pro Val Val Phe Glu Gln Phe Leu His Asn
                645                 650                 655

Asn Glu Asn Ile Glu Asn Glu Asp Leu Val Ala Trp Val Thr Val Gly
            660                 665                 670

Phe Leu His Ile Pro His Ser Glu Asp Ile Pro Asn Thr Ala Thr Pro
        675                 680                 685

Gly Asn Ser Val Gly Phe Leu Leu Arg Pro Phe Asn Phe Phe Pro Glu
    690                 695                 700

Asp Pro Ser Leu Ala Ser Arg Asp Thr Val Ile Val Trp Pro Arg Asp
705                 710                 715                 720

Asn Gly Pro Asn Tyr Val Gln Arg Trp Ile Pro Glu Asp Arg Asp Cys
                725                 730                 735

Ser Met Pro Pro Pro Phe Ser Tyr Asn Gly Thr Tyr Arg Pro Val
            740                 745                 750
```

<210> SEQ ID NO 16
<211> LENGTH: 751
<212> TYPE: PRT
<213> ORGANISM: Artificial Sequence
<220> FEATURE:
<223> OTHER INFORMATION: hDAO-Hepmut7-Cysmut

<400> SEQUENCE: 16

```
Met Pro Ala Leu Gly Trp Ala Val Ala Ala Ile Leu Met Leu Gln Thr
1               5                   10                  15

Ala Met Ala Glu Pro Ser Pro Gly Thr Leu Pro Arg Lys Ala Gly Val
            20                  25                  30

Phe Ser Asp Leu Ser Asn Gln Glu Leu Lys Ala Val His Ser Phe Leu
        35                  40                  45

Trp Ser Lys Lys Glu Leu Arg Leu Gln Pro Ser Ser Thr Thr Thr Met
    50                  55                  60

Ala Lys Asn Thr Val Phe Leu Ile Glu Met Leu Leu Pro Lys Lys Tyr
65                  70                  75                  80

His Val Leu Arg Phe Leu Asp Lys Gly Glu Arg His Pro Val Arg Glu
                85                  90                  95

Ala Arg Ala Val Ile Phe Phe Gly Asp Gln Glu His Pro Asn Val Thr
            100                 105                 110

Glu Phe Ala Val Gly Pro Leu Pro Gly Pro Ala Tyr Met Arg Ala Leu
        115                 120                 125

Ser Pro Arg Pro Gly Tyr Gln Ser Ser Trp Ala Ser Arg Pro Ile Ser
    130                 135                 140

Thr Ala Glu Tyr Ala Leu Leu Tyr His Thr Leu Gln Glu Ala Thr Lys
145                 150                 155                 160

Pro Leu His Gln Phe Phe Leu Asn Thr Thr Gly Phe Ser Phe Gln Asp
                165                 170                 175

Cys His Asp Arg Cys Leu Ala Phe Thr Asp Val Ala Pro Arg Gly Val
            180                 185                 190

Ala Ser Gly Gln Arg Arg Ser Trp Leu Ile Ile Gln Arg Tyr Val Glu
        195                 200                 205

Gly Tyr Phe Leu His Pro Thr Gly Leu Glu Leu Leu Val Asp His Gly
    210                 215                 220

Ser Thr Asp Ala Gly His Trp Ala Val Glu Gln Val Trp Tyr Asn Gly
225                 230                 235                 240

Lys Phe Tyr Gly Ser Pro Glu Glu Leu Ala Arg Lys Tyr Ala Asp Gly
                245                 250                 255

Glu Val Asp Val Val Val Leu Glu Asp Pro Leu Pro Gly Gly Lys Gly
            260                 265                 270

His Asp Ser Thr Glu Glu Pro Pro Leu Phe Ser Ser His Lys Pro Arg
        275                 280                 285

Gly Asp Phe Pro Ser Pro Ile His Val Ser Gly Pro Arg Leu Val Gln
    290                 295                 300

Pro His Gly Pro Arg Phe Arg Leu Glu Gly Asn Ala Val Leu Tyr Gly
305                 310                 315                 320

Gly Trp Ser Phe Ala Phe Arg Leu Arg Ser Ser Ser Gly Leu Gln Val
                325                 330                 335

Leu Asn Val His Phe Gly Gly Glu Arg Ile Ala Tyr Glu Val Ser Val
            340                 345                 350

Gln Glu Ala Val Ala Leu Tyr Gly Gly His Thr Pro Ala Gly Met Gln
        355                 360                 365

Thr Lys Tyr Leu Asp Val Gly Trp Gly Leu Gly Ser Val Thr His Glu
    370                 375                 380

Leu Ala Pro Gly Ile Asp Cys Pro Glu Thr Ala Thr Phe Leu Asp Thr
385                 390                 395                 400

Phe His Tyr Tyr Asp Ala Asp Asp Pro Val His Tyr Pro Arg Ala Leu
                405                 410                 415
```

-continued

```
Cys Leu Phe Glu Met Pro Thr Gly Val Pro Leu Arg Arg His Phe Asn
            420                 425                 430

Ser Asn Phe Lys Gly Gly Phe Asn Phe Tyr Ala Gly Leu Lys Gly Gln
        435                 440                 445

Val Leu Val Leu Arg Thr Thr Ser Thr Val Tyr Asn Tyr Asp Tyr Ile
    450                 455                 460

Trp Asp Phe Ile Phe Tyr Pro Asn Gly Val Met Glu Ala Lys Met His
465                 470                 475                 480

Ala Thr Gly Tyr Val His Ala Thr Phe Tyr Thr Pro Glu Gly Leu Arg
                485                 490                 495

His Gly Thr Arg Leu His Thr His Leu Ile Gly Asn Ile His Thr His
            500                 505                 510

Leu Val His Tyr Arg Val Asp Leu Asp Val Ala Gly Thr Lys Asn Ser
        515                 520                 525

Phe Gln Thr Leu Gln Met Lys Leu Glu Asn Ile Thr Asn Pro Trp Ser
    530                 535                 540

Pro Arg His Arg Val Val Gln Pro Thr Leu Glu Gln Thr Gln Tyr Ser
545                 550                 555                 560

Trp Glu Arg Gln Ala Ala Phe Ser Phe Lys Arg Lys Leu Pro Thr Tyr
                565                 570                 575

Leu Leu Phe Thr Ser Pro Gln Glu Asn Pro Trp Gly His Lys Arg Ser
            580                 585                 590

Tyr Arg Leu Gln Ile His Ser Met Ala Asp Gln Val Leu Pro Pro Gly
        595                 600                 605

Trp Gln Glu Glu Gln Ala Ile Thr Trp Ala Arg Tyr Pro Leu Ala Val
    610                 615                 620

Thr Lys Tyr Arg Glu Ser Glu Leu Cys Ser Ser Ser Ile Tyr His Gln
625                 630                 635                 640

Asn Asp Pro Trp His Pro Pro Val Val Phe Glu Gln Phe Leu His Asn
                645                 650                 655

Asn Glu Asn Ile Glu Asn Glu Asp Leu Val Ala Trp Val Thr Val Gly
            660                 665                 670

Phe Leu His Ile Pro His Ser Glu Asp Ile Pro Asn Thr Ala Thr Pro
        675                 680                 685

Gly Asn Ser Val Gly Phe Leu Leu Arg Pro Phe Asn Phe Phe Pro Glu
    690                 695                 700

Asp Pro Ser Leu Ala Ser Arg Asp Thr Val Ile Val Trp Pro Arg Asp
705                 710                 715                 720

Asn Gly Pro Asn Tyr Val Gln Arg Trp Ile Pro Glu Asp Arg Asp Cys
                725                 730                 735

Ser Met Pro Pro Pro Phe Ser Tyr Asn Gly Thr Tyr Arg Pro Val
            740                 745                 750
```

<210> SEQ ID NO 17
<211> LENGTH: 2256
<212> TYPE: DNA
<213> ORGANISM: Homo sapiens

<400> SEQUENCE: 17

```
atgccggccc tgggctgggc cgtggctgcc atcctgatgc tgcagacggc catggcggag      60

ccctccccgg ggactctgcc caggaaggca ggggtgtttt cagacctaag caaccaagag     120

ctgaaggcag tgcacagctt cctctggtcc aagaaggagc tgaggctgca gccctccagt     180

accaccacca tggccaagaa caccgtgttt ctcatcgaga tgctgctgcc caagaagtac     240
```

```
catgtgctga ggtttctgga taaaggtgaa aggcatcctg tgcgggaagc ccgtgccgtc    300
atcttctttg gtgaccagga gcatcccaat gtcaccgagt ttgctgtggg gcccctgcca    360
gggccctgct acatgcgagc actgtccccc aggcctgggt accagtcctc ctgggcatcg    420
aggcccatct ccacagcaga gtatgccctc ctctaccaca ccctgcagga agccaccaag    480
cccctgcatc agttcttcct caataccaca ggcttctcat tccaagactg ccatgacaga    540
tgcctggcct tcaccgatgt ggcccccgg ggtgtggctt ctggccagcg ccgcagttgg    600
cttatcatac agcgctatgt agaaggctac tttctgcacc ccactgggct ggagctcctc    660
gtggatcatg ggagcacaga tgctgggcac tgggccgtgg agcaggtgtg gtacaacggg    720
aagttctatg ggagcccaga ggaactggct cggaagtatg cagatggaga ggtggacgtg    780
gtggtcctgg aggacccgct gcctgggggc aaggggcatg acagcacaga ggagccgccc    840
ctcttctcct cccacaagcc ccgcggggac ttccccagcc ccatccatgt gagcggcccc    900
cgcttggtcc agccccacgg ccctcgcttc aggctggagg gcaacgctgt gctctacggc    960
ggctggagct ttgccttccg gctgcgctcc tcctccgggc tgcaggtcct gaacgtgcac   1020
ttcggcggag agcgcattgc ctatgaggtc agcgtgcaag aggcagtggc gctgtatgga   1080
ggacacacac ctgcaggcat gcagaccaag tacctcgatg tcggctgggg cctgggcagc   1140
gtcactcatg agttagcccc cggcatcgac tgcccggaga ccgccacctt cctggacact   1200
ttccactact atgatgccga tgacccggtc cattatcccc gagccctctg cctctttgaa   1260
atgcccacag ggtgcccct tcggcggcac tttaattcca actttaaagg tggcttcaac   1320
ttctatgcgg ggctgaaggg ccaggtgctg gtgctgcgga caacttcaac tgtctacaat   1380
tatgattaca tttgggactt tatcttctac cccaacgggg tgatggaggc caagatgcat   1440
gccactggct acgtccacgc caccttctac accccgagg ggctgcgcca cggcactcgc   1500
ctgcacaccc acctgattgg caacatacac actcacttgg tgcactaccg cgtagacctg   1560
gatgtggcag gcaccaagaa cagcttccag acactgcaga tgaagctaga aaacatcacc   1620
aacccctgga gcccaagaca ccgcgtggtc cagccaactc tggagcagac gcagtactcc   1680
tgggagcgcc aggcggcctt ccgcttcaaa aggaagctgc ccaagtacct gctctttacc   1740
agcccccagg agaaccctg gggccacaag cgcagctacc gcctgcagat ccactccatg   1800
gccgaccagg tgctgccccc aggctggcag gaggagcagg ccatcacctg ggcaaggtac   1860
cccctggcag tgaccaagta ccgggagtcg gagctgtgca gcagcagcat ctaccaccag   1920
aacgacccct ggcacccgcc cgtggtcttt gagcagtttc ttcacaacaa cgagaacatt   1980
gaaaatgagg acctggtggc ctgggtgacg gtgggcttcc tgcacatccc ccactcagag   2040
gacattccca acacagccac acctgggaac tccgtgggct tcctgctccg gccattcaac   2100
ttcttcccag aggaccctc cctggcatcc agagacactg tgatcgtgtg gcctcgggac   2160
aacggcccca actacgtcca gcgctggatc cctgaggaca gggactgctc gatgcctccc   2220
ccttttagct acaatgggac ctatagacct gtgtga                              2256
```

```
<210> SEQ ID NO 18
<211> LENGTH: 2256
<212> TYPE: DNA
<213> ORGANISM: Artificial Sequence
<220> FEATURE:
<223> OTHER INFORMATION: hDAO-Hepmut1

<400> SEQUENCE: 18
```

```
atgccggccc tgggctgggc cgtggctgcc atcctgatgc tgcagacggc catggcggag     60
ccctccccgg ggactctgcc caggaaggca ggggtgtttt cagacctaag caaccaagag    120
ctgaaggcag tgcacagctt cctctggtcc aagaaggagc tgaggctgca gccctccagt    180
accaccacca tggccaagaa caccgtgttt ctcatcgaga tgctgctgcc caagaagtac    240
catgtgctga ggtttctgga taaaggtgaa aggcatcctg tgcgggaagc ccgtgccgtc    300
atcttctttg gtgaccagga gcatcccaat gtcaccgagt ttgctgtggg gcccctgcca    360
gggccctgct acatgcgagc actgtccccc aggcctgggt accagtcctc ctgggcatcg    420
aggcccatct ccacagcaga gtatgccctc ctctaccaca ccctgcagga agccaccaag    480
cccctgcatc agttcttcct caataccaca ggcttctcat tccaagactg ccatgacaga    540
tgcctggcct tcaccgatgt ggcccccggg ggtgtggctt ctggccagcg ccgcagttgg    600
cttatcatac agcgctatgt agaaggctac tttctgcacc ccactgggct ggagctcctc    660
gtggatcatg ggagcacaga tgctgggcac tgggccgtgg agcaggtgtg gtacaacggg    720
aagttctatg ggagcccaga ggaactggct cggaagtatg cagatggaga ggtggacgtg    780
gtggtcctgg aggacccgct gcctgggggc aaggggcatg acagcacaga ggagccgccc    840
ctcttctcct cccacaagcc ccgcggggac ttccccagcc ccatccatgt gagcggcccc    900
cgcttggtcc agccccacgg ccctcgcttc aggctggagg gcaacgctgt gctctacggc    960
ggctggagct ttgccttccg gctgcgctcc tcctccgggc tgcaggtcct gaacgtgcac   1020
ttcggcggag agcgcattgc ctatgaggtc agcgtgcaag aggcagtggc gctgtatgga   1080
ggacacacac ctgcaggcat gcagaccaag tacctcgatg tcggctgggg cctgggcagc   1140
gtcactcatg agttagcccc cggcatcgac tgcccggaga ccgccacctt cctggacact   1200
ttccactact atgatgccga tgacccggtc cattatcccc gagccctctg cctctttgaa   1260
atgcccacag ggtgcccct tcggcggcac tttaattcca actttaaagg tggcttcaac   1320
ttctatgcgg ggctgaaggg ccaggtgctg gtgctgcgga caacttcaac tgtctacaat   1380
tatgattaca tttgggactt tatcttctac cccaacgggg tgatggaggc caagatgcat   1440
gccactggct acgtccacgc caccttctac acccccgagg ggctgcgcca cggcactcgc   1500
ctgcacaccc acctgattgg caacatacac actcacttgg tgcactaccg cgtagacctg   1560
gatgtggcag gcaccaagaa cagcttccag acactgcaga tgaagctaga aaacatcacc   1620
aacccctgga gcccaagaca ccgcgtggtc cagccaactc tggagcagac gcagtactcc   1680
tgggagcgcc aggcggcctt cagcttcaaa aggaagctgc ccaagtacct gctctttacc   1740
agcccccagg agaacccctg ggccacaag cgcagctacc gcctgcagat ccactccatg   1800
gccgaccagg tgctgcccc aggctggcag gaggagcagg ccatcacctg ggcaaggtac   1860
cccctggcag tgaccaagta ccgggagtcg gagctgtgca gcagcagcat ctaccaccag   1920
aacgacccct ggcacccgcc cgtggtcttt gagcagtttc ttcacaacaa cgagaacatt   1980
gaaaatgagg acctggtggc ctgggtgacg gtgggcttcc tgcacatccc ccactcagag   2040
gacattccca acacagccac acctgggaac tccgtgggct tcctgctccg gccattcaac   2100
ttcttcccag aggacccctc cctggcatcc agagacactg tgatcgtgtg gcctcgggac   2160
aacggcccca actacgtcca gcgctggatc cctgaggaca gggactgctc gatgcctccc   2220
ccttttagct acaatgggac ctatagacct gtgtga                              2256
```

<210> SEQ ID NO 19
<211> LENGTH: 2256

```
<212> TYPE: DNA
<213> ORGANISM: Artificial Sequence
<220> FEATURE:
<223> OTHER INFORMATION: hDAO-Hepmut2

<400> SEQUENCE: 19

atgccggccc tgggctgggc cgtggctgcc atcctgatgc tgcagacggc catggcggag     60

ccctccccgg ggactctgcc caggaaggca ggggtgtttt cagacctaag caaccaagag    120

ctgaaggcag tgcacagctt cctctggtcc aagaaggagc tgaggctgca gccctccagt    180

accaccacca tggccaagaa caccgtgttt ctcatcgaga tgctgctgcc caagaagtac    240

catgtgctga ggtttctgga taaaggtgaa aggcatcctg tgcgggaagc ccgtgccgtc    300

atcttctttg gtgaccagga gcatcccaat gtcaccgagt ttgctgtggg gcccctgcca    360

gggccctgct acatgcgagc actgtccccc aggcctgggt accagtcctc ctgggcatcg    420

aggcccatct ccacagcaga gtatgccctc ctctaccaca ccctgcagga agccaccaag    480

cccctgcatc agttcttcct caataccaca ggcttctcat tccaagactg ccatgacaga    540

tgcctggcct tcaccgatgt ggcccccogg ggtgtggctt ctggccagcg ccgcagttgg    600

cttatcatac agcgctatgt agaaggctac tttctgcacc ccactgggct ggagctcctc    660

gtggatcatg ggagcacaga tgctgggcac tgggccgtgg agcaggtgtg gtacaacggg    720

aagttctatg ggagcccaga ggaactggct cggaagtatg cagatggaga ggtggacgtg    780

gtggtcctgg aggacccgct gcctgggggc aaggggcatg acagcacaga ggagccgccc    840

ctcttctcct cccacaagcc ccgcggggac ttccccagcc ccatccatgt gagcggcccc    900

cgcttggtcc agccccacgg ccctcgcttc aggctggagg gcaacgctgt gctctacggc    960

ggctggagct ttgccttccg gctgcgctcc tcctccgggc tgcaggtcct gaacgtgcac   1020

ttcggcggag agcgcattgc ctatgaggtc agcgtgcaag aggcagtggc gctgtatgga   1080

ggacacacac ctgcaggcat gcagaccaag tacctcgatg tcggctgggg cctgggcagc   1140

gtcactcatg agttagcccc cggcatcgac tgcccggaga ccgccacctt cctggacact   1200

ttccactact atgatgccga tgacccggtc cattatcccc gagccctctg cctctttgaa   1260

atgcccacag ggtgcccct tcggcggcac tttaattcca actttaaagg tggcttcaac   1320

ttctatgcgg ggctgaaggg ccaggtgctg gtgctgcgga caacttcaac tgtctacaat   1380

tatgattaca tttgggactt tatcttctac cccaacgggg tgatggaggc caagatgcat   1440

gccactggct acgtccacgc caccttctac acccccgagg ggctgcgcca cggcactcgc   1500

ctgcacaccc acctgattgg caacatacac actcacttgg tgcactaccg cgtagacctg   1560

gatgtggcag gcaccaagaa cagcttccag acactgcaga tgaagctaga aaacatcacc   1620

aacccctgga gcccaagaca ccgcgtggtc cagccaactc tggagcagac gcagtactcc   1680

tgggagcgcc aggcggcctt ccgcttcaaa aggaagctgc ccacgtacct gctctttacc   1740

agcccccagg agaaccctg gggccacaag cgcagctacc gcctgcagat ccactccatg   1800

gccgaccagg tgctgccccc aggctggcag gaggagcagg ccatcacctg ggcaaggtac   1860

cccctggcag tgaccaagta ccgggagtcg gagctgtgca gcagcagcat ctaccaccag   1920

aacgacccct ggcacccgcc cgtggtcttt gagcagtttc ttcacaacaa cgagaacatt   1980

gaaaatgagg acctggtggc ctgggtgacg gtgggcttcc tgcacatccc ccactcagag   2040

gacattccca acacagccac acctgggaac tccgtgggct tcctgctccg gccattcaac   2100

ttcttcccag aggacccctc cctggcatcc agagacactg tgatcgtgtg gcctcgggac   2160
```

aacggcccca actacgtcca gcgctggatc cctgaggaca gggactgctc gatgcctccc 2220
ccttttagct acaatgggac ctatagacct gtgtga 2256

<210> SEQ ID NO 20
<211> LENGTH: 2256
<212> TYPE: DNA
<213> ORGANISM: Artificial Sequence
<220> FEATURE:
<223> OTHER INFORMATION: hDAO-Hepmut3

<400> SEQUENCE: 20
atgccggccc tgggctgggc cgtggctgcc atcctgatgc tgcagacggc catggcggag 60
ccctccccgg ggactctgcc caggaaggca ggggtgtttt cagacctaag caaccaagag 120
ctgaaggcag tgcacagctt cctctggtcc aagaaggagc tgaggctgca gccctccagt 180
accaccacca tggccaagaa caccgtgttt ctcatcgaga tgctgctgcc caagaagtac 240
catgtgctga ggtttctgga taaaggtgaa aggcatcctg tgcgggaagc ccgtgccgtc 300
atcttctttg gtgaccagga gcatcccaat gtcaccgagt ttgctgtggg gcccctgcca 360
gggccctgct acatgcgagc actgtccccc aggcctgggt accagtcctc ctgggcatcg 420
aggcccatct ccacagcaga gtatgccctc ctctaccaca ccctgcagga agccaccaag 480
cccctgcatc agttcttcct caataccaca ggcttctcat tccaagactg ccatgacaga 540
tgcctggcct tcaccgatgt ggccccccgg ggtgtggctt ctggccagcg ccgcagttgg 600
cttatcatac agcgctatgt agaaggctac tttctgcacc ccactgggct ggagctcctc 660
gtggatcatg ggagcacaga tgctgggcac tgggccgtgg agcaggtgtg gtacaacggg 720
aagttctatg ggagcccaga ggaactggct cggaagtatg cagatggaga ggtggacgtg 780
gtggtcctgg aggacccgct gcctgggggc aaggggcatg acagcacaga ggagccgccc 840
ctcttctcct cccacaagcc ccgcggggac ttccccagcc ccatccatgt gagcggcccc 900
cgcttggtcc agccccacgg ccctcgcttc aggctggagg gcaacgctgt gctctacggc 960
ggctggagct ttgccttccg gctgcgctcc tcctccgggc tgcaggtcct gaacgtgcac 1020
ttcggcggag agcgcattgc ctatgaggtc agcgtgcaag aggcagtggc gctgtatgga 1080
ggacacacac ctgcaggcat gcagaccaag tacctcgatg tcggctgggg cctgggcagc 1140
gtcactcatg agttagcccc cggcatcgac tgcccggaga ccgccacctt cctggacact 1200
ttccactact atgatgccga tgacccggtc cattatcccc gagccctctg cctctttgaa 1260
atgcccacag ggtgcccct tcggcggcac tttaattcca actttaaagg tggcttcaac 1320
ttctatgcgg ggctgaaggg ccaggtgctg gtgctgcgga caacttcaac tgtctacaat 1380
tatgattaca tttgggactt tatcttctac cccaacgggg tgatggaggc caagatgcat 1440
gccactggct acgtccacgc caccttctac acccccgagg ggctgcgcca cggcactcgc 1500
ctgcacaccc acctgattgg caacatacac actcacttgg tgcactaccg cgtagacctg 1560
gatgtggcag gcaccaagaa cagcttccag acactgcaga tgaagctaga aaacatcacc 1620
aacccctgga gcccaagaca ccgcgtggtc cagccaactc tggagcagac gcagtactcc 1680
tgggagcgcc aggcggcctt ccgcttcaaa acgaagctgc ccaagtacct gctctttacc 1740
agcccccagg agaacccctg ggccacaag cgcagctacc gcctgcagat ccactccatg 1800
gccgaccagg tgctgccccc aggctggcag gaggagcagg ccatcacctg ggcaaggtac 1860
cccctggcag tgaccaagta ccgggagtcg gagctgtgca gcagcagcat ctaccaccag 1920
aacgacccct ggcacccgcc cgtggtcttt gagcagtttc ttcacaacaa cgagaacatt 1980
gaaaatgagg acctggtggc ctgggtgacg gtgggcttcc tgcacatccc ccactcagag 2040
gacattccca acacagccac acctgggaac tccgtgggct tcctgctccg gccattcaac 2100
ttcttcccag aggacccctc cctggcatcc agagacactg tgatcgtgtg gcctcgggac 2160
aacggcccca actacgtcca gcgctggatc cctgaggaca gggactgctc gatgcctccc 2220
ccttttagct acaatgggac ctatagacct gtgtga 2256

<210> SEQ ID NO 21
<211> LENGTH: 2256
<212> TYPE: DNA
<213> ORGANISM: Artificial Sequence
<220> FEATURE:
<223> OTHER INFORMATION: hDAO-Hepmut4

<400> SEQUENCE: 21
atgccggccc tgggctgggc cgtggctgcc atcctgatgc tgcagacggc catggcggag 60
ccctccccgg ggactctgcc caggaaggca ggggtgtttt cagacctaag caaccaagag 120
ctgaaggcag tgcacagctt cctctggtcc aagaaggagc tgaggctgca gccctccagt 180
accaccacca tggccaagaa caccgtgttt ctcatcgaga tgctgctgcc caagaagtac 240
catgtgctga ggtttctgga taaaggtgaa aggcatcctg tgcgggaagc ccgtgccgtc 300
atcttctttg gtgaccagga gcatcccaat gtcaccgagt ttgctgtggg gcccctgcca 360
gggccctgct acatgcgagc actgtccccc aggcctgggt accagtcctc ctgggcatcg 420
aggcccatct ccacagcaga gtatgccctc ctctaccaca ccctgcagga agccaccaag 480
cccctgcatc agttcttcct caataccaca ggcttctcat tccaagactg ccatgacaga 540
tgcctggcct tcaccgatgt ggccccccgg ggtgtggctt ctggccagcg ccgcagttgg 600
cttatcatac agcgctatgt agaaggctac tttctgcacc ccactgggct ggagctcctc 660
gtggatcatg ggagcacaga tgctgggcac tgggccgtgg agcaggtgtg gtacaacggg 720
aagttctatg ggagcccaga ggaactggct cggaagtatg cagatggaga ggtggacgtg 780
gtggtcctgg aggacccgct gcctgggggc aaggggcatg acagcacaga ggagccgccc 840
ctcttctcct cccacaagcc ccgcggggac ttccccagcc ccatccatgt gagcggcccc 900
cgcttggtcc agccccacgg ccctcgcttc aggctggagg gcaacgctgt gctctacggc 960
ggctggagct ttgccttccg gctgcgctcc tcctccgggc tgcaggtcct gaacgtgcac 1020
ttcggcggag agcgcattgc ctatgaggtc agcgtgcaag aggcagtggc gctgtatgga 1080
ggacacacac ctgcaggcat gcagaccaag tacctcgatg tcggctgggg cctgggcagc 1140
gtcactcatg agttagcccc cggcatcgac tgcccggaga ccgccacctt cctggacact 1200
ttccactact atgatgccga tgacccggtc cattatcccc gagccctctg cctctttgaa 1260
atgcccacag ggtgcccct tcggcggcac tttaattcca actttaaagg tggcttcaac 1320
ttctatgcgg ggctgaaggg ccaggtgctg gtgctgcgga caacttcaac tgtctacaat 1380
tatgattaca tttgggactt tatcttctac cccaacgggg tgatggaggc caagatgcat 1440
gccactggct acgtccacgc caccttctac acccccgagg ggctgcgcca cggcactcgc 1500
ctgcacaccc acctgattgg caacatacac actcacttgg tgcactaccg cgtagacctg 1560
gatgtggcag gcaccaagaa cagcttccag acactgcaga tgaagctaga aaacatcacc 1620
aacccctgga gcccaagaca ccgcgtggtc cagccaactc tggagcagac gcagtactcc 1680
tgggagcgcc aggcggcctt cagcttcaaa acgaagctgc ccaagtacct gctctttacc 1740

```
agcccccagg agaacccctg gggccacaag cgcagctacc gcctgcagat ccactccatg   1800

gccgaccagg tgctgccccc aggctggcag gaggagcagg ccatcacctg ggcaaggtac   1860

cccctggcag tgaccaagta ccgggagtcg gagctgtgca gcagcagcat ctaccaccag   1920

aacgacccct ggcacccgcc cgtggtcttt gagcagtttc ttcacaacaa cgagaacatt   1980

gaaaatgagg acctggtggc ctgggtgacg gtgggcttcc tgcacatccc ccactcagag   2040

gacattccca acacagccac acctgggaac tccgtgggct tcctgctccg gccattcaac   2100

ttcttcccag aggacccctc cctggcatcc agagacactg tgatcgtgtg gcctcgggac   2160

aacggcccca actacgtcca gcgctggatc cctgaggaca gggactgctc gatgcctccc   2220

ccttttagct acaatgggac ctatagacct gtgtga                             2256
```

<210> SEQ ID NO 22
<211> LENGTH: 2256
<212> TYPE: DNA
<213> ORGANISM: Artificial Sequence
<220> FEATURE:
<223> OTHER INFORMATION: hDAO-Hepmut5

<400> SEQUENCE: 22

```
atgccggccc tgggctgggc cgtggctgcc atcctgatgc tgcagacggc catggcggag     60

ccctccccgg ggactctgcc caggaaggca ggggtgtttt cagacctaag caaccaagag    120

ctgaaggcag tgcacagctt cctctggtcc aagaaggagc tgaggctgca gccctccagt    180

accaccacca tggccaagaa caccgtgttt ctcatcgaga tgctgctgcc caagaagtac    240

catgtgctga ggtttctgga taaaggtgaa aggcatcctg tgcgggaagc ccgtgccgtc    300

atcttctttg gtgaccagga gcatcccaat gtcaccgagt ttgctgtggg gcccctgcca    360

gggccctgct acatgcgagc actgtccccc aggcctgggt accagtcctc ctgggcatcg    420

aggcccatct ccacagcaga gtatgccctc ctctaccaca ccctgcagga agccaccaag    480

cccctgcatc agttcttcct caataccaca ggcttctcat tccaagactg ccatgacaga    540

tgcctggcct tcaccgatgt ggcccccgg ggtgtggctt ctggccagcg ccgcagttgg     600

cttatcatac agcgctatgt agaaggctac tttctgcacc ccactgggct ggagctcctc    660

gtggatcatg ggagcacaga tgctgggcac tgggccgtgg agcaggtgtg gtacaacggg    720

aagttctatg ggagcccaga ggaactggct cggaagtatg cagatggaga ggtggacgtg    780

gtggtcctgg aggacccgct gcctgggggc aaggggcatg acagcacaga ggagccgccc    840

ctcttctcct cccacaagcc ccgcggggac ttccccagcc ccatccatgt gagcggcccc    900

cgcttggtcc agccccacgg ccctcgcttc aggctggagg gcaacgctgt gctctacggc    960

ggctggagct ttgccttccg gctgcgctcc tcctccgggc tgcaggtcct gaacgtgcac   1020

ttcggcggag agcgcattgc ctatgaggtc agcgtgcaag aggcagtggc gctgtatgga   1080

ggacacacac ctgcaggcat gcagaccaag tacctcgatg tcggctgggg cctgggcagc   1140

gtcactcatg agttagcccc cggcatcgac tgcccggaga ccgccacctt cctggacact   1200

ttccactact atgatgccga tgacccggtc cattatcccc gagccctctg cctctttgaa   1260

atgcccacag ggtgcccct tcggcggcac tttaattcca actttaaagg tggcttcaac    1320

ttctatgcgg ggctgaaggg ccaggtgctg gtgctgcgga caacttcaac tgtctacaat   1380

tatgattaca tttgggactt tatcttctac ccccaacgggg tgatggaggc caagatgcat  1440

gccactggct acgtccacgc caccttctac acccccgagg ggctgcgcca cggcactcgc   1500

ctgcacaccc acctgattgg caacatacac actcacttgg tgcactaccg cgtagacctg   1560
```

```
gatgtggcag gcaccaagaa cagcttccag acactgcaga tgaagctaga aaacatcacc   1620

aacccctgga gcccaagaca ccgcgtggtc cagccaactc tggagcagac gcagtactcc   1680

tgggagcgcc aggcggcctt ccgcttcaaa acgaagctgc ccacgtacct gctctttacc   1740

agcccccagg agaacccctg gggccacaag cgcagctacc gcctgcagat ccactccatg   1800

gccgaccagg tgctgccccc aggctggcag gaggagcagg ccatcacctg ggcaaggtac   1860

cccctggcag tgaccaagta ccgggagtcg gagctgtgca gcagcagcat ctaccaccag   1920

aacgacccct ggcacccgcc cgtggtcttt gagcagtttc ttcacaacaa cgagaacatt   1980

gaaaatgagg acctggtggc ctgggtgacg gtgggcttcc tgcacatccc ccactcagag   2040

gacattccca acacagccac acctgggaac tccgtgggct tcctgctccg gccattcaac   2100

ttcttcccag aggacccctc cctggcatcc agagacactg tgatcgtgtg gcctcgggac   2160

aacggcccca actacgtcca gcgctggatc cctgaggaca gggactgctc gatgcctccc   2220

ccttttagct acaatgggac ctatagacct gtgtga                             2256
```

<210> SEQ ID NO 23
<211> LENGTH: 2256
<212> TYPE: DNA
<213> ORGANISM: Artificial Sequence
<220> FEATURE:
<223> OTHER INFORMATION: hDAO-Hepmut6

<400> SEQUENCE: 23

```
atgccggccc tgggctgggc cgtggctgcc atcctgatgc tgcagacggc catggcggag     60

ccctccccgg ggactctgcc caggaaggca ggggtgtttt cagacctaag caaccaagag    120

ctgaaggcag tgcacagctt cctctggtcc aagaaggagc tgaggctgca gccctccagt    180

accaccacca tggccaagaa caccgtgttt ctcatcgaga tgctgctgcc caagaagtac    240

catgtgctga ggtttctgga taaaggtgaa aggcatcctg tgcgggaagc ccgtgccgtc    300

atcttctttg gtgaccagga gcatcccaat gtcaccgagt ttgctgtggg gcccctgcca    360

gggccctgct acatgcgagc actgtccccc aggcctgggt accagtcctc ctgggcatcg    420

aggcccatct ccacagcaga gtatgccctc ctctaccaca ccctgcagga agccaccaag    480

cccctgcatc agttcttcct caataccaca ggcttctcat tccaagactg ccatgacaga    540

tgcctggcct tcaccgatgt ggccccccgg ggtgtggctt ctggccagcg ccgcagttgg    600

cttatcatac agcgctatgt agaaggctac tttctgcacc ccactgggct ggagctcctc    660

gtggatcatg ggagcacaga tgctgggcac tgggccgtgg agcaggtgtg gtacaacggg    720

aagttctatg ggagcccaga ggaactggct cggaagtatg cagatggaga ggtggacgtg    780

gtggtcctgg aggacccgct gcctgggggc aaggggcatg acagcacaga ggagccgccc    840

ctcttctcct cccacaagcc ccgcggggac ttccccagcc ccatccatgt gagcggcccc    900

cgcttggtcc agccccacgg ccctcgcttc aggctggagg gcaacgctgt gctctacggc    960

ggctggagct ttgccttccg gctgcgctcc tcctccgggc tgcaggtcct gaacgtgcac   1020

ttcggcggag agcgcattgc ctatgaggtc agcgtgcaag aggcagtggc gctgtatgga   1080

ggacacacac ctgcaggcat gcagaccaag tacctcgatg tcggctgggg cctgggcagc   1140

gtcactcatg agttagcccc cggcatcgac tgcccggaga ccgccacctt cctggacact   1200

ttccactact atgatgccga tgacccggtc cattatcccc gagccctctg cctctttgaa   1260

atgcccacag ggtgcccct tcggcggcac tttaattcca actttaaagg tggcttcaac   1320
```

```
ttctatgcgg ggctgaaggg ccaggtgctg gtgctgcgga caacttcaac tgtctacaat   1380

tatgattaca tttgggactt tatcttctac cccaacgggg tgatggaggc caagatgcat   1440

gccactggct acgtccacgc caccttctac acccccgagg ggctgcgcca cggcactcgc   1500

ctgcacaccc acctgattgg caacatacac actcacttgg tgcactaccg cgtagacctg   1560

gatgtggcag gcaccaagaa cagcttccag acactgcaga tgaagctaga aaacatcacc   1620

aacccctgga gcccaagaca ccgcgtggtc cagccaactc tggagcagac gcagtactcc   1680

tgggagcgcc aggcggcctt ccgcttcgga cagacgctgc ccaagtacct gctctttacc   1740

agcccccagg agaacccctg ggccacaag cgcagctacc gcctgcagat ccactccatg   1800

gccgaccagg tgctgccccc aggctggcag gaggagcagg ccatcacctg ggcaaggtac   1860

cccctggcag tgaccaagta ccgggagtcg gagctgtgca gcagcagcat ctaccaccag   1920

aacgacccct ggcacccgcc cgtggtcttt gagcagtttc ttcacaacaa cgagaacatt   1980

gaaaatgagg acctggtggc ctgggtgacg gtgggcttcc tgcacatccc ccactcagag   2040

gacattccca acacagccac acctgggaac tccgtgggct tcctgctccg gccattcaac   2100

ttcttcccag aggacccctc cctggcatcc agagacactg tgatcgtgtg gcctcgggac   2160

aacggcccca actacgtcca gcgctggatc cctgaggaca gggactgctc gatgcctccc   2220

ccttttagct acaatgggac ctatagacct gtgtga                            2256
```

<210> SEQ ID NO 24
<211> LENGTH: 2256
<212> TYPE: DNA
<213> ORGANISM: Artificial Sequence
<220> FEATURE:
<223> OTHER INFORMATION: hDAO-Hepmut7

<400> SEQUENCE: 24

```
atgccggccc tgggctgggc cgtggctgcc atcctgatgc tgcagacggc catggcggag     60

ccctccccgg ggactctgcc caggaaggca ggggtgtttt cagacctaag caaccaagag    120

ctgaaggcag tgcacagctt cctctggtcc aagaaggagc tgaggctgca gccctccagt    180

accaccacca tggccaagaa caccgtgttt ctcatcgaga tgctgctgcc caagaagtac    240

catgtgctga ggtttctgga taaaggtgaa aggcatcctg tgcgggaagc ccgtgccgtc    300

atcttctttg gtgaccagga gcatcccaat gtcaccgagt ttgctgtggg gcccctgcca    360

gggccctgct acatgcgagc actgtccccc aggcctgggt accagtcctc ctgggcatcg    420

aggcccatct ccacagcaga gtatgccctc ctctaccaca ccctgcagga agccaccaag    480

cccctgcatc agttcttcct caataccaca ggcttctcat tccaagactg ccatgacaga    540

tgcctggcct tcaccgatgt ggccccccgg ggtgtggctt ctggccagcg ccgcagttgg    600

cttatcatac agcgctatgt agaaggctac tttctgcacc ccactgggct ggagctcctc    660

gtggatcatg ggagcacaga tgctgggcac tgggccgtgg agcaggtgtg gtacaacggg    720

aagttctatg ggagcccaga ggaactggct cggaagtatg cagatggaga ggtggacgtg    780

gtggtcctgg aggacccgct gcctgggggc aaggggcatg acagcacaga ggagccgccc    840

ctcttctcct cccacaagcc ccgcggggac ttccccagcc ccatccatgt gagcggcccc    900

cgcttggtcc agccccacgg ccctcgcttc aggctggagg gcaacgctgt gctctacggc    960

ggctggagct ttgccttccg gctgcgctcc tcctccgggc tgcaggtcct gaacgtgcac   1020

ttcggcggag agcgcattgc ctatgaggtc agcgtgcaag aggcagtggc gctgtatgga   1080

ggacacacac ctgcaggcat gcagaccaag tacctcgatg tcggctgggg cctgggcagc   1140
```

gtcactcatg agttagcccc cggcatcgac tgcccggaga ccgccacctt cctggacact 1200
ttccactact atgatgccga tgacccggtc cattatcccc gagccctctg cctctttgaa 1260
atgcccacag gggtgcccct tcggcggcac tttaattcca actttaaagg tggcttcaac 1320
ttctatgcgg ggctgaaggg ccaggtgctg gtgctgcgga caacttcaac tgtctacaat 1380
tatgattaca tttgggactt tatcttctac cccaacgggg tgatggaggc caagatgcat 1440
gccactggct acgtccacgc caccttctac acccccgagg ggctgcgcca cggcactcgc 1500
ctgcacaccc acctgattgg caacatacac actcacttgg tgcactaccg cgtagacctg 1560
gatgtggcag gcaccaagaa cagcttccag acactgcaga tgaagctaga aaacatcacc 1620
aacccctgga gcccaagaca ccgcgtggtc cagccaactc tggagcagac gcagtactcc 1680
tgggagcgcc aggcggcctt cagcttcaaa aggaagctgc ccacgtacct gctctttacc 1740
agcccccagg agaacccctg ggccacaag cgcagctacc gcctgcagat ccactccatg 1800
gccgaccagg tgctgccccc aggctggcag gaggagcagg ccatcacctg ggcaaggtac 1860
cccctggcag tgaccaagta ccgggagtcg gagctgtgca gcagcagcat ctaccaccag 1920
aacgacccct ggcacccgcc cgtggtcttt gagcagtttc ttcacaacaa cgagaacatt 1980
gaaaatgagg acctggtggc ctgggtgacg gtgggcttcc tgcacatccc ccactcagag 2040
gacattccca acacagccac acctgggaac tccgtgggct tcctgctccg gccattcaac 2100
ttcttcccag aggacccctc cctggcatcc agagacactg tgatcgtgtg gcctcgggac 2160
aacggcccca actacgtcca gcgctggatc cctgaggaca gggactgctc gatgcctccc 2220
ccttttagct acaatgggac ctatagacct gtgtga 2256

<210> SEQ ID NO 25
<211> LENGTH: 2256
<212> TYPE: DNA
<213> ORGANISM: Artificial Sequence
<220> FEATURE:
<223> OTHER INFORMATION: hDAO-Cysmut

<400> SEQUENCE: 25
atgccggccc tgggctgggc cgtggctgcc atcctgatgc tgcagacggc catggcggag 60
ccctccccgg ggactctgcc caggaaggca ggggtgtttt cagacctaag caaccaagag 120
ctgaaggcag tgcacagctt cctctggtcc aagaaggagc tgaggctgca gccctccagt 180
accaccacca tggccaagaa caccgtgttt ctcatcgaga tgctgctgcc caagaagtac 240
catgtgctga ggtttctgga taaaggtgaa aggcatcctg tgcgggaagc ccgtgccgtc 300
atcttctttg gtgaccagga gcatcccaat gtcaccgagt ttgctgtggg gcccctgcca 360
gggcccgcct acatgcgagc actgtccccc aggcctgggt accagtcctc ctgggcatcg 420
aggcccatct ccacagcaga gtatgccctc ctctaccaca ccctgcagga agccaccaag 480
cccctgcatc agttcttcct caataccaca ggcttctcat tccaagactg ccatgacaga 540
tgcctggcct tcaccgatgt ggcccccegg ggtgtggctt ctggccagcg ccgcagttgg 600
cttatcatac agcgctatgt agaaggctac tttctgcacc ccactgggct ggagctcctc 660
gtggatcatg ggagcacaga tgctgggcac tgggccgtgg agcaggtgtg gtacaacggg 720
aagttctatg ggagcccaga ggaactggct cggaagtatg cagatggaga ggtggacgtg 780
gtggtcctgg aggacccgct gcctgggggc aaggggcatg acagcacaga ggagccgccc 840
ctcttctcct cccacaagcc ccgcggggac ttccccagcc ccatccatgt gagcggcccc 900

```
cgcttggtcc agccccacgg ccctcgcttc aggctggagg gcaacgctgt gctctacggc    960
ggctggagct ttgccttccg gctgcgctcc tcctccgggc tgcaggtcct gaacgtgcac   1020
ttcggcggag agcgcattgc ctatgaggtc agcgtgcaag aggcagtggc gctgtatgga   1080
ggacacacac ctgcaggcat gcagaccaag tacctcgatg tcggctgggg cctgggcagc   1140
gtcactcatg agttagcccc cggcatcgac tgcccggaga ccgccacctt cctggacact   1200
ttccactact atgatgccga tgacccggtc cattatcccc gagccctctg cctctttgaa   1260
atgcccacag ggtgcccct tcggcggcac tttaattcca actttaaagg tggcttcaac   1320
ttctatgcgg ggctgaaggg ccaggtgctg gtgctgcgga caacttcaac tgtctacaat   1380
tatgattaca tttgggactt tatcttctac cccaacgggg tgatggaggc caagatgcat   1440
gccactggct acgtccacgc caccttctac acccccgagg ggctgcgcca cggcactcgc   1500
ctgcacaccc acctgattgg caacatacac actcacttgg tgcactaccg cgtagacctg   1560
gatgtggcag gcaccaagaa cagcttccag acactgcaga tgaagctaga aaacatcacc   1620
aacccctgga gcccaagaca ccgcgtggtc cagccaactc tggagcagac gcagtactcc   1680
tgggagcgcc aggcggcctt ccgcttcaaa aggaagctgc ccaagtacct gctctttacc   1740
agcccccagg agaaccctg ggccacaag cgcagctacc gcctgcagat ccactccatg    1800
gccgaccagg tgctgccccc aggctggcag gaggagcagg ccatcacctg ggcaaggtac   1860
cccctggcag tgaccaagta ccgggagtcg gagctgtgca gcagcagcat ctaccaccag   1920
aacgacccct ggcacccgcc cgtggtcttt gagcagtttc ttcacaacaa cgagaacatt   1980
gaaaatgagg acctggtggc ctgggtgacg gtgggcttcc tgcacatccc ccactcagag   2040
gacattccca acacagccac acctgggaac tccgtgggct tcctgctccg gccattcaac   2100
ttcttcccag aggacccctc cctggcatcc agagacactg tgatcgtgtg gcctcgggac   2160
aacggcccca actacgtcca gcgctggatc cctgaggaca gggactgctc gatgcctccc   2220
ccttttagct acaatgggac ctatagacct gtgtga                             2256
```

<210> SEQ ID NO 26
<211> LENGTH: 2256
<212> TYPE: DNA
<213> ORGANISM: Artificial Sequence
<220> FEATURE:
<223> OTHER INFORMATION: hDAO-Hepmut1-Cysmut

<400> SEQUENCE: 26

```
atgccggccc tgggctgggc cgtggctgcc atcctgatgc tgcagacggc catggcggag     60
ccctccccgg ggactctgcc caggaaggca ggggtgtttt cagacctaag caaccaagag    120
ctgaaggcag tgcacagctt cctctggtcc aagaaggagc tgaggctgca gccctccagt    180
accaccacca tggccaagaa caccgtgttt ctcatcgaga tgctgctgcc caagaagtac    240
catgtgctga ggtttctgga taaaggtgaa aggcatcctg tgcgggaagc ccgtgccgtc    300
atcttctttg gtgaccagga gcatcccaat gtcaccgagt ttgctgtggg gcccctgcca    360
gggcccgcct acatgcgagc actgtccccc aggcctgggt accagtcctc ctgggcatcg    420
aggcccatct ccacagcaga gtatgccctc ctctaccaca ccctgcagga agccaccaag    480
cccctgcatc agttcttcct caataccaca ggcttctcat tccaagactg ccatgacaga    540
tgcctggcct tcaccgatgt ggcccccgg ggtgtggctt ctggccagcg ccgcagttgg     600
cttatcatac agcgctatgt agaaggctac tttctgcacc ccactgggct ggagctcctc    660
gtggatcatg ggagcacaga tgctgggcac tgggccgtgg agcaggtgtg gtacaacggg    720
```

```
aagttctatg ggagcccaga ggaactggct cggaagtatg cagatggaga ggtggacgtg    780

gtggtcctgg aggacccgct gcctgggggc aaggggcatg acagcacaga ggagccgccc    840

ctcttctcct cccacaagcc ccgcggggac ttccccagcc ccatccatgt gagcggcccc    900

cgcttggtcc agccccacgg ccctcgcttc aggctggagg gcaacgctgt gctctacggc    960

ggctggagct ttgccttccg gctgcgctcc tcctccgggc tgcaggtcct gaacgtgcac   1020

ttcggcggag agcgcattgc ctatgaggtc agcgtgcaag aggcagtggc gctgtatgga   1080

ggacacacac ctgcaggcat gcagaccaag tacctcgatg tcggctgggg cctgggcagc   1140

gtcactcatg agttagcccc cggcatcgac tgcccggaga ccgccacctt cctggacact   1200

ttccactact atgatgccga tgacccggtc cattatcccc gagccctctg cctctttgaa   1260

atgcccacag ggggtgcccct tcggcggcac tttaattcca actttaaagg tggcttcaac   1320

ttctatgcgg ggctgaaggg ccaggtgctg gtgctgcgga caacttcaac tgtctacaat   1380

tatgattaca tttgggactt tatcttctac cccaacgggg tgatggaggc caagatgcat   1440

gccactggct acgtccacgc caccttctac acccccgagg ggctgcgcca cggcactcgc   1500

ctgcacaccc acctgattgg caacatacac actcacttgg tgcactaccg cgtagacctg   1560

gatgtggcag gcaccaagaa cagcttccag acactgcaga tgaagctaga aaacatcacc   1620

aacccctgga gcccaagaca ccgcgtggtc cagccaactc tggagcagac gcagtactcc   1680

tgggagcgcc aggcggcctt cagcttcaaa aggaagctgc ccaagtacct gctctttacc   1740

agcccccagg agaacccctg ggccacaaag cgcagctacc gcctgcagat ccactccatg   1800

gccgaccagg tgctgccccc aggctggcag gaggagcagg ccatcacctg ggcaaggtac   1860

cccctggcag tgaccaagta ccgggagtcg gagctgtgca gcagcagcat ctaccaccag   1920

aacgacccct ggcacccgcc cgtggtcttt gagcagtttc ttcacaacaa cgagaacatt   1980

gaaaatgagg acctggtggc ctgggtgacg gtgggcttcc tgcacatccc ccactcagag   2040

gacattccca acacagccac acctgggaac tccgtgggct tcctgctccg gccattcaac   2100

ttcttcccag aggacccctc cctggcatcc agagacactg tgatcgtgtg gcctcgggac   2160

aacggcccca actacgtcca gcgctggatc cctgaggaca gggactgctc gatgcctccc   2220

ccttttagct acaatgggac ctatagacct gtgtga                             2256


<210> SEQ ID NO 27
<211> LENGTH: 2256
<212> TYPE: DNA
<213> ORGANISM: Artificial Sequence
<220> FEATURE:
<223> OTHER INFORMATION: hDAO-Hepmut2-Cysmut

<400> SEQUENCE: 27

atgccggccc tgggctgggc cgtggctgcc atcctgatgc tgcagacggc catggcggag     60

ccctccccgg ggactctgcc caggaaggca ggggtgtttt cagacctaag caaccaagag    120

ctgaaggcag tgcacagctt cctctggtcc aagaaggagc tgaggctgca gccctccagt    180

accaccacca tggccaagaa caccgtgttt ctcatcgaga tgctgctgcc caagaagtac    240

catgtgctga ggtttctgga taaaggtgaa aggcatcctg tgcgggaagc ccgtgccgtc    300

atcttctttg gtgaccagga gcatcccaat gtcaccgagt ttgctgtggg gcccctgcca    360

gggcccgcct acatgcgagc actgtccccc aggcctgggt accagtcctc ctgggcatcg    420

aggcccatct ccacagcaga gtatgccctc ctctaccaca ccctgcagga agccaccaag    480
```

cccctgcatc agttcttcct caataccaca ggcttctcat tccaagactg ccatgacaga 540
tgcctggcct tcaccgatgt ggccccccgg ggtgtggctt ctggccagcg ccgcagttgg 600
cttatcatac agcgctatgt agaaggctac tttctgcacc ccactgggct ggagctcctc 660
gtggatcatg ggagcacaga tgctgggcac tgggccgtgg agcaggtgtg gtacaacggg 720
aagttctatg ggagcccaga ggaactggct cggaagtatg cagatggaga ggtggacgtg 780
gtggtcctgg aggacccgct gcctgggggc aaggggcatg acagcacaga ggagccgccc 840
ctcttctcct cccacaagcc ccgcggggac ttccccagcc ccatccatgt gagcggcccc 900
cgcttggtcc agccccacgg ccctcgcttc aggctggagg gcaacgctgt gctctacggc 960
ggctggagct ttgccttccg gctgcgctcc tcctccgggc tgcaggtcct gaacgtgcac 1020
ttcggcggag agcgcattgc ctatgaggtc agcgtgcaag aggcagtggc gctgtatgga 1080
ggacacacac ctgcaggcat gcagaccaag tacctcgatg tcggctgggg cctgggcagc 1140
gtcactcatg agttagcccc cggcatcgac tgcccggaga ccgccacctt cctggacact 1200
ttccactact atgatgccga tgacccggtc cattatcccc gagccctctg cctctttgaa 1260
atgcccacag ggtgcccct tcggcggcac tttaattcca actttaaagg tggcttcaac 1320
ttctatgcgg ggctgaaggg ccaggtgctg gtgctgcgga caacttcaac tgtctacaat 1380
tatgattaca tttgggactt tatcttctac cccaacgggg tgatggaggc caagatgcat 1440
gccactggct acgtccacgc caccttctac acccccgagg ggctgcgcca cggcactcgc 1500
ctgcacaccc acctgattgg caacatacac actcacttgg tgcactaccg cgtagacctg 1560
gatgtggcag gcaccaagaa cagcttccag acactgcaga tgaagctaga aaacatcacc 1620
aacccctgga gcccaagaca ccgcgtggtc cagccaactc tggagcagac gcagtactcc 1680
tgggagcgcc aggcggcctt ccgcttcaaa aggaagctgc ccacgtacct gctctttacc 1740
agcccccagg agaaccctg ggccacaag cgcagctacc gcctgcagat ccactccatg 1800
gccgaccagg tgctgccccc aggctggcag gaggagcagg ccatcacctg ggcaaggtac 1860
cccctggcag tgaccaagta ccgggagtcg gagctgtgca gcagcagcat ctaccaccag 1920
aacgacccct ggcacccgcc cgtggtcttt gagcagtttc ttcacaacaa cgagaacatt 1980
gaaaatgagg acctggtggc ctgggtgacg gtgggcttcc tgcacatccc ccactcagag 2040
gacattccca acacagccac acctgggaac tccgtgggct tcctgctccg gccattcaac 2100
ttcttcccag aggacccctc cctggcatcc agagacactg tgatcgtgtg gcctcgggac 2160
aacggcccca actacgtcca gcgctggatc cctgaggaca gggactgctc gatgcctccc 2220
ccttttagct acaatgggac ctatagacct gtgtga 2256

<210> SEQ ID NO 28
<211> LENGTH: 2256
<212> TYPE: DNA
<213> ORGANISM: Artificial Sequence
<220> FEATURE:
<223> OTHER INFORMATION: hDAO-Hepmut3-Cysmut

<400> SEQUENCE: 28
atgccggccc tgggctgggc cgtggctgcc atcctgatgc tgcagacggc catggcggag 60
ccctccccgg ggactctgcc caggaaggca ggggtgtttt cagacctaag caaccaagag 120
ctgaaggcag tgcacagctt cctctggtcc aagaaggagc tgaggctgca gccctccagt 180
accaccacca tggccaagaa caccgtgttt ctcatcgaga tgctgctgcc caagaagtac 240
catgtgctga ggtttctgga taaaggtgaa aggcatcctg tgcgggaagc ccgtgccgtc 300

```
atcttctttg gtgaccagga gcatcccaat gtcaccgagt ttgctgtggg gcccctgcca    360
gggcccgcct acatgcgagc actgtccccc aggcctgggt accagtcctc ctgggcatcg    420
aggcccatct ccacagcaga gtatgccctc ctctaccaca ccctgcagga agccaccaag    480
cccctgcatc agttcttcct caataccaca ggcttctcat tccaagactg ccatgacaga    540
tgcctggcct tcaccgatgt ggccccccgg ggtgtggctt ctggccagcg ccgcagttgg    600
cttatcatac agcgctatgt agaaggctac tttctgcacc ccactgggct ggagctcctc    660
gtggatcatg ggagcacaga tgctgggcac tgggccgtgg agcaggtgtg gtacaacggg    720
aagttctatg ggagcccaga ggaactggct cggaagtatg cagatggaga ggtggacgtg    780
gtggtcctgg aggacccgct gcctgggggc aaggggcatg acagcacaga ggagccgccc    840
ctcttctcct cccacaagcc ccgcggggac ttccccagcc ccatccatgt gagcggcccc    900
cgcttggtcc agccccacgg ccctcgcttc aggctggagg gcaacgctgt gctctacggc    960
ggctggagct ttgccttccg gctgcgctcc tcctccgggc tgcaggtcct gaacgtgcac   1020
ttcggcggag agcgcattgc ctatgaggtc agcgtgcaag aggcagtggc gctgtatgga   1080
ggacacacac ctgcaggcat gcagaccaag tacctcgatg tcggctgggg cctgggcagc   1140
gtcactcatg agttagcccc cggcatcgac tgcccggaga ccgccacctt cctggacact   1200
ttccactact atgatgccga tgacccggtc cattatcccc gagccctctg cctctttgaa   1260
atgcccacag gggtgcccct tcggcggcac tttaattcca actttaaagg tggcttcaac   1320
ttctatgcgg ggctgaaggg ccaggtgctg gtgctgcgga caacttcaac tgtctacaat   1380
tatgattaca tttgggactt tatcttctac cccaacgggg tgatggaggc caagatgcat   1440
gccactggct acgtccacgc caccttctac acccccgagg ggctgcgcca cggcactcgc   1500
ctgcacaccc acctgattgg caacatacac actcacttgg tgcactaccg cgtagacctg   1560
gatgtggcag gcaccaagaa cagcttccag acactgcaga tgaagctaga aaacatcacc   1620
aacccctgga gcccaagaca ccgcgtggtc cagccaactc tggagcagac gcagtactcc   1680
tgggagcgcc aggcggcctt ccgcttcaaa acgaagctgc ccaagtacct gctctttacc   1740
agcccccagg agaacccctg ggccacaaag cgcagctacc gcctgcagat ccactccatg   1800
gccgaccagg tgctgccccc aggctggcag gaggagcagg ccatcacctg ggcaaggtac   1860
cccctggcag tgaccaagta ccgggagtcg gagctgtgca gcagcagcat ctaccaccag   1920
aacgacccct ggcacccgcc cgtggtcttt gagcagtttc ttcacaacaa cgagaacatt   1980
gaaaatgagg acctggtggc ctgggtgacg gtgggcttcc tgcacatccc ccactcagag   2040
gacattccca acacagccac acctgggaac tccgtgggct tcctgctccg gccattcaac   2100
ttcttcccag aggacccctc cctggcatcc agagacactg tgatcgtgtg gcctcgggac   2160
aacggcccca actacgtcca gcgctggatc cctgaggaca gggactgctc gatgcctccc   2220
ccttttagct acaatgggac ctatagacct gtgtga                             2256
```

<210> SEQ ID NO 29
<211> LENGTH: 2256
<212> TYPE: DNA
<213> ORGANISM: Artificial Sequence
<220> FEATURE:
<223> OTHER INFORMATION: hDAO-Hepmut4-Cysmut

<400> SEQUENCE: 29

```
atgccggccc tgggctgggc cgtggctgcc atcctgatgc tgcagacggc catggcggag     60
```

```
ccctccccgg ggactctgcc caggaaggca ggggtgtttt cagacctaag caaccaagag    120

ctgaaggcag tgcacagctt cctctggtcc aagaaggagc tgaggctgca gccctccagt    180

accaccacca tggccaagaa caccgtgttt ctcatcgaga tgctgctgcc caagaagtac    240

catgtgctga ggtttctgga taaaggtgaa aggcatcctg tgcgggaagc ccgtgccgtc    300

atcttctttg gtgaccagga gcatcccaat gtcaccgagt ttgctgtggg gcccctgcca    360

gggcccgcct acatgcgagc actgtccccc aggcctgggt accagtcctc ctgggcatcg    420

aggcccatct ccacagcaga gtatgccctc ctctaccaca ccctgcagga agccaccaag    480

cccctgcatc agttcttcct caataccaca ggcttctcat tccaagactg ccatgacaga    540

tgcctggcct tcaccgatgt ggcccccgg ggtgtggctt ctggccagcg ccgcagttgg    600

cttatcatac agcgctatgt agaaggctac tttctgcacc ccactgggct ggagctcctc    660

gtggatcatg ggagcacaga tgctgggcac tgggccgtgg agcaggtgtg gtacaacggg    720

aagttctatg ggagcccaga ggaactggct cggaagtatg cagatggaga ggtggacgtg    780

gtggtcctgg aggacccgct gcctgggggc aaggggcatg acagcacaga ggagccgccc    840

ctcttctcct cccacaagcc ccgcggggac ttccccagcc ccatccatgt gagcggcccc    900

cgcttggtcc agccccacgg ccctcgcttc aggctggagg gcaacgctgt gctctacggc    960

ggctggagct ttgccttccg gctgcgctcc tcctccgggc tgcaggtcct gaacgtgcac   1020

ttcggcggag agcgcattgc ctatgaggtc agcgtgcaag aggcagtggc gctgtatgga   1080

ggacacacac ctgcaggcat gcagaccaag tacctcgatg tcggctgggg cctgggcagc   1140

gtcactcatg agttagcccc cggcatcgac tgcccggaga ccgccacctt cctggacact   1200

ttccactact atgatgccga tgacccggtc cattatcccc gagccctctg cctctttgaa   1260

atgcccacag ggtgcccct tcggcggcac tttaattcca actttaaagg tggcttcaac   1320

ttctatgcgg ggctgaaggg ccaggtgctg gtgctgcgga caacttcaac tgtctacaat   1380

tatgattaca tttgggactt tatcttctac cccaacgggg tgatggaggc caagatgcat   1440

gccactggct acgtccacgc caccttctac acccccgagg ggctgcgcca cggcactcgc   1500

ctgcacaccc acctgattgg caacatacac actcacttgg tgcactaccg cgtagacctg   1560

gatgtggcag gcaccaagaa cagcttccag acactgcaga tgaagctaga aaacatcacc   1620

aacccctgga gcccaagaca ccgcgtggtc cagccaactc tggagcagac gcagtactcc   1680

tgggagcgcc aggcggcctt cagcttcaaa acgaagctgc ccaagtacct gctctttacc   1740

agcccccagg agaacccctg ggccacaag cgcagctacc gcctgcagat ccactccatg    1800

gccgaccagg tgctgccccc aggctggcag gaggagcagg ccatcacctg ggcaaggtac   1860

cccctggcag tgaccaagta ccgggagtcg gagctgtgca gcagcagcat ctaccaccag   1920

aacgacccct ggcacccgcc cgtggtcttt gagcagtttc ttcacaacaa cgagaacatt   1980

gaaaatgagg acctggtggc ctgggtgacg gtgggcttcc tgcacatccc ccactcagag   2040

gacattccca acacagccac acctgggaac tccgtgggct tcctgctccg gccattcaac   2100

ttcttcccag aggacccctc cctggcatcc agagacactg tgatcgtgtg gcctcgggac   2160

aacggcccca actacgtcca gcgctggatc cctgaggaca gggactgctc gatgcctccc   2220

ccttttagct acaatgggac ctatagacct gtgtga                             2256
```

<210> SEQ ID NO 30
<211> LENGTH: 2256
<212> TYPE: DNA
<213> ORGANISM: Artificial Sequence
<220> FEATURE:
<223> OTHER INFORMATION: hDAO-Hepmut5-Cysmut

<400> SEQUENCE: 30

```
atgccggccc tgggctgggc cgtggctgcc atcctgatgc tgcagacggc catggcggag     60
ccctccccgg ggactctgcc caggaaggca ggggtgtttt cagacctaag caaccaagag    120
ctgaaggcag tgcacagctt cctctggtcc aagaaggagc tgaggctgca gccctccagt    180
accaccacca tggccaagaa caccgtgttt ctcatcgaga tgctgctgcc caagaagtac    240
catgtgctga ggtttctgga taaaggtgaa aggcatcctg tgcgggaagc ccgtgccgtc    300
atcttctttg gtgaccagga gcatcccaat gtcaccgagt ttgctgtggg gccccctgcca    360
gggcccgcct acatgcgagc actgtccccc aggcctgggt accagtcctc ctgggcatcg    420
aggcccatct ccacagcaga gtatgccctc ctctaccaca ccctgcagga agccaccaag    480
cccctgcatc agttcttcct caataccaca ggcttctcat tccaagactg ccatgacaga    540
tgcctggcct tcaccgatgt ggccccccgg ggtgtggctt ctggccagcg ccgcagttgg    600
cttatcatac agcgctatgt agaaggctac tttctgcacc ccactgggct ggagctcctc    660
gtggatcatg ggagcacaga tgctgggcac tgggccgtgg agcaggtgtg gtacaacggg    720
aagttctatg ggagcccaga ggaactggct cggaagtatg cagatggaga ggtggacgtg    780
gtggtcctgg aggacccgct gcctgggggc aaggggcatg acagcacaga ggagccgccc    840
ctcttctcct cccacaagcc ccgcggggac ttccccagcc ccatccatgt gagcggcccc    900
cgcttggtcc agccccacgg ccctcgcttc aggctggagg gcaacgctgt gctctacggc    960
ggctggagct ttgccttccg gctgcgctcc tcctccgggc tgcaggtcct gaacgtgcac   1020
ttcggcggag agcgcattgc ctatgaggtc agcgtgcaag aggcagtggc gctgtatgga   1080
ggacacacac ctgcaggcat gcagaccaag tacctcgatg tcggctgggg cctgggcagc   1140
gtcactcatg agttagcccc cggcatcgac tgcccggaga ccgccacctt cctggacact   1200
ttccactact atgatgccga tgacccggtc cattatcccc gagccctctg cctctttgaa   1260
atgcccacag gggtgcccct tcggcggcac tttaattcca actttaaagg tggcttcaac   1320
ttctatgcgg ggctgaaggg ccaggtgctg gtgctgcgga caacttcaac tgtctacaat   1380
tatgattaca tttgggactt tatcttctac cccaacgggg tgatggaggc caagatgcat   1440
gccactggct acgtccacgc caccttctac acccccgagg ggctgcgcca cggcactcgc   1500
ctgcacaccc acctgattgg caacatacac actcacttgg tgcactaccg cgtagacctg   1560
gatgtggcag gcaccaagaa cagcttccag acactgcaga tgaagctaga aaacatcacc   1620
aacccctgga gcccaagaca ccgcgtggtc cagccaactc tggagcagac gcagtactcc   1680
tgggagcgcc aggcggcctt ccgcttcaaa acgaagctgc ccacgtacct gctctttacc   1740
agcccccagg agaacccctg ggccacaag cgcagctacc gcctgcagat ccactccatg   1800
gccgaccagg tgctgccccc aggctggcag gaggagcagg ccatcacctg ggcaaggtac   1860
cccctggcag tgaccaagta ccgggagtcg gagctgtgca gcagcagcat ctaccaccag   1920
aacgacccct ggcacccgcc cgtggtcttt gagcagtttc ttcacaacaa cgagaacatt   1980
gaaaatgagg acctggtggc ctgggtgacg gtgggcttcc tgcacatccc ccactcagag   2040
gacattccca acacagccac acctgggaac tccgtgggct tcctgctccg gccattcaac   2100
ttcttcccag aggacccctc cctggcatcc agagacactg tgatcgtgtg gcctcgggac   2160
aacggcccca actacgtcca gcgctggatc cctgaggaca gggactgctc gatgcctccc   2220
```

cctttttagct acaatgggac ctatagacct gtgtga 2256

<210> SEQ ID NO 31
<211> LENGTH: 2256
<212> TYPE: DNA
<213> ORGANISM: Artificial Sequence
<220> FEATURE:
<223> OTHER INFORMATION: hDAO-Hepmut6-Cysmut

<400> SEQUENCE: 31
atgccggccc tgggctgggc cgtggctgcc atcctgatgc tgcagacggc catggcggag 60
ccctccccgg ggactctgcc caggaaggca ggggtgtttt cagacctaag caaccaagag 120
ctgaaggcag tgcacagctt cctctggtcc aagaaggagc tgaggctgca gccctccagt 180
accaccacca tggccaagaa caccgtgttt ctcatcgaga tgctgctgcc caagaagtac 240
catgtgctga ggtttctgga taaaggtgaa aggcatcctg tgcgggaagc ccgtgccgtc 300
atcttctttg gtgaccagga gcatcccaat gtcaccgagt ttgctgtggg gcccctgcca 360
gggcccgcct acatgcgagc actgtccccc aggcctgggt accagtcctc ctgggcatcg 420
aggcccatct ccacagcaga gtatgccctc ctctaccaca ccctgcagga agccaccaag 480
cccctgcatc agttcttcct caataccaca ggcttctcat tccaagactg ccatgacaga 540
tgcctggcct tcaccgatgt ggccccccgg ggtgtggctt ctggccagcg ccgcagttgg 600
cttatcatac agcgctatgt agaaggctac tttctgcacc ccactgggct ggagctcctc 660
gtggatcatg ggagcacaga tgctgggcac tgggccgtgg agcaggtgtg gtacaacggg 720
aagttctatg ggagcccaga ggaactggct cggaagtatg cagatggaga ggtggacgtg 780
gtggtcctgg aggacccgct gcctgggggc aaggggcatg acagcacaga ggagccgccc 840
ctcttctcct cccacaagcc ccgcggggac ttccccagcc ccatccatgt gagcggcccc 900
cgcttggtcc agccccacgg ccctcgcttc aggctggagg gcaacgctgt gctctacggc 960
ggctggagct ttgccttccg gctgcgctcc tcctccgggc tgcaggtcct gaacgtgcac 1020
ttcggcggag agcgcattgc ctatgaggtc agcgtgcaag aggcagtggc gctgtatgga 1080
ggacacacac ctgcaggcat gcagaccaag tacctcgatg tcggctgggg cctgggcagc 1140
gtcactcatg agttagcccc cggcatcgac tgcccggaga ccgccacctt cctggacact 1200
ttccactact atgatgccga tgacccggtc cattatcccc gagccctctg cctctttgaa 1260
atgcccacag ggtgcccct tcggcggcac tttaattcca actttaaagg tggcttcaac 1320
ttctatgcgg ggctgaaggg ccaggtgctg gtgctgcgga caacttcaac tgtctacaat 1380
tatgattaca tttgggactt tatcttctac cccaacgggg tgatggaggc caagatgcat 1440
gccactggct acgtccacgc caccttctac acccccgagg ggctgcgcca cggcactcgc 1500
ctgcacaccc acctgattgg caacatacac actcacttgg tgcactaccg cgtagacctg 1560
gatgtggcag gcaccaagaa cagcttccag acactgcaga tgaagctaga aaacatcacc 1620
aacccctgga gcccaagaca ccgcgtggtc cagccaactc tggagcagac gcagtactcc 1680
tgggagcgcc aggcggcctt ccgcttcgga cagacgctgc ccaagtacct gctctttacc 1740
agcccccagg agaaccctg gggccacaag cgcagctacc gcctgcagat ccactccatg 1800
gccgaccagg tgctgccccc aggctggcag gaggagcagg ccatcacctg ggcaaggtac 1860
cccctggcag tgaccaagta ccgggagtcg gagctgtgca gcagcagcat ctaccaccag 1920
aacgacccct ggcacccgcc cgtggtcttt gagcagtttc ttcacaacaa cgagaacatt 1980
gaaaatgagg acctggtggc ctgggtgacg gtgggcttcc tgcacatccc ccactcagag 2040

```
gacattccca acacagccac acctgggaac tccgtgggct tcctgctccg gccattcaac   2100

ttcttcccag aggacccctc cctggcatcc agagacactg tgatcgtgtg gcctcgggac   2160

aacggcccca actacgtcca gcgctggatc cctgaggaca gggactgctc gatgcctccc   2220

ccttttagct acaatgggac ctatagacct gtgtga                             2256
```

```
<210> SEQ ID NO 32
<211> LENGTH: 2256
<212> TYPE: DNA
<213> ORGANISM: Artificial Sequence
<220> FEATURE:
<223> OTHER INFORMATION: hDAO-Hepmut7-Cysmut

<400> SEQUENCE: 32

atgccggccc tgggctgggc cgtggctgcc atcctgatgc tgcagacggc catggcggag     60

ccctccccgg ggactctgcc caggaaggca ggggtgtttt cagacctaag caaccaagag    120

ctgaaggcag tgcacagctt cctctggtcc aagaaggagc tgaggctgca gccctccagt    180

accaccacca tggccaagaa caccgtgttt ctcatcgaga tgctgctgcc caagaagtac    240

catgtgctga ggtttctgga taaaggtgaa aggcatcctg tgcgggaagc ccgtgccgtc    300

atcttctttg gtgaccagga gcatcccaat gtcaccgagt ttgctgtggg gccccctgcca    360

gggcccgcct acatgcgagc actgtccccc aggcctgggt accagtcctc ctgggcatcg    420

aggcccatct ccacagcaga gtatgccctc ctctaccaca ccctgcagga agccaccaag    480

cccctgcatc agttcttcct caataccaca ggcttctcat tccaagactg ccatgacaga    540

tgcctggcct tcaccgatgt ggcccccccgg ggtgtggctt ctggccagcg ccgcagttgg    600

cttatcatac agcgctatgt agaaggctac tttctgcacc ccactgggct ggagctcctc    660

gtggatcatg ggagcacaga tgctgggcac tgggccgtgg agcaggtgtg gtacaacggg    720

aagttctatg ggagcccaga ggaactggct cggaagtatg cagatggaga ggtggacgtg    780

gtggtcctgg aggacccgct gcctgggggc aaggggcatg acagcacaga ggagccgccc    840

ctcttctcct cccacaagcc ccgcggggac ttccccagcc ccatccatgt gagcggcccc    900

cgcttggtcc agccccacgg ccctcgcttc aggctggagg gcaacgctgt gctctacggc    960

ggctggagct ttgccttccg gctgcgctcc tcctccgggc tgcaggtcct gaacgtgcac   1020

ttcggcggag agcgcattgc ctatgaggtc agcgtgcaag aggcagtggc gctgtatgga   1080

ggacacacac ctgcaggcat gcagaccaag tacctcgatg tcggctgggg cctgggcagc   1140

gtcactcatg agttagcccc cggcatcgac tgcccggaga ccgccacctt cctggacact   1200

ttccactact atgatgccga tgacccggtc cattatcccc gagccctctg cctctttgaa   1260

atgcccacag ggtgccccct tcggcggcac tttaattcca actttaaagg tggcttcaac   1320

ttctatgcgg ggctgaaggg ccaggtgctg gtgctgcgga caacttcaac tgtctacaat   1380

tatgattaca tttgggactt tatcttctac cccaacgggg tgatggaggc caagatgcat   1440

gccactggct acgtccacgc caccttctac acccccgagg ggctgcgcca cggcactcgc   1500

ctgcacaccc acctgattgg caacatacac actcacttgg tgcactaccg cgtagacctg   1560

gatgtggcag gcaccaagaa cagcttccag acactgcaga tgaagctaga aaacatcacc   1620

aacccctgga gcccaagaca ccgcgtggtc cagccaactc tggagcagac gcagtactcc   1680

tgggagcgcc aggcggcctt cagcttcaaa aggaagctgc ccacgtacct gctctttacc   1740

agcccccagg agaacccctg gggccacaag cgcagctacc gcctgcagat ccactccatg   1800
```

```
gccgaccagg tgctgccccc aggctggcag gaggagcagg ccatcacctg ggcaaggtac   1860

cccctggcag tgaccaagta ccgggagtcg gagctgtgca gcagcagcat ctaccaccag   1920

aacgacccct ggcacccgcc cgtggtcttt gagcagtttc ttcacaacaa cgagaacatt   1980

gaaaatgagg acctggtggc ctgggtgacg gtgggcttcc tgcacatccc ccactcagag   2040

gacattccca acacagccac acctgggaac tccgtgggct tcctgctccg gccattcaac   2100

ttcttcccag aggacccctc cctggcatcc agagacactg tgatcgtgtg gcctcgggac   2160

aacggcccca actacgtcca gcgctggatc cctgaggaca gggactgctc gatgcctccc   2220

ccttttagct acaatgggac ctatagacct gtgtga                             2256


<210> SEQ ID NO 33
<211> LENGTH: 8
<212> TYPE: PRT
<213> ORGANISM: Artificial Sequence
<220> FEATURE:
<223> OTHER INFORMATION: DAO polypeptide

<400> SEQUENCE: 33

Ser Phe Lys Ala Lys Leu Pro Lys
1               5


<210> SEQ ID NO 34
<211> LENGTH: 8
<212> TYPE: PRT
<213> ORGANISM: Artificial Sequence
<220> FEATURE:
<223> OTHER INFORMATION: DAO polypeptide

<400> SEQUENCE: 34

Ala Phe Lys Ala Lys Leu Pro Thr
1               5


<210> SEQ ID NO 35
<211> LENGTH: 8
<212> TYPE: PRT
<213> ORGANISM: Artificial Sequence
<220> FEATURE:
<223> OTHER INFORMATION: DAO polypeptide

<400> SEQUENCE: 35

Ala Phe Lys Thr Lys Leu Pro Lys
1               5


<210> SEQ ID NO 36
<211> LENGTH: 8
<212> TYPE: PRT
<213> ORGANISM: Artificial Sequence
<220> FEATURE:
<223> OTHER INFORMATION: DAO polypeptide

<400> SEQUENCE: 36

Ser Phe Lys Thr Lys Leu Pro Lys
1               5


<210> SEQ ID NO 37
<211> LENGTH: 8
<212> TYPE: PRT
<213> ORGANISM: Artificial Sequence
<220> FEATURE:
<223> OTHER INFORMATION: DAO polypeptide

<400> SEQUENCE: 37

Ala Phe Lys Thr Lys Leu Pro Thr
```

1 5

<210> SEQ ID NO 38
<211> LENGTH: 8
<212> TYPE: PRT
<213> ORGANISM: Artificial Sequence
<220> FEATURE:
<223> OTHER INFORMATION: DAO polypeptide

<400> SEQUENCE: 38

Ser Phe Lys Ala Lys Leu Pro Lys
1 5

<210> SEQ ID NO 39
<211> LENGTH: 983
<212> TYPE: PRT
<213> ORGANISM: Artificial Sequence
<220> FEATURE:
<223> OTHER INFORMATION: Fc-hDAO

<400> SEQUENCE: 39

Met Pro Ala Leu Gly Trp Ala Val Ala Ala Ile Leu Met Leu Gln Thr
1 5 10 15

Ala Met Ala Glu Cys Pro Pro Cys Pro Ala Pro Pro Val Ala Gly Pro
20 25 30

Ser Val Phe Leu Phe Pro Pro Lys Pro Lys Asp Thr Leu Met Ile Ser
35 40 45

Arg Thr Pro Glu Val Thr Cys Val Val Val Asp Val Ser His Glu Asp
50 55 60

Pro Glu Val Lys Phe Asn Trp Tyr Val Asp Gly Val Glu Val His Asn
65 70 75 80

Ala Lys Thr Lys Pro Arg Glu Glu Gln Tyr Asn Ser Thr Tyr Arg Val
85 90 95

Val Ser Val Leu Thr Val Leu His Gln Asp Trp Leu Asn Gly Lys Glu
100 105 110

Tyr Lys Cys Lys Val Ser Asn Lys Gly Leu Pro Ser Ser Ile Glu Lys
115 120 125

Thr Ile Ser Lys Ala Lys Gly Gln Pro Arg Glu Pro Gln Val Tyr Thr
130 135 140

Leu Pro Pro Ser Arg Glu Glu Met Thr Lys Asn Gln Val Ser Leu Thr
145 150 155 160

Cys Leu Val Lys Gly Phe Tyr Pro Ser Asp Ile Ala Val Glu Trp Glu
165 170 175

Ser Asn Gly Gln Pro Glu Asn Asn Tyr Lys Thr Thr Pro Pro Val Leu
180 185 190

Asp Ser Asp Gly Ser Phe Phe Leu Tyr Ser Lys Leu Thr Val Asp Lys
195 200 205

Ser Arg Trp Gln Gln Gly Asn Val Phe Ser Cys Ser Val Met His Glu
210 215 220

Ala Leu His Asn His Tyr Thr Gln Lys Ser Leu Ser Leu Ser Pro Gly
225 230 235 240

Lys Glu Pro Lys Ser Ala Asp Lys Thr His Thr Glu Pro Ser Pro Gly
245 250 255

Thr Leu Pro Arg Lys Ala Gly Val Phe Ser Asp Leu Ser Asn Gln Glu
260 265 270

Leu Lys Ala Val His Ser Phe Leu Trp Ser Lys Lys Glu Leu Arg Leu
275 280 285

```
Gln Pro Ser Ser Thr Thr Thr Met Ala Lys Asn Thr Val Phe Leu Ile
    290                 295                 300

Glu Met Leu Leu Pro Lys Lys Tyr His Val Leu Arg Phe Leu Asp Lys
305                 310                 315                 320

Gly Glu Arg His Pro Val Arg Glu Ala Arg Ala Val Ile Phe Phe Gly
                325                 330                 335

Asp Gln Glu His Pro Asn Val Thr Glu Phe Ala Val Gly Pro Leu Pro
            340                 345                 350

Gly Pro Cys Tyr Met Arg Ala Leu Ser Pro Arg Pro Gly Tyr Gln Ser
        355                 360                 365

Ser Trp Ala Ser Arg Pro Ile Ser Thr Ala Glu Tyr Ala Leu Leu Tyr
    370                 375                 380

His Thr Leu Gln Glu Ala Thr Lys Pro Leu His Gln Phe Phe Leu Asn
385                 390                 395                 400

Thr Thr Gly Phe Ser Phe Gln Asp Cys His Asp Arg Cys Leu Ala Phe
                405                 410                 415

Thr Asp Val Ala Pro Arg Gly Val Ala Ser Gly Gln Arg Arg Ser Trp
            420                 425                 430

Leu Ile Ile Gln Arg Tyr Val Glu Gly Tyr Phe Leu His Pro Thr Gly
        435                 440                 445

Leu Glu Leu Leu Val Asp His Gly Ser Thr Asp Ala Gly His Trp Ala
    450                 455                 460

Val Glu Gln Val Trp Tyr Asn Gly Lys Phe Tyr Gly Ser Pro Glu Glu
465                 470                 475                 480

Leu Ala Arg Lys Tyr Ala Asp Gly Glu Val Asp Val Val Val Leu Glu
                485                 490                 495

Asp Pro Leu Pro Gly Gly Lys Gly His Asp Ser Thr Glu Glu Pro Pro
            500                 505                 510

Leu Phe Ser Ser His Lys Pro Arg Gly Asp Phe Pro Ser Pro Ile His
        515                 520                 525

Val Ser Gly Pro Arg Leu Val Gln Pro His Gly Pro Arg Phe Arg Leu
    530                 535                 540

Glu Gly Asn Ala Val Leu Tyr Gly Gly Trp Ser Phe Ala Phe Arg Leu
545                 550                 555                 560

Arg Ser Ser Ser Gly Leu Gln Val Leu Asn Val His Phe Gly Gly Glu
                565                 570                 575

Arg Ile Ala Tyr Glu Val Ser Val Gln Glu Ala Val Ala Leu Tyr Gly
            580                 585                 590

Gly His Thr Pro Ala Gly Met Gln Thr Lys Tyr Leu Asp Val Gly Trp
        595                 600                 605

Gly Leu Gly Ser Val Thr His Glu Leu Ala Pro Gly Ile Asp Cys Pro
    610                 615                 620

Glu Thr Ala Thr Phe Leu Asp Thr Phe His Tyr Tyr Asp Ala Asp Asp
625                 630                 635                 640

Pro Val His Tyr Pro Arg Ala Leu Cys Leu Phe Glu Met Pro Thr Gly
                645                 650                 655

Val Pro Leu Arg Arg His Phe Asn Ser Asn Phe Lys Gly Gly Phe Asn
            660                 665                 670

Phe Tyr Ala Gly Leu Lys Gly Gln Val Leu Val Leu Arg Thr Thr Ser
        675                 680                 685

Thr Val Tyr Asn Tyr Asp Tyr Ile Trp Asp Phe Ile Phe Tyr Pro Asn
    690                 695                 700

Gly Val Met Glu Ala Lys Met His Ala Thr Gly Tyr Val His Ala Thr
```

```
705                 710                 715                 720

Phe Tyr Thr Pro Glu Gly Leu Arg His Gly Thr Arg Leu His Thr His
                725                 730                 735

Leu Ile Gly Asn Ile His Thr His Leu Val His Tyr Arg Val Asp Leu
            740                 745                 750

Asp Val Ala Gly Thr Lys Asn Ser Phe Gln Thr Leu Gln Met Lys Leu
        755                 760                 765

Glu Asn Ile Thr Asn Pro Trp Ser Pro Arg His Arg Val Val Gln Pro
    770                 775                 780

Thr Leu Glu Gln Thr Gln Tyr Ser Trp Glu Arg Gln Ala Ala Phe Arg
785                 790                 795                 800

Phe Lys Arg Lys Leu Pro Lys Tyr Leu Leu Phe Thr Ser Pro Gln Glu
                805                 810                 815

Asn Pro Trp Gly His Lys Arg Ser Tyr Arg Leu Gln Ile His Ser Met
            820                 825                 830

Ala Asp Gln Val Leu Pro Pro Gly Trp Gln Glu Glu Gln Ala Ile Thr
        835                 840                 845

Trp Ala Arg Tyr Pro Leu Ala Val Thr Lys Tyr Arg Glu Ser Glu Leu
    850                 855                 860

Cys Ser Ser Ser Ile Tyr His Gln Asn Asp Pro Trp His Pro Pro Val
865                 870                 875                 880

Val Phe Glu Gln Phe Leu His Asn Asn Glu Asn Ile Glu Asn Glu Asp
                885                 890                 895

Leu Val Ala Trp Val Thr Val Gly Phe Leu His Ile Pro His Ser Glu
            900                 905                 910

Asp Ile Pro Asn Thr Ala Thr Pro Gly Asn Ser Val Gly Phe Leu Leu
        915                 920                 925

Arg Pro Phe Asn Phe Phe Pro Glu Asp Pro Ser Leu Ala Ser Arg Asp
    930                 935                 940

Thr Val Ile Val Trp Pro Arg Asp Asn Gly Pro Asn Tyr Val Gln Arg
945                 950                 955                 960

Trp Ile Pro Glu Asp Arg Asp Cys Ser Met Pro Pro Pro Phe Ser Tyr
                965                 970                 975

Asn Gly Thr Tyr Arg Pro Val
            980


<210> SEQ ID NO 40
<211> LENGTH: 983
<212> TYPE: PRT
<213> ORGANISM: Artificial Sequence
<220> FEATURE:
<223> OTHER INFORMATION: Fc-hDAO-Hepmut1

<400> SEQUENCE: 40

Met Pro Ala Leu Gly Trp Ala Val Ala Ala Ile Leu Met Leu Gln Thr
1               5                   10                  15

Ala Met Ala Glu Cys Pro Pro Cys Pro Ala Pro Pro Val Ala Gly Pro
            20                  25                  30

Ser Val Phe Leu Phe Pro Pro Lys Pro Lys Asp Thr Leu Met Ile Ser
        35                  40                  45

Arg Thr Pro Glu Val Thr Cys Val Val Val Asp Val Ser His Glu Asp
    50                  55                  60

Pro Glu Val Lys Phe Asn Trp Tyr Val Asp Gly Val Glu Val His Asn
65                  70                  75                  80

Ala Lys Thr Lys Pro Arg Glu Glu Gln Tyr Asn Ser Thr Tyr Arg Val
```

```
                85                  90                  95

Val Ser Val Leu Thr Val Leu His Gln Asp Trp Leu Asn Gly Lys Glu
            100                 105                 110

Tyr Lys Cys Lys Val Ser Asn Lys Gly Leu Pro Ser Ser Ile Glu Lys
        115                 120                 125

Thr Ile Ser Lys Ala Lys Gly Gln Pro Arg Glu Pro Gln Val Tyr Thr
    130                 135                 140

Leu Pro Pro Ser Arg Glu Glu Met Thr Lys Asn Gln Val Ser Leu Thr
145                 150                 155                 160

Cys Leu Val Lys Gly Phe Tyr Pro Ser Asp Ile Ala Val Glu Trp Glu
                165                 170                 175

Ser Asn Gly Gln Pro Glu Asn Asn Tyr Lys Thr Thr Pro Pro Val Leu
            180                 185                 190

Asp Ser Asp Gly Ser Phe Phe Leu Tyr Ser Lys Leu Thr Val Asp Lys
        195                 200                 205

Ser Arg Trp Gln Gln Gly Asn Val Phe Ser Cys Ser Val Met His Glu
    210                 215                 220

Ala Leu His Asn His Tyr Thr Gln Lys Ser Leu Ser Leu Ser Pro Gly
225                 230                 235                 240

Lys Glu Pro Lys Ser Ala Asp Lys Thr His Thr Glu Pro Ser Pro Gly
                245                 250                 255

Thr Leu Pro Arg Lys Ala Gly Val Phe Ser Asp Leu Ser Asn Gln Glu
            260                 265                 270

Leu Lys Ala Val His Ser Phe Leu Trp Ser Lys Lys Glu Leu Arg Leu
        275                 280                 285

Gln Pro Ser Ser Thr Thr Thr Met Ala Lys Asn Thr Val Phe Leu Ile
    290                 295                 300

Glu Met Leu Leu Pro Lys Lys Tyr His Val Leu Arg Phe Leu Asp Lys
305                 310                 315                 320

Gly Glu Arg His Pro Val Arg Glu Ala Arg Ala Val Ile Phe Phe Gly
                325                 330                 335

Asp Gln Glu His Pro Asn Val Thr Glu Phe Ala Val Gly Pro Leu Pro
            340                 345                 350

Gly Pro Cys Tyr Met Arg Ala Leu Ser Pro Arg Pro Gly Tyr Gln Ser
        355                 360                 365

Ser Trp Ala Ser Arg Pro Ile Ser Thr Ala Glu Tyr Ala Leu Leu Tyr
    370                 375                 380

His Thr Leu Gln Glu Ala Thr Lys Pro Leu His Gln Phe Phe Leu Asn
385                 390                 395                 400

Thr Thr Gly Phe Ser Phe Gln Asp Cys His Asp Arg Cys Leu Ala Phe
                405                 410                 415

Thr Asp Val Ala Pro Arg Gly Val Ala Ser Gly Gln Arg Arg Ser Trp
            420                 425                 430

Leu Ile Ile Gln Arg Tyr Val Glu Gly Tyr Phe Leu His Pro Thr Gly
        435                 440                 445

Leu Glu Leu Leu Val Asp His Gly Ser Thr Asp Ala Gly His Trp Ala
    450                 455                 460

Val Glu Gln Val Trp Tyr Asn Gly Lys Phe Tyr Gly Ser Pro Glu Glu
465                 470                 475                 480

Leu Ala Arg Lys Tyr Ala Asp Gly Glu Val Asp Val Val Val Leu Glu
                485                 490                 495

Asp Pro Leu Pro Gly Gly Lys Gly His Asp Ser Thr Glu Glu Pro Pro
            500                 505                 510
```

```
Leu Phe Ser Ser His Lys Pro Arg Gly Asp Phe Pro Ser Pro Ile His
        515                 520                 525

Val Ser Gly Pro Arg Leu Val Gln Pro His Gly Pro Arg Phe Arg Leu
    530                 535                 540

Glu Gly Asn Ala Val Leu Tyr Gly Gly Trp Ser Phe Ala Phe Arg Leu
545                 550                 555                 560

Arg Ser Ser Ser Gly Leu Gln Val Leu Asn Val His Phe Gly Gly Glu
                565                 570                 575

Arg Ile Ala Tyr Glu Val Ser Val Gln Glu Ala Val Ala Leu Tyr Gly
            580                 585                 590

Gly His Thr Pro Ala Gly Met Gln Thr Lys Tyr Leu Asp Val Gly Trp
        595                 600                 605

Gly Leu Gly Ser Val Thr His Glu Leu Ala Pro Gly Ile Asp Cys Pro
    610                 615                 620

Glu Thr Ala Thr Phe Leu Asp Thr Phe His Tyr Tyr Asp Ala Asp Asp
625                 630                 635                 640

Pro Val His Tyr Pro Arg Ala Leu Cys Leu Phe Glu Met Pro Thr Gly
                645                 650                 655

Val Pro Leu Arg Arg His Phe Asn Ser Asn Phe Lys Gly Gly Phe Asn
            660                 665                 670

Phe Tyr Ala Gly Leu Lys Gly Gln Val Leu Val Leu Arg Thr Thr Ser
        675                 680                 685

Thr Val Tyr Asn Tyr Asp Tyr Ile Trp Asp Phe Ile Phe Tyr Pro Asn
    690                 695                 700

Gly Val Met Glu Ala Lys Met His Ala Thr Gly Tyr Val His Ala Thr
705                 710                 715                 720

Phe Tyr Thr Pro Glu Gly Leu Arg His Gly Thr Arg Leu His Thr His
                725                 730                 735

Leu Ile Gly Asn Ile His Thr His Leu Val His Tyr Arg Val Asp Leu
            740                 745                 750

Asp Val Ala Gly Thr Lys Asn Ser Phe Gln Thr Leu Gln Met Lys Leu
        755                 760                 765

Glu Asn Ile Thr Asn Pro Trp Ser Pro Arg His Arg Val Val Gln Pro
    770                 775                 780

Thr Leu Glu Gln Thr Gln Tyr Ser Trp Glu Arg Gln Ala Ala Phe Ser
785                 790                 795                 800

Phe Lys Arg Lys Leu Pro Lys Tyr Leu Leu Phe Thr Ser Pro Gln Glu
                805                 810                 815

Asn Pro Trp Gly His Lys Arg Ser Tyr Arg Leu Gln Ile His Ser Met
            820                 825                 830

Ala Asp Gln Val Leu Pro Pro Gly Trp Gln Glu Glu Gln Ala Ile Thr
        835                 840                 845

Trp Ala Arg Tyr Pro Leu Ala Val Thr Lys Tyr Arg Glu Ser Glu Leu
    850                 855                 860

Cys Ser Ser Ser Ile Tyr His Gln Asn Asp Pro Trp His Pro Pro Val
865                 870                 875                 880

Val Phe Glu Gln Phe Leu His Asn Asn Glu Asn Ile Glu Asn Glu Asp
                885                 890                 895

Leu Val Ala Trp Val Thr Val Gly Phe Leu His Ile Pro His Ser Glu
            900                 905                 910

Asp Ile Pro Asn Thr Ala Thr Pro Gly Asn Ser Val Gly Phe Leu Leu
        915                 920                 925
```

Arg Pro Phe Asn Phe Phe Pro Glu Asp Pro Ser Leu Ala Ser Arg Asp
    930                 935                 940

Thr Val Ile Val Trp Pro Arg Asp Asn Gly Pro Asn Tyr Val Gln Arg
945                 950                 955                 960

Trp Ile Pro Glu Asp Arg Asp Cys Ser Met Pro Pro Pro Phe Ser Tyr
                965                 970                 975

Asn Gly Thr Tyr Arg Pro Val
            980

<210> SEQ ID NO 41
<211> LENGTH: 983
<212> TYPE: PRT
<213> ORGANISM: Artificial Sequence
<220> FEATURE:
<223> OTHER INFORMATION: Fc-hDAO-Hepmut2

<400> SEQUENCE: 41

Met Pro Ala Leu Gly Trp Ala Val Ala Ala Ile Leu Met Leu Gln Thr
1               5                   10                  15

Ala Met Ala Glu Cys Pro Pro Cys Pro Ala Pro Pro Val Ala Gly Pro
            20                  25                  30

Ser Val Phe Leu Phe Pro Pro Lys Pro Lys Asp Thr Leu Met Ile Ser
        35                  40                  45

Arg Thr Pro Glu Val Thr Cys Val Val Val Asp Val Ser His Glu Asp
    50                  55                  60

Pro Glu Val Lys Phe Asn Trp Tyr Val Asp Gly Val Glu Val His Asn
65                  70                  75                  80

Ala Lys Thr Lys Pro Arg Glu Glu Gln Tyr Asn Ser Thr Tyr Arg Val
                85                  90                  95

Val Ser Val Leu Thr Val Leu His Gln Asp Trp Leu Asn Gly Lys Glu
            100                 105                 110

Tyr Lys Cys Lys Val Ser Asn Lys Gly Leu Pro Ser Ser Ile Glu Lys
        115                 120                 125

Thr Ile Ser Lys Ala Lys Gly Gln Pro Arg Glu Pro Gln Val Tyr Thr
    130                 135                 140

Leu Pro Pro Ser Arg Glu Glu Met Thr Lys Asn Gln Val Ser Leu Thr
145                 150                 155                 160

Cys Leu Val Lys Gly Phe Tyr Pro Ser Asp Ile Ala Val Glu Trp Glu
                165                 170                 175

Ser Asn Gly Gln Pro Glu Asn Asn Tyr Lys Thr Thr Pro Pro Val Leu
            180                 185                 190

Asp Ser Asp Gly Ser Phe Phe Leu Tyr Ser Lys Leu Thr Val Asp Lys
        195                 200                 205

Ser Arg Trp Gln Gln Gly Asn Val Phe Ser Cys Ser Val Met His Glu
    210                 215                 220

Ala Leu His Asn His Tyr Thr Gln Lys Ser Leu Ser Leu Ser Pro Gly
225                 230                 235                 240

Lys Glu Pro Lys Ser Ala Asp Lys Thr His Thr Glu Pro Ser Pro Gly
                245                 250                 255

Thr Leu Pro Arg Lys Ala Gly Val Phe Ser Asp Leu Ser Asn Gln Glu
            260                 265                 270

Leu Lys Ala Val His Ser Phe Leu Trp Ser Lys Lys Glu Leu Arg Leu
        275                 280                 285

Gln Pro Ser Ser Thr Thr Thr Met Ala Lys Asn Thr Val Phe Leu Ile
    290                 295                 300

```
Glu Met Leu Leu Pro Lys Lys Tyr His Val Leu Arg Phe Leu Asp Lys
305                 310                 315                 320

Gly Glu Arg His Pro Val Arg Glu Ala Arg Ala Val Ile Phe Phe Gly
                325                 330                 335

Asp Gln Glu His Pro Asn Val Thr Glu Phe Ala Val Gly Pro Leu Pro
            340                 345                 350

Gly Pro Cys Tyr Met Arg Ala Leu Ser Pro Arg Pro Gly Tyr Gln Ser
        355                 360                 365

Ser Trp Ala Ser Arg Pro Ile Ser Thr Ala Glu Tyr Ala Leu Leu Tyr
    370                 375                 380

His Thr Leu Gln Glu Ala Thr Lys Pro Leu His Gln Phe Phe Leu Asn
385                 390                 395                 400

Thr Thr Gly Phe Ser Phe Gln Asp Cys His Asp Arg Cys Leu Ala Phe
                405                 410                 415

Thr Asp Val Ala Pro Arg Gly Val Ala Ser Gly Gln Arg Arg Ser Trp
            420                 425                 430

Leu Ile Ile Gln Arg Tyr Val Glu Gly Tyr Phe Leu His Pro Thr Gly
        435                 440                 445

Leu Glu Leu Leu Val Asp His Gly Ser Thr Asp Ala Gly His Trp Ala
    450                 455                 460

Val Glu Gln Val Trp Tyr Asn Gly Lys Phe Tyr Gly Ser Pro Glu Glu
465                 470                 475                 480

Leu Ala Arg Lys Tyr Ala Asp Gly Glu Val Asp Val Val Val Leu Glu
                485                 490                 495

Asp Pro Leu Pro Gly Gly Lys Gly His Asp Ser Thr Glu Glu Pro Pro
            500                 505                 510

Leu Phe Ser Ser His Lys Pro Arg Gly Asp Phe Pro Ser Pro Ile His
        515                 520                 525

Val Ser Gly Pro Arg Leu Val Gln Pro His Gly Pro Arg Phe Arg Leu
    530                 535                 540

Glu Gly Asn Ala Val Leu Tyr Gly Gly Trp Ser Phe Ala Phe Arg Leu
545                 550                 555                 560

Arg Ser Ser Ser Gly Leu Gln Val Leu Asn Val His Phe Gly Gly Glu
                565                 570                 575

Arg Ile Ala Tyr Glu Val Ser Val Gln Glu Ala Val Ala Leu Tyr Gly
            580                 585                 590

Gly His Thr Pro Ala Gly Met Gln Thr Lys Tyr Leu Asp Val Gly Trp
        595                 600                 605

Gly Leu Gly Ser Val Thr His Glu Leu Ala Pro Gly Ile Asp Cys Pro
    610                 615                 620

Glu Thr Ala Thr Phe Leu Asp Thr Phe His Tyr Tyr Asp Ala Asp Asp
625                 630                 635                 640

Pro Val His Tyr Pro Arg Ala Leu Cys Leu Phe Glu Met Pro Thr Gly
                645                 650                 655

Val Pro Leu Arg Arg His Phe Asn Ser Asn Phe Lys Gly Gly Phe Asn
            660                 665                 670

Phe Tyr Ala Gly Leu Lys Gly Gln Val Leu Val Leu Arg Thr Thr Ser
        675                 680                 685

Thr Val Tyr Asn Tyr Asp Tyr Ile Trp Asp Phe Ile Phe Tyr Pro Asn
    690                 695                 700

Gly Val Met Glu Ala Lys Met His Ala Thr Gly Tyr Val His Ala Thr
705                 710                 715                 720

Phe Tyr Thr Pro Glu Gly Leu Arg His Gly Thr Arg Leu His Thr His
```

```
                725                 730                 735

Leu Ile Gly Asn Ile His Thr His Leu Val His Tyr Arg Val Asp Leu
            740                 745                 750

Asp Val Ala Gly Thr Lys Asn Ser Phe Gln Thr Leu Gln Met Lys Leu
        755                 760                 765

Glu Asn Ile Thr Asn Pro Trp Ser Pro Arg His Arg Val Val Gln Pro
    770                 775                 780

Thr Leu Glu Gln Thr Gln Tyr Ser Trp Glu Arg Gln Ala Ala Phe Arg
785                 790                 795                 800

Phe Lys Arg Lys Leu Pro Thr Tyr Leu Leu Phe Thr Ser Pro Gln Glu
                805                 810                 815

Asn Pro Trp Gly His Lys Arg Ser Tyr Arg Leu Gln Ile His Ser Met
            820                 825                 830

Ala Asp Gln Val Leu Pro Pro Gly Trp Gln Glu Glu Gln Ala Ile Thr
        835                 840                 845

Trp Ala Arg Tyr Pro Leu Ala Val Thr Lys Tyr Arg Glu Ser Glu Leu
    850                 855                 860

Cys Ser Ser Ser Ile Tyr His Gln Asn Asp Pro Trp His Pro Pro Val
865                 870                 875                 880

Val Phe Glu Gln Phe Leu His Asn Asn Glu Asn Ile Glu Asn Glu Asp
                885                 890                 895

Leu Val Ala Trp Val Thr Val Gly Phe Leu His Ile Pro His Ser Glu
            900                 905                 910

Asp Ile Pro Asn Thr Ala Thr Pro Gly Asn Ser Val Gly Phe Leu Leu
        915                 920                 925

Arg Pro Phe Asn Phe Phe Pro Glu Asp Pro Ser Leu Ala Ser Arg Asp
    930                 935                 940

Thr Val Ile Val Trp Pro Arg Asp Asn Gly Pro Asn Tyr Val Gln Arg
945                 950                 955                 960

Trp Ile Pro Glu Asp Arg Asp Cys Ser Met Pro Pro Pro Phe Ser Tyr
                965                 970                 975

Asn Gly Thr Tyr Arg Pro Val
            980


<210> SEQ ID NO 42
<211> LENGTH: 983
<212> TYPE: PRT
<213> ORGANISM: Artificial Sequence
<220> FEATURE:
<223> OTHER INFORMATION: Fc-hDAO-Hepmut3

<400> SEQUENCE: 42

Met Pro Ala Leu Gly Trp Ala Val Ala Ala Ile Leu Met Leu Gln Thr
1               5                   10                  15

Ala Met Ala Glu Cys Pro Pro Cys Pro Ala Pro Pro Val Ala Gly Pro
            20                  25                  30

Ser Val Phe Leu Phe Pro Pro Lys Pro Lys Asp Thr Leu Met Ile Ser
        35                  40                  45

Arg Thr Pro Glu Val Thr Cys Val Val Val Asp Val Ser His Glu Asp
    50                  55                  60

Pro Glu Val Lys Phe Asn Trp Tyr Val Asp Gly Val Glu Val His Asn
65                  70                  75                  80

Ala Lys Thr Lys Pro Arg Glu Glu Gln Tyr Asn Ser Thr Tyr Arg Val
                85                  90                  95

Val Ser Val Leu Thr Val Leu His Gln Asp Trp Leu Asn Gly Lys Glu
```

```
            100                 105                 110

Tyr Lys Cys Lys Val Ser Asn Lys Gly Leu Pro Ser Ser Ile Glu Lys
        115                 120                 125

Thr Ile Ser Lys Ala Lys Gly Gln Pro Arg Glu Pro Gln Val Tyr Thr
    130                 135                 140

Leu Pro Pro Ser Arg Glu Glu Met Thr Lys Asn Gln Val Ser Leu Thr
145                 150                 155                 160

Cys Leu Val Lys Gly Phe Tyr Pro Ser Asp Ile Ala Val Glu Trp Glu
                165                 170                 175

Ser Asn Gly Gln Pro Glu Asn Asn Tyr Lys Thr Thr Pro Pro Val Leu
            180                 185                 190

Asp Ser Asp Gly Ser Phe Phe Leu Tyr Ser Lys Leu Thr Val Asp Lys
        195                 200                 205

Ser Arg Trp Gln Gln Gly Asn Val Phe Ser Cys Ser Val Met His Glu
    210                 215                 220

Ala Leu His Asn His Tyr Thr Gln Lys Ser Leu Ser Leu Ser Pro Gly
225                 230                 235                 240

Lys Glu Pro Lys Ser Ala Asp Lys Thr His Thr Glu Pro Ser Pro Gly
                245                 250                 255

Thr Leu Pro Arg Lys Ala Gly Val Phe Ser Asp Leu Ser Asn Gln Glu
            260                 265                 270

Leu Lys Ala Val His Ser Phe Leu Trp Ser Lys Lys Glu Leu Arg Leu
        275                 280                 285

Gln Pro Ser Ser Thr Thr Thr Met Ala Lys Asn Thr Val Phe Leu Ile
    290                 295                 300

Glu Met Leu Leu Pro Lys Lys Tyr His Val Leu Arg Phe Leu Asp Lys
305                 310                 315                 320

Gly Glu Arg His Pro Val Arg Glu Ala Arg Ala Val Ile Phe Phe Gly
                325                 330                 335

Asp Gln Glu His Pro Asn Val Thr Glu Phe Ala Val Gly Pro Leu Pro
            340                 345                 350

Gly Pro Cys Tyr Met Arg Ala Leu Ser Pro Arg Pro Gly Tyr Gln Ser
        355                 360                 365

Ser Trp Ala Ser Arg Pro Ile Ser Thr Ala Glu Tyr Ala Leu Leu Tyr
    370                 375                 380

His Thr Leu Gln Glu Ala Thr Lys Pro Leu His Gln Phe Phe Leu Asn
385                 390                 395                 400

Thr Thr Gly Phe Ser Phe Gln Asp Cys His Asp Arg Cys Leu Ala Phe
                405                 410                 415

Thr Asp Val Ala Pro Arg Gly Val Ala Ser Gly Gln Arg Arg Ser Trp
            420                 425                 430

Leu Ile Ile Gln Arg Tyr Val Glu Gly Tyr Phe Leu His Pro Thr Gly
        435                 440                 445

Leu Glu Leu Leu Val Asp His Gly Ser Thr Asp Ala Gly His Trp Ala
    450                 455                 460

Val Glu Gln Val Trp Tyr Asn Gly Lys Phe Tyr Gly Ser Pro Glu Glu
465                 470                 475                 480

Leu Ala Arg Lys Tyr Ala Asp Gly Glu Val Asp Val Val Val Leu Glu
                485                 490                 495

Asp Pro Leu Pro Gly Gly Lys Gly His Asp Ser Thr Glu Glu Pro Pro
            500                 505                 510

Leu Phe Ser Ser His Lys Pro Arg Gly Asp Phe Pro Ser Pro Ile His
        515                 520                 525
```

```
Val Ser Gly Pro Arg Leu Val Gln Pro His Gly Pro Arg Phe Arg Leu
    530                 535                 540

Glu Gly Asn Ala Val Leu Tyr Gly Gly Trp Ser Phe Ala Phe Arg Leu
545                 550                 555                 560

Arg Ser Ser Ser Gly Leu Gln Val Leu Asn Val His Phe Gly Gly Glu
                565                 570                 575

Arg Ile Ala Tyr Glu Val Ser Val Gln Glu Ala Val Ala Leu Tyr Gly
            580                 585                 590

Gly His Thr Pro Ala Gly Met Gln Thr Lys Tyr Leu Asp Val Gly Trp
        595                 600                 605

Gly Leu Gly Ser Val Thr His Glu Leu Ala Pro Gly Ile Asp Cys Pro
    610                 615                 620

Glu Thr Ala Thr Phe Leu Asp Thr Phe His Tyr Tyr Asp Ala Asp Asp
625                 630                 635                 640

Pro Val His Tyr Pro Arg Ala Leu Cys Leu Phe Glu Met Pro Thr Gly
                645                 650                 655

Val Pro Leu Arg Arg His Phe Asn Ser Asn Phe Lys Gly Gly Phe Asn
            660                 665                 670

Phe Tyr Ala Gly Leu Lys Gly Gln Val Leu Val Leu Arg Thr Thr Ser
        675                 680                 685

Thr Val Tyr Asn Tyr Asp Tyr Ile Trp Asp Phe Ile Phe Tyr Pro Asn
    690                 695                 700

Gly Val Met Glu Ala Lys Met His Ala Thr Gly Tyr Val His Ala Thr
705                 710                 715                 720

Phe Tyr Thr Pro Glu Gly Leu Arg His Gly Thr Arg Leu His Thr His
                725                 730                 735

Leu Ile Gly Asn Ile His Thr His Leu Val His Tyr Arg Val Asp Leu
            740                 745                 750

Asp Val Ala Gly Thr Lys Asn Ser Phe Gln Thr Leu Gln Met Lys Leu
        755                 760                 765

Glu Asn Ile Thr Asn Pro Trp Ser Pro Arg His Arg Val Val Gln Pro
    770                 775                 780

Thr Leu Glu Gln Thr Gln Tyr Ser Trp Glu Arg Gln Ala Ala Phe Arg
785                 790                 795                 800

Phe Lys Thr Lys Leu Pro Lys Tyr Leu Leu Phe Thr Ser Pro Gln Glu
                805                 810                 815

Asn Pro Trp Gly His Lys Arg Ser Tyr Arg Leu Gln Ile His Ser Met
            820                 825                 830

Ala Asp Gln Val Leu Pro Pro Gly Trp Gln Glu Glu Gln Ala Ile Thr
        835                 840                 845

Trp Ala Arg Tyr Pro Leu Ala Val Thr Lys Tyr Arg Glu Ser Glu Leu
    850                 855                 860

Cys Ser Ser Ser Ile Tyr His Gln Asn Asp Pro Trp His Pro Pro Val
865                 870                 875                 880

Val Phe Glu Gln Phe Leu His Asn Asn Glu Asn Ile Glu Asn Glu Asp
                885                 890                 895

Leu Val Ala Trp Val Thr Val Gly Phe Leu His Ile Pro His Ser Glu
            900                 905                 910

Asp Ile Pro Asn Thr Ala Thr Pro Gly Asn Ser Val Gly Phe Leu Leu
        915                 920                 925

Arg Pro Phe Asn Phe Phe Pro Glu Asp Pro Ser Leu Ala Ser Arg Asp
    930                 935                 940
```

```
Thr Val Ile Val Trp Pro Arg Asp Asn Gly Pro Asn Tyr Val Gln Arg
945                 950                 955                 960

Trp Ile Pro Glu Asp Arg Asp Cys Ser Met Pro Pro Pro Phe Ser Tyr
                965                 970                 975

Asn Gly Thr Tyr Arg Pro Val
            980


<210> SEQ ID NO 43
<211> LENGTH: 983
<212> TYPE: PRT
<213> ORGANISM: Artificial Sequence
<220> FEATURE:
<223> OTHER INFORMATION: Fc-hDAO-Hepmut4

<400> SEQUENCE: 43

Met Pro Ala Leu Gly Trp Ala Val Ala Ala Ile Leu Met Leu Gln Thr
1               5                   10                  15

Ala Met Ala Glu Cys Pro Pro Cys Pro Ala Pro Pro Val Ala Gly Pro
            20                  25                  30

Ser Val Phe Leu Phe Pro Pro Lys Pro Lys Asp Thr Leu Met Ile Ser
        35                  40                  45

Arg Thr Pro Glu Val Thr Cys Val Val Val Asp Val Ser His Glu Asp
    50                  55                  60

Pro Glu Val Lys Phe Asn Trp Tyr Val Asp Gly Val Glu Val His Asn
65                  70                  75                  80

Ala Lys Thr Lys Pro Arg Glu Glu Gln Tyr Asn Ser Thr Tyr Arg Val
                85                  90                  95

Val Ser Val Leu Thr Val Leu His Gln Asp Trp Leu Asn Gly Lys Glu
            100                 105                 110

Tyr Lys Cys Lys Val Ser Asn Lys Gly Leu Pro Ser Ser Ile Glu Lys
        115                 120                 125

Thr Ile Ser Lys Ala Lys Gly Gln Pro Arg Glu Pro Gln Val Tyr Thr
    130                 135                 140

Leu Pro Pro Ser Arg Glu Glu Met Thr Lys Asn Gln Val Ser Leu Thr
145                 150                 155                 160

Cys Leu Val Lys Gly Phe Tyr Pro Ser Asp Ile Ala Val Glu Trp Glu
                165                 170                 175

Ser Asn Gly Gln Pro Glu Asn Asn Tyr Lys Thr Thr Pro Pro Val Leu
            180                 185                 190

Asp Ser Asp Gly Ser Phe Phe Leu Tyr Ser Lys Leu Thr Val Asp Lys
        195                 200                 205

Ser Arg Trp Gln Gln Gly Asn Val Phe Ser Cys Ser Val Met His Glu
    210                 215                 220

Ala Leu His Asn His Tyr Thr Gln Lys Ser Leu Ser Leu Ser Pro Gly
225                 230                 235                 240

Lys Glu Pro Lys Ser Ala Asp Lys Thr His Thr Glu Pro Ser Pro Gly
                245                 250                 255

Thr Leu Pro Arg Lys Ala Gly Val Phe Ser Asp Leu Ser Asn Gln Glu
            260                 265                 270

Leu Lys Ala Val His Ser Phe Leu Trp Ser Lys Lys Glu Leu Arg Leu
        275                 280                 285

Gln Pro Ser Ser Thr Thr Thr Met Ala Lys Asn Thr Val Phe Leu Ile
    290                 295                 300

Glu Met Leu Leu Pro Lys Lys Tyr His Val Leu Arg Phe Leu Asp Lys
305                 310                 315                 320
```

```
Gly Glu Arg His Pro Val Arg Glu Ala Arg Ala Val Ile Phe Phe Gly
                325                 330                 335

Asp Gln Glu His Pro Asn Val Thr Glu Phe Ala Val Gly Pro Leu Pro
            340                 345                 350

Gly Pro Cys Tyr Met Arg Ala Leu Ser Pro Arg Pro Gly Tyr Gln Ser
        355                 360                 365

Ser Trp Ala Ser Arg Pro Ile Ser Thr Ala Glu Tyr Ala Leu Leu Tyr
    370                 375                 380

His Thr Leu Gln Glu Ala Thr Lys Pro Leu His Gln Phe Phe Leu Asn
385                 390                 395                 400

Thr Thr Gly Phe Ser Phe Gln Asp Cys His Asp Arg Cys Leu Ala Phe
                405                 410                 415

Thr Asp Val Ala Pro Arg Gly Val Ala Ser Gly Gln Arg Arg Ser Trp
            420                 425                 430

Leu Ile Ile Gln Arg Tyr Val Glu Gly Tyr Phe Leu His Pro Thr Gly
        435                 440                 445

Leu Glu Leu Leu Val Asp His Gly Ser Thr Asp Ala Gly His Trp Ala
    450                 455                 460

Val Glu Gln Val Trp Tyr Asn Gly Lys Phe Tyr Gly Ser Pro Glu Glu
465                 470                 475                 480

Leu Ala Arg Lys Tyr Ala Asp Gly Glu Val Asp Val Val Val Leu Glu
                485                 490                 495

Asp Pro Leu Pro Gly Gly Lys Gly His Asp Ser Thr Glu Glu Pro Pro
            500                 505                 510

Leu Phe Ser Ser His Lys Pro Arg Gly Asp Phe Pro Ser Pro Ile His
        515                 520                 525

Val Ser Gly Pro Arg Leu Val Gln Pro His Gly Pro Arg Phe Arg Leu
    530                 535                 540

Glu Gly Asn Ala Val Leu Tyr Gly Gly Trp Ser Phe Ala Phe Arg Leu
545                 550                 555                 560

Arg Ser Ser Ser Gly Leu Gln Val Leu Asn Val His Phe Gly Gly Glu
                565                 570                 575

Arg Ile Ala Tyr Glu Val Ser Val Gln Glu Ala Val Ala Leu Tyr Gly
            580                 585                 590

Gly His Thr Pro Ala Gly Met Gln Thr Lys Tyr Leu Asp Val Gly Trp
        595                 600                 605

Gly Leu Gly Ser Val Thr His Glu Leu Ala Pro Gly Ile Asp Cys Pro
    610                 615                 620

Glu Thr Ala Thr Phe Leu Asp Thr Phe His Tyr Tyr Asp Ala Asp Asp
625                 630                 635                 640

Pro Val His Tyr Pro Arg Ala Leu Cys Leu Phe Glu Met Pro Thr Gly
                645                 650                 655

Val Pro Leu Arg Arg His Phe Asn Ser Asn Phe Lys Gly Gly Phe Asn
            660                 665                 670

Phe Tyr Ala Gly Leu Lys Gly Gln Val Leu Val Leu Arg Thr Thr Ser
        675                 680                 685

Thr Val Tyr Asn Tyr Asp Tyr Ile Trp Asp Phe Ile Phe Tyr Pro Asn
    690                 695                 700

Gly Val Met Glu Ala Lys Met His Ala Thr Gly Tyr Val His Ala Thr
705                 710                 715                 720

Phe Tyr Thr Pro Glu Gly Leu Arg His Gly Thr Arg Leu His Thr His
                725                 730                 735

Leu Ile Gly Asn Ile His Thr His Leu Val His Tyr Arg Val Asp Leu
```

```
            740                 745                 750

Asp Val Ala Gly Thr Lys Asn Ser Phe Gln Thr Leu Gln Met Lys Leu
        755                 760                 765

Glu Asn Ile Thr Asn Pro Trp Ser Pro Arg His Arg Val Val Gln Pro
    770                 775                 780

Thr Leu Glu Gln Thr Gln Tyr Ser Trp Glu Arg Gln Ala Ala Phe Ser
785                 790                 795                 800

Phe Lys Thr Lys Leu Pro Lys Tyr Leu Leu Phe Thr Ser Pro Gln Glu
                805                 810                 815

Asn Pro Trp Gly His Lys Arg Ser Tyr Arg Leu Gln Ile His Ser Met
            820                 825                 830

Ala Asp Gln Val Leu Pro Pro Gly Trp Gln Glu Glu Gln Ala Ile Thr
        835                 840                 845

Trp Ala Arg Tyr Pro Leu Ala Val Thr Lys Tyr Arg Glu Ser Glu Leu
    850                 855                 860

Cys Ser Ser Ser Ile Tyr His Gln Asn Asp Pro Trp His Pro Pro Val
865                 870                 875                 880

Val Phe Glu Gln Phe Leu His Asn Asn Glu Asn Ile Glu Asn Glu Asp
                885                 890                 895

Leu Val Ala Trp Val Thr Val Gly Phe Leu His Ile Pro His Ser Glu
            900                 905                 910

Asp Ile Pro Asn Thr Ala Thr Pro Gly Asn Ser Val Gly Phe Leu Leu
        915                 920                 925

Arg Pro Phe Asn Phe Phe Pro Glu Asp Pro Ser Leu Ala Ser Arg Asp
    930                 935                 940

Thr Val Ile Val Trp Pro Arg Asp Asn Gly Pro Asn Tyr Val Gln Arg
945                 950                 955                 960

Trp Ile Pro Glu Asp Arg Asp Cys Ser Met Pro Pro Pro Phe Ser Tyr
                965                 970                 975

Asn Gly Thr Tyr Arg Pro Val
            980


<210> SEQ ID NO 44
<211> LENGTH: 983
<212> TYPE: PRT
<213> ORGANISM: Artificial Sequence
<220> FEATURE:
<223> OTHER INFORMATION: Fc-hDAO-Hepmut5

<400> SEQUENCE: 44

Met Pro Ala Leu Gly Trp Ala Val Ala Ala Ile Leu Met Leu Gln Thr
1               5                   10                  15

Ala Met Ala Glu Cys Pro Pro Cys Pro Ala Pro Pro Val Ala Gly Pro
            20                  25                  30

Ser Val Phe Leu Phe Pro Pro Lys Pro Lys Asp Thr Leu Met Ile Ser
        35                  40                  45

Arg Thr Pro Glu Val Thr Cys Val Val Val Asp Val Ser His Glu Asp
    50                  55                  60

Pro Glu Val Lys Phe Asn Trp Tyr Val Asp Gly Val Glu Val His Asn
65                  70                  75                  80

Ala Lys Thr Lys Pro Arg Glu Glu Gln Tyr Asn Ser Thr Tyr Arg Val
                85                  90                  95

Val Ser Val Leu Thr Val Leu His Gln Asp Trp Leu Asn Gly Lys Glu
            100                 105                 110

Tyr Lys Cys Lys Val Ser Asn Lys Gly Leu Pro Ser Ser Ile Glu Lys
```

```
        115                 120                 125

Thr Ile Ser Lys Ala Lys Gly Gln Pro Arg Glu Pro Gln Val Tyr Thr
    130                 135                 140

Leu Pro Pro Ser Arg Glu Glu Met Thr Lys Asn Gln Val Ser Leu Thr
145                 150                 155                 160

Cys Leu Val Lys Gly Phe Tyr Pro Ser Asp Ile Ala Val Glu Trp Glu
                165                 170                 175

Ser Asn Gly Gln Pro Glu Asn Asn Tyr Lys Thr Thr Pro Pro Val Leu
            180                 185                 190

Asp Ser Asp Gly Ser Phe Phe Leu Tyr Ser Lys Leu Thr Val Asp Lys
        195                 200                 205

Ser Arg Trp Gln Gln Gly Asn Val Phe Ser Cys Ser Val Met His Glu
    210                 215                 220

Ala Leu His Asn His Tyr Thr Gln Lys Ser Leu Ser Leu Ser Pro Gly
225                 230                 235                 240

Lys Glu Pro Lys Ser Ala Asp Lys Thr His Thr Glu Pro Ser Pro Gly
                245                 250                 255

Thr Leu Pro Arg Lys Ala Gly Val Phe Ser Asp Leu Ser Asn Gln Glu
            260                 265                 270

Leu Lys Ala Val His Ser Phe Leu Trp Ser Lys Lys Glu Leu Arg Leu
        275                 280                 285

Gln Pro Ser Ser Thr Thr Thr Met Ala Lys Asn Thr Val Phe Leu Ile
    290                 295                 300

Glu Met Leu Leu Pro Lys Lys Tyr His Val Leu Arg Phe Leu Asp Lys
305                 310                 315                 320

Gly Glu Arg His Pro Val Arg Glu Ala Arg Ala Val Ile Phe Phe Gly
                325                 330                 335

Asp Gln Glu His Pro Asn Val Thr Glu Phe Ala Val Gly Pro Leu Pro
            340                 345                 350

Gly Pro Cys Tyr Met Arg Ala Leu Ser Pro Arg Pro Gly Tyr Gln Ser
        355                 360                 365

Ser Trp Ala Ser Arg Pro Ile Ser Thr Ala Glu Tyr Ala Leu Leu Tyr
    370                 375                 380

His Thr Leu Gln Glu Ala Thr Lys Pro Leu His Gln Phe Phe Leu Asn
385                 390                 395                 400

Thr Thr Gly Phe Ser Phe Gln Asp Cys His Asp Arg Cys Leu Ala Phe
                405                 410                 415

Thr Asp Val Ala Pro Arg Gly Val Ala Ser Gly Gln Arg Arg Ser Trp
            420                 425                 430

Leu Ile Ile Gln Arg Tyr Val Glu Gly Tyr Phe Leu His Pro Thr Gly
        435                 440                 445

Leu Glu Leu Leu Val Asp His Gly Ser Thr Asp Ala Gly His Trp Ala
    450                 455                 460

Val Glu Gln Val Trp Tyr Asn Gly Lys Phe Tyr Gly Ser Pro Glu Glu
465                 470                 475                 480

Leu Ala Arg Lys Tyr Ala Asp Gly Glu Val Asp Val Val Val Leu Glu
                485                 490                 495

Asp Pro Leu Pro Gly Gly Lys Gly His Asp Ser Thr Glu Glu Pro Pro
            500                 505                 510

Leu Phe Ser Ser His Lys Pro Arg Gly Asp Phe Pro Ser Pro Ile His
        515                 520                 525

Val Ser Gly Pro Arg Leu Val Gln Pro His Gly Pro Arg Phe Arg Leu
    530                 535                 540
```

```
Glu Gly Asn Ala Val Leu Tyr Gly Gly Trp Ser Phe Ala Phe Arg Leu
545                 550                 555                 560

Arg Ser Ser Ser Gly Leu Gln Val Leu Asn Val His Phe Gly Gly Glu
                565                 570                 575

Arg Ile Ala Tyr Glu Val Ser Val Gln Glu Ala Val Ala Leu Tyr Gly
            580                 585                 590

Gly His Thr Pro Ala Gly Met Gln Thr Lys Tyr Leu Asp Val Gly Trp
        595                 600                 605

Gly Leu Gly Ser Val Thr His Glu Leu Ala Pro Gly Ile Asp Cys Pro
    610                 615                 620

Glu Thr Ala Thr Phe Leu Asp Thr Phe His Tyr Tyr Asp Ala Asp Asp
625                 630                 635                 640

Pro Val His Tyr Pro Arg Ala Leu Cys Leu Phe Glu Met Pro Thr Gly
                645                 650                 655

Val Pro Leu Arg Arg His Phe Asn Ser Asn Phe Lys Gly Gly Phe Asn
            660                 665                 670

Phe Tyr Ala Gly Leu Lys Gly Gln Val Leu Val Leu Arg Thr Thr Ser
        675                 680                 685

Thr Val Tyr Asn Tyr Asp Tyr Ile Trp Asp Phe Ile Phe Tyr Pro Asn
    690                 695                 700

Gly Val Met Glu Ala Lys Met His Ala Thr Gly Tyr Val His Ala Thr
705                 710                 715                 720

Phe Tyr Thr Pro Glu Gly Leu Arg His Gly Thr Arg Leu His Thr His
                725                 730                 735

Leu Ile Gly Asn Ile His Thr His Leu Val His Tyr Arg Val Asp Leu
            740                 745                 750

Asp Val Ala Gly Thr Lys Asn Ser Phe Gln Thr Leu Gln Met Lys Leu
        755                 760                 765

Glu Asn Ile Thr Asn Pro Trp Ser Pro Arg His Arg Val Val Gln Pro
    770                 775                 780

Thr Leu Glu Gln Thr Gln Tyr Ser Trp Glu Arg Gln Ala Ala Phe Arg
785                 790                 795                 800

Phe Lys Thr Lys Leu Pro Thr Tyr Leu Leu Phe Thr Ser Pro Gln Glu
                805                 810                 815

Asn Pro Trp Gly His Lys Arg Ser Tyr Arg Leu Gln Ile His Ser Met
            820                 825                 830

Ala Asp Gln Val Leu Pro Pro Gly Trp Gln Glu Glu Gln Ala Ile Thr
        835                 840                 845

Trp Ala Arg Tyr Pro Leu Ala Val Thr Lys Tyr Arg Glu Ser Glu Leu
    850                 855                 860

Cys Ser Ser Ser Ile Tyr His Gln Asn Asp Pro Trp His Pro Pro Val
865                 870                 875                 880

Val Phe Glu Gln Phe Leu His Asn Asn Glu Asn Ile Glu Asn Glu Asp
                885                 890                 895

Leu Val Ala Trp Val Thr Val Gly Phe Leu His Ile Pro His Ser Glu
            900                 905                 910

Asp Ile Pro Asn Thr Ala Thr Pro Gly Asn Ser Val Gly Phe Leu Leu
        915                 920                 925

Arg Pro Phe Asn Phe Phe Pro Glu Asp Pro Ser Leu Ala Ser Arg Asp
    930                 935                 940

Thr Val Ile Val Trp Pro Arg Asp Asn Gly Pro Asn Tyr Val Gln Arg
945                 950                 955                 960
```

```
Trp Ile Pro Glu Asp Arg Asp Cys Ser Met Pro Pro Pro Phe Ser Tyr
                965                 970                 975

Asn Gly Thr Tyr Arg Pro Val
            980
```

<210> SEQ ID NO 45
<211> LENGTH: 983
<212> TYPE: PRT
<213> ORGANISM: Artificial Sequence
<220> FEATURE:
<223> OTHER INFORMATION: Fc-hDAO-Hepmut6

<400> SEQUENCE: 45

```
Met Pro Ala Leu Gly Trp Ala Val Ala Ala Ile Leu Met Leu Gln Thr
1               5                   10                  15

Ala Met Ala Glu Cys Pro Pro Cys Pro Ala Pro Pro Val Ala Gly Pro
            20                  25                  30

Ser Val Phe Leu Phe Pro Pro Lys Pro Lys Asp Thr Leu Met Ile Ser
        35                  40                  45

Arg Thr Pro Glu Val Thr Cys Val Val Val Asp Val Ser His Glu Asp
    50                  55                  60

Pro Glu Val Lys Phe Asn Trp Tyr Val Asp Gly Val Glu Val His Asn
65                  70                  75                  80

Ala Lys Thr Lys Pro Arg Glu Glu Gln Tyr Asn Ser Thr Tyr Arg Val
                85                  90                  95

Val Ser Val Leu Thr Val Leu His Gln Asp Trp Leu Asn Gly Lys Glu
            100                 105                 110

Tyr Lys Cys Lys Val Ser Asn Lys Gly Leu Pro Ser Ser Ile Glu Lys
        115                 120                 125

Thr Ile Ser Lys Ala Lys Gly Gln Pro Arg Glu Pro Gln Val Tyr Thr
    130                 135                 140

Leu Pro Pro Ser Arg Glu Glu Met Thr Lys Asn Gln Val Ser Leu Thr
145                 150                 155                 160

Cys Leu Val Lys Gly Phe Tyr Pro Ser Asp Ile Ala Val Glu Trp Glu
                165                 170                 175

Ser Asn Gly Gln Pro Glu Asn Asn Tyr Lys Thr Thr Pro Pro Val Leu
            180                 185                 190

Asp Ser Asp Gly Ser Phe Phe Leu Tyr Ser Lys Leu Thr Val Asp Lys
        195                 200                 205

Ser Arg Trp Gln Gln Gly Asn Val Phe Ser Cys Ser Val Met His Glu
    210                 215                 220

Ala Leu His Asn His Tyr Thr Gln Lys Ser Leu Ser Leu Ser Pro Gly
225                 230                 235                 240

Lys Glu Pro Lys Ser Ala Asp Lys Thr His Thr Glu Pro Ser Pro Gly
                245                 250                 255

Thr Leu Pro Arg Lys Ala Gly Val Phe Ser Asp Leu Ser Asn Gln Glu
            260                 265                 270

Leu Lys Ala Val His Ser Phe Leu Trp Ser Lys Lys Glu Leu Arg Leu
        275                 280                 285

Gln Pro Ser Ser Thr Thr Thr Met Ala Lys Asn Thr Val Phe Leu Ile
    290                 295                 300

Glu Met Leu Leu Pro Lys Lys Tyr His Val Leu Arg Phe Leu Asp Lys
305                 310                 315                 320

Gly Glu Arg His Pro Val Arg Glu Ala Arg Ala Val Ile Phe Phe Gly
                325                 330                 335
```

```
Asp Gln Glu His Pro Asn Val Thr Glu Phe Ala Val Gly Pro Leu Pro
            340                 345                 350

Gly Pro Cys Tyr Met Arg Ala Leu Ser Pro Arg Pro Gly Tyr Gln Ser
        355                 360                 365

Ser Trp Ala Ser Arg Pro Ile Ser Thr Ala Glu Tyr Ala Leu Leu Tyr
    370                 375                 380

His Thr Leu Gln Glu Ala Thr Lys Pro Leu His Gln Phe Phe Leu Asn
385                 390                 395                 400

Thr Thr Gly Phe Ser Phe Gln Asp Cys His Asp Arg Cys Leu Ala Phe
                405                 410                 415

Thr Asp Val Ala Pro Arg Gly Val Ala Ser Gly Gln Arg Arg Ser Trp
            420                 425                 430

Leu Ile Ile Gln Arg Tyr Val Glu Gly Tyr Phe Leu His Pro Thr Gly
        435                 440                 445

Leu Glu Leu Leu Val Asp His Gly Ser Thr Asp Ala Gly His Trp Ala
    450                 455                 460

Val Glu Gln Val Trp Tyr Asn Gly Lys Phe Tyr Gly Ser Pro Glu Glu
465                 470                 475                 480

Leu Ala Arg Lys Tyr Ala Asp Gly Glu Val Asp Val Val Val Leu Glu
                485                 490                 495

Asp Pro Leu Pro Gly Gly Lys Gly His Asp Ser Thr Glu Glu Pro Pro
            500                 505                 510

Leu Phe Ser Ser His Lys Pro Arg Gly Asp Phe Pro Ser Pro Ile His
        515                 520                 525

Val Ser Gly Pro Arg Leu Val Gln Pro His Gly Pro Arg Phe Arg Leu
    530                 535                 540

Glu Gly Asn Ala Val Leu Tyr Gly Gly Trp Ser Phe Ala Phe Arg Leu
545                 550                 555                 560

Arg Ser Ser Ser Gly Leu Gln Val Leu Asn Val His Phe Gly Gly Glu
                565                 570                 575

Arg Ile Ala Tyr Glu Val Ser Val Gln Glu Ala Val Ala Leu Tyr Gly
            580                 585                 590

Gly His Thr Pro Ala Gly Met Gln Thr Lys Tyr Leu Asp Val Gly Trp
        595                 600                 605

Gly Leu Gly Ser Val Thr His Glu Leu Ala Pro Gly Ile Asp Cys Pro
    610                 615                 620

Glu Thr Ala Thr Phe Leu Asp Thr Phe His Tyr Tyr Asp Ala Asp Asp
625                 630                 635                 640

Pro Val His Tyr Pro Arg Ala Leu Cys Leu Phe Glu Met Pro Thr Gly
                645                 650                 655

Val Pro Leu Arg Arg His Phe Asn Ser Asn Phe Lys Gly Gly Phe Asn
            660                 665                 670

Phe Tyr Ala Gly Leu Lys Gly Gln Val Leu Val Leu Arg Thr Thr Ser
        675                 680                 685

Thr Val Tyr Asn Tyr Asp Tyr Ile Trp Asp Phe Ile Phe Tyr Pro Asn
    690                 695                 700

Gly Val Met Glu Ala Lys Met His Ala Thr Gly Tyr Val His Ala Thr
705                 710                 715                 720

Phe Tyr Thr Pro Glu Gly Leu Arg His Gly Thr Arg Leu His Thr His
                725                 730                 735

Leu Ile Gly Asn Ile His Thr His Leu Val His Tyr Arg Val Asp Leu
            740                 745                 750

Asp Val Ala Gly Thr Lys Asn Ser Phe Gln Thr Leu Gln Met Lys Leu
```

755 760 765

Glu Asn Ile Thr Asn Pro Trp Ser Pro Arg His Arg Val Val Gln Pro
770 775 780

Thr Leu Glu Gln Thr Gln Tyr Ser Trp Glu Arg Gln Ala Ala Phe Arg
785 790 795 800

Phe Gly Gln Thr Leu Pro Lys Tyr Leu Leu Phe Thr Ser Pro Gln Glu
805 810 815

Asn Pro Trp Gly His Lys Arg Ser Tyr Arg Leu Gln Ile His Ser Met
820 825 830

Ala Asp Gln Val Leu Pro Pro Gly Trp Gln Glu Glu Gln Ala Ile Thr
835 840 845

Trp Ala Arg Tyr Pro Leu Ala Val Thr Lys Tyr Arg Glu Ser Glu Leu
850 855 860

Cys Ser Ser Ser Ile Tyr His Gln Asn Asp Pro Trp His Pro Pro Val
865 870 875 880

Val Phe Glu Gln Phe Leu His Asn Asn Glu Asn Ile Glu Asn Glu Asp
885 890 895

Leu Val Ala Trp Val Thr Val Gly Phe Leu His Ile Pro His Ser Glu
900 905 910

Asp Ile Pro Asn Thr Ala Thr Pro Gly Asn Ser Val Gly Phe Leu Leu
915 920 925

Arg Pro Phe Asn Phe Phe Pro Glu Asp Pro Ser Leu Ala Ser Arg Asp
930 935 940

Thr Val Ile Val Trp Pro Arg Asp Asn Gly Pro Asn Tyr Val Gln Arg
945 950 955 960

Trp Ile Pro Glu Asp Arg Asp Cys Ser Met Pro Pro Pro Phe Ser Tyr
965 970 975

Asn Gly Thr Tyr Arg Pro Val
980

<210> SEQ ID NO 46
<211> LENGTH: 983
<212> TYPE: PRT
<213> ORGANISM: Artificial Sequence
<220> FEATURE:
<223> OTHER INFORMATION: Fc-hDAO-Hepmut7

<400> SEQUENCE: 46

Met Pro Ala Leu Gly Trp Ala Val Ala Ala Ile Leu Met Leu Gln Thr
1 5 10 15

Ala Met Ala Glu Cys Pro Pro Cys Pro Ala Pro Pro Val Ala Gly Pro
20 25 30

Ser Val Phe Leu Phe Pro Pro Lys Pro Lys Asp Thr Leu Met Ile Ser
35 40 45

Arg Thr Pro Glu Val Thr Cys Val Val Val Asp Val Ser His Glu Asp
50 55 60

Pro Glu Val Lys Phe Asn Trp Tyr Val Asp Gly Val Glu Val His Asn
65 70 75 80

Ala Lys Thr Lys Pro Arg Glu Glu Gln Tyr Asn Ser Thr Tyr Arg Val
85 90 95

Val Ser Val Leu Thr Val Leu His Gln Asp Trp Leu Asn Gly Lys Glu
100 105 110

Tyr Lys Cys Lys Val Ser Asn Lys Gly Leu Pro Ser Ser Ile Glu Lys
115 120 125

Thr Ile Ser Lys Ala Lys Gly Gln Pro Arg Glu Pro Gln Val Tyr Thr

```
    130                 135                 140

Leu Pro Pro Ser Arg Glu Glu Met Thr Lys Asn Gln Val Ser Leu Thr
145                 150                 155                 160

Cys Leu Val Lys Gly Phe Tyr Pro Ser Asp Ile Ala Val Glu Trp Glu
                165                 170                 175

Ser Asn Gly Gln Pro Glu Asn Asn Tyr Lys Thr Thr Pro Pro Val Leu
            180                 185                 190

Asp Ser Asp Gly Ser Phe Phe Leu Tyr Ser Lys Leu Thr Val Asp Lys
        195                 200                 205

Ser Arg Trp Gln Gln Gly Asn Val Phe Ser Cys Ser Val Met His Glu
    210                 215                 220

Ala Leu His Asn His Tyr Thr Gln Lys Ser Leu Ser Leu Ser Pro Gly
225                 230                 235                 240

Lys Glu Pro Lys Ser Ala Asp Lys Thr His Thr Glu Pro Ser Pro Gly
                245                 250                 255

Thr Leu Pro Arg Lys Ala Gly Val Phe Ser Asp Leu Ser Asn Gln Glu
            260                 265                 270

Leu Lys Ala Val His Ser Phe Leu Trp Ser Lys Lys Glu Leu Arg Leu
        275                 280                 285

Gln Pro Ser Ser Thr Thr Thr Met Ala Lys Asn Thr Val Phe Leu Ile
    290                 295                 300

Glu Met Leu Leu Pro Lys Lys Tyr His Val Leu Arg Phe Leu Asp Lys
305                 310                 315                 320

Gly Glu Arg His Pro Val Arg Glu Ala Arg Ala Val Ile Phe Phe Gly
                325                 330                 335

Asp Gln Glu His Pro Asn Val Thr Glu Phe Ala Val Gly Pro Leu Pro
            340                 345                 350

Gly Pro Cys Tyr Met Arg Ala Leu Ser Pro Arg Pro Gly Tyr Gln Ser
        355                 360                 365

Ser Trp Ala Ser Arg Pro Ile Ser Thr Ala Glu Tyr Ala Leu Leu Tyr
    370                 375                 380

His Thr Leu Gln Glu Ala Thr Lys Pro Leu His Gln Phe Phe Leu Asn
385                 390                 395                 400

Thr Thr Gly Phe Ser Phe Gln Asp Cys His Asp Arg Cys Leu Ala Phe
                405                 410                 415

Thr Asp Val Ala Pro Arg Gly Val Ala Ser Gly Gln Arg Arg Ser Trp
            420                 425                 430

Leu Ile Ile Gln Arg Tyr Val Glu Gly Tyr Phe Leu His Pro Thr Gly
        435                 440                 445

Leu Glu Leu Leu Val Asp His Gly Ser Thr Asp Ala Gly His Trp Ala
    450                 455                 460

Val Glu Gln Val Trp Tyr Asn Gly Lys Phe Tyr Gly Ser Pro Glu Glu
465                 470                 475                 480

Leu Ala Arg Lys Tyr Ala Asp Gly Glu Val Asp Val Val Val Leu Glu
                485                 490                 495

Asp Pro Leu Pro Gly Gly Lys Gly His Asp Ser Thr Glu Glu Pro Pro
            500                 505                 510

Leu Phe Ser Ser His Lys Pro Arg Gly Asp Phe Pro Ser Pro Ile His
        515                 520                 525

Val Ser Gly Pro Arg Leu Val Gln Pro His Gly Pro Arg Phe Arg Leu
    530                 535                 540

Glu Gly Asn Ala Val Leu Tyr Gly Gly Trp Ser Phe Ala Phe Arg Leu
545                 550                 555                 560
```

```
Arg Ser Ser Ser Gly Leu Gln Val Leu Asn Val His Phe Gly Gly Glu
                565                 570                 575

Arg Ile Ala Tyr Glu Val Ser Val Gln Glu Ala Val Ala Leu Tyr Gly
            580                 585                 590

Gly His Thr Pro Ala Gly Met Gln Thr Lys Tyr Leu Asp Val Gly Trp
        595                 600                 605

Gly Leu Gly Ser Val Thr His Glu Leu Ala Pro Gly Ile Asp Cys Pro
    610                 615                 620

Glu Thr Ala Thr Phe Leu Asp Thr Phe His Tyr Tyr Asp Ala Asp Asp
625                 630                 635                 640

Pro Val His Tyr Pro Arg Ala Leu Cys Leu Phe Glu Met Pro Thr Gly
                645                 650                 655

Val Pro Leu Arg Arg His Phe Asn Ser Asn Phe Lys Gly Gly Phe Asn
            660                 665                 670

Phe Tyr Ala Gly Leu Lys Gly Gln Val Leu Val Leu Arg Thr Thr Ser
        675                 680                 685

Thr Val Tyr Asn Tyr Asp Tyr Ile Trp Asp Phe Ile Phe Tyr Pro Asn
    690                 695                 700

Gly Val Met Glu Ala Lys Met His Ala Thr Gly Tyr Val His Ala Thr
705                 710                 715                 720

Phe Tyr Thr Pro Glu Gly Leu Arg His Gly Thr Arg Leu His Thr His
                725                 730                 735

Leu Ile Gly Asn Ile His Thr His Leu Val His Tyr Arg Val Asp Leu
            740                 745                 750

Asp Val Ala Gly Thr Lys Asn Ser Phe Gln Thr Leu Gln Met Lys Leu
        755                 760                 765

Glu Asn Ile Thr Asn Pro Trp Ser Pro Arg His Arg Val Val Gln Pro
    770                 775                 780

Thr Leu Glu Gln Thr Gln Tyr Ser Trp Glu Arg Gln Ala Ala Phe Ser
785                 790                 795                 800

Phe Lys Arg Lys Leu Pro Thr Tyr Leu Leu Phe Thr Ser Pro Gln Glu
                805                 810                 815

Asn Pro Trp Gly His Lys Arg Ser Tyr Arg Leu Gln Ile His Ser Met
            820                 825                 830

Ala Asp Gln Val Leu Pro Pro Gly Trp Gln Glu Glu Gln Ala Ile Thr
        835                 840                 845

Trp Ala Arg Tyr Pro Leu Ala Val Thr Lys Tyr Arg Glu Ser Glu Leu
    850                 855                 860

Cys Ser Ser Ser Ile Tyr His Gln Asn Asp Pro Trp His Pro Pro Val
865                 870                 875                 880

Val Phe Glu Gln Phe Leu His Asn Asn Glu Asn Ile Glu Asn Glu Asp
                885                 890                 895

Leu Val Ala Trp Val Thr Val Gly Phe Leu His Ile Pro His Ser Glu
            900                 905                 910

Asp Ile Pro Asn Thr Ala Thr Pro Gly Asn Ser Val Gly Phe Leu Leu
        915                 920                 925

Arg Pro Phe Asn Phe Phe Pro Glu Asp Pro Ser Leu Ala Ser Arg Asp
    930                 935                 940

Thr Val Ile Val Trp Pro Arg Asp Asn Gly Pro Asn Tyr Val Gln Arg
945                 950                 955                 960

Trp Ile Pro Glu Asp Arg Asp Cys Ser Met Pro Pro Pro Phe Ser Tyr
                965                 970                 975
```

Asn Gly Thr Tyr Arg Pro Val
980

<210> SEQ ID NO 47
<211> LENGTH: 983
<212> TYPE: PRT
<213> ORGANISM: Artificial Sequence
<220> FEATURE:
<223> OTHER INFORMATION: Fc-hDAO-Cysmut

<400> SEQUENCE: 47

Met Pro Ala Leu Gly Trp Ala Val Ala Ala Ile Leu Met Leu Gln Thr
1 5 10 15

Ala Met Ala Glu Cys Pro Pro Cys Pro Ala Pro Pro Val Ala Gly Pro
20 25 30

Ser Val Phe Leu Phe Pro Pro Lys Pro Lys Asp Thr Leu Met Ile Ser
35 40 45

Arg Thr Pro Glu Val Thr Cys Val Val Val Asp Val Ser His Glu Asp
50 55 60

Pro Glu Val Lys Phe Asn Trp Tyr Val Asp Gly Val Glu Val His Asn
65 70 75 80

Ala Lys Thr Lys Pro Arg Glu Glu Gln Tyr Asn Ser Thr Tyr Arg Val
85 90 95

Val Ser Val Leu Thr Val Leu His Gln Asp Trp Leu Asn Gly Lys Glu
100 105 110

Tyr Lys Cys Lys Val Ser Asn Lys Gly Leu Pro Ser Ser Ile Glu Lys
115 120 125

Thr Ile Ser Lys Ala Lys Gly Gln Pro Arg Glu Pro Gln Val Tyr Thr
130 135 140

Leu Pro Pro Ser Arg Glu Glu Met Thr Lys Asn Gln Val Ser Leu Thr
145 150 155 160

Cys Leu Val Lys Gly Phe Tyr Pro Ser Asp Ile Ala Val Glu Trp Glu
165 170 175

Ser Asn Gly Gln Pro Glu Asn Asn Tyr Lys Thr Thr Pro Pro Val Leu
180 185 190

Asp Ser Asp Gly Ser Phe Phe Leu Tyr Ser Lys Leu Thr Val Asp Lys
195 200 205

Ser Arg Trp Gln Gln Gly Asn Val Phe Ser Cys Ser Val Met His Glu
210 215 220

Ala Leu His Asn His Tyr Thr Gln Lys Ser Leu Ser Leu Ser Pro Gly
225 230 235 240

Lys Glu Pro Lys Ser Ala Asp Lys Thr His Thr Glu Pro Ser Pro Gly
245 250 255

Thr Leu Pro Arg Lys Ala Gly Val Phe Ser Asp Leu Ser Asn Gln Glu
260 265 270

Leu Lys Ala Val His Ser Phe Leu Trp Ser Lys Lys Glu Leu Arg Leu
275 280 285

Gln Pro Ser Ser Thr Thr Thr Met Ala Lys Asn Thr Val Phe Leu Ile
290 295 300

Glu Met Leu Leu Pro Lys Lys Tyr His Val Leu Arg Phe Leu Asp Lys
305 310 315 320

Gly Glu Arg His Pro Val Arg Glu Ala Arg Ala Val Ile Phe Phe Gly
325 330 335

Asp Gln Glu His Pro Asn Val Thr Glu Phe Ala Val Gly Pro Leu Pro
340 345 350

```
Gly Pro Ala Tyr Met Arg Ala Leu Ser Pro Arg Pro Gly Tyr Gln Ser
        355                 360                 365

Ser Trp Ala Ser Arg Pro Ile Ser Thr Ala Glu Tyr Ala Leu Leu Tyr
    370                 375                 380

His Thr Leu Gln Glu Ala Thr Lys Pro Leu His Gln Phe Phe Leu Asn
385                 390                 395                 400

Thr Thr Gly Phe Ser Phe Gln Asp Cys His Asp Arg Cys Leu Ala Phe
                405                 410                 415

Thr Asp Val Ala Pro Arg Gly Val Ala Ser Gly Gln Arg Arg Ser Trp
            420                 425                 430

Leu Ile Ile Gln Arg Tyr Val Glu Gly Tyr Phe Leu His Pro Thr Gly
        435                 440                 445

Leu Glu Leu Leu Val Asp His Gly Ser Thr Asp Ala Gly His Trp Ala
    450                 455                 460

Val Glu Gln Val Trp Tyr Asn Gly Lys Phe Tyr Gly Ser Pro Glu Glu
465                 470                 475                 480

Leu Ala Arg Lys Tyr Ala Asp Gly Glu Val Asp Val Val Val Leu Glu
                485                 490                 495

Asp Pro Leu Pro Gly Gly Lys Gly His Asp Ser Thr Glu Glu Pro Pro
            500                 505                 510

Leu Phe Ser Ser His Lys Pro Arg Gly Asp Phe Pro Ser Pro Ile His
        515                 520                 525

Val Ser Gly Pro Arg Leu Val Gln Pro His Gly Pro Arg Phe Arg Leu
    530                 535                 540

Glu Gly Asn Ala Val Leu Tyr Gly Gly Trp Ser Phe Ala Phe Arg Leu
545                 550                 555                 560

Arg Ser Ser Ser Gly Leu Gln Val Leu Asn Val His Phe Gly Gly Glu
                565                 570                 575

Arg Ile Ala Tyr Glu Val Ser Val Gln Glu Ala Val Ala Leu Tyr Gly
            580                 585                 590

Gly His Thr Pro Ala Gly Met Gln Thr Lys Tyr Leu Asp Val Gly Trp
        595                 600                 605

Gly Leu Gly Ser Val Thr His Glu Leu Ala Pro Gly Ile Asp Cys Pro
    610                 615                 620

Glu Thr Ala Thr Phe Leu Asp Thr Phe His Tyr Tyr Asp Ala Asp Asp
625                 630                 635                 640

Pro Val His Tyr Pro Arg Ala Leu Cys Leu Phe Glu Met Pro Thr Gly
                645                 650                 655

Val Pro Leu Arg Arg His Phe Asn Ser Asn Phe Lys Gly Gly Phe Asn
            660                 665                 670

Phe Tyr Ala Gly Leu Lys Gly Gln Val Leu Val Leu Arg Thr Thr Ser
        675                 680                 685

Thr Val Tyr Asn Tyr Asp Tyr Ile Trp Asp Phe Ile Phe Tyr Pro Asn
    690                 695                 700

Gly Val Met Glu Ala Lys Met His Ala Thr Gly Tyr Val His Ala Thr
705                 710                 715                 720

Phe Tyr Thr Pro Glu Gly Leu Arg His Gly Thr Arg Leu His Thr His
                725                 730                 735

Leu Ile Gly Asn Ile His Thr His Leu Val His Tyr Arg Val Asp Leu
            740                 745                 750

Asp Val Ala Gly Thr Lys Asn Ser Phe Gln Thr Leu Gln Met Lys Leu
        755                 760                 765

Glu Asn Ile Thr Asn Pro Trp Ser Pro Arg His Arg Val Val Gln Pro
```

770 775 780

Thr Leu Glu Gln Thr Gln Tyr Ser Trp Glu Arg Gln Ala Ala Phe Arg
785 790 795 800

Phe Lys Arg Lys Leu Pro Lys Tyr Leu Leu Phe Thr Ser Pro Gln Glu
805 810 815

Asn Pro Trp Gly His Lys Arg Ser Tyr Arg Leu Gln Ile His Ser Met
820 825 830

Ala Asp Gln Val Leu Pro Pro Gly Trp Gln Glu Glu Gln Ala Ile Thr
835 840 845

Trp Ala Arg Tyr Pro Leu Ala Val Thr Lys Tyr Arg Glu Ser Glu Leu
850 855 860

Cys Ser Ser Ser Ile Tyr His Gln Asn Asp Pro Trp His Pro Pro Val
865 870 875 880

Val Phe Glu Gln Phe Leu His Asn Asn Glu Asn Ile Glu Asn Glu Asp
885 890 895

Leu Val Ala Trp Val Thr Val Gly Phe Leu His Ile Pro His Ser Glu
900 905 910

Asp Ile Pro Asn Thr Ala Thr Pro Gly Asn Ser Val Gly Phe Leu Leu
915 920 925

Arg Pro Phe Asn Phe Phe Pro Glu Asp Pro Ser Leu Ala Ser Arg Asp
930 935 940

Thr Val Ile Val Trp Pro Arg Asp Asn Gly Pro Asn Tyr Val Gln Arg
945 950 955 960

Trp Ile Pro Glu Asp Arg Asp Cys Ser Met Pro Pro Pro Phe Ser Tyr
965 970 975

Asn Gly Thr Tyr Arg Pro Val
980

<210> SEQ ID NO 48
<211> LENGTH: 983
<212> TYPE: PRT
<213> ORGANISM: Artificial Sequence
<220> FEATURE:
<223> OTHER INFORMATION: Fc-hDAO-Hepmut1-Cysmut

<400> SEQUENCE: 48

Met Pro Ala Leu Gly Trp Ala Val Ala Ala Ile Leu Met Leu Gln Thr
1 5 10 15

Ala Met Ala Glu Cys Pro Pro Cys Pro Ala Pro Pro Val Ala Gly Pro
20 25 30

Ser Val Phe Leu Phe Pro Pro Lys Pro Lys Asp Thr Leu Met Ile Ser
35 40 45

Arg Thr Pro Glu Val Thr Cys Val Val Val Asp Val Ser His Glu Asp
50 55 60

Pro Glu Val Lys Phe Asn Trp Tyr Val Asp Gly Val Glu Val His Asn
65 70 75 80

Ala Lys Thr Lys Pro Arg Glu Glu Gln Tyr Asn Ser Thr Tyr Arg Val
85 90 95

Val Ser Val Leu Thr Val Leu His Gln Asp Trp Leu Asn Gly Lys Glu
100 105 110

Tyr Lys Cys Lys Val Ser Asn Lys Gly Leu Pro Ser Ser Ile Glu Lys
115 120 125

Thr Ile Ser Lys Ala Lys Gly Gln Pro Arg Glu Pro Gln Val Tyr Thr
130 135 140

Leu Pro Pro Ser Arg Glu Glu Met Thr Lys Asn Gln Val Ser Leu Thr

-continued

```
145                 150                 155                 160

Cys Leu Val Lys Gly Phe Tyr Pro Ser Asp Ile Ala Val Glu Trp Glu
                165                 170                 175

Ser Asn Gly Gln Pro Glu Asn Asn Tyr Lys Thr Thr Pro Pro Val Leu
            180                 185                 190

Asp Ser Asp Gly Ser Phe Phe Leu Tyr Ser Lys Leu Thr Val Asp Lys
        195                 200                 205

Ser Arg Trp Gln Gln Gly Asn Val Phe Ser Cys Ser Val Met His Glu
    210                 215                 220

Ala Leu His Asn His Tyr Thr Gln Lys Ser Leu Ser Leu Ser Pro Gly
225                 230                 235                 240

Lys Glu Pro Lys Ser Ala Asp Lys Thr His Thr Glu Pro Ser Pro Gly
                245                 250                 255

Thr Leu Pro Arg Lys Ala Gly Val Phe Ser Asp Leu Ser Asn Gln Glu
            260                 265                 270

Leu Lys Ala Val His Ser Phe Leu Trp Ser Lys Lys Glu Leu Arg Leu
        275                 280                 285

Gln Pro Ser Ser Thr Thr Thr Met Ala Lys Asn Thr Val Phe Leu Ile
    290                 295                 300

Glu Met Leu Leu Pro Lys Lys Tyr His Val Leu Arg Phe Leu Asp Lys
305                 310                 315                 320

Gly Glu Arg His Pro Val Arg Glu Ala Arg Ala Val Ile Phe Phe Gly
                325                 330                 335

Asp Gln Glu His Pro Asn Val Thr Glu Phe Ala Val Gly Pro Leu Pro
            340                 345                 350

Gly Pro Ala Tyr Met Arg Ala Leu Ser Pro Arg Pro Gly Tyr Gln Ser
        355                 360                 365

Ser Trp Ala Ser Arg Pro Ile Ser Thr Ala Glu Tyr Ala Leu Leu Tyr
    370                 375                 380

His Thr Leu Gln Glu Ala Thr Lys Pro Leu His Gln Phe Phe Leu Asn
385                 390                 395                 400

Thr Thr Gly Phe Ser Phe Gln Asp Cys His Asp Arg Cys Leu Ala Phe
                405                 410                 415

Thr Asp Val Ala Pro Arg Gly Val Ala Ser Gly Gln Arg Arg Ser Trp
            420                 425                 430

Leu Ile Ile Gln Arg Tyr Val Glu Gly Tyr Phe Leu His Pro Thr Gly
        435                 440                 445

Leu Glu Leu Leu Val Asp His Gly Ser Thr Asp Ala Gly His Trp Ala
    450                 455                 460

Val Glu Gln Val Trp Tyr Asn Gly Lys Phe Tyr Gly Ser Pro Glu Glu
465                 470                 475                 480

Leu Ala Arg Lys Tyr Ala Asp Gly Glu Val Asp Val Val Val Leu Glu
                485                 490                 495

Asp Pro Leu Pro Gly Gly Lys Gly His Asp Ser Thr Glu Glu Pro Pro
            500                 505                 510

Leu Phe Ser Ser His Lys Pro Arg Gly Asp Phe Pro Ser Pro Ile His
        515                 520                 525

Val Ser Gly Pro Arg Leu Val Gln Pro His Gly Pro Arg Phe Arg Leu
    530                 535                 540

Glu Gly Asn Ala Val Leu Tyr Gly Gly Trp Ser Phe Ala Phe Arg Leu
545                 550                 555                 560

Arg Ser Ser Ser Gly Leu Gln Val Leu Asn Val His Phe Gly Gly Glu
                565                 570                 575
```

```
Arg Ile Ala Tyr Glu Val Ser Val Gln Glu Ala Val Ala Leu Tyr Gly
            580                 585                 590

Gly His Thr Pro Ala Gly Met Gln Thr Lys Tyr Leu Asp Val Gly Trp
        595                 600                 605

Gly Leu Gly Ser Val Thr His Glu Leu Ala Pro Gly Ile Asp Cys Pro
    610                 615                 620

Glu Thr Ala Thr Phe Leu Asp Thr Phe His Tyr Tyr Asp Ala Asp Asp
625                 630                 635                 640

Pro Val His Tyr Pro Arg Ala Leu Cys Leu Phe Glu Met Pro Thr Gly
                645                 650                 655

Val Pro Leu Arg Arg His Phe Asn Ser Asn Phe Lys Gly Gly Phe Asn
            660                 665                 670

Phe Tyr Ala Gly Leu Lys Gly Gln Val Leu Val Leu Arg Thr Thr Ser
        675                 680                 685

Thr Val Tyr Asn Tyr Asp Tyr Ile Trp Asp Phe Ile Phe Tyr Pro Asn
    690                 695                 700

Gly Val Met Glu Ala Lys Met His Ala Thr Gly Tyr Val His Ala Thr
705                 710                 715                 720

Phe Tyr Thr Pro Glu Gly Leu Arg His Gly Thr Arg Leu His Thr His
                725                 730                 735

Leu Ile Gly Asn Ile His Thr His Leu Val His Tyr Arg Val Asp Leu
            740                 745                 750

Asp Val Ala Gly Thr Lys Asn Ser Phe Gln Thr Leu Gln Met Lys Leu
        755                 760                 765

Glu Asn Ile Thr Asn Pro Trp Ser Pro Arg His Arg Val Val Gln Pro
    770                 775                 780

Thr Leu Glu Gln Thr Gln Tyr Ser Trp Glu Arg Gln Ala Ala Phe Ser
785                 790                 795                 800

Phe Lys Arg Lys Leu Pro Lys Tyr Leu Leu Phe Thr Ser Pro Gln Glu
                805                 810                 815

Asn Pro Trp Gly His Lys Arg Ser Tyr Arg Leu Gln Ile His Ser Met
            820                 825                 830

Ala Asp Gln Val Leu Pro Pro Gly Trp Gln Glu Glu Gln Ala Ile Thr
        835                 840                 845

Trp Ala Arg Tyr Pro Leu Ala Val Thr Lys Tyr Arg Glu Ser Glu Leu
    850                 855                 860

Cys Ser Ser Ser Ile Tyr His Gln Asn Asp Pro Trp His Pro Pro Val
865                 870                 875                 880

Val Phe Glu Gln Phe Leu His Asn Asn Glu Asn Ile Glu Asn Glu Asp
                885                 890                 895

Leu Val Ala Trp Val Thr Val Gly Phe Leu His Ile Pro His Ser Glu
            900                 905                 910

Asp Ile Pro Asn Thr Ala Thr Pro Gly Asn Ser Val Gly Phe Leu Leu
        915                 920                 925

Arg Pro Phe Asn Phe Phe Pro Glu Asp Pro Ser Leu Ala Ser Arg Asp
    930                 935                 940

Thr Val Ile Val Trp Pro Arg Asp Asn Gly Pro Asn Tyr Val Gln Arg
945                 950                 955                 960

Trp Ile Pro Glu Asp Arg Asp Cys Ser Met Pro Pro Pro Phe Ser Tyr
                965                 970                 975

Asn Gly Thr Tyr Arg Pro Val
            980
```

<210> SEQ ID NO 49
<211> LENGTH: 983
<212> TYPE: PRT
<213> ORGANISM: Artificial Sequence
<220> FEATURE:
<223> OTHER INFORMATION: Fc-hDAO-Hepmut2-Cysmut

<400> SEQUENCE: 49

```
Met Pro Ala Leu Gly Trp Ala Val Ala Ala Ile Leu Met Leu Gln Thr
1               5                   10                  15

Ala Met Ala Glu Cys Pro Pro Cys Pro Ala Pro Pro Val Ala Gly Pro
            20                  25                  30

Ser Val Phe Leu Phe Pro Pro Lys Pro Lys Asp Thr Leu Met Ile Ser
        35                  40                  45

Arg Thr Pro Glu Val Thr Cys Val Val Val Asp Val Ser His Glu Asp
    50                  55                  60

Pro Glu Val Lys Phe Asn Trp Tyr Val Asp Gly Val Glu Val His Asn
65                  70                  75                  80

Ala Lys Thr Lys Pro Arg Glu Glu Gln Tyr Asn Ser Thr Tyr Arg Val
                85                  90                  95

Val Ser Val Leu Thr Val Leu His Gln Asp Trp Leu Asn Gly Lys Glu
            100                 105                 110

Tyr Lys Cys Lys Val Ser Asn Lys Gly Leu Pro Ser Ser Ile Glu Lys
        115                 120                 125

Thr Ile Ser Lys Ala Lys Gly Gln Pro Arg Glu Pro Gln Val Tyr Thr
    130                 135                 140

Leu Pro Pro Ser Arg Glu Glu Met Thr Lys Asn Gln Val Ser Leu Thr
145                 150                 155                 160

Cys Leu Val Lys Gly Phe Tyr Pro Ser Asp Ile Ala Val Glu Trp Glu
                165                 170                 175

Ser Asn Gly Gln Pro Glu Asn Asn Tyr Lys Thr Thr Pro Pro Val Leu
            180                 185                 190

Asp Ser Asp Gly Ser Phe Phe Leu Tyr Ser Lys Leu Thr Val Asp Lys
        195                 200                 205

Ser Arg Trp Gln Gln Gly Asn Val Phe Ser Cys Ser Val Met His Glu
    210                 215                 220

Ala Leu His Asn His Tyr Thr Gln Lys Ser Leu Ser Leu Ser Pro Gly
225                 230                 235                 240

Lys Glu Pro Lys Ser Ala Asp Lys Thr His Thr Glu Pro Ser Pro Gly
                245                 250                 255

Thr Leu Pro Arg Lys Ala Gly Val Phe Ser Asp Leu Ser Asn Gln Glu
            260                 265                 270

Leu Lys Ala Val His Ser Phe Leu Trp Ser Lys Lys Glu Leu Arg Leu
        275                 280                 285

Gln Pro Ser Ser Thr Thr Thr Met Ala Lys Asn Thr Val Phe Leu Ile
    290                 295                 300

Glu Met Leu Leu Pro Lys Lys Tyr His Val Leu Arg Phe Leu Asp Lys
305                 310                 315                 320

Gly Glu Arg His Pro Val Arg Glu Ala Arg Ala Val Ile Phe Phe Gly
                325                 330                 335

Asp Gln Glu His Pro Asn Val Thr Glu Phe Ala Val Gly Pro Leu Pro
            340                 345                 350

Gly Pro Ala Tyr Met Arg Ala Leu Ser Pro Arg Pro Gly Tyr Gln Ser
        355                 360                 365
```

```
Ser Trp Ala Ser Arg Pro Ile Ser Thr Ala Glu Tyr Ala Leu Leu Tyr
    370                 375                 380

His Thr Leu Gln Glu Ala Thr Lys Pro Leu His Gln Phe Phe Leu Asn
385                 390                 395                 400

Thr Thr Gly Phe Ser Phe Gln Asp Cys His Asp Arg Cys Leu Ala Phe
                405                 410                 415

Thr Asp Val Ala Pro Arg Gly Val Ala Ser Gly Gln Arg Arg Ser Trp
            420                 425                 430

Leu Ile Ile Gln Arg Tyr Val Glu Gly Tyr Phe Leu His Pro Thr Gly
        435                 440                 445

Leu Glu Leu Leu Val Asp His Gly Ser Thr Asp Ala Gly His Trp Ala
    450                 455                 460

Val Glu Gln Val Trp Tyr Asn Gly Lys Phe Tyr Gly Ser Pro Glu Glu
465                 470                 475                 480

Leu Ala Arg Lys Tyr Ala Asp Gly Glu Val Asp Val Val Val Leu Glu
                485                 490                 495

Asp Pro Leu Pro Gly Gly Lys Gly His Asp Ser Thr Glu Glu Pro Pro
            500                 505                 510

Leu Phe Ser Ser His Lys Pro Arg Gly Asp Phe Pro Ser Pro Ile His
        515                 520                 525

Val Ser Gly Pro Arg Leu Val Gln Pro His Gly Pro Arg Phe Arg Leu
    530                 535                 540

Glu Gly Asn Ala Val Leu Tyr Gly Gly Trp Ser Phe Ala Phe Arg Leu
545                 550                 555                 560

Arg Ser Ser Ser Gly Leu Gln Val Leu Asn Val His Phe Gly Gly Glu
                565                 570                 575

Arg Ile Ala Tyr Glu Val Ser Val Gln Glu Ala Val Ala Leu Tyr Gly
            580                 585                 590

Gly His Thr Pro Ala Gly Met Gln Thr Lys Tyr Leu Asp Val Gly Trp
        595                 600                 605

Gly Leu Gly Ser Val Thr His Glu Leu Ala Pro Gly Ile Asp Cys Pro
    610                 615                 620

Glu Thr Ala Thr Phe Leu Asp Thr Phe His Tyr Tyr Asp Ala Asp Asp
625                 630                 635                 640

Pro Val His Tyr Pro Arg Ala Leu Cys Leu Phe Glu Met Pro Thr Gly
                645                 650                 655

Val Pro Leu Arg Arg His Phe Asn Ser Asn Phe Lys Gly Gly Phe Asn
            660                 665                 670

Phe Tyr Ala Gly Leu Lys Gly Gln Val Leu Val Leu Arg Thr Thr Ser
        675                 680                 685

Thr Val Tyr Asn Tyr Asp Tyr Ile Trp Asp Phe Ile Phe Tyr Pro Asn
    690                 695                 700

Gly Val Met Glu Ala Lys Met His Ala Thr Gly Tyr Val His Ala Thr
705                 710                 715                 720

Phe Tyr Thr Pro Glu Gly Leu Arg His Gly Thr Arg Leu His Thr His
                725                 730                 735

Leu Ile Gly Asn Ile His Thr His Leu Val His Tyr Arg Val Asp Leu
            740                 745                 750

Asp Val Ala Gly Thr Lys Asn Ser Phe Gln Thr Leu Gln Met Lys Leu
        755                 760                 765

Glu Asn Ile Thr Asn Pro Trp Ser Pro Arg His Arg Val Val Gln Pro
    770                 775                 780

Thr Leu Glu Gln Thr Gln Tyr Ser Trp Glu Arg Gln Ala Ala Phe Arg
```

```
785                 790                 795                 800

Phe Lys Arg Lys Leu Pro Thr Tyr Leu Leu Phe Thr Ser Pro Gln Glu
                805                 810                 815

Asn Pro Trp Gly His Lys Arg Ser Tyr Arg Leu Gln Ile His Ser Met
            820                 825                 830

Ala Asp Gln Val Leu Pro Pro Gly Trp Gln Glu Glu Gln Ala Ile Thr
        835                 840                 845

Trp Ala Arg Tyr Pro Leu Ala Val Thr Lys Tyr Arg Glu Ser Glu Leu
    850                 855                 860

Cys Ser Ser Ser Ile Tyr His Gln Asn Asp Pro Trp His Pro Pro Val
865                 870                 875                 880

Val Phe Glu Gln Phe Leu His Asn Asn Glu Asn Ile Glu Asn Glu Asp
                885                 890                 895

Leu Val Ala Trp Val Thr Val Gly Phe Leu His Ile Pro His Ser Glu
            900                 905                 910

Asp Ile Pro Asn Thr Ala Thr Pro Gly Asn Ser Val Gly Phe Leu Leu
        915                 920                 925

Arg Pro Phe Asn Phe Phe Pro Glu Asp Pro Ser Leu Ala Ser Arg Asp
    930                 935                 940

Thr Val Ile Val Trp Pro Arg Asp Asn Gly Pro Asn Tyr Val Gln Arg
945                 950                 955                 960

Trp Ile Pro Glu Asp Arg Asp Cys Ser Met Pro Pro Pro Phe Ser Tyr
                965                 970                 975

Asn Gly Thr Tyr Arg Pro Val
            980


<210> SEQ ID NO 50
<211> LENGTH: 983
<212> TYPE: PRT
<213> ORGANISM: Artificial Sequence
<220> FEATURE:
<223> OTHER INFORMATION: Fc-hDAO-Hepmut3-Cysmut

<400> SEQUENCE: 50

Met Pro Ala Leu Gly Trp Ala Val Ala Ala Ile Leu Met Leu Gln Thr
1               5                   10                  15

Ala Met Ala Glu Cys Pro Pro Cys Pro Ala Pro Pro Val Ala Gly Pro
            20                  25                  30

Ser Val Phe Leu Phe Pro Pro Lys Pro Lys Asp Thr Leu Met Ile Ser
        35                  40                  45

Arg Thr Pro Glu Val Thr Cys Val Val Val Asp Val Ser His Glu Asp
    50                  55                  60

Pro Glu Val Lys Phe Asn Trp Tyr Val Asp Gly Val Glu Val His Asn
65                  70                  75                  80

Ala Lys Thr Lys Pro Arg Glu Glu Gln Tyr Asn Ser Thr Tyr Arg Val
                85                  90                  95

Val Ser Val Leu Thr Val Leu His Gln Asp Trp Leu Asn Gly Lys Glu
            100                 105                 110

Tyr Lys Cys Lys Val Ser Asn Lys Gly Leu Pro Ser Ser Ile Glu Lys
        115                 120                 125

Thr Ile Ser Lys Ala Lys Gly Gln Pro Arg Glu Pro Gln Val Tyr Thr
    130                 135                 140

Leu Pro Pro Ser Arg Glu Glu Met Thr Lys Asn Gln Val Ser Leu Thr
145                 150                 155                 160

Cys Leu Val Lys Gly Phe Tyr Pro Ser Asp Ile Ala Val Glu Trp Glu
```

-continued

```
                165                 170                 175

Ser Asn Gly Gln Pro Glu Asn Asn Tyr Lys Thr Thr Pro Pro Val Leu
            180                 185                 190

Asp Ser Asp Gly Ser Phe Phe Leu Tyr Ser Lys Leu Thr Val Asp Lys
        195                 200                 205

Ser Arg Trp Gln Gln Gly Asn Val Phe Ser Cys Ser Val Met His Glu
    210                 215                 220

Ala Leu His Asn His Tyr Thr Gln Lys Ser Leu Ser Leu Ser Pro Gly
225                 230                 235                 240

Lys Glu Pro Lys Ser Ala Asp Lys Thr His Thr Glu Pro Ser Pro Gly
                245                 250                 255

Thr Leu Pro Arg Lys Ala Gly Val Phe Ser Asp Leu Ser Asn Gln Glu
            260                 265                 270

Leu Lys Ala Val His Ser Phe Leu Trp Ser Lys Lys Glu Leu Arg Leu
        275                 280                 285

Gln Pro Ser Ser Thr Thr Thr Met Ala Lys Asn Thr Val Phe Leu Ile
    290                 295                 300

Glu Met Leu Leu Pro Lys Lys Tyr His Val Leu Arg Phe Leu Asp Lys
305                 310                 315                 320

Gly Glu Arg His Pro Val Arg Glu Ala Arg Ala Val Ile Phe Phe Gly
                325                 330                 335

Asp Gln Glu His Pro Asn Val Thr Glu Phe Ala Val Gly Pro Leu Pro
            340                 345                 350

Gly Pro Ala Tyr Met Arg Ala Leu Ser Pro Arg Pro Gly Tyr Gln Ser
        355                 360                 365

Ser Trp Ala Ser Arg Pro Ile Ser Thr Ala Glu Tyr Ala Leu Leu Tyr
    370                 375                 380

His Thr Leu Gln Glu Ala Thr Lys Pro Leu His Gln Phe Phe Leu Asn
385                 390                 395                 400

Thr Thr Gly Phe Ser Phe Gln Asp Cys His Asp Arg Cys Leu Ala Phe
                405                 410                 415

Thr Asp Val Ala Pro Arg Gly Val Ala Ser Gly Gln Arg Arg Ser Trp
            420                 425                 430

Leu Ile Ile Gln Arg Tyr Val Glu Gly Tyr Phe Leu His Pro Thr Gly
        435                 440                 445

Leu Glu Leu Leu Val Asp His Gly Ser Thr Asp Ala Gly His Trp Ala
    450                 455                 460

Val Glu Gln Val Trp Tyr Asn Gly Lys Phe Tyr Gly Ser Pro Glu Glu
465                 470                 475                 480

Leu Ala Arg Lys Tyr Ala Asp Gly Glu Val Asp Val Val Val Leu Glu
                485                 490                 495

Asp Pro Leu Pro Gly Gly Lys Gly His Asp Ser Thr Glu Glu Pro Pro
            500                 505                 510

Leu Phe Ser Ser His Lys Pro Arg Gly Asp Phe Pro Ser Pro Ile His
        515                 520                 525

Val Ser Gly Pro Arg Leu Val Gln Pro His Gly Pro Arg Phe Arg Leu
    530                 535                 540

Glu Gly Asn Ala Val Leu Tyr Gly Gly Trp Ser Phe Ala Phe Arg Leu
545                 550                 555                 560

Arg Ser Ser Ser Gly Leu Gln Val Leu Asn Val His Phe Gly Gly Glu
                565                 570                 575

Arg Ile Ala Tyr Glu Val Ser Val Gln Glu Ala Val Ala Leu Tyr Gly
            580                 585                 590
```

```
Gly His Thr Pro Ala Gly Met Gln Thr Lys Tyr Leu Asp Val Gly Trp
        595                 600                 605

Gly Leu Gly Ser Val Thr His Glu Leu Ala Pro Gly Ile Asp Cys Pro
    610                 615                 620

Glu Thr Ala Thr Phe Leu Asp Thr Phe His Tyr Tyr Asp Ala Asp Asp
625                 630                 635                 640

Pro Val His Tyr Pro Arg Ala Leu Cys Leu Phe Glu Met Pro Thr Gly
                645                 650                 655

Val Pro Leu Arg Arg His Phe Asn Ser Asn Phe Lys Gly Gly Phe Asn
            660                 665                 670

Phe Tyr Ala Gly Leu Lys Gly Gln Val Leu Val Leu Arg Thr Thr Ser
        675                 680                 685

Thr Val Tyr Asn Tyr Asp Tyr Ile Trp Asp Phe Ile Phe Tyr Pro Asn
    690                 695                 700

Gly Val Met Glu Ala Lys Met His Ala Thr Gly Tyr Val His Ala Thr
705                 710                 715                 720

Phe Tyr Thr Pro Glu Gly Leu Arg His Gly Thr Arg Leu His Thr His
                725                 730                 735

Leu Ile Gly Asn Ile His Thr His Leu Val His Tyr Arg Val Asp Leu
            740                 745                 750

Asp Val Ala Gly Thr Lys Asn Ser Phe Gln Thr Leu Gln Met Lys Leu
        755                 760                 765

Glu Asn Ile Thr Asn Pro Trp Ser Pro Arg His Arg Val Val Gln Pro
    770                 775                 780

Thr Leu Glu Gln Thr Gln Tyr Ser Trp Glu Arg Gln Ala Ala Phe Arg
785                 790                 795                 800

Phe Lys Thr Lys Leu Pro Lys Tyr Leu Leu Phe Thr Ser Pro Gln Glu
                805                 810                 815

Asn Pro Trp Gly His Lys Arg Ser Tyr Arg Leu Gln Ile His Ser Met
            820                 825                 830

Ala Asp Gln Val Leu Pro Pro Gly Trp Gln Glu Glu Gln Ala Ile Thr
        835                 840                 845

Trp Ala Arg Tyr Pro Leu Ala Val Thr Lys Tyr Arg Glu Ser Glu Leu
    850                 855                 860

Cys Ser Ser Ser Ile Tyr His Gln Asn Asp Pro Trp His Pro Pro Val
865                 870                 875                 880

Val Phe Glu Gln Phe Leu His Asn Asn Glu Asn Ile Glu Asn Glu Asp
                885                 890                 895

Leu Val Ala Trp Val Thr Val Gly Phe Leu His Ile Pro His Ser Glu
            900                 905                 910

Asp Ile Pro Asn Thr Ala Thr Pro Gly Asn Ser Val Gly Phe Leu Leu
        915                 920                 925

Arg Pro Phe Asn Phe Phe Pro Glu Asp Pro Ser Leu Ala Ser Arg Asp
    930                 935                 940

Thr Val Ile Val Trp Pro Arg Asp Asn Gly Pro Asn Tyr Val Gln Arg
945                 950                 955                 960

Trp Ile Pro Glu Asp Arg Asp Cys Ser Met Pro Pro Pro Phe Ser Tyr
                965                 970                 975

Asn Gly Thr Tyr Arg Pro Val
            980
```

<210> SEQ ID NO 51
<211> LENGTH: 983

```
<212> TYPE: PRT
<213> ORGANISM: Artificial Sequence
<220> FEATURE:
<223> OTHER INFORMATION: Fc-hDAO-Hepmut4-Cysmut

<400> SEQUENCE: 51

Met Pro Ala Leu Gly Trp Ala Val Ala Ala Ile Leu Met Leu Gln Thr
1               5                   10                  15

Ala Met Ala Glu Cys Pro Pro Cys Pro Ala Pro Pro Val Ala Gly Pro
            20                  25                  30

Ser Val Phe Leu Phe Pro Pro Lys Pro Lys Asp Thr Leu Met Ile Ser
        35                  40                  45

Arg Thr Pro Glu Val Thr Cys Val Val Val Asp Val Ser His Glu Asp
    50                  55                  60

Pro Glu Val Lys Phe Asn Trp Tyr Val Asp Gly Val Glu Val His Asn
65                  70                  75                  80

Ala Lys Thr Lys Pro Arg Glu Glu Gln Tyr Asn Ser Thr Tyr Arg Val
                85                  90                  95

Val Ser Val Leu Thr Val Leu His Gln Asp Trp Leu Asn Gly Lys Glu
            100                 105                 110

Tyr Lys Cys Lys Val Ser Asn Lys Gly Leu Pro Ser Ser Ile Glu Lys
        115                 120                 125

Thr Ile Ser Lys Ala Lys Gly Gln Pro Arg Glu Pro Gln Val Tyr Thr
    130                 135                 140

Leu Pro Pro Ser Arg Glu Glu Met Thr Lys Asn Gln Val Ser Leu Thr
145                 150                 155                 160

Cys Leu Val Lys Gly Phe Tyr Pro Ser Asp Ile Ala Val Glu Trp Glu
                165                 170                 175

Ser Asn Gly Gln Pro Glu Asn Asn Tyr Lys Thr Thr Pro Pro Val Leu
            180                 185                 190

Asp Ser Asp Gly Ser Phe Phe Leu Tyr Ser Lys Leu Thr Val Asp Lys
        195                 200                 205

Ser Arg Trp Gln Gln Gly Asn Val Phe Ser Cys Ser Val Met His Glu
    210                 215                 220

Ala Leu His Asn His Tyr Thr Gln Lys Ser Leu Ser Leu Ser Pro Gly
225                 230                 235                 240

Lys Glu Pro Lys Ser Ala Asp Lys Thr His Thr Glu Pro Ser Pro Gly
                245                 250                 255

Thr Leu Pro Arg Lys Ala Gly Val Phe Ser Asp Leu Ser Asn Gln Glu
            260                 265                 270

Leu Lys Ala Val His Ser Phe Leu Trp Ser Lys Lys Glu Leu Arg Leu
        275                 280                 285

Gln Pro Ser Ser Thr Thr Thr Met Ala Lys Asn Thr Val Phe Leu Ile
    290                 295                 300

Glu Met Leu Leu Pro Lys Lys Tyr His Val Leu Arg Phe Leu Asp Lys
305                 310                 315                 320

Gly Glu Arg His Pro Val Arg Glu Ala Arg Ala Val Ile Phe Phe Gly
                325                 330                 335

Asp Gln Glu His Pro Asn Val Thr Glu Phe Ala Val Gly Pro Leu Pro
            340                 345                 350

Gly Pro Ala Tyr Met Arg Ala Leu Ser Pro Arg Pro Gly Tyr Gln Ser
        355                 360                 365

Ser Trp Ala Ser Arg Pro Ile Ser Thr Ala Glu Tyr Ala Leu Leu Tyr
    370                 375                 380
```

```
His Thr Leu Gln Glu Ala Thr Lys Pro Leu His Gln Phe Phe Leu Asn
385                 390                 395                 400

Thr Thr Gly Phe Ser Phe Gln Asp Cys His Asp Arg Cys Leu Ala Phe
                405                 410                 415

Thr Asp Val Ala Pro Arg Gly Val Ala Ser Gly Gln Arg Arg Ser Trp
            420                 425                 430

Leu Ile Ile Gln Arg Tyr Val Glu Gly Tyr Phe Leu His Pro Thr Gly
        435                 440                 445

Leu Glu Leu Leu Val Asp His Gly Ser Thr Asp Ala Gly His Trp Ala
    450                 455                 460

Val Glu Gln Val Trp Tyr Asn Gly Lys Phe Tyr Gly Ser Pro Glu Glu
465                 470                 475                 480

Leu Ala Arg Lys Tyr Ala Asp Gly Glu Val Asp Val Val Val Leu Glu
                485                 490                 495

Asp Pro Leu Pro Gly Gly Lys Gly His Asp Ser Thr Glu Glu Pro Pro
            500                 505                 510

Leu Phe Ser Ser His Lys Pro Arg Gly Asp Phe Pro Ser Pro Ile His
        515                 520                 525

Val Ser Gly Pro Arg Leu Val Gln Pro His Gly Pro Arg Phe Arg Leu
    530                 535                 540

Glu Gly Asn Ala Val Leu Tyr Gly Gly Trp Ser Phe Ala Phe Arg Leu
545                 550                 555                 560

Arg Ser Ser Ser Gly Leu Gln Val Leu Asn Val His Phe Gly Gly Glu
                565                 570                 575

Arg Ile Ala Tyr Glu Val Ser Val Gln Glu Ala Val Ala Leu Tyr Gly
            580                 585                 590

Gly His Thr Pro Ala Gly Met Gln Thr Lys Tyr Leu Asp Val Gly Trp
        595                 600                 605

Gly Leu Gly Ser Val Thr His Glu Leu Ala Pro Gly Ile Asp Cys Pro
    610                 615                 620

Glu Thr Ala Thr Phe Leu Asp Thr Phe His Tyr Tyr Asp Ala Asp Asp
625                 630                 635                 640

Pro Val His Tyr Pro Arg Ala Leu Cys Leu Phe Glu Met Pro Thr Gly
                645                 650                 655

Val Pro Leu Arg Arg His Phe Asn Ser Asn Phe Lys Gly Gly Phe Asn
            660                 665                 670

Phe Tyr Ala Gly Leu Lys Gly Gln Val Leu Val Leu Arg Thr Thr Ser
        675                 680                 685

Thr Val Tyr Asn Tyr Asp Tyr Ile Trp Asp Phe Ile Phe Tyr Pro Asn
    690                 695                 700

Gly Val Met Glu Ala Lys Met His Ala Thr Gly Tyr Val His Ala Thr
705                 710                 715                 720

Phe Tyr Thr Pro Glu Gly Leu Arg His Gly Thr Arg Leu His Thr His
                725                 730                 735

Leu Ile Gly Asn Ile His Thr His Leu Val His Tyr Arg Val Asp Leu
            740                 745                 750

Asp Val Ala Gly Thr Lys Asn Ser Phe Gln Thr Leu Gln Met Lys Leu
        755                 760                 765

Glu Asn Ile Thr Asn Pro Trp Ser Pro Arg His Arg Val Val Gln Pro
    770                 775                 780

Thr Leu Glu Gln Thr Gln Tyr Ser Trp Glu Arg Gln Ala Ala Phe Ser
785                 790                 795                 800

Phe Lys Thr Lys Leu Pro Lys Tyr Leu Leu Phe Thr Ser Pro Gln Glu
```

```
                805                 810                 815

Asn Pro Trp Gly His Lys Arg Ser Tyr Arg Leu Gln Ile His Ser Met
            820                 825                 830

Ala Asp Gln Val Leu Pro Pro Gly Trp Gln Glu Glu Gln Ala Ile Thr
        835                 840                 845

Trp Ala Arg Tyr Pro Leu Ala Val Thr Lys Tyr Arg Glu Ser Glu Leu
    850                 855                 860

Cys Ser Ser Ser Ile Tyr His Gln Asn Asp Pro Trp His Pro Pro Val
865                 870                 875                 880

Val Phe Glu Gln Phe Leu His Asn Asn Glu Asn Ile Glu Asn Glu Asp
                885                 890                 895

Leu Val Ala Trp Val Thr Val Gly Phe Leu His Ile Pro His Ser Glu
            900                 905                 910

Asp Ile Pro Asn Thr Ala Thr Pro Gly Asn Ser Val Gly Phe Leu Leu
        915                 920                 925

Arg Pro Phe Asn Phe Phe Pro Glu Asp Pro Ser Leu Ala Ser Arg Asp
    930                 935                 940

Thr Val Ile Val Trp Pro Arg Asp Asn Gly Pro Asn Tyr Val Gln Arg
945                 950                 955                 960

Trp Ile Pro Glu Asp Arg Asp Cys Ser Met Pro Pro Pro Phe Ser Tyr
                965                 970                 975

Asn Gly Thr Tyr Arg Pro Val
            980


<210> SEQ ID NO 52
<211> LENGTH: 983
<212> TYPE: PRT
<213> ORGANISM: Artificial Sequence
<220> FEATURE:
<223> OTHER INFORMATION: Fc-hDAO-Hepmut5-Cysmut

<400> SEQUENCE: 52

Met Pro Ala Leu Gly Trp Ala Val Ala Ala Ile Leu Met Leu Gln Thr
1               5                   10                  15

Ala Met Ala Glu Cys Pro Pro Cys Pro Ala Pro Pro Val Ala Gly Pro
            20                  25                  30

Ser Val Phe Leu Phe Pro Pro Lys Pro Lys Asp Thr Leu Met Ile Ser
        35                  40                  45

Arg Thr Pro Glu Val Thr Cys Val Val Val Asp Val Ser His Glu Asp
    50                  55                  60

Pro Glu Val Lys Phe Asn Trp Tyr Val Asp Gly Val Glu Val His Asn
65                  70                  75                  80

Ala Lys Thr Lys Pro Arg Glu Glu Gln Tyr Asn Ser Thr Tyr Arg Val
                85                  90                  95

Val Ser Val Leu Thr Val Leu His Gln Asp Trp Leu Asn Gly Lys Glu
            100                 105                 110

Tyr Lys Cys Lys Val Ser Asn Lys Gly Leu Pro Ser Ser Ile Glu Lys
        115                 120                 125

Thr Ile Ser Lys Ala Lys Gly Gln Pro Arg Glu Pro Gln Val Tyr Thr
    130                 135                 140

Leu Pro Pro Ser Arg Glu Glu Met Thr Lys Asn Gln Val Ser Leu Thr
145                 150                 155                 160

Cys Leu Val Lys Gly Phe Tyr Pro Ser Asp Ile Ala Val Glu Trp Glu
                165                 170                 175

Ser Asn Gly Gln Pro Glu Asn Asn Tyr Lys Thr Thr Pro Pro Val Leu
```

```
            180                 185                 190

Asp Ser Asp Gly Ser Phe Phe Leu Tyr Ser Lys Leu Thr Val Asp Lys
        195                 200                 205

Ser Arg Trp Gln Gln Gly Asn Val Phe Ser Cys Ser Val Met His Glu
    210                 215                 220

Ala Leu His Asn His Tyr Thr Gln Lys Ser Leu Ser Leu Ser Pro Gly
225                 230                 235                 240

Lys Glu Pro Lys Ser Ala Asp Lys Thr His Thr Glu Pro Ser Pro Gly
                245                 250                 255

Thr Leu Pro Arg Lys Ala Gly Val Phe Ser Asp Leu Ser Asn Gln Glu
            260                 265                 270

Leu Lys Ala Val His Ser Phe Leu Trp Ser Lys Lys Glu Leu Arg Leu
        275                 280                 285

Gln Pro Ser Ser Thr Thr Thr Met Ala Lys Asn Thr Val Phe Leu Ile
    290                 295                 300

Glu Met Leu Leu Pro Lys Lys Tyr His Val Leu Arg Phe Leu Asp Lys
305                 310                 315                 320

Gly Glu Arg His Pro Val Arg Glu Ala Arg Ala Val Ile Phe Phe Gly
                325                 330                 335

Asp Gln Glu His Pro Asn Val Thr Glu Phe Ala Val Gly Pro Leu Pro
            340                 345                 350

Gly Pro Ala Tyr Met Arg Ala Leu Ser Pro Arg Pro Gly Tyr Gln Ser
        355                 360                 365

Ser Trp Ala Ser Arg Pro Ile Ser Thr Ala Glu Tyr Ala Leu Leu Tyr
    370                 375                 380

His Thr Leu Gln Glu Ala Thr Lys Pro Leu His Gln Phe Phe Leu Asn
385                 390                 395                 400

Thr Thr Gly Phe Ser Phe Gln Asp Cys His Asp Arg Cys Leu Ala Phe
                405                 410                 415

Thr Asp Val Ala Pro Arg Gly Val Ala Ser Gly Gln Arg Arg Ser Trp
            420                 425                 430

Leu Ile Ile Gln Arg Tyr Val Glu Gly Tyr Phe Leu His Pro Thr Gly
        435                 440                 445

Leu Glu Leu Leu Val Asp His Gly Ser Thr Asp Ala Gly His Trp Ala
    450                 455                 460

Val Glu Gln Val Trp Tyr Asn Gly Lys Phe Tyr Gly Ser Pro Glu Glu
465                 470                 475                 480

Leu Ala Arg Lys Tyr Ala Asp Gly Glu Val Asp Val Val Val Leu Glu
                485                 490                 495

Asp Pro Leu Pro Gly Gly Lys Gly His Asp Ser Thr Glu Glu Pro Pro
            500                 505                 510

Leu Phe Ser Ser His Lys Pro Arg Gly Asp Phe Pro Ser Pro Ile His
        515                 520                 525

Val Ser Gly Pro Arg Leu Val Gln Pro His Gly Pro Arg Phe Arg Leu
    530                 535                 540

Glu Gly Asn Ala Val Leu Tyr Gly Gly Trp Ser Phe Ala Phe Arg Leu
545                 550                 555                 560

Arg Ser Ser Ser Gly Leu Gln Val Leu Asn Val His Phe Gly Gly Glu
                565                 570                 575

Arg Ile Ala Tyr Glu Val Ser Val Gln Glu Ala Val Ala Leu Tyr Gly
            580                 585                 590

Gly His Thr Pro Ala Gly Met Gln Thr Lys Tyr Leu Asp Val Gly Trp
        595                 600                 605
```

```
Gly Leu Gly Ser Val Thr His Glu Leu Ala Pro Gly Ile Asp Cys Pro
    610                 615                 620

Glu Thr Ala Thr Phe Leu Asp Thr Phe His Tyr Tyr Asp Ala Asp Asp
625                 630                 635                 640

Pro Val His Tyr Pro Arg Ala Leu Cys Leu Phe Glu Met Pro Thr Gly
                645                 650                 655

Val Pro Leu Arg Arg His Phe Asn Ser Asn Phe Lys Gly Gly Phe Asn
            660                 665                 670

Phe Tyr Ala Gly Leu Lys Gly Gln Val Leu Val Leu Arg Thr Thr Ser
        675                 680                 685

Thr Val Tyr Asn Tyr Asp Tyr Ile Trp Asp Phe Ile Phe Tyr Pro Asn
    690                 695                 700

Gly Val Met Glu Ala Lys Met His Ala Thr Gly Tyr Val His Ala Thr
705                 710                 715                 720

Phe Tyr Thr Pro Glu Gly Leu Arg His Gly Thr Arg Leu His Thr His
                725                 730                 735

Leu Ile Gly Asn Ile His Thr His Leu Val His Tyr Arg Val Asp Leu
            740                 745                 750

Asp Val Ala Gly Thr Lys Asn Ser Phe Gln Thr Leu Gln Met Lys Leu
        755                 760                 765

Glu Asn Ile Thr Asn Pro Trp Ser Pro Arg His Arg Val Val Gln Pro
    770                 775                 780

Thr Leu Glu Gln Thr Gln Tyr Ser Trp Glu Arg Gln Ala Ala Phe Arg
785                 790                 795                 800

Phe Lys Thr Lys Leu Pro Thr Tyr Leu Leu Phe Thr Ser Pro Gln Glu
                805                 810                 815

Asn Pro Trp Gly His Lys Arg Ser Tyr Arg Leu Gln Ile His Ser Met
            820                 825                 830

Ala Asp Gln Val Leu Pro Pro Gly Trp Gln Glu Glu Gln Ala Ile Thr
        835                 840                 845

Trp Ala Arg Tyr Pro Leu Ala Val Thr Lys Tyr Arg Glu Ser Glu Leu
    850                 855                 860

Cys Ser Ser Ser Ile Tyr His Gln Asn Asp Pro Trp His Pro Pro Val
865                 870                 875                 880

Val Phe Glu Gln Phe Leu His Asn Asn Glu Asn Ile Glu Asn Glu Asp
                885                 890                 895

Leu Val Ala Trp Val Thr Val Gly Phe Leu His Ile Pro His Ser Glu
            900                 905                 910

Asp Ile Pro Asn Thr Ala Thr Pro Gly Asn Ser Val Gly Phe Leu Leu
        915                 920                 925

Arg Pro Phe Asn Phe Phe Pro Glu Asp Pro Ser Leu Ala Ser Arg Asp
    930                 935                 940

Thr Val Ile Val Trp Pro Arg Asp Asn Gly Pro Asn Tyr Val Gln Arg
945                 950                 955                 960

Trp Ile Pro Glu Asp Arg Asp Cys Ser Met Pro Pro Pro Phe Ser Tyr
                965                 970                 975

Asn Gly Thr Tyr Arg Pro Val
            980
```

<210> SEQ ID NO 53
<211> LENGTH: 983
<212> TYPE: PRT
<213> ORGANISM: Artificial Sequence
<220> FEATURE:

<223> OTHER INFORMATION: Fc-hDAO-Hepmut6-Cysmut

<400> SEQUENCE: 53

```
Met Pro Ala Leu Gly Trp Ala Val Ala Ala Ile Leu Met Leu Gln Thr
1               5                   10                  15

Ala Met Ala Glu Cys Pro Pro Cys Pro Ala Pro Pro Val Ala Gly Pro
            20                  25                  30

Ser Val Phe Leu Phe Pro Pro Lys Pro Lys Asp Thr Leu Met Ile Ser
        35                  40                  45

Arg Thr Pro Glu Val Thr Cys Val Val Val Asp Val Ser His Glu Asp
    50                  55                  60

Pro Glu Val Lys Phe Asn Trp Tyr Val Asp Gly Val Glu Val His Asn
65                  70                  75                  80

Ala Lys Thr Lys Pro Arg Glu Glu Gln Tyr Asn Ser Thr Tyr Arg Val
                85                  90                  95

Val Ser Val Leu Thr Val Leu His Gln Asp Trp Leu Asn Gly Lys Glu
            100                 105                 110

Tyr Lys Cys Lys Val Ser Asn Lys Gly Leu Pro Ser Ser Ile Glu Lys
        115                 120                 125

Thr Ile Ser Lys Ala Lys Gly Gln Pro Arg Glu Pro Gln Val Tyr Thr
    130                 135                 140

Leu Pro Pro Ser Arg Glu Glu Met Thr Lys Asn Gln Val Ser Leu Thr
145                 150                 155                 160

Cys Leu Val Lys Gly Phe Tyr Pro Ser Asp Ile Ala Val Glu Trp Glu
                165                 170                 175

Ser Asn Gly Gln Pro Glu Asn Asn Tyr Lys Thr Thr Pro Pro Val Leu
            180                 185                 190

Asp Ser Asp Gly Ser Phe Phe Leu Tyr Ser Lys Leu Thr Val Asp Lys
        195                 200                 205

Ser Arg Trp Gln Gln Gly Asn Val Phe Ser Cys Ser Val Met His Glu
    210                 215                 220

Ala Leu His Asn His Tyr Thr Gln Lys Ser Leu Ser Leu Ser Pro Gly
225                 230                 235                 240

Lys Glu Pro Lys Ser Ala Asp Lys Thr His Thr Glu Pro Ser Pro Gly
                245                 250                 255

Thr Leu Pro Arg Lys Ala Gly Val Phe Ser Asp Leu Ser Asn Gln Glu
            260                 265                 270

Leu Lys Ala Val His Ser Phe Leu Trp Ser Lys Lys Glu Leu Arg Leu
        275                 280                 285

Gln Pro Ser Ser Thr Thr Thr Met Ala Lys Asn Thr Val Phe Leu Ile
    290                 295                 300

Glu Met Leu Leu Pro Lys Lys Tyr His Val Leu Arg Phe Leu Asp Lys
305                 310                 315                 320

Gly Glu Arg His Pro Val Arg Glu Ala Arg Ala Val Ile Phe Phe Gly
                325                 330                 335

Asp Gln Glu His Pro Asn Val Thr Glu Phe Ala Val Gly Pro Leu Pro
            340                 345                 350

Gly Pro Ala Tyr Met Arg Ala Leu Ser Pro Arg Pro Gly Tyr Gln Ser
        355                 360                 365

Ser Trp Ala Ser Arg Pro Ile Ser Thr Ala Glu Tyr Ala Leu Leu Tyr
    370                 375                 380

His Thr Leu Gln Glu Ala Thr Lys Pro Leu His Gln Phe Phe Leu Asn
385                 390                 395                 400
```

-continued

```
Thr Thr Gly Phe Ser Phe Gln Asp Cys His Asp Arg Cys Leu Ala Phe
                405                 410                 415

Thr Asp Val Ala Pro Arg Gly Val Ala Ser Gly Gln Arg Arg Ser Trp
            420                 425                 430

Leu Ile Ile Gln Arg Tyr Val Glu Gly Tyr Phe Leu His Pro Thr Gly
        435                 440                 445

Leu Glu Leu Leu Val Asp His Gly Ser Thr Asp Ala Gly His Trp Ala
    450                 455                 460

Val Glu Gln Val Trp Tyr Asn Gly Lys Phe Tyr Gly Ser Pro Glu Glu
465                 470                 475                 480

Leu Ala Arg Lys Tyr Ala Asp Gly Glu Val Asp Val Val Val Leu Glu
                485                 490                 495

Asp Pro Leu Pro Gly Gly Lys Gly His Asp Ser Thr Glu Glu Pro Pro
            500                 505                 510

Leu Phe Ser Ser His Lys Pro Arg Gly Asp Phe Pro Ser Pro Ile His
        515                 520                 525

Val Ser Gly Pro Arg Leu Val Gln Pro His Gly Pro Arg Phe Arg Leu
    530                 535                 540

Glu Gly Asn Ala Val Leu Tyr Gly Gly Trp Ser Phe Ala Phe Arg Leu
545                 550                 555                 560

Arg Ser Ser Ser Gly Leu Gln Val Leu Asn Val His Phe Gly Gly Glu
                565                 570                 575

Arg Ile Ala Tyr Glu Val Ser Val Gln Glu Ala Val Ala Leu Tyr Gly
            580                 585                 590

Gly His Thr Pro Ala Gly Met Gln Thr Lys Tyr Leu Asp Val Gly Trp
        595                 600                 605

Gly Leu Gly Ser Val Thr His Glu Leu Ala Pro Gly Ile Asp Cys Pro
    610                 615                 620

Glu Thr Ala Thr Phe Leu Asp Thr Phe His Tyr Tyr Asp Ala Asp Asp
625                 630                 635                 640

Pro Val His Tyr Pro Arg Ala Leu Cys Leu Phe Glu Met Pro Thr Gly
                645                 650                 655

Val Pro Leu Arg Arg His Phe Asn Ser Asn Phe Lys Gly Gly Phe Asn
            660                 665                 670

Phe Tyr Ala Gly Leu Lys Gly Gln Val Leu Val Leu Arg Thr Thr Ser
        675                 680                 685

Thr Val Tyr Asn Tyr Asp Tyr Ile Trp Asp Phe Ile Phe Tyr Pro Asn
    690                 695                 700

Gly Val Met Glu Ala Lys Met His Ala Thr Gly Tyr Val His Ala Thr
705                 710                 715                 720

Phe Tyr Thr Pro Glu Gly Leu Arg His Gly Thr Arg Leu His Thr His
                725                 730                 735

Leu Ile Gly Asn Ile His Thr His Leu Val His Tyr Arg Val Asp Leu
            740                 745                 750

Asp Val Ala Gly Thr Lys Asn Ser Phe Gln Thr Leu Gln Met Lys Leu
        755                 760                 765

Glu Asn Ile Thr Asn Pro Trp Ser Pro Arg His Arg Val Val Gln Pro
    770                 775                 780

Thr Leu Glu Gln Thr Gln Tyr Ser Trp Glu Arg Gln Ala Ala Phe Arg
785                 790                 795                 800

Phe Gly Gln Thr Leu Pro Lys Tyr Leu Leu Phe Thr Ser Pro Gln Glu
                805                 810                 815

Asn Pro Trp Gly His Lys Arg Ser Tyr Arg Leu Gln Ile His Ser Met
```

```
            820                 825                 830

Ala Asp Gln Val Leu Pro Pro Gly Trp Gln Glu Glu Gln Ala Ile Thr
        835                 840                 845

Trp Ala Arg Tyr Pro Leu Ala Val Thr Lys Tyr Arg Glu Ser Glu Leu
    850                 855                 860

Cys Ser Ser Ser Ile Tyr His Gln Asn Asp Pro Trp His Pro Pro Val
865                 870                 875                 880

Val Phe Glu Gln Phe Leu His Asn Asn Glu Asn Ile Glu Asn Glu Asp
                885                 890                 895

Leu Val Ala Trp Val Thr Val Gly Phe Leu His Ile Pro His Ser Glu
            900                 905                 910

Asp Ile Pro Asn Thr Ala Thr Pro Gly Asn Ser Val Gly Phe Leu Leu
        915                 920                 925

Arg Pro Phe Asn Phe Phe Pro Glu Asp Pro Ser Leu Ala Ser Arg Asp
    930                 935                 940

Thr Val Ile Val Trp Pro Arg Asp Asn Gly Pro Asn Tyr Val Gln Arg
945                 950                 955                 960

Trp Ile Pro Glu Asp Arg Asp Cys Ser Met Pro Pro Pro Phe Ser Tyr
                965                 970                 975

Asn Gly Thr Tyr Arg Pro Val
            980


<210> SEQ ID NO 54
<211> LENGTH: 983
<212> TYPE: PRT
<213> ORGANISM: Artificial Sequence
<220> FEATURE:
<223> OTHER INFORMATION: Fc-hDAO-Hepmut7-Cysmut

<400> SEQUENCE: 54

Met Pro Ala Leu Gly Trp Ala Val Ala Ala Ile Leu Met Leu Gln Thr
1               5                   10                  15

Ala Met Ala Glu Cys Pro Pro Cys Pro Ala Pro Pro Val Ala Gly Pro
            20                  25                  30

Ser Val Phe Leu Phe Pro Pro Lys Pro Lys Asp Thr Leu Met Ile Ser
        35                  40                  45

Arg Thr Pro Glu Val Thr Cys Val Val Val Asp Val Ser His Glu Asp
    50                  55                  60

Pro Glu Val Lys Phe Asn Trp Tyr Val Asp Gly Val Glu Val His Asn
65                  70                  75                  80

Ala Lys Thr Lys Pro Arg Glu Glu Gln Tyr Asn Ser Thr Tyr Arg Val
                85                  90                  95

Val Ser Val Leu Thr Val Leu His Gln Asp Trp Leu Asn Gly Lys Glu
            100                 105                 110

Tyr Lys Cys Lys Val Ser Asn Lys Gly Leu Pro Ser Ser Ile Glu Lys
        115                 120                 125

Thr Ile Ser Lys Ala Lys Gly Gln Pro Arg Glu Pro Gln Val Tyr Thr
    130                 135                 140

Leu Pro Pro Ser Arg Glu Glu Met Thr Lys Asn Gln Val Ser Leu Thr
145                 150                 155                 160

Cys Leu Val Lys Gly Phe Tyr Pro Ser Asp Ile Ala Val Glu Trp Glu
                165                 170                 175

Ser Asn Gly Gln Pro Glu Asn Asn Tyr Lys Thr Thr Pro Pro Val Leu
            180                 185                 190

Asp Ser Asp Gly Ser Phe Phe Leu Tyr Ser Lys Leu Thr Val Asp Lys
```

-continued

```
        195                 200                 205

Ser Arg Trp Gln Gln Gly Asn Val Phe Ser Cys Ser Val Met His Glu
    210                 215                 220

Ala Leu His Asn His Tyr Thr Gln Lys Ser Leu Ser Leu Ser Pro Gly
225                 230                 235                 240

Lys Glu Pro Lys Ser Ala Asp Lys Thr His Thr Glu Pro Ser Pro Gly
                245                 250                 255

Thr Leu Pro Arg Lys Ala Gly Val Phe Ser Asp Leu Ser Asn Gln Glu
            260                 265                 270

Leu Lys Ala Val His Ser Phe Leu Trp Ser Lys Lys Glu Leu Arg Leu
        275                 280                 285

Gln Pro Ser Ser Thr Thr Thr Met Ala Lys Asn Thr Val Phe Leu Ile
    290                 295                 300

Glu Met Leu Leu Pro Lys Lys Tyr His Val Leu Arg Phe Leu Asp Lys
305                 310                 315                 320

Gly Glu Arg His Pro Val Arg Glu Ala Arg Ala Val Ile Phe Phe Gly
                325                 330                 335

Asp Gln Glu His Pro Asn Val Thr Glu Phe Ala Val Gly Pro Leu Pro
            340                 345                 350

Gly Pro Ala Tyr Met Arg Ala Leu Ser Pro Arg Pro Gly Tyr Gln Ser
        355                 360                 365

Ser Trp Ala Ser Arg Pro Ile Ser Thr Ala Glu Tyr Ala Leu Leu Tyr
    370                 375                 380

His Thr Leu Gln Glu Ala Thr Lys Pro Leu His Gln Phe Phe Leu Asn
385                 390                 395                 400

Thr Thr Gly Phe Ser Phe Gln Asp Cys His Asp Arg Cys Leu Ala Phe
                405                 410                 415

Thr Asp Val Ala Pro Arg Gly Val Ala Ser Gly Gln Arg Arg Ser Trp
            420                 425                 430

Leu Ile Ile Gln Arg Tyr Val Glu Gly Tyr Phe Leu His Pro Thr Gly
        435                 440                 445

Leu Glu Leu Leu Val Asp His Gly Ser Thr Asp Ala Gly His Trp Ala
    450                 455                 460

Val Glu Gln Val Trp Tyr Asn Gly Lys Phe Tyr Gly Ser Pro Glu Glu
465                 470                 475                 480

Leu Ala Arg Lys Tyr Ala Asp Gly Glu Val Asp Val Val Val Leu Glu
                485                 490                 495

Asp Pro Leu Pro Gly Gly Lys Gly His Asp Ser Thr Glu Glu Pro Pro
            500                 505                 510

Leu Phe Ser Ser His Lys Pro Arg Gly Asp Phe Pro Ser Pro Ile His
        515                 520                 525

Val Ser Gly Pro Arg Leu Val Gln Pro His Gly Pro Arg Phe Arg Leu
    530                 535                 540

Glu Gly Asn Ala Val Leu Tyr Gly Gly Trp Ser Phe Ala Phe Arg Leu
545                 550                 555                 560

Arg Ser Ser Ser Gly Leu Gln Val Leu Asn Val His Phe Gly Gly Glu
                565                 570                 575

Arg Ile Ala Tyr Glu Val Ser Val Gln Glu Ala Val Ala Leu Tyr Gly
            580                 585                 590

Gly His Thr Pro Ala Gly Met Gln Thr Lys Tyr Leu Asp Val Gly Trp
        595                 600                 605

Gly Leu Gly Ser Val Thr His Glu Leu Ala Pro Gly Ile Asp Cys Pro
    610                 615                 620
```

Glu Thr Ala Thr Phe Leu Asp Thr Phe His Tyr Tyr Asp Ala Asp Asp
625 630 635 640

Pro Val His Tyr Pro Arg Ala Leu Cys Leu Phe Glu Met Pro Thr Gly
645 650 655

Val Pro Leu Arg Arg His Phe Asn Ser Asn Phe Lys Gly Gly Phe Asn
660 665 670

Phe Tyr Ala Gly Leu Lys Gly Gln Val Leu Val Leu Arg Thr Thr Ser
675 680 685

Thr Val Tyr Asn Tyr Asp Tyr Ile Trp Asp Phe Ile Phe Tyr Pro Asn
690 695 700

Gly Val Met Glu Ala Lys Met His Ala Thr Gly Tyr Val His Ala Thr
705 710 715 720

Phe Tyr Thr Pro Glu Gly Leu Arg His Gly Thr Arg Leu His Thr His
725 730 735

Leu Ile Gly Asn Ile His Thr His Leu Val His Tyr Arg Val Asp Leu
740 745 750

Asp Val Ala Gly Thr Lys Asn Ser Phe Gln Thr Leu Gln Met Lys Leu
755 760 765

Glu Asn Ile Thr Asn Pro Trp Ser Pro Arg His Arg Val Val Gln Pro
770 775 780

Thr Leu Glu Gln Thr Gln Tyr Ser Trp Glu Arg Gln Ala Ala Phe Ser
785 790 795 800

Phe Lys Arg Lys Leu Pro Thr Tyr Leu Leu Phe Thr Ser Pro Gln Glu
805 810 815

Asn Pro Trp Gly His Lys Arg Ser Tyr Arg Leu Gln Ile His Ser Met
820 825 830

Ala Asp Gln Val Leu Pro Pro Gly Trp Gln Glu Glu Gln Ala Ile Thr
835 840 845

Trp Ala Arg Tyr Pro Leu Ala Val Thr Lys Tyr Arg Glu Ser Glu Leu
850 855 860

Cys Ser Ser Ser Ile Tyr His Gln Asn Asp Pro Trp His Pro Pro Val
865 870 875 880

Val Phe Glu Gln Phe Leu His Asn Asn Glu Asn Ile Glu Asn Glu Asp
885 890 895

Leu Val Ala Trp Val Thr Val Gly Phe Leu His Ile Pro His Ser Glu
900 905 910

Asp Ile Pro Asn Thr Ala Thr Pro Gly Asn Ser Val Gly Phe Leu Leu
915 920 925

Arg Pro Phe Asn Phe Phe Pro Glu Asp Pro Ser Leu Ala Ser Arg Asp
930 935 940

Thr Val Ile Val Trp Pro Arg Asp Asn Gly Pro Asn Tyr Val Gln Arg
945 950 955 960

Trp Ile Pro Glu Asp Arg Asp Cys Ser Met Pro Pro Pro Phe Ser Tyr
965 970 975

Asn Gly Thr Tyr Arg Pro Val
980

<210> SEQ ID NO 55
<211> LENGTH: 982
<212> TYPE: PRT
<213> ORGANISM: Artificial Sequence
<220> FEATURE:
<223> OTHER INFORMATION: hDAO-Fc

<400> SEQUENCE: 55

```
Met Pro Ala Leu Gly Trp Ala Val Ala Ala Ile Leu Met Leu Gln Thr
1               5                   10                  15

Ala Met Ala Glu Pro Ser Pro Gly Thr Leu Pro Arg Lys Ala Gly Val
            20                  25                  30

Phe Ser Asp Leu Ser Asn Gln Glu Leu Lys Ala Val His Ser Phe Leu
        35                  40                  45

Trp Ser Lys Lys Glu Leu Arg Leu Gln Pro Ser Ser Thr Thr Thr Met
    50                  55                  60

Ala Lys Asn Thr Val Phe Leu Ile Glu Met Leu Leu Pro Lys Lys Tyr
65                  70                  75                  80

His Val Leu Arg Phe Leu Asp Lys Gly Glu Arg His Pro Val Arg Glu
                85                  90                  95

Ala Arg Ala Val Ile Phe Phe Gly Asp Gln Glu His Pro Asn Val Thr
            100                 105                 110

Glu Phe Ala Val Gly Pro Leu Pro Gly Pro Cys Tyr Met Arg Ala Leu
        115                 120                 125

Ser Pro Arg Pro Gly Tyr Gln Ser Ser Trp Ala Ser Arg Pro Ile Ser
    130                 135                 140

Thr Ala Glu Tyr Ala Leu Leu Tyr His Thr Leu Gln Glu Ala Thr Lys
145                 150                 155                 160

Pro Leu His Gln Phe Phe Leu Asn Thr Thr Gly Phe Ser Phe Gln Asp
                165                 170                 175

Cys His Asp Arg Cys Leu Ala Phe Thr Asp Val Ala Pro Arg Gly Val
            180                 185                 190

Ala Ser Gly Gln Arg Arg Ser Trp Leu Ile Ile Gln Arg Tyr Val Glu
        195                 200                 205

Gly Tyr Phe Leu His Pro Thr Gly Leu Glu Leu Leu Val Asp His Gly
    210                 215                 220

Ser Thr Asp Ala Gly His Trp Ala Val Glu Gln Val Trp Tyr Asn Gly
225                 230                 235                 240

Lys Phe Tyr Gly Ser Pro Glu Glu Leu Ala Arg Lys Tyr Ala Asp Gly
                245                 250                 255

Glu Val Asp Val Val Val Leu Glu Asp Pro Leu Pro Gly Gly Lys Gly
            260                 265                 270

His Asp Ser Thr Glu Glu Pro Pro Leu Phe Ser Ser His Lys Pro Arg
        275                 280                 285

Gly Asp Phe Pro Ser Pro Ile His Val Ser Gly Pro Arg Leu Val Gln
    290                 295                 300

Pro His Gly Pro Arg Phe Arg Leu Glu Gly Asn Ala Val Leu Tyr Gly
305                 310                 315                 320

Gly Trp Ser Phe Ala Phe Arg Leu Arg Ser Ser Ser Gly Leu Gln Val
                325                 330                 335

Leu Asn Val His Phe Gly Gly Glu Arg Ile Ala Tyr Glu Val Ser Val
            340                 345                 350

Gln Glu Ala Val Ala Leu Tyr Gly Gly His Thr Pro Ala Gly Met Gln
        355                 360                 365

Thr Lys Tyr Leu Asp Val Gly Trp Gly Leu Gly Ser Val Thr His Glu
    370                 375                 380

Leu Ala Pro Gly Ile Asp Cys Pro Glu Thr Ala Thr Phe Leu Asp Thr
385                 390                 395                 400

Phe His Tyr Tyr Asp Ala Asp Asp Pro Val His Tyr Pro Arg Ala Leu
                405                 410                 415
```

```
Cys Leu Phe Glu Met Pro Thr Gly Val Pro Leu Arg Arg His Phe Asn
            420                 425                 430

Ser Asn Phe Lys Gly Gly Phe Asn Phe Tyr Ala Gly Leu Lys Gly Gln
        435                 440                 445

Val Leu Val Leu Arg Thr Thr Ser Thr Val Tyr Asn Tyr Asp Tyr Ile
    450                 455                 460

Trp Asp Phe Ile Phe Tyr Pro Asn Gly Val Met Glu Ala Lys Met His
465                 470                 475                 480

Ala Thr Gly Tyr Val His Ala Thr Phe Tyr Thr Pro Glu Gly Leu Arg
                485                 490                 495

His Gly Thr Arg Leu His Thr His Leu Ile Gly Asn Ile His Thr His
            500                 505                 510

Leu Val His Tyr Arg Val Asp Leu Asp Val Ala Gly Thr Lys Asn Ser
        515                 520                 525

Phe Gln Thr Leu Gln Met Lys Leu Glu Asn Ile Thr Asn Pro Trp Ser
    530                 535                 540

Pro Arg His Arg Val Val Gln Pro Thr Leu Glu Gln Thr Gln Tyr Ser
545                 550                 555                 560

Trp Glu Arg Gln Ala Ala Phe Arg Phe Lys Arg Lys Leu Pro Lys Tyr
                565                 570                 575

Leu Leu Phe Thr Ser Pro Gln Glu Asn Pro Trp Gly His Lys Arg Ser
            580                 585                 590

Tyr Arg Leu Gln Ile His Ser Met Ala Asp Gln Val Leu Pro Pro Gly
        595                 600                 605

Trp Gln Glu Glu Gln Ala Ile Thr Trp Ala Arg Tyr Pro Leu Ala Val
    610                 615                 620

Thr Lys Tyr Arg Glu Ser Glu Leu Cys Ser Ser Ser Ile Tyr His Gln
625                 630                 635                 640

Asn Asp Pro Trp His Pro Pro Val Val Phe Glu Gln Phe Leu His Asn
                645                 650                 655

Asn Glu Asn Ile Glu Asn Glu Asp Leu Val Ala Trp Val Thr Val Gly
            660                 665                 670

Phe Leu His Ile Pro His Ser Glu Asp Ile Pro Asn Thr Ala Thr Pro
        675                 680                 685

Gly Asn Ser Val Gly Phe Leu Leu Arg Pro Phe Asn Phe Phe Pro Glu
    690                 695                 700

Asp Pro Ser Leu Ala Ser Arg Asp Thr Val Ile Val Trp Pro Arg Asp
705                 710                 715                 720

Asn Gly Pro Asn Tyr Val Gln Arg Trp Ile Pro Glu Asp Arg Asp Cys
                725                 730                 735

Ser Met Pro Pro Pro Phe Ser Tyr Asn Gly Thr Tyr Arg Pro Val Glu
            740                 745                 750

Pro Lys Ser Ala Asp Lys Thr His Thr Cys Pro Pro Cys Pro Ala Pro
        755                 760                 765

Pro Val Ala Gly Pro Ser Val Phe Leu Phe Pro Pro Lys Pro Lys Asp
    770                 775                 780

Thr Leu Met Ile Ser Arg Thr Pro Glu Val Thr Cys Val Val Val Asp
785                 790                 795                 800

Val Ser His Glu Asp Pro Glu Val Lys Phe Asn Trp Tyr Val Asp Gly
                805                 810                 815

Val Glu Val His Asn Ala Lys Thr Lys Pro Arg Glu Glu Gln Tyr Asn
            820                 825                 830

Ser Thr Tyr Arg Val Val Ser Val Leu Thr Val Leu His Gln Asp Trp
```

835 840 845

Leu Asn Gly Lys Glu Tyr Lys Cys Lys Val Ser Asn Lys Gly Leu Pro
850 855 860

Ser Ser Ile Glu Lys Thr Ile Ser Lys Ala Lys Gly Gln Pro Arg Glu
865 870 875 880

Pro Gln Val Tyr Thr Leu Pro Pro Ser Arg Glu Glu Met Thr Lys Asn
885 890 895

Gln Val Ser Leu Thr Cys Leu Val Lys Gly Phe Tyr Pro Ser Asp Ile
900 905 910

Ala Val Glu Trp Glu Ser Asn Gly Gln Pro Glu Asn Asn Tyr Lys Thr
915 920 925

Thr Pro Pro Val Leu Asp Ser Asp Gly Ser Phe Phe Leu Tyr Ser Lys
930 935 940

Leu Thr Val Asp Lys Ser Arg Trp Gln Gln Gly Asn Val Phe Ser Cys
945 950 955 960

Ser Val Met His Glu Ala Leu His Asn His Tyr Thr Gln Lys Ser Leu
965 970 975

Ser Leu Ser Pro Gly Lys
980

<210> SEQ ID NO 56
<211> LENGTH: 982
<212> TYPE: PRT
<213> ORGANISM: Artificial Sequence
<220> FEATURE:
<223> OTHER INFORMATION: hDAO-Fc-Hepmut1

<400> SEQUENCE: 56

Met Pro Ala Leu Gly Trp Ala Val Ala Ala Ile Leu Met Leu Gln Thr
1 5 10 15

Ala Met Ala Glu Pro Ser Pro Gly Thr Leu Pro Arg Lys Ala Gly Val
20 25 30

Phe Ser Asp Leu Ser Asn Gln Glu Leu Lys Ala Val His Ser Phe Leu
35 40 45

Trp Ser Lys Lys Glu Leu Arg Leu Gln Pro Ser Ser Thr Thr Thr Met
50 55 60

Ala Lys Asn Thr Val Phe Leu Ile Glu Met Leu Leu Pro Lys Lys Tyr
65 70 75 80

His Val Leu Arg Phe Leu Asp Lys Gly Glu Arg His Pro Val Arg Glu
85 90 95

Ala Arg Ala Val Ile Phe Phe Gly Asp Gln Glu His Pro Asn Val Thr
100 105 110

Glu Phe Ala Val Gly Pro Leu Pro Gly Pro Cys Tyr Met Arg Ala Leu
115 120 125

Ser Pro Arg Pro Gly Tyr Gln Ser Ser Trp Ala Ser Arg Pro Ile Ser
130 135 140

Thr Ala Glu Tyr Ala Leu Leu Tyr His Thr Leu Gln Glu Ala Thr Lys
145 150 155 160

Pro Leu His Gln Phe Phe Leu Asn Thr Thr Gly Phe Ser Phe Gln Asp
165 170 175

Cys His Asp Arg Cys Leu Ala Phe Thr Asp Val Ala Pro Arg Gly Val
180 185 190

Ala Ser Gly Gln Arg Arg Ser Trp Leu Ile Ile Gln Arg Tyr Val Glu
195 200 205

Gly Tyr Phe Leu His Pro Thr Gly Leu Glu Leu Leu Val Asp His Gly

```
    210                 215                 220

Ser Thr Asp Ala Gly His Trp Ala Val Glu Gln Val Trp Tyr Asn Gly
225                 230                 235                 240

Lys Phe Tyr Gly Ser Pro Glu Glu Leu Ala Arg Lys Tyr Ala Asp Gly
                245                 250                 255

Glu Val Asp Val Val Val Leu Glu Asp Pro Leu Pro Gly Gly Lys Gly
            260                 265                 270

His Asp Ser Thr Glu Glu Pro Pro Leu Phe Ser Ser His Lys Pro Arg
        275                 280                 285

Gly Asp Phe Pro Ser Pro Ile His Val Ser Gly Pro Arg Leu Val Gln
    290                 295                 300

Pro His Gly Pro Arg Phe Arg Leu Glu Gly Asn Ala Val Leu Tyr Gly
305                 310                 315                 320

Gly Trp Ser Phe Ala Phe Arg Leu Arg Ser Ser Ser Gly Leu Gln Val
                325                 330                 335

Leu Asn Val His Phe Gly Gly Glu Arg Ile Ala Tyr Glu Val Ser Val
            340                 345                 350

Gln Glu Ala Val Ala Leu Tyr Gly Gly His Thr Pro Ala Gly Met Gln
        355                 360                 365

Thr Lys Tyr Leu Asp Val Gly Trp Gly Leu Gly Ser Val Thr His Glu
    370                 375                 380

Leu Ala Pro Gly Ile Asp Cys Pro Glu Thr Ala Thr Phe Leu Asp Thr
385                 390                 395                 400

Phe His Tyr Tyr Asp Ala Asp Asp Pro Val His Tyr Pro Arg Ala Leu
                405                 410                 415

Cys Leu Phe Glu Met Pro Thr Gly Val Pro Leu Arg Arg His Phe Asn
            420                 425                 430

Ser Asn Phe Lys Gly Gly Phe Asn Phe Tyr Ala Gly Leu Lys Gly Gln
        435                 440                 445

Val Leu Val Leu Arg Thr Thr Ser Thr Val Tyr Asn Tyr Asp Tyr Ile
    450                 455                 460

Trp Asp Phe Ile Phe Tyr Pro Asn Gly Val Met Glu Ala Lys Met His
465                 470                 475                 480

Ala Thr Gly Tyr Val His Ala Thr Phe Tyr Thr Pro Glu Gly Leu Arg
                485                 490                 495

His Gly Thr Arg Leu His Thr His Leu Ile Gly Asn Ile His Thr His
            500                 505                 510

Leu Val His Tyr Arg Val Asp Leu Asp Val Ala Gly Thr Lys Asn Ser
        515                 520                 525

Phe Gln Thr Leu Gln Met Lys Leu Glu Asn Ile Thr Asn Pro Trp Ser
    530                 535                 540

Pro Arg His Arg Val Val Gln Pro Thr Leu Glu Gln Thr Gln Tyr Ser
545                 550                 555                 560

Trp Glu Arg Gln Ala Ala Phe Ser Phe Lys Arg Lys Leu Pro Lys Tyr
                565                 570                 575

Leu Leu Phe Thr Ser Pro Gln Glu Asn Pro Trp Gly His Lys Arg Ser
            580                 585                 590

Tyr Arg Leu Gln Ile His Ser Met Ala Asp Gln Val Leu Pro Pro Gly
        595                 600                 605

Trp Gln Glu Glu Gln Ala Ile Thr Trp Ala Arg Tyr Pro Leu Ala Val
    610                 615                 620

Thr Lys Tyr Arg Glu Ser Glu Leu Cys Ser Ser Ser Ile Tyr His Gln
625                 630                 635                 640
```

Asn Asp Pro Trp His Pro Pro Val Val Phe Glu Gln Phe Leu His Asn
645 650 655

Asn Glu Asn Ile Glu Asn Glu Asp Leu Val Ala Trp Val Thr Val Gly
660 665 670

Phe Leu His Ile Pro His Ser Glu Asp Ile Pro Asn Thr Ala Thr Pro
675 680 685

Gly Asn Ser Val Gly Phe Leu Leu Arg Pro Phe Asn Phe Phe Pro Glu
690 695 700

Asp Pro Ser Leu Ala Ser Arg Asp Thr Val Ile Val Trp Pro Arg Asp
705 710 715 720

Asn Gly Pro Asn Tyr Val Gln Arg Trp Ile Pro Glu Asp Arg Asp Cys
725 730 735

Ser Met Pro Pro Pro Phe Ser Tyr Asn Gly Thr Tyr Arg Pro Val Glu
740 745 750

Pro Lys Ser Ala Asp Lys Thr His Thr Cys Pro Pro Cys Pro Ala Pro
755 760 765

Pro Val Ala Gly Pro Ser Val Phe Leu Phe Pro Pro Lys Pro Lys Asp
770 775 780

Thr Leu Met Ile Ser Arg Thr Pro Glu Val Thr Cys Val Val Val Asp
785 790 795 800

Val Ser His Glu Asp Pro Glu Val Lys Phe Asn Trp Tyr Val Asp Gly
805 810 815

Val Glu Val His Asn Ala Lys Thr Lys Pro Arg Glu Glu Gln Tyr Asn
820 825 830

Ser Thr Tyr Arg Val Val Ser Val Leu Thr Val Leu His Gln Asp Trp
835 840 845

Leu Asn Gly Lys Glu Tyr Lys Cys Lys Val Ser Asn Lys Gly Leu Pro
850 855 860

Ser Ser Ile Glu Lys Thr Ile Ser Lys Ala Lys Gly Gln Pro Arg Glu
865 870 875 880

Pro Gln Val Tyr Thr Leu Pro Pro Ser Arg Glu Glu Met Thr Lys Asn
885 890 895

Gln Val Ser Leu Thr Cys Leu Val Lys Gly Phe Tyr Pro Ser Asp Ile
900 905 910

Ala Val Glu Trp Glu Ser Asn Gly Gln Pro Glu Asn Asn Tyr Lys Thr
915 920 925

Thr Pro Pro Val Leu Asp Ser Asp Gly Ser Phe Phe Leu Tyr Ser Lys
930 935 940

Leu Thr Val Asp Lys Ser Arg Trp Gln Gln Gly Asn Val Phe Ser Cys
945 950 955 960

Ser Val Met His Glu Ala Leu His Asn His Tyr Thr Gln Lys Ser Leu
965 970 975

Ser Leu Ser Pro Gly Lys
980

<210> SEQ ID NO 57
<211> LENGTH: 982
<212> TYPE: PRT
<213> ORGANISM: Artificial Sequence
<220> FEATURE:
<223> OTHER INFORMATION: hDAO-Fc-Hepmut2

<400> SEQUENCE: 57

Met Pro Ala Leu Gly Trp Ala Val Ala Ala Ile Leu Met Leu Gln Thr
1 5 10 15

```
Ala Met Ala Glu Pro Ser Pro Gly Thr Leu Pro Arg Lys Ala Gly Val
            20                  25                  30

Phe Ser Asp Leu Ser Asn Gln Glu Leu Lys Ala Val His Ser Phe Leu
        35                  40                  45

Trp Ser Lys Lys Glu Leu Arg Leu Gln Pro Ser Ser Thr Thr Thr Met
    50                  55                  60

Ala Lys Asn Thr Val Phe Leu Ile Glu Met Leu Leu Pro Lys Lys Tyr
65                  70                  75                  80

His Val Leu Arg Phe Leu Asp Lys Gly Glu Arg His Pro Val Arg Glu
                85                  90                  95

Ala Arg Ala Val Ile Phe Phe Gly Asp Gln Glu His Pro Asn Val Thr
            100                 105                 110

Glu Phe Ala Val Gly Pro Leu Pro Gly Pro Cys Tyr Met Arg Ala Leu
        115                 120                 125

Ser Pro Arg Pro Gly Tyr Gln Ser Ser Trp Ala Ser Arg Pro Ile Ser
    130                 135                 140

Thr Ala Glu Tyr Ala Leu Leu Tyr His Thr Leu Gln Glu Ala Thr Lys
145                 150                 155                 160

Pro Leu His Gln Phe Phe Leu Asn Thr Thr Gly Phe Ser Phe Gln Asp
                165                 170                 175

Cys His Asp Arg Cys Leu Ala Phe Thr Asp Val Ala Pro Arg Gly Val
            180                 185                 190

Ala Ser Gly Gln Arg Arg Ser Trp Leu Ile Ile Gln Arg Tyr Val Glu
        195                 200                 205

Gly Tyr Phe Leu His Pro Thr Gly Leu Glu Leu Leu Val Asp His Gly
    210                 215                 220

Ser Thr Asp Ala Gly His Trp Ala Val Glu Gln Val Trp Tyr Asn Gly
225                 230                 235                 240

Lys Phe Tyr Gly Ser Pro Glu Glu Leu Ala Arg Lys Tyr Ala Asp Gly
                245                 250                 255

Glu Val Asp Val Val Val Leu Glu Asp Pro Leu Pro Gly Gly Lys Gly
            260                 265                 270

His Asp Ser Thr Glu Glu Pro Pro Leu Phe Ser Ser His Lys Pro Arg
        275                 280                 285

Gly Asp Phe Pro Ser Pro Ile His Val Ser Gly Pro Arg Leu Val Gln
    290                 295                 300

Pro His Gly Pro Arg Phe Arg Leu Glu Gly Asn Ala Val Leu Tyr Gly
305                 310                 315                 320

Gly Trp Ser Phe Ala Phe Arg Leu Arg Ser Ser Ser Gly Leu Gln Val
                325                 330                 335

Leu Asn Val His Phe Gly Gly Glu Arg Ile Ala Tyr Glu Val Ser Val
            340                 345                 350

Gln Glu Ala Val Ala Leu Tyr Gly Gly His Thr Pro Ala Gly Met Gln
        355                 360                 365

Thr Lys Tyr Leu Asp Val Gly Trp Gly Leu Gly Ser Val Thr His Glu
    370                 375                 380

Leu Ala Pro Gly Ile Asp Cys Pro Glu Thr Ala Thr Phe Leu Asp Thr
385                 390                 395                 400

Phe His Tyr Tyr Asp Ala Asp Asp Pro Val His Tyr Pro Arg Ala Leu
                405                 410                 415

Cys Leu Phe Glu Met Pro Thr Gly Val Pro Leu Arg Arg His Phe Asn
            420                 425                 430
```

```
Ser Asn Phe Lys Gly Gly Phe Asn Phe Tyr Ala Gly Leu Lys Gly Gln
        435                 440                 445

Val Leu Val Leu Arg Thr Thr Ser Thr Val Tyr Asn Tyr Asp Tyr Ile
    450                 455                 460

Trp Asp Phe Ile Phe Tyr Pro Asn Gly Val Met Glu Ala Lys Met His
465                 470                 475                 480

Ala Thr Gly Tyr Val His Ala Thr Phe Tyr Thr Pro Glu Gly Leu Arg
                485                 490                 495

His Gly Thr Arg Leu His Thr His Leu Ile Gly Asn Ile His Thr His
            500                 505                 510

Leu Val His Tyr Arg Val Asp Leu Asp Val Ala Gly Thr Lys Asn Ser
        515                 520                 525

Phe Gln Thr Leu Gln Met Lys Leu Glu Asn Ile Thr Asn Pro Trp Ser
    530                 535                 540

Pro Arg His Arg Val Val Gln Pro Thr Leu Glu Gln Thr Gln Tyr Ser
545                 550                 555                 560

Trp Glu Arg Gln Ala Ala Phe Arg Phe Lys Arg Lys Leu Pro Thr Tyr
                565                 570                 575

Leu Leu Phe Thr Ser Pro Gln Glu Asn Pro Trp Gly His Lys Arg Ser
            580                 585                 590

Tyr Arg Leu Gln Ile His Ser Met Ala Asp Gln Val Leu Pro Pro Gly
        595                 600                 605

Trp Gln Glu Glu Gln Ala Ile Thr Trp Ala Arg Tyr Pro Leu Ala Val
    610                 615                 620

Thr Lys Tyr Arg Glu Ser Glu Leu Cys Ser Ser Ser Ile Tyr His Gln
625                 630                 635                 640

Asn Asp Pro Trp His Pro Pro Val Val Phe Glu Gln Phe Leu His Asn
                645                 650                 655

Asn Glu Asn Ile Glu Asn Glu Asp Leu Val Ala Trp Val Thr Val Gly
            660                 665                 670

Phe Leu His Ile Pro His Ser Glu Asp Ile Pro Asn Thr Ala Thr Pro
        675                 680                 685

Gly Asn Ser Val Gly Phe Leu Leu Arg Pro Phe Asn Phe Phe Pro Glu
    690                 695                 700

Asp Pro Ser Leu Ala Ser Arg Asp Thr Val Ile Val Trp Pro Arg Asp
705                 710                 715                 720

Asn Gly Pro Asn Tyr Val Gln Arg Trp Ile Pro Glu Asp Arg Asp Cys
                725                 730                 735

Ser Met Pro Pro Pro Phe Ser Tyr Asn Gly Thr Tyr Arg Pro Val Glu
            740                 745                 750

Pro Lys Ser Ala Asp Lys Thr His Thr Cys Pro Pro Cys Pro Ala Pro
        755                 760                 765

Pro Val Ala Gly Pro Ser Val Phe Leu Phe Pro Pro Lys Pro Lys Asp
    770                 775                 780

Thr Leu Met Ile Ser Arg Thr Pro Glu Val Thr Cys Val Val Val Asp
785                 790                 795                 800

Val Ser His Glu Asp Pro Glu Val Lys Phe Asn Trp Tyr Val Asp Gly
                805                 810                 815

Val Glu Val His Asn Ala Lys Thr Lys Pro Arg Glu Glu Gln Tyr Asn
            820                 825                 830

Ser Thr Tyr Arg Val Val Ser Val Leu Thr Val Leu His Gln Asp Trp
        835                 840                 845

Leu Asn Gly Lys Glu Tyr Lys Cys Lys Val Ser Asn Lys Gly Leu Pro
```

```
    850                 855                 860

Ser Ser Ile Glu Lys Thr Ile Ser Lys Ala Lys Gly Gln Pro Arg Glu
865                 870                 875                 880

Pro Gln Val Tyr Thr Leu Pro Pro Ser Arg Glu Glu Met Thr Lys Asn
                885                 890                 895

Gln Val Ser Leu Thr Cys Leu Val Lys Gly Phe Tyr Pro Ser Asp Ile
            900                 905                 910

Ala Val Glu Trp Glu Ser Asn Gly Gln Pro Glu Asn Asn Tyr Lys Thr
        915                 920                 925

Thr Pro Pro Val Leu Asp Ser Asp Gly Ser Phe Phe Leu Tyr Ser Lys
    930                 935                 940

Leu Thr Val Asp Lys Ser Arg Trp Gln Gln Gly Asn Val Phe Ser Cys
945                 950                 955                 960

Ser Val Met His Glu Ala Leu His Asn His Tyr Thr Gln Lys Ser Leu
                965                 970                 975

Ser Leu Ser Pro Gly Lys
            980


<210> SEQ ID NO 58
<211> LENGTH: 982
<212> TYPE: PRT
<213> ORGANISM: Artificial Sequence
<220> FEATURE:
<223> OTHER INFORMATION: hDAO-Fc-Hepmut3

<400> SEQUENCE: 58

Met Pro Ala Leu Gly Trp Ala Val Ala Ala Ile Leu Met Leu Gln Thr
1               5                   10                  15

Ala Met Ala Glu Pro Ser Pro Gly Thr Leu Pro Arg Lys Ala Gly Val
            20                  25                  30

Phe Ser Asp Leu Ser Asn Gln Glu Leu Lys Ala Val His Ser Phe Leu
        35                  40                  45

Trp Ser Lys Lys Glu Leu Arg Leu Gln Pro Ser Ser Thr Thr Thr Met
    50                  55                  60

Ala Lys Asn Thr Val Phe Leu Ile Glu Met Leu Leu Pro Lys Lys Tyr
65                  70                  75                  80

His Val Leu Arg Phe Leu Asp Lys Gly Glu Arg His Pro Val Arg Glu
                85                  90                  95

Ala Arg Ala Val Ile Phe Phe Gly Asp Gln Glu His Pro Asn Val Thr
            100                 105                 110

Glu Phe Ala Val Gly Pro Leu Pro Gly Pro Cys Tyr Met Arg Ala Leu
        115                 120                 125

Ser Pro Arg Pro Gly Tyr Gln Ser Ser Trp Ala Ser Arg Pro Ile Ser
    130                 135                 140

Thr Ala Glu Tyr Ala Leu Leu Tyr His Thr Leu Gln Glu Ala Thr Lys
145                 150                 155                 160

Pro Leu His Gln Phe Phe Leu Asn Thr Thr Gly Phe Ser Phe Gln Asp
                165                 170                 175

Cys His Asp Arg Cys Leu Ala Phe Thr Asp Val Ala Pro Arg Gly Val
            180                 185                 190

Ala Ser Gly Gln Arg Arg Ser Trp Leu Ile Ile Gln Arg Tyr Val Glu
        195                 200                 205

Gly Tyr Phe Leu His Pro Thr Gly Leu Glu Leu Leu Val Asp His Gly
    210                 215                 220

Ser Thr Asp Ala Gly His Trp Ala Val Glu Gln Val Trp Tyr Asn Gly
```

```
225                 230                 235                 240

Lys Phe Tyr Gly Ser Pro Glu Glu Leu Ala Arg Lys Tyr Ala Asp Gly
                245                 250                 255

Glu Val Asp Val Val Val Leu Glu Asp Pro Leu Pro Gly Gly Lys Gly
            260                 265                 270

His Asp Ser Thr Glu Glu Pro Pro Leu Phe Ser Ser His Lys Pro Arg
        275                 280                 285

Gly Asp Phe Pro Ser Pro Ile His Val Ser Gly Pro Arg Leu Val Gln
    290                 295                 300

Pro His Gly Pro Arg Phe Arg Leu Glu Gly Asn Ala Val Leu Tyr Gly
305                 310                 315                 320

Gly Trp Ser Phe Ala Phe Arg Leu Arg Ser Ser Ser Gly Leu Gln Val
                325                 330                 335

Leu Asn Val His Phe Gly Gly Glu Arg Ile Ala Tyr Glu Val Ser Val
            340                 345                 350

Gln Glu Ala Val Ala Leu Tyr Gly Gly His Thr Pro Ala Gly Met Gln
        355                 360                 365

Thr Lys Tyr Leu Asp Val Gly Trp Gly Leu Gly Ser Val Thr His Glu
    370                 375                 380

Leu Ala Pro Gly Ile Asp Cys Pro Glu Thr Ala Thr Phe Leu Asp Thr
385                 390                 395                 400

Phe His Tyr Tyr Asp Ala Asp Asp Pro Val His Tyr Pro Arg Ala Leu
                405                 410                 415

Cys Leu Phe Glu Met Pro Thr Gly Val Pro Leu Arg Arg His Phe Asn
            420                 425                 430

Ser Asn Phe Lys Gly Gly Phe Asn Phe Tyr Ala Gly Leu Lys Gly Gln
        435                 440                 445

Val Leu Val Leu Arg Thr Thr Ser Thr Val Tyr Asn Tyr Asp Tyr Ile
    450                 455                 460

Trp Asp Phe Ile Phe Tyr Pro Asn Gly Val Met Glu Ala Lys Met His
465                 470                 475                 480

Ala Thr Gly Tyr Val His Ala Thr Phe Tyr Thr Pro Glu Gly Leu Arg
                485                 490                 495

His Gly Thr Arg Leu His Thr His Leu Ile Gly Asn Ile His Thr His
            500                 505                 510

Leu Val His Tyr Arg Val Asp Leu Asp Val Ala Gly Thr Lys Asn Ser
        515                 520                 525

Phe Gln Thr Leu Gln Met Lys Leu Glu Asn Ile Thr Asn Pro Trp Ser
    530                 535                 540

Pro Arg His Arg Val Val Gln Pro Thr Leu Glu Gln Thr Gln Tyr Ser
545                 550                 555                 560

Trp Glu Arg Gln Ala Ala Phe Arg Phe Lys Thr Lys Leu Pro Lys Tyr
                565                 570                 575

Leu Leu Phe Thr Ser Pro Gln Glu Asn Pro Trp Gly His Lys Arg Ser
            580                 585                 590

Tyr Arg Leu Gln Ile His Ser Met Ala Asp Gln Val Leu Pro Pro Gly
        595                 600                 605

Trp Gln Glu Glu Gln Ala Ile Thr Trp Ala Arg Tyr Pro Leu Ala Val
    610                 615                 620

Thr Lys Tyr Arg Glu Ser Glu Leu Cys Ser Ser Ser Ile Tyr His Gln
625                 630                 635                 640

Asn Asp Pro Trp His Pro Pro Val Val Phe Glu Gln Phe Leu His Asn
                645                 650                 655
```

Asn Glu Asn Ile Glu Asn Glu Asp Leu Val Ala Trp Val Thr Val Gly
660 665 670

Phe Leu His Ile Pro His Ser Glu Asp Ile Pro Asn Thr Ala Thr Pro
675 680 685

Gly Asn Ser Val Gly Phe Leu Leu Arg Pro Phe Asn Phe Phe Pro Glu
690 695 700

Asp Pro Ser Leu Ala Ser Arg Asp Thr Val Ile Val Trp Pro Arg Asp
705 710 715 720

Asn Gly Pro Asn Tyr Val Gln Arg Trp Ile Pro Glu Asp Arg Asp Cys
725 730 735

Ser Met Pro Pro Pro Phe Ser Tyr Asn Gly Thr Tyr Arg Pro Val Glu
740 745 750

Pro Lys Ser Ala Asp Lys Thr His Thr Cys Pro Pro Cys Pro Ala Pro
755 760 765

Pro Val Ala Gly Pro Ser Val Phe Leu Phe Pro Pro Lys Pro Lys Asp
770 775 780

Thr Leu Met Ile Ser Arg Thr Pro Glu Val Thr Cys Val Val Val Asp
785 790 795 800

Val Ser His Glu Asp Pro Glu Val Lys Phe Asn Trp Tyr Val Asp Gly
805 810 815

Val Glu Val His Asn Ala Lys Thr Lys Pro Arg Glu Glu Gln Tyr Asn
820 825 830

Ser Thr Tyr Arg Val Val Ser Val Leu Thr Val Leu His Gln Asp Trp
835 840 845

Leu Asn Gly Lys Glu Tyr Lys Cys Lys Val Ser Asn Lys Gly Leu Pro
850 855 860

Ser Ser Ile Glu Lys Thr Ile Ser Lys Ala Lys Gly Gln Pro Arg Glu
865 870 875 880

Pro Gln Val Tyr Thr Leu Pro Pro Ser Arg Glu Glu Met Thr Lys Asn
885 890 895

Gln Val Ser Leu Thr Cys Leu Val Lys Gly Phe Tyr Pro Ser Asp Ile
900 905 910

Ala Val Glu Trp Glu Ser Asn Gly Gln Pro Glu Asn Asn Tyr Lys Thr
915 920 925

Thr Pro Pro Val Leu Asp Ser Asp Gly Ser Phe Phe Leu Tyr Ser Lys
930 935 940

Leu Thr Val Asp Lys Ser Arg Trp Gln Gln Gly Asn Val Phe Ser Cys
945 950 955 960

Ser Val Met His Glu Ala Leu His Asn His Tyr Thr Gln Lys Ser Leu
965 970 975

Ser Leu Ser Pro Gly Lys
980

<210> SEQ ID NO 59
<211> LENGTH: 982
<212> TYPE: PRT
<213> ORGANISM: Artificial Sequence
<220> FEATURE:
<223> OTHER INFORMATION: hDAO-Fc-Hepmut4

<400> SEQUENCE: 59

Met Pro Ala Leu Gly Trp Ala Val Ala Ala Ile Leu Met Leu Gln Thr
1 5 10 15

Ala Met Ala Glu Pro Ser Pro Gly Thr Leu Pro Arg Lys Ala Gly Val
20 25 30

```
Phe Ser Asp Leu Ser Asn Gln Glu Leu Lys Ala Val His Ser Phe Leu
        35                  40                  45

Trp Ser Lys Lys Glu Leu Arg Leu Gln Pro Ser Ser Thr Thr Thr Met
    50                  55                  60

Ala Lys Asn Thr Val Phe Leu Ile Glu Met Leu Leu Pro Lys Lys Tyr
65                  70                  75                  80

His Val Leu Arg Phe Leu Asp Lys Gly Glu Arg His Pro Val Arg Glu
                85                  90                  95

Ala Arg Ala Val Ile Phe Phe Gly Asp Gln Glu His Pro Asn Val Thr
            100                 105                 110

Glu Phe Ala Val Gly Pro Leu Pro Gly Pro Cys Tyr Met Arg Ala Leu
        115                 120                 125

Ser Pro Arg Pro Gly Tyr Gln Ser Ser Trp Ala Ser Arg Pro Ile Ser
    130                 135                 140

Thr Ala Glu Tyr Ala Leu Leu Tyr His Thr Leu Gln Glu Ala Thr Lys
145                 150                 155                 160

Pro Leu His Gln Phe Phe Leu Asn Thr Thr Gly Phe Ser Phe Gln Asp
                165                 170                 175

Cys His Asp Arg Cys Leu Ala Phe Thr Asp Val Ala Pro Arg Gly Val
            180                 185                 190

Ala Ser Gly Gln Arg Arg Ser Trp Leu Ile Ile Gln Arg Tyr Val Glu
        195                 200                 205

Gly Tyr Phe Leu His Pro Thr Gly Leu Glu Leu Leu Val Asp His Gly
    210                 215                 220

Ser Thr Asp Ala Gly His Trp Ala Val Glu Gln Val Trp Tyr Asn Gly
225                 230                 235                 240

Lys Phe Tyr Gly Ser Pro Glu Glu Leu Ala Arg Lys Tyr Ala Asp Gly
                245                 250                 255

Glu Val Asp Val Val Val Leu Glu Asp Pro Leu Pro Gly Gly Lys Gly
            260                 265                 270

His Asp Ser Thr Glu Glu Pro Pro Leu Phe Ser Ser His Lys Pro Arg
        275                 280                 285

Gly Asp Phe Pro Ser Pro Ile His Val Ser Gly Pro Arg Leu Val Gln
    290                 295                 300

Pro His Gly Pro Arg Phe Arg Leu Glu Gly Asn Ala Val Leu Tyr Gly
305                 310                 315                 320

Gly Trp Ser Phe Ala Phe Arg Leu Arg Ser Ser Ser Gly Leu Gln Val
                325                 330                 335

Leu Asn Val His Phe Gly Gly Glu Arg Ile Ala Tyr Glu Val Ser Val
            340                 345                 350

Gln Glu Ala Val Ala Leu Tyr Gly Gly His Thr Pro Ala Gly Met Gln
        355                 360                 365

Thr Lys Tyr Leu Asp Val Gly Trp Gly Leu Gly Ser Val Thr His Glu
    370                 375                 380

Leu Ala Pro Gly Ile Asp Cys Pro Glu Thr Ala Thr Phe Leu Asp Thr
385                 390                 395                 400

Phe His Tyr Tyr Asp Ala Asp Asp Pro Val His Tyr Pro Arg Ala Leu
                405                 410                 415

Cys Leu Phe Glu Met Pro Thr Gly Val Pro Leu Arg Arg His Phe Asn
            420                 425                 430

Ser Asn Phe Lys Gly Gly Phe Asn Phe Tyr Ala Gly Leu Lys Gly Gln
        435                 440                 445
```

```
Val Leu Val Leu Arg Thr Thr Ser Thr Val Tyr Asn Tyr Asp Tyr Ile
    450                 455                 460

Trp Asp Phe Ile Phe Tyr Pro Asn Gly Val Met Glu Ala Lys Met His
465                 470                 475                 480

Ala Thr Gly Tyr Val His Ala Thr Phe Tyr Thr Pro Glu Gly Leu Arg
                485                 490                 495

His Gly Thr Arg Leu His Thr His Leu Ile Gly Asn Ile His Thr His
            500                 505                 510

Leu Val His Tyr Arg Val Asp Leu Asp Val Ala Gly Thr Lys Asn Ser
        515                 520                 525

Phe Gln Thr Leu Gln Met Lys Leu Glu Asn Ile Thr Asn Pro Trp Ser
    530                 535                 540

Pro Arg His Arg Val Val Gln Pro Thr Leu Glu Gln Thr Gln Tyr Ser
545                 550                 555                 560

Trp Glu Arg Gln Ala Ala Phe Ser Phe Lys Thr Lys Leu Pro Lys Tyr
                565                 570                 575

Leu Leu Phe Thr Ser Pro Gln Glu Asn Pro Trp Gly His Lys Arg Ser
            580                 585                 590

Tyr Arg Leu Gln Ile His Ser Met Ala Asp Gln Val Leu Pro Pro Gly
        595                 600                 605

Trp Gln Glu Glu Gln Ala Ile Thr Trp Ala Arg Tyr Pro Leu Ala Val
    610                 615                 620

Thr Lys Tyr Arg Glu Ser Glu Leu Cys Ser Ser Ser Ile Tyr His Gln
625                 630                 635                 640

Asn Asp Pro Trp His Pro Pro Val Val Phe Glu Gln Phe Leu His Asn
                645                 650                 655

Asn Glu Asn Ile Glu Asn Glu Asp Leu Val Ala Trp Val Thr Val Gly
            660                 665                 670

Phe Leu His Ile Pro His Ser Glu Asp Ile Pro Asn Thr Ala Thr Pro
        675                 680                 685

Gly Asn Ser Val Gly Phe Leu Leu Arg Pro Phe Asn Phe Phe Pro Glu
    690                 695                 700

Asp Pro Ser Leu Ala Ser Arg Asp Thr Val Ile Val Trp Pro Arg Asp
705                 710                 715                 720

Asn Gly Pro Asn Tyr Val Gln Arg Trp Ile Pro Glu Asp Arg Asp Cys
                725                 730                 735

Ser Met Pro Pro Pro Phe Ser Tyr Asn Gly Thr Tyr Arg Pro Val Glu
            740                 745                 750

Pro Lys Ser Ala Asp Lys Thr His Thr Cys Pro Pro Cys Pro Ala Pro
        755                 760                 765

Pro Val Ala Gly Pro Ser Val Phe Leu Phe Pro Pro Lys Pro Lys Asp
    770                 775                 780

Thr Leu Met Ile Ser Arg Thr Pro Glu Val Thr Cys Val Val Val Asp
785                 790                 795                 800

Val Ser His Glu Asp Pro Glu Val Lys Phe Asn Trp Tyr Val Asp Gly
                805                 810                 815

Val Glu Val His Asn Ala Lys Thr Lys Pro Arg Glu Glu Gln Tyr Asn
            820                 825                 830

Ser Thr Tyr Arg Val Val Ser Val Leu Thr Val Leu His Gln Asp Trp
        835                 840                 845

Leu Asn Gly Lys Glu Tyr Lys Cys Lys Val Ser Asn Lys Gly Leu Pro
    850                 855                 860

Ser Ser Ile Glu Lys Thr Ile Ser Lys Ala Lys Gly Gln Pro Arg Glu
```

865 870 875 880

Pro Gln Val Tyr Thr Leu Pro Pro Ser Arg Glu Glu Met Thr Lys Asn
885 890 895

Gln Val Ser Leu Thr Cys Leu Val Lys Gly Phe Tyr Pro Ser Asp Ile
900 905 910

Ala Val Glu Trp Glu Ser Asn Gly Gln Pro Glu Asn Asn Tyr Lys Thr
915 920 925

Thr Pro Pro Val Leu Asp Ser Asp Gly Ser Phe Phe Leu Tyr Ser Lys
930 935 940

Leu Thr Val Asp Lys Ser Arg Trp Gln Gln Gly Asn Val Phe Ser Cys
945 950 955 960

Ser Val Met His Glu Ala Leu His Asn His Tyr Thr Gln Lys Ser Leu
965 970 975

Ser Leu Ser Pro Gly Lys
980

<210> SEQ ID NO 60
<211> LENGTH: 982
<212> TYPE: PRT
<213> ORGANISM: Artificial Sequence
<220> FEATURE:
<223> OTHER INFORMATION: hDAO-Fc-Hepmut5

<400> SEQUENCE: 60

Met Pro Ala Leu Gly Trp Ala Val Ala Ala Ile Leu Met Leu Gln Thr
1 5 10 15

Ala Met Ala Glu Pro Ser Pro Gly Thr Leu Pro Arg Lys Ala Gly Val
20 25 30

Phe Ser Asp Leu Ser Asn Gln Glu Leu Lys Ala Val His Ser Phe Leu
35 40 45

Trp Ser Lys Lys Glu Leu Arg Leu Gln Pro Ser Ser Thr Thr Thr Met
50 55 60

Ala Lys Asn Thr Val Phe Leu Ile Glu Met Leu Leu Pro Lys Lys Tyr
65 70 75 80

His Val Leu Arg Phe Leu Asp Lys Gly Glu Arg His Pro Val Arg Glu
85 90 95

Ala Arg Ala Val Ile Phe Phe Gly Asp Gln Glu His Pro Asn Val Thr
100 105 110

Glu Phe Ala Val Gly Pro Leu Pro Gly Pro Cys Tyr Met Arg Ala Leu
115 120 125

Ser Pro Arg Pro Gly Tyr Gln Ser Ser Trp Ala Ser Arg Pro Ile Ser
130 135 140

Thr Ala Glu Tyr Ala Leu Leu Tyr His Thr Leu Gln Glu Ala Thr Lys
145 150 155 160

Pro Leu His Gln Phe Phe Leu Asn Thr Thr Gly Phe Ser Phe Gln Asp
165 170 175

Cys His Asp Arg Cys Leu Ala Phe Thr Asp Val Ala Pro Arg Gly Val
180 185 190

Ala Ser Gly Gln Arg Arg Ser Trp Leu Ile Ile Gln Arg Tyr Val Glu
195 200 205

Gly Tyr Phe Leu His Pro Thr Gly Leu Glu Leu Leu Val Asp His Gly
210 215 220

Ser Thr Asp Ala Gly His Trp Ala Val Glu Gln Val Trp Tyr Asn Gly
225 230 235 240

Lys Phe Tyr Gly Ser Pro Glu Glu Leu Ala Arg Lys Tyr Ala Asp Gly

```
                245                 250                 255

Glu Val Asp Val Val Val Leu Glu Asp Pro Leu Pro Gly Gly Lys Gly
            260                 265                 270

His Asp Ser Thr Glu Glu Pro Pro Leu Phe Ser Ser His Lys Pro Arg
        275                 280                 285

Gly Asp Phe Pro Ser Pro Ile His Val Ser Gly Pro Arg Leu Val Gln
    290                 295                 300

Pro His Gly Pro Arg Phe Arg Leu Glu Gly Asn Ala Val Leu Tyr Gly
305                 310                 315                 320

Gly Trp Ser Phe Ala Phe Arg Leu Arg Ser Ser Ser Gly Leu Gln Val
                325                 330                 335

Leu Asn Val His Phe Gly Gly Glu Arg Ile Ala Tyr Glu Val Ser Val
            340                 345                 350

Gln Glu Ala Val Ala Leu Tyr Gly Gly His Thr Pro Ala Gly Met Gln
        355                 360                 365

Thr Lys Tyr Leu Asp Val Gly Trp Gly Leu Gly Ser Val Thr His Glu
    370                 375                 380

Leu Ala Pro Gly Ile Asp Cys Pro Glu Thr Ala Thr Phe Leu Asp Thr
385                 390                 395                 400

Phe His Tyr Tyr Asp Ala Asp Asp Pro Val His Tyr Pro Arg Ala Leu
                405                 410                 415

Cys Leu Phe Glu Met Pro Thr Gly Val Pro Leu Arg Arg His Phe Asn
            420                 425                 430

Ser Asn Phe Lys Gly Gly Phe Asn Phe Tyr Ala Gly Leu Lys Gly Gln
        435                 440                 445

Val Leu Val Leu Arg Thr Thr Ser Thr Val Tyr Asn Tyr Asp Tyr Ile
    450                 455                 460

Trp Asp Phe Ile Phe Tyr Pro Asn Gly Val Met Glu Ala Lys Met His
465                 470                 475                 480

Ala Thr Gly Tyr Val His Ala Thr Phe Tyr Thr Pro Glu Gly Leu Arg
                485                 490                 495

His Gly Thr Arg Leu His Thr His Leu Ile Gly Asn Ile His Thr His
            500                 505                 510

Leu Val His Tyr Arg Val Asp Leu Asp Val Ala Gly Thr Lys Asn Ser
        515                 520                 525

Phe Gln Thr Leu Gln Met Lys Leu Glu Asn Ile Thr Asn Pro Trp Ser
    530                 535                 540

Pro Arg His Arg Val Val Gln Pro Thr Leu Glu Gln Thr Gln Tyr Ser
545                 550                 555                 560

Trp Glu Arg Gln Ala Ala Phe Arg Phe Lys Thr Lys Leu Pro Thr Tyr
                565                 570                 575

Leu Leu Phe Thr Ser Pro Gln Glu Asn Pro Trp Gly His Lys Arg Ser
            580                 585                 590

Tyr Arg Leu Gln Ile His Ser Met Ala Asp Gln Val Leu Pro Pro Gly
        595                 600                 605

Trp Gln Glu Glu Gln Ala Ile Thr Trp Ala Arg Tyr Pro Leu Ala Val
    610                 615                 620

Thr Lys Tyr Arg Glu Ser Glu Leu Cys Ser Ser Ser Ile Tyr His Gln
625                 630                 635                 640

Asn Asp Pro Trp His Pro Pro Val Val Phe Glu Gln Phe Leu His Asn
                645                 650                 655

Asn Glu Asn Ile Glu Asn Glu Asp Leu Val Ala Trp Val Thr Val Gly
            660                 665                 670
```

Phe Leu His Ile Pro His Ser Glu Asp Ile Pro Asn Thr Ala Thr Pro
675 680 685

Gly Asn Ser Val Gly Phe Leu Leu Arg Pro Phe Asn Phe Phe Pro Glu
690 695 700

Asp Pro Ser Leu Ala Ser Arg Asp Thr Val Ile Val Trp Pro Arg Asp
705 710 715 720

Asn Gly Pro Asn Tyr Val Gln Arg Trp Ile Pro Glu Asp Arg Asp Cys
725 730 735

Ser Met Pro Pro Pro Phe Ser Tyr Asn Gly Thr Tyr Arg Pro Val Glu
740 745 750

Pro Lys Ser Ala Asp Lys Thr His Thr Cys Pro Pro Cys Pro Ala Pro
755 760 765

Pro Val Ala Gly Pro Ser Val Phe Leu Phe Pro Pro Lys Pro Lys Asp
770 775 780

Thr Leu Met Ile Ser Arg Thr Pro Glu Val Thr Cys Val Val Val Asp
785 790 795 800

Val Ser His Glu Asp Pro Glu Val Lys Phe Asn Trp Tyr Val Asp Gly
805 810 815

Val Glu Val His Asn Ala Lys Thr Lys Pro Arg Glu Glu Gln Tyr Asn
820 825 830

Ser Thr Tyr Arg Val Val Ser Val Leu Thr Val Leu His Gln Asp Trp
835 840 845

Leu Asn Gly Lys Glu Tyr Lys Cys Lys Val Ser Asn Lys Gly Leu Pro
850 855 860

Ser Ser Ile Glu Lys Thr Ile Ser Lys Ala Lys Gly Gln Pro Arg Glu
865 870 875 880

Pro Gln Val Tyr Thr Leu Pro Pro Ser Arg Glu Glu Met Thr Lys Asn
885 890 895

Gln Val Ser Leu Thr Cys Leu Val Lys Gly Phe Tyr Pro Ser Asp Ile
900 905 910

Ala Val Glu Trp Glu Ser Asn Gly Gln Pro Glu Asn Asn Tyr Lys Thr
915 920 925

Thr Pro Pro Val Leu Asp Ser Asp Gly Ser Phe Phe Leu Tyr Ser Lys
930 935 940

Leu Thr Val Asp Lys Ser Arg Trp Gln Gln Gly Asn Val Phe Ser Cys
945 950 955 960

Ser Val Met His Glu Ala Leu His Asn His Tyr Thr Gln Lys Ser Leu
965 970 975

Ser Leu Ser Pro Gly Lys
980

<210> SEQ ID NO 61
<211> LENGTH: 982
<212> TYPE: PRT
<213> ORGANISM: Artificial Sequence
<220> FEATURE:
<223> OTHER INFORMATION: hDAO-Fc-Hepmut6

<400> SEQUENCE: 61

Met Pro Ala Leu Gly Trp Ala Val Ala Ala Ile Leu Met Leu Gln Thr
1 5 10 15

Ala Met Ala Glu Pro Ser Pro Gly Thr Leu Pro Arg Lys Ala Gly Val
20 25 30

Phe Ser Asp Leu Ser Asn Gln Glu Leu Lys Ala Val His Ser Phe Leu
35 40 45

```
Trp Ser Lys Lys Glu Leu Arg Leu Gln Pro Ser Ser Thr Thr Thr Met
    50                  55                  60

Ala Lys Asn Thr Val Phe Leu Ile Glu Met Leu Leu Pro Lys Lys Tyr
65                  70                  75                  80

His Val Leu Arg Phe Leu Asp Lys Gly Glu Arg His Pro Val Arg Glu
                85                  90                  95

Ala Arg Ala Val Ile Phe Phe Gly Asp Gln Glu His Pro Asn Val Thr
            100                 105                 110

Glu Phe Ala Val Gly Pro Leu Pro Gly Pro Cys Tyr Met Arg Ala Leu
        115                 120                 125

Ser Pro Arg Pro Gly Tyr Gln Ser Ser Trp Ala Ser Arg Pro Ile Ser
    130                 135                 140

Thr Ala Glu Tyr Ala Leu Leu Tyr His Thr Leu Gln Glu Ala Thr Lys
145                 150                 155                 160

Pro Leu His Gln Phe Phe Leu Asn Thr Thr Gly Phe Ser Phe Gln Asp
                165                 170                 175

Cys His Asp Arg Cys Leu Ala Phe Thr Asp Val Ala Pro Arg Gly Val
            180                 185                 190

Ala Ser Gly Gln Arg Arg Ser Trp Leu Ile Ile Gln Arg Tyr Val Glu
        195                 200                 205

Gly Tyr Phe Leu His Pro Thr Gly Leu Glu Leu Leu Val Asp His Gly
    210                 215                 220

Ser Thr Asp Ala Gly His Trp Ala Val Glu Gln Val Trp Tyr Asn Gly
225                 230                 235                 240

Lys Phe Tyr Gly Ser Pro Glu Glu Leu Ala Arg Lys Tyr Ala Asp Gly
                245                 250                 255

Glu Val Asp Val Val Val Leu Glu Asp Pro Leu Pro Gly Gly Lys Gly
            260                 265                 270

His Asp Ser Thr Glu Glu Pro Pro Leu Phe Ser Ser His Lys Pro Arg
        275                 280                 285

Gly Asp Phe Pro Ser Pro Ile His Val Ser Gly Pro Arg Leu Val Gln
    290                 295                 300

Pro His Gly Pro Arg Phe Arg Leu Glu Gly Asn Ala Val Leu Tyr Gly
305                 310                 315                 320

Gly Trp Ser Phe Ala Phe Arg Leu Arg Ser Ser Ser Gly Leu Gln Val
                325                 330                 335

Leu Asn Val His Phe Gly Gly Glu Arg Ile Ala Tyr Glu Val Ser Val
            340                 345                 350

Gln Glu Ala Val Ala Leu Tyr Gly Gly His Thr Pro Ala Gly Met Gln
        355                 360                 365

Thr Lys Tyr Leu Asp Val Gly Trp Gly Leu Gly Ser Val Thr His Glu
    370                 375                 380

Leu Ala Pro Gly Ile Asp Cys Pro Glu Thr Ala Thr Phe Leu Asp Thr
385                 390                 395                 400

Phe His Tyr Tyr Asp Ala Asp Asp Pro Val His Tyr Pro Arg Ala Leu
                405                 410                 415

Cys Leu Phe Glu Met Pro Thr Gly Val Pro Leu Arg Arg His Phe Asn
            420                 425                 430

Ser Asn Phe Lys Gly Gly Phe Asn Phe Tyr Ala Gly Leu Lys Gly Gln
        435                 440                 445

Val Leu Val Leu Arg Thr Thr Ser Thr Val Tyr Asn Tyr Asp Tyr Ile
    450                 455                 460
```

```
Trp Asp Phe Ile Phe Tyr Pro Asn Gly Val Met Glu Ala Lys Met His
465                 470                 475                 480

Ala Thr Gly Tyr Val His Ala Thr Phe Tyr Thr Pro Glu Gly Leu Arg
                485                 490                 495

His Gly Thr Arg Leu His Thr His Leu Ile Gly Asn Ile His Thr His
            500                 505                 510

Leu Val His Tyr Arg Val Asp Leu Asp Val Ala Gly Thr Lys Asn Ser
        515                 520                 525

Phe Gln Thr Leu Gln Met Lys Leu Glu Asn Ile Thr Asn Pro Trp Ser
    530                 535                 540

Pro Arg His Arg Val Val Gln Pro Thr Leu Glu Gln Thr Gln Tyr Ser
545                 550                 555                 560

Trp Glu Arg Gln Ala Ala Phe Arg Phe Gly Gln Thr Leu Pro Lys Tyr
                565                 570                 575

Leu Leu Phe Thr Ser Pro Gln Glu Asn Pro Trp Gly His Lys Arg Ser
            580                 585                 590

Tyr Arg Leu Gln Ile His Ser Met Ala Asp Gln Val Leu Pro Pro Gly
        595                 600                 605

Trp Gln Glu Glu Gln Ala Ile Thr Trp Ala Arg Tyr Pro Leu Ala Val
    610                 615                 620

Thr Lys Tyr Arg Glu Ser Glu Leu Cys Ser Ser Ser Ile Tyr His Gln
625                 630                 635                 640

Asn Asp Pro Trp His Pro Pro Val Val Phe Glu Gln Phe Leu His Asn
                645                 650                 655

Asn Glu Asn Ile Glu Asn Glu Asp Leu Val Ala Trp Val Thr Val Gly
            660                 665                 670

Phe Leu His Ile Pro His Ser Glu Asp Ile Pro Asn Thr Ala Thr Pro
        675                 680                 685

Gly Asn Ser Val Gly Phe Leu Leu Arg Pro Phe Asn Phe Phe Pro Glu
    690                 695                 700

Asp Pro Ser Leu Ala Ser Arg Asp Thr Val Ile Val Trp Pro Arg Asp
705                 710                 715                 720

Asn Gly Pro Asn Tyr Val Gln Arg Trp Ile Pro Glu Asp Arg Asp Cys
                725                 730                 735

Ser Met Pro Pro Pro Phe Ser Tyr Asn Gly Thr Tyr Arg Pro Val Glu
            740                 745                 750

Pro Lys Ser Ala Asp Lys Thr His Thr Cys Pro Pro Cys Pro Ala Pro
        755                 760                 765

Pro Val Ala Gly Pro Ser Val Phe Leu Phe Pro Pro Lys Pro Lys Asp
    770                 775                 780

Thr Leu Met Ile Ser Arg Thr Pro Glu Val Thr Cys Val Val Val Asp
785                 790                 795                 800

Val Ser His Glu Asp Pro Glu Val Lys Phe Asn Trp Tyr Val Asp Gly
                805                 810                 815

Val Glu Val His Asn Ala Lys Thr Lys Pro Arg Glu Glu Gln Tyr Asn
            820                 825                 830

Ser Thr Tyr Arg Val Val Ser Val Leu Thr Val Leu His Gln Asp Trp
        835                 840                 845

Leu Asn Gly Lys Glu Tyr Lys Cys Lys Val Ser Asn Lys Gly Leu Pro
    850                 855                 860

Ser Ser Ile Glu Lys Thr Ile Ser Lys Ala Lys Gly Gln Pro Arg Glu
865                 870                 875                 880

Pro Gln Val Tyr Thr Leu Pro Pro Ser Arg Glu Glu Met Thr Lys Asn
```

```
                885                 890                 895

Gln Val Ser Leu Thr Cys Leu Val Lys Gly Phe Tyr Pro Ser Asp Ile
            900                 905                 910

Ala Val Glu Trp Glu Ser Asn Gly Gln Pro Glu Asn Asn Tyr Lys Thr
        915                 920                 925

Thr Pro Pro Val Leu Asp Ser Asp Gly Ser Phe Phe Leu Tyr Ser Lys
    930                 935                 940

Leu Thr Val Asp Lys Ser Arg Trp Gln Gln Gly Asn Val Phe Ser Cys
945                 950                 955                 960

Ser Val Met His Glu Ala Leu His Asn His Tyr Thr Gln Lys Ser Leu
                965                 970                 975

Ser Leu Ser Pro Gly Lys
            980


<210> SEQ ID NO 62
<211> LENGTH: 982
<212> TYPE: PRT
<213> ORGANISM: Artificial Sequence
<220> FEATURE:
<223> OTHER INFORMATION: hDAO-Fc-Hepmut7

<400> SEQUENCE: 62

Met Pro Ala Leu Gly Trp Ala Val Ala Ala Ile Leu Met Leu Gln Thr
1               5                   10                  15

Ala Met Ala Glu Pro Ser Pro Gly Thr Leu Pro Arg Lys Ala Gly Val
            20                  25                  30

Phe Ser Asp Leu Ser Asn Gln Glu Leu Lys Ala Val His Ser Phe Leu
        35                  40                  45

Trp Ser Lys Lys Glu Leu Arg Leu Gln Pro Ser Ser Thr Thr Thr Met
    50                  55                  60

Ala Lys Asn Thr Val Phe Leu Ile Glu Met Leu Leu Pro Lys Lys Tyr
65                  70                  75                  80

His Val Leu Arg Phe Leu Asp Lys Gly Glu Arg His Pro Val Arg Glu
                85                  90                  95

Ala Arg Ala Val Ile Phe Phe Gly Asp Gln Glu His Pro Asn Val Thr
            100                 105                 110

Glu Phe Ala Val Gly Pro Leu Pro Gly Pro Cys Tyr Met Arg Ala Leu
        115                 120                 125

Ser Pro Arg Pro Gly Tyr Gln Ser Ser Trp Ala Ser Arg Pro Ile Ser
    130                 135                 140

Thr Ala Glu Tyr Ala Leu Leu Tyr His Thr Leu Gln Glu Ala Thr Lys
145                 150                 155                 160

Pro Leu His Gln Phe Phe Leu Asn Thr Thr Gly Phe Ser Phe Gln Asp
                165                 170                 175

Cys His Asp Arg Cys Leu Ala Phe Thr Asp Val Ala Pro Arg Gly Val
            180                 185                 190

Ala Ser Gly Gln Arg Arg Ser Trp Leu Ile Ile Gln Arg Tyr Val Glu
        195                 200                 205

Gly Tyr Phe Leu His Pro Thr Gly Leu Glu Leu Leu Val Asp His Gly
    210                 215                 220

Ser Thr Asp Ala Gly His Trp Ala Val Glu Gln Val Trp Tyr Asn Gly
225                 230                 235                 240

Lys Phe Tyr Gly Ser Pro Glu Glu Leu Ala Arg Lys Tyr Ala Asp Gly
                245                 250                 255

Glu Val Asp Val Val Val Leu Glu Asp Pro Leu Pro Gly Gly Lys Gly
```

```
            260                 265                 270

His Asp Ser Thr Glu Glu Pro Pro Leu Phe Ser Ser His Lys Pro Arg
        275                 280                 285

Gly Asp Phe Pro Ser Pro Ile His Val Ser Gly Pro Arg Leu Val Gln
    290                 295                 300

Pro His Gly Pro Arg Phe Arg Leu Glu Gly Asn Ala Val Leu Tyr Gly
305                 310                 315                 320

Gly Trp Ser Phe Ala Phe Arg Leu Arg Ser Ser Ser Gly Leu Gln Val
                325                 330                 335

Leu Asn Val His Phe Gly Gly Glu Arg Ile Ala Tyr Glu Val Ser Val
            340                 345                 350

Gln Glu Ala Val Ala Leu Tyr Gly Gly His Thr Pro Ala Gly Met Gln
        355                 360                 365

Thr Lys Tyr Leu Asp Val Gly Trp Gly Leu Gly Ser Val Thr His Glu
    370                 375                 380

Leu Ala Pro Gly Ile Asp Cys Pro Glu Thr Ala Thr Phe Leu Asp Thr
385                 390                 395                 400

Phe His Tyr Tyr Asp Ala Asp Asp Pro Val His Tyr Pro Arg Ala Leu
                405                 410                 415

Cys Leu Phe Glu Met Pro Thr Gly Val Pro Leu Arg Arg His Phe Asn
            420                 425                 430

Ser Asn Phe Lys Gly Gly Phe Asn Phe Tyr Ala Gly Leu Lys Gly Gln
        435                 440                 445

Val Leu Val Leu Arg Thr Thr Ser Thr Val Tyr Asn Tyr Asp Tyr Ile
    450                 455                 460

Trp Asp Phe Ile Phe Tyr Pro Asn Gly Val Met Glu Ala Lys Met His
465                 470                 475                 480

Ala Thr Gly Tyr Val His Ala Thr Phe Tyr Thr Pro Glu Gly Leu Arg
                485                 490                 495

His Gly Thr Arg Leu His Thr His Leu Ile Gly Asn Ile His Thr His
            500                 505                 510

Leu Val His Tyr Arg Val Asp Leu Asp Val Ala Gly Thr Lys Asn Ser
        515                 520                 525

Phe Gln Thr Leu Gln Met Lys Leu Glu Asn Ile Thr Asn Pro Trp Ser
    530                 535                 540

Pro Arg His Arg Val Val Gln Pro Thr Leu Glu Gln Thr Gln Tyr Ser
545                 550                 555                 560

Trp Glu Arg Gln Ala Ala Phe Ser Phe Lys Arg Lys Leu Pro Thr Tyr
                565                 570                 575

Leu Leu Phe Thr Ser Pro Gln Glu Asn Pro Trp Gly His Lys Arg Ser
            580                 585                 590

Tyr Arg Leu Gln Ile His Ser Met Ala Asp Gln Val Leu Pro Pro Gly
        595                 600                 605

Trp Gln Glu Glu Gln Ala Ile Thr Trp Ala Arg Tyr Pro Leu Ala Val
    610                 615                 620

Thr Lys Tyr Arg Glu Ser Glu Leu Cys Ser Ser Ser Ile Tyr His Gln
625                 630                 635                 640

Asn Asp Pro Trp His Pro Pro Val Val Phe Glu Gln Phe Leu His Asn
                645                 650                 655

Asn Glu Asn Ile Glu Asn Glu Asp Leu Val Ala Trp Val Thr Val Gly
            660                 665                 670

Phe Leu His Ile Pro His Ser Glu Asp Ile Pro Asn Thr Ala Thr Pro
        675                 680                 685
```

Gly Asn Ser Val Gly Phe Leu Leu Arg Pro Phe Asn Phe Phe Pro Glu
690 695 700

Asp Pro Ser Leu Ala Ser Arg Asp Thr Val Ile Val Trp Pro Arg Asp
705 710 715 720

Asn Gly Pro Asn Tyr Val Gln Arg Trp Ile Pro Glu Asp Arg Asp Cys
725 730 735

Ser Met Pro Pro Pro Phe Ser Tyr Asn Gly Thr Tyr Arg Pro Val Glu
740 745 750

Pro Lys Ser Ala Asp Lys Thr His Thr Cys Pro Pro Cys Pro Ala Pro
755 760 765

Pro Val Ala Gly Pro Ser Val Phe Leu Phe Pro Pro Lys Pro Lys Asp
770 775 780

Thr Leu Met Ile Ser Arg Thr Pro Glu Val Thr Cys Val Val Val Asp
785 790 795 800

Val Ser His Glu Asp Pro Glu Val Lys Phe Asn Trp Tyr Val Asp Gly
805 810 815

Val Glu Val His Asn Ala Lys Thr Lys Pro Arg Glu Glu Gln Tyr Asn
820 825 830

Ser Thr Tyr Arg Val Val Ser Val Leu Thr Val Leu His Gln Asp Trp
835 840 845

Leu Asn Gly Lys Glu Tyr Lys Cys Lys Val Ser Asn Lys Gly Leu Pro
850 855 860

Ser Ser Ile Glu Lys Thr Ile Ser Lys Ala Lys Gly Gln Pro Arg Glu
865 870 875 880

Pro Gln Val Tyr Thr Leu Pro Pro Ser Arg Glu Glu Met Thr Lys Asn
885 890 895

Gln Val Ser Leu Thr Cys Leu Val Lys Gly Phe Tyr Pro Ser Asp Ile
900 905 910

Ala Val Glu Trp Glu Ser Asn Gly Gln Pro Glu Asn Asn Tyr Lys Thr
915 920 925

Thr Pro Pro Val Leu Asp Ser Asp Gly Ser Phe Phe Leu Tyr Ser Lys
930 935 940

Leu Thr Val Asp Lys Ser Arg Trp Gln Gln Gly Asn Val Phe Ser Cys
945 950 955 960

Ser Val Met His Glu Ala Leu His Asn His Tyr Thr Gln Lys Ser Leu
965 970 975

Ser Leu Ser Pro Gly Lys
980

<210> SEQ ID NO 63
<211> LENGTH: 982
<212> TYPE: PRT
<213> ORGANISM: Artificial Sequence
<220> FEATURE:
<223> OTHER INFORMATION: hDAO-Fc-Cysmut

<400> SEQUENCE: 63

Met Pro Ala Leu Gly Trp Ala Val Ala Ala Ile Leu Met Leu Gln Thr
1 5 10 15

Ala Met Ala Glu Pro Ser Pro Gly Thr Leu Pro Arg Lys Ala Gly Val
20 25 30

Phe Ser Asp Leu Ser Asn Gln Glu Leu Lys Ala Val His Ser Phe Leu
35 40 45

Trp Ser Lys Lys Glu Leu Arg Leu Gln Pro Ser Ser Thr Thr Thr Met
50 55 60

Ala Lys Asn Thr Val Phe Leu Ile Glu Met Leu Leu Pro Lys Lys Tyr
65 70 75 80

His Val Leu Arg Phe Leu Asp Lys Gly Glu Arg His Pro Val Arg Glu
85 90 95

Ala Arg Ala Val Ile Phe Phe Gly Asp Gln Glu His Pro Asn Val Thr
100 105 110

Glu Phe Ala Val Gly Pro Leu Pro Gly Pro Ala Tyr Met Arg Ala Leu
115 120 125

Ser Pro Arg Pro Gly Tyr Gln Ser Ser Trp Ala Ser Arg Pro Ile Ser
130 135 140

Thr Ala Glu Tyr Ala Leu Leu Tyr His Thr Leu Gln Glu Ala Thr Lys
145 150 155 160

Pro Leu His Gln Phe Phe Leu Asn Thr Thr Gly Phe Ser Phe Gln Asp
165 170 175

Cys His Asp Arg Cys Leu Ala Phe Thr Asp Val Ala Pro Arg Gly Val
180 185 190

Ala Ser Gly Gln Arg Arg Ser Trp Leu Ile Ile Gln Arg Tyr Val Glu
195 200 205

Gly Tyr Phe Leu His Pro Thr Gly Leu Glu Leu Leu Val Asp His Gly
210 215 220

Ser Thr Asp Ala Gly His Trp Ala Val Glu Gln Val Trp Tyr Asn Gly
225 230 235 240

Lys Phe Tyr Gly Ser Pro Glu Glu Leu Ala Arg Lys Tyr Ala Asp Gly
245 250 255

Glu Val Asp Val Val Val Leu Glu Asp Pro Leu Pro Gly Gly Lys Gly
260 265 270

His Asp Ser Thr Glu Glu Pro Pro Leu Phe Ser Ser His Lys Pro Arg
275 280 285

Gly Asp Phe Pro Ser Pro Ile His Val Ser Gly Pro Arg Leu Val Gln
290 295 300

Pro His Gly Pro Arg Phe Arg Leu Glu Gly Asn Ala Val Leu Tyr Gly
305 310 315 320

Gly Trp Ser Phe Ala Phe Arg Leu Arg Ser Ser Ser Gly Leu Gln Val
325 330 335

Leu Asn Val His Phe Gly Gly Glu Arg Ile Ala Tyr Glu Val Ser Val
340 345 350

Gln Glu Ala Val Ala Leu Tyr Gly Gly His Thr Pro Ala Gly Met Gln
355 360 365

Thr Lys Tyr Leu Asp Val Gly Trp Gly Leu Gly Ser Val Thr His Glu
370 375 380

Leu Ala Pro Gly Ile Asp Cys Pro Glu Thr Ala Thr Phe Leu Asp Thr
385 390 395 400

Phe His Tyr Tyr Asp Ala Asp Asp Pro Val His Tyr Pro Arg Ala Leu
405 410 415

Cys Leu Phe Glu Met Pro Thr Gly Val Pro Leu Arg Arg His Phe Asn
420 425 430

Ser Asn Phe Lys Gly Gly Phe Asn Phe Tyr Ala Gly Leu Lys Gly Gln
435 440 445

Val Leu Val Leu Arg Thr Thr Ser Thr Val Tyr Asn Tyr Asp Tyr Ile
450 455 460

Trp Asp Phe Ile Phe Tyr Pro Asn Gly Val Met Glu Ala Lys Met His
465 470 475 480

```
Ala Thr Gly Tyr Val His Ala Thr Phe Tyr Thr Pro Glu Gly Leu Arg
                485                 490                 495

His Gly Thr Arg Leu His Thr His Leu Ile Gly Asn Ile His Thr His
            500                 505                 510

Leu Val His Tyr Arg Val Asp Leu Asp Val Ala Gly Thr Lys Asn Ser
        515                 520                 525

Phe Gln Thr Leu Gln Met Lys Leu Glu Asn Ile Thr Asn Pro Trp Ser
    530                 535                 540

Pro Arg His Arg Val Val Gln Pro Thr Leu Glu Gln Thr Gln Tyr Ser
545                 550                 555                 560

Trp Glu Arg Gln Ala Ala Phe Arg Phe Lys Arg Lys Leu Pro Lys Tyr
                565                 570                 575

Leu Leu Phe Thr Ser Pro Gln Glu Asn Pro Trp Gly His Lys Arg Ser
            580                 585                 590

Tyr Arg Leu Gln Ile His Ser Met Ala Asp Gln Val Leu Pro Pro Gly
        595                 600                 605

Trp Gln Glu Glu Gln Ala Ile Thr Trp Ala Arg Tyr Pro Leu Ala Val
    610                 615                 620

Thr Lys Tyr Arg Glu Ser Glu Leu Cys Ser Ser Ser Ile Tyr His Gln
625                 630                 635                 640

Asn Asp Pro Trp His Pro Pro Val Val Phe Glu Gln Phe Leu His Asn
                645                 650                 655

Asn Glu Asn Ile Glu Asn Glu Asp Leu Val Ala Trp Val Thr Val Gly
            660                 665                 670

Phe Leu His Ile Pro His Ser Glu Asp Ile Pro Asn Thr Ala Thr Pro
        675                 680                 685

Gly Asn Ser Val Gly Phe Leu Leu Arg Pro Phe Asn Phe Phe Pro Glu
    690                 695                 700

Asp Pro Ser Leu Ala Ser Arg Asp Thr Val Ile Val Trp Pro Arg Asp
705                 710                 715                 720

Asn Gly Pro Asn Tyr Val Gln Arg Trp Ile Pro Glu Asp Arg Asp Cys
                725                 730                 735

Ser Met Pro Pro Pro Phe Ser Tyr Asn Gly Thr Tyr Arg Pro Val Glu
            740                 745                 750

Pro Lys Ser Ala Asp Lys Thr His Thr Cys Pro Pro Cys Pro Ala Pro
        755                 760                 765

Pro Val Ala Gly Pro Ser Val Phe Leu Phe Pro Pro Lys Pro Lys Asp
    770                 775                 780

Thr Leu Met Ile Ser Arg Thr Pro Glu Val Thr Cys Val Val Val Asp
785                 790                 795                 800

Val Ser His Glu Asp Pro Glu Val Lys Phe Asn Trp Tyr Val Asp Gly
                805                 810                 815

Val Glu Val His Asn Ala Lys Thr Lys Pro Arg Glu Glu Gln Tyr Asn
            820                 825                 830

Ser Thr Tyr Arg Val Val Ser Val Leu Thr Val Leu His Gln Asp Trp
        835                 840                 845

Leu Asn Gly Lys Glu Tyr Lys Cys Lys Val Ser Asn Lys Gly Leu Pro
    850                 855                 860

Ser Ser Ile Glu Lys Thr Ile Ser Lys Ala Lys Gly Gln Pro Arg Glu
865                 870                 875                 880

Pro Gln Val Tyr Thr Leu Pro Pro Ser Arg Glu Glu Met Thr Lys Asn
                885                 890                 895

Gln Val Ser Leu Thr Cys Leu Val Lys Gly Phe Tyr Pro Ser Asp Ile
```

900 905 910

Ala Val Glu Trp Glu Ser Asn Gly Gln Pro Glu Asn Asn Tyr Lys Thr
915 920 925

Thr Pro Pro Val Leu Asp Ser Asp Gly Ser Phe Phe Leu Tyr Ser Lys
930 935 940

Leu Thr Val Asp Lys Ser Arg Trp Gln Gln Gly Asn Val Phe Ser Cys
945 950 955 960

Ser Val Met His Glu Ala Leu His Asn His Tyr Thr Gln Lys Ser Leu
965 970 975

Ser Leu Ser Pro Gly Lys
980

<210> SEQ ID NO 64
<211> LENGTH: 982
<212> TYPE: PRT
<213> ORGANISM: Artificial Sequence
<220> FEATURE:
<223> OTHER INFORMATION: hDAO-Fc-Hepmut1-Cysmut

<400> SEQUENCE: 64

Met Pro Ala Leu Gly Trp Ala Val Ala Ala Ile Leu Met Leu Gln Thr
1 5 10 15

Ala Met Ala Glu Pro Ser Pro Gly Thr Leu Pro Arg Lys Ala Gly Val
20 25 30

Phe Ser Asp Leu Ser Asn Gln Glu Leu Lys Ala Val His Ser Phe Leu
35 40 45

Trp Ser Lys Lys Glu Leu Arg Leu Gln Pro Ser Ser Thr Thr Thr Met
50 55 60

Ala Lys Asn Thr Val Phe Leu Ile Glu Met Leu Leu Pro Lys Lys Tyr
65 70 75 80

His Val Leu Arg Phe Leu Asp Lys Gly Glu Arg His Pro Val Arg Glu
85 90 95

Ala Arg Ala Val Ile Phe Phe Gly Asp Gln Glu His Pro Asn Val Thr
100 105 110

Glu Phe Ala Val Gly Pro Leu Pro Gly Pro Ala Tyr Met Arg Ala Leu
115 120 125

Ser Pro Arg Pro Gly Tyr Gln Ser Ser Trp Ala Ser Arg Pro Ile Ser
130 135 140

Thr Ala Glu Tyr Ala Leu Leu Tyr His Thr Leu Gln Glu Ala Thr Lys
145 150 155 160

Pro Leu His Gln Phe Phe Leu Asn Thr Thr Gly Phe Ser Phe Gln Asp
165 170 175

Cys His Asp Arg Cys Leu Ala Phe Thr Asp Val Ala Pro Arg Gly Val
180 185 190

Ala Ser Gly Gln Arg Arg Ser Trp Leu Ile Ile Gln Arg Tyr Val Glu
195 200 205

Gly Tyr Phe Leu His Pro Thr Gly Leu Glu Leu Leu Val Asp His Gly
210 215 220

Ser Thr Asp Ala Gly His Trp Ala Val Glu Gln Val Trp Tyr Asn Gly
225 230 235 240

Lys Phe Tyr Gly Ser Pro Glu Glu Leu Ala Arg Lys Tyr Ala Asp Gly
245 250 255

Glu Val Asp Val Val Val Leu Glu Asp Pro Leu Pro Gly Gly Lys Gly
260 265 270

His Asp Ser Thr Glu Glu Pro Pro Leu Phe Ser Ser His Lys Pro Arg

```
        275                 280                 285

Gly Asp Phe Pro Ser Pro Ile His Val Ser Gly Pro Arg Leu Val Gln
    290                 295                 300

Pro His Gly Pro Arg Phe Arg Leu Glu Gly Asn Ala Val Leu Tyr Gly
305                 310                 315                 320

Gly Trp Ser Phe Ala Phe Arg Leu Arg Ser Ser Ser Gly Leu Gln Val
                325                 330                 335

Leu Asn Val His Phe Gly Gly Glu Arg Ile Ala Tyr Glu Val Ser Val
            340                 345                 350

Gln Glu Ala Val Ala Leu Tyr Gly Gly His Thr Pro Ala Gly Met Gln
        355                 360                 365

Thr Lys Tyr Leu Asp Val Gly Trp Gly Leu Gly Ser Val Thr His Glu
    370                 375                 380

Leu Ala Pro Gly Ile Asp Cys Pro Glu Thr Ala Thr Phe Leu Asp Thr
385                 390                 395                 400

Phe His Tyr Tyr Asp Ala Asp Asp Pro Val His Tyr Pro Arg Ala Leu
                405                 410                 415

Cys Leu Phe Glu Met Pro Thr Gly Val Pro Leu Arg Arg His Phe Asn
            420                 425                 430

Ser Asn Phe Lys Gly Gly Phe Asn Phe Tyr Ala Gly Leu Lys Gly Gln
        435                 440                 445

Val Leu Val Leu Arg Thr Thr Ser Thr Val Tyr Asn Tyr Asp Tyr Ile
    450                 455                 460

Trp Asp Phe Ile Phe Tyr Pro Asn Gly Val Met Glu Ala Lys Met His
465                 470                 475                 480

Ala Thr Gly Tyr Val His Ala Thr Phe Tyr Thr Pro Glu Gly Leu Arg
                485                 490                 495

His Gly Thr Arg Leu His Thr His Leu Ile Gly Asn Ile His Thr His
            500                 505                 510

Leu Val His Tyr Arg Val Asp Leu Asp Val Ala Gly Thr Lys Asn Ser
        515                 520                 525

Phe Gln Thr Leu Gln Met Lys Leu Glu Asn Ile Thr Asn Pro Trp Ser
    530                 535                 540

Pro Arg His Arg Val Val Gln Pro Thr Leu Glu Gln Thr Gln Tyr Ser
545                 550                 555                 560

Trp Glu Arg Gln Ala Ala Phe Ser Phe Lys Arg Lys Leu Pro Lys Tyr
                565                 570                 575

Leu Leu Phe Thr Ser Pro Gln Glu Asn Pro Trp Gly His Lys Arg Ser
            580                 585                 590

Tyr Arg Leu Gln Ile His Ser Met Ala Asp Gln Val Leu Pro Pro Gly
        595                 600                 605

Trp Gln Glu Glu Gln Ala Ile Thr Trp Ala Arg Tyr Pro Leu Ala Val
    610                 615                 620

Thr Lys Tyr Arg Glu Ser Glu Leu Cys Ser Ser Ser Ile Tyr His Gln
625                 630                 635                 640

Asn Asp Pro Trp His Pro Pro Val Val Phe Glu Gln Phe Leu His Asn
                645                 650                 655

Asn Glu Asn Ile Glu Asn Glu Asp Leu Val Ala Trp Val Thr Val Gly
            660                 665                 670

Phe Leu His Ile Pro His Ser Glu Asp Ile Pro Asn Thr Ala Thr Pro
        675                 680                 685

Gly Asn Ser Val Gly Phe Leu Leu Arg Pro Phe Asn Phe Phe Pro Glu
    690                 695                 700
```

Asp Pro Ser Leu Ala Ser Arg Asp Thr Val Ile Val Trp Pro Arg Asp
705 710 715 720

Asn Gly Pro Asn Tyr Val Gln Arg Trp Ile Pro Glu Asp Arg Asp Cys
725 730 735

Ser Met Pro Pro Pro Phe Ser Tyr Asn Gly Thr Tyr Arg Pro Val Glu
740 745 750

Pro Lys Ser Ala Asp Lys Thr His Thr Cys Pro Pro Cys Pro Ala Pro
755 760 765

Pro Val Ala Gly Pro Ser Val Phe Leu Phe Pro Pro Lys Pro Lys Asp
770 775 780

Thr Leu Met Ile Ser Arg Thr Pro Glu Val Thr Cys Val Val Val Asp
785 790 795 800

Val Ser His Glu Asp Pro Glu Val Lys Phe Asn Trp Tyr Val Asp Gly
805 810 815

Val Glu Val His Asn Ala Lys Thr Lys Pro Arg Glu Glu Gln Tyr Asn
820 825 830

Ser Thr Tyr Arg Val Val Ser Val Leu Thr Val Leu His Gln Asp Trp
835 840 845

Leu Asn Gly Lys Glu Tyr Lys Cys Lys Val Ser Asn Lys Gly Leu Pro
850 855 860

Ser Ser Ile Glu Lys Thr Ile Ser Lys Ala Lys Gly Gln Pro Arg Glu
865 870 875 880

Pro Gln Val Tyr Thr Leu Pro Pro Ser Arg Glu Glu Met Thr Lys Asn
885 890 895

Gln Val Ser Leu Thr Cys Leu Val Lys Gly Phe Tyr Pro Ser Asp Ile
900 905 910

Ala Val Glu Trp Glu Ser Asn Gly Gln Pro Glu Asn Asn Tyr Lys Thr
915 920 925

Thr Pro Pro Val Leu Asp Ser Asp Gly Ser Phe Phe Leu Tyr Ser Lys
930 935 940

Leu Thr Val Asp Lys Ser Arg Trp Gln Gln Gly Asn Val Phe Ser Cys
945 950 955 960

Ser Val Met His Glu Ala Leu His Asn His Tyr Thr Gln Lys Ser Leu
965 970 975

Ser Leu Ser Pro Gly Lys
980

<210> SEQ ID NO 65
<211> LENGTH: 982
<212> TYPE: PRT
<213> ORGANISM: Artificial Sequence
<220> FEATURE:
<223> OTHER INFORMATION: hDAO-Fc-Hepmut2-Cysmut

<400> SEQUENCE: 65

Met Pro Ala Leu Gly Trp Ala Val Ala Ala Ile Leu Met Leu Gln Thr
1 5 10 15

Ala Met Ala Glu Pro Ser Pro Gly Thr Leu Pro Arg Lys Ala Gly Val
20 25 30

Phe Ser Asp Leu Ser Asn Gln Glu Leu Lys Ala Val His Ser Phe Leu
35 40 45

Trp Ser Lys Lys Glu Leu Arg Leu Gln Pro Ser Ser Thr Thr Thr Met
50 55 60

Ala Lys Asn Thr Val Phe Leu Ile Glu Met Leu Leu Pro Lys Lys Tyr
65 70 75 80

```
His Val Leu Arg Phe Leu Asp Lys Gly Glu Arg His Pro Val Arg Glu
                85                  90                  95

Ala Arg Ala Val Ile Phe Phe Gly Asp Gln Glu His Pro Asn Val Thr
            100                 105                 110

Glu Phe Ala Val Gly Pro Leu Pro Gly Pro Ala Tyr Met Arg Ala Leu
        115                 120                 125

Ser Pro Arg Pro Gly Tyr Gln Ser Ser Trp Ala Ser Arg Pro Ile Ser
    130                 135                 140

Thr Ala Glu Tyr Ala Leu Leu Tyr His Thr Leu Gln Glu Ala Thr Lys
145                 150                 155                 160

Pro Leu His Gln Phe Phe Leu Asn Thr Thr Gly Phe Ser Phe Gln Asp
                165                 170                 175

Cys His Asp Arg Cys Leu Ala Phe Thr Asp Val Ala Pro Arg Gly Val
            180                 185                 190

Ala Ser Gly Gln Arg Arg Ser Trp Leu Ile Ile Gln Arg Tyr Val Glu
        195                 200                 205

Gly Tyr Phe Leu His Pro Thr Gly Leu Glu Leu Leu Val Asp His Gly
    210                 215                 220

Ser Thr Asp Ala Gly His Trp Ala Val Glu Gln Val Trp Tyr Asn Gly
225                 230                 235                 240

Lys Phe Tyr Gly Ser Pro Glu Glu Leu Ala Arg Lys Tyr Ala Asp Gly
                245                 250                 255

Glu Val Asp Val Val Val Leu Glu Asp Pro Leu Pro Gly Gly Lys Gly
            260                 265                 270

His Asp Ser Thr Glu Glu Pro Pro Leu Phe Ser Ser His Lys Pro Arg
        275                 280                 285

Gly Asp Phe Pro Ser Pro Ile His Val Ser Gly Pro Arg Leu Val Gln
    290                 295                 300

Pro His Gly Pro Arg Phe Arg Leu Glu Gly Asn Ala Val Leu Tyr Gly
305                 310                 315                 320

Gly Trp Ser Phe Ala Phe Arg Leu Arg Ser Ser Ser Gly Leu Gln Val
                325                 330                 335

Leu Asn Val His Phe Gly Gly Glu Arg Ile Ala Tyr Glu Val Ser Val
            340                 345                 350

Gln Glu Ala Val Ala Leu Tyr Gly Gly His Thr Pro Ala Gly Met Gln
        355                 360                 365

Thr Lys Tyr Leu Asp Val Gly Trp Gly Leu Gly Ser Val Thr His Glu
    370                 375                 380

Leu Ala Pro Gly Ile Asp Cys Pro Glu Thr Ala Thr Phe Leu Asp Thr
385                 390                 395                 400

Phe His Tyr Tyr Asp Ala Asp Asp Pro Val His Tyr Pro Arg Ala Leu
                405                 410                 415

Cys Leu Phe Glu Met Pro Thr Gly Val Pro Leu Arg Arg His Phe Asn
            420                 425                 430

Ser Asn Phe Lys Gly Gly Phe Asn Phe Tyr Ala Gly Leu Lys Gly Gln
        435                 440                 445

Val Leu Val Leu Arg Thr Thr Ser Thr Val Tyr Asn Tyr Asp Tyr Ile
    450                 455                 460

Trp Asp Phe Ile Phe Tyr Pro Asn Gly Val Met Glu Ala Lys Met His
465                 470                 475                 480

Ala Thr Gly Tyr Val His Ala Thr Phe Tyr Thr Pro Glu Gly Leu Arg
                485                 490                 495
```

```
His Gly Thr Arg Leu His Thr His Leu Ile Gly Asn Ile His Thr His
            500                 505                 510

Leu Val His Tyr Arg Val Asp Leu Asp Val Ala Gly Thr Lys Asn Ser
        515                 520                 525

Phe Gln Thr Leu Gln Met Lys Leu Glu Asn Ile Thr Asn Pro Trp Ser
    530                 535                 540

Pro Arg His Arg Val Val Gln Pro Thr Leu Glu Gln Thr Gln Tyr Ser
545                 550                 555                 560

Trp Glu Arg Gln Ala Ala Phe Arg Phe Lys Arg Lys Leu Pro Thr Tyr
                565                 570                 575

Leu Leu Phe Thr Ser Pro Gln Glu Asn Pro Trp Gly His Lys Arg Ser
            580                 585                 590

Tyr Arg Leu Gln Ile His Ser Met Ala Asp Gln Val Leu Pro Pro Gly
        595                 600                 605

Trp Gln Glu Glu Gln Ala Ile Thr Trp Ala Arg Tyr Pro Leu Ala Val
    610                 615                 620

Thr Lys Tyr Arg Glu Ser Glu Leu Cys Ser Ser Ser Ile Tyr His Gln
625                 630                 635                 640

Asn Asp Pro Trp His Pro Pro Val Val Phe Glu Gln Phe Leu His Asn
                645                 650                 655

Asn Glu Asn Ile Glu Asn Glu Asp Leu Val Ala Trp Val Thr Val Gly
            660                 665                 670

Phe Leu His Ile Pro His Ser Glu Asp Ile Pro Asn Thr Ala Thr Pro
        675                 680                 685

Gly Asn Ser Val Gly Phe Leu Leu Arg Pro Phe Asn Phe Phe Pro Glu
    690                 695                 700

Asp Pro Ser Leu Ala Ser Arg Asp Thr Val Ile Val Trp Pro Arg Asp
705                 710                 715                 720

Asn Gly Pro Asn Tyr Val Gln Arg Trp Ile Pro Glu Asp Arg Asp Cys
                725                 730                 735

Ser Met Pro Pro Pro Phe Ser Tyr Asn Gly Thr Tyr Arg Pro Val Glu
            740                 745                 750

Pro Lys Ser Ala Asp Lys Thr His Thr Cys Pro Pro Cys Pro Ala Pro
        755                 760                 765

Pro Val Ala Gly Pro Ser Val Phe Leu Phe Pro Pro Lys Pro Lys Asp
    770                 775                 780

Thr Leu Met Ile Ser Arg Thr Pro Glu Val Thr Cys Val Val Val Asp
785                 790                 795                 800

Val Ser His Glu Asp Pro Glu Val Lys Phe Asn Trp Tyr Val Asp Gly
                805                 810                 815

Val Glu Val His Asn Ala Lys Thr Lys Pro Arg Glu Glu Gln Tyr Asn
            820                 825                 830

Ser Thr Tyr Arg Val Val Ser Val Leu Thr Val Leu His Gln Asp Trp
        835                 840                 845

Leu Asn Gly Lys Glu Tyr Lys Cys Lys Val Ser Asn Lys Gly Leu Pro
    850                 855                 860

Ser Ser Ile Glu Lys Thr Ile Ser Lys Ala Lys Gly Gln Pro Arg Glu
865                 870                 875                 880

Pro Gln Val Tyr Thr Leu Pro Pro Ser Arg Glu Glu Met Thr Lys Asn
                885                 890                 895

Gln Val Ser Leu Thr Cys Leu Val Lys Gly Phe Tyr Pro Ser Asp Ile
            900                 905                 910

Ala Val Glu Trp Glu Ser Asn Gly Gln Pro Glu Asn Asn Tyr Lys Thr
```

```
        915                 920                 925

Thr Pro Pro Val Leu Asp Ser Asp Gly Ser Phe Phe Leu Tyr Ser Lys
    930                 935                 940

Leu Thr Val Asp Lys Ser Arg Trp Gln Gln Gly Asn Val Phe Ser Cys
945                 950                 955                 960

Ser Val Met His Glu Ala Leu His Asn His Tyr Thr Gln Lys Ser Leu
                965                 970                 975

Ser Leu Ser Pro Gly Lys
            980


<210> SEQ ID NO 66
<211> LENGTH: 982
<212> TYPE: PRT
<213> ORGANISM: Artificial Sequence
<220> FEATURE:
<223> OTHER INFORMATION: hDAO-Fc-Hepmut3-Cysmut

<400> SEQUENCE: 66

Met Pro Ala Leu Gly Trp Ala Val Ala Ala Ile Leu Met Leu Gln Thr
1               5                   10                  15

Ala Met Ala Glu Pro Ser Pro Gly Thr Leu Pro Arg Lys Ala Gly Val
            20                  25                  30

Phe Ser Asp Leu Ser Asn Gln Glu Leu Lys Ala Val His Ser Phe Leu
        35                  40                  45

Trp Ser Lys Lys Glu Leu Arg Leu Gln Pro Ser Ser Thr Thr Thr Met
    50                  55                  60

Ala Lys Asn Thr Val Phe Leu Ile Glu Met Leu Leu Pro Lys Lys Tyr
65                  70                  75                  80

His Val Leu Arg Phe Leu Asp Lys Gly Glu Arg His Pro Val Arg Glu
                85                  90                  95

Ala Arg Ala Val Ile Phe Phe Gly Asp Gln Glu His Pro Asn Val Thr
            100                 105                 110

Glu Phe Ala Val Gly Pro Leu Pro Gly Pro Ala Tyr Met Arg Ala Leu
        115                 120                 125

Ser Pro Arg Pro Gly Tyr Gln Ser Ser Trp Ala Ser Arg Pro Ile Ser
    130                 135                 140

Thr Ala Glu Tyr Ala Leu Leu Tyr His Thr Leu Gln Glu Ala Thr Lys
145                 150                 155                 160

Pro Leu His Gln Phe Phe Leu Asn Thr Thr Gly Phe Ser Phe Gln Asp
                165                 170                 175

Cys His Asp Arg Cys Leu Ala Phe Thr Asp Val Ala Pro Arg Gly Val
            180                 185                 190

Ala Ser Gly Gln Arg Arg Ser Trp Leu Ile Ile Gln Arg Tyr Val Glu
        195                 200                 205

Gly Tyr Phe Leu His Pro Thr Gly Leu Glu Leu Leu Val Asp His Gly
    210                 215                 220

Ser Thr Asp Ala Gly His Trp Ala Val Glu Gln Val Trp Tyr Asn Gly
225                 230                 235                 240

Lys Phe Tyr Gly Ser Pro Glu Glu Leu Ala Arg Lys Tyr Ala Asp Gly
                245                 250                 255

Glu Val Asp Val Val Val Leu Glu Asp Pro Leu Pro Gly Gly Lys Gly
            260                 265                 270

His Asp Ser Thr Glu Glu Pro Pro Leu Phe Ser Ser His Lys Pro Arg
        275                 280                 285

Gly Asp Phe Pro Ser Pro Ile His Val Ser Gly Pro Arg Leu Val Gln
```

```
290                 295                 300

Pro His Gly Pro Arg Phe Arg Leu Glu Gly Asn Ala Val Leu Tyr Gly
305                 310                 315                 320

Gly Trp Ser Phe Ala Phe Arg Leu Arg Ser Ser Ser Gly Leu Gln Val
                325                 330                 335

Leu Asn Val His Phe Gly Gly Glu Arg Ile Ala Tyr Glu Val Ser Val
            340                 345                 350

Gln Glu Ala Val Ala Leu Tyr Gly Gly His Thr Pro Ala Gly Met Gln
        355                 360                 365

Thr Lys Tyr Leu Asp Val Gly Trp Gly Leu Gly Ser Val Thr His Glu
    370                 375                 380

Leu Ala Pro Gly Ile Asp Cys Pro Glu Thr Ala Thr Phe Leu Asp Thr
385                 390                 395                 400

Phe His Tyr Tyr Asp Ala Asp Asp Pro Val His Tyr Pro Arg Ala Leu
                405                 410                 415

Cys Leu Phe Glu Met Pro Thr Gly Val Pro Leu Arg Arg His Phe Asn
            420                 425                 430

Ser Asn Phe Lys Gly Gly Phe Asn Phe Tyr Ala Gly Leu Lys Gly Gln
        435                 440                 445

Val Leu Val Leu Arg Thr Thr Ser Thr Val Tyr Asn Tyr Asp Tyr Ile
    450                 455                 460

Trp Asp Phe Ile Phe Tyr Pro Asn Gly Val Met Glu Ala Lys Met His
465                 470                 475                 480

Ala Thr Gly Tyr Val His Ala Thr Phe Tyr Thr Pro Glu Gly Leu Arg
                485                 490                 495

His Gly Thr Arg Leu His Thr His Leu Ile Gly Asn Ile His Thr His
            500                 505                 510

Leu Val His Tyr Arg Val Asp Leu Asp Val Ala Gly Thr Lys Asn Ser
        515                 520                 525

Phe Gln Thr Leu Gln Met Lys Leu Glu Asn Ile Thr Asn Pro Trp Ser
    530                 535                 540

Pro Arg His Arg Val Val Gln Pro Thr Leu Glu Gln Thr Gln Tyr Ser
545                 550                 555                 560

Trp Glu Arg Gln Ala Ala Phe Arg Phe Lys Thr Lys Leu Pro Lys Tyr
                565                 570                 575

Leu Leu Phe Thr Ser Pro Gln Glu Asn Pro Trp Gly His Lys Arg Ser
            580                 585                 590

Tyr Arg Leu Gln Ile His Ser Met Ala Asp Gln Val Leu Pro Pro Gly
        595                 600                 605

Trp Gln Glu Glu Gln Ala Ile Thr Trp Ala Arg Tyr Pro Leu Ala Val
    610                 615                 620

Thr Lys Tyr Arg Glu Ser Glu Leu Cys Ser Ser Ser Ile Tyr His Gln
625                 630                 635                 640

Asn Asp Pro Trp His Pro Pro Val Val Phe Glu Gln Phe Leu His Asn
                645                 650                 655

Asn Glu Asn Ile Glu Asn Glu Asp Leu Val Ala Trp Val Thr Val Gly
            660                 665                 670

Phe Leu His Ile Pro His Ser Glu Asp Ile Pro Asn Thr Ala Thr Pro
        675                 680                 685

Gly Asn Ser Val Gly Phe Leu Leu Arg Pro Phe Asn Phe Phe Pro Glu
    690                 695                 700

Asp Pro Ser Leu Ala Ser Arg Asp Thr Val Ile Val Trp Pro Arg Asp
705                 710                 715                 720
```

Asn Gly Pro Asn Tyr Val Gln Arg Trp Ile Pro Glu Asp Arg Asp Cys
725 730 735

Ser Met Pro Pro Pro Phe Ser Tyr Asn Gly Thr Tyr Arg Pro Val Glu
740 745 750

Pro Lys Ser Ala Asp Lys Thr His Thr Cys Pro Pro Cys Pro Ala Pro
755 760 765

Pro Val Ala Gly Pro Ser Val Phe Leu Phe Pro Pro Lys Pro Lys Asp
770 775 780

Thr Leu Met Ile Ser Arg Thr Pro Glu Val Thr Cys Val Val Val Asp
785 790 795 800

Val Ser His Glu Asp Pro Glu Val Lys Phe Asn Trp Tyr Val Asp Gly
805 810 815

Val Glu Val His Asn Ala Lys Thr Lys Pro Arg Glu Glu Gln Tyr Asn
820 825 830

Ser Thr Tyr Arg Val Val Ser Val Leu Thr Val Leu His Gln Asp Trp
835 840 845

Leu Asn Gly Lys Glu Tyr Lys Cys Lys Val Ser Asn Lys Gly Leu Pro
850 855 860

Ser Ser Ile Glu Lys Thr Ile Ser Lys Ala Lys Gly Gln Pro Arg Glu
865 870 875 880

Pro Gln Val Tyr Thr Leu Pro Pro Ser Arg Glu Glu Met Thr Lys Asn
885 890 895

Gln Val Ser Leu Thr Cys Leu Val Lys Gly Phe Tyr Pro Ser Asp Ile
900 905 910

Ala Val Glu Trp Glu Ser Asn Gly Gln Pro Glu Asn Asn Tyr Lys Thr
915 920 925

Thr Pro Pro Val Leu Asp Ser Asp Gly Ser Phe Phe Leu Tyr Ser Lys
930 935 940

Leu Thr Val Asp Lys Ser Arg Trp Gln Gln Gly Asn Val Phe Ser Cys
945 950 955 960

Ser Val Met His Glu Ala Leu His Asn His Tyr Thr Gln Lys Ser Leu
965 970 975

Ser Leu Ser Pro Gly Lys
980

<210> SEQ ID NO 67
<211> LENGTH: 982
<212> TYPE: PRT
<213> ORGANISM: Artificial Sequence
<220> FEATURE:
<223> OTHER INFORMATION: hDAO-Fc-Hepmut4-Cysmut

<400> SEQUENCE: 67

Met Pro Ala Leu Gly Trp Ala Val Ala Ala Ile Leu Met Leu Gln Thr
1 5 10 15

Ala Met Ala Glu Pro Ser Pro Gly Thr Leu Pro Arg Lys Ala Gly Val
20 25 30

Phe Ser Asp Leu Ser Asn Gln Glu Leu Lys Ala Val His Ser Phe Leu
35 40 45

Trp Ser Lys Lys Glu Leu Arg Leu Gln Pro Ser Ser Thr Thr Thr Met
50 55 60

Ala Lys Asn Thr Val Phe Leu Ile Glu Met Leu Leu Pro Lys Lys Tyr
65 70 75 80

His Val Leu Arg Phe Leu Asp Lys Gly Glu Arg His Pro Val Arg Glu
85 90 95

```
Ala Arg Ala Val Ile Phe Phe Gly Asp Gln Glu His Pro Asn Val Thr
            100                 105                 110

Glu Phe Ala Val Gly Pro Leu Pro Gly Pro Ala Tyr Met Arg Ala Leu
        115                 120                 125

Ser Pro Arg Pro Gly Tyr Gln Ser Ser Trp Ala Ser Arg Pro Ile Ser
    130                 135                 140

Thr Ala Glu Tyr Ala Leu Leu Tyr His Thr Leu Gln Glu Ala Thr Lys
145                 150                 155                 160

Pro Leu His Gln Phe Phe Leu Asn Thr Thr Gly Phe Ser Phe Gln Asp
                165                 170                 175

Cys His Asp Arg Cys Leu Ala Phe Thr Asp Val Ala Pro Arg Gly Val
            180                 185                 190

Ala Ser Gly Gln Arg Arg Ser Trp Leu Ile Ile Gln Arg Tyr Val Glu
        195                 200                 205

Gly Tyr Phe Leu His Pro Thr Gly Leu Glu Leu Leu Val Asp His Gly
    210                 215                 220

Ser Thr Asp Ala Gly His Trp Ala Val Glu Gln Val Trp Tyr Asn Gly
225                 230                 235                 240

Lys Phe Tyr Gly Ser Pro Glu Glu Leu Ala Arg Lys Tyr Ala Asp Gly
                245                 250                 255

Glu Val Asp Val Val Val Leu Glu Asp Pro Leu Pro Gly Gly Lys Gly
            260                 265                 270

His Asp Ser Thr Glu Glu Pro Pro Leu Phe Ser Ser His Lys Pro Arg
        275                 280                 285

Gly Asp Phe Pro Ser Pro Ile His Val Ser Gly Pro Arg Leu Val Gln
    290                 295                 300

Pro His Gly Pro Arg Phe Arg Leu Glu Gly Asn Ala Val Leu Tyr Gly
305                 310                 315                 320

Gly Trp Ser Phe Ala Phe Arg Leu Arg Ser Ser Ser Gly Leu Gln Val
                325                 330                 335

Leu Asn Val His Phe Gly Gly Glu Arg Ile Ala Tyr Glu Val Ser Val
            340                 345                 350

Gln Glu Ala Val Ala Leu Tyr Gly Gly His Thr Pro Ala Gly Met Gln
        355                 360                 365

Thr Lys Tyr Leu Asp Val Gly Trp Gly Leu Gly Ser Val Thr His Glu
    370                 375                 380

Leu Ala Pro Gly Ile Asp Cys Pro Glu Thr Ala Thr Phe Leu Asp Thr
385                 390                 395                 400

Phe His Tyr Tyr Asp Ala Asp Asp Pro Val His Tyr Pro Arg Ala Leu
                405                 410                 415

Cys Leu Phe Glu Met Pro Thr Gly Val Pro Leu Arg Arg His Phe Asn
            420                 425                 430

Ser Asn Phe Lys Gly Gly Phe Asn Phe Tyr Ala Gly Leu Lys Gly Gln
        435                 440                 445

Val Leu Val Leu Arg Thr Thr Ser Thr Val Tyr Asn Tyr Asp Tyr Ile
    450                 455                 460

Trp Asp Phe Ile Phe Tyr Pro Asn Gly Val Met Glu Ala Lys Met His
465                 470                 475                 480

Ala Thr Gly Tyr Val His Ala Thr Phe Tyr Thr Pro Glu Gly Leu Arg
                485                 490                 495

His Gly Thr Arg Leu His Thr His Leu Ile Gly Asn Ile His Thr His
            500                 505                 510
```

```
Leu Val His Tyr Arg Val Asp Leu Asp Val Ala Gly Thr Lys Asn Ser
        515                 520                 525

Phe Gln Thr Leu Gln Met Lys Leu Glu Asn Ile Thr Asn Pro Trp Ser
    530                 535                 540

Pro Arg His Arg Val Val Gln Pro Thr Leu Glu Gln Thr Gln Tyr Ser
545                 550                 555                 560

Trp Glu Arg Gln Ala Ala Phe Ser Phe Lys Thr Lys Leu Pro Lys Tyr
                565                 570                 575

Leu Leu Phe Thr Ser Pro Gln Glu Asn Pro Trp Gly His Lys Arg Ser
            580                 585                 590

Tyr Arg Leu Gln Ile His Ser Met Ala Asp Gln Val Leu Pro Pro Gly
        595                 600                 605

Trp Gln Glu Glu Gln Ala Ile Thr Trp Ala Arg Tyr Pro Leu Ala Val
    610                 615                 620

Thr Lys Tyr Arg Glu Ser Glu Leu Cys Ser Ser Ser Ile Tyr His Gln
625                 630                 635                 640

Asn Asp Pro Trp His Pro Pro Val Val Phe Glu Gln Phe Leu His Asn
                645                 650                 655

Asn Glu Asn Ile Glu Asn Glu Asp Leu Val Ala Trp Val Thr Val Gly
            660                 665                 670

Phe Leu His Ile Pro His Ser Glu Asp Ile Pro Asn Thr Ala Thr Pro
        675                 680                 685

Gly Asn Ser Val Gly Phe Leu Leu Arg Pro Phe Asn Phe Phe Pro Glu
    690                 695                 700

Asp Pro Ser Leu Ala Ser Arg Asp Thr Val Ile Val Trp Pro Arg Asp
705                 710                 715                 720

Asn Gly Pro Asn Tyr Val Gln Arg Trp Ile Pro Glu Asp Arg Asp Cys
                725                 730                 735

Ser Met Pro Pro Pro Phe Ser Tyr Asn Gly Thr Tyr Arg Pro Val Glu
            740                 745                 750

Pro Lys Ser Ala Asp Lys Thr His Thr Cys Pro Pro Cys Pro Ala Pro
        755                 760                 765

Pro Val Ala Gly Pro Ser Val Phe Leu Phe Pro Pro Lys Pro Lys Asp
    770                 775                 780

Thr Leu Met Ile Ser Arg Thr Pro Glu Val Thr Cys Val Val Val Asp
785                 790                 795                 800

Val Ser His Glu Asp Pro Glu Val Lys Phe Asn Trp Tyr Val Asp Gly
                805                 810                 815

Val Glu Val His Asn Ala Lys Thr Lys Pro Arg Glu Glu Gln Tyr Asn
            820                 825                 830

Ser Thr Tyr Arg Val Val Ser Val Leu Thr Val Leu His Gln Asp Trp
        835                 840                 845

Leu Asn Gly Lys Glu Tyr Lys Cys Lys Val Ser Asn Lys Gly Leu Pro
    850                 855                 860

Ser Ser Ile Glu Lys Thr Ile Ser Lys Ala Lys Gly Gln Pro Arg Glu
865                 870                 875                 880

Pro Gln Val Tyr Thr Leu Pro Pro Ser Arg Glu Glu Met Thr Lys Asn
                885                 890                 895

Gln Val Ser Leu Thr Cys Leu Val Lys Gly Phe Tyr Pro Ser Asp Ile
            900                 905                 910

Ala Val Glu Trp Glu Ser Asn Gly Gln Pro Glu Asn Asn Tyr Lys Thr
        915                 920                 925

Thr Pro Pro Val Leu Asp Ser Asp Gly Ser Phe Phe Leu Tyr Ser Lys
```

930 935 940

Leu Thr Val Asp Lys Ser Arg Trp Gln Gln Gly Asn Val Phe Ser Cys
945 950 955 960

Ser Val Met His Glu Ala Leu His Asn His Tyr Thr Gln Lys Ser Leu
965 970 975

Ser Leu Ser Pro Gly Lys
980

<210> SEQ ID NO 68
<211> LENGTH: 982
<212> TYPE: PRT
<213> ORGANISM: Artificial Sequence
<220> FEATURE:
<223> OTHER INFORMATION: hDAO-Fc-Hepmut5-Cysmut

<400> SEQUENCE: 68

Met Pro Ala Leu Gly Trp Ala Val Ala Ala Ile Leu Met Leu Gln Thr
1 5 10 15

Ala Met Ala Glu Pro Ser Pro Gly Thr Leu Pro Arg Lys Ala Gly Val
20 25 30

Phe Ser Asp Leu Ser Asn Gln Glu Leu Lys Ala Val His Ser Phe Leu
35 40 45

Trp Ser Lys Lys Glu Leu Arg Leu Gln Pro Ser Ser Thr Thr Thr Met
50 55 60

Ala Lys Asn Thr Val Phe Leu Ile Glu Met Leu Leu Pro Lys Lys Tyr
65 70 75 80

His Val Leu Arg Phe Leu Asp Lys Gly Glu Arg His Pro Val Arg Glu
85 90 95

Ala Arg Ala Val Ile Phe Phe Gly Asp Gln Glu His Pro Asn Val Thr
100 105 110

Glu Phe Ala Val Gly Pro Leu Pro Gly Pro Ala Tyr Met Arg Ala Leu
115 120 125

Ser Pro Arg Pro Gly Tyr Gln Ser Ser Trp Ala Ser Arg Pro Ile Ser
130 135 140

Thr Ala Glu Tyr Ala Leu Leu Tyr His Thr Leu Gln Glu Ala Thr Lys
145 150 155 160

Pro Leu His Gln Phe Phe Leu Asn Thr Thr Gly Phe Ser Phe Gln Asp
165 170 175

Cys His Asp Arg Cys Leu Ala Phe Thr Asp Val Ala Pro Arg Gly Val
180 185 190

Ala Ser Gly Gln Arg Arg Ser Trp Leu Ile Ile Gln Arg Tyr Val Glu
195 200 205

Gly Tyr Phe Leu His Pro Thr Gly Leu Glu Leu Leu Val Asp His Gly
210 215 220

Ser Thr Asp Ala Gly His Trp Ala Val Glu Gln Val Trp Tyr Asn Gly
225 230 235 240

Lys Phe Tyr Gly Ser Pro Glu Glu Leu Ala Arg Lys Tyr Ala Asp Gly
245 250 255

Glu Val Asp Val Val Val Leu Glu Asp Pro Leu Pro Gly Gly Lys Gly
260 265 270

His Asp Ser Thr Glu Glu Pro Pro Leu Phe Ser Ser His Lys Pro Arg
275 280 285

Gly Asp Phe Pro Ser Pro Ile His Val Ser Gly Pro Arg Leu Val Gln
290 295 300

Pro His Gly Pro Arg Phe Arg Leu Glu Gly Asn Ala Val Leu Tyr Gly

```
305                 310                 315                 320

Gly Trp Ser Phe Ala Phe Arg Leu Arg Ser Ser Ser Gly Leu Gln Val
                325                 330                 335

Leu Asn Val His Phe Gly Gly Glu Arg Ile Ala Tyr Glu Val Ser Val
            340                 345                 350

Gln Glu Ala Val Ala Leu Tyr Gly Gly His Thr Pro Ala Gly Met Gln
        355                 360                 365

Thr Lys Tyr Leu Asp Val Gly Trp Gly Leu Gly Ser Val Thr His Glu
    370                 375                 380

Leu Ala Pro Gly Ile Asp Cys Pro Glu Thr Ala Thr Phe Leu Asp Thr
385                 390                 395                 400

Phe His Tyr Tyr Asp Ala Asp Asp Pro Val His Tyr Pro Arg Ala Leu
                405                 410                 415

Cys Leu Phe Glu Met Pro Thr Gly Val Pro Leu Arg Arg His Phe Asn
            420                 425                 430

Ser Asn Phe Lys Gly Gly Phe Asn Phe Tyr Ala Gly Leu Lys Gly Gln
        435                 440                 445

Val Leu Val Leu Arg Thr Thr Ser Thr Val Tyr Asn Tyr Asp Tyr Ile
    450                 455                 460

Trp Asp Phe Ile Phe Tyr Pro Asn Gly Val Met Glu Ala Lys Met His
465                 470                 475                 480

Ala Thr Gly Tyr Val His Ala Thr Phe Tyr Thr Pro Glu Gly Leu Arg
                485                 490                 495

His Gly Thr Arg Leu His Thr His Leu Ile Gly Asn Ile His Thr His
            500                 505                 510

Leu Val His Tyr Arg Val Asp Leu Asp Val Ala Gly Thr Lys Asn Ser
        515                 520                 525

Phe Gln Thr Leu Gln Met Lys Leu Glu Asn Ile Thr Asn Pro Trp Ser
    530                 535                 540

Pro Arg His Arg Val Val Gln Pro Thr Leu Glu Gln Thr Gln Tyr Ser
545                 550                 555                 560

Trp Glu Arg Gln Ala Ala Phe Arg Phe Lys Thr Lys Leu Pro Thr Tyr
                565                 570                 575

Leu Leu Phe Thr Ser Pro Gln Glu Asn Pro Trp Gly His Lys Arg Ser
            580                 585                 590

Tyr Arg Leu Gln Ile His Ser Met Ala Asp Gln Val Leu Pro Pro Gly
        595                 600                 605

Trp Gln Glu Glu Gln Ala Ile Thr Trp Ala Arg Tyr Pro Leu Ala Val
    610                 615                 620

Thr Lys Tyr Arg Glu Ser Glu Leu Cys Ser Ser Ser Ile Tyr His Gln
625                 630                 635                 640

Asn Asp Pro Trp His Pro Pro Val Val Phe Glu Gln Phe Leu His Asn
                645                 650                 655

Asn Glu Asn Ile Glu Asn Glu Asp Leu Val Ala Trp Val Thr Val Gly
            660                 665                 670

Phe Leu His Ile Pro His Ser Glu Asp Ile Pro Asn Thr Ala Thr Pro
        675                 680                 685

Gly Asn Ser Val Gly Phe Leu Leu Arg Pro Phe Asn Phe Phe Pro Glu
    690                 695                 700

Asp Pro Ser Leu Ala Ser Arg Asp Thr Val Ile Val Trp Pro Arg Asp
705                 710                 715                 720

Asn Gly Pro Asn Tyr Val Gln Arg Trp Ile Pro Glu Asp Arg Asp Cys
                725                 730                 735
```

Ser Met Pro Pro Pro Phe Ser Tyr Asn Gly Thr Tyr Arg Pro Val Glu
740 745 750

Pro Lys Ser Ala Asp Lys Thr His Thr Cys Pro Pro Cys Pro Ala Pro
755 760 765

Pro Val Ala Gly Pro Ser Val Phe Leu Phe Pro Pro Lys Pro Lys Asp
770 775 780

Thr Leu Met Ile Ser Arg Thr Pro Glu Val Thr Cys Val Val Val Asp
785 790 795 800

Val Ser His Glu Asp Pro Glu Val Lys Phe Asn Trp Tyr Val Asp Gly
805 810 815

Val Glu Val His Asn Ala Lys Thr Lys Pro Arg Glu Glu Gln Tyr Asn
820 825 830

Ser Thr Tyr Arg Val Val Ser Val Leu Thr Val Leu His Gln Asp Trp
835 840 845

Leu Asn Gly Lys Glu Tyr Lys Cys Lys Val Ser Asn Lys Gly Leu Pro
850 855 860

Ser Ser Ile Glu Lys Thr Ile Ser Lys Ala Lys Gly Gln Pro Arg Glu
865 870 875 880

Pro Gln Val Tyr Thr Leu Pro Pro Ser Arg Glu Glu Met Thr Lys Asn
885 890 895

Gln Val Ser Leu Thr Cys Leu Val Lys Gly Phe Tyr Pro Ser Asp Ile
900 905 910

Ala Val Glu Trp Glu Ser Asn Gly Gln Pro Glu Asn Asn Tyr Lys Thr
915 920 925

Thr Pro Pro Val Leu Asp Ser Asp Gly Ser Phe Phe Leu Tyr Ser Lys
930 935 940

Leu Thr Val Asp Lys Ser Arg Trp Gln Gln Gly Asn Val Phe Ser Cys
945 950 955 960

Ser Val Met His Glu Ala Leu His Asn His Tyr Thr Gln Lys Ser Leu
965 970 975

Ser Leu Ser Pro Gly Lys
980

<210> SEQ ID NO 69
<211> LENGTH: 982
<212> TYPE: PRT
<213> ORGANISM: Artificial Sequence
<220> FEATURE:
<223> OTHER INFORMATION: hDAO-Fc-Hepmut6-Cysmut

<400> SEQUENCE: 69

Met Pro Ala Leu Gly Trp Ala Val Ala Ala Ile Leu Met Leu Gln Thr
1 5 10 15

Ala Met Ala Glu Pro Ser Pro Gly Thr Leu Pro Arg Lys Ala Gly Val
20 25 30

Phe Ser Asp Leu Ser Asn Gln Glu Leu Lys Ala Val His Ser Phe Leu
35 40 45

Trp Ser Lys Lys Glu Leu Arg Leu Gln Pro Ser Ser Thr Thr Thr Met
50 55 60

Ala Lys Asn Thr Val Phe Leu Ile Glu Met Leu Leu Pro Lys Lys Tyr
65 70 75 80

His Val Leu Arg Phe Leu Asp Lys Gly Glu Arg His Pro Val Arg Glu
85 90 95

Ala Arg Ala Val Ile Phe Phe Gly Asp Gln Glu His Pro Asn Val Thr
100 105 110

```
Glu Phe Ala Val Gly Pro Leu Pro Gly Pro Ala Tyr Met Arg Ala Leu
        115                 120                 125

Ser Pro Arg Pro Gly Tyr Gln Ser Ser Trp Ala Ser Arg Pro Ile Ser
    130                 135                 140

Thr Ala Glu Tyr Ala Leu Leu Tyr His Thr Leu Gln Glu Ala Thr Lys
145                 150                 155                 160

Pro Leu His Gln Phe Phe Leu Asn Thr Thr Gly Phe Ser Phe Gln Asp
                165                 170                 175

Cys His Asp Arg Cys Leu Ala Phe Thr Asp Val Ala Pro Arg Gly Val
            180                 185                 190

Ala Ser Gly Gln Arg Arg Ser Trp Leu Ile Ile Gln Arg Tyr Val Glu
        195                 200                 205

Gly Tyr Phe Leu His Pro Thr Gly Leu Glu Leu Leu Val Asp His Gly
    210                 215                 220

Ser Thr Asp Ala Gly His Trp Ala Val Glu Gln Val Trp Tyr Asn Gly
225                 230                 235                 240

Lys Phe Tyr Gly Ser Pro Glu Glu Leu Ala Arg Lys Tyr Ala Asp Gly
                245                 250                 255

Glu Val Asp Val Val Val Leu Glu Asp Pro Leu Pro Gly Gly Lys Gly
            260                 265                 270

His Asp Ser Thr Glu Glu Pro Pro Leu Phe Ser Ser His Lys Pro Arg
        275                 280                 285

Gly Asp Phe Pro Ser Pro Ile His Val Ser Gly Pro Arg Leu Val Gln
    290                 295                 300

Pro His Gly Pro Arg Phe Arg Leu Glu Gly Asn Ala Val Leu Tyr Gly
305                 310                 315                 320

Gly Trp Ser Phe Ala Phe Arg Leu Arg Ser Ser Ser Gly Leu Gln Val
                325                 330                 335

Leu Asn Val His Phe Gly Gly Glu Arg Ile Ala Tyr Glu Val Ser Val
            340                 345                 350

Gln Glu Ala Val Ala Leu Tyr Gly Gly His Thr Pro Ala Gly Met Gln
        355                 360                 365

Thr Lys Tyr Leu Asp Val Gly Trp Gly Leu Gly Ser Val Thr His Glu
    370                 375                 380

Leu Ala Pro Gly Ile Asp Cys Pro Glu Thr Ala Thr Phe Leu Asp Thr
385                 390                 395                 400

Phe His Tyr Tyr Asp Ala Asp Asp Pro Val His Tyr Pro Arg Ala Leu
                405                 410                 415

Cys Leu Phe Glu Met Pro Thr Gly Val Pro Leu Arg Arg His Phe Asn
            420                 425                 430

Ser Asn Phe Lys Gly Gly Phe Asn Phe Tyr Ala Gly Leu Lys Gly Gln
        435                 440                 445

Val Leu Val Leu Arg Thr Thr Ser Thr Val Tyr Asn Tyr Asp Tyr Ile
    450                 455                 460

Trp Asp Phe Ile Phe Tyr Pro Asn Gly Val Met Glu Ala Lys Met His
465                 470                 475                 480

Ala Thr Gly Tyr Val His Ala Thr Phe Tyr Thr Pro Glu Gly Leu Arg
                485                 490                 495

His Gly Thr Arg Leu His Thr His Leu Ile Gly Asn Ile His Thr His
            500                 505                 510

Leu Val His Tyr Arg Val Asp Leu Asp Val Ala Gly Thr Lys Asn Ser
        515                 520                 525
```

```
Phe Gln Thr Leu Gln Met Lys Leu Glu Asn Ile Thr Asn Pro Trp Ser
    530                 535                 540

Pro Arg His Arg Val Val Gln Pro Thr Leu Glu Gln Thr Gln Tyr Ser
545                 550                 555                 560

Trp Glu Arg Gln Ala Ala Phe Arg Phe Gly Gln Thr Leu Pro Lys Tyr
                565                 570                 575

Leu Leu Phe Thr Ser Pro Gln Glu Asn Pro Trp Gly His Lys Arg Ser
            580                 585                 590

Tyr Arg Leu Gln Ile His Ser Met Ala Asp Gln Val Leu Pro Pro Gly
        595                 600                 605

Trp Gln Glu Glu Gln Ala Ile Thr Trp Ala Arg Tyr Pro Leu Ala Val
    610                 615                 620

Thr Lys Tyr Arg Glu Ser Glu Leu Cys Ser Ser Ser Ile Tyr His Gln
625                 630                 635                 640

Asn Asp Pro Trp His Pro Pro Val Val Phe Glu Gln Phe Leu His Asn
                645                 650                 655

Asn Glu Asn Ile Glu Asn Glu Asp Leu Val Ala Trp Val Thr Val Gly
            660                 665                 670

Phe Leu His Ile Pro His Ser Glu Asp Ile Pro Asn Thr Ala Thr Pro
        675                 680                 685

Gly Asn Ser Val Gly Phe Leu Leu Arg Pro Phe Asn Phe Phe Pro Glu
    690                 695                 700

Asp Pro Ser Leu Ala Ser Arg Asp Thr Val Ile Val Trp Pro Arg Asp
705                 710                 715                 720

Asn Gly Pro Asn Tyr Val Gln Arg Trp Ile Pro Glu Asp Arg Asp Cys
                725                 730                 735

Ser Met Pro Pro Pro Phe Ser Tyr Asn Gly Thr Tyr Arg Pro Val Glu
            740                 745                 750

Pro Lys Ser Ala Asp Lys Thr His Thr Cys Pro Pro Cys Pro Ala Pro
        755                 760                 765

Pro Val Ala Gly Pro Ser Val Phe Leu Phe Pro Pro Lys Pro Lys Asp
    770                 775                 780

Thr Leu Met Ile Ser Arg Thr Pro Glu Val Thr Cys Val Val Val Asp
785                 790                 795                 800

Val Ser His Glu Asp Pro Glu Val Lys Phe Asn Trp Tyr Val Asp Gly
                805                 810                 815

Val Glu Val His Asn Ala Lys Thr Lys Pro Arg Glu Glu Gln Tyr Asn
            820                 825                 830

Ser Thr Tyr Arg Val Val Ser Val Leu Thr Val Leu His Gln Asp Trp
        835                 840                 845

Leu Asn Gly Lys Glu Tyr Lys Cys Lys Val Ser Asn Lys Gly Leu Pro
    850                 855                 860

Ser Ser Ile Glu Lys Thr Ile Ser Lys Ala Lys Gly Gln Pro Arg Glu
865                 870                 875                 880

Pro Gln Val Tyr Thr Leu Pro Pro Ser Arg Glu Glu Met Thr Lys Asn
                885                 890                 895

Gln Val Ser Leu Thr Cys Leu Val Lys Gly Phe Tyr Pro Ser Asp Ile
            900                 905                 910

Ala Val Glu Trp Glu Ser Asn Gly Gln Pro Glu Asn Asn Tyr Lys Thr
        915                 920                 925

Thr Pro Pro Val Leu Asp Ser Asp Gly Ser Phe Phe Leu Tyr Ser Lys
    930                 935                 940

Leu Thr Val Asp Lys Ser Arg Trp Gln Gln Gly Asn Val Phe Ser Cys
```

945 950 955 960

Ser Val Met His Glu Ala Leu His Asn His Tyr Thr Gln Lys Ser Leu
965 970 975

Ser Leu Ser Pro Gly Lys
980

<210> SEQ ID NO 70
<211> LENGTH: 982
<212> TYPE: PRT
<213> ORGANISM: Artificial Sequence
<220> FEATURE:
<223> OTHER INFORMATION: hDAO-Fc-Hepmut7-Cysmut

<400> SEQUENCE: 70

Met Pro Ala Leu Gly Trp Ala Val Ala Ala Ile Leu Met Leu Gln Thr
1 5 10 15

Ala Met Ala Glu Pro Ser Pro Gly Thr Leu Pro Arg Lys Ala Gly Val
20 25 30

Phe Ser Asp Leu Ser Asn Gln Glu Leu Lys Ala Val His Ser Phe Leu
35 40 45

Trp Ser Lys Lys Glu Leu Arg Leu Gln Pro Ser Ser Thr Thr Thr Met
50 55 60

Ala Lys Asn Thr Val Phe Leu Ile Glu Met Leu Leu Pro Lys Lys Tyr
65 70 75 80

His Val Leu Arg Phe Leu Asp Lys Gly Glu Arg His Pro Val Arg Glu
85 90 95

Ala Arg Ala Val Ile Phe Phe Gly Asp Gln Glu His Pro Asn Val Thr
100 105 110

Glu Phe Ala Val Gly Pro Leu Pro Gly Pro Ala Tyr Met Arg Ala Leu
115 120 125

Ser Pro Arg Pro Gly Tyr Gln Ser Ser Trp Ala Ser Arg Pro Ile Ser
130 135 140

Thr Ala Glu Tyr Ala Leu Leu Tyr His Thr Leu Gln Glu Ala Thr Lys
145 150 155 160

Pro Leu His Gln Phe Phe Leu Asn Thr Thr Gly Phe Ser Phe Gln Asp
165 170 175

Cys His Asp Arg Cys Leu Ala Phe Thr Asp Val Ala Pro Arg Gly Val
180 185 190

Ala Ser Gly Gln Arg Arg Ser Trp Leu Ile Ile Gln Arg Tyr Val Glu
195 200 205

Gly Tyr Phe Leu His Pro Thr Gly Leu Glu Leu Leu Val Asp His Gly
210 215 220

Ser Thr Asp Ala Gly His Trp Ala Val Glu Gln Val Trp Tyr Asn Gly
225 230 235 240

Lys Phe Tyr Gly Ser Pro Glu Glu Leu Ala Arg Lys Tyr Ala Asp Gly
245 250 255

Glu Val Asp Val Val Val Leu Glu Asp Pro Leu Pro Gly Gly Lys Gly
260 265 270

His Asp Ser Thr Glu Glu Pro Pro Leu Phe Ser Ser His Lys Pro Arg
275 280 285

Gly Asp Phe Pro Ser Pro Ile His Val Ser Gly Pro Arg Leu Val Gln
290 295 300

Pro His Gly Pro Arg Phe Arg Leu Glu Gly Asn Ala Val Leu Tyr Gly
305 310 315 320

Gly Trp Ser Phe Ala Phe Arg Leu Arg Ser Ser Ser Gly Leu Gln Val

```
            325                 330                 335

Leu Asn Val His Phe Gly Gly Glu Arg Ile Ala Tyr Glu Val Ser Val
        340                 345                 350

Gln Glu Ala Val Ala Leu Tyr Gly Gly His Thr Pro Ala Gly Met Gln
    355                 360                 365

Thr Lys Tyr Leu Asp Val Gly Trp Gly Leu Gly Ser Val Thr His Glu
    370                 375                 380

Leu Ala Pro Gly Ile Asp Cys Pro Glu Thr Ala Thr Phe Leu Asp Thr
385                 390                 395                 400

Phe His Tyr Tyr Asp Ala Asp Asp Pro Val His Tyr Pro Arg Ala Leu
                405                 410                 415

Cys Leu Phe Glu Met Pro Thr Gly Val Pro Leu Arg Arg His Phe Asn
            420                 425                 430

Ser Asn Phe Lys Gly Gly Phe Asn Phe Tyr Ala Gly Leu Lys Gly Gln
        435                 440                 445

Val Leu Val Leu Arg Thr Thr Ser Thr Val Tyr Asn Tyr Asp Tyr Ile
    450                 455                 460

Trp Asp Phe Ile Phe Tyr Pro Asn Gly Val Met Glu Ala Lys Met His
465                 470                 475                 480

Ala Thr Gly Tyr Val His Ala Thr Phe Tyr Thr Pro Glu Gly Leu Arg
                485                 490                 495

His Gly Thr Arg Leu His Thr His Leu Ile Gly Asn Ile His Thr His
            500                 505                 510

Leu Val His Tyr Arg Val Asp Leu Asp Val Ala Gly Thr Lys Asn Ser
        515                 520                 525

Phe Gln Thr Leu Gln Met Lys Leu Glu Asn Ile Thr Asn Pro Trp Ser
    530                 535                 540

Pro Arg His Arg Val Val Gln Pro Thr Leu Glu Gln Thr Gln Tyr Ser
545                 550                 555                 560

Trp Glu Arg Gln Ala Ala Phe Ser Phe Lys Arg Lys Leu Pro Thr Tyr
                565                 570                 575

Leu Leu Phe Thr Ser Pro Gln Glu Asn Pro Trp Gly His Lys Arg Ser
            580                 585                 590

Tyr Arg Leu Gln Ile His Ser Met Ala Asp Gln Val Leu Pro Pro Gly
        595                 600                 605

Trp Gln Glu Glu Gln Ala Ile Thr Trp Ala Arg Tyr Pro Leu Ala Val
    610                 615                 620

Thr Lys Tyr Arg Glu Ser Glu Leu Cys Ser Ser Ser Ile Tyr His Gln
625                 630                 635                 640

Asn Asp Pro Trp His Pro Pro Val Val Phe Glu Gln Phe Leu His Asn
                645                 650                 655

Asn Glu Asn Ile Glu Asn Glu Asp Leu Val Ala Trp Val Thr Val Gly
            660                 665                 670

Phe Leu His Ile Pro His Ser Glu Asp Ile Pro Asn Thr Ala Thr Pro
        675                 680                 685

Gly Asn Ser Val Gly Phe Leu Leu Arg Pro Phe Asn Phe Phe Pro Glu
    690                 695                 700

Asp Pro Ser Leu Ala Ser Arg Asp Thr Val Ile Val Trp Pro Arg Asp
705                 710                 715                 720

Asn Gly Pro Asn Tyr Val Gln Arg Trp Ile Pro Glu Asp Arg Asp Cys
                725                 730                 735

Ser Met Pro Pro Pro Phe Ser Tyr Asn Gly Thr Tyr Arg Pro Val Glu
            740                 745                 750
```

```
Pro Lys Ser Ala Asp Lys Thr His Thr Cys Pro Pro Cys Pro Ala Pro
        755                 760                 765

Pro Val Ala Gly Pro Ser Val Phe Leu Phe Pro Pro Lys Pro Lys Asp
    770                 775                 780

Thr Leu Met Ile Ser Arg Thr Pro Glu Val Thr Cys Val Val Val Asp
785                 790                 795                 800

Val Ser His Glu Asp Pro Glu Val Lys Phe Asn Trp Tyr Val Asp Gly
                805                 810                 815

Val Glu Val His Asn Ala Lys Thr Lys Pro Arg Glu Glu Gln Tyr Asn
            820                 825                 830

Ser Thr Tyr Arg Val Val Ser Val Leu Thr Val Leu His Gln Asp Trp
        835                 840                 845

Leu Asn Gly Lys Glu Tyr Lys Cys Lys Val Ser Asn Lys Gly Leu Pro
    850                 855                 860

Ser Ser Ile Glu Lys Thr Ile Ser Lys Ala Lys Gly Gln Pro Arg Glu
865                 870                 875                 880

Pro Gln Val Tyr Thr Leu Pro Pro Ser Arg Glu Glu Met Thr Lys Asn
                885                 890                 895

Gln Val Ser Leu Thr Cys Leu Val Lys Gly Phe Tyr Pro Ser Asp Ile
            900                 905                 910

Ala Val Glu Trp Glu Ser Asn Gly Gln Pro Glu Asn Asn Tyr Lys Thr
        915                 920                 925

Thr Pro Pro Val Leu Asp Ser Asp Gly Ser Phe Phe Leu Tyr Ser Lys
    930                 935                 940

Leu Thr Val Asp Lys Ser Arg Trp Gln Gln Gly Asn Val Phe Ser Cys
945                 950                 955                 960

Ser Val Met His Glu Ala Leu His Asn His Tyr Thr Gln Lys Ser Leu
                965                 970                 975

Ser Leu Ser Pro Gly Lys
            980


<210> SEQ ID NO 71
<211> LENGTH: 2952
<212> TYPE: DNA
<213> ORGANISM: Artificial Sequence
<220> FEATURE:
<223> OTHER INFORMATION: Fc-hDAO

<400> SEQUENCE: 71

atgccggccc tgggctgggc cgtggctgcc atcctgatgc tgcagacggc catggcggag      60

tgcccccccct gccccgcccc ccccgtggcc ggcccctccg tgttcctgtt cccccccaag     120

cccaaggaca ccctgatgat ctccaggacc cccgaggtga cctgcgtggt ggtggacgtg     180

tcccacgagg accccgaggt gaagttcaac tggtacgtgg acggcgtgga ggtgcacaac     240

gccaagacca agcccaggga ggagcagtac aactccacct acagggtggt gtccgtgctg     300

accgtgctgc accaggactg gctgaacggc aaggagtaca agtgcaaggt gtccaacaag     360

ggcctgccct cctccatcga gaagaccatc tccaaggcca agggccagcc cagggagccc     420

caggtgtaca ccctgccccc ctccagggag gagatgacca agaaccaggt gtccctgacc     480

tgcctggtga agggcttcta cccctccgac atcgccgtgg agtgggagtc caacggccag     540

cccgagaaca actacaagac cacccccccc gtgctggact ccgacggctc cttcttcctg     600

tactccaagc tgaccgtgga caagtccagg tggcagcagg gcaacgtgtt ctcctgctcc     660

gtgatgcacg aggccctgca caaccactac acccagaagt ccctgtccct gtcccccggc     720
```

```
aaggagccca agtccgccga caagacccac accgagccct ccccggggac tctgcccagg    780
aaggcagggg tgttttcaga cctaagcaac caagagctga aggcagtgca cagcttcctc    840
tggtccaaga aggagctgag gctgcagccc tccagtacca ccaccatggc caagaacacc    900
gtgtttctca tcgagatgct gctgcccaag aagtaccatg tgctgaggtt tctggataaa    960
ggtgaaaggc atcctgtgcg ggaagcccgt gccgtcatct tctttggtga ccaggagcat   1020
cccaatgtca ccgagtttgc tgtggggccc ctgccaggcc cctgctacat gcgagcactg   1080
tcccccaggc ctgggtacca gtcctcctgg gcatcgaggc ccatctccac agcagagtat   1140
gccctcctct accacaccct gcaggaagcc accaagcccc tgcatcagtt cttcctcaat   1200
accacaggct tctcattcca agactgccat gacagatgcc tggccttcac cgatgtggcc   1260
ccccggggtg tggcttctgg ccagcgccgc agttggctta tcatacagcg ctatgtagaa   1320
ggctactttc tgcaccccac tgggctggag ctcctcgtgg atcatgggag cacagatgct   1380
gggcactggg ccgtggagca ggtgtggtac aacgggaagt tctatgggag cccagaggaa   1440
ctggctcgga agtatgcaga tggagaggtg gacgtggtgg tcctggagga cccgctgcct   1500
gggggcaagg ggcatgacag cacagaggag ccgcccctct tctcctccca caagccccgc   1560
ggggacttcc ccagccccat ccatgtgagc ggcccccgct tggtccagcc ccacggccct   1620
cgcttcaggc tggagggcaa cgctgtgctc tacggcggct ggagctttgc cttccggctg   1680
cgctcctcct ccgggctgca ggtcctgaac gtgcacttcg gcggagagcg cattgcctat   1740
gaggtcagcg tgcaagaggc agtggcgctg tatggaggac acacacctgc aggcatgcag   1800
accaagtacc tcgatgtcgg ctggggcctg ggcagcgtca ctcatgagtt agccccccggc  1860
atcgactgcc cggagaccgc caccttcctg gacactttcc actactatga tgccgatgac   1920
ccggtccatt atccccgagc cctctgcctc tttgaaatgc ccacaggggt gccccttcgg   1980
cggcacttta attccaactt taaaggtggc ttcaacttct atgcggggct gaagggccag   2040
gtgctggtgc tgcggacaac ttcaactgtc tacaattatg attacatttg ggactttatc   2100
ttctacccca acggggtgat ggaggccaag atgcatgcca ctggctacgt ccacgccacc   2160
ttctacaccc ccgaggggct gcgccacggc actcgcctgc acacccacct gattggcaac   2220
atacacactc acttggtgca ctaccgcgta gacctggatg tggcaggcac caagaacagc   2280
ttccagacac tgcagatgaa gctagaaaac atcaccaacc cctggagccc aagacaccgc   2340
gtggtccagc caactctgga gcagacgcag tactcctggg agcgccaggc ggccttccgc   2400
ttcaaaagga agctgcccaa gtacctgctc tttaccagcc cccaggagaa cccctggggc   2460
cacaagcgca gctaccgcct gcagatccac tccatggccg accaggtgct gcccccaggc   2520
tggcaggagg agcaggccat cacctgggca aggtaccccc tggcagtgac caagtaccgg   2580
gagtcggagc tgtgcagcag cagcatctac caccagaacg acccctggca cccgcccgtg   2640
gtctttgagc agtttcttca caacaacgag aacattgaaa atgaggacct ggtggcctgg   2700
gtgacggtgg gcttcctgca catcccccac tcagaggaca ttcccaacac agccacacct   2760
gggaactccg tgggcttcct gctccggcca ttcaacttct tcccagagga cccctccctg   2820
gcatccagag acactgtgat cgtgtggcct cgggacaacg gccccaacta cgtccagcgc   2880
tggatccctg aggacaggga ctgctcgatg cctccccctt ttagctacaa tgggacctat   2940
agacctgtgt ga                                                        2952
```

<210> SEQ ID NO 72

<211> LENGTH: 2952
<212> TYPE: DNA
<213> ORGANISM: Artificial Sequence
<220> FEATURE:
<223> OTHER INFORMATION: Fc-hDAO-Hepmut1

<400> SEQUENCE: 72
atgccggccc tgggctgggc cgtggctgcc atcctgatgc tgcagacggc catggcggag 60 tgcccccct gccccgcccc ccccgtggcc ggcccctccg tgttcctgtt ccccccaag 120 cccaaggaca ccctgatgat ctccaggacc cccgaggtga cctgcgtggt ggtggacgtg 180
tcccacgagg accccgaggt gaagttcaac tggtacgtgg acggcgtgga ggtgcacaac 240
gccaagacca agcccaggga ggagcagtac aactccacct acagggtggt gtccgtgctg 300
accgtgctgc accaggactg gctgaacggc aaggagtaca agtgcaaggt gtccaacaag 360
ggcctgccct cctccatcga gaagaccatc tccaaggcca agggccagcc cagggagccc 420
caggtgtaca ccctgccccc ctccagggag gagatgacca agaaccaggt gtccctgacc 480
tgcctggtga agggcttcta cccctccgac atcgccgtgg agtgggagtc caacggccag 540
cccgagaaca actacaagac cacccccccc gtgctggact ccgacggctc cttcttcctg 600
tactccaagc tgaccgtgga caagtccagg tggcagcagg gcaacgtgtt ctcctgctcc 660
gtgatgcacg aggccctgca caaccactac acccagaagt ccctgtccct gtcccccggc 720
aaggagccca agtccgccga caagacccac accgagccct ccccggggac tctgcccagg 780
aaggcagggg tgttttcaga cctaagcaac caagagctga aggcagtgca cagcttcctc 840
tggtccaaga aggagctgag gctgcagccc tccagtacca ccaccatggc caagaacacc 900
gtgtttctca tcgagatgct gctgcccaag aagtaccatg tgctgaggtt tctggataaa 960
ggtgaaaggc atcctgtgcg ggaagcccgt gccgtcatct tctttggtga ccaggagcat 1020
cccaatgtca ccgagtttgc tgtggggccc ctgccaggcc cctgctacat gcgagcactg 1080
tcccccaggc ctgggtacca gtcctcctgg gcatcgaggc ccatctccac agcagagtat 1140
gccctcctct accacaccct gcaggaagcc accaagcccc tgcatcagtt cttcctcaat 1200
accacaggct tctcattcca agactgccat gacagatgcc tggccttcac cgatgtggcc 1260
ccccggggtg tggcttctgg ccagcgccgc agttggctta tcatacagcg ctatgtagaa 1320
ggctactttc tgcaccccac tgggctggag ctcctcgtgg atcatgggag cacagatgct 1380
gggcactggg ccgtggagca ggtgtggtac aacgggaagt tctatgggag cccagaggaa 1440
ctggctcgga agtatgcaga tggagaggtg gacgtggtgg tcctggagga cccgctgcct 1500
gggggcaagg ggcatgacag cacagaggag ccgcccctct tctcctccca caagccccgc 1560
ggggacttcc ccagccccat ccatgtgagc ggcccccgct tggtccagcc ccacggccct 1620
cgcttcaggc tggagggcaa cgctgtgctc tacggcggct ggagctttgc cttccggctg 1680
cgctcctcct ccgggctgca ggtcctgaac gtgcacttcg gcggagagcg cattgcctat 1740
gaggtcagcg tgcaagaggc agtggcgctg tatggaggac acacacctgc aggcatgcag 1800
accaagtacc tcgatgtcgg ctggggcctg ggcagcgtca ctcatgagtt agcccccggc 1860
atcgactgcc cggagaccgc caccttcctg gacactttcc actactatga tgccgatgac 1920
ccggtccatt atccccgagc cctctgcctc tttgaaatgc ccacaggggt gccccttcgg 1980
cggcacttta attccaactt taaaggtggc ttcaacttct atgcggggct gaagggccag 2040
gtgctggtgc tgcggacaac ttcaactgtc tacaattatg attacatttg ggactttatc 2100
ttctacccca acggggtgat ggaggccaag atgcatgcca ctggctacgt ccacgccacc 2160
ttctacaccc ccgaggggct gcgccacggc actcgcctgc acacccacct gattggcaac 2220
atacacactc acttggtgca ctaccgcgta gacctggatg tggcaggcac caagaacagc 2280
ttccagacac tgcagatgaa gctagaaaac atcaccaacc cctggagccc aagacaccgc 2340
gtggtccagc caactctgga gcagacgcag tactcctggg agcgccaggc ggccttcagc 2400
ttcaaaagga agctgcccaa gtacctgctc tttaccagcc cccaggagaa cccctggggc 2460
cacaagcgca gctaccgcct gcagatccac tccatggccg accaggtgct gcccccaggc 2520
tggcaggagg agcaggccat cacctgggca aggtaccccc tggcagtgac caagtaccgg 2580
gagtcggagc tgtgcagcag cagcatctac caccagaacg acccctggca cccgcccgtg 2640
gtctttgagc agtttcttca caacaacgag aacattgaaa atgaggacct ggtggcctgg 2700
gtgacggtgg gcttcctgca catcccccac tcagaggaca ttcccaacac agccacacct 2760
gggaactccg tgggcttcct gctccggcca ttcaacttct tcccagagga cccctccctg 2820
gcatccagag acactgtgat cgtgtggcct cgggacaacg gccccaacta cgtccagcgc 2880
tggatccctg aggacaggga ctgctcgatg cctcccccctt ttagctacaa tgggacctat 2940
agacctgtgt ga 2952

<210> SEQ ID NO 73
<211> LENGTH: 2952
<212> TYPE: DNA
<213> ORGANISM: Artificial Sequence
<220> FEATURE:
<223> OTHER INFORMATION: Fc-hDAO-Hepmut2

<400> SEQUENCE: 73
atgccggccc tgggctgggc cgtggctgcc atcctgatgc tgcagacggc catggcggag 60
tgccccccct gccccgcccc ccccgtggcc ggcccctccg tgttcctgtt ccccccccaag 120 cccaaggaca ccctgatgat ctccaggacc cccgaggtga cctgcgtggt ggtggacgtg 180
tcccacgagg accccgaggt gaagttcaac tggtacgtgg acggcgtgga ggtgcacaac 240
gccaagacca agcccaggga ggagcagtac aactccacct acagggtggt gtccgtgctg 300
accgtgctgc accaggactg gctgaacggc aaggagtaca agtgcaaggt gtccaacaag 360
ggcctgccct cctccatcga gaagaccatc tccaaggcca agggccagcc cagggagccc 420
caggtgtaca ccctgccccc ctccagggag gagatgacca agaaccaggt gtccctgacc 480
tgcctggtga agggcttcta cccctccgac atcgccgtgg agtgggagtc caacggccag 540
cccgagaaca actacaagac cacccccccc gtgctggact ccgacggctc cttcttcctg 600
tactccaagc tgaccgtgga caagtccagg tggcagcagg gcaacgtgtt ctcctgctcc 660
gtgatgcacg aggccctgca caaccactac acccagaagt ccctgtccct gtcccccggc 720
aaggagccca agtccgccga caagacccac accgagccct ccccggggac tctgcccagg 780
aaggcagggg tgttttcaga cctaagcaac caagagctga aggcagtgca cagcttcctc 840
tggtccaaga aggagctgag gctgcagccc tccagtacca ccaccatggc caagaacacc 900
gtgtttctca tcgagatgct gctgcccaag aagtaccatg tgctgaggtt tctggataaa 960
ggtgaaaggc atcctgtgcg ggaagcccgt gccgtcatct tctttggtga ccaggagcat 1020
cccaatgtca ccgagtttgc tgtggggccc ctgccaggcc cctgctacat gcgagcactg 1080
tcccccaggc ctgggtacca gtcctcctgg gcatcgaggc ccatctccac agcagagtat 1140
gccctcctct accacaccct gcaggaagcc accaagcccc tgcatcagtt cttcctcaat 1200
accacaggct tctcattcca agactgccat gacagatgcc tggccttcac cgatgtggcc 1260
ccccggggtg tggcttctgg ccagcgccgc agttggctta tcatacagcg ctatgtagaa 1320
ggctactttc tgcaccccac tgggctggag ctcctcgtgg atcatgggag cacagatgct 1380
gggcactggg ccgtggagca ggtgtggtac aacgggaagt tctatgggag cccagaggaa 1440
ctggctcgga agtatgcaga tggagaggtg gacgtggtgg tcctggagga cccgctgcct 1500
gggggcaagg ggcatgacag cacagaggag ccgcccctct tctcctccca caagccccgc 1560
ggggacttcc ccagccccat ccatgtgagc ggcccccgct tggtccagcc ccacggccct 1620
cgcttcaggc tggagggcaa cgctgtgctc tacggcggct ggagctttgc cttccggctg 1680
cgctcctcct ccgggctgca ggtcctgaac gtgcacttcg gcggagagcg cattgcctat 1740
gaggtcagcg tgcaagaggc agtggcgctg tatggaggac acacacctgc aggcatgcag 1800
accaagtacc tcgatgtcgg ctggggcctg ggcagcgtca ctcatgagtt agcccccggc 1860
atcgactgcc cggagaccgc caccttcctg gacactttcc actactatga tgccgatgac 1920
ccggtccatt atccccgagc cctctgcctc tttgaaatgc ccacaggggt gccccttcgg 1980
cggcacttta attccaactt taaaggtggc ttcaacttct atgcggggct gaagggccag 2040
gtgctggtgc tgcggacaac ttcaactgtc tacaattatg attacatttg ggactttatc 2100
ttctacccca acggggtgat ggaggccaag atgcatgcca ctggctacgt ccacgccacc 2160
ttctacaccc ccgaggggct gcgccacggc actcgcctgc acacccacct gattggcaac 2220
atacacactc acttggtgca ctaccgcgta gacctggatg tggcaggcac caagaacagc 2280
ttccagacac tgcagatgaa gctagaaaac atcaccaacc cctggagccc aagacaccgc 2340
gtggtccagc caactctgga gcagacgcag tactcctggg agcgccaggc ggccttccgc 2400
ttcaaaagga agctgcccac gtacctgctc tttaccagcc cccaggagaa cccctggggc 2460
cacaagcgca gctaccgcct gcagatccac tccatggccg accaggtgct gcccccaggc 2520
tggcaggagg agcaggccat cacctgggca aggtaccccc tggcagtgac caagtaccgg 2580
gagtcggagc tgtgcagcag cagcatctac caccagaacg acccctggca cccgcccgtg 2640
gtctttgagc agtttcttca caacaacgag aacattgaaa atgaggacct ggtggcctgg 2700
gtgacggtgg gcttcctgca catcccccac tcagaggaca ttcccaacac agccacacct 2760
gggaactccg tgggcttcct gctccggcca ttcaacttct tcccagagga cccctccctg 2820
gcatccagag acactgtgat cgtgtggcct cgggacaacg gccccaacta cgtccagcgc 2880
tggatccctg aggacaggga ctgctcgatg cctcccccctt ttagctacaa tgggacctat 2940
agacctgtgt ga 2952

<210> SEQ ID NO 74
<211> LENGTH: 2952
<212> TYPE: DNA
<213> ORGANISM: Artificial Sequence
<220> FEATURE:
<223> OTHER INFORMATION: Fc-hDAO-Hepmut3

<400> SEQUENCE: 74
atgccggccc tgggctgggc cgtggctgcc atcctgatgc tgcagacggc catggcggag 60 tgcccccccct gccccgcccc ccccgtggcc ggcccctccg tgttcctgtt cccccccaag 120
cccaaggaca ccctgatgat ctccaggacc cccgaggtga cctgcgtggt ggtggacgtg 180
tcccacgagg accccgaggt gaagttcaac tggtacgtgg acggcgtgga ggtgcacaac 240
gccaagacca agcccaggga ggagcagtac aactccacct acagggtggt gtccgtgctg 300

-continued

```
accgtgctgc accaggactg gctgaacggc aaggagtaca agtgcaaggt gtccaacaag    360
ggcctgccct cctccatcga gaagaccatc tccaaggcca agggccagcc cagggagccc    420
caggtgtaca ccctgccccc ctccagggag gagatgacca agaaccaggt gtccctgacc    480
tgcctggtga agggcttcta cccctccgac atcgccgtgg agtgggagtc caacggccag    540
cccgagaaca actacaagac caccccccc gtgctggact ccgacggctc cttcttcctg     600
tactccaagc tgaccgtgga caagtccagg tggcagcagg gcaacgtgtt ctcctgctcc    660
gtgatgcacg aggccctgca caaccactac acccagaagt ccctgtccct gtcccccggc    720
aaggagccca agtccgccga caagacccac accgagccct ccccggggac tctgcccagg    780
aaggcagggg tgttttcaga cctaagcaac caagagctga aggcagtgca cagcttcctc    840
tggtccaaga aggagctgag gctgcagccc tccagtacca ccaccatggc caagaacacc    900
gtgtttctca tcgagatgct gctgcccaag aagtaccatg tgctgaggtt tctggataaa    960
ggtgaaaggc atcctgtgcg ggaagcccgt gccgtcatct tctttggtga ccaggagcat   1020
cccaatgtca ccgagtttgc tgtggggccc ctgccaggcc cctgctacat gcgagcactg   1080
tcccccaggc ctgggtacca gtcctcctgg gcatcgaggc ccatctccac agcagagtat   1140
gccctcctct accacaccct gcaggaagcc accaagcccc tgcatcagtt cttcctcaat   1200
accacaggct tctcattcca agactgccat gacagatgcc tggccttcac cgatgtggcc   1260
ccccggggtg tggcttctgg ccagcgccgc agttggctta tcatacagcg ctatgtagaa   1320
ggctactttc tgcaccccac tgggctggag ctcctcgtgg atcatgggag cacagatgct   1380
gggcactggg ccgtggagca ggtgtggtac aacgggaagt tctatgggag cccagaggaa   1440
ctggctcgga agtatgcaga tggagaggtg gacgtggtgg tcctggagga cccgctgcct   1500
gggggcaagg ggcatgacag cacagaggag ccgcccctct tctcctccca caagccccgc   1560
ggggacttcc ccagccccat ccatgtgagc ggcccccgct tggtccagcc ccacggccct   1620
cgcttcaggc tggagggcaa cgctgtgctc tacggcggct ggagctttgc cttccggctg   1680
cgctcctcct ccgggctgca ggtcctgaac gtgcacttcg gcggagagcg cattgcctat   1740
gaggtcagcg tgcaagaggc agtggcgctg tatggaggac acacacctgc aggcatgcag   1800
accaagtacc tcgatgtcgg ctggggcctg ggcagcgtca ctcatgagtt agcccccggc   1860
atcgactgcc cggagaccgc caccttcctg gacactttcc actactatga tgccgatgac   1920
ccggtccatt atccccgagc cctctgcctc tttgaaatgc ccacaggggt gccccttcgg   1980
cggcacttta attccaactt taaaggtggc ttcaacttct atgcggggct gaagggccag   2040
gtgctggtgc tgcggacaac ttcaactgtc tacaattatg attacatttg ggactttatc   2100
ttctacccca acggggtgat ggaggccaag atgcatgcca ctggctacgt ccacgccacc   2160
ttctacaccc ccgaggggct gcgccacggc actcgcctgc acacccacct gattggcaac   2220
atacacactc acttggtgca ctaccgcgta gacctggatg tggcaggcac caagaacagc   2280
ttccagacac tgcagatgaa gctagaaaac atcaccaacc cctggagccc aagacaccgc   2340
gtggtccagc caactctgga gcagacgcag tactcctggg agcgccaggc ggccttccgc   2400
ttcaaaacga agctgcccaa gtacctgctc tttaccagcc cccaggagaa cccctggggc   2460
cacaagcgca gctaccgcct gcagatccac tccatggccg accaggtgct gcccccaggc   2520
tggcaggagg agcaggccat cacctgggca aggtaccccc tggcagtgac caagtaccgg   2580
gagtcggagc tgtgcagcag cagcatctac caccagaacg acccctggca cccgcccgtg   2640
```

```
gtctttgagc agtttcttca caacaacgag aacattgaaa atgaggacct ggtggcctgg   2700

gtgacggtgg gcttcctgca catcccccac tcagaggaca ttcccaacac agccacacct   2760

gggaactccg tgggcttcct gctccggcca ttcaacttct tcccagagga cccctccctg   2820

gcatccagag acactgtgat cgtgtggcct cgggacaacg gccccaacta cgtccagcgc   2880

tggatccctg aggacaggga ctgctcgatg cctcccccctt ttagctacaa tgggacctat   2940

agacctgtgt ga                                                        2952
```

<210> SEQ ID NO 75
<211> LENGTH: 2952
<212> TYPE: DNA
<213> ORGANISM: Artificial Sequence
<220> FEATURE:
<223> OTHER INFORMATION: Fc-hDAO-Hepmut4

<400> SEQUENCE: 75

```
atgccggccc tgggctgggc cgtggctgcc atcctgatgc tgcagacggc catggcggag     60

tgcccccccct gccccgcccc ccccgtggcc ggcccctccg tgttcctgtt cccccccaag    120

cccaaggaca ccctgatgat ctccaggacc cccgaggtga cctgcgtggt ggtggacgtg    180

tcccacgagg accccgaggt gaagttcaac tggtacgtgg acggcgtgga ggtgcacaac    240

gccaagacca agcccaggga ggagcagtac aactccacct acagggtggt gtccgtgctg    300

accgtgctgc accaggactg gctgaacggc aaggagtaca agtgcaaggt gtccaacaag    360

ggcctgccct cctccatcga gaagaccatc tccaaggcca agggccagcc cagggagccc    420

caggtgtaca ccctgccccc ctccagggag gagatgacca agaaccaggt gtccctgacc    480

tgcctggtga agggcttcta cccctccgac atcgccgtgg agtgggagtc caacggccag    540

cccgagaaca actacaagac cacccccccc gtgctggact ccgacggctc cttcttcctg    600

tactccaagc tgaccgtgga caagtccagg tggcagcagg gcaacgtgtt ctcctgctcc    660

gtgatgcacg aggccctgca caaccactac acccagaagt ccctgtccct gtcccccggc    720

aaggagccca agtccgccga caagacccac accgagccct ccccggggac tctgcccagg    780

aaggcagggg tgttttcaga cctaagcaac caagagctga aggcagtgca cagcttcctc    840

tggtccaaga aggagctgag gctgcagccc tccagtacca ccaccatggc caagaacacc    900

gtgtttctca tcgagatgct gctgcccaag aagtaccatg tgctgaggtt tctggataaa    960

ggtgaaaggc atcctgtgcg ggaagcccgt gccgtcatct tctttggtga ccaggagcat   1020

cccaatgtca ccgagtttgc tgtggggccc ctgccaggcc cctgctacat gcgagcactg   1080

tcccccaggc ctgggtacca gtcctcctgg gcatcgaggc ccatctccac agcagagtat   1140

gccctcctct accacaccct gcaggaagcc accaagcccc tgcatcagtt cttcctcaat   1200

accacaggct tctcattcca agactgccat gacagatgcc tggccttcac cgatgtggcc   1260

ccccggggtg tggcttctgg ccagcgccgc agttggctta tcatacagcg ctatgtagaa   1320

ggctactttc tgcaccccac tgggctggag ctcctcgtgg atcatgggag cacagatgct   1380

gggcactggg ccgtggagca ggtgtggtac aacgggaagt tctatgggag cccagaggaa   1440

ctggctcgga agtatgcaga tggagaggtg gacgtggtgg tcctggagga cccgctgcct   1500

gggggcaagg ggcatgacag cacagaggag ccgcccctct tctcctccca caagccccgc   1560

ggggacttcc ccagccccat ccatgtgagc ggcccccgct tggtccagcc ccacggccct   1620

cgcttcaggc tggagggcaa cgctgtgctc tacggcggct ggagctttgc cttccggctg   1680

cgctcctcct ccgggctgca ggtcctgaac gtgcacttcg gcggagagcg cattgcctat   1740
```

gaggtcagcg tgcaagaggc agtggcgctg tatggaggac acacacctgc aggcatgcag 1800
accaagtacc tcgatgtcgg ctggggcctg ggcagcgtca ctcatgagtt agcccccggc 1860
atcgactgcc cggagaccgc caccttcctg gacactttcc actactatga tgccgatgac 1920
ccggtccatt atccccgagc cctctgcctc tttgaaatgc ccacaggggt gccccttcgg 1980
cggcacttta attccaactt taaaggtggc ttcaacttct atgcggggct gaagggccag 2040
gtgctggtgc tgcggacaac ttcaactgtc tacaattatg attacatttg ggactttatc 2100
ttctacccca acggggtgat ggaggccaag atgcatgcca ctggctacgt ccacgccacc 2160
ttctacaccc ccgaggggct gcgccacggc actcgcctgc acacccacct gattggcaac 2220
atacacactc acttggtgca ctaccgcgta gacctggatg tggcaggcac caagaacagc 2280
ttccagacac tgcagatgaa gctagaaaac atcaccaacc cctggagccc aagacaccgc 2340
gtggtccagc caactctgga gcagacgcag tactcctggg agcgccaggc ggccttcagc 2400
ttcaaaacga agctgcccaa gtacctgctc tttaccagcc cccaggagaa cccctggggc 2460
cacaagcgca gctaccgcct gcagatccac tccatggccg accaggtgct gcccccaggc 2520
tggcaggagg agcaggccat cacctgggca aggtaccccc tggcagtgac caagtaccgg 2580
gagtcggagc tgtgcagcag cagcatctac caccagaacg acccctggca cccgcccgtg 2640
gtctttgagc agtttcttca caacaacgag aacattgaaa atgaggacct ggtggcctgg 2700
gtgacggtgg gcttcctgca catcccccac tcagaggaca ttcccaacac agccacacct 2760
gggaactccg tgggcttcct gctccggcca ttcaacttct tcccagagga cccctccctg 2820
gcatccagag acactgtgat cgtgtggcct cgggacaacg gccccaacta cgtccagcgc 2880
tggatccctg aggacaggga ctgctcgatg cctcccccctt ttagctacaa tgggacctat 2940
agacctgtgt ga 2952

<210> SEQ ID NO 76
<211> LENGTH: 2952
<212> TYPE: DNA
<213> ORGANISM: Artificial Sequence
<220> FEATURE:
<223> OTHER INFORMATION: Fc-hDAO-Hepmut5

<400> SEQUENCE: 76
atgccggccc tgggctgggc cgtggctgcc atcctgatgc tgcagacggc catggcggag 60
tgccccccct gccccgcccc ccccgtggcc ggcccctccg tgttcctgtt cccccccaag 120
cccaaggaca ccctgatgat ctccaggacc cccgaggtga cctgcgtggt ggtggacgtg 180
tcccacgagg accccgaggt gaagttcaac tggtacgtgg acggcgtgga ggtgcacaac 240
gccaagacca agcccaggga ggagcagtac aactccacct acagggtggt gtccgtgctg 300
accgtgctgc accaggactg gctgaacggc aaggagtaca agtgcaaggt gtccaacaag 360
ggcctgccct cctccatcga gaagaccatc tccaaggcca agggccagcc cagggagccc 420
caggtgtaca ccctgccccc ctccagggag gagatgacca agaaccaggt gtccctgacc 480
tgcctggtga agggcttcta cccctccgac atcgccgtgg agtgggagtc caacggccag 540
cccgagaaca actacaagac caccccccccc gtgctggact ccgacggctc cttcttcctg 600
tactccaagc tgaccgtgga caagtccagg tggcagcagg gcaacgtgtt ctcctgctcc 660
gtgatgcacg aggccctgca caaccactac acccagaagt ccctgtccct gtcccccggc 720
aaggagccca agtccgccga caagacccac accgagccct ccccggggac tctgcccagg 780
aaggcagggg tgttttcaga cctaagcaac caagagctga aggcagtgca cagcttcctc 840
tggtccaaga aggagctgag gctgcagccc tccagtacca ccaccatggc caagaacacc 900
gtgtttctca tcgagatgct gctgcccaag aagtaccatg tgctgaggtt tctggataaa 960
ggtgaaaggc atcctgtgcg ggaagcccgt gccgtcatct tctttggtga ccaggagcat 1020
cccaatgtca ccgagtttgc tgtggggccc ctgccaggcc cctgctacat gcgagcactg 1080
tcccccaggc ctgggtacca gtcctcctgg gcatcgaggc ccatctccac agcagagtat 1140
gccctcctct accacaccct gcaggaagcc accaagcccc tgcatcagtt cttcctcaat 1200
accacaggct tctcattcca agactgccat gacagatgcc tggccttcac cgatgtggcc 1260
ccccggggtg tggcttctgg ccagcgccgc agttggctta tcatacagcg ctatgtagaa 1320
ggctactttc tgcaccccac tgggctggag ctcctcgtgg atcatgggag cacagatgct 1380
gggcactggg ccgtggagca ggtgtggtac aacgggaagt tctatgggag cccagaggaa 1440
ctggctcgga agtatgcaga tggagaggtg gacgtggtgg tcctggagga cccgctgcct 1500
gggggcaagg ggcatgacag cacagaggag ccgcccctct tctcctccca caagccccgc 1560
ggggacttcc ccagccccat ccatgtgagc ggcccccgct tggtccagcc ccacggccct 1620
cgcttcaggc tggagggcaa cgctgtgctc tacggcggct ggagctttgc cttccggctg 1680
cgctcctcct ccgggctgca ggtcctgaac gtgcacttcg gcggagagcg cattgcctat 1740
gaggtcagcg tgcaagaggc agtggcgctg tatggaggac acacacctgc aggcatgcag 1800
accaagtacc tcgatgtcgg ctggggcctg ggcagcgtca ctcatgagtt agcccccggc 1860
atcgactgcc cggagaccgc caccttcctg gacactttcc actactatga tgccgatgac 1920
ccggtccatt atccccgagc cctctgcctc tttgaaatgc ccacaggggt gccccttcgg 1980
cggcacttta attccaactt taaaggtggc ttcaacttct atgcggggct gaagggccag 2040
gtgctggtgc tgcggacaac ttcaactgtc tacaattatg attacatttg ggactttatc 2100
ttctacccca acggggtgat ggaggccaag atgcatgcca ctggctacgt ccacgccacc 2160
ttctacaccc ccgaggggct gcgccacggc actcgcctgc acacccacct gattggcaac 2220
atacacactc acttggtgca ctaccgcgta gacctggatg tggcaggcac caagaacagc 2280
ttccagacac tgcagatgaa gctagaaaac atcaccaacc cctggagccc aagacaccgc 2340
gtggtccagc caactctgga gcagacgcag tactcctggg agcgccaggc ggccttccgc 2400
ttcaaaacga agctgcccac gtacctgctc tttaccagcc cccaggagaa cccctggggc 2460
cacaagcgca gctaccgcct gcagatccac tccatggccg accaggtgct gcccccaggc 2520
tggcaggagg agcaggccat cacctgggca aggtaccccc tggcagtgac caagtaccgg 2580
gagtcggagc tgtgcagcag cagcatctac caccagaacg acccctggca cccgcccgtg 2640
gtctttgagc agtttcttca caacaacgag aacattgaaa atgaggacct ggtggcctgg 2700
gtgacggtgg gcttcctgca catcccccac tcagaggaca ttcccaacac agccacacct 2760
gggaactccg tgggcttcct gctccggcca ttcaacttct tcccagagga cccctccctg 2820
gcatccagag acactgtgat cgtgtggcct cgggacaacg gccccaacta cgtccagcgc 2880
tggatccctg aggacaggga ctgctcgatg cctcccccct ttagctacaa tgggacctat 2940
agacctgtgt ga 2952

<210> SEQ ID NO 77
<211> LENGTH: 2952
<212> TYPE: DNA
<213> ORGANISM: Artificial Sequence
<220> FEATURE:
<223> OTHER INFORMATION: Fc-hDAO-Hepmut6

<400> SEQUENCE: 77

```
atgccggccc tgggctgggc cgtggctgcc atcctgatgc tgcagacggc catggcggag     60

tgcccccccct gccccgcccc ccccgtggcc ggcccctccg tgttcctgtt cccccccaag    120

cccaaggaca ccctgatgat ctccaggacc cccgaggtga cctgcgtggt ggtggacgtg    180

tcccacgagg accccgaggt gaagttcaac tggtacgtgg acggcgtgga ggtgcacaac    240

gccaagacca agcccaggga ggagcagtac aactccacct acagggtggt gtccgtgctg    300

accgtgctgc accaggactg gctgaacggc aaggagtaca agtgcaaggt gtccaacaag    360

ggcctgccct cctccatcga gaagaccatc tccaaggcca agggccagcc cagggagccc    420

caggtgtaca ccctgccccc ctccagggag gagatgacca agaaccaggt gtccctgacc    480

tgcctggtga agggcttcta cccctccgac atcgccgtgg agtgggagtc caacggccag    540

cccgagaaca actacaagac cacccccccc gtgctggact ccgacggctc cttcttcctg    600

tactccaagc tgaccgtgga caagtccagg tggcagcagg gcaacgtgtt ctcctgctcc    660

gtgatgcacg aggccctgca caaccactac acccagaagt ccctgtccct gtcccccggc    720

aaggagccca agtccgccga caagacccac accgagccct ccccggggac tctgcccagg    780

aaggcagggg tgttttcaga cctaagcaac caagagctga aggcagtgca cagcttcctc    840

tggtccaaga aggagctgag gctgcagccc tccagtacca ccaccatggc caagaacacc    900

gtgtttctca tcgagatgct gctgcccaag aagtaccatg tgctgaggtt tctggataaa    960

ggtgaaaggc atcctgtgcg ggaagcccgt gccgtcatct tctttggtga ccaggagcat   1020

cccaatgtca ccgagtttgc tgtggggccc ctgccaggcc cctgctacat gcgagcactg   1080

tcccccaggc ctgggtacca gtcctcctgg gcatcgaggc ccatctccac agcagagtat   1140

gccctcctct accacaccct gcaggaagcc accaagcccc tgcatcagtt cttcctcaat   1200

accacaggct tctcattcca agactgccat gacagatgcc tggccttcac cgatgtggcc   1260

ccccggggtg tggcttctgg ccagcgccgc agttggctta tcatacagcg ctatgtagaa   1320

ggctactttc tgcaccccac tgggctggag ctcctcgtgg atcatgggag cacagatgct   1380

gggcactggg ccgtggagca ggtgtggtac aacgggaagt tctatgggag cccagaggaa   1440

ctggctcgga agtatgcaga tggagaggtg gacgtggtgg tcctggagga cccgctgcct   1500

gggggcaagg ggcatgacag cacagaggag ccgcccctct tctcctccca caagccccgc   1560

ggggacttcc ccagccccat ccatgtgagc ggcccccgct tggtccagcc ccacggccct   1620

cgcttcaggc tggagggcaa cgctgtgctc tacggcggct ggagctttgc cttccggctg   1680

cgctcctcct ccgggctgca ggtcctgaac gtgcacttcg gcggagagcg cattgcctat   1740

gaggtcagcg tgcaagaggc agtggcgctg tatggaggac acacacctgc aggcatgcag   1800

accaagtacc tcgatgtcgg ctggggcctg ggcagcgtca ctcatgagtt agcccccggc   1860

atcgactgcc cggagaccgc caccttcctg gacactttcc actactatga tgccgatgac   1920

ccggtccatt atccccgagc cctctgcctc tttgaaatgc ccacaggggt gccccttcgg   1980

cggcacttta attccaactt taaaggtggc ttcaacttct atgcggggct gaagggccag   2040

gtgctggtgc tgcggacaac ttcaactgtc tacaattatg attacatttg ggactttatc   2100

ttctacccca acggggtgat ggaggccaag atgcatgcca ctggctacgt ccacgccacc   2160

ttctacaccc ccgaggggct gcgccacggc actcgcctgc acacccacct gattggcaac   2220
```

atacacactc acttggtgca ctaccgcgta gacctggatg tggcaggcac caagaacagc 2280
ttccagacac tgcagatgaa gctagaaaac atcaccaacc cctggagccc aagacaccgc 2340
gtggtccagc caactctgga gcagacgcag tactcctggg agcgccaggc ggccttccgc 2400
ttcggacaga cgctgcccaa gtacctgctc tttaccagcc cccaggagaa cccctggggc 2460
cacaagcgca gctaccgcct gcagatccac tccatggccg accaggtgct gcccccaggc 2520
tggcaggagg agcaggccat cacctgggca aggtacccc tggcagtgac caagtaccgg 2580
gagtcggagc tgtgcagcag cagcatctac caccagaacg acccctggca cccgcccgtg 2640
gtctttgagc agtttcttca caacaacgag aacattgaaa atgaggacct ggtggcctgg 2700
gtgacggtgg gcttcctgca catcccccac tcagaggaca ttcccaacac agccacacct 2760
gggaactccg tgggcttcct gctccggcca ttcaacttct tcccagagga cccctccctg 2820
gcatccagag acactgtgat cgtgtggcct cgggacaacg gccccaacta cgtccagcgc 2880
tggatccctg aggacaggga ctgctcgatg cctcccctt ttagctacaa tgggacctat 2940
agacctgtgt ga 2952

<210> SEQ ID NO 78
<211> LENGTH: 2952
<212> TYPE: DNA
<213> ORGANISM: Artificial Sequence
<220> FEATURE:
<223> OTHER INFORMATION: Fc-hDAO-Hepmut7

<400> SEQUENCE: 78
atgccggccc tgggctgggc cgtggctgcc atcctgatgc tgcagacggc catggcggag 60 tgcccccct gccccgcccc ccccgtggcc ggcccctccg tgttcctgtt cccccccaag 120
cccaaggaca ccctgatgat ctccaggacc cccgaggtga cctgcgtggt ggtggacgtg 180
tcccacgagg accccgaggt gaagttcaac tggtacgtgg acggcgtgga ggtgcacaac 240
gccaagacca agcccaggga ggagcagtac aactccacct acagggtggt gtccgtgctg 300
accgtgctgc accaggactg gctgaacggc aaggagtaca agtgcaaggt gtccaacaag 360
ggcctgccct cctccatcga gaagaccatc tccaaggcca agggccagcc cagggagccc 420
caggtgtaca ccctgccccc ctccagggag gagatgacca agaaccaggt gtccctgacc 480
tgcctggtga agggcttcta ccccctccgac atcgccgtgg agtgggagtc caacggccag 540
cccgagaaca actacaagac caccccccc gtgctggact ccgacggctc cttcttcctg 600
tactccaagc tgaccgtgga caagtccagg tggcagcagg gcaacgtgtt ctcctgctcc 660
gtgatgcacg aggccctgca caaccactac acccagaagt ccctgtccct gtcccccggc 720
aaggagccca agtccgccga caagacccac accgagccct ccccggggac tctgcccagg 780
aaggcagggg tgttttcaga cctaagcaac caagagctga aggcagtgca cagcttcctc 840
tggtccaaga aggagctgag gctgcagccc tccagtacca ccaccatggc caagaacacc 900
gtgtttctca tcgagatgct gctgcccaag aagtaccatg tgctgaggtt tctggataaa 960
ggtgaaaggc atcctgtgcg ggaagcccgt gccgtcatct tctttggtga ccaggagcat 1020
cccaatgtca ccgagtttgc tgtggggccc ctgccaggcc cctgctacat gcgagcactg 1080
tcccccaggc ctgggtacca gtcctcctgg gcatcgaggc ccatctccac agcagagtat 1140
gccctcctct accacaccct gcaggaagcc accaagcccc tgcatcagtt cttcctcaat 1200
accacaggct tctcattcca agactgccat gacagatgcc tggccttcac cgatgtggcc 1260
ccccggggtg tggcttctgg ccagcgccgc agttggctta tcatacagcg ctatgtagaa 1320
ggctactttc tgcaccccac tgggctggag ctcctcgtgg atcatgggag cacagatgct 1380
gggcactggg ccgtggagca ggtgtggtac aacgggaagt tctatgggag cccagaggaa 1440
ctggctcgga agtatgcaga tggagaggtg gacgtggtgg tcctggagga cccgctgcct 1500
gggggcaagg ggcatgacag cacagaggag ccgcccctct tctcctccca caagccccgc 1560
ggggacttcc ccagccccat ccatgtgagc ggcccccgct tggtccagcc ccacggccct 1620
cgcttcaggc tggagggcaa cgctgtgctc tacggcggct ggagctttgc cttccggctg 1680
cgctcctcct ccgggctgca ggtcctgaac gtgcacttcg gcggagagcg cattgcctat 1740
gaggtcagcg tgcaagaggc agtggcgctg tatggaggac acacacctgc aggcatgcag 1800
accaagtacc tcgatgtcgg ctggggcctg ggcagcgtca ctcatgagtt agcccccggc 1860
atcgactgcc cggagaccgc caccttcctg gacactttcc actactatga tgccgatgac 1920
ccggtccatt atccccgagc cctctgcctc tttgaaatgc ccacaggggt gccccttcgg 1980
cggcacttta attccaactt taaaggtggc ttcaacttct atgcggggct gaagggccag 2040
gtgctggtgc tgcggacaac ttcaactgtc tacaattatg attacatttg ggactttatc 2100
ttctacccca acggggtgat ggaggccaag atgcatgcca ctggctacgt ccacgccacc 2160
ttctacaccc ccgaggggct gcgccacggc actcgcctgc acacccacct gattggcaac 2220
atacacactc acttggtgca ctaccgcgta gacctggatg tggcaggcac caagaacagc 2280
ttccagacac tgcagatgaa gctagaaaac atcaccaacc cctggagccc aagacaccgc 2340
gtggtccagc caactctgga gcagacgcag tactcctggg agcgccaggc ggccttcagc 2400
ttcaaaagga agctgcccac gtacctgctc tttaccagcc cccaggagaa cccctggggc 2460
cacaagcgca gctaccgcct gcagatccac tccatggccg accaggtgct gcccccaggc 2520
tggcaggagg agcaggccat cacctgggca aggtaccccc tggcagtgac caagtaccgg 2580
gagtcggagc tgtgcagcag cagcatctac caccagaacg acccctggca cccgcccgtg 2640
gtctttgagc agtttcttca caacaacgag aacattgaaa atgaggacct ggtggcctgg 2700
gtgacggtgg gcttcctgca catcccccac tcagaggaca ttcccaacac agccacacct 2760
gggaactccg tgggcttcct gctccggcca ttcaacttct tcccagagga cccctccctg 2820
gcatccagag acactgtgat cgtgtggcct cgggacaacg gccccaacta cgtccagcgc 2880
tggatccctg aggacaggga ctgctcgatg cctcccccctt ttagctacaa tgggacctat 2940
agacctgtgt ga 2952

<210> SEQ ID NO 79
<211> LENGTH: 2952
<212> TYPE: DNA
<213> ORGANISM: Artificial Sequence
<220> FEATURE:
<223> OTHER INFORMATION: Fc-hDAO-Cysmut

<400> SEQUENCE: 79
atgccggccc tgggctgggc cgtggctgcc atcctgatgc tgcagacggc catggcggag 60 tgcccccccct gccccgcccc ccccgtggcc ggcccctccg tgttcctgtt cccccccaag 120
cccaaggaca ccctgatgat ctccaggacc cccgaggtga cctgcgtggt ggtggacgtg 180
tcccacgagg accccgaggt gaagttcaac tggtacgtgg acggcgtgga ggtgcacaac 240
gccaagacca agcccaggga ggagcagtac aactccacct acagggtggt gtccgtgctg 300
accgtgctgc accaggactg gctgaacggc aaggagtaca agtgcaaggt gtccaacaag 360

```
ggcctgccct cctccatcga gaagaccatc tccaaggcca agggccagcc cagggagccc    420
caggtgtaca ccctgccccc ctccagggag gagatgacca agaaccaggt gtccctgacc    480
tgcctggtga agggcttcta cccctccgac atcgccgtgg agtgggagtc caacggccag    540
cccgagaaca actacaagac caccccccc gtgctggact ccgacggctc cttcttcctg    600
tactccaagc tgaccgtgga caagtccagg tggcagcagg gcaacgtgtt ctcctgctcc    660
gtgatgcacg aggccctgca caaccactac acccagaagt ccctgtccct gtcccccggc    720
aaggagccca agtccgccga caagacccac accgagccct ccccggggac tctgcccagg    780
aaggcagggg tgttttcaga cctaagcaac caagagctga aggcagtgca cagcttcctc    840
tggtccaaga aggagctgag gctgcagccc tccagtacca ccaccatggc caagaacacc    900
gtgtttctca tcgagatgct gctgcccaag aagtaccatg tgctgaggtt tctggataaa    960
ggtgaaaggc atcctgtgcg ggaagcccgt gccgtcatct tctttggtga ccaggagcat   1020
cccaatgtca ccgagtttgc tgtggggccc ctgccaggcc ccgcctacat gcgagcactg   1080
tcccccaggc ctgggtacca gtcctcctgg gcatcgaggc ccatctccac agcagagtat   1140
gccctcctct accacaccct gcaggaagcc accaagcccc tgcatcagtt cttcctcaat   1200
accacaggct tctcattcca agactgccat gacagatgcc tggccttcac cgatgtggcc   1260
ccccggggtg tggcttctgg ccagcgccgc agttggctta tcatacagcg ctatgtagaa   1320
ggctactttc tgcaccccac tgggctggag ctcctcgtgg atcatgggag cacagatgct   1380
gggcactggg ccgtggagca ggtgtggtac aacgggaagt tctatgggag cccagaggaa   1440
ctggctcgga agtatgcaga tggagaggtg gacgtggtgg tcctggagga cccgctgcct   1500
gggggcaagg ggcatgacag cacagaggag ccgcccctct tctcctccca caagccccgc   1560
ggggacttcc ccagccccat ccatgtgagc ggcccccgct tggtccagcc ccacggccct   1620
cgcttcaggc tggagggcaa cgctgtgctc tacggcggct ggagctttgc cttccggctg   1680
cgctcctcct ccgggctgca ggtcctgaac gtgcacttcg gcggagagcg cattgcctat   1740
gaggtcagcg tgcaagaggc agtggcgctg tatggaggac acacacctgc aggcatgcag   1800
accaagtacc tcgatgtcgg ctggggcctg ggcagcgtca ctcatgagtt agcccccggc   1860
atcgactgcc cggagaccgc caccttcctg gacactttcc actactatga tgccgatgac   1920
ccggtccatt atccccgagc cctctgcctc tttgaaatgc ccacaggggt gccccttcgg   1980
cggcacttta attccaactt taaaggtggc ttcaacttct atgcggggct gaagggccag   2040
gtgctggtgc tgcggacaac ttcaactgtc tacaattatg attacatttg ggactttatc   2100
ttctacccca acggggtgat ggaggccaag atgcatgcca ctggctacgt ccacgccacc   2160
ttctacaccc ccgaggggct gcgccacggc actcgcctgc acacccacct gattggcaac   2220
atacacactc acttggtgca ctaccgcgta gacctggatg tggcaggcac caagaacagc   2280
ttccagacac tgcagatgaa gctagaaaac atcaccaacc cctggagccc aagacaccgc   2340
gtggtccagc caactctgga gcagacgcag tactcctggg agcgccaggc ggccttccgc   2400
ttcaaaagga agctgcccaa gtacctgctc tttaccagcc cccaggagaa cccctggggc   2460
cacaagcgca gctaccgcct gcagatccac tccatggccg accaggtgct gcccccaggc   2520
tggcaggagg agcaggccat cacctgggca aggtaccccc tggcagtgac caagtaccgg   2580
gagtcggagc tgtgcagcag cagcatctac caccagaacg acccctggca cccgcccgtg   2640
gtctttgagc agtttcttca caacaacgag aacattgaaa atgaggacct ggtggcctgg   2700
gtgacggtgg gcttcctgca catcccccac tcagaggaca ttcccaacac agccacacct   2760
```

gggaactccg tgggcttcct gctccggcca ttcaacttct tcccagagga cccctccctg 2820
gcatccagag acactgtgat cgtgtggcct cgggacaacg gccccaacta cgtccagcgc 2880
tggatccctg aggacaggga ctgctcgatg cctccccctt ttagctacaa tgggacctat 2940
agacctgtgt ga 2952

<210> SEQ ID NO 80
<211> LENGTH: 2952
<212> TYPE: DNA
<213> ORGANISM: Artificial Sequence
<220> FEATURE:
<223> OTHER INFORMATION: Fc-hDAO-Hepmut1-Cysmut

<400> SEQUENCE: 80
atgccggccc tgggctgggc cgtggctgcc atcctgatgc tgcagacggc catggcggag 60
tgccccccct gccccgcccc ccccgtggcc ggcccctccg tgttcctgtt ccccccccaag 120 cccaaggaca ccctgatgat ctccaggacc cccgaggtga cctgcgtggt ggtggacgtg 180
tcccacgagg accccgaggt gaagttcaac tggtacgtgg acggcgtgga ggtgcacaac 240
gccaagacca agcccaggga ggagcagtac aactccacct acagggtggt gtccgtgctg 300
accgtgctgc accaggactg gctgaacggc aaggagtaca agtgcaaggt gtccaacaag 360
ggcctgccct cctccatcga gaagaccatc tccaaggcca agggccagcc cagggagccc 420
caggtgtaca ccctgccccc ctccagggag gagatgacca agaaccaggt gtccctgacc 480
tgcctggtga agggcttcta cccctccgac atcgccgtgg agtgggagtc caacggccag 540
cccgagaaca actacaagac caccccccc gtgctggact ccgacggctc cttcttcctg 600
tactccaagc tgaccgtgga caagtccagg tggcagcagg gcaacgtgtt ctcctgctcc 660
gtgatgcacg aggccctgca caaccactac acccagaagt ccctgtccct gtcccccggc 720
aaggagccca agtccgccga caagacccac accgagccct ccccggggac tctgcccagg 780
aaggcagggg tgttttcaga cctaagcaac caagagctga aggcagtgca cagcttcctc 840
tggtccaaga aggagctgag gctgcagccc tccagtacca ccaccatggc caagaacacc 900
gtgtttctca tcgagatgct gctgcccaag aagtaccatg tgctgaggtt tctggataaa 960
ggtgaaaggc atcctgtgcg ggaagcccgt gccgtcatct tctttggtga ccaggagcat 1020
cccaatgtca ccgagtttgc tgtggggccc ctgccaggcc ccgcctacat gcgagcactg 1080
tcccccaggc ctgggtacca gtcctcctgg gcatcgaggc ccatctccac agcagagtat 1140
gccctcctct accacaccct gcaggaagcc accaagcccc tgcatcagtt cttcctcaat 1200
accacaggct tctcattcca agactgccat gacagatgcc tggccttcac cgatgtggcc 1260
ccccggggtg tggcttctgg ccagcgccgc agttggctta tcatacagcg ctatgtagaa 1320
ggctactttc tgcaccccac tgggctggag ctcctcgtgg atcatgggag cacagatgct 1380
gggcactggg ccgtggagca ggtgtggtac aacgggaagt tctatgggag cccagaggaa 1440
ctggctcgga agtatgcaga tggagaggtg gacgtggtgg tcctggagga cccgctgcct 1500
gggggcaagg ggcatgacag cacagaggag ccgcccctct tctcctccca caagccccgc 1560
ggggacttcc ccagccccat ccatgtgagc ggcccccgct tggtccagcc ccacggccct 1620
cgcttcaggc tggagggcaa cgctgtgctc tacggcggct ggagctttgc cttccggctg 1680
cgctcctcct ccgggctgca ggtcctgaac gtgcacttcg gcggagagcg cattgcctat 1740
gaggtcagcg tgcaagaggc agtggcgctg tatggaggac acacacctgc aggcatgcag 1800
accaagtacc tcgatgtcgg ctggggcctg ggcagcgtca ctcatgagtt agccccggc 1860 atcgactgcc cggagaccgc caccttcctg gacactttcc actactatga tgccgatgac 1920
ccggtccatt atccccgagc cctctgcctc tttgaaatgc ccacaggggt gccccttcgg 1980
cggcacttta attccaactt taaaggtggc ttcaacttct atgcggggct gaagggccag 2040
gtgctggtgc tgcggacaac ttcaactgtc tacaattatg attacatttg ggactttatc 2100
ttctacccca acggggtgat ggaggccaag atgcatgcca ctggctacgt ccacgccacc 2160
ttctacaccc ccgaggggct gcgccacggc actcgcctgc acacccacct gattggcaac 2220
atacacactc acttggtgca ctaccgcgta gacctggatg tggcaggcac caagaacagc 2280
ttccagacac tgcagatgaa gctagaaaac atcaccaacc cctggagccc aagacaccgc 2340
gtggtccagc caactctgga gcagacgcag tactcctggg agcgccaggc ggccttcagc 2400
ttcaaaagga agctgcccaa gtacctgctc tttaccagcc cccaggagaa cccctggggc 2460
cacaagcgca gctaccgcct gcagatccac tccatggccg accaggtgct gcccccaggc 2520
tggcaggagg agcaggccat cacctgggca aggtaccccc tggcagtgac caagtaccgg 2580
gagtcggagc tgtgcagcag cagcatctac caccagaacg acccctggca cccgcccgtg 2640
gtctttgagc agtttcttca caacaacgag aacattgaaa atgaggacct ggtggcctgg 2700
gtgacggtgg gcttcctgca catcccccac tcagaggaca ttcccaacac agccacacct 2760
gggaactccg tgggcttcct gctccggcca ttcaacttct tcccagagga cccctccctg 2820
gcatccagag acactgtgat cgtgtggcct cgggacaacg gccccaacta cgtccagcgc 2880
tggatccctg aggacaggga ctgctcgatg cctcccccctt ttagctacaa tgggacctat 2940
agacctgtgt ga 2952

<210> SEQ ID NO 81
<211> LENGTH: 2952
<212> TYPE: DNA
<213> ORGANISM: Artificial Sequence
<220> FEATURE:
<223> OTHER INFORMATION: Fc-hDAO-Hepmut2-Cysmut

<400> SEQUENCE: 81
atgccggccc tgggctgggc cgtggctgcc atcctgatgc tgcagacggc catggcggag 60
tgccccccct gccccgcccc ccccgtggcc ggcccctccg tgttcctgtt cccccccaag 120
cccaaggaca ccctgatgat ctccaggacc cccgaggtga cctgcgtggt ggtggacgtg 180
tcccacgagg accccgaggt gaagttcaac tggtacgtgg acggcgtgga ggtgcacaac 240
gccaagacca agcccaggga ggagcagtac aactccacct acagggtggt gtccgtgctg 300
accgtgctgc accaggactg gctgaacggc aaggagtaca agtgcaaggt gtccaacaag 360
ggcctgccct cctccatcga gaagaccatc tccaaggcca agggccagcc cagggagccc 420
caggtgtaca ccctgccccc ctccagggag gagatgacca agaaccaggt gtccctgacc 480
tgcctggtga agggcttcta cccctccgac atcgccgtgg agtgggagtc caacggccag 540
cccgagaaca actacaagac caccccccc gtgctggact ccgacggctc cttcttcctg 600
tactccaagc tgaccgtgga caagtccagg tggcagcagg gcaacgtgtt ctcctgctcc 660
gtgatgcacg aggccctgca caaccactac acccagaagt ccctgtccct gtcccccggc 720
aaggagccca agtccgccga caagacccac accgagccct ccccggggac tctgcccagg 780
aaggcagggg tgttttcaga cctaagcaac caagagctga aggcagtgca cagcttcctc 840
tggtccaaga aggagctgag gctgcagccc tccagtacca ccaccatggc caagaacacc 900

```
gtgtttctca tcgagatgct gctgcccaag aagtaccatg tgctgaggtt tctggataaa    960
ggtgaaaggc atcctgtgcg ggaagcccgt gccgtcatct tctttggtga ccaggagcat   1020
cccaatgtca ccgagtttgc tgtggggccc ctgccaggcc ccgcctacat gcgagcactg   1080
tcccccaggc ctgggtacca gtcctcctgg gcatcgaggc ccatctccac agcagagtat   1140
gccctcctct accacacct gcaggaagcc accaagcccc tgcatcagtt cttcctcaat    1200
accacaggct tctcattcca agactgccat gacagatgcc tggccttcac cgatgtggcc   1260
ccccggggtg tggcttctgg ccagcgccgc agttggctta tcatacagcg ctatgtagaa   1320
ggctactttc tgcaccccac tgggctggag ctcctcgtgg atcatgggag cacagatgct   1380
gggcactggg ccgtggagca ggtgtggtac aacgggaagt tctatgggag cccagaggaa   1440
ctggctcgga agtatgcaga tggagaggtg gacgtggtgg tcctggagga cccgctgcct   1500
gggggcaagg ggcatgacag cacagaggag ccgcccctct tctcctccca caagccccgc   1560
ggggacttcc ccagccccat ccatgtgagc ggcccccgct tggtccagcc ccacggccct   1620
cgcttcaggc tggagggcaa cgctgtgctc tacggcggct ggagctttgc cttccggctg   1680
cgctcctcct ccgggctgca ggtcctgaac gtgcacttcg gcggagagcg cattgcctat   1740
gaggtcagcg tgcaagaggc agtggcgctg tatggaggac acacacctgc aggcatgcag   1800
accaagtacc tcgatgtcgg ctggggcctg ggcagcgtca ctcatgagtt agcccccggc   1860
atcgactgcc cggagaccgc caccttcctg gacactttcc actactatga tgccgatgac   1920
ccggtccatt atccccgagc cctctgcctc tttgaaatgc ccacaggggt gccccttcgg   1980
cggcacttta attccaactt taaaggtggc ttcaacttct atgcggggct gaagggccag   2040
gtgctggtgc tgcggacaac ttcaactgtc tacaattatg attacatttg ggactttatc   2100
ttctacccca acggggtgat ggaggccaag atgcatgcca ctggctacgt ccacgccacc   2160
ttctacaccc ccgaggggct gcgccacggc actcgcctgc acacccacct gattggcaac   2220
atacacactc acttggtgca ctaccgcgta gacctggatg tggcaggcac caagaacagc   2280
ttccagacac tgcagatgaa gctagaaaac atcaccaacc cctggagccc aagacaccgc   2340
gtggtccagc caactctgga gcagacgcag tactcctggg agcgccaggc ggccttccgc   2400
ttcaaaagga agctgcccac gtacctgctc tttaccagcc cccaggagaa cccctggggc   2460
cacaagcgca gctaccgcct gcagatccac tccatggccg accaggtgct gcccccaggc   2520
tggcaggagg agcaggccat cacctgggca aggtaccccc tggcagtgac caagtaccgg   2580
gagtcggagc tgtgcagcag cagcatctac caccagaacg accccctggca cccgcccgtg   2640
gtctttgagc agtttcttca caacaacgag aacattgaaa atgaggacct ggtggcctgg   2700
gtgacggtgg gcttcctgca catcccccac tcagaggaca ttcccaacac agccacacct   2760
gggaactccg tgggcttcct gctccggcca ttcaacttct tcccagagga cccctccctg   2820
gcatccagag acactgtgat cgtgtggcct cgggacaacg gccccaacta cgtccagcgc   2880
tggatccctg aggacaggga ctgctcgatg cctcccccctt ttagctacaa tgggacctat   2940
agacctgtgt ga                                                       2952
```

<210> SEQ ID NO 82
<211> LENGTH: 2952
<212> TYPE: DNA
<213> ORGANISM: Artificial Sequence
<220> FEATURE:
<223> OTHER INFORMATION: Fc-hDAO-Hepmut3-Cysmut

<400> SEQUENCE: 82

```
atgccggccc tgggctgggc cgtggctgcc atcctgatgc tgcagacggc catggcggag      60
tgcccccccct gccccgcccc ccccgtggcc ggcccctccg tgttcctgtt ccccccccaag    120
cccaaggaca ccctgatgat ctccaggacc cccgaggtga cctgcgtggt ggtggacgtg    180
tcccacgagg accccgaggt gaagttcaac tggtacgtgg acggcgtgga ggtgcacaac    240
gccaagacca agcccaggga ggagcagtac aactccacct acagggtggt gtccgtgctg    300
accgtgctgc accaggactg gctgaacggc aaggagtaca agtgcaaggt gtccaacaag    360
ggcctgccct cctccatcga gaagaccatc tccaaggcca agggccagcc cagggagccc    420
caggtgtaca ccctgccccc ctccagggag gagatgacca agaaccaggt gtccctgacc    480
tgcctggtga agggcttcta cccctccgac atcgccgtgg agtgggagtc caacggccag    540
cccgagaaca actacaagac cacccccccc gtgctggact ccgacggctc cttcttcctg    600
tactccaagc tgaccgtgga caagtccagg tggcagcagg gcaacgtgtt ctcctgctcc    660
gtgatgcacg aggccctgca caaccactac acccagaagt ccctgtccct gtcccccggc    720
aaggagccca agtccgccga caagacccac accgagccct ccccggggac tctgcccagg    780
aaggcagggg tgttttcaga cctaagcaac caagagctga aggcagtgca cagcttcctc    840
tggtccaaga aggagctgag gctgcagccc tccagtacca ccaccatggc caagaacacc    900
gtgtttctca tcgagatgct gctgcccaag aagtaccatg tgctgaggtt tctggataaa    960
ggtgaaaggc atcctgtgcg ggaagcccgt gccgtcatct tctttggtga ccaggagcat   1020
cccaatgtca ccgagtttgc tgtggggccc ctgccaggcc ccgcctacat gcgagcactg   1080
tcccccaggc ctgggtacca gtcctcctgg gcatcgaggc ccatctccac agcagagtat   1140
gccctcctct accacaccct gcaggaagcc accaagcccc tgcatcagtt cttcctcaat   1200
accacaggct tctcattcca agactgccat gacagatgcc tggccttcac cgatgtggcc   1260
ccccggggtg tggcttctgg ccagcgccgc agttggctta tcatacagcg ctatgtagaa   1320
ggctactttc tgcaccccac tgggctggag ctcctcgtgg atcatgggag cacagatgct   1380
gggcactggg ccgtggagca ggtgtggtac aacgggaagt tctatgggag cccagaggaa   1440
ctggctcgga agtatgcaga tggagaggtg gacgtggtgg tcctggagga cccgctgcct   1500
gggggcaagg ggcatgacag cacagaggag ccgcccctct tctcctccca caagccccgc   1560
ggggacttcc ccagccccat ccatgtgagc ggcccccgct tggtccagcc ccacggccct   1620
cgcttcaggc tggagggcaa cgctgtgctc tacggcggct ggagctttgc cttccggctg   1680
cgctcctcct ccgggctgca ggtcctgaac gtgcacttcg gcggagagcg cattgcctat   1740
gaggtcagcg tgcaagaggc agtggcgctg tatggaggac acacacctgc aggcatgcag   1800
accaagtacc tcgatgtcgg ctggggcctg ggcagcgtca ctcatgagtt agcccccggc   1860
atcgactgcc cggagaccgc caccttcctg gacactttcc actactatga tgccgatgac   1920
ccggtccatt atccccgagc cctctgcctc tttgaaatgc ccacaggggt gccccttcgg   1980
cggcacttta attccaactt taaaggtggc ttcaacttct atgcggggct gaagggccag   2040
gtgctggtgc tgcggacaac ttcaactgtc tacaattatg attacatttg ggactttatc   2100
ttctacccca acggggtgat ggaggccaag atgcatgcca ctggctacgt ccacgccacc   2160
ttctacaccc ccgagggggct gcgccacggc actcgcctgc acacccacct gattggcaac   2220
atacacactc acttggtgca ctaccgcgta gacctggatg tggcaggcac caagaacagc   2280
ttccagacac tgcagatgaa gctagaaaac atcaccaacc cctggagccc aagacaccgc   2340
```

gtggtccagc caactctgga gcagacgcag tactcctggg agcgccaggc ggccttccgc 2400
ttcaaaacga agctgcccaa gtacctgctc tttaccagcc cccaggagaa cccctggggc 2460
cacaagcgca gctaccgcct gcagatccac tccatggccg accaggtgct gcccccaggc 2520
tggcaggagg agcaggccat cacctgggca aggtaccccc tggcagtgac caagtaccgg 2580
gagtcggagc tgtgcagcag cagcatctac caccagaacg acccctggca cccgcccgtg 2640
gtctttgagc agtttcttca caacaacgag aacattgaaa atgaggacct ggtggcctgg 2700
gtgacggtgg gcttcctgca catcccccac tcagaggaca ttcccaacac agccacacct 2760
gggaactccg tgggcttcct gctccggcca ttcaacttct tcccagagga cccctccctg 2820
gcatccagag acactgtgat cgtgtggcct cgggacaacg gccccaacta cgtccagcgc 2880
tggatccctg aggacaggga ctgctcgatg cctcccccctt ttagctacaa tgggacctat 2940
agacctgtgt ga 2952

<210> SEQ ID NO 83
<211> LENGTH: 2952
<212> TYPE: DNA
<213> ORGANISM: Artificial Sequence
<220> FEATURE:
<223> OTHER INFORMATION: Fc-hDAO-Hepmut4-Cysmut

<400> SEQUENCE: 83
atgccggccc tgggctgggc cgtggctgcc atcctgatgc tgcagacggc catggcggag 60 tgcccccccct gccccgcccc ccccgtggcc ggcccctccg tgttcctgtt cccccccaag 120
cccaaggaca ccctgatgat ctccaggacc cccgaggtga cctgcgtggt ggtggacgtg 180
tcccacgagg accccgaggt gaagttcaac tggtacgtgg acggcgtgga ggtgcacaac 240
gccaagacca agcccaggga ggagcagtac aactccacct acagggtggt gtccgtgctg 300
accgtgctgc accaggactg gctgaacggc aaggagtaca agtgcaaggt gtccaacaag 360
ggcctgccct cctccatcga gaagaccatc tccaaggcca agggccagcc cagggagccc 420
caggtgtaca ccctgccccc ctccagggag gagatgacca agaaccaggt gtccctgacc 480
tgcctggtga agggcttcta cccctccgac atcgccgtgg agtgggagtc caacggccag 540
cccgagaaca actacaagac cacccccccc gtgctggact ccgacggctc cttcttcctg 600
tactccaagc tgaccgtgga caagtccagg tggcagcagg gcaacgtgtt ctcctgctcc 660
gtgatgcacg aggccctgca caaccactac acccagaagt ccctgtccct gtcccccggc 720
aaggagccca agtccgccga caagacccac accgagccct ccccggggac tctgcccagg 780
aaggcagggg tgttttcaga cctaagcaac caagagctga aggcagtgca cagcttcctc 840
tggtccaaga aggagctgag gctgcagccc tccagtacca ccaccatggc caagaacacc 900
gtgtttctca tcgagatgct gctgcccaag aagtaccatg tgctgaggtt tctggataaa 960
ggtgaaaggc atcctgtgcg ggaagcccgt gccgtcatct tctttggtga ccaggagcat 1020
cccaatgtca ccgagtttgc tgtggggccc ctgccaggcc ccgcctacat gcgagcactg 1080
tcccccaggc ctgggtacca gtcctcctgg gcatcgaggc ccatctccac agcagagtat 1140
gccctcctct accacaccct gcaggaagcc accaagcccc tgcatcagtt cttcctcaat 1200
accacaggct tctcattcca agactgccat gacagatgcc tggccttcac cgatgtggcc 1260
ccccggggtg tggcttctgg ccagcgccgc agttggctta tcatacagcg ctatgtagaa 1320
ggctactttc tgcaccccac tgggctggag ctcctcgtgg atcatgggag cacagatgct 1380
gggcactggg ccgtggagca ggtgtggtac aacgggaagt tctatgggag cccagaggaa 1440
ctggctcgga agtatgcaga tggagaggtg gacgtggtgg tcctggagga cccgctgcct 1500
gggggcaagg ggcatgacag cacagaggag ccgcccctct tctcctccca caagccccgc 1560
ggggacttcc ccagccccat ccatgtgagc ggcccccgct tggtccagcc ccacggccct 1620
cgcttcaggc tggagggcaa cgctgtgctc tacggcggct ggagctttgc cttccggctg 1680
cgctcctcct ccgggctgca ggtcctgaac gtgcacttcg gcggagagcg cattgcctat 1740
gaggtcagcg tgcaagaggc agtggcgctg tatggaggac acacacctgc aggcatgcag 1800
accaagtacc tcgatgtcgg ctggggcctg ggcagcgtca ctcatgagtt agccccccggc 1860
atcgactgcc cggagaccgc caccttcctg gacactttcc actactatga tgccgatgac 1920
ccggtccatt atccccgagc cctctgcctc tttgaaatgc ccacaggggt gccccttcgg 1980
cggcacttta attccaactt taaaggtggc ttcaacttct atgcggggct gaagggccag 2040
gtgctggtgc tgcggacaac ttcaactgtc tacaattatg attacatttg ggactttatc 2100
ttctacccca acggggtgat ggaggccaag atgcatgcca ctggctacgt ccacgccacc 2160
ttctacaccc ccgaggggct gcgccacggc actcgcctgc acacccacct gattggcaac 2220
atacacactc acttggtgca ctaccgcgta gacctggatg tggcaggcac caagaacagc 2280
ttccagacac tgcagatgaa gctagaaaac atcaccaacc cctggagccc aagacaccgc 2340
gtggtccagc caactctgga gcagacgcag tactcctggg agcgccaggc ggccttcagc 2400
ttcaaaacga agctgcccaa gtacctgctc tttaccagcc cccaggagaa cccctggggc 2460
cacaagcgca gctaccgcct gcagatccac tccatggccg accaggtgct gcccccaggc 2520
tggcaggagg agcaggccat cacctgggca aggtaccccc tggcagtgac caagtaccgg 2580
gagtcggagc tgtgcagcag cagcatctac caccagaacg acccctggca cccgcccgtg 2640
gtctttgagc agtttcttca caacaacgag aacattgaaa atgaggacct ggtggcctgg 2700
gtgacggtgg gcttcctgca catcccccac tcagaggaca ttcccaacac agccacacct 2760
gggaactccg tgggcttcct gctccggcca ttcaacttct tcccagagga cccctccctg 2820
gcatccagag acactgtgat cgtgtggcct cgggacaacg gccccaacta cgtccagcgc 2880
tggatccctg aggacaggga ctgctcgatg cctcccccctt ttagctacaa tgggacctat 2940
agacctgtgt ga 2952

<210> SEQ ID NO 84
<211> LENGTH: 2952
<212> TYPE: DNA
<213> ORGANISM: Artificial Sequence
<220> FEATURE:
<223> OTHER INFORMATION: Fc-hDAO-Hepmut5-Cysmut

<400> SEQUENCE: 84
atgccggccc tgggctgggc cgtggctgcc atcctgatgc tgcagacggc catggcggag 60
tgcccccccct gccccgcccc ccccgtggcc ggcccctccg tgttcctgtt cccccccaag 120
cccaaggaca ccctgatgat ctccaggacc cccgaggtga cctgcgtggt ggtggacgtg 180
tcccacgagg accccgaggt gaagttcaac tggtacgtgg acggcgtgga ggtgcacaac 240
gccaagacca agcccaggga ggagcagtac aactccacct acagggtggt gtccgtgctg 300
accgtgctgc accaggactg gctgaacggc aaggagtaca agtgcaaggt gtccaacaag 360
ggcctgccct cctccatcga gaagaccatc tccaaggcca agggccagcc cagggagccc 420
caggtgtaca ccctgccccc ctccagggag gagatgacca agaaccaggt gtccctgacc 480

```
tgcctggtga agggcttcta cccctccgac atcgccgtgg agtgggagtc caacggccag    540
cccgagaaca actacaagac cacccccccc gtgctggact ccgacggctc cttcttcctg    600
tactccaagc tgaccgtgga caagtccagg tggcagcagg gcaacgtgtt ctcctgctcc    660
gtgatgcacg aggccctgca caaccactac acccagaagt ccctgtccct gtcccccggc    720
aaggagccca agtccgccga caagacccac accgagccct ccccggggac tctgcccagg    780
aaggcagggg tgttttcaga cctaagcaac caagagctga aggcagtgca cagcttcctc    840
tggtccaaga aggagctgag gctgcagccc tccagtacca ccaccatggc caagaacacc    900
gtgtttctca tcgagatgct gctgcccaag aagtaccatg tgctgaggtt tctggataaa    960
ggtgaaaggc atcctgtgcg ggaagcccgt gccgtcatct tctttggtga ccaggagcat   1020
cccaatgtca ccgagtttgc tgtggggccc ctgccaggcc ccgcctacat gcgagcactg   1080
tcccccaggc ctgggtacca gtcctcctgg gcatcgaggc ccatctccac agcagagtat   1140
gccctcctct accacaccct gcaggaagcc accaagcccc tgcatcagtt cttcctcaat   1200
accacaggct tctcattcca agactgccat gacagatgcc tggccttcac cgatgtggcc   1260
ccccggggtg tggcttctgg ccagcgccgc agttggctta tcatacagcg ctatgtagaa   1320
ggctactttc tgcaccccac tgggctggag ctcctcgtgg atcatgggag cacagatgct   1380
gggcactggg ccgtggagca ggtgtggtac aacgggaagt tctatgggag cccagaggaa   1440
ctggctcgga agtatgcaga tggagaggtg gacgtggtgg tcctggagga cccgctgcct   1500
gggggcaagg ggcatgacag cacagaggag ccgcccctct tctcctccca caagccccgc   1560
ggggacttcc ccagccccat ccatgtgagc ggcccccgct tggtccagcc ccacggccct   1620
cgcttcaggc tggagggcaa cgctgtgctc tacggcggct ggagctttgc cttccggctg   1680
cgctcctcct ccgggctgca ggtcctgaac gtgcacttcg gcggagagcg cattgcctat   1740
gaggtcagcg tgcaagaggc agtggcgctg tatggaggac acacacctgc aggcatgcag   1800
accaagtacc tcgatgtcgg ctggggcctg ggcagcgtca ctcatgagtt agcccccggc   1860
atcgactgcc cggagaccgc caccttcctg gacactttcc actactatga tgccgatgac   1920
ccggtccatt atccccgagc cctctgcctc tttgaaatgc ccacaggggt gccccttcgg   1980
cggcacttta attccaactt taaaggtggc ttcaacttct atgcggggct gaagggccag   2040
gtgctggtgc tgcggacaac ttcaactgtc tacaattatg attacatttg ggactttatc   2100
ttctacccca acggggtgat ggaggccaag atgcatgcca ctggctacgt ccacgccacc   2160
ttctacaccc ccgaggggct gcgccacggc actcgcctgc acacccacct gattggcaac   2220
atacacactc acttggtgca ctaccgcgta gacctggatg tggcaggcac caagaacagc   2280
ttccagacac tgcagatgaa gctagaaaac atcaccaacc cctggagccc aagacaccgc   2340
gtggtccagc caactctgga gcagacgcag tactcctggg agcgccaggc ggccttccgc   2400
ttcaaaacga agctgcccac gtacctgctc tttaccagcc cccaggagaa cccctggggc   2460
cacaagcgca gctaccgcct gcagatccac tccatggccg accaggtgct gcccccaggc   2520
tggcaggagg agcaggccat cacctgggca aggtaccccc tggcagtgac caagtaccgg   2580
gagtcggagc tgtgcagcag cagcatctac caccagaacg acccctggca cccgcccgtg   2640
gtctttgagc agtttcttca caacaacgag aacattgaaa atgaggacct ggtggcctgg   2700
gtgacggtgg gcttcctgca catcccccac tcagaggaca ttcccaacac agccacacct   2760
gggaactccg tgggcttcct gctccggcca ttcaacttct tcccagagga cccctccctg   2820
```

gcatccagag acactgtgat cgtgtggcct cgggacaacg gccccaacta cgtccagcgc 2880
tggatccctg aggacaggga ctgctcgatg cctccccctt ttagctacaa tgggacctat 2940
agacctgtgt ga 2952

<210> SEQ ID NO 85
<211> LENGTH: 2952
<212> TYPE: DNA
<213> ORGANISM: Artificial Sequence
<220> FEATURE:
<223> OTHER INFORMATION: Fc-hDAO-Hepmut6-Cysmut

<400> SEQUENCE: 85
atgccggccc tgggctgggc cgtggctgcc atcctgatgc tgcagacggc catggcggag 60
tgccccccct gccccgcccc ccccgtggcc ggcccctccg tgttcctgtt cccccccaag 120
cccaaggaca ccctgatgat ctccaggacc cccgaggtga cctgcgtggt ggtggacgtg 180
tcccacgagg accccgaggt gaagttcaac tggtacgtgg acggcgtgga ggtgcacaac 240
gccaagacca agcccaggga ggagcagtac aactccacct acagggtggt gtccgtgctg 300
accgtgctgc accaggactg gctgaacggc aaggagtaca agtgcaaggt gtccaacaag 360
ggcctgccct cctccatcga gaagaccatc tccaaggcca agggccagcc cagggagccc 420
caggtgtaca ccctgccccc ctccagggag gagatgacca agaaccaggt gtccctgacc 480
tgcctggtga agggcttcta cccctccgac atcgccgtgg agtgggagtc caacggccag 540
cccgagaaca actacaagac caccccccccc gtgctggact ccgacggctc cttcttcctg 600
tactccaagc tgaccgtgga caagtccagg tggcagcagg gcaacgtgtt ctcctgctcc 660
gtgatgcacg aggccctgca caaccactac acccagaagt ccctgtccct gtcccccggc 720
aaggagccca agtccgccga caagacccac accgagccct ccccggggac tctgcccagg 780
aaggcagggg tgttttcaga cctaagcaac caagagctga aggcagtgca cagcttcctc 840
tggtccaaga aggagctgag gctgcagccc tccagtacca ccaccatggc caagaacacc 900
gtgtttctca tcgagatgct gctgcccaag aagtaccatg tgctgaggtt tctggataaa 960
ggtgaaaggc atcctgtgcg ggaagcccgt gccgtcatct tctttggtga ccaggagcat 1020
cccaatgtca ccgagtttgc tgtggggccc ctgccaggcc ccgcctacat gcgagcactg 1080
tcccccaggc ctgggtacca gtcctcctgg gcatcgaggc ccatctccac agcagagtat 1140
gccctcctct accacaccct gcaggaagcc accaagcccc tgcatcagtt cttcctcaat 1200
accacaggct tctcattcca agactgccat gacagatgcc tggccttcac cgatgtggcc 1260
ccccggggtg tggcttctgg ccagcgccgc agttggctta tcatacagcg ctatgtagaa 1320
ggctactttc tgcaccccac tgggctggag ctcctcgtgg atcatgggag cacagatgct 1380
gggcactggg ccgtggagca ggtgtggtac aacgggaagt tctatgggag cccagaggaa 1440
ctggctcgga agtatgcaga tggagaggtg gacgtggtgg tcctggagga cccgctgcct 1500
gggggcaagg ggcatgacag cacagaggag ccgcccctct tctcctccca caagccccgc 1560
ggggacttcc ccagccccat ccatgtgagc ggcccccgct tggtccagcc ccacggccct 1620
cgcttcaggc tggagggcaa cgctgtgctc tacggcggct ggagctttgc cttccggctg 1680
cgctcctcct ccgggctgca ggtcctgaac gtgcacttcg gcggagagcg cattgcctat 1740
gaggtcagcg tgcaagaggc agtggcgctg tatggaggac acacacctgc aggcatgcag 1800
accaagtacc tcgatgtcgg ctggggcctg ggcagcgtca ctcatgagtt agcccccggc 1860
atcgactgcc cggagaccgc caccttcctg gacactttcc actactatga tgccgatgac 1920
ccggtccatt atccccgagc cctctgcctc tttgaaatgc ccacaggggt gccccttcgg 1980
cggcacttta attccaactt taaaggtggc ttcaacttct atgcggggct gaagggccag 2040
gtgctggtgc tgcggacaac ttcaactgtc tacaattatg attacatttg ggactttatc 2100
ttctacccca acggggtgat ggaggccaag atgcatgcca ctggctacgt ccacgccacc 2160
ttctacaccc ccgaggggct gcgccacggc actcgcctgc acacccacct gattggcaac 2220
atacacactc acttggtgca ctaccgcgta gacctggatg tggcaggcac caagaacagc 2280
ttccagacac tgcagatgaa gctagaaaac atcaccaacc cctggagccc aagacaccgc 2340
gtggtccagc caactctgga gcagacgcag tactcctggg agcgccaggc ggccttccgc 2400
ttcggacaga cgctgcccaa gtacctgctc tttaccagcc cccaggagaa cccctggggc 2460
cacaagcgca gctaccgcct gcagatccac tccatggccg accaggtgct gccccccaggc 2520 tggcaggagg agcaggccat cacctgggca aggtaccccc tggcagtgac caagtaccgg 2580
gagtcggagc tgtgcagcag cagcatctac caccagaacg acccctggca cccgcccgtg 2640
gtctttgagc agtttcttca caacaacgag aacattgaaa atgaggacct ggtggcctgg 2700
gtgacggtgg gcttcctgca catcccccac tcagaggaca ttcccaacac agccacacct 2760
gggaactccg tgggcttcct gctccggcca ttcaacttct tcccagagga cccctccctg 2820
gcatccagag acactgtgat cgtgtggcct cgggacaacg gccccaacta cgtccagcgc 2880
tggatccctg aggacaggga ctgctcgatg cctcccccctt ttagctacaa tgggacctat 2940
agacctgtgt ga 2952

<210> SEQ ID NO 86
<211> LENGTH: 2952
<212> TYPE: DNA
<213> ORGANISM: Artificial Sequence
<220> FEATURE:
<223> OTHER INFORMATION: Fc-hDAO-Hepmut7-Cysmut

<400> SEQUENCE: 86
atgccggccc tgggctgggc cgtggctgcc atcctgatgc tgcagacggc catggcggag 60
tgccccccct gccccgcccc ccccgtggcc ggcccctccg tgttcctgtt ccccccccaag 120 cccaaggaca ccctgatgat ctccaggacc cccgaggtga cctgcgtggt ggtggacgtg 180
tcccacgagg accccgaggt gaagttcaac tggtacgtgg acggcgtgga ggtgcacaac 240
gccaagacca agcccaggga ggagcagtac aactccacct acagggtggt gtccgtgctg 300
accgtgctgc accaggactg gctgaacggc aaggagtaca agtgcaaggt gtccaacaag 360
ggcctgccct cctccatcga gaagaccatc tccaaggcca agggccagcc cagggagccc 420
caggtgtaca ccctgccccc ctccagggag gagatgacca agaaccaggt gtccctgacc 480
tgcctggtga agggcttcta cccctccgac atcgccgtgg agtgggagtc caacggccag 540
cccgagaaca actacaagac cacccccccc gtgctggact ccgacggctc cttcttcctg 600
tactccaagc tgaccgtgga caagtccagg tggcagcagg gcaacgtgtt ctcctgctcc 660
gtgatgcacg aggccctgca caaccactac acccagaagt ccctgtccct gtcccccggc 720
aaggagccca agtccgccga caagacccac accgagccct ccccggggac tctgcccagg 780
aaggcagggg tgttttcaga cctaagcaac caagagctga aggcagtgca cagcttcctc 840
tggtccaaga aggagctgag gctgcagccc tccagtacca ccaccatggc caagaacacc 900
gtgtttctca tcgagatgct gctgcccaag aagtaccatg tgctgaggtt tctggataaa 960

```
ggtgaaaggc atcctgtgcg ggaagcccgt gccgtcatct tctttggtga ccaggagcat   1020
cccaatgtca ccgagtttgc tgtggggccc ctgccaggcc ccgcctacat gcgagcactg   1080
tcccccaggc ctgggtacca gtcctcctgg gcatcgaggc ccatctccac agcagagtat   1140
gccctcctct accacaccct gcaggaagcc accaagcccc tgcatcagtt cttcctcaat   1200
accacaggct tctcattcca agactgccat gacagatgcc tggccttcac cgatgtggcc   1260
ccccggggtg tggcttctgg ccagcgccgc agttggctta tcatacagcg ctatgtagaa   1320
ggctactttc tgcaccccac tgggctggag ctcctcgtgg atcatgggag cacagatgct   1380
gggcactggg ccgtggagca ggtgtggtac aacgggaagt tctatgggag cccagaggaa   1440
ctggctcgga agtatgcaga tggagaggtg gacgtggtgg tcctggagga cccgctgcct   1500
gggggcaagg ggcatgacag cacagaggag ccgcccctct tctcctccca caagccccgc   1560
ggggacttcc ccagccccat ccatgtgagc ggcccccgct tggtccagcc ccacggccct   1620
cgcttcaggc tggagggcaa cgctgtgctc tacggcggct ggagctttgc cttccggctg   1680
cgctcctcct ccgggctgca ggtcctgaac gtgcacttcg gcggagagcg cattgcctat   1740
gaggtcagcg tgcaagaggc agtggcgctg tatggaggac acacacctgc aggcatgcag   1800
accaagtacc tcgatgtcgg ctggggcctg ggcagcgtca ctcatgagtt agcccccggc   1860
atcgactgcc cggagaccgc caccttcctg gacactttcc actactatga tgccgatgac   1920
ccggtccatt atccccgagc cctctgcctc tttgaaatgc ccacaggggt gccccttcgg   1980
cggcacttta attccaactt taaaggtggc ttcaacttct atgcggggct gaagggccag   2040
gtgctggtgc tgcggacaac ttcaactgtc tacaattatg attacatttg ggactttatc   2100
ttctacccca acggggtgat ggaggccaag atgcatgcca ctggctacgt ccacgccacc   2160
ttctacaccc ccgaggggct gcgccacggc actcgcctgc acacccacct gattggcaac   2220
atacacactc acttggtgca ctaccgcgta gacctggatg tggcaggcac caagaacagc   2280
ttccagacac tgcagatgaa gctagaaaac atcaccaacc cctggagccc aagacaccgc   2340
gtggtccagc caactctgga gcagacgcag tactcctggg agcgccaggc ggccttcagc   2400
ttcaaaagga agctgcccac gtacctgctc tttaccagcc cccaggagaa cccctggggc   2460
cacaagcgca gctaccgcct gcagatccac tccatggccg accaggtgct gcccccaggc   2520
tggcaggagg agcaggccat cacctgggca aggtaccccc tggcagtgac caagtaccgg   2580
gagtcggagc tgtgcagcag cagcatctac caccagaacg acccctggca cccgcccgtg   2640
gtctttgagc agtttcttca caacaacgag aacattgaaa atgaggacct ggtggcctgg   2700
gtgacggtgg gcttcctgca catcccccac tcagaggaca ttcccaacac agccacacct   2760
gggaactccg tgggcttcct gctccggcca ttcaacttct tcccagagga cccctccctg   2820
gcatccagag acactgtgat cgtgtggcct cgggacaacg gccccaacta cgtccagcgc   2880
tggatccctg aggacaggga ctgctcgatg cctcccccct ttagctacaa tgggacctat   2940
agacctgtgt ga                                                       2952
```

<210> SEQ ID NO 87
<211> LENGTH: 2949
<212> TYPE: DNA
<213> ORGANISM: Artificial Sequence
<220> FEATURE:
<223> OTHER INFORMATION: hDAO-Fc

<400> SEQUENCE: 87

```
atgccggccc tgggctgggc cgtggctgcc atcctgatgc tgcagacggc catggcggag     60
```

```
ccctccccgg ggactctgcc caggaaggca ggggtgtttt cagacctaag caaccaagag    120
ctgaaggcag tgcacagctt cctctggtcc aagaaggagc tgaggctgca gccctccagt    180
accaccacca tggccaagaa caccgtgttt ctcatcgaga tgctgctgcc caagaagtac    240
catgtgctga ggtttctgga taaaggtgaa aggcatcctg tgcgggaagc ccgtgccgtc    300
atcttctttg gtgaccagga gcatcccaat gtcaccgagt ttgctgtggg gcccctgcca    360
gggccctgct acatgcgagc actgtccccc aggcctgggt accagtcctc ctgggcatcg    420
aggcccatct ccacagcaga gtatgccctc ctctaccaca ccctgcagga agccaccaag    480
cccctgcatc agttcttcct caataccaca ggcttctcat tccaagactg ccatgacaga    540
tgcctggcct tcaccgatgt ggccccccgg ggtgtggctt ctggccagcg ccgcagttgg    600
cttatcatac agcgctatgt agaaggctac tttctgcacc ccactgggct ggagctcctc    660
gtggatcatg ggagcacaga tgctgggcac tgggccgtgg agcaggtgtg gtacaacggg    720
aagttctatg ggagcccaga ggaactggct cggaagtatg cagatggaga ggtggacgtg    780
gtggtcctgg aggacccgct gcctgggggc aaggggcatg acagcacaga ggagccgccc    840
ctcttctcct cccacaagcc ccgcggggac ttccccagcc ccatccatgt gagcggcccc    900
cgcttggtcc agccccacgg ccctcgcttc aggctggagg gcaacgctgt gctctacggc    960
ggctggagct ttgccttccg gctgcgctcc tcctccgggc tgcaggtcct gaacgtgcac   1020
ttcggcggag agcgcattgc ctatgaggtc agcgtgcaag aggcagtggc gctgtatgga   1080
ggacacacac ctgcaggcat gcagaccaag tacctcgatg tcggctgggg cctgggcagc   1140
gtcactcatg agttagcccc cggcatcgac tgcccggaga ccgccacctt cctggacact   1200
ttccactact atgatgccga tgacccggtc cattatcccc gagccctctg cctctttgaa   1260
atgcccacag gggtgcccct tcggcggcac tttaattcca actttaaagg tggcttcaac   1320
ttctatgcgg ggctgaaggg ccaggtgctg gtgctgcgga caacttcaac tgtctacaat   1380
tatgattaca tttgggactt tatcttctac cccaacgggg tgatggaggc caagatgcat   1440
gccactggct acgtccacgc caccttctac acccccgagg ggctgcgcca cggcactcgc   1500
ctgcacaccc acctgattgg caacatacac actcacttgg tgcactaccg cgtagacctg   1560
gatgtggcag gcaccaagaa cagcttccag acactgcaga tgaagctaga aaacatcacc   1620
aacccctgga gcccaagaca ccgcgtggtc cagccaactc tggagcagac gcagtactcc   1680
tgggagcgcc aggcggcctt ccgcttcaaa aggaagctgc ccaagtacct gctctttacc   1740
agcccccagg agaaccccctg ggccacaag cgcagctacc gcctgcagat ccactccatg   1800
gccgaccagg tgctgccccc aggctggcag gaggagcagg ccatcacctg ggcaaggtac   1860
cccctggcag tgaccaagta ccgggagtcg gagctgtgca gcagcagcat ctaccaccag   1920
aacgacccct ggcacccgcc cgtggtcttt gagcagtttc ttcacaacaa cgagaacatt   1980
gaaaatgagg acctggtggc ctgggtgacg gtgggcttcc tgcacatccc ccactcagag   2040
gacattccca acacagccac acctgggaac tccgtgggct tcctgctccg gccattcaac   2100
ttcttcccag aggacccctc cctggcatcc agagacactg tgatcgtgtg gcctcgggac   2160
aacggcccca actacgtcca gcgctggatc cctgaggaca gggactgctc gatgcctccc   2220
ccttttagct acaatgggac ctatagacct gtggagccca agtccgccga caagacccac   2280
acctgccccc cctgccccgc cccccccgtg gccggcccct ccgtgttcct gttccccccc   2340
aagcccaagg acaccctgat gatctccagg acccccgagg tgacctgcgt ggtggtggac   2400
```

gtgtcccacg aggaccccga ggtgaagttc aactggtacg tggacggcgt ggaggtgcac 2460
aacgccaaga ccaagcccag ggaggagcag tacaactcca cctacagggt ggtgtccgtg 2520
ctgaccgtgc tgcaccagga ctggctgaac ggcaaggagt acaagtgcaa ggtgtccaac 2580
aagggcctgc cctcctccat cgagaagacc atctccaagg ccaagggcca gcccagggag 2640
ccccaggtgt acaccctgcc cccctccagg gaggagatga ccaagaacca ggtgtccctg 2700
acctgcctgg tgaagggctt ctacccctcc gacatcgccg tggagtggga gtccaacggc 2760
cagcccgaga acaactacaa gaccaccccc cccgtgctgg actccgacgg ctccttcttc 2820
ctgtactcca agctgaccgt ggacaagtcc aggtggcagc agggcaacgt gttctcctgc 2880
tccgtgatgc acgaggccct gcacaaccac tacacccaga agtccctgtc cctgtccccc 2940
ggcaagtga 2949

<210> SEQ ID NO 88
<211> LENGTH: 2949
<212> TYPE: DNA
<213> ORGANISM: Artificial Sequence
<220> FEATURE:
<223> OTHER INFORMATION: hDAO-Fc-Hepmut1

<400> SEQUENCE: 88
atgccggccc tgggctgggc cgtggctgcc atcctgatgc tgcagacggc catggcggag 60
ccctccccgg ggactctgcc caggaaggca ggggtgtttt cagacctaag caaccaagag 120
ctgaaggcag tgcacagctt cctctggtcc aagaaggagc tgaggctgca gccctccagt 180
accaccacca tggccaagaa caccgtgttt ctcatcgaga tgctgctgcc caagaagtac 240
catgtgctga ggtttctgga taaaggtgaa aggcatcctg tgcgggaagc ccgtgccgtc 300
atcttctttg gtgaccagga gcatcccaat gtcaccgagt ttgctgtggg gcccctgcca 360
gggccctgct acatgcgagc actgtccccc aggcctgggt accagtcctc ctgggcatcg 420
aggcccatct ccacagcaga gtatgccctc ctctaccaca ccctgcagga agccaccaag 480
cccctgcatc agttcttcct caataccaca ggcttctcat tccaagactg ccatgacaga 540
tgcctggcct tcaccgatgt ggcccccggg ggtgtggctt ctggccagcg ccgcagttgg 600
cttatcatac agcgctatgt agaaggctac tttctgcacc ccactgggct ggagctcctc 660
gtggatcatg ggagcacaga tgctgggcac tgggccgtgg agcaggtgtg gtacaacggg 720
aagttctatg ggagcccaga ggaactggct cggaagtatg cagatggaga ggtggacgtg 780
gtggtcctgg aggacccgct gcctgggggc aaggggcatg acagcacaga ggagccgccc 840
ctcttctcct cccacaagcc ccgcggggac ttccccagcc ccatccatgt gagcggcccc 900
cgcttggtcc agccccacgg ccctcgcttc aggctggagg gcaacgctgt gctctacggc 960
ggctggagct ttgccttccg gctgcgctcc tcctccgggc tgcaggtcct gaacgtgcac 1020
ttcggcggag agcgcattgc ctatgaggtc agcgtgcaag aggcagtggc gctgtatgga 1080
ggacacacac ctgcaggcat gcagaccaag tacctcgatg tcggctgggg cctgggcagc 1140
gtcactcatg agttagcccc cggcatcgac tgcccggaga ccgccacctt cctggacact 1200
ttccactact atgatgccga tgacccggtc cattatcccc gagccctctg cctctttgaa 1260
atgcccacag ggtgccccct tcggcggcac tttaattcca actttaaagg tggcttcaac 1320
ttctatgcgg ggctgaaggg ccaggtgctg gtgctgcgga caacttcaac tgtctacaat 1380
tatgattaca tttgggactt tatcttctac cccaacgggg tgatggaggc caagatgcat 1440
gccactggct acgtccacgc caccttctac acccccgagg ggctgcgcca cggcactcgc 1500

```
ctgcacaccc acctgattgg caacatacac actcacttgg tgcactaccg cgtagacctg   1560

gatgtggcag gcaccaagaa cagcttccag acactgcaga tgaagctaga aaacatcacc   1620

aaccccctgga gcccaagaca ccgcgtggtc cagccaactc tggagcagac gcagtactcc   1680

tgggagcgcc aggcggcctt cagcttcaaa aggaagctgc ccaagtacct gctctttacc   1740

agcccccagg agaacccctg gggccacaag cgcagctacc gcctgcagat ccactccatg   1800

gccgaccagg tgctgccccc aggctggcag gaggagcagg ccatcacctg ggcaaggtac   1860

cccctggcag tgaccaagta ccgggagtcg gagctgtgca gcagcagcat ctaccaccag   1920

aacgacccct ggcacccgcc cgtggtcttt gagcagtttc ttcacaacaa cgagaacatt   1980

gaaaatgagg acctggtggc ctgggtgacg gtgggcttcc tgcacatccc ccactcagag   2040

gacattccca acacagccac acctgggaac tccgtgggct tcctgctccg gccattcaac   2100

ttcttcccag aggacccctc cctggcatcc agagacactg tgatcgtgtg gcctcgggac   2160

aacggcccca actacgtcca gcgctggatc cctgaggaca gggactgctc gatgcctccc   2220

ccttttagct acaatgggac ctatagacct gtggagccca agtccgccga caagacccac   2280

acctgccccc cctgccccgc cccccccgtg gccggcccct ccgtgttcct gttccccccc   2340

aagcccaagg acaccctgat gatctccagg acccccgagg tgacctgcgt ggtggtggac   2400

gtgtcccacg aggaccccga ggtgaagttc aactggtacg tggacggcgt ggaggtgcac   2460

aacgccaaga ccaagcccag ggaggagcag tacaactcca cctacagggt ggtgtccgtg   2520

ctgaccgtgc tgcaccagga ctggctgaac ggcaaggagt acaagtgcaa ggtgtccaac   2580

aagggcctgc cctcctccat cgagaagacc atctccaagg ccaagggcca gcccagggag   2640

ccccaggtgt acaccctgcc cccctccagg gaggagatga ccaagaacca ggtgtccctg   2700

acctgcctgg tgaagggctt ctacccctcc gacatcgccg tggagtggga gtccaacggc   2760

cagcccgaga acaactacaa gaccaccccc cccgtgctgg actccgacgg ctccttcttc   2820

ctgtactcca agctgaccgt ggacaagtcc aggtggcagc agggcaacgt gttctcctgc   2880

tccgtgatgc acgaggccct gcacaaccac tacacccaga agtccctgtc cctgtccccc   2940

ggcaagtga                                                           2949
```

```
<210> SEQ ID NO 89
<211> LENGTH: 2949
<212> TYPE: DNA
<213> ORGANISM: Artificial Sequence
<220> FEATURE:
<223> OTHER INFORMATION: hDAO-Fc-Hepmut2

<400> SEQUENCE: 89

atgccggccc tgggctgggc cgtggctgcc atcctgatgc tgcagacggc catggcggag     60

ccctccccgg ggactctgcc caggaaggca ggggtgtttt cagacctaag caaccaagag    120

ctgaaggcag tgcacagctt cctctggtcc aagaaggagc tgaggctgca gccctccagt    180

accaccacca tggccaagaa caccgtgttt ctcatcgaga tgctgctgcc caagaagtac    240

catgtgctga ggtttctgga taaaggtgaa aggcatcctg tgcgggaagc ccgtgccgtc    300

atcttctttg gtgaccagga gcatcccaat gtcaccgagt ttgctgtggg gcccctgcca    360

gggccctgct acatgcgagc actgtccccc aggcctgggt accagtcctc ctgggcatcg    420

aggcccatct ccacagcaga gtatgccctc ctctaccaca ccctgcagga agccaccaag    480

cccctgcatc agttcttcct caataccaca ggcttctcat tccaagactg ccatgacaga    540
```

```
tgcctggcct tcaccgatgt ggccccccgg ggtgtggctt ctggccagcg ccgcagttgg    600
cttatcatac agcgctatgt agaaggctac tttctgcacc ccactgggct ggagctcctc    660
gtggatcatg ggagcacaga tgctgggcac tgggccgtgg agcaggtgtg gtacaacggg    720
aagttctatg ggagcccaga ggaactggct cggaagtatg cagatggaga ggtggacgtg    780
gtggtcctgg aggacccgct gcctgggggc aaggggcatg acagcacaga ggagccgccc    840
ctcttctcct cccacaagcc ccgcggggac ttccccagcc ccatccatgt gagcggcccc    900
cgcttggtcc agccccacgg ccctcgcttc aggctggagg gcaacgctgt gctctacggc    960
ggctggagct ttgccttccg gctgcgctcc tcctccgggc tgcaggtcct gaacgtgcac   1020
ttcggcggag agcgcattgc ctatgaggtc agcgtgcaag aggcagtggc gctgtatgga   1080
ggacacacac ctgcaggcat gcagaccaag tacctcgatg tcggctgggg cctgggcagc   1140
gtcactcatg agttagcccc cggcatcgac tgcccggaga ccgccacctt cctggacact   1200
ttccactact atgatgccga tgacccggtc cattatcccc gagccctctg cctctttgaa   1260
atgcccacag gggtgcccct tcggcggcac tttaattcca actttaaagg tggcttcaac   1320
ttctatgcgg ggctgaaggg ccaggtgctg gtgctgcgga caacttcaac tgtctacaat   1380
tatgattaca tttgggactt tatcttctac cccaacgggg tgatggaggc caagatgcat   1440
gccactggct acgtccacgc caccttctac acccccgagg ggctgcgcca cggcactcgc   1500
ctgcacaccc acctgattgg caacatacac actcacttgg tgcactaccg cgtagacctg   1560
gatgtggcag gcaccaagaa cagcttccag acactgcaga tgaagctaga aaacatcacc   1620
aacccctgga gcccaagaca ccgcgtggtc cagccaactc tggagcagac gcagtactcc   1680
tgggagcgcc aggcggcctt ccgcttcaaa aggaagctgc ccacgtacct gctctttacc   1740
agcccccagg agaacccctg gggccacaag cgcagctacc gcctgcagat ccactccatg   1800
gccgaccagg tgctgccccc aggctggcag gaggagcagg ccatcacctg ggcaaggtac   1860
cccctggcag tgaccaagta ccgggagtcg gagctgtgca gcagcagcat ctaccaccag   1920
aacgacccct ggcacccgcc cgtggtcttt gagcagtttc ttcacaacaa cgagaacatt   1980
gaaaatgagg acctggtggc ctgggtgacg gtgggcttcc tgcacatccc ccactcagag   2040
gacattccca acacagccac acctgggaac tccgtgggct tcctgctccg gccattcaac   2100
ttcttcccag aggacccctc cctggcatcc agagacactg tgatcgtgtg gcctcgggac   2160
aacggcccca actacgtcca gcgctggatc cctgaggaca gggactgctc gatgcctccc   2220
ccttttagct acaatgggac ctatagacct gtggagccca agtccgccga caagacccac   2280
acctgccccc cctgccccgc ccccccccgtg gccggcccct ccgtgttcct gttccccccc   2340
aagcccaagg acaccctgat gatctccagg acccccgagg tgacctgcgt ggtggtggac   2400
gtgtcccacg aggaccccga ggtgaagttc aactggtacg tggacggcgt ggaggtgcac   2460
aacgccaaga ccaagcccag ggaggagcag tacaactcca cctacagggt ggtgtccgtg   2520
ctgaccgtgc tgcaccagga ctggctgaac ggcaaggagt acaagtgcaa ggtgtccaac   2580
aagggcctgc cctcctccat cgagaagacc atctccaagg ccaagggcca gcccagggag   2640
ccccaggtgt acaccctgcc cccctccagg gaggagatga ccaagaacca ggtgtccctg   2700
acctgcctgg tgaagggctt ctacccctcc gacatcgccg tggagtggga gtccaacggc   2760
cagcccgaga acaactacaa gaccaccccc cccgtgctgg actccgacgg ctccttcttc   2820
ctgtactcca agctgaccgt ggacaagtcc aggtggcagc agggcaacgt gttctcctgc   2880
tccgtgatgc acgaggccct gcacaaccac tacacccaga agtccctgtc cctgtccccc   2940
```

ggcaagtga 2949

<210> SEQ ID NO 90
<211> LENGTH: 2949
<212> TYPE: DNA
<213> ORGANISM: Artificial Sequence
<220> FEATURE:
<223> OTHER INFORMATION: hDAO-Fc-Hepmut3

<400> SEQUENCE: 90
atgccggccc tgggctgggc cgtggctgcc atcctgatgc tgcagacggc catggcggag 60
ccctccccgg ggactctgcc caggaaggca ggggtgtttt cagacctaag caaccaagag 120
ctgaaggcag tgcacagctt cctctggtcc aagaaggagc tgaggctgca gccctccagt 180
accaccacca tggccaagaa caccgtgttt ctcatcgaga tgctgctgcc caagaagtac 240
catgtgctga ggtttctgga taaaggtgaa aggcatcctg tgcgggaagc ccgtgccgtc 300
atcttctttg gtgaccagga gcatcccaat gtcaccgagt ttgctgtggg gcccctgcca 360
gggccctgct acatgcgagc actgtccccc aggcctgggt accagtcctc ctgggcatcg 420
aggcccatct ccacagcaga gtatgccctc ctctaccaca ccctgcagga agccaccaag 480
cccctgcatc agttcttcct caataccaca ggcttctcat tccaagactg ccatgacaga 540
tgcctggcct tcaccgatgt ggcccccggg ggtgtggctt ctggccagcg ccgcagttgg 600
cttatcatac agcgctatgt agaaggctac tttctgcacc ccactgggct ggagctcctc 660
gtggatcatg ggagcacaga tgctgggcac tgggccgtgg agcaggtgtg gtacaacggg 720
aagttctatg ggagcccaga ggaactggct cggaagtatg cagatggaga ggtggacgtg 780
gtggtcctgg aggacccgct gcctgggggc aaggggcatg acagcacaga ggagccgccc 840
ctcttctcct cccacaagcc ccgcggggac ttccccagcc ccatccatgt gagcggcccc 900
cgcttggtcc agccccacgg ccctcgcttc aggctggagg gcaacgctgt gctctacggc 960
ggctggagct ttgccttccg gctgcgctcc tcctccgggc tgcaggtcct gaacgtgcac 1020
ttcggcggag agcgcattgc ctatgaggtc agcgtgcaag aggcagtggc gctgtatgga 1080
ggacacacac ctgcaggcat gcagaccaag tacctcgatg tcggctgggg cctgggcagc 1140
gtcactcatg agttagcccc cggcatcgac tgcccggaga ccgccacctt cctggacact 1200
ttccactact atgatgccga tgacccggtc cattatcccc gagccctctg cctctttgaa 1260
atgcccacag gggtgcccct tcggcggcac tttaattcca actttaaagg tggcttcaac 1320
ttctatgcgg ggctgaaggg ccaggtgctg gtgctgcgga caacttcaac tgtctacaat 1380
tatgattaca tttgggactt tatcttctac cccaacgggg tgatggaggc caagatgcat 1440
gccactggct acgtccacgc caccttctac acccccgagg ggctgcgcca cggcactcgc 1500
ctgcacaccc acctgattgg caacatacac actcacttgg tgcactaccg cgtagacctg 1560
gatgtggcag gcaccaagaa cagcttccag acactgcaga tgaagctaga aaacatcacc 1620
aacccctgga gcccaagaca ccgcgtggtc cagccaactc tggagcagac gcagtactcc 1680
tgggagcgcc aggcggcctt ccgcttcaaa acgaagctgc ccaagtacct gctctttacc 1740
agcccccagg agaacccctg ggccacaagg cgcagctacc gcctgcagat ccactccatg 1800
gccgaccagg tgctgccccc aggctggcag gaggagcagg ccatcacctg ggcaaggtac 1860
cccctggcag tgaccaagta ccgggagtcg gagctgtgca gcagcagcat ctaccaccag 1920
aacgacccct ggcacccgcc cgtggtcttt gagcagtttc ttcacaacaa cgagaacatt 1980

```
gaaaatgagg acctggtggc ctgggtgacg gtgggcttcc tgcacatccc ccactcagag   2040
gacattccca acacagccac acctgggaac tccgtgggct tcctgctccg gccattcaac   2100
ttcttcccag aggacccctc cctggcatcc agagacactg tgatcgtgtg gcctcgggac   2160
aacggcccca actacgtcca gcgctggatc cctgaggaca gggactgctc gatgcctccc   2220
ccttttagct acaatgggac ctatagacct gtggagccca agtccgccga caagacccac   2280
acctgccccc cctgccccgc ccccccgtg gccggcccct ccgtgttcct gttccccccc   2340
aagcccaagg acaccctgat gatctccagg acccccgagg tgacctgcgt ggtggtggac   2400
gtgtcccacg aggaccccga ggtgaagttc aactggtacg tggacggcgt ggaggtgcac   2460
aacgccaaga ccaagcccag ggaggagcag tacaactcca cctacagggt ggtgtccgtg   2520
ctgaccgtgc tgcaccagga ctggctgaac ggcaaggagt acaagtgcaa ggtgtccaac   2580
aagggcctgc cctcctccat cgagaagacc atctccaagg ccaagggcca gcccagggag   2640
ccccaggtgt acaccctgcc cccctccagg gaggagatga ccaagaacca ggtgtccctg   2700
acctgcctgg tgaagggctt ctacccctcc gacatcgccg tggagtggga gtccaacggc   2760
cagcccgaga acaactacaa gaccaccccc cccgtgctgg actccgacgg ctccttcttc   2820
ctgtactcca agctgaccgt ggacaagtcc aggtggcagc agggcaacgt gttctcctgc   2880
tccgtgatgc acgaggccct gcacaaccac tacacccaga agtccctgtc cctgtccccc   2940
ggcaagtga                                                           2949
```

```
<210> SEQ ID NO 91
<211> LENGTH: 2949
<212> TYPE: DNA
<213> ORGANISM: Artificial Sequence
<220> FEATURE:
<223> OTHER INFORMATION: hDAO-Fc-Hepmut4

<400> SEQUENCE: 91
```

```
atgccggccc tgggctgggc cgtggctgcc atcctgatgc tgcagacggc catggcggag     60
ccctccccgg ggactctgcc caggaaggca ggggtgtttt cagacctaag caaccaagag    120
ctgaaggcag tgcacagctt cctctggtcc aagaaggagc tgaggctgca gccctccagt    180
accaccacca tggccaagaa caccgtgttt ctcatcgaga tgctgctgcc caagaagtac    240
catgtgctga ggtttctgga taaaggtgaa aggcatcctg tgcgggaagc ccgtgccgtc    300
atcttctttg gtgaccagga gcatcccaat gtcaccgagt ttgctgtggg gcccctgcca    360
gggccctgct acatgcgagc actgtccccc aggcctgggt accagtcctc ctgggcatcg    420
aggcccatct ccacagcaga gtatgccctc ctctaccaca ccctgcagga agccaccaag    480
cccctgcatc agttcttcct caataccaca ggcttctcat tccaagactg ccatgacaga    540
tgcctggcct tcaccgatgt ggcccccccgg ggtgtggctt ctggccagcg ccgcagttgg    600
cttatcatac agcgctatgt agaaggctac tttctgcacc ccactgggct ggagctcctc    660
gtggatcatg ggagcacaga tgctgggcac tgggccgtgg agcaggtgtg gtacaacggg    720
aagttctatg ggagcccaga ggaactggct cggaagtatg cagatggaga ggtggacgtg    780
gtggtcctgg aggacccgct gcctgggggc aaggggcatg acagcacaga ggagccgccc    840
ctcttctcct cccacaagcc ccgcggggac ttccccagcc ccatccatgt gagcggcccc    900
cgcttggtcc agccccacgg ccctcgcttc aggctggagg gcaacgctgt gctctacggc    960
ggctggagct ttgccttccg gctgcgctcc tcctccgggc tgcaggtcct gaacgtgcac   1020
ttcggcggag agcgcattgc ctatgaggtc agcgtgcaag aggcagtggc gctgtatgga   1080
```

ggacacacac ctgcaggcat gcagaccaag tacctcgatg tcggctgggg cctgggcagc 1140
gtcactcatg agttagcccc cggcatcgac tgcccggaga ccgccacctt cctggacact 1200
ttccactact atgatgccga tgacccggtc cattatcccc gagccctctg cctctttgaa 1260
atgcccacag ggtgcccct tcggcggcac tttaattcca actttaaagg tggcttcaac 1320
ttctatgcgg ggctgaaggg ccaggtgctg gtgctgcgga caacttcaac tgtctacaat 1380
tatgattaca tttgggactt tatcttctac cccaacgggg tgatggaggc caagatgcat 1440
gccactggct acgtccacgc caccttctac acccccgagg ggctgcgcca cggcactcgc 1500
ctgcacaccc acctgattgg caacatacac actcacttgg tgcactaccg cgtagacctg 1560
gatgtggcag gcaccaagaa cagcttccag acactgcaga tgaagctaga aaacatcacc 1620
aacccctgga gcccaagaca ccgcgtggtc cagccaactc tggagcagac gcagtactcc 1680
tgggagcgcc aggcggcctt cagcttcaaa acgaagctgc ccaagtacct gctctttacc 1740
agcccccagg agaacccctg ggccacaag cgcagctacc gcctgcagat ccactccatg 1800
gccgaccagg tgctgccccc aggctggcag gaggagcagg ccatcacctg ggcaaggtac 1860
cccctggcag tgaccaagta ccgggagtcg gagctgtgca gcagcagcat ctaccaccag 1920
aacgacccct ggcacccgcc cgtggtcttt gagcagtttc ttcacaacaa cgagaacatt 1980
gaaaatgagg acctggtggc ctgggtgacg gtgggcttcc tgcacatccc ccactcagag 2040
gacattccca acacagccac acctgggaac tccgtgggct tcctgctccg gccattcaac 2100
ttcttcccag aggacccctc cctggcatcc agagacactg tgatcgtgtg gcctcgggac 2160
aacggcccca actacgtcca gcgctggatc cctgaggaca gggactgctc gatgcctccc 2220
ccttttagct acaatgggac ctatagacct gtggagccca agtccgccga caagacccac 2280
acctgccccc cctgccccgc ccccccgtg gccggcccct ccgtgttcct gttccccccc 2340
aagcccaagg acaccctgat gatctccagg acccccgagg tgacctgcgt ggtggtggac 2400
gtgtcccacg aggaccccga ggtgaagttc aactggtacg tggacggcgt ggaggtgcac 2460
aacgccaaga ccaagcccag ggaggagcag tacaactcca cctacagggt ggtgtccgtg 2520
ctgaccgtgc tgcaccagga ctggctgaac ggcaaggagt acaagtgcaa ggtgtccaac 2580
aagggcctgc cctcctccat cgagaagacc atctccaagg ccaagggcca gcccagggag 2640
ccccaggtgt acaccctgcc cccctccagg gaggagatga ccaagaacca ggtgtccctg 2700
acctgcctgg tgaagggctt ctacccctcc gacatcgccg tggagtggga gtccaacggc 2760
cagcccgaga acaactacaa gaccaccccc cccgtgctgg actccgacgg ctccttcttc 2820
ctgtactcca agctgaccgt ggacaagtcc aggtggcagc agggcaacgt gttctcctgc 2880
tccgtgatgc acgaggccct gcacaaccac tacacccaga agtccctgtc cctgtccccc 2940
ggcaagtga 2949

<210> SEQ ID NO 92
<211> LENGTH: 2949
<212> TYPE: DNA
<213> ORGANISM: Artificial Sequence
<220> FEATURE:
<223> OTHER INFORMATION: hDAO-Fc-Hepmut5

<400> SEQUENCE: 92
atgccggccc tgggctgggc cgtggctgcc atcctgatgc tgcagacggc catggcggag 60
ccctccccgg ggactctgcc caggaaggca ggggtgtttt cagacctaag caaccaagag 120

```
ctgaaggcag tgcacagctt cctctggtcc aagaaggagc tgaggctgca gccctccagt    180
accaccacca tggccaagaa caccgtgttt ctcatcgaga tgctgctgcc caagaagtac    240
catgtgctga ggtttctgga taaaggtgaa aggcatcctg tgcgggaagc ccgtgccgtc    300
atcttctttg gtgaccagga gcatcccaat gtcaccgagt ttgctgtggg gcccctgcca    360
gggccctgct acatgcgagc actgtccccc aggcctgggt accagtcctc ctgggcatcg    420
aggcccatct ccacagcaga gtatgccctc ctctaccaca ccctgcagga agccaccaag    480
cccctgcatc agttcttcct caataccaca ggcttctcat tccaagactg ccatgacaga    540
tgcctggcct tcaccgatgt ggcccccgg ggtgtggctt ctggccagcg ccgcagttgg    600
cttatcatac agcgctatgt agaaggctac tttctgcacc ccactgggct ggagctcctc    660
gtggatcatg ggagcacaga tgctgggcac tgggccgtgg agcaggtgtg gtacaacggg    720
aagttctatg ggagcccaga ggaactggct cggaagtatg cagatggaga ggtggacgtg    780
gtggtcctgg aggacccgct gcctgggggc aaggggcatg acagcacaga ggagccgccc    840
ctcttctcct cccacaagcc ccgcggggac ttccccagcc ccatccatgt gagcggcccc    900
cgcttggtcc agccccacgg ccctcgcttc aggctggagg gcaacgctgt gctctacggc    960
ggctggagct ttgccttccg gctgcgctcc tcctccgggc tgcaggtcct gaacgtgcac   1020
ttcggcggag agcgcattgc ctatgaggtc agcgtgcaag aggcagtggc gctgtatgga   1080
ggacacacac ctgcaggcat gcagaccaag tacctcgatg tcggctgggg cctgggcagc   1140
gtcactcatg agttagcccc cggcatcgac tgcccggaga ccgccacctt cctggacact   1200
ttccactact atgatgccga tgacccggtc cattatcccc gagccctctg cctctttgaa   1260
atgcccacag ggtgcccct tcggcggcac tttaattcca actttaaagg tggcttcaac   1320
ttctatgcgg ggctgaaggg ccaggtgctg gtgctgcgga caacttcaac tgtctacaat   1380
tatgattaca tttgggactt tatcttctac cccaacgggg tgatggaggc caagatgcat   1440
gccactggct acgtccacgc caccttctac acccccgagg ggctgcgcca cggcactcgc   1500
ctgcacaccc acctgattgg caacatacac actcacttgg tgcactaccg cgtagacctg   1560
gatgtggcag gcaccaagaa cagcttccag acactgcaga tgaagctaga aaacatcacc   1620
aacccctgga gcccaagaca ccgcgtggtc cagccaactc tggagcagac gcagtactcc   1680
tgggagcgcc aggcggcctt ccgcttcaaa acgaagctgc ccacgtacct gctctttacc   1740
agcccccagg agaacccctg ggccacaag cgcagctacc gcctgcagat ccactccatg    1800
gccgaccagg tgctgccccc aggctggcag gaggagcagg ccatcacctg ggcaaggtac   1860
cccctggcag tgaccaagta ccgggagtcg gagctgtgca gcagcagcat ctaccaccag   1920
aacgacccct ggcacccgcc cgtggtcttt gagcagtttc ttcacaacaa cgagaacatt   1980
gaaaatgagg acctggtggc ctgggtgacg gtgggcttcc tgcacatccc ccactcagag   2040
gacattccca acacagccac acctgggaac tccgtgggct tcctgctccg gccattcaac   2100
ttcttcccag aggacccctc cctggcatcc agagacactg tgatcgtgtg gcctcgggac   2160
aacggcccca actacgtcca gcgctggatc cctgaggaca gggactgctc gatgcctccc   2220
ccttttagct acaatgggac ctatagacct gtggagccca agtccgccga caagacccac   2280
acctgccccc cctgccccgc ccccccgtg gccggcccct ccgtgttcct gttccccccc   2340
aagcccaagg acaccctgat gatctccagg acccccgagg tgacctgcgt ggtggtggac   2400
gtgtcccacg aggaccccga ggtgaagttc aactggtacg tggacggcgt ggaggtgcac   2460
aacgccaaga ccaagcccag ggaggagcag tacaactcca cctacagggt ggtgtccgtg   2520
```

ctgaccgtgc tgcaccagga ctggctgaac ggcaaggagt acaagtgcaa ggtgtccaac 2580
aagggcctgc cctcctccat cgagaagacc atctccaagg ccaagggcca gcccagggag 2640
ccccaggtgt acaccctgcc cccctccagg gaggagatga ccaagaacca ggtgtccctg 2700
acctgcctgg tgaagggctt ctacccctcc gacatcgccg tggagtggga gtccaacggc 2760
cagcccgaga acaactacaa gaccaccccc cccgtgctgg actccgacgg ctccttcttc 2820
ctgtactcca agctgaccgt ggacaagtcc aggtggcagc agggcaacgt gttctcctgc 2880
tccgtgatgc acgaggccct gcacaaccac tacacccaga agtccctgtc cctgtccccc 2940
ggcaagtga 2949

<210> SEQ ID NO 93
<211> LENGTH: 2949
<212> TYPE: DNA
<213> ORGANISM: Artificial Sequence
<220> FEATURE:
<223> OTHER INFORMATION: hDAO-Fc-Hepmut6

<400> SEQUENCE: 93
atgccggccc tgggctgggc cgtggctgcc atcctgatgc tgcagacggc catggcggag 60
ccctccccgg ggactctgcc caggaaggca ggggtgtttt cagacctaag caaccaagag 120
ctgaaggcag tgcacagctt cctctggtcc aagaaggagc tgaggctgca gccctccagt 180
accaccacca tggccaagaa caccgtgttt ctcatcgaga tgctgctgcc caagaagtac 240
catgtgctga ggtttctgga taaaggtgaa aggcatcctg tgcgggaagc ccgtgccgtc 300
atcttctttg gtgaccagga gcatcccaat gtcaccgagt ttgctgtggg gcccctgcca 360
gggccctgct acatgcgagc actgtccccc aggcctgggt accagtcctc ctgggcatcg 420
aggcccatct ccacagcaga gtatgccctc ctctaccaca ccctgcagga agccaccaag 480
cccctgcatc agttcttcct caataccaca ggcttctcat tccaagactg ccatgacaga 540
tgcctggcct tcaccgatgt ggccccccgg ggtgtggctt ctggccagcg ccgcagttgg 600
cttatcatac agcgctatgt agaaggctac tttctgcacc ccactgggct ggagctcctc 660
gtggatcatg ggagcacaga tgctgggcac tgggccgtgg agcaggtgtg gtacaacggg 720
aagttctatg ggagcccaga ggaactggct cggaagtatg cagatggaga ggtggacgtg 780
gtggtcctgg aggacccgct gcctgggggc aaggggcatg acagcacaga ggagccgccc 840
ctcttctcct cccacaagcc ccgcggggac ttccccagcc ccatccatgt gagcggcccc 900
cgcttggtcc agccccacgg ccctcgcttc aggctggagg gcaacgctgt gctctacggc 960
ggctggagct ttgccttccg gctgcgctcc tcctccgggc tgcaggtcct gaacgtgcac 1020
ttcggcggag agcgcattgc ctatgaggtc agcgtgcaag aggcagtggc gctgtatgga 1080
ggacacacac ctgcaggcat gcagaccaag tacctcgatg tcggctgggg cctgggcagc 1140
gtcactcatg agttagcccc cggcatcgac tgcccggaga ccgccacctt cctggacact 1200
ttccactact atgatgccga tgacccggtc cattatcccc gagccctctg cctctttgaa 1260
atgcccacag gggtgcccct tcggcggcac tttaattcca actttaaagg tggcttcaac 1320
ttctatgcgg ggctgaaggg ccaggtgctg gtgctgcgga caacttcaac tgtctacaat 1380
tatgattaca tttgggactt tatcttctac cccaacgggg tgatggaggc caagatgcat 1440
gccactggct acgtccacgc caccttctac acccccgagg ggctgcgcca cggcactcgc 1500
ctgcacaccc acctgattgg caacatacac actcacttgg tgcactaccg cgtagacctg 1560
gatgtggcag gcaccaagaa cagcttccag acactgcaga tgaagctaga aaacatcacc 1620 aaccccctgga gcccaagaca ccgcgtggtc cagccaactc tggagcagac gcagtactcc 1680
tgggagcgcc aggcggcctt ccgcttcgga cagacgctgc ccaagtacct gctctttacc 1740
agcccccagg agaaccccctg gggccacaag cgcagctacc gcctgcagat ccactccatg 1800
gccgaccagg tgctgccccc aggctggcag gaggagcagg ccatcacctg ggcaaggtac 1860
cccctggcag tgaccaagta ccgggagtcg gagctgtgca gcagcagcat ctaccaccag 1920
aacgacccct ggcacccgcc cgtggtcttt gagcagtttc ttcacaacaa cgagaacatt 1980
gaaaatgagg acctggtggc ctgggtgacg gtgggcttcc tgcacatccc ccactcagag 2040
gacattccca acacagccac acctgggaac tccgtgggct tcctgctccg gccattcaac 2100
ttcttcccag aggacccctc cctggcatcc agagacactg tgatcgtgtg gcctcgggac 2160
aacggcccca actacgtcca gcgctggatc cctgaggaca gggactgctc gatgcctccc 2220
ccttttagct acaatgggac ctatagacct gtggagccca agtccgccga caagacccac 2280
acctgccccc cctgccccgc cccccccgtg gccggcccct ccgtgttcct gttccccccc 2340
aagcccaagg acaccctgat gatctccagg acccccgagg tgacctgcgt ggtggtggac 2400
gtgtcccacg aggaccccga ggtgaagttc aactggtacg tggacggcgt ggaggtgcac 2460
aacgccaaga ccaagcccag ggaggagcag tacaactcca cctacagggt ggtgtccgtg 2520
ctgaccgtgc tgcaccagga ctggctgaac ggcaaggagt acaagtgcaa ggtgtccaac 2580
aagggcctgc cctcctccat cgagaagacc atctccaagg ccaagggcca gcccagggag 2640
ccccaggtgt acaccctgcc cccctccagg gaggagatga ccaagaacca ggtgtccctg 2700
acctgcctgg tgaagggctt ctacccctcc gacatcgccg tggagtggga gtccaacggc 2760
cagcccgaga acaactacaa gaccaccccc cccgtgctgg actccgacgg ctccttcttc 2820
ctgtactcca agctgaccgt ggacaagtcc aggtggcagc agggcaacgt gttctcctgc 2880
tccgtgatgc acgaggccct gcacaaccac tacacccaga agtccctgtc cctgtccccc 2940
ggcaagtga 2949

<210> SEQ ID NO 94
<211> LENGTH: 2949
<212> TYPE: DNA
<213> ORGANISM: Artificial Sequence
<220> FEATURE:
<223> OTHER INFORMATION: hDAO-Fc-Hepmut7

<400> SEQUENCE: 94
atgccggccc tgggctgggc cgtggctgcc atcctgatgc tgcagacggc catggcggag 60
ccctccccgg ggactctgcc caggaaggca ggggtgtttt cagacctaag caaccaagag 120
ctgaaggcag tgcacagctt cctctggtcc aagaaggagc tgaggctgca gccctccagt 180
accaccacca tggccaagaa caccgtgttt ctcatcgaga tgctgctgcc caagaagtac 240
catgtgctga ggtttctgga taaaggtgaa aggcatcctg tgcgggaagc ccgtgccgtc 300
atcttctttg gtgaccagga gcatcccaat gtcaccgagt ttgctgtggg gcccctgcca 360
gggccctgct acatgcgagc actgtccccc aggcctgggt accagtcctc ctgggcatcg 420
aggcccatct ccacagcaga gtatgccctc ctctaccaca ccctgcagga agccaccaag 480
cccctgcatc agttcttcct caataccaca ggcttctcat tccaagactg ccatgacaga 540
tgcctggcct tcaccgatgt ggcccccggg ggtgtggctt ctggccagcg ccgcagttgg 600
cttatcatac agcgctatgt agaaggctac tttctgcacc ccactgggct ggagctcctc 660

```
gtggatcatg ggagcacaga tgctgggcac tgggccgtgg agcaggtgtg gtacaacggg    720
aagttctatg ggagcccaga ggaactggct cggaagtatg cagatggaga ggtggacgtg    780
gtggtcctgg aggacccgct gcctgggggc aaggggcatg acagcacaga ggagccgccc    840
ctcttctcct cccacaagcc ccgcggggac ttccccagcc ccatccatgt gagcggcccc    900
cgcttggtcc agccccacgg ccctcgcttc aggctggagg gcaacgctgt gctctacggc    960
ggctggagct ttgccttccg gctgcgctcc tcctccgggc tgcaggtcct gaacgtgcac   1020
ttcggcggag agcgcattgc ctatgaggtc agcgtgcaag aggcagtggc gctgtatgga   1080
ggacacacac ctgcaggcat gcagaccaag tacctcgatg tcggctgggg cctgggcagc   1140
gtcactcatg agttagcccc cggcatcgac tgcccggaga ccgccacctt cctggacact   1200
ttccactact atgatgccga tgacccggtc cattatcccc gagccctctg cctctttgaa   1260
atgcccacag gggtgcccct tcggcggcac tttaattcca actttaaagg tggcttcaac   1320
ttctatgcgg ggctgaaggg ccaggtgctg gtgctgcgga caacttcaac tgtctacaat   1380
tatgattaca tttgggactt tatcttctac cccaacgggg tgatggaggc caagatgcat   1440
gccactggct acgtccacgc caccttctac acccccgagg ggctgcgcca cggcactcgc   1500
ctgcacaccc acctgattgg caacatacac actcacttgg tgcactaccg cgtagacctg   1560
gatgtggcag gcaccaagaa cagcttccag acactgcaga tgaagctaga aaacatcacc   1620
aacccctgga gcccaagaca ccgcgtggtc cagccaactc tggagcagac gcagtactcc   1680
tgggagcgcc aggcggcctt cagcttcaaa aggaagctgc ccacgtacct gctctttacc   1740
agcccccagg agaacccctg gggccacaag cgcagctacc gcctgcagat ccactccatg   1800
gccgaccagg tgctgccccc aggctggcag gaggagcagg ccatcacctg ggcaaggtac   1860
cccctggcag tgaccaagta ccgggagtcg gagctgtgca gcagcagcat ctaccaccag   1920
aacgacccct ggcacccgcc cgtggtcttt gagcagtttc ttcacaacaa cgagaacatt   1980
gaaaatgagg acctggtggc ctgggtgacg gtgggcttcc tgcacatccc ccactcagag   2040
gacattccca acacagccac acctgggaac tccgtgggct tcctgctccg gccattcaac   2100
ttcttcccag aggacccctc cctggcatcc agagacactg tgatcgtgtg gcctcgggac   2160
aacggcccca actacgtcca gcgctggatc cctgaggaca gggactgctc gatgcctccc   2220
ccttttagct acaatgggac ctatagacct gtggagccca agtccgccga caagacccac   2280
acctgccccc cctgccccgc cccccccgtg gccggcccct ccgtgttcct gttccccccc   2340
aagcccaagg acaccctgat gatctccagg acccccgagg tgacctgcgt ggtggtggac   2400
gtgtcccacg aggaccccga ggtgaagttc aactggtacg tggacggcgt ggaggtgcac   2460
aacgccaaga ccaagcccag ggaggagcag tacaactcca cctacagggt ggtgtccgtg   2520
ctgaccgtgc tgcaccagga ctggctgaac ggcaaggagt acaagtgcaa ggtgtccaac   2580
aagggcctgc cctcctccat cgagaagacc atctccaagg ccaagggcca gcccagggag   2640
ccccaggtgt acaccctgcc cccctccagg gaggagatga ccaagaacca ggtgtccctg   2700
acctgcctgg tgaagggctt ctacccctcc gacatcgccg tggagtggga gtccaacggc   2760
cagcccgaga acaactacaa gaccaccccc cccgtgctgg actccgacgg ctccttcttc   2820
ctgtactcca agctgaccgt ggacaagtcc aggtggcagc agggcaacgt gttctcctgc   2880
tccgtgatgc acgaggccct gcacaaccac tacacccaga agtccctgtc cctgtccccc   2940
ggcaagtga                                                           2949
```

<210> SEQ ID NO 95
<211> LENGTH: 2949
<212> TYPE: DNA
<213> ORGANISM: Artificial Sequence
<220> FEATURE:
<223> OTHER INFORMATION: hDAO-Fc-Cysmut

<400> SEQUENCE: 95
atgccggccc tgggctgggc cgtggctgcc atcctgatgc tgcagacggc catggcggag 60
ccctccccgg ggactctgcc caggaaggca ggggtgtttt cagacctaag caaccaagag 120
ctgaaggcag tgcacagctt cctctggtcc aagaaggagc tgaggctgca gccctccagt 180
accaccacca tggccaagaa caccgtgttt ctcatcgaga tgctgctgcc caagaagtac 240
catgtgctga ggtttctgga taaaggtgaa aggcatcctg tgcgggaagc ccgtgccgtc 300
atcttctttg gtgaccagga gcatcccaat gtcaccgagt ttgctgtggg gccccctgcca 360 gggcccgcct acatgcgagc actgtccccc aggcctgggt accagtcctc ctgggcatcg 420
aggcccatct ccacagcaga gtatgccctc ctctaccaca ccctgcagga agccaccaag 480
cccctgcatc agttcttcct caataccaca ggcttctcat tccaagactg ccatgacaga 540
tgcctggcct tcaccgatgt ggcccccccgg ggtgtggctt ctggccagcg ccgcagttgg 600
cttatcatac agcgctatgt agaaggctac tttctgcacc ccactgggct ggagctcctc 660
gtggatcatg ggagcacaga tgctgggcac tgggccgtgg agcaggtgtg gtacaacggg 720
aagttctatg ggagcccaga ggaactggct cggaagtatg cagatggaga ggtggacgtg 780
gtggtcctgg aggacccgct gcctgggggc aaggggcatg acagcacaga ggagccgccc 840
ctcttctcct cccacaagcc ccgcggggac ttccccagcc ccatccatgt gagcggcccc 900
cgcttggtcc agccccacgg ccctcgcttc aggctggagg gcaacgctgt gctctacggc 960
ggctggagct ttgccttccg gctgcgctcc tcctccgggc tgcaggtcct gaacgtgcac 1020
ttcggcggag agcgcattgc ctatgaggtc agcgtgcaag aggcagtggc gctgtatgga 1080
ggacacacac ctgcaggcat gcagaccaag tacctcgatg tcggctgggg cctgggcagc 1140
gtcactcatg agttagcccc cggcatcgac tgcccggaga ccgccacctt cctggacact 1200
ttccactact atgatgccga tgacccggtc cattatcccc gagccctctg cctctttgaa 1260
atgcccacag ggtgcccct tcggcggcac tttaattcca actttaaagg tggcttcaac 1320
ttctatgcgg ggctgaaggg ccaggtgctg gtgctgcgga caacttcaac tgtctacaat 1380
tatgattaca tttgggactt tatcttctac cccaacgggg tgatggaggc caagatgcat 1440
gccactggct acgtccacgc caccttctac acccccgagg ggctgcgcca cggcactcgc 1500
ctgcacaccc acctgattgg caacatacac actcacttgg tgcactaccg cgtagacctg 1560
gatgtggcag gcaccaagaa cagcttccag acactgcaga tgaagctaga aaacatcacc 1620
aacccctgga gcccaagaca ccgcgtggtc cagccaactc tggagcagac gcagtactcc 1680
tgggagcgcc aggcggcctt ccgcttcaaa aggaagctgc ccaagtacct gctctttacc 1740
agcccccagg agaacccctg gggccacaag cgcagctacc gcctgcagat ccactccatg 1800
gccgaccagg tgctgccccc aggctggcag gaggagcagg ccatcacctg ggcaaggtac 1860
cccctggcag tgaccaagta ccgggagtcg gagctgtgca gcagcagcat ctaccaccag 1920
aacgacccct ggcacccgcc cgtggtcttt gagcagtttc ttcacaacaa cgagaacatt 1980
gaaaatgagg acctggtggc ctgggtgacg gtgggcttcc tgcacatccc ccactcagag 2040
gacattccca acacagccac acctgggaac tccgtgggct tcctgctccg gccattcaac 2100
ttcttcccag aggacccctc cctggcatcc agagacactg tgatcgtgtg gcctcgggac 2160
aacggcccca actacgtcca gcgctggatc cctgaggaca gggactgctc gatgcctccc 2220
ccttttagct acaatgggac ctatagacct gtggagccca agtccgccga caagacccac 2280
acctgccccc cctgccccgc ccccccgtg gccggcccct ccgtgttcct gttccccccc 2340
aagcccaagg acaccctgat gatctccagg acccccgagg tgacctgcgt ggtggtggac 2400
gtgtcccacg aggaccccga ggtgaagttc aactggtacg tggacggcgt ggaggtgcac 2460
aacgccaaga ccaagcccag ggaggagcag tacaactcca cctacagggt ggtgtccgtg 2520
ctgaccgtgc tgcaccagga ctggctgaac ggcaaggagt acaagtgcaa ggtgtccaac 2580
aagggcctgc cctcctccat cgagaagacc atctccaagg ccaagggcca gcccagggag 2640
ccccaggtgt acaccctgcc cccctccagg gaggagatga ccaagaacca ggtgtccctg 2700
acctgcctgg tgaagggctt ctacccctcc gacatcgccg tggagtggga gtccaacggc 2760
cagcccgaga acaactacaa gaccaccccc cccgtgctgg actccgacgg ctccttcttc 2820
ctgtactcca agctgaccgt ggacaagtcc aggtggcagc agggcaacgt gttctcctgc 2880
tccgtgatgc acgaggccct gcacaaccac tacacccaga agtccctgtc cctgtccccc 2940
ggcaagtga 2949

<210> SEQ ID NO 96
<211> LENGTH: 2949
<212> TYPE: DNA
<213> ORGANISM: Artificial Sequence
<220> FEATURE:
<223> OTHER INFORMATION: hDAO-Fc-Hepmut1-Cysmut

<400> SEQUENCE: 96
atgccggccc tgggctgggc cgtggctgcc atcctgatgc tgcagacggc catggcggag 60
ccctccccgg ggactctgcc caggaaggca ggggtgtttt cagacctaag caaccaagag 120
ctgaaggcag tgcacagctt cctctggtcc aagaaggagc tgaggctgca gccctccagt 180
accaccacca tggccaagaa caccgtgttt ctcatcgaga tgctgctgcc caagaagtac 240
catgtgctga ggtttctgga taaaggtgaa aggcatcctg tgcgggaagc ccgtgccgtc 300
atcttctttg gtgaccagga gcatcccaat gtcaccgagt ttgctgtggg gcccctgcca 360
gggcccgcct acatgcgagc actgtccccc aggcctgggt accagtcctc ctgggcatcg 420
aggcccatct ccacagcaga gtatgccctc ctctaccaca ccctgcagga agccaccaag 480
cccctgcatc agttcttcct caataccaca ggcttctcat tccaagactg ccatgacaga 540
tgcctggcct tcaccgatgt ggcccccgg ggtgtggctt ctggccagcg ccgcagttgg 600
cttatcatac agcgctatgt agaaggctac tttctgcacc ccactgggct ggagctcctc 660
gtggatcatg ggagcacaga tgctgggcac tgggccgtgg agcaggtgtg gtacaacggg 720
aagttctatg ggagcccaga ggaactggct cggaagtatg cagatggaga ggtggacgtg 780
gtggtcctgg aggacccgct gcctgggggc aaggggcatg acagcacaga ggagccgccc 840
ctcttctcct cccacaagcc ccgcggggac ttccccagcc ccatccatgt gagcggcccc 900
cgcttggtcc agccccacgg ccctcgcttc aggctggagg gcaacgctgt gctctacggc 960
ggctggagct ttgccttccg gctgcgctcc tcctccgggc tgcaggtcct gaacgtgcac 1020
ttcggcggag agcgcattgc ctatgaggtc agcgtgcaag aggcagtggc gctgtatgga 1080
ggacacacac ctgcaggcat gcagaccaag tacctcgatg tcggctgggg cctgggcagc 1140
gtcactcatg agttagcccc cggcatcgac tgcccggaga ccgccacctt cctggacact 1200
ttccactact atgatgccga tgacccggtc cattatcccc gagccctctg cctctttgaa 1260
atgcccacag gggtgcccct tcggcggcac tttaattcca actttaaagg tggcttcaac 1320
ttctatgcgg ggctgaaggg ccaggtgctg gtgctgcgga caacttcaac tgtctacaat 1380
tatgattaca tttgggactt tatcttctac cccaacgggg tgatggaggc caagatgcat 1440
gccactggct acgtccacgc caccttctac accccgagg ggctgcgcca cggcactcgc 1500
ctgcacaccc acctgattgg caacatacac actcacttgg tgcactaccg cgtagacctg 1560
gatgtggcag gcaccaagaa cagcttccag acactgcaga tgaagctaga aaacatcacc 1620
aacccctgga gcccaagaca ccgcgtggtc cagccaactc tggagcagac gcagtactcc 1680
tgggagcgcc aggcggcctt cagcttcaaa aggaagctgc ccaagtacct gctctttacc 1740
agcccccagg agaacccctg gggccacaag cgcagctacc gcctgcagat ccactccatg 1800
gccgaccagg tgctgcccc aggctggcag gaggagcagg ccatcacctg ggcaaggtac 1860
cccctggcag tgaccaagta ccgggagtcg gagctgtgca gcagcagcat ctaccaccag 1920
aacgacccct ggcacccgcc cgtggtcttt gagcagtttc ttcacaacaa cgagaacatt 1980
gaaaatgagg acctggtggc ctgggtgacg gtgggcttcc tgcacatccc ccactcagag 2040
gacattccca acacagccac acctgggaac tccgtgggct tcctgctccg gccattcaac 2100
ttcttcccag aggacccctc cctggcatcc agagacactg tgatcgtgtg gcctcgggac 2160
aacggcccca actacgtcca gcgctggatc cctgaggaca gggactgctc gatgcctccc 2220
ccttttagct acaatgggac ctatagacct gtggagccca agtccgccga caagacccac 2280
acctgccccc cctgccccgc cccccccgtg gccggcccct ccgtgttcct gttcccccc 2340 aagcccaagg acaccctgat gatctccagg acccccgagg tgacctgcgt ggtggtggac 2400
gtgtcccacg aggaccccga ggtgaagttc aactggtacg tggacggcgt ggaggtgcac 2460
aacgccaaga ccaagcccag ggaggagcag tacaactcca cctacagggt ggtgtccgtg 2520
ctgaccgtgc tgcaccagga ctggctgaac ggcaaggagt acaagtgcaa ggtgtccaac 2580
aagggcctgc cctcctccat cgagaagacc atctccaagg ccaagggcca gcccagggag 2640
ccccaggtgt acaccctgcc cccctccagg gaggagatga ccaagaacca ggtgtccctg 2700
acctgcctgg tgaagggctt ctacccctcc gacatcgccg tggagtggga gtccaacggc 2760
cagcccgaga acaactacaa gaccaccccc cccgtgctgg actccgacgg ctccttcttc 2820
ctgtactcca agctgaccgt ggacaagtcc aggtggcagc agggcaacgt gttctcctgc 2880
tccgtgatgc acgaggccct gcacaaccac tacacccaga agtccctgtc cctgtccccc 2940
ggcaagtga 2949

<210> SEQ ID NO 97
<211> LENGTH: 2949
<212> TYPE: DNA
<213> ORGANISM: Artificial Sequence
<220> FEATURE:
<223> OTHER INFORMATION: hDAO-Fc-Hepmut2-Cysmut

<400> SEQUENCE: 97
atgccggccc tgggctgggc cgtggctgcc atcctgatgc tgcagacggc catggcggag 60
ccctccccgg ggactctgcc caggaaggca ggggtgtttt cagacctaag caaccaagag 120
ctgaaggcag tgcacagctt cctctggtcc aagaaggagc tgaggctgca gccctccagt 180
accaccacca tggccaagaa caccgtgttt ctcatcgaga tgctgctgcc caagaagtac 240

```
catgtgctga ggtttctgga taaaggtgaa aggcatcctg tgcgggaagc ccgtgccgtc    300
atcttctttg gtgaccagga gcatcccaat gtcaccgagt ttgctgtggg gcccctgcca    360
gggcccgcct acatgcgagc actgtccccc aggcctgggt accagtcctc ctgggcatcg    420
aggcccatct ccacagcaga gtatgccctc ctctaccaca ccctgcagga agccaccaag    480
cccctgcatc agttcttcct caataccaca ggcttctcat tccaagactg ccatgacaga    540
tgcctggcct tcaccgatgt ggcccccccgg ggtgtggctt ctggccagcg ccgcagttgg    600
cttatcatac agcgctatgt agaaggctac tttctgcacc ccactgggct ggagctcctc    660
gtggatcatg ggagcacaga tgctgggcac tgggccgtgg agcaggtgtg gtacaacggg    720
aagttctatg ggagcccaga ggaactggct cggaagtatg cagatggaga ggtggacgtg    780
gtggtcctgg aggacccgct gcctgggggc aaggggcatg acagcacaga ggagccgccc    840
ctcttctcct cccacaagcc ccgcggggac ttccccagcc ccatccatgt gagcggcccc    900
cgcttggtcc agccccacgg ccctcgcttc aggctggagg gcaacgctgt gctctacggc    960
ggctggagct ttgccttccg gctgcgctcc tcctccgggc tgcaggtcct gaacgtgcac   1020
ttcggcggag agcgcattgc ctatgaggtc agcgtgcaag aggcagtggc gctgtatgga   1080
ggacacacac ctgcaggcat gcagaccaag tacctcgatg tcggctgggg cctgggcagc   1140
gtcactcatg agttagcccc cggcatcgac tgcccggaga ccgccacctt cctggacact   1200
ttccactact atgatgccga tgacccggtc cattatcccc gagccctctg cctctttgaa   1260
atgcccacag ggtgcccct tcggcggcac tttaattcca actttaaagg tggcttcaac   1320
ttctatgcgg ggctgaaggg ccaggtgctg gtgctgcgga caacttcaac tgtctacaat   1380
tatgattaca tttgggactt tatcttctac cccaacgggg tgatggaggc caagatgcat   1440
gccactggct acgtccacgc caccttctac acccccgagg ggctgcgcca cggcactcgc   1500
ctgcacaccc acctgattgg caacatacac actcacttgg tgcactaccg cgtagacctg   1560
gatgtggcag gcaccaagaa cagcttccag acactgcaga tgaagctaga aaacatcacc   1620
aacccctgga gcccaagaca ccgcgtggtc cagccaactc tggagcagac gcagtactcc   1680
tgggagcgcc aggcggcctt ccgcttcaaa aggaagctgc ccacgtacct gctctttacc   1740
agcccccagg agaaccccctg gggccacaag cgcagctacc gcctgcagat ccactccatg   1800
gccgaccagg tgctgccccc aggctggcag gaggagcagg ccatcacctg ggcaaggtac   1860
cccctggcag tgaccaagta ccgggagtcg gagctgtgca gcagcagcat ctaccaccag   1920
aacgacccct ggcacccgcc cgtggtcttt gagcagtttc ttcacaacaa cgagaacatt   1980
gaaaatgagg acctggtggc ctgggtgacg gtgggcttcc tgcacatccc ccactcagag   2040
gacattccca acacagccac acctgggaac tccgtgggct tcctgctccg gccattcaac   2100
ttcttcccag aggacccctc cctggcatcc agagacactg tgatcgtgtg gcctcgggac   2160
aacggcccca actacgtcca gcgctggatc cctgaggaca gggactgctc gatgcctccc   2220
ccttttagct acaatgggac ctatagacct gtggagccca agtccgccga caagacccac   2280
acctgccccc cctgccccgc ccccccgtg gccggcccct ccgtgttcct gttccccccc   2340
aagcccaagg acaccctgat gatctccagg acccccgagg tgacctgcgt ggtggtggac   2400
gtgtcccacg aggaccccga ggtgaagttc aactggtacg tggacggcgt ggaggtgcac   2460
aacgccaaga ccaagcccag ggaggagcag tacaactcca cctacagggt ggtgtccgtg   2520
ctgaccgtgc tgcaccagga ctggctgaac ggcaaggagt acaagtgcaa ggtgtccaac   2580
```

aagggcctgc cctcctccat cgagaagacc atctccaagg ccaagggcca gcccagggag 2640
ccccaggtgt acaccctgcc cccctccagg gaggagatga ccaagaacca ggtgtccctg 2700
acctgcctgg tgaagggctt ctacccctcc gacatcgccg tggagtggga gtccaacggc 2760
cagcccgaga acaactacaa gaccaccccc cccgtgctgg actccgacgg ctccttcttc 2820
ctgtactcca agctgaccgt ggacaagtcc aggtggcagc agggcaacgt gttctcctgc 2880
tccgtgatgc acgaggccct gcacaaccac tacacccaga agtccctgtc cctgtccccc 2940
ggcaagtga 2949

<210> SEQ ID NO 98
<211> LENGTH: 2949
<212> TYPE: DNA
<213> ORGANISM: Artificial Sequence
<220> FEATURE:
<223> OTHER INFORMATION: hDAO-Fc-Hepmut3-Cysmut

<400> SEQUENCE: 98
atgccggccc tgggctgggc cgtggctgcc atcctgatgc tgcagacggc catggcggag 60
ccctccccgg ggactctgcc caggaaggca ggggtgtttt cagacctaag caaccaagag 120
ctgaaggcag tgcacagctt cctctggtcc aagaaggagc tgaggctgca gccctccagt 180
accaccacca tggccaagaa caccgtgttt ctcatcgaga tgctgctgcc caagaagtac 240
catgtgctga ggtttctgga taaaggtgaa aggcatcctg tgcgggaagc ccgtgccgtc 300
atcttctttg gtgaccagga gcatcccaat gtcaccgagt ttgctgtggg gcccctgcca 360
gggcccgcct acatgcgagc actgtccccc aggcctgggt accagtcctc ctgggcatcg 420
aggcccatct ccacagcaga gtatgccctc ctctaccaca ccctgcagga agccaccaag 480
cccctgcatc agttcttcct caataccaca ggcttctcat tccaagactg ccatgacaga 540
tgcctggcct tcaccgatgt ggccccccgg ggtgtggctt ctggccagcg ccgcagttgg 600
cttatcatac agcgctatgt agaaggctac tttctgcacc ccactgggct ggagctcctc 660
gtggatcatg ggagcacaga tgctgggcac tgggccgtgg agcaggtgtg gtacaacggg 720
aagttctatg ggagcccaga ggaactggct cggaagtatg cagatggaga ggtggacgtg 780
gtggtcctgg aggacccgct gcctgggggc aaggggcatg acagcacaga ggagccgccc 840
ctcttctcct cccacaagcc ccgcggggac ttccccagcc ccatccatgt gagcggcccc 900
cgcttggtcc agccccacgg ccctcgcttc aggctggagg gcaacgctgt gctctacggc 960
ggctggagct ttgccttccg gctgcgctcc tcctccgggc tgcaggtcct gaacgtgcac 1020
ttcggcggag agcgcattgc ctatgaggtc agcgtgcaag aggcagtggc gctgtatgga 1080
ggacacacac ctgcaggcat gcagaccaag tacctcgatg tcggctgggg cctgggcagc 1140
gtcactcatg agttagcccc cggcatcgac tgcccggaga ccgccacctt cctggacact 1200
ttccactact atgatgccga tgacccggtc cattatcccc gagccctctg cctctttgaa 1260
atgcccacag ggtgccccct tcggcggcac tttaattcca actttaaagg tggcttcaac 1320
ttctatgcgg ggctgaaggg ccaggtgctg gtgctgcgga caacttcaac tgtctacaat 1380
tatgattaca tttgggactt tatcttctac cccaacgggg tgatggaggc caagatgcat 1440
gccactggct acgtccacgc caccttctac acccccgagg ggctgcgcca cggcactcgc 1500
ctgcacaccc acctgattgg caacatacac actcacttgg tgcactaccg cgtagacctg 1560
gatgtggcag gcaccaagaa cagcttccag acactgcaga tgaagctaga aaacatcacc 1620
aacccctgga gcccaagaca ccgcgtggtc cagccaactc tggagcagac gcagtactcc 1680
tgggagcgcc aggcggcctt ccgcttcaaa acgaagctgc ccaagtacct gctctttacc 1740
agcccccagg agaacccctg gggccacaag cgcagctacc gcctgcagat ccactccatg 1800
gccgaccagg tgctgccccc aggctggcag gaggagcagg ccatcacctg ggcaaggtac 1860
cccctggcag tgaccaagta ccgggagtcg gagctgtgca gcagcagcat ctaccaccag 1920
aacgacccct ggcacccgcc cgtggtcttt gagcagtttc ttcacaacaa cgagaacatt 1980
gaaaatgagg acctggtggc ctgggtgacg gtgggcttcc tgcacatccc ccactcagag 2040
gacattccca acacagccac acctgggaac tccgtgggct tcctgctccg gccattcaac 2100
ttcttcccag aggacccctc cctggcatcc agagacactg tgatcgtgtg gcctcgggac 2160
aacggcccca actacgtcca gcgctggatc cctgaggaca gggactgctc gatgcctccc 2220
ccttttagct acaatgggac ctatagacct gtggagccca agtccgccga caagacccac 2280
acctgccccc cctgccccgc ccccccgtg gccggcccct ccgtgttcct gttccccccc 2340
aagcccaagg acaccctgat gatctccagg acccccgagg tgacctgcgt ggtggtggac 2400
gtgtcccacg aggaccccga ggtgaagttc aactggtacg tggacggcgt ggaggtgcac 2460
aacgccaaga ccaagcccag ggaggagcag tacaactcca cctacagggt ggtgtccgtg 2520
ctgaccgtgc tgcaccagga ctggctgaac ggcaaggagt acaagtgcaa ggtgtccaac 2580
aagggcctgc cctcctccat cgagaagacc atctccaagg ccaagggcca gcccagggag 2640
ccccaggtgt acaccctgcc cccctccagg gaggagatga ccaagaacca ggtgtccctg 2700
acctgcctgg tgaagggctt ctacccctcc gacatcgccg tggagtggga gtccaacggc 2760
cagcccgaga acaactacaa gaccaccccc cccgtgctgg actccgacgg ctccttcttc 2820
ctgtactcca agctgaccgt ggacaagtcc aggtggcagc agggcaacgt gttctcctgc 2880
tccgtgatgc acgaggccct gcacaaccac tacacccaga agtccctgtc cctgtccccc 2940
ggcaagtga 2949

<210> SEQ ID NO 99
<211> LENGTH: 2949
<212> TYPE: DNA
<213> ORGANISM: Artificial Sequence
<220> FEATURE:
<223> OTHER INFORMATION: hDAO-Fc-Hepmut4-Cysmut

<400> SEQUENCE: 99
atgccggccc tgggctgggc cgtggctgcc atcctgatgc tgcagacggc catggcggag 60
ccctccccgg ggactctgcc caggaaggca ggggtgtttt cagacctaag caaccaagag 120
ctgaaggcag tgcacagctt cctctggtcc aagaaggagc tgaggctgca gccctccagt 180
accaccacca tggccaagaa caccgtgttt ctcatcgaga tgctgctgcc caagaagtac 240
catgtgctga ggtttctgga taaaggtgaa aggcatcctg tgcgggaagc ccgtgccgtc 300
atcttctttg gtgaccagga gcatcccaat gtcaccgagt ttgctgtggg gcccctgcca 360
gggcccgcct acatgcgagc actgtccccc aggcctgggt accagtcctc ctgggcatcg 420
aggcccatct ccacagcaga gtatgccctc ctctaccaca ccctgcagga agccaccaag 480
cccctgcatc agttcttcct caataccaca ggcttctcat tccaagactg ccatgacaga 540
tgcctggcct tcaccgatgt ggccccccgg ggtgtggctt ctggccagcg ccgcagttgg 600
cttatcatac agcgctatgt agaaggctac tttctgcacc ccactgggct ggagctcctc 660
gtggatcatg ggagcacaga tgctgggcac tgggccgtgg agcaggtgtg gtacaacggg 720

```
aagttctatg ggagcccaga ggaactggct cggaagtatg cagatggaga ggtggacgtg    780
gtggtcctgg aggacccgct gcctgggggc aaggggcatg acagcacaga ggagccgccc    840
ctcttctcct cccacaagcc ccgcggggac ttccccagcc ccatccatgt gagcggcccc    900
cgcttggtcc agccccacgg ccctcgcttc aggctggagg gcaacgctgt gctctacggc    960
ggctggagct ttgccttccg gctgcgctcc tcctccgggc tgcaggtcct gaacgtgcac   1020
ttcggcggag agcgcattgc ctatgaggtc agcgtgcaag aggcagtggc gctgtatgga   1080
ggacacacac ctgcaggcat gcagaccaag tacctcgatg tcggctgggg cctgggcagc   1140
gtcactcatg agttagcccc cggcatcgac tgcccggaga ccgccacctt cctggacact   1200
ttccactact atgatgccga tgacccggtc cattatcccc gagccctctg cctctttgaa   1260
atgcccacag ggggtgcccct tcggcggcac tttaattcca actttaaagg tggcttcaac   1320
ttctatgcgg ggctgaaggg ccaggtgctg gtgctgcgga caacttcaac tgtctacaat   1380
tatgattaca tttgggactt tatcttctac cccaacgggg tgatggaggc caagatgcat   1440
gccactggct acgtccacgc caccttctac acccccgagg ggctgcgcca cggcactcgc   1500
ctgcacaccc acctgattgg caacatacac actcacttgg tgcactaccg cgtagacctg   1560
gatgtggcag gcaccaagaa cagcttccag acactgcaga tgaagctaga aaacatcacc   1620
aacccctgga gcccaagaca ccgcgtggtc cagccaactc tggagcagac gcagtactcc   1680
tgggagcgcc aggcggcctt cagcttcaaa acgaagctgc ccaagtacct gctctttacc   1740
agcccccagg agaacccctg gggccacaag cgcagctacc gcctgcagat ccactccatg   1800
gccgaccagg tgctgccccc aggctggcag gaggagcagg ccatcacctg ggcaaggtac   1860
cccctggcag tgaccaagta ccgggagtcg gagctgtgca gcagcagcat ctaccaccag   1920
aacgacccct ggcacccgcc cgtggtcttt gagcagtttc ttcacaacaa cgagaacatt   1980
gaaaatgagg acctggtggc ctgggtgacg gtgggcttcc tgcacatccc ccactcagag   2040
gacattccca acacagccac acctgggaac tccgtgggct tcctgctccg gccattcaac   2100
ttcttcccag aggacccctc cctggcatcc agagacactg tgatcgtgtg gcctcgggac   2160
aacggcccca actacgtcca gcgctggatc cctgaggaca gggactgctc gatgcctccc   2220
ccttttagct acaatgggac ctatagacct gtggagccca agtccgccga caagacccac   2280
acctgccccc cctgccccgc cccccccgtg gccggcccct ccgtgttcct gttccccccc   2340
aagcccaagg acaccctgat gatctccagg acccccgagg tgacctgcgt ggtggtggac   2400
gtgtcccacg aggaccccga ggtgaagttc aactggtacg tggacggcgt ggaggtgcac   2460
aacgccaaga ccaagcccag ggaggagcag tacaactcca cctacagggt ggtgtccgtg   2520
ctgaccgtgc tgcaccagga ctggctgaac ggcaaggagt acaagtgcaa ggtgtccaac   2580
aagggcctgc cctcctccat cgagaagacc atctccaagg ccaagggcca gcccagggag   2640
ccccaggtgt acaccctgcc cccctccagg gaggagatga ccaagaacca ggtgtccctg   2700
acctgcctgg tgaagggctt ctacccctcc gacatcgccg tggagtggga gtccaacggc   2760
cagcccgaga acaactacaa gaccaccccc cccgtgctgg actccgacgg ctccttcttc   2820
ctgtactcca agctgaccgt ggacaagtcc aggtggcagc agggcaacgt gttctcctgc   2880
tccgtgatgc acgaggccct gcacaaccac tacacccaga agtccctgtc cctgtccccc   2940
ggcaagtga                                                           2949
```

<210> SEQ ID NO 100
<211> LENGTH: 2949

<212> TYPE: DNA
<213> ORGANISM: Artificial Sequence
<220> FEATURE:
<223> OTHER INFORMATION: hDAO-Fc-Hepmut5-Cysmut

<400> SEQUENCE: 100

```
atgccggccc tgggctgggc cgtggctgcc atcctgatgc tgcagacggc catggcggag     60

ccctccccgg ggactctgcc caggaaggca ggggtgtttt cagacctaag caaccaagag    120

ctgaaggcag tgcacagctt cctctggtcc aagaaggagc tgaggctgca gccctccagt    180

accaccacca tggccaagaa caccgtgttt ctcatcgaga tgctgctgcc caagaagtac    240

catgtgctga ggtttctgga taaaggtgaa aggcatcctg tgcgggaagc ccgtgccgtc    300

atcttctttg gtgaccagga gcatcccaat gtcaccgagt ttgctgtggg gcccctgcca    360

gggcccgcct acatgcgagc actgtccccc aggcctgggt accagtcctc ctgggcatcg    420

aggcccatct ccacagcaga gtatgccctc ctctaccaca ccctgcagga agccaccaag    480

cccctgcatc agttcttcct caataccaca ggcttctcat tccaagactg ccatgacaga    540

tgcctggcct tcaccgatgt ggcccccggg ggtgtggctt ctggccagcg ccgcagttgg    600

cttatcatac agcgctatgt agaaggctac tttctgcacc ccactgggct ggagctcctc    660

gtggatcatg ggagcacaga tgctgggcac tgggccgtgg agcaggtgtg gtacaacggg    720

aagttctatg ggagcccaga ggaactggct cggaagtatg cagatggaga ggtggacgtg    780

gtggtcctgg aggacccgct gcctgggggc aaggggcatg acagcacaga ggagccgccc    840

ctcttctcct cccacaagcc ccgcggggac ttccccagcc ccatccatgt gagcggcccc    900

cgcttggtcc agccccacgg ccctcgcttc aggctggagg gcaacgctgt gctctacggc    960

ggctggagct ttgccttccg gctgcgctcc tcctccgggc tgcaggtcct gaacgtgcac   1020

ttcggcggag agcgcattgc ctatgaggtc agcgtgcaag aggcagtggc gctgtatgga   1080

ggacacacac ctgcaggcat gcagaccaag tacctcgatg tcggctgggg cctgggcagc   1140

gtcactcatg agttagcccc cggcatcgac tgcccggaga ccgccacctt cctggacact   1200

ttccactact atgatgccga tgacccggtc cattatcccc gagccctctg cctctttgaa   1260

atgcccacag ggtgcccct tcggcggcac tttaattcca actttaaagg tggcttcaac   1320

ttctatgcgg ggctgaaggg ccaggtgctg gtgctgcgga caacttcaac tgtctacaat   1380

tatgattaca tttgggactt tatcttctac cccaacgggg tgatggaggc caagatgcat   1440

gccactggct acgtccacgc caccttctac acccccgagg ggctgcgcca cggcactcgc   1500

ctgcacaccc acctgattgg caacatacac actcacttgg tgcactaccg cgtagacctg   1560

gatgtggcag gcaccaagaa cagcttccag acactgcaga tgaagctaga aaacatcacc   1620

aacccctgga gcccaagaca ccgcgtggtc cagccaactc tggagcagac gcagtactcc   1680

tgggagcgcc aggcggcctt ccgcttcaaa acgaagctgc ccacgtacct gctctttacc   1740

agcccccagg agaaccctg gggccacaag cgcagctacc gcctgcagat ccactccatg   1800

gccgaccagg tgctgccccc aggctggcag gaggagcagg ccatcacctg ggcaaggtac   1860

cccctggcag tgaccaagta ccgggagtcg gagctgtgca gcagcagcat ctaccaccag   1920

aacgacccct ggcacccgcc cgtggtcttt gagcagtttc ttcacaacaa cgagaacatt   1980

gaaaatgagg acctggtggc ctgggtgacg gtgggcttcc tgcacatccc ccactcagag   2040

gacattccca acacagccac acctgggaac tccgtgggct tcctgctccg gccattcaac   2100

ttcttcccag aggacccctc cctggcatcc agagacactg tgatcgtgtg gcctcgggac   2160
```

aacggcccca actacgtcca gcgctggatc cctgaggaca gggactgctc gatgcctccc 2220
ccttttagct acaatgggac ctatagacct gtggagccca agtccgccga caagacccac 2280
acctgccccc cctgccccgc cccccccgtg gccggcccct ccgtgttcct gttccccccc 2340
aagcccaagg acaccctgat gatctccagg acccccgagg tgacctgcgt ggtggtggac 2400
gtgtcccacg aggaccccga ggtgaagttc aactggtacg tggacggcgt ggaggtgcac 2460
aacgccaaga ccaagcccag ggaggagcag tacaactcca cctacagggt ggtgtccgtg 2520
ctgaccgtgc tgcaccagga ctggctgaac ggcaaggagt acaagtgcaa ggtgtccaac 2580
aagggcctgc cctcctccat cgagaagacc atctccaagg ccaagggcca gcccagggag 2640
ccccaggtgt acaccctgcc cccctccagg gaggagatga ccaagaacca ggtgtccctg 2700
acctgcctgg tgaagggctt ctacccctcc gacatcgccg tggagtggga gtccaacggc 2760
cagcccgaga acaactacaa gaccaccccc cccgtgctgg actccgacgg ctccttcttc 2820
ctgtactcca agctgaccgt ggacaagtcc aggtggcagc agggcaacgt gttctcctgc 2880
tccgtgatgc acgaggccct gcacaaccac tacacccaga agtccctgtc cctgtccccc 2940
ggcaagtga 2949

<210> SEQ ID NO 101
<211> LENGTH: 2949
<212> TYPE: DNA
<213> ORGANISM: Artificial Sequence
<220> FEATURE:
<223> OTHER INFORMATION: hDAO-Fc-Hepmut6-Cysmut

<400> SEQUENCE: 101
atgccggccc tgggctgggc cgtggctgcc atcctgatgc tgcagacggc catggcggag 60
ccctccccgg ggactctgcc caggaaggca ggggtgtttt cagacctaag caaccaagag 120
ctgaaggcag tgcacagctt cctctggtcc aagaaggagc tgaggctgca gccctccagt 180
accaccacca tggccaagaa caccgtgttt ctcatcgaga tgctgctgcc caagaagtac 240
catgtgctga ggtttctgga taaaggtgaa aggcatcctg tgcgggaagc ccgtgccgtc 300
atcttctttg gtgaccagga gcatcccaat gtcaccgagt ttgctgtggg gccccctgcca 360 gggcccgcct acatgcgagc actgtccccc aggcctgggt accagtcctc ctgggcatcg 420
aggcccatct ccacagcaga gtatgccctc ctctaccaca ccctgcagga agccaccaag 480
cccctgcatc agttcttcct caataccaca ggcttctcat tccaagactg ccatgacaga 540
tgcctggcct tcaccgatgt ggccccccgg ggtgtggctt ctggccagcg ccgcagttgg 600
cttatcatac agcgctatgt agaaggctac tttctgcacc ccactgggct ggagctcctc 660
gtggatcatg ggagcacaga tgctgggcac tgggccgtgg agcaggtgtg gtacaacggg 720
aagttctatg ggagcccaga ggaactggct cggaagtatg cagatggaga ggtggacgtg 780
gtggtcctgg aggacccgct gcctgggggc aaggggcatg acagcacaga ggagccgccc 840
ctcttctcct cccacaagcc ccgcggggac ttccccagcc ccatccatgt gagcggcccc 900
cgcttggtcc agccccacgg ccctcgcttc aggctggagg gcaacgctgt gctctacggc 960
ggctggagct ttgccttccg gctgcgctcc tcctccgggc tgcaggtcct gaacgtgcac 1020
ttcggcggag agcgcattgc ctatgaggtc agcgtgcaag aggcagtggc gctgtatgga 1080
ggacacacac ctgcaggcat gcagaccaag tacctcgatg tcggctgggg cctgggcagc 1140
gtcactcatg agttagcccc cggcatcgac tgcccggaga ccgccacctt cctggacact 1200
ttccactact atgatgccga tgacccggtc cattatcccc gagccctctg cctctttgaa 1260
atgcccacag gggtgcccct tcggcggcac tttaattcca actttaaagg tggcttcaac 1320
ttctatgcgg ggctgaaggg ccaggtgctg gtgctgcgga caacttcaac tgtctacaat 1380
tatgattaca tttgggactt tatcttctac cccaacgggg tgatggaggc caagatgcat 1440
gccactggct acgtccacgc caccttctac acccccgagg ggctgcgcca cggcactcgc 1500
ctgcacaccc acctgattgg caacatacac actcacttgg tgcactaccg cgtagacctg 1560
gatgtggcag gcaccaagaa cagcttccag acactgcaga tgaagctaga aaacatcacc 1620
aacccctgga gcccaagaca ccgcgtggtc cagccaactc tggagcagac gcagtactcc 1680
tgggagcgcc aggcggcctt ccgcttcgga cagacgctgc ccaagtacct gctctttacc 1740
agcccccagg agaacccctg gggccacaag cgcagctacc gcctgcagat ccactccatg 1800
gccgaccagg tgctgccccc aggctggcag gaggagcagg ccatcacctg ggcaaggtac 1860
cccctggcag tgaccaagta ccgggagtcg gagctgtgca gcagcagcat ctaccaccag 1920
aacgacccct ggcacccgcc cgtggtcttt gagcagtttc ttcacaacaa cgagaacatt 1980
gaaaatgagg acctggtggc ctgggtgacg gtgggcttcc tgcacatccc ccactcagag 2040
gacattccca acacagccac acctgggaac tccgtgggct tcctgctccg gccattcaac 2100
ttcttcccag aggacccctc cctggcatcc agagacactg tgatcgtgtg gcctcgggac 2160
aacggcccca actacgtcca gcgctggatc cctgaggaca gggactgctc gatgcctccc 2220
ccttttagct acaatgggac ctatagacct gtggagccca agtccgccga caagacccac 2280
acctgccccc cctgccccgc cccccccgtg gccggcccct ccgtgttcct gttccccccc 2340
aagcccaagg acaccctgat gatctccagg acccccgagg tgacctgcgt ggtggtggac 2400
gtgtcccacg aggaccccga ggtgaagttc aactggtacg tggacggcgt ggaggtgcac 2460
aacgccaaga ccaagcccag ggaggagcag tacaactcca cctacagggt ggtgtccgtg 2520
ctgaccgtgc tgcaccagga ctggctgaac ggcaaggagt acaagtgcaa ggtgtccaac 2580
aagggcctgc cctcctccat cgagaagacc atctccaagg ccaagggcca gcccagggag 2640
ccccaggtgt acaccctgcc cccctccagg gaggagatga ccaagaacca ggtgtccctg 2700
acctgcctgg tgaagggctt ctacccctcc gacatcgccg tggagtggga gtccaacggc 2760
cagcccgaga acaactacaa gaccaccccc cccgtgctgg actccgacgg ctccttcttc 2820
ctgtactcca agctgaccgt ggacaagtcc aggtggcagc agggcaacgt gttctcctgc 2880
tccgtgatgc acgaggccct gcacaaccac tacacccaga agtccctgtc cctgtccccc 2940
ggcaagtga 2949

<210> SEQ ID NO 102
<211> LENGTH: 2949
<212> TYPE: DNA
<213> ORGANISM: Artificial Sequence
<220> FEATURE:
<223> OTHER INFORMATION: hDAO-Fc-Hepmut7-Cysmut

<400> SEQUENCE: 102
atgccggccc tgggctgggc cgtggctgcc atcctgatgc tgcagacggc catggcggag 60
ccctccccgg ggactctgcc caggaaggca ggggtgtttt cagacctaag caaccaagag 120
ctgaaggcag tgcacagctt cctctggtcc aagaaggagc tgaggctgca gccctccagt 180
accaccacca tggccaagaa caccgtgttt ctcatcgaga tgctgctgcc caagaagtac 240
catgtgctga ggtttctgga taaaggtgaa aggcatcctg tgcgggaagc ccgtgccgtc 300

```
atcttctttg gtgaccagga gcatcccaat gtcaccgagt ttgctgtggg gcccctgcca    360
gggcccgcct acatgcgagc actgtccccc aggcctgggt accagtcctc ctgggcatcg    420
aggcccatct ccacagcaga gtatgccctc ctctaccaca ccctgcagga agccaccaag    480
cccctgcatc agttcttcct caataccaca ggcttctcat tccaagactg ccatgacaga    540
tgcctggcct tcaccgatgt ggccccccgg ggtgtggctt ctggccagcg ccgcagttgg    600
cttatcatac agcgctatgt agaaggctac tttctgcacc ccactgggct ggagctcctc    660
gtggatcatg ggagcacaga tgctgggcac tgggccgtgg agcaggtgtg gtacaacggg    720
aagttctatg ggagcccaga ggaactggct cggaagtatg cagatggaga ggtggacgtg    780
gtggtcctgg aggacccgct gcctgggggc aaggggcatg acagcacaga ggagccgccc    840
ctcttctcct cccacaagcc ccgcggggac ttccccagcc ccatccatgt gagcggcccc    900
cgcttggtcc agccccacgg ccctcgcttc aggctggagg gcaacgctgt gctctacggc    960
ggctggagct ttgccttccg gctgcgctcc tcctccgggc tgcaggtcct gaacgtgcac   1020
ttcggcggag agcgcattgc ctatgaggtc agcgtgcaag aggcagtggc gctgtatgga   1080
ggacacacac ctgcaggcat gcagaccaag tacctcgatg tcggctgggg cctgggcagc   1140
gtcactcatg agttagcccc cggcatcgac tgcccggaga ccgccacctt cctggacact   1200
ttccactact atgatgccga tgacccggtc cattatcccc gagccctctg cctctttgaa   1260
atgcccacag ggtgcccct tcggcggcac tttaattcca actttaaagg tggcttcaac   1320
ttctatgcgg ggctgaaggg ccaggtgctg gtgctgcgga caacttcaac tgtctacaat   1380
tatgattaca tttgggactt tatcttctac cccaacgggg tgatggaggc caagatgcat   1440
gccactggct acgtccacgc caccttctac acccccgagg ggctgcgcca cggcactcgc   1500
ctgcacaccc acctgattgg caacatacac actcacttgg tgcactaccg cgtagacctg   1560
gatgtggcag gcaccaagaa cagcttccag acactgcaga tgaagctaga aaacatcacc   1620
aacccctgga gcccaagaca ccgcgtggtc cagccaactc tggagcagac gcagtactcc   1680
tgggagcgcc aggcggcctt cagcttcaaa aggaagctgc ccacgtacct gctctttacc   1740
agcccccagg agaacccctg ggccacaag cgcagctacc gcctgcagat ccactccatg   1800
gccgaccagg tgctgccccc aggctggcag gaggagcagg ccatcacctg ggcaaggtac   1860
cccctggcag tgaccaagta ccgggagtcg gagctgtgca gcagcagcat ctaccaccag   1920
aacgacccct ggcacccgcc cgtggtcttt gagcagtttc ttcacaacaa cgagaacatt   1980
gaaaatgagg acctggtggc ctgggtgacg gtgggcttcc tgcacatccc ccactcagag   2040
gacattccca acacagccac acctgggaac tccgtgggct tcctgctccg gccattcaac   2100
ttcttcccag aggacccctc cctggcatcc agagacactg tgatcgtgtg gcctcgggac   2160
aacggcccca actacgtcca gcgctggatc cctgaggaca gggactgctc gatgcctccc   2220
ccttttagct acaatgggac ctatagacct gtggagccca agtccgccga caagacccac   2280
acctgccccc cctgccccgc ccccccgtg gccggcccct ccgtgttcct gttccccccc   2340
aagcccaagg acaccctgat gatctccagg acccccgagg tgacctgcgt ggtggtggac   2400
gtgtcccacg aggaccccga ggtgaagttc aactggtacg tggacggcgt ggaggtgcac   2460
aacgccaaga ccaagcccag ggaggagcag tacaactcca cctacagggt ggtgtccgtg   2520
ctgaccgtgc tgcaccagga ctggctgaac ggcaaggagt acaagtgcaa ggtgtccaac   2580
aagggcctgc cctcctccat cgagaagacc atctccaagg ccaagggcca gcccagggag   2640
ccccaggtgt acaccctgcc cccctccagg gaggagatga ccaagaacca ggtgtccctg   2700
```

acctgcctgg tgaagggctt ctacccctcc gacatcgccg tggagtggga gtccaacggc 2760
cagcccgaga acaactacaa gaccaccccc cccgtgctgg actccgacgg ctccttcttc 2820
ctgtactcca agctgaccgt ggacaagtcc aggtggcagc agggcaacgt gttctcctgc 2880
tccgtgatgc acgaggccct gcacaaccac tacacccaga agtccctgtc cctgtccccc 2940
ggcaagtga 2949

<210> SEQ ID NO 103
<211> LENGTH: 585
<212> TYPE: PRT
<213> ORGANISM: Homo sapiens

<400> SEQUENCE: 103

Asp Ala His Lys Ser Glu Val Ala His Arg Phe Lys Asp Leu Gly Glu
1 5 10 15

Glu Asn Phe Lys Ala Leu Val Leu Ile Ala Phe Ala Gln Tyr Leu Gln
20 25 30

Gln Cys Pro Phe Glu Asp His Val Lys Leu Val Asn Glu Val Thr Glu
35 40 45

Phe Ala Lys Thr Cys Val Ala Asp Glu Ser Ala Glu Asn Cys Asp Lys
50 55 60

Ser Leu His Thr Leu Phe Gly Asp Lys Leu Cys Thr Val Ala Thr Leu
65 70 75 80

Arg Glu Thr Tyr Gly Glu Met Ala Asp Cys Cys Ala Lys Gln Glu Pro
85 90 95

Glu Arg Asn Glu Cys Phe Leu Gln His Lys Asp Asp Asn Pro Asn Leu
100 105 110

Pro Arg Leu Val Arg Pro Glu Val Asp Val Met Cys Thr Ala Phe His
115 120 125

Asp Asn Glu Glu Thr Phe Leu Lys Lys Tyr Leu Tyr Glu Ile Ala Arg
130 135 140

Arg His Pro Tyr Phe Tyr Ala Pro Glu Leu Leu Phe Phe Ala Lys Arg
145 150 155 160

Tyr Lys Ala Ala Phe Thr Glu Cys Cys Gln Ala Ala Asp Lys Ala Ala
165 170 175

Cys Leu Leu Pro Lys Leu Asp Glu Leu Arg Asp Glu Gly Lys Ala Ser
180 185 190

Ser Ala Lys Gln Arg Leu Lys Cys Ala Ser Leu Gln Lys Phe Gly Glu
195 200 205

Arg Ala Phe Lys Ala Trp Ala Val Ala Arg Leu Ser Gln Arg Phe Pro
210 215 220

Lys Ala Glu Phe Ala Glu Val Ser Lys Leu Val Thr Asp Leu Thr Lys
225 230 235 240

Val His Thr Glu Cys Cys His Gly Asp Leu Leu Glu Cys Ala Asp Asp
245 250 255

Arg Ala Asp Leu Ala Lys Tyr Ile Cys Glu Asn Gln Asp Ser Ile Ser
260 265 270

Ser Lys Leu Lys Glu Cys Cys Glu Lys Pro Leu Leu Glu Lys Ser His
275 280 285

Cys Ile Ala Glu Val Glu Asn Asp Glu Met Pro Ala Asp Leu Pro Ser
290 295 300

Leu Ala Ala Asp Phe Val Glu Ser Lys Asp Val Cys Lys Asn Tyr Ala
305 310 315 320

```
Glu Ala Lys Asp Val Phe Leu Gly Met Phe Leu Tyr Glu Tyr Ala Arg
            325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
            405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
            485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
            565                 570                 575

Ala Ala Ser Gln Ala Ala Leu Gly Leu
            580                 585
```

<210> SEQ ID NO 104
<211> LENGTH: 21
<212> TYPE: DNA
<213> ORGANISM: Artificial Sequence
<220> FEATURE:
<223> OTHER INFORMATION: forward primer

<400> SEQUENCE: 104
cagaccacag gcttctcatt c 21

<210> SEQ ID NO 105
<211> LENGTH: 18
<212> TYPE: DNA
<213> ORGANISM: Artificial Sequence
<220> FEATURE:
<223> OTHER INFORMATION: reverse primer

<400> SEQUENCE: 105
gaggaagaac tgatgcag 18

<210> SEQ ID NO 106
<211> LENGTH: 751
<212> TYPE: PRT

<213> ORGANISM: Artificial Sequence
<220> FEATURE:
<223> OTHER INFORMATION: hDAO-Hepmut4 Asn168Gln

<400> SEQUENCE: 106

Met Pro Ala Leu Gly Trp Ala Val Ala Ala Ile Leu Met Leu Gln Thr
1               5                   10                  15

Ala Met Ala Glu Pro Ser Pro Gly Thr Leu Pro Arg Lys Ala Gly Val
            20                  25                  30

Phe Ser Asp Leu Ser Asn Gln Glu Leu Lys Ala Val His Ser Phe Leu
        35                  40                  45

Trp Ser Lys Lys Glu Leu Arg Leu Gln Pro Ser Ser Thr Thr Thr Met
    50                  55                  60

Ala Lys Asn Thr Val Phe Leu Ile Glu Met Leu Leu Pro Lys Lys Tyr
65                  70                  75                  80

His Val Leu Arg Phe Leu Asp Lys Gly Glu Arg His Pro Val Arg Glu
                85                  90                  95

Ala Arg Ala Val Ile Phe Phe Gly Asp Gln Glu His Pro Asn Val Thr
            100                 105                 110

Glu Phe Ala Val Gly Pro Leu Pro Gly Pro Cys Tyr Met Arg Ala Leu
        115                 120                 125

Ser Pro Arg Pro Gly Tyr Gln Ser Ser Trp Ala Ser Arg Pro Ile Ser
    130                 135                 140

Thr Ala Glu Tyr Ala Leu Leu Tyr His Thr Leu Gln Glu Ala Thr Lys
145                 150                 155                 160

Pro Leu His Gln Phe Phe Leu Gln Thr Thr Gly Phe Ser Phe Gln Asp
                165                 170                 175

Cys His Asp Arg Cys Leu Ala Phe Thr Asp Val Ala Pro Arg Gly Val
            180                 185                 190

Ala Ser Gly Gln Arg Arg Ser Trp Leu Ile Ile Gln Arg Tyr Val Glu
        195                 200                 205

Gly Tyr Phe Leu His Pro Thr Gly Leu Glu Leu Leu Val Asp His Gly
    210                 215                 220

Ser Thr Asp Ala Gly His Trp Ala Val Glu Gln Val Trp Tyr Asn Gly
225                 230                 235                 240

Lys Phe Tyr Gly Ser Pro Glu Glu Leu Ala Arg Lys Tyr Ala Asp Gly
                245                 250                 255

Glu Val Asp Val Val Val Leu Glu Asp Pro Leu Pro Gly Gly Lys Gly
            260                 265                 270

His Asp Ser Thr Glu Glu Pro Pro Leu Phe Ser Ser His Lys Pro Arg
        275                 280                 285

Gly Asp Phe Pro Ser Pro Ile His Val Ser Gly Pro Arg Leu Val Gln
    290                 295                 300

Pro His Gly Pro Arg Phe Arg Leu Glu Gly Asn Ala Val Leu Tyr Gly
305                 310                 315                 320

Gly Trp Ser Phe Ala Phe Arg Leu Arg Ser Ser Ser Gly Leu Gln Val
                325                 330                 335

Leu Asn Val His Phe Gly Gly Glu Arg Ile Ala Tyr Glu Val Ser Val
            340                 345                 350

Gln Glu Ala Val Ala Leu Tyr Gly Gly His Thr Pro Ala Gly Met Gln
        355                 360                 365

Thr Lys Tyr Leu Asp Val Gly Trp Gly Leu Gly Ser Val Thr His Glu
    370                 375                 380

Leu Ala Pro Gly Ile Asp Cys Pro Glu Thr Ala Thr Phe Leu Asp Thr

```
385                 390                 395                 400

Phe His Tyr Tyr Asp Ala Asp Asp Pro Val His Tyr Pro Arg Ala Leu
                405                 410                 415

Cys Leu Phe Glu Met Pro Thr Gly Val Pro Leu Arg Arg His Phe Asn
            420                 425                 430

Ser Asn Phe Lys Gly Gly Phe Asn Phe Tyr Ala Gly Leu Lys Gly Gln
        435                 440                 445

Val Leu Val Leu Arg Thr Thr Ser Thr Val Tyr Asn Tyr Asp Tyr Ile
    450                 455                 460

Trp Asp Phe Ile Phe Tyr Pro Asn Gly Val Met Glu Ala Lys Met His
465                 470                 475                 480

Ala Thr Gly Tyr Val His Ala Thr Phe Tyr Thr Pro Glu Gly Leu Arg
                485                 490                 495

His Gly Thr Arg Leu His Thr His Leu Ile Gly Asn Ile His Thr His
            500                 505                 510

Leu Val His Tyr Arg Val Asp Leu Asp Val Ala Gly Thr Lys Asn Ser
        515                 520                 525

Phe Gln Thr Leu Gln Met Lys Leu Glu Asn Ile Thr Asn Pro Trp Ser
    530                 535                 540

Pro Arg His Arg Val Val Gln Pro Thr Leu Glu Gln Thr Gln Tyr Ser
545                 550                 555                 560

Trp Glu Arg Gln Ala Ala Phe Ser Phe Lys Thr Lys Leu Pro Lys Tyr
                565                 570                 575

Leu Leu Phe Thr Ser Pro Gln Glu Asn Pro Trp Gly His Lys Arg Ser
            580                 585                 590

Tyr Arg Leu Gln Ile His Ser Met Ala Asp Gln Val Leu Pro Pro Gly
        595                 600                 605

Trp Gln Glu Glu Gln Ala Ile Thr Trp Ala Arg Tyr Pro Leu Ala Val
    610                 615                 620

Thr Lys Tyr Arg Glu Ser Glu Leu Cys Ser Ser Ser Ile Tyr His Gln
625                 630                 635                 640

Asn Asp Pro Trp His Pro Pro Val Val Phe Glu Gln Phe Leu His Asn
                645                 650                 655

Asn Glu Asn Ile Glu Asn Glu Asp Leu Val Ala Trp Val Thr Val Gly
            660                 665                 670

Phe Leu His Ile Pro His Ser Glu Asp Ile Pro Asn Thr Ala Thr Pro
        675                 680                 685

Gly Asn Ser Val Gly Phe Leu Leu Arg Pro Phe Asn Phe Phe Pro Glu
    690                 695                 700

Asp Pro Ser Leu Ala Ser Arg Asp Thr Val Ile Val Trp Pro Arg Asp
705                 710                 715                 720

Asn Gly Pro Asn Tyr Val Gln Arg Trp Ile Pro Glu Asp Arg Asp Cys
                725                 730                 735

Ser Met Pro Pro Pro Phe Ser Tyr Asn Gly Thr Tyr Arg Pro Val
            740                 745                 750
```